US008779235B2

(12) United States Patent
Gallie et al.

(10) Patent No.: US 8,779,235 B2
(45) Date of Patent: *Jul. 15, 2014

(54) ENGINEERING SINGLE-GENE-CONTROLLED STAYGREEN POTENTIAL INTO PLANTS

(75) Inventors: Daniel R. Gallie, Riverside, CA (US); Robert Meeley, Des Moines, IA (US); Todd Young, Palm Springs, CA (US)

(73) Assignees: Pioneer Hi-Bred International, Inc., Des Moines, IA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,911

(22) Filed: Feb. 14, 2012

(65) Prior Publication Data
US 2012/0144525 A1 Jun. 7, 2012

Related U.S. Application Data

(60) Continuation of application No. 12/800,466, filed on May 14, 2010, now Pat. No. 8,129,587, which is a division of application No. 11/698,310, filed on Jan. 24, 2007, now Pat. No. 7,763,773, which is a continuation of application No. 10/875,127, filed on Jun. 22, 2004, now Pat. No. 7,230,161.

(60) Provisional application No. 60/480,861, filed on Jun. 23, 2003.

(51) Int. Cl.
C12N 15/113 (2010.01)
C12N 15/82 (2006.01)
C12N 5/10 (2006.01)
A01H 5/00 (2006.01)

(52) U.S. Cl.
USPC ........... 800/283; 800/278; 800/285; 800/320; 536/24.5; 435/419

(58) Field of Classification Search
None
See application file for complete search history.

(56) References Cited

U.S. PATENT DOCUMENTS

| | | | |
|---|---|---|---|
| 5,304,712 A | 4/1994 | Harper, II | |
| 5,449,764 A | 9/1995 | Bird et al. | |
| 5,484,906 A | 1/1996 | Bird et al. | |
| 5,536,659 A | 7/1996 | Fukuda | |
| 5,702,933 A | 12/1997 | Klee et al. | |
| 5,723,766 A | 3/1998 | Theologis et al. | |
| 5,750,864 A | 5/1998 | Bestwick et al. | |
| 5,824,875 A | 10/1998 | Ranu | |
| 5,886,164 A | 3/1999 | Bird et al. | |
| 5,908,971 A | 6/1999 | Van Der Straeten | |
| 6,156,956 A | 12/2000 | Theologis et al. | |
| 6,194,639 B1 * | 2/2001 | Botella et al. | 800/298 |
| 6,207,881 B1 | 3/2001 | Theologis et al. | |
| 6,262,346 B1 | 7/2001 | Bird | |
| 7,230,161 B2 | 6/2007 | Gallie et al. | |
| 7,763,773 B2 | 7/2010 | Gallie et al. | |
| 7,838,730 B2 | 11/2010 | Gallie et al. | |
| 2002/0058340 A1 | 5/2002 | Clemente et al. | |
| 2004/0034888 A1 * | 2/2004 | Liu et al. | 800/289 |
| 2004/0214272 A1 | 10/2004 | La Rosa et al. | |
| 2009/0019601 A1 | 1/2009 | Kovalic | |

FOREIGN PATENT DOCUMENTS

| | | |
|---|---|---|
| EP | 0482053 B1 | 4/2003 |
| WO | WO 92/04456 | 3/1992 |
| WO | WO 9621027 A1 | 7/1996 |
| WO | WO 96/35792 | 11/1996 |
| WO | WO 01/25455 | 4/2001 |
| WO | WO 01/57063 | 8/2001 |
| WO | WO 03/000906 | 1/2003 |

OTHER PUBLICATIONS

Guo et al. (2004) PNAS 101: 9205-9210.*
Thomas et al. (2001) Plant J. 25, pp. 417-425.*
Klahre et al. (2002) PNAS 99, pp. 11981-11986.*
Waterhouse et al. (1998) PNAS 95: 13959-13964.*
Bhalla and Singh (1999) Molecular control of male fertility in Brassica Proc. 10$^{th}$ Annual Rapeseed Congress, Canberra, Australia.
Borrell and Douglas (1996) Maintaining green leaf area in grain sorghum increases yield in a water-limited environment. In: Foale MA, Henzell RG, Kneipp JF, eds. Proceedings of the third Australian sorghum conference. Melbourne: Australian Institute of Agricultural Science, Occasional Publication No. 93.
Bruce et al. (2002), "Molecular and physiological approaches to maize improvement for drought tolerance" *Journal of Experimental Botany*, 53 (366): 13-25.
Chuang et al. (2000) "Specific and heritable genetic interference by double-stranded RNA in Arabidopsis thaliana." *Proceedings of the National Academy of Sciences, USA*, 97: 4985-4990.
Colliver et al. (1997) "Different modification of flavonoid and isoflavonoid biosynthesis with an antisense chalcone synthase construct in transgenic Lotus corniculatus." *PBM*, 35: 509-522.
Database EMBL Apr. 5, 1996, Subramaniam, L. "Triticum aestivum ACC synthase (TA-ACS2) gene, complete cds." Retrieved from EBI Database accession No. U42336.

(Continued)

Primary Examiner — Anne Kubelik
Assistant Examiner — Steven Bernacki
(74) Attorney, Agent, or Firm — Monica Elrod-Erickson; Quine Intellectual Property Law Group, P.C.

(57) ABSTRACT

The enzymes of the ACC synthase family are used in producing ethylene. Nucleotide and polypeptide sequences of ACC synthases are provided along with knockout plant cells having inhibition in expression and/or activity in an ACC synthase and knockout plants displaying a staygreen phenotype, a male sterility phenotype, or an inhibition in ethylene production. Methods for modulating staygreen potential in plants, methods for modulating sterility in plants, and methods for inhibiting ethylene production in plants are also provided.

8 Claims, 59 Drawing Sheets
(2 of 59 Drawing Sheet(s) Filed in Color)

(56) References Cited

OTHER PUBLICATIONS

Davis and Grierson(1989) Identification of cDNA clones for tomato (*Lycopersicon esculentum* Mill.) mRNAs that accumulate during fruit ripening and leaf senescence in response to ethylene. *Planta* 179: 73-80.
Desai et al. (2002) "Expression and Affinity Purification of Recombinant Proteins from Plants." *Protein Expression and Purification*, 25:195-202.
Duncan, et al. (1981) "Descriptive comparison of senescent and non-senescent sorghum genotypes." *Agronomy Journal* 73: 849-853.
Elomaa et al. (1996) "Transformation of antisense constructs of the chslcone synthase gene superfamily into Gerbera hybrida: differential effect on the expression of family members." *Molecular Breeding*, 2: 41-50.
EP examination report dated Apr. 19, 2011 from corresponding EP application No. 04801865.9.
Gallie and Young (2004) The ethylene biosynthetic and perception machinery is differentially expressed during endosperm and embryo development Mol Gen Genomics 271:267-281.
Gan and Amasino (1995) Inhibition of leaf senescence by autoregulated production of cytokinin. *Science* 270: 1986-1988.
Gan et al. (1997) "Making Sense of Senescence." *Plant Physiology*, 113:313-319.
Gen Bank Accession No. AY104732 "*Zea mays* PC0143423 mRNA sequence," May 2008.
Gen Bank Accession No. CC651994, Jun. 19, 2003.
Gen Bank Accession No. CC680933, Jun. 19, 2003.
Gen Bank Accession No. CC730134, Jun. 20, 2003.
GenBank Accession No. AX659868, "Sequence 225 from Patent WO 03000906," Mar. 22, 2003.
GenBank Accession No. M96673, "*Oryza sativa* 1-aminocyclopropane-1 carboxylate synthase (ACC1) gene, complete cds," Jun. 12, 1993.
Genbank accession No. AAAA01003833, date of publication Apr. 4, 2002, date of retrieval Feb. 9, 2005.
Genbank accession No. AAAA01005233, date of publication Apr. 4, 2002, date of retrieval Feb. 9, 2005.
Genbank accession No. AAAA01009261, date of publication Apr. 4, 2002, date of retrieval Feb. 9, 2005.
Genbank accession No. AAAA01016483, date of publication Apr. 4, 2002, date of retrieval Feb. 9, 2005.
Genbank accession No. AAAA01021286, date of publication Apr. 4, 2002, date of retrieval Feb. 9, 2005.
Genbank accession No. AAAA01027795, date of publication Apr. 4, 2002, date of retrieval Feb. 9, 2005.
Genbank accession No. AB085172, date of publication Feb. 26, 2006, date of retrieval Aug. 3, 2006.
Genbank accession No. AC090973, date of publication Mar. 21, 2001, date of retrieval Feb. 9, 2005.
Genbank accession No. AF008942, date of publication Oct. 16, 2003, date of retrieval Feb. 9, 2005.
Genbank accession No. AF129508, date of publication Apr. 7, 2000, date of retrieval Feb. 9, 2005.
Genbank accession No. AF179248, date of publication Jul. 13, 2001, date of retrieval Feb. 9, 2005.
Genbank accession No. AF179249, date of publication Jul. 13, 2001, date of retrieval Feb. 9, 2005.
Genbank accession No. AF332390.1, date of publication May 7, 2003, date of retrieval Feb. 9, 2005.
Genbank accession No. AF332391.1, date of publication May 7, 2003, date of retrieval Feb. 9, 2005.
Genbank accession No. AF334712.1, date of publication Dec. 11, 2003, date of retrieval Feb. 9, 2005.
Genbank accession No. AF334720, date of publication Dec. 11, 2003, date of retrieval Feb. 9, 2005.
Genbank accession No. AL606624, date of publication Feb. 10, 2004, date of retrieval Feb. 9, 2005.
Genbank accession No. AP000559, date of publication Nov. 30, 2004, date of retrieval Feb. 9, 2005.
Genbank accession No. AP002746, date of publication Nov. 16, 2004, date of retrieval Feb. 9, 2005.
Genbank accession No. AY133715, date of publication Sep. 18, 2002, date of retrieval Feb. 9, 2005.
Genbank accession No. AY702076, date of publication Sep. 6, 2004, date of retrieval Feb. 9, 2005.
Genbank accession No. M96672, date of publication Jun 12, 1993, date of retrieval Aug. 3, 2006.
Genbank accession No. NM_100030, date of publication Feb. 19, 2004, date of retrieval Feb. 9, 2005.
Genbank accession No. NM_127846, date of publication Jan. 25, 2005, date of retrieval Feb. 9, 2005.
Genbank accession No. T13019, date of publication Mar. 28, 1995, date of retrieval Feb. 9, 2005.
Genbank accession No. U17972, date of publication Mar. 8, 1997, date of retrieval Feb. 9, 2005.
Genbank accession No. U26544, date of publication Apr. 3, 1996, date of retrieval Feb. 9, 2005.
Genbank accession No. U42336, date of publication Nov. 7, 1996, date of retrieval Feb. 9, 2005.
Genbank accession No. U72389, date of publication Oct. 22, 1996, date of retrieval Feb. 9, 2005.
Genbank accession No. U72390, date of publication Oct. 22, 1996, date of retrieval Feb. 9, 2005.
Genbank accession No. U79999, date of publication Jan. 5, 1999, date of retrieval Feb. 9, 2005.
Genbank accession No. X59139, date of publication Jan. 30, 1992, date of retrieval Jan. 13, 2006.
Genbank accession No. X59145, date of publication Jan. 30, 1992, date of retrieval Feb. 9, 2005.
Genbank accession No. X59145, date of publication Jan. 30, 1992, date of retrieval Jan. 13, 2006.
Genbank accession No. X59146, date of publication Apr. 18, 2005, date of retrieval Jan. 13, 2006.
Genbank accession No. X59146, date of publication Jan. 30, 1992, date of retrieval Feb. 9, 2005.
Grbic V and Bleeker AB (1995) Ethylene regulates the timing of leaf senescence in *Arabidopsis*. *The Plant Journal* 8: 95-102.
Horesh et al. (2003) "A rapid method for detection of putative RAi target genes in genomic data." *Bioinformatics*, 19: ii73-ii80.
Jeon et al. (1999) Isolation and characterization of an anther-specific gene, RA8, from rice (*Oryza sativa* L). *Plant Molecular Biology* 39:35-44.
John I, et al. (1995) Delayed leaf senescence in ethylene-deficient ACC-oxidase antisense tomato plants: molecular and physiological analysis. *The Plant Journal* 7: 483-490.
Kim et al. (2000) Tissue-Specific Expression of the Gus Gene Driven by the Gban215-6 Promoter in Cabbage and Tobacco Plants, International Plant & Animal Genome Conference, San Diego, CA Jan. 9-12, 2000, Abstract.
Kolkman, et al. (2005) "Distribution of Activator (Ac) Throughout the Maize Genome for Use in Regional Mutagenesis" Genetics, 169: 981-995.
Matsui et al. (2003) Phyllostachys edulis BA-ACS mRNA for ACC synthase, complete cds. GenBank. Accession AB085172, pp. 1-2.
McBee et al. (1983) Effect of senescence and non-senescence on carbohydrates in sorghum during late kernel maturity states. Crop Science 23: 372-377.
Mendipweb Plant Hormones (2003) ; pp. 1.
New England BioLabs 1988-1989 Catalog, p. 62, catalog #1230, "Random Primer".
New England BioLabs 2000-2001 Catalog, S1257S, "Random Primer 36", accessed on Aug. 13, 2011.
Oeller et al. (1991) "Reversible Inhibition of Tomato Fruit Senescence by Antisense RNA." *Science*, 254:437-439.
Pepescu and Turner (2004) "Silencing of ribosomal protein L3 genes in N tabacum reveals coordinate expression and significant alterations in plant growth, develepment and ribosome biogenesis." *The Plant Journal* 39:29-44.
Picton et al. (1993) Altered fruit ripening and leaf senescence in tomatoes expressing an antisense ethylene-forming enzyme transgene. *The Plant Journal* 3: 469-481.

(56) References Cited

OTHER PUBLICATIONS

Protein Information Resource accession No. F46376, date of publication Jul. 9, 2004, date of retrieval Feb. 8, 2005.
Protein Information Resource accession No. G46376, date of publication Jul. 9, 2004, date of retrieval Feb. 8, 200.
Protein Information Resource accession No. S71174, date of publication Jul. 9, 2004, date of retrieval Feb. 9, 2005.
Protein Information Resource accession No. T13019, date of publication Jul. 9, 2004, date of retrieval Feb. 9, 2005.
Protein Information Resource accession No. T47943, date of publication Jul. 9, 2004, date of retrieval Feb. 9, 2005.
Rosenow DT, Quisenberry JE, Wendt CW, Clark LE (1983) Drought-tolerant sorghum and cotton germplasm. *Agricultural Water Management* 7: 207-222.
Rottmann et al. (1991) 1-Aminocyclopropane-1-carboxylate synthase in tomato is encoded by a multigene family whose transcription is induced during fruit and floral sensescence *Journal of Molecular Biology* 222:937-961.
Rougon et al. (1975) "Insertion of rabbit B-globin gene sequence into an *E. coli* plasmid." *Nucleic Acids Research.* 2:2365-2378.
Russell (1991) Genetic improvement of maize yields. *Advances in Agronomy* 46: 245-298.
Smith et al. (2000) "Total silencing by intron-spliced hairpin RNAs." *Nature*, 407:319-320.
Sozzi et al. (2002) Gibberellic acid, synthetic auxins, and ethylene differentially modulate α-L-arabinofuranosidase activites in antisense 1-aminocyclopropane-1-carboxylic acid synthase tomato pericarp discs *Plant Physiology* 129:1330-1340.
Spano et al. (2003) "Physiological characterization of 'stay-green' mutants in durum wheat." *Journal of Experimental Botany*, 54:1415-1420.
Subramaniam et al. (1996) "Isolation of two differently expressed wheat ACC synthase cDNAs and the characterization of one of their genes with root-predominant expression." *Plant Molecular Biology* 31:1009-1020.
SwissProt accession No. AAG48754, date of publication May 7, 2003, date of retrieval Mar. 8, 2005.
SwissProt accession No. AAG48755, date of publication May 7, 2003, date of retrieval Mar. 8, 2005.
SwissProt accession No. AAG50090, date of publication Dec. 11, 2003, date of retrieval Mar. 8, 2005.
SwissProt accession No. Q06402, date of publication Jan. 25, 2005, date of retrieval Mar. 8, 2005.
Tada et al. (2003) "Effect of an Antisense Sequence on Rice Allergen Genes Comprising a Multigene Family." *Breeding Science* 53:61-67.
Thomas and Howarth (2000) "Five ways to stay green" *Journal of Experimental Botany* 51: 329-337.
Thomas and Smart (1993) "Crops that stay green," *Annals of Applied Biology* 123: 193-219.
Thomas et al. (2001) "Size constraints for targeting post-transcriptional gene silencing and for RNA-directed methylation in Nicotana benthamiana using a potato virus X vector." *The Plant Journal*, 25:417-425.
Tsuchisaka and Theologis (2004) "Unique and overlapping expression patterns among the Arabidopsis 1-amino-cyclopropane-1-carboxylate synthase gene family members" *Plant Physiology*, 136: 2982-3000.
Twell et al. (1993) "Activation and developmental regulation of an Arabidopsis anther-specific promoter in microspores and pollen of Nicotiana tabacum."*Sex. Plant Reprod.* 6:217-224.
Van Tunen et al. (1990) "Pollen- and anther-specific chi promoters from petunia: tandem promoter regulation of the chiA gene". *Plant Cell* 2:393-40.
Young, et al. (2004) "ACC Synthase Expression Regulates Leaf Performance and Drought Tolerance in Maize" The Plant Journal, 40:813-825.
Zarembinski and Theologis (1993) "Anaerobiosis and Plant Growth Hormones Induce Two Genes Encoding I-Aminocyclopropane-l-Carboxylate Synthase in Rice (*Oryza sativa* L.)" Molecular Biology of the Cell vol. 4, 363-373.
Zarembinski et al. (1993) "*Oryza sativa* 1-aminocyclopropane-1 carboxylate synthase (ACC1) mRNA," complete cds. GenBank Accession M96672, pp. 1-2.
Beltrano, et al. (1999) "Drought Stress Syndrome in Wheat Is Provoked by Ethylene Evolution Imbalance and Reversed by Rewatering, Aminoethoxyvinylglycine, or Sodium Benzoate," *Journal of Plant Growth Regulation*, 18: 59-64.
Bensen, et al. (1995) "Cloning and Characterization of the Maize Ani Gene," *The Plant Cell*, 7: 75-84.
Gan, et al. (1997) "Making Sense of Senescence: Molecular Genetic Regulation and Manipulation of leaf Senescence," *Plant Physiology*, 113(2): 313-319.
Stearns, et al. "Transgenic plants with altered ethylene biosynthesis or perception," *Biotechnology Advances*, 21(3): 193-210, 2003.
The Arabidopsis Genome Initiative (2000) "Analysis of the genome sequence of the flowering plant Arabidopsis thaliana," Nature, 408: 796-815.
Wang, et al. (2002) "Ethylene Biosynthesis and Signaling Networks," The Plant Cell, Supplement: S131-S151.
Wi, et al. (2002) "Antisense Expression of Carnation cDNA Encoding ACC Synthase or ACC Oxidase Enhances Polyamine Content and Abiotic Stress Tolerance in Transgenic Tobacco," *Molecules and Cells*, 13(2): 209-220.
Zarembinski, et al. (1997) "Expression characteristics of OS-ACS1 and OS-ACS2, two members of the 1-aminocyclopropane-i-carboxylate synthase gene family in rice (*Oryza sativa* L. cv. Habiganj Aman It) during partial submergence," *Plant Molecular Biology*, 33: 71-77.

\* cited by examiner

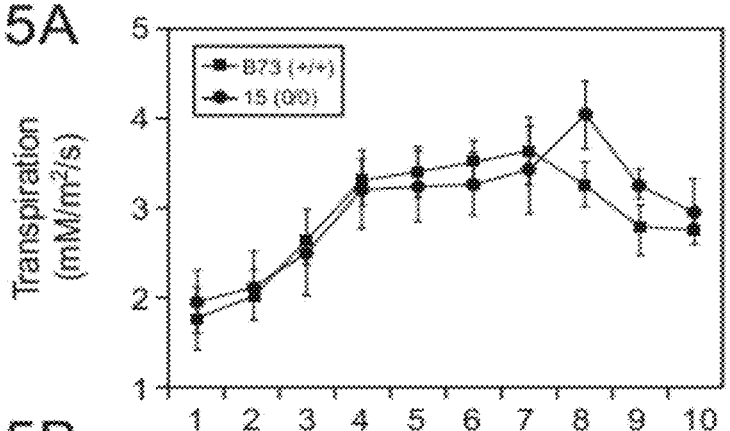
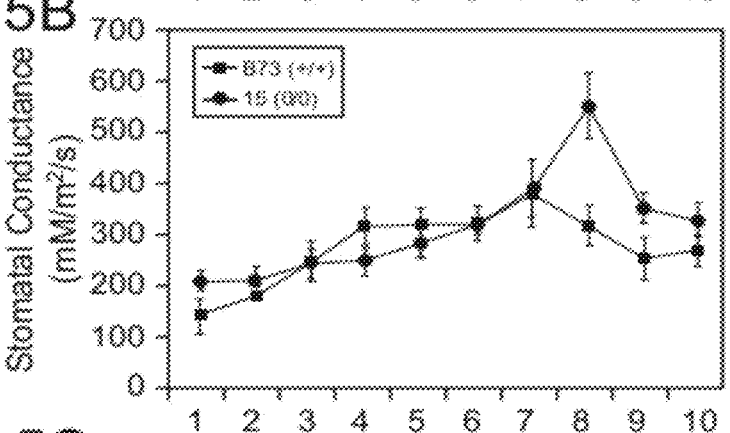
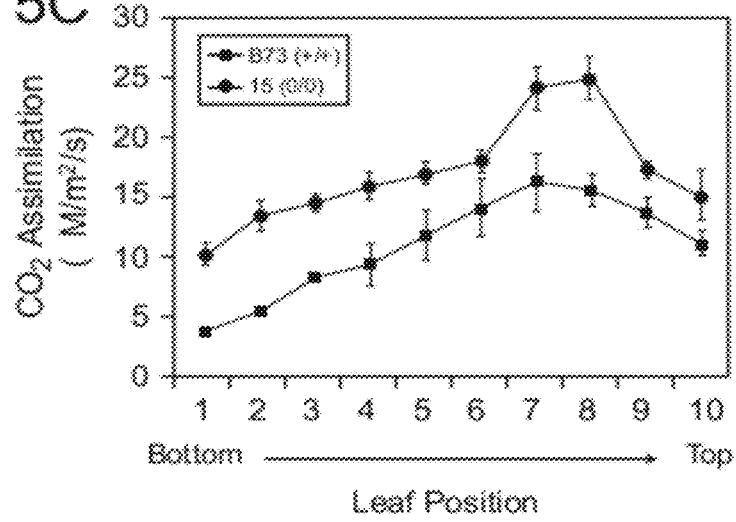

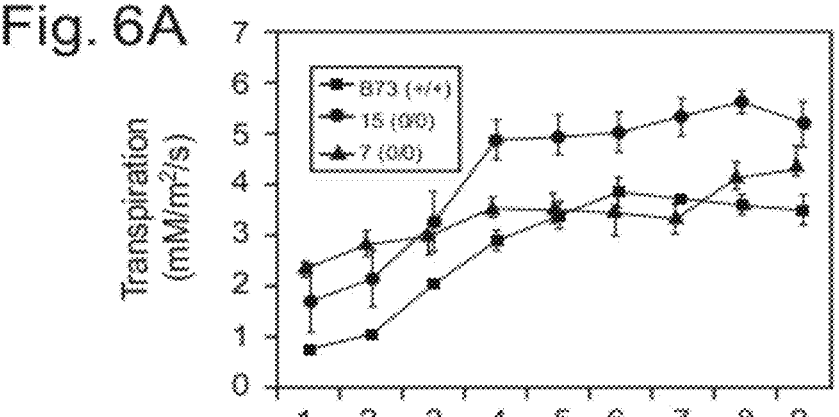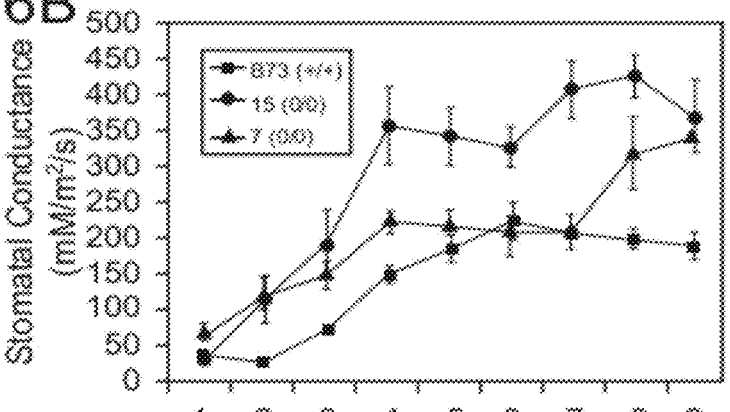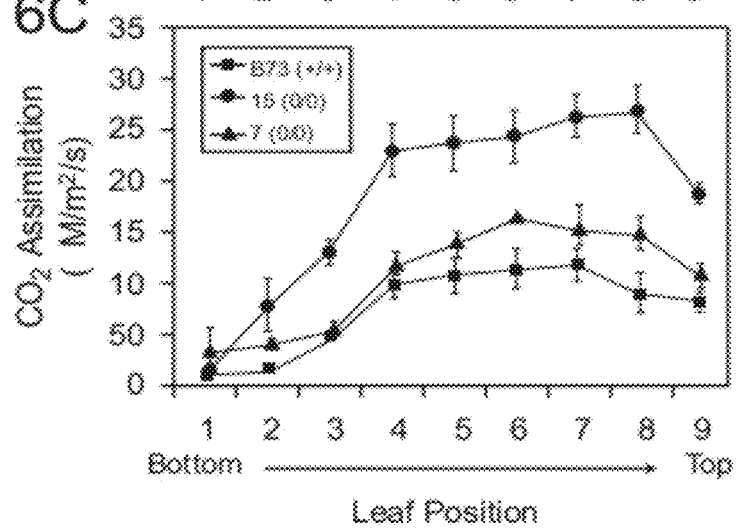

Consensus Sequence (identical amino acid residues)

Fig. 8

```
AtACS4pep  PQGIIQMGLA  ENQLCFDLLE  SWLAQ.NTDA  ACFKRD..GQ  SVFRELALFQ
  AtACS8   PDGIIQMGLA  ENQLSFDLIE  SWLAK.NPDA  ANFQRE..GQ  SIFRELALFQ
MaACS2pep  -------MGFT  ENQLCFDLIE  SWLEN.RPDF  AAFKKD..GA  LLFRELALFQ
MaACS3pep  -------MGFA  ENNVSFDLIE  SWLED.RPDL  TGFKKD..GG  LVFRELALFQ
LeACS3pep  PKGIIQMGLA  ENQLSFDLLE  SWLAQ.NPDA  AGFKRN..GE  SIFRELALFQ
LeACS7pep  PKGIIQMGLA  ENQLSFDLLE  SWLTL.NPDA  SAFKRN..GH  SIFRELSLFQ
OsjACS2pep PDGVIQMGLA  ENQVSFDLLE  AYL.RDHPEA  AGWSTGGAGA  GSFRDNALFQ
  OsjACS3  PDGVIQMGLA  ENQVSFDLLE  AYL.RDHPEA  AGWSTGGAGA  GSFRDNALFQ
OsiACS3pep PDGVIQMGLA  ENQVSFDLLE  AYL.RDHPEA  AGWSTGGAGA  GSFRDNALFQ
  AtACS7   PSGVIQMGLA  ENQVSFDLLE  TYLKKNPEG   SNW..GSKGA  PGFRENALFQ
Consensus  --G-IQMGLA  ENQ----DL--  ----------P--  -----------G-  ---F---A-FQ 101                                              150
   A47pep  DYHGLPEFRK  AMAKFMGQVR  AGKVTFDPDR  VVMCGGATGA  QDTLAFCLAD
   A80pep  DYHGLPEFRK  AMAKFMGQVR  GGKVTFDPDR  VVMCGGATGA  QDTLAFCLAD
osiacs1pep DYHGLPEFRK  AMAQFMGQVR  GGKATFDPDR  VVMSGGATGA  QETLAFCLAN
osjacs1pep DYHGLPEFRK  AMAQFMGQVR  GGKATFDPDR  VVMSGGATGA  QETLAFCLAN
TaACS2pep  DYHGLPEFRQ  AMAQFMGQVR  GNKARFDPDR  VVMSGGATGA  QETLAFCLAN
AtACS1pep  DYHGLKQFRQ  AIATFMERAR  GGRVRFEAER  VVMSGGATSA  NETIMFCLAD
AtACS2pep  DYHGLKKFRQ  AIAHFMGKAR  GGRVTFDPER  VVMSGGATSA  NETIIFCLAD
LeACS2pep  dyhglpefrk  aiakfmektr  ggrvrfdper  vvmaggatga  netlifclad
LeACS4pep  dyhglpeftn  aiakfmektr  ggkvkfdakr  vvsaggatga  netlilclad
MaACS1pep  DYHGLPTFRK  AIAQFMEKVR  GGRARFDPDR  IVMSGGATGA  QETIAFCLAD
MaACS3pep  DYHGLPAFRK  AIAQFMEKVR  GGRARFDPDR  IVMSGGATGA  QETIAFCLAD
LeACS1Apep dyhglpefrq  avarfmekvr  gdrvtfdgnr  ivmsggatga  hemlafclad
LeACS1Bpep dyhglpefrq  avarfmekvr  gdrvtfdpnr  ivmsggatga  hemlafclad
MaACS6pep  DYHGLPEFRK  AVARFMEKVR  GDRVRFDPER  IVMSGGATSA  HESLAFCLAD
AtACS6pep  DYHGLPEFRQ  AVAKFMEKTR  NNKVKFDPDR  IVMSGGATSA  HETVAFCLAN
   A65pep  DYHGMPAFRN  ALARFMSEQR  GYRVTFDPSN  IVLTAGATSA  NEALMFCLAD
osiacs2pep DYHGLPAFKQ  ALAPFMSEQR  GYRVVFDPSN  IVLTAGATSA  NEALMFCLAD
AtACS5pep  DYHGNPEFKK  AMASFMEEIR  GNRVTFDPKK  IVLAAGSTSA  NETLMFCLAE
  AtACS9   DYHGLPEFKK  ALAEFMEEIR  GNRVTFDPGK  IVLAAGSTSA  NETLMFCLAE
AtACS4pep  DYRGLSSFRN  AFADFMSENR  GNRVSFDSNN  LVLTAGATSA  NETLMFCLAD
  AtACS8   DYHGLPSFKN  AMADFMGENR  GNRVSFNPNK  LVLTAGATPA  NETLMFCLAD
MaACS2pep  DYHGLPAFKR  ALTKYMGEVR  GNKVAFDPNR  LVLTAGATSA  NETLMFCLAE
MaACS3pep  DYHGLPAFRN  ALARYMGEVR  GNKVSFEPSK  LVLTAGATSA  NETLMFCLAD
LeACS3pep  DYHGLPAFKN  AMEKFMSEIR  GNRVSFDSNN  LVLTAGATSA  NETLMFCLAN
LeACS7pep  DYHGLPAFKD  ALVQFMSEIR  GNKVSFDSNK  LVLTAGATSA  NETLMFCLAD
OsjACS2pep DYHGLKSFRK  AMASFMGEIR  GGKARFDPDN  IVLTAGATAA  NELLTFILAN
  OsjACS3  DYHGLKSFRK  AMASFMGKIR  GGKARFDPDN  IVLTAGATAA  NELLTFILAN
OsiACS3pep DYHGLKSFRK  AMASFMGKIR  GGKARFDPDN  IVLTAGATAA  NELLTFILAN
  AtACS7   DYHGLKTFRQ  AMASFMEQIR  GGKARFDPDR  IVLTAGATAA  NELLTFILAD
Consensus  DYHGL---F--  A-A-FM----R  G-----FD----  -V---GAT-A  -E---F-LA- 151                                              200
   A47pep  PGDAYLVPTP  YYPAFDRDCC  WRSGVKLLPI  ECHSSNNFTL  TREALVSAYD
   A80pep  PGDAYLVPTP  YYPAFDRDCC  WRSGVKLLPI  ECHSSNNFTL  TREALVSAYD
osiacs1pep PGEAFLVPTP  YYPAFDRDCC  WRSGIKLLPI  ECHSSNDFRL  TREALVSAYD
osjacs1pep PGEAFLVPTP  YYPAFDRDCC  WRSGIKLLPI  ECHSSNDFRL  TREALVSAYD
TaACS2pep  PGEAFLVPTP  YYPGFDRDCC  WRSGVRLLPI  ECHSSNDFRI  TREAVVAAYE
AtACS1pep  PGDAFLVPTP  YYAAFDRDLR  WRTGVRIIPV  ECSSSNNFQI  TEQALESAYL
AtACS2pep  PGDVFLIPSP  YYAAFDRDLN  WRTGVEIIPV  PCSSSNDFKL  TVDAAEWAYK
LeACS2pep  pgdaflvpsp  yypafdrdlr  wrtgvqlipi  bcessnnfki  takavksays
LeACS4pep  pgdaflvptp  yypgfdrdlr  wrsgvqlipi  scksccnfki  tiealesaye
MaACS1pep  PGEAFLIPTP  YYPGFDRDFR  WRTGVQLLPI  HCHSSNNFKI  TQAALETAYR
```

```
MaACS5pep PGEAFLIPTP YYPGFDRDFR WRTGVQLLPI HCRSSNKFKI TQAALETAYR
LeACS1Apep pgdaflvptp yypgfdrdlr wrtgvqlfpv vcesscndfkv ttkaleeaye
LeACS1Bpep pgdaflvptp yypgfdrdlr wrtgvqlfpv vcesscndfkv ttkaleeaye
LeACS6pep PGDAFLVPTP YYPGFDRDLR WRTGVQLFPV VCESSNNFKV TEEALEEAYE
AtACS6pep PGDGFLVPTP YYPGFDRDLR WRTGVNLVPV TCRSSNGFRI TVEALEAAYE
A6pep SGDAFLIPTP YYPGFDRDLK WRTGAEIVPV HCTSONGFRL TRAALGDAYR
osiacs2pep NGDAFLIPTP YYPGFDRDLK WRTGAEIVPI HCASANGFRV TRAALGDAYR
AtACS5pep PGDAFLLPTP YYPGFDRDLK WRTGAEIVPI HCSSSNGFQI TESALQQAYQ
AtACS9 PGDAFLLPTP YYPGFDRDLK WRTGAEIVPI HCSSSNGFQI TESALQQAYQ
AtACS4pep PGDAFLLPTP YYPGFDRDLK WRTGVEIVPI QSSSTNGFRI TRLALEEAYE
AtACS8 PGDAFLLPTP YYPGFDRDLK WRTGAEIVPI QCKSANGFRI TKVALEEAYE
MaACS2pep PGEAFLLPTP YYPGFDRDLK WRTGAEIVPI HCSSSNGFRI TKPALEAAYQ
NaACS3pep PGEAFLLPTP YYPGFDRDLK WRTGVEIVPI RCSSSNGFRI TRAALEAALR
LeACS3pep QGDAFLLPTP YYPGFDRDLK WRTGAEIVPI RCSSSNGFRI TESALEEAYL
LeACS7pep PGHAFLLPTP YYPGFDRDLK WRTGAEIVPI QCTSSNGFRI TESALEEAYT
OsjACS2pep PGDALLIPTP YYPGFDRDLR WRTGVNIVPV RCDSANGFQV TVAALQAAYD
OsjACS3 PGDALLIPTP YYPGFDRDLR WRTGVNIVPV RCDSANGFQV TVAALQAAYD
OsiACS3pep PGDALLIPTP YYPGFDRDLR WRTGVNIVPV RCDSANGFQV TVAALQAAYD
AtACS7 PNDALLVPTP YYPGFDRDLR WRTGVKIVPI RCDSSNRFQI TPEALESAYQ
Consensus PG-A-L-PTP YYP-FDRD-- WR-G----P- -C-S-N-F-- ?--A----AY- 201                                                    250
     A47pep GARRQGVRVK GVLITNPSNP LGTTMDRATL AMLARFAT.E HRVHLICDEI
     A50pep GARSQGVRVR GILITNPSNP LGTTMDRGTL AMLAAFAT.E RRVELICDEI
osiacs1pep GARRQGISVK GILITNPSNP LGTITDRDTL AMLATFAT.E HRVHLVCDEI
osjacs1pep GARRQGISVK GILITNPSNP LGTITDRDTL AMLATFAT.E HRVHLVCDEI
 TaACS2pep GARSSGVRVR GILITNPSNP LGTTADRATL AMLATFAT.E HRVHLICDEI
 AtACS1pep KAQETGIKIK GLII...SNP LGTSLDRETL KSLVSFIN.D RQIRLVCDEI
 AtACS2pep SAQESNKKVK GLILTSPSNP LGTMLDKDTL TNLVRFVT.R SNIRLVVDEI
 LeACS2pep saqksnikvk gliitnpsnp lgttidkdtl ksvisftn.q bnihlvcdei
 LeACS4pep bggganvkik gliltnpcnp lgttildrdtl kkistftn.e bnihlvcdei
 MaACS1pep KARNSHIRVK GILVTNPSKP LGTTMDRETL RTLVSFVN.E KRNHLVCDEI
 NaACS5pep KARNSHIRVK GIVVTKPSNP LGTTMDRDTL RTLVSFVN.E KRNHLVCDEV
 LeACS1Apep kaqqsnikik gliinpsnp lgtiildkdtl rdivtfin.s knihlvcdei
 LeACS1Bpep kaqqsnikik gliinpsnp lgtiildkdtl rdivtfin.s knihlvcdei
 LeACS6pep KAQESNIRVK GLLINNPSNP LGTILDKETL KDILRFIN.D KNIRLVCDEI
 AtACS6pep NARRSNIPVK GLLVTNPSNP LGTTLDRECL KSLVNFTN.D KGISLIADEI
     A6pep RAQRLRLRVK GVLITNPSNP LGTTSPRADL EMLVDFVA.A RGISLVSDEI
osiacs2pep RAQKRRLRVK GVLITNPSNP LGTASPRADL ETIVDFVA.A KGISLISDEI
 AtACS5pep QAQKLDLKVK GVLVTNPSNP LGTALTRREL NLLVDFIT.S KNISLISDEI
 AtACS9 QAQKLDLKVK GVLVTNPSNP LGTMLTRREL NLLVDFIT.S KNISLISDEI
 AtACS4pep QARKLDLRVK GILITNPSNP LGTTTQTEL NILFDFITKN KNIRLVSDEI
 AtACS8 QAQKINLRVK GVLITNPSNP LGTTTRTEL NRLLDFISR. KRISLISDEI
 MaACS2pep DAQKRSLRVK GVLVTNPSNP LGTTLRHEL DILVDFVV.S KDISLISDEI
 NaACS3pep RAQKRRLRVK GVLVTNPSNP LGTTLTRQEL DTLVDFAV.A NDISLISDEI
 LeACS3pep DARRRNLRVR GVLVTNPSNP LGTTLNRNEL ELLLTFID.E KGISLISDEI
 LeACS7pep EAERRNLRVK GVLVTNPSNP LGTTLRKKEL QLLLTFVS.T KQISLISDEI
OsjACS2pep EAAAVGNRAR AVLITNPSNP LGTVRRRML DSILDFVSR. NDISLISDEI
OsjACS3 EAAAVGNRAR AVLITNPSNP LGTTVRRRML DDILDFVSR. NDISLISDEI
OsiACS3pep EAAAAGNRAR AVLITNPSNP LGTTVRRKVL DDILDFVSR. NDISLISDEI
 AtACS7 TARDAHIRVR GVLITNPSNP LGATVQKKVL EDLLDFCVR. RRISLVSDEI
 Consensus -A-------- G-----NPSNP LGT-------L ------F----  ----SL--DEI 251                                                    300
     A47pep YAGSVFAKPD ..FVSIAEVI ER.DVPGCNR .......DLI HIAYSLSKDF
```

Fig. 8 (cont.)

```
      A50pep  YAGSVFAKPG  ..FVSIAEVI  ERGDAPGCNR  ........DLV  HIAYSLSKDF
  osiacs1pep  YAGSVFATPE  ..YVSIAEVI  ER.DVPWCNR  ........DLI  HVVYSLSKDF
  osjacs1pep  YAGSVFATPE  ..YVSIAEVI  ER.DVPWCNR  ........DLI  HVVYSLSKDF
     TaACS2pep YAGGVFAKPE  ..YVSIAEVI  ER.DAPGADR  ........DLI  HIAYSLSKDF
     AtACS1pep YAATVFASPG  ..FISVAEII  Q..EMYYVNR  ........DLI  HIVYSLSKDM
     AtACS2pep YAATVFAGGD  ..FVSVAEVV  NDVDISEVNV  ........DLI  HIVYSLSKDM
     LeACS2pep yaatvfdtpq  ..fvsiaeil  deqemtycnk  ........dlv  hivyslskdm
     LeACS4pep yaatvfoppk  ..fvsiaeil  nednc..ink  ........dlv  hivsslskdl
     MaACS1pep FSGTVFDKPS  ..YVSVSEVI  ED..DPYCDR  ........DLI  HIAYSLSKDL
     MaACS5pep FSGTVFDKPS  ..YVSVAEVI  QD..DPYCDR  ........DLI  HIAYSLSKDL
    LeACS1Apep yaatvfdqpr  ..fisvseiv  ed..miecnk  ........dli  hivyslskdl
    LeACS1Bpep yaatvfdqpr  ..fisvsemv  ee..miecnt  ........dli  hivyslskdi
     LeACS6pep YAATAFSQFS  ..FISISEVK  SE..VVGCND  ........DLV  HIVYSLSKDL
     AtACS6pep YAATTFGQSE  ..FISVAEVI  EE..IRDCNR  ........DLI  HIVYSLSKDM
         A65pep YSGTVFADP.  .GFVSVLEVV  AARAATDDGV  VGVGPLSDRV  HVVYSLSKDL
   osiacs2pep  YAGTAFAEPP  AGFVSALEVV  AGR....DG.  .GGADVSDRV  HVVYSLSKDL
     AtACS5pep YSGTMPGFE.  .QFISVMDVL  KDKKLRD...  ...TEVSKRV  HVVYSLSKDL
        AtACS9 YSGTVPGFE.  .QFVSVMDVL  KDKNLEN...  ...SEVSKRV  HIVYSLSKDL
     AtACS4pep YSGTVFNSS.  .EFISVMEIL  KNNQLEN...  ...TDVLNRV  HIVCSLSKDL
        AtACS8 YSGTVFTNP.  .GFISVMEVL  KDRKLEN...  ...TDVFDRV  SIVYSLSKDL
     MaACS2pep YSGTNFDSP.  .GFISIAEAT  KIRN......  ....NVSHRI  HIVCSLSKDL
     MaACS3pep YSGTTFGSP.  .GFVSIAEAT  KGRD......  ....DVSHRI  HIVCSLSKDL
     LeACS3pep YSGTVFNSP.  .GLVSVMEVL  IEKNYMK...  ...TRVMERV  HIVYSLSKDL
     LeACS7pep YSGTVFNSP.  .KFVSVMSVL  IERNYMY...  ...TDVNDRV  HIVYSLSKDL
    OsjACS2pep YSGSVFAAPD  ..LVSVAELV  EAR.......  .GGDGIAGRV  HIVYSLSKDL
       OsjACS3 YSGSVFAAPD  ..LVSVAELV  EAR.......  .GGDGIAGRV  HIVYSLSKDL
    OsiACS3pep YSGSVFAAPD  ..LVSVAELV  EAR.......  .DGDGIAGRV  HIVYSLSKDL
        AtACS7 YSGSVFWASE  ..FTSVARIV  ENI.......  .DDVSVKERV  HIVYSLSKDL
     Consensus Y------F--  ------S--E  ----------  ----------  H----SLSKD- 301                                                      350
      A47pep  GLPGFRVGIV  YSYNDDVVAC  ARKMSSFGLV  SSQTQHFLAK  MLSDAEFMAR
      A50pep  GLPGFRVGIV  YSYNDDVVAC  ARKMSSFGLV  SSQTQHFLAM  MLADAEFMAR
  osiacs1pep  GLPGFRVGII  YSYNDAVVAA  ARRMSSFGLV  SSQTQYFLAR  MLSDEEFIGR
  osjacs1pep  GLPGFRVGII  YSYNDAVVAA  ARRMSSFGLV  SSQTQYFLAR  MLGDEEFIGR
     TaACS2pep GLPGFRVGIV  YSYNDAVVAC  ARKMSSFGLV  SSQTQLFLAK  MLGDEEFNSR
     AtACS1pep GLPGFRVGVV  YSYNDVVSC   ARRMSSFGLV  SSQTQSFLAA  MLSDQGFVDN
     AtACS2pep GLPGFRVGIV  YSFNDSVVSC  ARKMSSFGLV  SSQTQLMLAS  MLSDMQFVDN
     LeACS2pep glpgfrvgli  ysfnddvvnc  arkmssfglv  stqtqyflaa  msdekfvdn
     LeACS4pep gfpgfrvgiv  ysfoddvvnc  arkmssfglv  stqtqhllaf  alsddefvee
     MaACS1pep GVPGFRVGVI  YSYNDAVVTC  ARKMSSFGLV  SSQTQHLLAS  MLGDEEFTTS
     MaACS5pep GVPGFRVGVI  YSYNDAVVSC  ARKMSSFGLV  SSQTQHLLAS  MLGDEEFTTS
    LeACS1Apep gfpgfrvgiv  ysyndtvvni  arkmssfglv  ssqtqhllas  alsdevfldk
    LeACS1Bpep gfpgfrvgiv  ysyndtvvni  arkmssfglv  stqtqhmlas  alsdeifvek
     LeACS6pep GFPGFRVGII  YSYNDAVVNI  ARKMSSFGLV  STQTQRLIAS  MLLDTIFVSD
     AtACS6pep GLPGLRVGIV  YSYNDRVVQI  ARKMSSFGLV  SSQTQHLIAK  MLSDEEFVDE
         A65pep GLPGFRVGAI  YSSNAGVVSA  ATKMGSFGLV  SSQTQHLLAS  LLGDRDFTSR
   osiacs2pep  GLPGFRVGAI  YSANAAVVSA  ATKMSSFGLV  SSQTQYLLAA  LLGDRDFTSG
     AtACS5pep GLPGFRVGAI  YSNDEMIVGA  ATKMGSFGLV  SSQTQYLLSA  LLSDKKFTSQ
        AtACS9 GLPGFRVGAI  YSNDEMVVSA  ATKMGSFGLV  SSQTQYLLSA  LLSDKKFTST
     AtACS4pep GLPGFRVGAI  YSNDKDVISA  ATKMGSFGLV  SSQTQYLLSS  LLSDKKFTRN
        AtACS9 GLPGFRVGVI  YSNDDFVVGA  ATKMGSFGLI  SSQTQYLLGA  LLSDKFTFTN
     MaACS2pep GLPGFRVGAI  YSENEAVVSA  ATKMSSFGNV  SSQTQYLLAA  LLSDREFTDK
     MaACS3pep GLPGFRVSAI  YSDNEAVVSA  ATKMSSFGLI  SSQTQYLLAA  LLSDKEFTEK
     LeACS3pep GLPGFRIGAI  YSNDEMVVSA  ATKMSSFGLV  SSQTQYLLSC  MLSDKKPTEK
```

Fig. 8 (cont.)

```
LeACS7pep    GLPGFRVGAI  YSNDDRVVGA  ATKMSSFGLI  SSQTQYLLSA  LLSDKKFTKN
OsjACS2pep   GLPGFRVGVV  YSYNDAVVTA  ARRMSSFTLV  SSQTQKTLAA  MLSDEAFAGE
OsjACS3      GLPGFRVGVV  YSYNDAVVTA  ARRMSSFTLV  SSQTQKTLAA  MLSDEAFAGE
OsiACS3pep   GLPGFRVGVV  YSYNDAVVTA  ARRMSSFTLV  SSQTQKTLAA  MLSDEAFAGE
AtACS7       GLPGFRVGTI  YSYNDNVVRT  ARRMSSFTLV  SSQTQHMLAS  MLSDEEFTEK
Consensus    G-PGFRVG--  YS-----VV--  A--MSSF-LV  S-QTQ---L--  -L-D--F---

351                                                    400
A47pep       FLAESARRLA  ARHDRFVAGL  REVGIACLPG  NAGLFSWMDL  RGMLRDK.TN
A50pep       FLAESARRLA  ARHDRFVAGL  REVGIACLPG  NAGLFSWMDL  RGMLREK.TN
osiacs1pep   FLQESKCRLV  ARHERFTSGL  REVGIGCLRG  NAGLFSWMDL  RRMLREK.TA
osjacs1pep   FLQESKCRLV  ARHERFTSGL  REVGIGCLRG  NAGLFSWMDL  RRMLREK.TA
TaACS2pep    FLRESARRLA  ARHELFTSGL  REVGIGCLGG  NAGLFSWMDL  RGMLREK.TA
AtACS1pep    FLVEVSKRVA  KRHDMFTEGL  EEMGISCLRS  NAGLFVLMDL  RHMLKDQ.TF
AtACS2pep    FLMESSRRLG  IRKKVFTTGI  KKADIACLTS  NAGLFAWMDL  RHLLRDKNSP
LeACS2pep    flresamrlg  krhkhftngl  evvgikclkn  naglfcwmdl  rpllre.atf
LeACS4pep    fliesakrlr  eryekftrgl  eeigikeles  nagvycwmdl  rsllke.atl
MaACS1pep    FLATSRTRLC  GRRRVFTDGL  KRVGIRCLDG  NAGLFCWMDL  RPLLKE.ATV
MaACS5pep    FLATSRTRLC  GRRSVFTDGL  KRVGIRCLDG  NAGLFCWMDL  RPLLKE.ATV
LeACS1Apep   flaessrlg   erqgmftkgl  aevgistlke  naglffwmdl  rrllke.atf
LeACS1Bpep   flaessrlg   krqgmftkgl  aqvgistlks  naglffwmdl  rrllke.atf
LeACS6pep    FIAKSSMRLL  QRHGLFTKGL  GQVGITTLKS  NAGLFIWMDL  RRFLSN.STF
AtACS6pep    FIRESKLRLA  ARHAEITTGL  DGLGIGWLKA  KAGLFLWMDL  RNLLKT.ATF
A65pep       YIAENTRRIR  ERREQLAEGL  AAVGIECLES  NAGLFCWVDM  RR.LMRSRSF
osiacs2pep   YVAENTRRIK  ERHDQLVEGL  RAIGIECLPS  NAGLFCWVDM  SH.LMRSRSF
AtACS5pep    YLEENQKRLK  SRQRRLVSGL  ESAGITCLRS  NAGLFCWVDM  RH.LLDTNTF
AtACS9       YLDENQKRLK  IRQKKLVSGL  EAAGITCLKS  NAGLFCWVDM  RH.LLDTNTF
AtACS4pep    YLRENQKRLK  NRQRKLVLGL  EAIGIRCLKS  NAGLFCWVDM  RP.LLRSNTF
AtACS8       YLEENQIRLK  NRHKKLVSGL  EAAGIECLKS  NAGLFCWVDM  RH.LLKSNTF
MaACS2pep    YLLENQKRLK  ERHDMLVEGL  RRIGIGCLKG  SAALFCWVDV  RH.LLKSNTF
MaACS3pep    YVRESQKRLK  ERRDMLVEGL  PRISIGCLES  NAGLFCWVDM  RH.LLRSNTF
LeACS3pep    YISENQKRLK  RPHAMLVKGL  KSAGINCLES  NAGLFCWVDM  RH.LLSSNNF
LeACS7pep    YVSENQKRLK  KRHEMLVGGL  KQIGIRCLES  NAGLFCWVDM  RH.LLSSNTF
OsjACS2pep   YIRTNRRRLR  EPHERVVAGL  ARAGVPCLRG  NAGLFVWMDM  RRLLIGGGGV
OsjACS3      YIRTNRRRLR  EPHERVVAGL  ARAGVPCLRG  NAGLFVWMDM  RRLLIGGGGV
OsiACS3pep   YIRTNRRRLR  EPHERVVAGL  ARAGVPCLRG  NAGLFVWMDM  RRLLIGGGGV
AtACS7       YIRINKERLR  RRYDTIVEGL  KKAGIECLRS  NAGLFCWMDL  .GFLLERKTK
Consensus    --------RL-  -R------GL  ----GI--L--  NAGLF-W-D-  R--L------

401                                                    450
A47pep       DAELELWRVI  VRRVKLNVSP  GTSFHCNEPG  WFRVCHANKD  DETMEVALGR
A50pep       DAELELWRVI  VRRVKLNVSP  GTSFHCHEPG  WFRVCYANMD  DDTMEVALGR
osiacs1pep   EAELELWRVI  VHQVKLNVSP  GTSFHCREPG  WFRVCHANKD  DETMEVALGR
osjacs1pep   EAELELWRVI  VHQVKLNVSP  GTSFHCREPG  WFRVCHANMD  DETMEVALGR
TaACS2pep    EAELELWRVI  IRKVKLNVSP  GTSFHCSEPG  WFRVCHANMD  DETMGVALSR
AtACS1pep    DSEMALWRVI  INKVKINVSP  GSSFHCSEPG  WFRVCFANMD  EDTLQIALER
AtACS2pep    ESEIELWHII  IDRVKLNVSP  GSSFRCTEPG  WFRICFANMD  DDTLRVALGR
LeACS2pep    dsemslwrvi  indvklnvsp  gssfecqepg  wfrvcfanmd  dgtvdialar
LeACS4pep    daemslwkli  inevklnvsp  gssfncsevg  wfrvcfanid  dqtmeialar
MaACS1pep    EAELRLWRVI  INDVKLNISP  GSSFHCSEPG  WFRVFANMD  DTAMKIALRR
MaACS5pep    EAELRLWRVI  INDVKLNISP  GSSFHCSEPG  WFRVCFANMD  DTAMKIALRR
LeACS1Apep   dselelwrli  inevklnvsp  gcsfhcsepg  wfrvcfanmd  detmrialkr
LeACS1Bpep   dgselelwrli  inevklnvsp  gcsfhcsepg  wfrvcfanmd  detmrialkr
LeACS6pep    DDELKLWHII  IDKVKLNVSP  GCSFHCSEPG  WFRVCFANMD  DATMKIALRR
AtACS6pep    DSETELWRVI  VHQVKLNVSP  GGSFHCREPG  WFRVCFANMD  SKTMETALER
```

Fig. 8 (cont.)

```
         A65pep   EGEMELWKKV  VFEVGLNISP  GSSCHCREPG  WFRVCFANMS  AKTLDVALQR
      osiacs2pep  AGEMELWKKV  VFEVGLNISP  GSSCHCREPG  WFRVCFANMS  AKTLDVAMQR
       AtACS6pep  EAELDLWKKI  VYNVKLNISP  GSSCHCTEPG  WFRVCFANMS  EDTLDLALKR
          AtACS9  EAELELWKKI  VYDVKLNISP  GSSCHCTEPG  WFRVCFANMS  EDTLDLANKR
       AtACS4pep  EAEMDLNKKI  VYEVKLNISP  GSSCHCREPG  WFRVCFANMI  DETLKLALKR
          AtACS8  EAEIELWKKI  VYEVKLNISP  GSSCHCNEPG  WFRVCFANLS  EETLKVALDR
       NaACS2pep  KGAMELKKKI  VYQVGLNISP  GSSCHCDEPG  WFSVTP----  ----------
       NaACS3pep  EGEMELWKKI  VYRVGLNVSP  GSSCHCDEPG  WFRVSF----  ----------
       LeACS3pep  DAEMDLWKKI  VYDVGLNISP  GSSCHCTEPG  WFRVCFANMS  EDTLDLAMRR
       LeACS7pep  DGEMELWKKI  VYEVGLNISA  GSSCHCTEPG  WFRACFANMS  EDTLNIAIQR
       OsjACS2pep GSELRLWEKL  LRQAKLNISP  GSSCHCSEAG  WFRVCFANMS  LDTLDLALHR
         OsjACS3  GGELRLWEKL  LRQAKLNISP  GSSCHCSEAG  WFRVCFANMS  LDTLDLALER
       OsiACS3pep GSELRLWEKL  LREAKLNISP  GSSCHCSEAG  WFRVCFANMS  LDTLDLALHR
           AtACS7 DKELQLWDVI  LKELNLNISP  GSSCHCSEVG  WFRVCFANMS  ENTLKIALKR
       Consensus  --E--L----  ------LN-SP G-S-HC-E-G  WFRVC-AN--  -------A--R 451                                                     500
         A47pep   IRRFVRQHQR  .KAKAERHAA  TRPMRLSLPR  RGGATASHLP  ISSPM.ALLS
         A50pep   IRRFVRQHQR  SKAKAERNAA  TRPLRLSLPR  RGATTASHLA  ISSPL.ALLS
      osiacs1pep  IRDFVRQHQQ  RRVKAERNAA  NRQLRLSLPH  RSHL.SPAH.  LSSPL.ALLS
       osjacs1pep IRDFVRQHQQ  RRVKAERNAA  NRQLRLSLPH  RSHL.SPAH.  LSSPL.ALLS
        TaACS2pep IRDFVRQRQQ  QKAKAQRNAA  RSRLRLSLQR  HGPNASQYRA  LSSPRAALLS
        AtACS1pep IKDFVVGSRA  NKNKNCNCIC  NNKR..ENKK  RKSF...QRN  LKLGLSSMR.
        AtACS2pep IQDFV...SK  NENKKIVEKAS ENDQVIQNRS  AKKLKNTQTN  LRLSFRRL..
       LeACS2pep  irrfvqvek.  .......sgdk as.......sm skkqqwkkna  lrlsfs..kr
       LeACS4pep  irmfmdayn.  ......nvnk  sg.......vm knkhsgrgtt  ydltpq..mg
       NaACS1pep  IESFVYREN.  .......DAA. ........VQA KNKKRWDKA.  LRLSLPR.RR
       NaACS3pep  IENFVYREN.  .......DAA. ........VQA KNKRKWDET.  LRLSLP..RR
       LeACS1Apep lsyfv.....  ..........lq p.kglsnlaa  lkkqc.arrk  lqisls..frr
       LeACS1Bpep lrnfv.....  ..........lq t.kglsnlaa  lkkqc.srsk  lqisls..frr
       LeACS6pep  IRRFV.....  .......YLQ  PRKGV.EVAT  RKQYCRTRSK  LEISLS.FRR
       AtACS6pep  IKVFTSQLR.  .......EETK PHAAYTMMAK  KKKKCW.QSM  LRLSFSDTRR
         A65pep   LGAFREAATG  G.......RR  VLAPARSISL  PVRFSWANRL  TPGGAADRKA
      osiacs3pep  LRSFVDSATG  GG.DNAALRR  AAVPVRSVSC  PLATKWALRL  TP.SIADRKA
       AtACS8pep  LKTFVKSTDC  GSMISRSSHR  RLKSLRKKT.  ..VSNWVFRV  ...SWTDKVP
          AtACS9  LKEYVESTCS  SRVISKSSHD  RIKSLRKRT.  ..VSNWVFRV  ...SWTDRVP
       AtACS4pep  LKMLVDDENS  SRKCQKSESE  RLNGSRKKTM  SNVSNWVFRL  ...SPEDREA
          AtACS8  LRRFVDGPSP  TRRSQ.SERQ  RLKRLRK...  NKVSNWVFRL  ...SPEDREP
       NaACS2pep  ----------  ----------  ----------  ----------  ----------
       NaACS3pep  ----------  ----------  ----------  ----------  ----------
       LeACS3pep  IRDFVESTAP  NATNRQNQQQ  SHANGKKKSF  ...SKWVFRL  ...SFNDQR
       LeACS7pep  LKAFVGSRVR  NEDDIQNQQQ  ..CSNEKKSF  ...SKWVFRL  ...SFNERQR
       OsjACS2pep ISRFMDTRNG  TKQQASCQQQ  EQQ-------  ----------  ----------
         OsjACS3  ISRFMDTRNG  TKQQASCQQQ  EQQ-------  ----------  ----------
       OsiACS3pep ISRFMDTRNG  TKQQASCQQQ  EQQ-------  ----------  ----------
           AtACS7 IHEFMDRKRR  F---------  ----------  ----------  ----------
       Consensus  ----------  ----------  ----------  ----------  ----------

501                    524
         A47pep   PQSPMVHAS~  ----------  -----
         A50pep   PQSPMVHAS~  ----------  -----
      osiacs1pep  PQSPMVRATS  ----------  -----
       osjacs1pep PQSPMVRATS  ----------  -----
        TaACS2pep PQSPLVHAAS  ----------  -----
        AtACS1pep .YEENVRSPK  .LNSFRSPLL  RR~~
```

Fig. 8 (cont.)

```
AtACS2pep   .YEDGLSSPG  .IMSPRSPLL  RA--
LeACS2pep   mydesvispi  sspippsplv  r---
LeACS4pep   stmkmlla--  ----------  ----
MaACS1pep   FEDPTIMTP.  RLMSPRSPLV  QAAT
MaACS5pep   FEDPTIMTP.  RLMSPRSPLV  QAAT
LeACS1Apep  ldhefmnspa  hspm.nsplv  rt--
LeACS1Bpep  ld.df.nspa  hspm.nsplv  rt--
LeACS6pep   LD.DFNNSP.  HSPM.SSPMV  QASR
AtACS6pep   FDDGFF.SP.  HSPVPPSPLV  RAQT
A65pep      ER--------  ----------  ----
osiacs2pep  ER--------  ----------  ----
AtACS5pep   DER-------  ----------  ----
AtACS9      DER-------  ----------  ----
AtACS4pep   EER-------  ----------  ----
AtACS8      EER-------  ----------  ----
MaACS2pep   ----------  ----------  ----
MaACS3pep   ----------  ----------  ----
LeACS3pep   ER--------  ----------  ----
LeACS7pep   ER--------  ----------  ----
OsjACS2pep  ----------  ----------  ----
OsjACS3     ----------  ----------  ----
OsiACS3pep  ----------  ----------  ----
AtACS7      ----------  ----------  ----
Consensus   ----------  ----------  ----
```

```
     MaACS5pep  PGEAFLIPTP  YYPGFDRDFR  WRTGVQLLPI  HCHSSNKFRI  TQAALETAYR
     LeACS1Apep pgdaflvptp  yypgfdrdlr  wrtgvqlfpv  vceesondfkv ttkaleeaye
     LeACS1Bpep pgdaflvptp  yypgfdrdlr  wrtgvqlfpv  vceesondfkv ttkaleeaye
      LeACS6pep PGDAFLVPTP  YYPGFDRDLR  WRTGVQLFPV  VCESSNNFKV  SKEALEEAYS
      AtACS6pep PGDGFLVPTP  YYPGFDRDLR  WRTGVNLVPV  TCRSSNGFKI  TVEALEAAYE
          A6pep HGDAFLIPTP  YYPGFDRDLK  WRTGAEIVPV  HCTSGNGFRL  TRAALDDAYR
      osiacs2pep HGDAFLIPTP YYPGFDRDLK  WRTGAEIVPV  HCASANGFRV  TRAALDDAYR
      AtACS5pep PGDAFLLPTP  YYPGFDRDLK  WRTGAEIVPI  HCSSSNGFQI  TESALQQAYQ
         AtACS9 PGDAFLLPTP  YYPGFDRDLK  WRTGAEIVPI  HCSSNGFQI   TESALQQAYQ
      AtACS4pep PGDAFLLPTP  YYPGFDRDLK  WRTGVEIVPI  QSSSTNGFRI  SKLALEEAYE
         AtACS8 PGDAFLLPTP  YYPGFDRDLK  WRTGAEIVPI  QCKSANGFRI  TKVALEEAYE
      MaACS2pep PGEAFLLPTP  YYPGFDRDLK  WRTGAEIVPI  HCSSSNGFRI  TKPALEAAYQ
      MaACS3pep PGEAFLLPTP  YYPGFDRDLK  WRTGVEIVPI  HCSSSNGFRI  TRAALEAALR
      LeACS3pep QGDAFLLPTP  YYPGFDRDLK  WRTGAEIVPI  HCSSSNGFRI  TESALEEAYL
      LeACS7pep PGHAFLLPTP  YYPGFDRDLK  WRTGAEIVPI  QCTSGNGFRI  TESALEEAYT
      OsjACS2pep PGDALLIPTP YYPGFDRDLR  WRTGVNIVPV  RCDSANGFQV  TVAALQAAYD
         OsjACS3 PGDALLIPTP YYPGFDRDLR  WRTGVNIVPV  RCDSANGFQV  TVAALQAAYD
      OsiACS3pep PGDALLIPTP YYPGFDRDLR  WRTGVNIVPV  RCDSANGFQV  TVAALQAAYD
         AtACS7 PHDALLVPTP  YYPGFDRDLR  WRTGVEIVPI  RCDSSNNFQI  TPEALESAYQ
      Consensus PGDA-LVPTP  YYP-FDRD--  WR-G---IVPI -C-S-N-F-I  T---AL---AY- 201                                                    250
      A47pep    GARRQGVRVK  GVLITNPSNP  LGTTMDRATL  AMLARFAT.E  HRVHLICDEI
      A50pep    GARRQGVRVK  GILITNPSNP  LGTTMDRGTL  AMLAAFAT.E  RRVHLICDEI
     osiacs1pep GARRQGISVK  QILITNPSNP  LGTITDRDTL  AMLATFAT.E  SRVHLVCDEI
     osjacs1pep GARRQGISVK  GILITNPSNP  LGTITDRDTL  AMLATFAT.E  SRVHLVCDEI
      7aACS3pep GARSSGVRVK  GILITNPSNP  LGTTADRATL  AMLATFAT.E  SRVHLICDEI
      AtACS1pep KAQETGIRIK  GLII...SNP  LGTSLDRETL  ESLVSFIN.D  RQIHLVCDEI
      AtACS2pep KAQESNKKVK  GLILTNPSNP  LGTMLDKDTL  TNLVRFVT.R  KNIHLVVDEI
      LeACS2pep naqksnikvk  gliltnpsnp  lgttldkdtl  kavlsfta.q  hnihlvcdei
      LeACS4pep kgqqanvklk  gliltxpcnp  lgtildrdtl  kkistftn.e  haihlvcdei
      MaACS1pep KARNSHIPVK  GILVTNPSKP  LGTTMDRETL  RTLVSFVN.E  KDMHLVCDEI
      MaACS5pep KAANSHIRVK  GIVVTKPSNP  LGTTMDRDTL  RTLVSFVN.E  KRMHLVCDEV
     LeACS1Apep kaqgsnikik  gllinxpsnp  lgtlldkdtl  rdivtfin.s  knihlvcdei
     LeACS1Bpep kaqgsnikik  gllinspsnp  lgtlldkdtl  rdivtfin.s  knihlvcdei
      LeACS6pep KAQESNIKVK  GLLINNPSNP  LGTTLDKETL  KDILRFIN.D  RNIHLVCDEI
      AtACS6pep NARKSNIPVK  GLLVTNPSNP  LGTTLDRSCL  KSLVNFTN.D  KGIHLIADEI
          A6pep RAQKLRLRVK  GVLITNPSNP  LGTTSFRADL  EMLVDFVA.A  KGIHLVSDEI
      osiacs2pep RAQKRRLRVK GVLITNPSNP  LGTASFRADL  ETIVDFVA.A  KGIHLISDEI
      AtACS5pep QAQKLDLKVK  GVLVTNPSNP  LGTALFRREL  NLLVDFIT.S  KNIHLISDEI
         AtACS9 QAQKLDLKVK  GVLVTNPSNP  LGTNLFRREL  NLLVDFIT.S  KNIHLISDEI
      AtACS4pep QAKKLDLNVK  GILITNPSNP  LGTTTQFEL   NILFDFITKN  KNIBLVSDEI
         AtACS8 QAQKLNLKVK  GVLITNPSNP  LGTTTRFEL   NHLLDFISR.  KKIHLISDEI
      MaACS3pep DAQKRSLRVK  GVLVTNPSNP  LGTTLFRHEL  DILVDFVV.S  KDIHLISDEI
      MaACS3pep RAQKRRLRVK  GVLVTNPSNP  LGTTLFRQEL  DTLVDFAV.A  NDIHLISDEI
      LeACS3pep DAKKRNLRVK  GVLVTNPSNP  LGTTLRRNEL  ELLLTFID.E  KGIHLISDEI
      LeACS7pep SAERRNLRVK  GVLVTNPSNP  LGTTLTKKEL  QLLLTFVS.T  RQIHLISDEI
      OsjACS2pep SAAAVGMRAR AVLITNPSNP  LGTTVRRKML  DDILDFVSR.  NDIHLISDEI
         OsjACS3 SAAAVGMRAR AVLITNPSNP  LGTTVRRKML  DDILDFVSR.  NDIHLISDEI
      OsiACS3pep SAAAAGMRAR AVLITNPSNP  LGTTVRRKVL  DDILDFVSR.  NDIHLISDEI
         AtACS7 TARDANIRVR  GVLITNPSNP  LGATVQKKVL  EDLLDFCVR.  KNIHLVSDEI
     Consensus  -A------VK  GVLI-NPSNP  LGT---R--L  --L--F----  ---IHLI-DEI 251                                                    300
      A47pep    YAGSVFAKPD  ..FVSIAEVI  ER.DVPGCNR  .......DLI  HIAYSLSKDF
```

Fig. 9 (cont.)

```
        A80pep  YAGSVFAKPG ..FVSIAEVI ERGDAPGCNR .......DLV HIAYSLSKDF
   osiacs1pep  YAGSVFATPE ..YVSIAEVI ER.DVPWCNR .......DLI HVVYSLSKDF
   osjacs1pep  YAGSVFATPE ..YVSIAEVI ER.DVPWCNR .......DLI HVVYSLSKDF
      TaACS2pep  YAGSVFAKPE ..YVSIAEVI ER.DAPGAIR .......DLI HIAYSLSKDF
      AtACS1pep  YAATVFAKPG ..FISVAEII Q..EMYVNR  .......DLI HIVYSLSKDM
      AtACS2pep  YAATVFAGGD ..FVSVAEVV NDVDISEVNV .......DLI HIVYSLSKDM
      LeACS2pep  yaatvfdtpq ..fvsiaeil deqemtycnk .......dlv hivyslskds
      LeACS4pep  yaatvfnppk ..fvsiaeil aednc..ink .......dlv hivsslskdi
      MaACS1pep  FSGTVFDKPS ..YVSVSEVI ED..DPYCNR .......DLI HIAYSLSKDL
      MaACS6pep  FSGTVFDKPS ..YVSVAEVI QD..DPYCDR .......DLI HIAYSLSKDL
     LeACS1Apep  yaatvfdqpr ..fisvsely ed..miecnk .......dli hivyslskdi
     LeACS1Bpep  yaatvfdqpr ..fisvsemv ae..miecnt .......dli hivyslskdi
      LeACS6pep  YAATAFSQPS ..FISISEVK SE..VVGCND .......DLV HIVYSLSKDL
      AtACS6pep  YAATTFGQSE ..FISVAEVI EE..IEDCNR .......DLI HIVYSLSKDM
           A65pep  YSGTVFADP. .GFVSVLEVY AARAATDKRV VGVGPLSDRV HVVYSLSKDL
    osiacs2pep  YAGTAFAEPP AGFVSALEVY AGR....DG. QGADVSDRV HVVYSLSKDL
      AtACS5pep  YSGTNFGFE. .QFISVNDVL KDRKLED... ...TEVSKRV HVVYSLSKDL
         AtACS9  YSGTVFGFE. .QFVSVMDVL KDRNLEN... ...SEVSKRV HIVYSLSKDL
      AtACS4pep  YSGTVFNSG. .EFISVMEIL KNNQLEN... ...TDVLNKV HIVCSLSKDL
         AtACS8  YSGTVFTNP. .GFISVNEVL KDRKLEN... ...TDVFDRV HIVYSLSKDL
      MaACS2pep  YSGTNFDSP. .GFISIAEAT KDRN...... ....NVSHRI HIVCSLSKDL
      MaACS3pep  YSGTTFGSP. .GFVSIAEAT KGRD...... ....DVSHRI HIVCSLSKDL
      LeACS5pep  YSGTVFNSP. .GLVSVNEVL IERNYMK... ...TRVWERV HIVYSLSKDL
      LeACS7pep  YSGTVFNSP. .KFVSVNEVL IENNYMY... ...TDVWDRV HIVYSLSKDL
     OsjACS2pep  YSGSVFAAPD ..LVSVAELV EAR....... .GGIKIAGRV HIVYSLSKDL
         OsjACS3  YSGSVFAAPD ..LVSVAELV EAR....... .GGDGIAGRV HIVYSLSKDL
     OsiACS3pep  YSGSVFAAPD ..LVSVAELV EAR....... .DGDGIAGRV HIVYSLSKDL
         AtACS7  YSGSVFHASE ..FTSVAEIV ENI....... .DDVSVKERV HIVYSLSKDL
      Consensus  Y----F---- ----VSV-EVI ---------- ----------V RI---SLSKD- 301                                                 350
       A47pep  GLPGFRVGIV YSYNDDVVAC ARKMSSFGLV SSQTQSFLAK MLSDAEFMAR
       A80pep  GLPGFRVGIV YSYNDDVVAC ARKMSSFGLV SSQTQHFLAM NLADASFMAR
   osiacs1pep  GLPGFRVGII YSYNDAVVAA ARRMSSFGLV SSQTQYFLAR MLSDEEFIGR
   osjacs1pep  GLPGFRVGII YSYNDAVVAA ARRMSSFGLV SSQTQYFLAR MLSDEEFIGR
      TaACS2pep  GLPGFRVGIV YSYNDAVVAC ARKMSSFGLV SSQTQLFLAK MLGDEEFMSR
      AtACS1pep  GLPGFRVGVV YSYNDVVVSC ARKMSSFGLV SSQTQSFLAA MLSDQSFVDN
      AtACS2pep  GLPGFRVGIV YSFNDSVVSC ARKMSSFGLV SSQTQLMLAS MLSDDQFVDN
      LeACS2pep  glpgfrvgli ysfnddvvnc arkmssfglv stqtqyflaa misdekfvdn
      LeACS4pep  gfpgfrvgiv ysfnddvvnc arkmssfglv stqtqhlilaf misdddefvee
      MaACS1pep  GVPGFRVGVI YSYNDAVVTC ARKMSSFGLV SSQTQSRLLAS MLGDEEFTTS
      MaACS6pep  GVPGFRVGVI YSYNDAVVSC ARKMSSFGLV SSQTQHLLAS MLGDEEFTTS
     LeACS1Apep  gfpgfrvgiv ysyndtvvni arkmssfglv saqtqhlilas misdevfidk
     LeACS1Bpep  gfpgfrvgiv ysyndtvvni arkmssfglv stqtqhmlas misdeifvek
      LeACS6pep  GFPGFRVGII YSYNDAVVNI ARKMSSFGLV STQTQRLIAS MLLDTIFVED
      AtACS6pep  GLPGLRVGIV YSYNDSVVQI ARKMSSFGLV SSQTQHLIAK MLSDEEFVDE
         A65pep  GLPGFRVGAI YSSNAGVVSA ATKMSSFGLV SSQTQRLLAS LLGDRDFTSR
    osiacs2pep  GLPGFRVGAI YSANAAVVSA ATKMGSFGLV SSQTQYLLAA LLGDRDFTRG
      AtACS5pep  GLPGFRVGAI YSNDEMIVSA ATKMSSFGLV SSQTQYLLSA LLSDKKFTSQ
         AtACS9  GLPGFRVGAI YSNDEMVVSA ATKMSSFGLV SSQTQYLLSA LLSDKEFTST
      AtACS4pep  GLPGFRVGAI YSNDKDVISA ATKMSSFGLV SSQTQYLLSS LLSDKKFTKN
         AtACS8  GLPGFRVGVI YSNDDFVVSA ATKMSSFGLI SSQTQYLLSA LLSDKTFTSN
      MaACS2pep  GLPGFRVGAI YSENEAVVSA ATKMSSFGMV SSQTQYLLAA LLSDKEFTDK
      MaACS3pep  GLPGFRVSAI YSDNEAVVSA ATKMSSFGLI SSQTQYLLAA LLSDKEFTEK
      LeACS3pep  GLPGFRIGAI YSNDEMVVSA ATKMSSFGLV SSQTQYLLSC MLSDKEFTKK
```

```
AtACS2pep  .YSDGLSSPG  .IMSPNSPLL  RA--
LeACS2pep  mydesvlspi  sspippsplv  r---
LeACS4pep  stmkmlls--  ----------  ----
MaACS1pep  FEDPTIMTP.  BLMSPNSPLV  QAAT
MaACS5pep  FEDPTIMTP.  BLMSPNSPLV  QAAT
LeACS1Apep  idssfmnspa  hspm.ssplv  rt--
LeACS1Bpep  id.df.nspa  hspm.ssplv  rt--
LeACS6pep  LD.SFNSSP.  RSPM.SSPMV  QRRS
AtACS6pep  FDSSFF.SP.  SSPVPPSPLV  RAQT
     A6pep  ER--------  ----------  ----
 osiacs2pep  ER--------  ----------  ----
 AtACS5pep  DER-------  ----------  ----
     AtACS9  DER-------  ----------  ----
 AtACS4pep  EER-------  ----------  ----
     AtACS8  EER-------  ----------  ----
 MaACS2pep  ----------  ----------  ----
 MaACS3pep  ----------  ----------  ----
 LeACS3pep  ER--------  ----------  ----
 LeACS7pep  ER--------  ----------  ----
 OsjACS2pep  ---------  ----------  ----
     OsjACS3  ---------  ----------  ----
 OsiACS3pep  ---------  ----------  ----
     AtACS7  ---------  ----------  ----
  Consensus  ---------  ----------  ----
```

```
   AtACS4pep  PQGIIQMGLA  ENQLCFDLLE  SWLAQ.NTDA  ACFKRD..GQ  SVFRELALFQ
      AtACS8  PDGIIQMGLA  ENQLSFDLIE  SWLAK.NPDA  ANFQRE..GQ  SIFRELALFQ
    MaACS2pep  -------MGFT  ENQLCFDLIE  SWLEN.HPDP  AAFKKD..GA  LLFRELALFQ
    MaACS3pep  -------NGFA  ENRVSFDLIE  SWLED.HPDL  TGFKKD..GG  LVFRELALFQ
    LeACS3pep  PKGIIQMGLA  ENQLSFDLLE  SWLAQ.NPDA  AGFKRN..GE  SIFRELALFQ
    LeACS7pep  PKGIIQMGLA  ENQLSFDLLE  SWLTL.NPDA  SAFKRN..GH  SIFRELSLFQ
   OsjACS2pep  PDGVIQMGLA  ENQVSFDLLE  AYL.RDHPEA  AGWSTGGAGA  GSFRDNALFQ
       OsjACS3 PDGVIQMGLA  ENQVSFDLLE  AYL.RDHPEA  AGWSTGGAGA  GSFRDNALFQ
   OsiACS3pep  PDGVIQMGLA  ENQVSFDLLE  AYL.RDHPEA  AGWSTGGAGA  GSFRDNALFQ
       AtACS7  PSGVIQMGLA  ENQVSFDLLE  TYLEKNPEG  SNW..SSKGA  PGFRENALFQ
    Consensus  PDGVIQMGLA  ENQL-FDLIE  SW-.-.NPEA  S--TRE..G-  --FRE-A-FQ 101                                                 150
       A47pep  DYHGLPEFRE  AMAKFMGQVR  AGKVTFDPDR  VVMCGGATGA  QDTLAFCLAD
       A50pep  DYRGLPEFRE  AMAKFMGQVR  GGKVTFDPDR  VVMCGGATGA  QDTLAFCLAD
   osiacs1pep  DYHGLPEFRK  AMAQFMGQVR  GGKATFDPDR  VVMSGGATGA  QETLAFCLAN
   osjacs1pep  DYHGLPEFRK  AMAQFMGQVR  GGKATFDPDR  VVMSGGATGA  QETLAFCLAN
    TaACS2pep  DYRGLPEFRQ  AMAQFMGQVR  GWKARFDPDR  VVMSGGATGA  QETLAFCLAN
    AtACS1pep  DYHGLKQFRQ  AIATFMEAAR  GGSVRFEASR  VVMSGGATGA  NETIMFCLAD
    AtACS2pep  DYHGLKEFRQ  AIAEFMGKAR  GGRVTFDPER  VVMSGGATGA  NETIIFCLAD
    LeACS2pep  dyhglpefrk  aiakfmektr  ggrvrfdper  vmsggatga   netiifclad
    LeACS4pep  dyhglpeftn  aiakfmektr  ggkvkfdakr  vvmsggatga  netlilclad
    MaACS1pep  DYRGLPTFRK  AIAQFMEKVR  GGRARFDPDR  IVMSGGATGA  QETIAFCLAD
    MaACS5pep  DYRGLPAFRK  AIAQFMEKVR  GGRARFDPDR  IVMSGGATGA  QETIAFCLAD
   LeACS1Apep  dyhglpefrq  avarfmekvr  gdrvtfdpsr  ivmsggatga  hemlafclad
   LeACS1Bpep  dyhglpefrq  avarfmekvr  gdrvtfdpnr  ivmsggatga  hemlafclad
    LeACS6pep  DYHGLPEFRK  AVARFMEKVR  GDRVRFDPSR  IVMSGGATGA  HESLAFCLAD
    AtACS6pep  DYHGLPEFRQ  AVAKFMEKTR  NNKVKFDPDR  IVMSGGATGA  HETVAFCLAN
       A65pep  DYHGMPAFKN  ALARFMSEQR  GYRVTFDPSN  IVLTAGATSA  NEALMFCLAD
   osiacs2pep  DYRGLPAFRQ  ALARFMSEQR  GYKVVFDPSN  IVLTAGATSA  NEALMFCLAD
    AtACS5pep  DYHGMPEFRK  AMAEFMEEIR  GNRVTFDPKK  IVLAAGSTSA  NETLMFCLAE
       AtACS9  DYHGLPEFRK  ALAEFMEEIR  GNRVTFDPSK  IVLAAGSTSA  NETLMFCLAE
    AtACS4pep  DYRGLSSFKN  AFADFMSENR  GNRVSFDSNN  LVLTAGATSA  NETLMFCLAD
       AtACS8  DYHGLPSFKN  AMADFMSENR  GNRVSFNPNK  LVLTAGATPA  NETLMFCLAD
    MaACS2pep  DYRGLPAFKR  ALTRYMGEVR  GNKVAFDPNR  LVLTAGATSA  NETLMFCLAE
    MaACS3pep  DYHGLPAFKN  ALARYMGEVR  GNKVSFEPSK  LVLTAGATSA  NETLMFCLAD
    LeACS3pep  DYHGLPAFKN  AMTRFMSEIR  GNRVSFDSNN  LVLTAGATSA  NETLMFCLAN
    LeACS7pep  DYHGLPAFKD  ALVQFMSEIR  GNKVSFDSNK  LVLTAGATSA  NETLMFCLAD
   OsjACS2pep  DYHGLKSFRK  AMASFMGKIR  GGKARFDPDR  IVLTAGATAA  NELLTFILAN
       OsjACS3 DYHGLKSFRK  AMASFMGKIR  GGKARFDPDR  IVLTAGATAA  NELLTFILAN
   OsiACS3pep  DYHGLKSFRK  AMASFMGKIR  GGKARFDPDR  IVLTAGATAA  NELLTFILAN
       AtACS7  DYHGLKTFRQ  AMASFMEQIR  GGKARFDPDR  IVLTAGATAA  NELLTFILAD
    Consensus  DYRGL-EFRK  AMAKFMEK-R  GGKV-FD-DR  IVMTGGATGA  NE-L-F-LAD 151                                                  200
       A47pep  PGDAYLVPTP  YYPAFDRDCC  WRSGVKLLPI  ECHSSNNFTL  TREALVSAYD
       A50pep  PGDAYLVPTP  YYPAFDRDCC  WRSGVKLLPI  ECHSSNNFTL  TREALVSAYD
   osiacs1pep  PGEAFLVPTP  YYPAFDRDCC  WRSGIKLLPI  ECSFNDFRL   TKEALVSAYD
   osjacs1pep  PGEAFLVPTP  YYPAFDRDCC  WRSGIKLLPI  ECHSFNDFRL  TKEALVSAYD
    TaACS2pep  PGEAFLVPTP  YYGFDRDCC   WRSGVKLLPI  ECSSNDFRI   TREAVVAAYE
    AtACS1pep  PGDAFLVPTP  YYAAFDRDLR  WRTGVRIIPV  ECSSNNFQI   TKQALESAYL
    AtACS2pep  PGDVFLIPSP  YYAAFDRDLR  WRTGVEIIPV  PCSGSDNFKL  TVDAAEKAYR
    LeACS2pep  pgdaflvpsp  yypafdrdlr  wrtgvqlipi  hcassnofki  tskavkeaye
    LeACS4pep  pgdaflvptp  yypgfnrdlr  wragvqlipi  scksonnfki  tlealeeaye
    MaACS1pep  PGEAFLIPTP  YYPGFDRDFR  WRTGVQLLPI  HCHSSNRFKI  TQAALETAYR
```

Fig. 10 (cont.)

```
MaACS5pep   PGEAFLIPTP  YYPGFDRDFR  WRTGVQLLFI  SCHSSNKFKI  TQAALETAYR
LeACS1Apep  pgdaflvptp  yypgfdrdlr  wrtgvqlfpv  vcescndfkv  ttkalesaye
LeACS1Bpep  pgdaflvptp  yypgfdrdlr  wrtgvqlfpv  vcescndfkv  ttkalesaye
LeACS6pep   PGDAFLVPTP  YYPGFDRDLR  WRTGVQLFPV  VCESSNNFKV  TKEALEEAYS
AtACS6pep   PGDGFLVPTP  YYPGFDRDLR  WRTGVNLVPV  TCHSSSNGFKI  TVEALEAAYN
A5pep       SGDAFLIPTP  YYPGFDRDLK  WRTGAEIVPV  SCTSGNGFRL  TRAALDDAYR
osiacs2pep  SGDAFLIPTP  YYPGFDRDLK  WRTGAKIVPV  HCAGANGFRV  TRAALDDAYR
AtACS5pep   PGDAFLLPTP  YYPGFDRDLK  WRTGAEIVPI  HCSSSNGFQI  TESALQQAYQ
AtACS9      PGDAFLLPTP  YYPGFDRDLK  WRTGAEIVPI  HCSSSNGFQI  TESALQQAYQ
AtACS4pep   PGDAFLLPTP  YYPGFDRDLK  WRTGVEIVPI  QSSGTNGFRI  TKLALEEAYE
AtACS8      PGDAFLLPTP  YYPGFDRDLK  WRTGAEIVPI  QCNSANGFRI  TKVALEEAYE
MaACS2pep   PGEAFLLPTP  YYPGFDRDLK  WRTGAEIVPI  HCSSSNGFRI  TKPALEAAYQ
MaACS3pep   PGEAFLLPTP  YYPGFDRDLK  WRTGVEIVPI  HCSSSNGFRI  TRAALEAALR
LeACS3pep   QGDAFLLPTP  YYPGFDRDLK  WRTGAEIVPI  HCSSSNGFRI  TESALEEAYL
LeACS7pep   PGRAFLLPTP  YYPGFDRDLK  WRTGAKIVPI  QCTSSNGFRI  TESALEEAYT
OsjACS2pep  PGDALLIPTP  YYPGFDRDLR  WRTGVNIVPV  RCDSANGFQV  TVAALQAAYD
OsjACS3     PGDALLIPTP  YYPGFDRDLR  WRTGVNIVPV  RCDSANGFQV  TVAALQAAYD
OsiACS3pep  PGDALLIPTP  YYPGFDRDLR  WRTGVNIVPV  RCDSANGFQV  TVAALQAAYD
AtACS7      PNDALLVPTP  YYPGFDRDLR  WRTGVEIVPI  HCDSSNHFQI  TPEALESAYQ
Consensus   PGDAFLVPTP  YYPGFDRD--  WRTGVEIVPI  -C-SSNGFRI  T-EAL-EAYE 201                                                250
A47pep      GARRQGVRVK  GVLITNPSNP  LGTTNDRATL  AMLARFAT.E  SRVHLICDEI
A56pep      GARRQGVRVR  GILITNPSNP  LGTTMDRGTL  AMLAAFAT.E  SRVHLICDEI
osiacs1pep  GARRQGISVK  GILITNPSNP  LGTTITDRDTL AMLATFAT.E  SRVHLVCDEI
osjacs1pep  GARRQGISVK  GILITNPSNP  LGTTITDRDTL AMLATFAT.E  SRVHLVCDEI
TaACS2pep   GANSGGVRVK  GILITNPSNP  LGTTADRATL  AMLATFAT.E  SRVHLICDEI
AtACS1pep   KAQETGIKIK  GLII...SNP  LGTSLDRETL  ESLVSFIN.D  KQIHLVCDEI
AtACS2pep   KAQESNKKVK  GLILTNPSNP  LGTMLDRDTL  TNLVSFVT.R  KNISLVVDEI
LeACS2pep   naqksnikvk  glilinpsnp  lgttldkdtl  ksvlsftn.q  hnihlvcdei
LeACS4pep   kgqqanvkik  glilsnpcnp  lgtlldrdtl  kkistftn.e  hnihlvcdei
MaACS1pep   KARNSHIRVK  GILVTNPSKP  LGTTMDRETL  RTLVSFVN.E  KRMHLVCDEI
MaACS5pep   KARNSHIRVK  GIVVTNPSNP  LGTTMDRDTL  RTLVSFVN.E  KRMHLVCDEV
LeACS1Apep  kaqqsnikik  glilnpsnp   igtlldkdtl  rdivtfin.s  knihlvcdei
LeACS1Bpep  kaqqsnikik  glilnpsnp   igtlldkdtl  rdivtfin.s  knihlvcdei
LeACS6pep   KAQESNIKVK  GLLISNPSNP  LGTTLDKETL  KDILRFIN.D  KNISLVCDEI
AtACS6pep   NARKSNIPVK  GLLVTNPSNP  LGTTLDRECL  KSLVNFTN.D  KGIHLIADEI
A5pep       RAQKLRLRVK  GVLITNPSNP  LGTTSPRADL  EMLVDFVA.A  KGIHLVSDEI
osiacs2pep  RAQKRRLRVK  GVLINPSNP   LGTAGPRADL  ETIVDFVA.A  KGIHLISDEI
AtACS5pep   QAQKLDLRVK  GVLVTNPSNP  LGTALTRREL  NLLVDFIT.S  KNIHLISDEI
AtACS9      QAQKLDLRVK  GVLVTNPSNP  LGTMLTRREL  NLLVDFIT.S  KNIHLISDEI
AtACS4pep   QAKKLDLNVK  GILITNPSNP  LGTTTQTEL   NILFDFITKN  KNIHLVSDEI
AtACS8      QAQKLNLRVK  GVLVTNPSNP  LGTTTRTEL   NHLLDFISR.  KRIHLISDEI
MaACS2pep   DAQKRSLRVK  GVLVTNPSNP  LGTTLTRNEL  DILVDFVV.S  KDIHLISDEI
MaACS3pep   RAQKRRLRVK  GVLVTNPSNP  LGTTLTRQEL  DTLVDFAV.A  NGIHLISDEI
LeACS3pep   DAKKRNLRVK  GVLVTNPSNP  LGTTLNRNEL  ELLLTFID.E  KGIHLISDEI
LeACS7pep   KAESRNLRVK  GVLVTNPSNP  LGTTLTKREL  QLLLTFVS.T  KQIRLISDEI
OsjACS3pep  EAAAVGNRAR  AVLITNPSNP  LGTTVRRKML  DDILDFVSR.  NDIHLISDEI
OsjACS3     EAAAVGMRAR  AVLITNPSNP  LGTTVRRKML  DDILDFVSR.  NDIHLISDEI
OsiACS3pep  EAAAAGMRAR  AVLITNPSNP  LGTTVKKVL   DDILDFVSR.  NDIHLISDEI
AtACS7      TARDANIRVR  GVLITNPSNP  LGATYQRKVL  EDLLDFCVR.  KNIHLVSDEI
Consensus   KAQK-NIRVK  GVLITNPSNP  LGT-LDR--L  --LVDFV-.E  KNIHLISDEI 251                                                300
A47pep      YAGSVFARPD  ..FVSIAEVI  ER.DVPGCNR  .......DLI  HIAYGLSKDF
```

Fig. 10 (cont.)

```
         A50pep  YAGSVFAKPG  ..FVSIAEVI  ERGDAPQCNR  .......DLV  HIAYSLSKDF
    osiacs1pep  YAGSVFATPK  ..YVSIAEVI  ER.DVPNCNR  .......DLI  HVVYSLSKDF
    osjacs1pep  YAGSVFATPK  ..YVSIAEVI  ER.DVPNCNR  .......DLI  HVVYSLSKDF
       TaACS2pep  YAGSVFAKPK  ..YVSIAEVI  EH.DAPGADR  .......DLI  HIAYSLSKDF
       AtACS1pep  YAATVFAKPG  ..FISVAEII  Q..EMYYVHR  .......DLI  HIVYSLSKDM
       AtACS2pep  YAATVFAGGD  ..FVSVAEVV  HDVDISEVHV  .......DLI  HIVYSLSKDM
       LeACS2pep  yaatvfdtpq  ..fvsiaeli  deqesmtycnk .......div  hivyslskde
       LeACS4pep  yaatvfnppk  ..fvsiaeli  nednc..ink  .......div  hivaslskdl
       MaACS1pep  FSGTVFDKPS  ..YVSVSEVI  ED..DPYCDR  .......DLI  HIAYSLSKDL
       MaACS5pep  FSGTVFDKPS  ..YVSVAEVI  QD..DPYCDR  .......DLI  HIAYSLSKDL
      LeACS1Apep  yaatvfdgpr  ..fisvseiv  ed..miecnk  .......dli  hivyslskdl
      LeACS1Bpep  yaatvfdgpr  ..fisvseiv  ee..miecnt  .......dli  hivyslskdl
       LeACS6pep  YAATAFSQPS  ..FISISEVK  SR..VVGCND  .......DLV  HIVYSLSKDL
       AtACS6pep  YAATTFGQSE  ..FISVAEVI  ER..IESCNR  .......DLI  HIVYSLSKDM
           A65pep  YSGTVFADP.  .GFVSVLEVV  AARAATHRGV  VGVGPLSDRV  HVVYSLSKDL
    osiacs2pep  YAGTAFAEPP  AGFVSALEVV  AGR....HC.  .GGADVSSRV  HVVYSLSKDL
       AtACS5pep  YSGTNFGFK.  .QFISVNDVL  KDKKLED...  ...TEVSRV  HVVYSLSKDL
           AtACS9  YSGTVFGFK.  .QFVSVMDVL  KDKNLEH...  ...SEVSRV  HIVYSLSKDL
       AtACS4pep  YSGTVFNSS.  .EFISVMEIL  KNNQLEH...  ...TDVLHRV  HIVCSLSKDL
           AtACS8  YSGTVFTNP.  .GFISVMEVL  KDRKLEH...  ...TDVFDRV  HIVYSLSKDL
       MaACS2pep  YSGTNFDSP.  .GFISIAEAT  KDRN......  ....NVSHRI  HIVCSLSKDL
       MaACS3pep  YSGTTFGSP.  .GFVSIAEAT  KGRD......  ....DVSHRI  HIVCSLSKDL
       LeACS3pep  YSGTVFNSP.  .GLVSVMEVL  IERNYMR...  ....TRVMERV HIVYSLSKDL
       LeACS7pep  YSGTVFNSP.  .KFVSVMEVL  IENNYMY...  ....TDVMDRV HIVYSLSKDL
       OsjACS2pep YSGSVFAAPD  ..LVSVAELV  EAR.......  .GGDGIAGRV  HIVYSLSKDL
           OsjACS3 YSGSVFAAPD  ..LVSVAELV  EAR.......  .GGDGIAGRV  HIVYSLSKDL
       OsiACS3pep YSGSVFAAPD  ..LVSVAELV  EAR.......  .DGDGIAGRV  HIVYSLSKDL
           AtACS7  YSGSVFRASE  ..FTSVAEIV  ENI.......  .DSVSVKERV  HIVYSLSKDL
       Consensus  YSGTVFA--.  ..FVSV-EVI  ED.........-.  ........S-V HIV-SLSKDL 301                                                   350
           A47pep  GLPGFRVGIV  YSYNDDVVAC  ARKMSSFGLV  SSQTQHFLAK  MLSDAEFMAR
           A50pep  GLPGFRVGIV  YSYNDDVVAC  ARKMSSFGLV  SSQTQHFLAN  MLADAEFMAR
    osiacs1pep  GLPGFRVGII  YSYNDAVVAA  ARKMSSFGLV  SSQTQYFLAR  MLSDEEFIGR
    osjacs1pep  GLPGFRVGII  YSYNDAVVAA  ARKMSSFGLV  SSQTQYFLAR  MLSDEEFIGR
       TaACS2pep  GLPGFRVGVV  YSYNDVVVSC  ARKMSSFGLV  SSQTQLFLAA  MLGDEEFVKR
       AtACS1pep  GLPGFRVGVV  YSYNDVVVSC  ARKMSSFGLV  SSQTQSFLAA  MLSDQSFVDN
       AtACS2pep  GLPGFRVGIV  YSFNDSVVSC  ARKMSSFGLV  SSQTQLMLAS  MLSDDQFVDN
       LeACS2pep  glpgfrvgii  ysfnddvvnc  arkmssfglv  stqtqyflaa  mlsdekfvda
       LeACS4pep  gfpgfrvgiv  ysfnddvvnc  arkmssfglv  stqtqhllaf  alsddefves
       MaACS1pep  GVPGFRVGVI  YSYNDAVVTC  ARKMSSFGLV  SSQTQHLLAS  MLGDEEFTTS
       MaACS5pep  GVPGFRVGVI  YSYNDAVVSC  ARKMSSFGLV  SSQTQHLLAS  MLGDEEFTTS
      LeACS1Apep  gfpgfrvgiv  ysyndvvvni  arkmssfglv  saqtqhllas  misdevfidk
      LeACS1Bpep  gfpgfrvgiv  ysyndvvvni  srkmssfglv  stqtqhmlas  misdeifvek
       LeACS6pep  GFPGFRVGII  YSYNDAVVNI  ARKMSSFGLV  STQTQRLIAS  MLLDTIFVSD
       AtACS6pep  GLPGLRVGIV  YSYNDRVVQI  ARKMSSFGLV  SSQTQRLIAK  MLSDEEFVDE
           A65pep  GLPGFRVGAI  YSSNAGVVSA  ATKMSSFGLV  SSQTQHLLAS  LLGDRDFTRR
    osiacs2pep  GLPGFRVGAI  YSANAAVVSA  ATKMSSFGLV  SSQTQYLLAA  LLGDRDFTRS
       AtACS5pep  GLPGFRVGAI  YSNDEMVVSA  ATKMSSFGLV  SSQTQYLLSA  LLSDKRFTSQ
           AtACS9  GLPGFRVGAI  YSNDEMVVSA  ATKMSSFGLV  SSQTQYLLSA  LLGDKRFTST
       AtACS4pep  GLPGFRVGCI  YSNDKDVISA  ATKMSSFGLV  SSQTQYLLSS  LLSDKRFTKN
           AtACS8  GLPGFRVGVI  YSNDDPVVSA  ATKMSSFGLI  SSQTQYLLSS  LLSDRRFTKN
       MaACS2pep  GLPGFRVGAI  YSENEAVVSA  ATKMSSFGNV  SSQTQYLLAA  LLSDKEFTSK
       MaACS3pep  GLPGFRVSAI  YSDNEAVVSA  ATKMSSFGLI  SSQTQYLLAA  LLSDKEFTSK
       LeACS3pep  GLPGFRIGAI  YSNDEMVVSA  ATKMSSFGLV  SSQTQYLLSC  MLSDKKFTKK
```

```
AtACS2pep    .YEDGLSSPG  .IMSPRSPLL  RA--
LeACS2pep    mydesvispl  sspigpsplv  r---
LeACS4pep    stskmlla--  ----------  ----
NaACS1pep    FEDPTINTP.  SLMSPRSPLV  QAAT
NaACS5pep    FEDPTINTP.  SLMSPHSPLV  QAAT
LeACS1Apep   ldhefsnspa  hspm.nsplv  rt--
LeACS1Bpep   ld.df.nspa  hspm.ssplv  rt--
LeACS6pep    LD.SFMNSP.  RSPM.SSPNV  QAPN
AtACS6pep    FDDSFF.SP.  RSPVPRSPLV  RAQT
AtACS5pep    ER--------  ----------  ----
osiacs2pep   ER--------  ----------  ----
AtACS3pep    DER-------  ----------  ----
AtACS9       DER-------  ----------  ----
AtACS4pep    EER-------  ----------  ----
AtACS8       EER-------  ----------  ----
NaACS2pep    ----------  ----------  ----
NaACS3pep    ----------  ----------  ----
LeACS3pep    ER--------  ----------  ----
LeACS7pep    ER--------  ----------  ----
OsjACS2pep   ----------  ----------  ----
OsjACS3      ----------  ----------  ----
OsiACS3pep   ----------  ----------  ----
AtACS7       ----------  ----------  ----
Consensus    ----------  ----------  ----
```

Fig. 10 (cont.)

Consensus Sequence (identical amino acid residues)

```
1                                                                    50
   A47pep    ------MAGG SSAEQLLSRI ASGDGHGENS SYFDGWKAYD KDPFDLRSNR
   A50pep    -------MAG SSAEQLLSRI AAGDGHGENS SYFDGWKAYD MNPFDLRSNR
 osiacs1pep  --------NA CQGIDLLSTK AAGDDHGENS SYFDGWKAYD TNPFDLRSNR
 osjacs1pep  --------MA YQGIDLLSTK AAGDGHGENS SYFDGWKAYD TNPFDLRSNR
   TaACS2pep ---------- ---------N AAGDGHGENS SYFDGWKAYD MNPFRPQDNR
   AtACS1pep ------MCQG ACENQLLSRI ALSDKHGEAS PYFHGWKAYD NNPFRPTSNP
   AtACS2pep ------MGLFG KNKGAVLSKI ATNNQHGENS KYFDGWKAYD KDPFHLSRNP
   LeACS2pep ------mgfei aktnailski atneehgens pyfdgwkayd sdpfhplkup
   LeACS4pep mdletseisn ykssavlski asneqhgens pyfdgwkayd sdpfhlvnnl
   MaACS1pep ---NRIYGEE SPNQQILSRI ATNDGHGENS SYFDGWKAYE RDPFHLTDNP
   MaACS5pep ---MRIYGEE SPNQEILSRI ATNDGHGENS SYFDGWKAYE NDPFHLTDNP
   LeACS1Apep ---mvsiskn nqkqgllski atndghgens pyfdgwkaya sspfhltdnp
   LeACS1Bpep ---mvsiskn nqkqqllski atndghgens pyfdgwkaya nnpfhptdnp
   LeACS6pep  ---------- ----MGILSKI ATNDGHGENS AYFDGWKAYE NDPFHPTQNP
   AtACS6pep  ---------- ---------- ---------- -YFDGWKAYE ENPFRPIDRP
   Consensus  ---------- ---------- A-----HGE~S -YFDGWKAY- --PF----N-

51                                                  100
   A47pep    DGVIQMGLAE NQLSLDLIEQ NSMEHPEASI CTAQGASQFR RIANFQDYHG
   A50pep    DGVIQMGLAE NQLSLDLIEQ NSVDHPEASI CTAQGAPQFR RIANFQDYHG
 osiacs1pep  GGVIQMGLAE NQLSLDLIEE NSKNHPEASI CTPEGVSQFK RIANFQDYHG
 osjacs1pep  GGVIQMGLAE NQLSLDLIEE NSKNHPEASI CTPEGVSQFK RIANFQDYHG
   TaACS2pep GGVIQMGLAE NQLSLDLIEE NSKAHPEASI CTAEGASQFR RIANFQDYHG
   AtACS1pep QGVIQMGLAE NQLCSDLIKE NIKENPQASI CTAEGIUSFS DIAVFQDYHG
   AtACS2pep HGIIQMGLAE NQLCLDLIKD WVKENPEASI CTLEGIHQFS DIANFQDYHG
   LeACS2pep ngviqmglae nqlcldlied wikrnpkgsi c.segiksfk alanfqdyhq
   LeACS4pep ngviqmglae nqlsvdliss wikrnpkasi ctndgiessfr rianfqdyhg
   MaACS1pep TGVIQMGLAE NQLSLDLIRD WMKKNPQASI CTEEGVSEFK AIANFQDYHG
   MaACS5pep TGVIQMGLAE NQLSLDLIQD WNKKNPQASI CTEEGVSEFK AIANFQDYHG
   LeACS1Apep tgviqmglae nqlcfdliqe wvvnnpkasi ctvegaenfq diaifqdyhq
   LeACS1Bpep tgviqmglae nqlcfdliqe wmvnnpkasi ctvegaenfq diaifqdyhq
   LeACS6pep  NGVIQMGLAE NQLCFDLIQE MIVNNPKASI CTYEGVQDFQ DTAIFQDYHG
   AtACS6pep  DGVIQMGLAE NQLCSDLMRK NVLKHPEASI CTSEGVNQFS DIAIFQDYHG
   Consensus  -G-IQMGLAE NQL--DL--- N-----P-SI C---G----F- --A-FQDYHG 101                                                 150
   A47pep    LPEFREAMAK FMGQVRAGKV TFDPDKVYMC GGATGAQDTL AFCLADPGDA
   A50pep    LPEFREAMAK FMGQVRGGKV TFDPDRVYMC GGATGAQDTL AFCLADPGDA
 osiacs1pep  LPEFRKAMAQ FMGQVRGGKA TFDPDKVYMS GGATGAQETL AFCLANPGEA
 osjacs1pep  LPEFRKAMAQ FMGQVRGGRA TFDPDKVYMS GGATGAQETL AFCLANPGEA
   TaACS2pep LPEFRQAMAQ FMGQVRGWKA RFDPDRVYMS GGATGAQETL AFCLANPGKA
   AtACS1pep LXQFRQAIAT FMERARGGRV RFEAERVYMS GGATGANETI MFCLADPGDA
   AtACS2pep LXHFRQAIAR FMGKARGGKV TFDPEKVYMS GGATGANETI IFCLADPGDV
   LeACS2pep lpefrkalak fmektrqgrv rfdpervyma ggatganeti ifcladpgda
   LeACS4pep lpeftnaiak fmektrqgkv kfdakrvyma ggatganeti llcladpgda
   MaACS1pep LPTFRKAIAQ FMEKVRGGRA RFDPDRIYMS GGATGAQETI AFCLADPGEA
   MaACS5pep LPAFRKAIAQ FMEKVRGGRA RFDPDRIYMS GGATGAQETI AFCLADPGEA
   LeACS1Apep lpefrqavar fmekvrgdrv tfdpnrivms ggatgaheml afcladpgda
   LeACS1Bpep lpefrqavar fmekvrgdrv tfdpnrivms ggatgaheml afcladpgda
   LeACS6pep  LPEFRKAVAR FMEKVRGDRV RFDPERIVMS GGATGANEGL AFCLADPGDA
```

Fig. 11

```
AtACS6pep    LPEFRQAVAK  FNEKTRNNKV  KFDPDRIVNS  GGATGAHETV  AFCLANPGDG
Consensus    L--F--A-A-  FN------V-  -F---R-VN-  GGATGA----  --CLA-PG--

151                                                     200
A47pep       YLVPTPYYPA  FDRDCCWRSG  VKLLPIECHS  SNNFTLTREA  LVSAYDGARR
A50pep       YLVPTPYYPA  FDRDCCWRSG  VKLLPIECHS  SNNFTLTREA  LVSAYDGARR
osiacs1pep   FLVPTPYYPA  FDRDCCWRSG  IKLLPIECHS  FNDFRLTKEA  LVSAYDGARR
osjacs1pep   FLVPTPYYPA  FDRDCCWRSG  IKLLPIECHS  FNDFRLTKEA  LVSAYDGARR
TaACS2pep    FLVPTPYYPG  FDRDCCWRSG  VKLLPIECHS  SNDFRITREA  VVAAYEGARS
AtACS1pep    FLVPTPYYAA  FDRDLSWRTG  VEIIPVECSS  SNNFQITKQA  LESAYLKAQE
AtACS2pep    FLIPSPYYAA  FDRDLSWRTG  VEIIPVPCSS  SDNFKLTVDA  AEWAYKKAQE
LeACS2pep    flvpspyypa  fordlswrtg  vqlipihces  snnfkitska  vkeayenaqk
LeACS4pep    flvptpyypg  fnrdlrwrsg  vqlipischs  cnnfkities  leeayekgqq
NaACS1pep    FLIPTPYYPG  FDRDFSWRTG  VQLLPIHCHS  SNKFKITQAA  LETAYRKARN
NaACS5pep    FLIPTPYYPG  FDRDFSWRTG  VQLLPIHCHS  SNKFKITQAA  LETAYRKARN
LeACS1Apep   flvptpyypg  fdrdlrwrtg  vqlfpvvces  cndfkvttka  leeayekaqg
LeACS1Bpep   flvptpyypg  fdrdlrwrtg  vqlfpvvces  cndfkvttka  leeayekaqg
LeACS6pep    FLVPTPYYPG  FDRDLSWRTG  VQLFPVVCES  SNNFKVTKEA  LEEAYSKAQE
AtACS6pep    FLVPTPYYPG  FDRDLSWRTG  VNLVPVTCHS  SNGFKITVEA  LEAAYENARK
Consensus    -L-P-PYY--  F-RD--WR-G  ----P--C-S  ---F---T--A  ---AY-----

201                                                     250
A47pep       QGVRVKGVLI  TNPSNPLGTT  MDRATLAMLA  RFATESRVHL  ICDEIYAGSV
A50pep       QGVRVKGILI  TNPSNPLGTT  NDRGTLAMLA  AFATERRVHL  ICDEIYAGSV
osiacs1pep   QGISVKGILI  TNPGNPLGTI  TDRDTLAMLA  TFATESRVHL  VCDEIYAGSV
osjacs1pep   QGISVKGILI  TNPSNPLGTI  TDRDTLAMLA  TFATESRVHL  VCDEIYAGSV
TaACS2pep    SGVRVKGILI  TNPSNPLGTT  ADRATLAMLA  TFATESRVHL  ICDEIYAGSV
AtACS1pep    TGIKIKGLII  ...SNPLGTS  LDRETLESLV  SFINDQIHL   VCDEIYAATV
AtACS2pep    SNKKVRGLIL  TNPSNPLGTM  LDKDTLTNLV  RFVTRKNIHL  VVDEIYAATV
LeACS2pep    snikvkglil  tnpsnplgtt  ldkdtlksvl  sftnqhnihl  vcdeiyaatv
LeACS4pep    asvkikglii  tnpcnplgti  ldrdtlkkis  tftnehnihl  vcdeiyaatv
NaACS1pep    SHIRVKGILV  TNPSKPLGTT  MDRETLRTLV  SFVNEKRMRL  VCDEIFSGTV
NaACS5pep    SHIRVKGIVV  TNPSNPLGTT  MDRSTLRTLV  SFVNEKRMRL  VCDEVFSGTV
LeACS1Apep   snikikglii  nnpsnplgti  ldkdtlrdiv  tfinskhihl  vcdeiyaatv
LeACS1Bpep   snikikglii  nnpsnplgti  ldkdtlrdiv  tfinskhihl  vcdeiyaatv
LeACS6pep    SNIKVKGLLI  NNPSNPLGTI  LDRETLRDIL  RFINDKNIRL  VCDEIYAATA
AtACS6pep    SNIPVRGLLV  TNPSNPLGTT  LDRECLKSLV  NFTNDKGIHL  IADEIYAATT
Consensus    ------G---  ------PLGT-  -D---L----  -F------HL  --DE------

251                                                     300
A47pep       FAKPDFVSIA  EVIER.DVPG  CNRDLIHIAY  SLSKDFGLPG  FRVGIVYSYN
A50pep       FAKPGFVSIA  EVIERGDAPG  CNRDLVHIAY  SLSKDFGLPG  FRVGIVYSYN
osiacs1pep   FATPEYVSIA  EVIER.DVPW  CNRDLIHVVY  SLSKDFGLPG  FRVGIIYSYN
osjacs1pep   FATPEYVSIA  EVIER.DVPW  CNRDLIHVVY  SLSKDFGLPG  FRVGIIYSYN
TaACS2pep    FAKPEYVSIA  EVIER.DAPG  ADRDLIHIAY  SLSKDFGLPG  FRVGIVYSYN
AtACS1pep    FAEPGFISVA  EIIQ..ENYY  VNRDLIHIVY  SLSKDMGLPG  FRVGVVYSYN
AtACS2pep    FAGGDFVSVA  EVVNDVDISE  VNVDLIHIVY  SLSKDMGLPG  FRVGIVYSFN
LeACS2pep    fdtpqfvaia  elldeqenty  cnkdlvhivy  slskdmglpg  frvgiiysfn
LeACS4pep    feppkfvsia  etinednc..  inkdlvhivs  slskdlgfpg  frvgivysfn
NaACS1pep    FDKPSYVSVS  EVIED..DPY  CDRDLIHIAY  SLSKDLGVPG  FRVGIIYSYN
NaACS5pep    FDKPSYVSVA  EVIQD..DPY  CDRDLIHIAY  SLSKDLGVPG  FRVGIIYSYN
LeACS1Apep   fdqprfisvs  eived..mie  cnkdlihivy  slskdlgfpg  frvgivysyn
LeACS1Bpep   fdqprfisvs  emvee..mie  cntdlihivy  slskdlgfpg  frvgivysyn
LeACS6pep    FGQPSFISIS  EVKSE..VVG  CNDDLVHIVY  SLSKDLGFPG  FRVGIIYSYN
AtACS6pep    FGQSEFISVA  EVISE..IED  CNRDLIHIVY  SLSKDMGLPG  LRVGIVYSYN
```

Fig. 11 (cont.)

```
Consensus    P-------S--  E----------  ----DL-S---  SLSKD-Q-PG  -RVG--YS-N 301                                                        350
     A47pep  DDVVACARKN   SSFGLVSSQT   QHFLAKNLSD   AKFMARFLAE   SARRLAARND
     A30pep  DDVVACARKN   SSFGLVSSQT   QHFLAKNLAD   AKFMARFLAE   SARRLAARND
 osiacs1pep  DAVVAAARKN   SSFGLVSSQT   QYFLARNLSD   KEFIGRFLQE   SKCRLVARHE
 osjacs1pep  DAVVAAARKN   SSFGLVSSQT   QYFLARNLSD   SEFIGRFLQE   SKCRLVARHE
    TaACS2pep DAVVACARKN   SSFGLVSSQT   QLFLARMLGD   EEFMSRFLEE   SARRLAARHE
    AtACS1pep DVVSCARKN    SSFGLVSSQT   QEFLAAMLSD   QSFVDNFLVE   VEKKVAKRHE
    AtACS2pep DSVVSCARRN   SSFGLVSSQT   QLMIASMLSD   DQFVDNFIME   SSRRLGIRKK
    LeACS2pep ddvvncarkn   ssfglvstqt   qyflaamlsd   ekfvdnflrs   aanrlqkrhk
    LeACS4pep ddvvscarkn   asfglvstqt   qhllafmlsd   defveeflis   aakrlrerye
    NaACS1pep DAVVTCARKN   SSFGLVSSQT   QHLLASMLGD   EEFTTSFLAT   SRTRLCGRES
    NaACS5pep DAVVTCARKN   SSFGLVSSQT   QHLLASMLGD   EEFTTSFLAT   SRTRLCGRES
   LeACS1Apep dtvvniarkn   asfglvsaqt   qhllasmlsd   evfidkflse   sserlgerqg
   LeACS1Bpep dtvvniarkn   asfglvstqt   qhmlasmlsd   eifvekflae   sserigkrgg
    LeACS6pep DAVVNIARKN   SSFGLVSTQT   QRLIASNLLD   TIFVEDFIAK   SSKRLLQKRG
    AtACS6pep DRVVQIARKN   SSFGLVSSQT   QRLIARMLSD   EEFVDEFIRE   SKLRLAARRA
  Consensus  D-VV---R-N   SSFGLVS-QT   Q----A-ML-D  --F----F---  ----R-----

351                                                        400
     A47pep  RFVAGLREVG   IACLPGNAGL   FSKMDLRGML   RDK.THDAEL   ELKRVIVEKV
     A30pep  RFVAGLREVG   IACLPGNAGL   FSKMDLRGML   REK.THDAEL   ELKRVIVERV
 osiacs1pep  RFTSGLREVG   IGCLRSNAGL   FSWMDLRRNL   SEK.TAEAEL   ELWRVIVRQV
 osjacs1pep  RFTSGLREVG   IGCLRSNAGL   FGWMDLRRNL   SEK.TAEAEL   ELWRVIVRQV
    TaACS2pep LFTSGLREVG   IGCLGSNAGL   FSWMDLRGNL   SEK.TAEAEL   ELWRVIIRKV
    AtACS1pep MFTEGLEENG   ISCLRSNAGL   FVLMDLRRNL   KIQ.TFDSEM   ALWRVIINKV
    AtACS2pep VFTTGIRKAD   IACLTSNAGL   FARMDLRRLL   KRNSFESEI    ELWRIIIDRV
    LeACS2pep hftnglevvg   iknlksnagl   fcwmdlrpll   rs.stfdsem  slwrviindv
    LeACS4pep kftrgleeig   iknlesnagv   ycwmdlrall   ks.atldaem  slwkliinev
    NaACS1pep VFTDGLRKVG   IKCLDGNAGL   FCKMDLRFLL   KE.ATVEAEL   RLRRVIINDV
    NaACS5pep VFTDGLRKVG   IKCLDGNAGL   FCKMDLRFLL   KE.ATVEAEL   RLRRVIINDV
   LeACS1Apep aftkglaevg   istlksnagl   ffwmdlrrll   ke.atfdsel  slwriiinev
   LeACS1Bpep aftkglaqvg   istlksnagl   ffwmdlrrll   ke.atfdgel  slwriiinev
    LeACS6pep LFTKGLOQVG   ITTLKSNAGL   FIWMDLRPFL   RN.STFDSEL   KLWRIIIDKV
    AtACS6pep EITTGLDGLG   IGWLRAKAGL   FLWMDLRNLL   KT.ATFESET   ELWRVIVHQV
  Consensus  -----G-----  I--L---AG-   ---MDLR--L   ----------S-  -LW--I----V 401                                                        450
     A47pep  KLNVSPGTSF   HCSEPGWFRV   CHANMDEETM   SVALDRIRRF   VRQHQR.KAK
     A30pep  KLNVSPGTSF   HCSEPGWFRV   CYANMDEETM   SVALDRIRRF   VRQHQRSKAK
 osiacs1pep  KLNVSPGTSF   HCRSPGWFRV   CHANMEEETM   SVALGRIHDF   VRQHQQRRVK
 osjacs1pep  KLNVSPGTSF   HCRSPGWFRV   CHANMEEETM   SVALGRIHDF   VRQHQQRRVK
    TaACS2pep KLNVSPGTSF   HCSEPGWFRV   CHANMEEETM   GVALGRIRDF   VRQHQQRKAK
    AtACS1pep KLNVSPGGSF   HCSEPGWFKV   CFANMDEDTL   QIALERIKDF   VVGDRANKNK
    AtACS2pep KLNVSPGSSF   RCTEPGWFKI   CFANMDDDTL   SVALGRIQDF   V...SKNKNK
    LeACS2pep klnvspgssf   scgepgwfrv   cfanmddgtv   dialarirrf   vgvek.....
    LeACS4pep klnvspgssf   ncsevgwfrv   cfaniddgtm   sialarismf   mdayn.....
    NaACS1pep KLNISPGSSF   HCSEPGWFRV   SFANMDDTAN   KIALARIESF   VYREN.....
    NaACS5pep KLNISPGSSF   HCSEPGWFRV   CFANMDDTAN   KIALARIESF   VYREN.....
   LeACS1Apep klnvspgssf   hcsepgqwfrv  cfanmddetm   rialkrisyf   v.........
   LeACS1Bpep klnvspgcsf   hcsepgqwfrv  cfanmddetm   rialrrinf    v.........
    LeACS6pep KLNVSPGCSF   HCSEPGWFRV   CFANMDDATM   KIALERIRRF   V.........
    AtACS6pep KLNVSPGSSF   HCSEPGWFRV   CFANMDSKTM   STALERIKVF   TSQLE.....
  Consensus  K-N-SPG-SF   -C-E-GWFR-   --AN-D----   --AL-RI--F   ----------
```

Fig. 11 (cont.)

```
              451                                                      500
    A47pep    AERWAATRPM RLSLPRRGGA TASHLPISSP M.ALLSPQSP MVHAS~~~~~
    A50pep    AERWAATRPL RLSLPRRGAT TASHLAISSP L.ALLSPQSP MVHAS~~~~~
osiacs1pep    AERWAANRQL RLSLPHHHL .SPAH.LSSP L.ALLSPQSP MVRATS~~~~
osjacs1pep    AERWAANRQL RLSLPHHHL .SPAH.LSSP L.ALLSPQSP MVRATS~~~~
  TaACS2pep   AQRWAARSHL HLSLQRHGPM ASQYHALSSP MAALLSPQSP LVHAAS~~~~
  AtACS1pep   NCNCICNNKR ..ENKKKKSF ...QKNLKLS LSSMR..YEE MVRSPK.LMS
  AtACS2pep   IVEKASENDQ VIQNKSAKKL KWTQTNLRLS FRRL...YED GLSSPG.IMS
  LeACS2pep   ..sgdkas.. ....smekkq qwkkmnlrls fs..krmyde svlsplsspi
  LeACS4pep   ..nvnkng.. ....vmkakh ngrgttydlt pq..mgstak mlla~~~~~~
  NaACS1pep   ..DAA..... ...VQAKNER RWDEA.LRLS LPR.RRFEDP TIMTP.SLMS
  NaACS3pep   ..DAA..... ...VQAKNER KWDET.LRLS LF..RRFEDP TIMTP.SLMS
 LeACS1Apep   ....lgp.kg lnnlaslkkq c.srrklqls ls.frrldha fmnspahspm
 LeACS1Bpep   ....lgt.kg lnnlaslkkq c.srsklqis ls.frrld.d f.nspahspm
  LeACS6pep   ...YLQPNRG V.EVATKRQY CRTRSKLEIS LS.FRRLD.D FMNSP.SSPM
  AtACS6pep   ..EETKPNAA TTMMAKKKKK CW.QSNLRLS FSDTRRFDSG FF.SP.HSPV
  Consensus   ~~~~~~~~~~ ~~~~~~~~~~ ~~~~~~~~~~ ~~~~~~~~~~ ~~~~~~~~~~

501
    A47pep    ~~~~~~~~~~
    A50pep    ~~~~~~~~~~
osiacs1pep    ~~~~~~~~~~
osjacs1pep    ~~~~~~~~~~
  TaACS2pep   ~~~~~~~~~~
  AtACS1pep   PHSPLLRA~~
  AtACS2pep   PHSPLLRA~~
  LeACS2pep   ppsplvr~~~
  LeACS4pep   ~~~~~~~~~~
  NaACS1pep   PHSPLVQAAT
  NaACS3pep   PHSPLVQAAT
 LeACS1Apep   .nsplvrt~~
 LeACS1Bpep   .nsplvrt~~
  LeACS6pep   .SSPMVQARN
  AtACS6pep   PPSPLVRAQT
  Consensus   ~~~~~~~~~~
```

Fig. 11 (cont.)

Consensus Sequence (similar amino acid residues)

```
               1                                                            50
      A47pep   -------MAGG SSAEQLLSRI ASGDGHGENS SYFDGWKAYD MDPFDLRHNR
      A50pep   --------MAG SSAEQLLSRI AAGDGHGENS SYFDGWKAYD MNPFDLRHNR
   osiacs1pep  ---------MA CQGIDLLSTK AAGDDHGENS SYFDGWKAYD TNPFDLRHNR
   osjacs1pep  ---------MA YQGIDLLSTK AAGDDHGENS SYFDGWKAYD TNPFDLRHNR
     TaACS2pep ----------- ----------M AAGDGHGENS SYFDGWKAYD MNPFSPQDNR
     AtACS1pep -------MSQG ACENQLLSKL ALSDKHGEAS PYFHGWKAYD MNPFHPTHNP
     AtACS2pep ------MGLPG KNRGAVLSKI ATNNQHGENS SYFDGWKAYD KDPFHLSRNP
     LeACS2pep ------mgfei aktnsilski atneehgens pyfdgwkayd sdpfhplknp
     LeACS4pep mdietseisn ykasavlski asneqhgens pyfdgwkayd ndpfhlvnnl
     MaACS1pep ----MRIYGEE HPNQQILSRI ATNDGHGENS SYFDGWKAYE RDPFHLTDNP
     MaACS3pep ----MRIYGEE HPNQEILSRI ATNDGHGENS SYFDGWKAYE NDPFHLTDNP
    LeACS1Apep ----avsiskn nqkqqllaki atndghgens pyfdgwkaya nnpfhltdnp
    LeACS1Bpep ----mvsiskn nqkqqllaki atndghgens pyfdgwkaya nnpfhptdnp
     LeACS6pep ----------- ----MGLISKI ATNDGHGENS AYFDGWKAYE NDPFHPTQNP
     AtACS6pep ----------- ---------- ---------- -YFDGWKAYE ENPFHPIDRP
     Consensus ----------- ---------- A-----HGE-S -YFDGWKAY- ---PF-----N-

51                                                           100
      A47pep   DGVIQMGLAE NQLSLDLIEQ WSMEHPEASI CTAQGASQFR RIANFQDYHG
      A50pep   DGVIQMGLAE NQLSLDLIEQ WSVDHPEASI CTAQGAPQFR RIANFQDYHG
   osiacs1pep  GGVIQMGLAE NQLSLDLIEE WSKNHPEASI CTPEGVSQFK RIANFQDYHG
   osjacs1pep  GGVIQMGLAE NQLSLDLIEE WSKNHPEASI CTPEGVSQFK RIANFQDYHG
     TaACS2pep GGVIQMGLAE NQLSLDLIEE WSKAHPEASI CTAEGASQFK RIANFQDYHG
     AtACS1pep QGVIQMGLAE NQLCSDLIKE WIKENPQASI CTAEGIDSFS DIAVFQDYHG
     AtACS2pep RGIIQMGLAE NQLCLDLIKD WVKENPEASI CTLEGIRQFS DIANFQDYHG
     LeACS2pep sgviqmglae nqlcldlied wikrnpkgsi c..aegiksfk aianfqdyhg
     LeACS4pep ngviqmglae nqisvdliee wikrnpkasi ctndgiesfr rianfqdyhg
     MaACS1pep TGVIQMGLAE NQLSLDLIRD WMKKNPQASI CTEEGVSEFK AIANFQDYHG
     MaACS3pep TGVIQMGLAE NQLSLDLIQD WMKKNPQASI CTKEGVSEFK AIANFQDYHG
    LeACS1Apep tgviqmglae nqlcfdlige wvvenpkasi ctvegaenfq diaifqdyhg
    LeACS1Bpep tgviqmglae nqlcfdlige wmvnnpkasi ctvegaenfq diaifqdyhg
     LeACS6pep NGVIQMGLAE NQLCFDLIQE WIVNNPKASI CTYEGVQDFQ DTAIFQDYHG
     AtACS6pep DGVIQMGLAE NQLCGDLMRK WVLKNPEASI CTSEGVRQFS DIAIFQDYHG
     Consensus -GVIQMGLAE NQL--DL---- W-----P--SI C--EG---F- ---A-FQDYHG 101                                                          150
      A47pep   LPEFREAMAK FMGQVRAGKV TFDPDKVYMC GGATGAQDTL AFCLADPGDA
      A50pep   LPEFREAMAK FMGQVRGGKV TFDPDRVVMC GGATGAQDTL AFCLADPGDA
   osiacs1pep  LPEFRKAMAQ FMGQVRGGKA TFDPDRVMS GGATGAQETL AFCLANPGEA
   osjacs1pep  LPEFRKAMAQ FMGQVRGGKA TFDPDRVMS GGATGAQETL AFCLANPGEA
     TaACS2pep LPEFRQAMAQ FMGQVRGMKA RFDPDKVYMS GGATGAQETL AFCLANPGEA
     AtACS1pep LKQFRQAIAK FMERARGGRV RFEAERVMS GGATGANETI MFCLADPGDA
     AtACS2pep LKKFRQAIAK FMGKARGGRV TFDPERVVMS GGATGANETI IFCLADPGDV
     LeACS2pep ipefxkaiak fmektrggrv rfdpervvsa ggatganeti ifcladpgda
     LeACS4pep ipeftnaiak fmektrggkv kfdakrvvma ggatganetl ilcladpgda
     MaACS1pep LPTFRKAIAQ FMEKVRGGRA RFDPDRIVMS GGATGAQETI AFCLADPGEA
     MaACS3pep LPAFRKAIAQ FMEKVRGGRA RFDPDRIVMS GGATGAQETI AFCLADPGEA
    LeACS1Apep ipefrqavar fmekvrgdrv tfdpxrivms ggatgahemi afcladpgda
    LeACS1Bpep ipefrqavar fmekvrgdrv tfdpnrivss ggatgaheml afcladpgda
     LeACS6pep LPEFRKAVAR FMEKVRGDRV RFDPERIVMS GGATGAHESL AFCLADPGDA
     AtACS6pep LPEFRQAVAK FMEKTRNNKV KFDPDRIVMS GGATGAHETV AFCLANPSDG
```

Fig. 12

```
   Consensus  L--F--A-A-  FM---R--R-  -FD--RVVM-  SGATGA-E-L  ---CLA-PGD- 151                                                      200
      A47pep  YLVPTPYYPA  FDRDCCNRSG  VKLLPIECHS  SNNFTLTREA  LVSAYDGARR
      A50pep  YLVPTPYYPA  FDRDCCNRSG  VKLLPIECHS  SNNFTLTREA  LVSAYDGARR
  osiacs1pep  FLVPTPYYPA  FDRDCCNRSG  IKLLPIECHS  FNDFRLTKEA  LVSAYDGARR
  osjacs1pep  FLVPTPYYPA  FDRDCCNRSG  IKLLPIECHS  FNDFRLTKEA  LVSAYDGARR
    TaACS2pep FLVPTPYYPG  FDRDCCNRSG  VKLLPIECHS  SNDFRITREA  VVAAYEGARS
    AtACS1pep FLVPTPYYAA  FDRDLRWRTG  VRITPVECSS  SNNFQITKQA  LESAYLRAQE
    AtACS2pep FLIPSFYYAA  FDRDLRNRTG  VETIPVPCSS  SDNFKLTVEA  AENAYKKAQS
    LeACS3pep flvpspyypa  fnrdlrwrtg  vqlipihces  snnfkitska  vksaynaqk
    LeACS4pep flvptpyypg  fnrdlrwrsg  vqllpiscks  cnnfkitiea  leeayekgqq
    MaACS1pep FLIPTPYYPG  FDRDFRNRTG  VQLLPIECHS  SNKFKITQAA  LETAYRKARN
    MaACS5pep FLIPTPYYPG  FDRDFRNRTG  VQLLPIECHS  SNKFKITQAA  LETAYRKARN
   LeACS1Apep flvptpyypg  fdrdlrwrtg  vqlfpvvces  cndfkvttka  leeayekagg
   LeACS1Bpep flvptpyypg  fdrdlrwrtg  vqlfpvvces  cndfkvttka  leeayekagg
    LeACS6pep FLVPTPYYPG  FDRDLRNRTG  VQLFPVVCES  SNNFKVTREA  LEEAYSKAQE
    AtACS6pep FLVPTPYYPG  FDRDLRWRTG  VNLVPVTCHS  SNGFKITVEA  LEAAYENARK
   Consensus  FLVP-PYY--  F-RD--NR-G  V-L-PI-C-S  ----F-IT--A  ----AY-----

201                                                      250
      A47pep  QGVRVKGVLI  TNPSNPLGTT  MDRATLAMLA  RFATEHRVHL  ICDEIYAGSV
      A50pep  QGVRVRGILI  TNPSNPLGTT  MDRGTLAMLA  AFATEHRVHL  ICDEIYAGSV
  osiacs1pep  QGISVKGILI  TNPSNPLGTI  TDRDTLAMLA  TFATEHRVHL  VCDEIYAGSV
  osjacs1pep  QGISVKGILI  TNPSNPLGTI  TDRDTLAMLA  TFATEHRVHL  VCDEIYAGSV
    TaACS2pep SGVRVKGILI  TNPSNPLGTT  ADRATLAMLA  TFATEHRVHL  ICDEIYAGSV
    AtACS1pep TGIKIKGLII  ...SNPLGTS  LDRETIESLV  SFINDKQIHL  VCDEIYAATV
    AtACS2pep SNKKVKGLIL  TNPSNPLGTM  LDRDTLTNLV  RPVTRKNIHL  VVDEIYAATV
    LeACS2pep snikvkglii  tpsnplgtt  ldkdtlksvl  sftnqhnihl  vcdeiyaatv
    LeACS4pep snvkikglii  tnpsnplgti  ldrdtikkis  tftnehnihl  vcdeiyaatv
    MaACS1pep SNIRVKGILV  TNPSNPLGTT  MDRETIRTLV  SFVNEKRMHL  VCDEIFSGTV
    MaACS5pep SHIRVKGIVV  TKPSNPLGTT  MDRDTLRTLV  SFVNEKRMHL  VCDEVFSGTV
   LeACS1Apep snikikglii  nnpsnplgti  ldkdtirdiv  tfinsknihl  vcdeiyaatv
   LeACS1Bpep snikikglii  nnpsnplgti  ldkdtirdiv  tfinsknihl  vcdeiyaatv
    LeACS6pep SNIKVKGLLI  NNPSNPLGTI  LDKETLKDIL  RFINDKNIHL  VCDEIYAATA
    AtACS6pep SNIPVKGLLV  TNPSNPLGTT  LDRECLKSLV  NFTNDKQIHL  IADEIYAATT
   Consensus  -----VKGLLI  ------PLGT-  -DR---L---  -F-------HL  V-DEIY-----

251                                                      300
      A47pep  FAKPDFVSIA  EVIER.DVPG  CNRDLIHIAY  SLSKDFGLPG  FRVGIVYSYN
      A50pep  FAKPDFVSIA  EVIERGDAPG  CNRDLVHIAY  SLSKDFGLPG  FRVGIVYSYN
  osiacs1pep  FATPEYVSIA  EVIER.DVPW  CNRDLIHVVY  SLSKDFGLPG  FRVGIIYSYN
  osjacs1pep  FATPEYVSIA  EVIER.DVPW  CNRDLIHVVY  SLSKDFGLPG  FRVGIIYSYN
    TaACS2pep FAKPEYVSIA  EVIER.DAPG  ADRDLIHIAY  SLSKDFGLPG  FRVGIVYSYN
    AtACS1pep FAKPGFISVA  ETIQ..EMYY  VNRDLIHIVY  SLSKDMGLPG  FRVGVVYSYN
    AtACS2pep FAGGDFVSVA  EVNDVDISE  VNVDLIHIVY  SLSKDMGLPG  FRVGIVYSFN
    LeACS2pep fdtpqfvsla  eildeqemty  cnkdlvhivy  slskdmglpg  frvgliyafn
    LeACS4pep fappkfvsla  elissdnc..  lnkdlvhivs  slskdlgfpg  frvgivysfn
    MaACS1pep FDKPSYVSVA  EVIED..DPY  CDRDLIHIAY  SLSKDLGVPG  FRVGVIYSYN
    MaACS5pep FDKPSYVSVA  EVIQD..DPY  CDRDLIHIAY  SLSKDLGVPG  FRVGVIYSYN
   LeACS1Apep fdqprfisvs  eived..mie  cnkdlihivy  slskdlgfpg  frvgivysyn
   LeACS1Bpep fdqprfisvs  emvee..mie  cntdlihivy  slskdlgfpg  frvgivysyn
    LeACS6pep FSQPSFISIS  EVKSE..VVS  CNDDLVHIVY  SLSKDLGFPG  FRVGIIYSYN
    AtACS6pep FGQSEFISVA  EVIEE..IED  CNRDLIHIVY  SLSKDMGLPG  LRVGIVYSYN
   Consensus  F----FVSI-  E---------  ---DLIHI--  SLSKD-G-PG  -RVGIVYSYN
```

Fig. 12 (cont.)

```
                    301                                                          350
        A47pep      DDVVACARKN  SSFGLVSSQT  QRFLARKLSD  AEFMARFLAE  SARRLAARHD
        A50pep      DDVVACARKN  SSFGLVSSQT  QRFLAMKLAD  AEFMARFLAE  SARRLAARHD
    osiacs1pep      DAVVAAARRM  SSFGLVSSQT  QYFLARMLSD  EEFIGRFLQE  SKCRLVARHE
    osjacs1pep      DAVVAAARRM  SSFGLVSSQT  QYFLARMLSD  EEFIGRFLQE  SKCRLVARHE
       TaACS2pep    DAVVACARKN  SSFGLVSSQT  QLFLARMLSD  EEFMSRFLRE  SARRLAARHE
       AtACS1pep    DVVVSCARRM  SSFGLVSSQT  QSFLAAMLSD  QSFVDNFLVE  VSKRVAKRSS
       AtACS2pep    DSVVSCARRM  SSFGLVSSQT  QLMLASMLSD  DQFVDNFLME  SSRRLGIRNK
       LeACS2pep    ddvvncarkm  ssfglvstqt  qyflaamlsd  ekfvdnfire  saarlgkrhk
       LeACS4pep    ddvvncarkm  ssfglvstqt  qhllafmlsd  defveeflie  sakrlrerye
       NaACS1pep    DAVVTCARKM  SSFGLVSSQT  QHLLASMLGD  EEFTTSFLAT  SRTRLCGRRR
       NaACS5pep    DAVVSCARKN  SSFGLVSSQT  QHLLASMLGD  EEFTTSFLAT  SRTRLCGRRR
      LeACS1Apep    dtvvniarkm  ssfglvsaqt  qhllasmlsd  evfidkfias  sserlgcrqg
      LeACS1Bpep    dtvvniarkm  ssfglvstqt  qhmlasmlsd  eifvekflae  sserlgkrqg
       LeACS6pep    DAVVNIARKN  SSFGLVSTQT  QRLIASMLLD  TIFVEDFIAK  SSMRLLQKHG
       AtACS6pep    DRVVQIARKN  SSFGLVSSQT  QHLIARMLSD  EEFVDEFIRE  SKLALAARSA
       Consensus    D-VV----RRM  SSFGLVS-QT  Q--LA-ML-D  --F----FL--  ----R----R--

351                                                          400
        A47pep      RFVAGLREVG  IACLPGNAGL  FSRMDLRQML  RDK.THDAEL  ELWRVIVRKV
        A50pep      RFVAGLREVG  IACLPGNAGL  FSNMDLRQML  REK.THDAEL  ELWRVIVRRV
    osiacs1pep      RFTSGLREVG  IGCLRGNAGL  FSWMDLRRML  SEK.TAEAEL  ELWRVIVRQV
    osjacs1pep      RFTSGLREVG  IGCLRGNAGL  FSWMDLRRML  REK.TAEAEL  ELWRVIVRQV
       TaACS2pep    LFTSGLREVG  IGCLGGNAGL  FSWMDLRQML  SEK.TAEAEL  ELWRVIIRKV
       AtACS1pep    MFTEGLEENG  ISCLRSNAGL  FVLMDLRHML  KDQ.TFDSEM  ALWRVIINKV
       AtACS2pep    VFTTGIRKAD  IACLTSNAGL  FANMDLRSLL  RDRNSFESEI  ELWRIIIDRV
       LeACS2pep    hftnglevvg  ikclknnagi  fcwmdlrpll  re.stfdsem  slwrviisdv
       LeACS4pep    kftrgleeig  ikclesnagv  ycwmdlrsll  ke.atidaem  slwkllinev
       NaACS1pep    VFTDGLRRVG  IRCLDGNAGL  FCWMDLRPLL  KE.ATVEAEL  RLWRVIINDV
       NaACS5pep    VFTDGLRRVG  ISCLDGNAGL  FCWMDLRPLL  KE.ATVEAEL  RLWRVIINDV
      LeACS1Apep    mftkglaevg  istlksnagl  ffwmdlrrll  ke.atfdsel  alwrillnev
      LeACS1Bpep    mftkglagvg  istlksnagl  ffwmdlrrll  ke.atfdgel  elwrillnev
       LeACS6pep    LFTKGLGQVG  ITYLKSNAGL  FIWMDLRSFL  EN.STFDREL  ELWRIIIDRV
       AtACS6pep    EITTGLDGLG  IGWLKAKAGL  FLWMDLRNLL  RT.ATFDGET  ELWRVIVRQV
       Consensus    -----GL----  I--L----AG-  F---MDLR--L  --------D-E-  -LW-VII---V 401                                                          450
        A47pep      KLNVSPGTSF  HCNEPGNFRV  CHANMDDETM  EVALDRIRRF  VRQHQH.KAK
        A50pep      KLNVSPGTSF  HCNEPGNFRV  CYANMDDDTM  EVALDRIRRF  VRQHQHSKAK
    osiacs1pep      KLNVSPGTSF  HCREPGNFRV  CHANMDDETM  EVALGRIHDF  VRQHQQRRVK
    osjacs1pep      KLNVSPGTSF  HCREPGNFRV  CHANMDDETM  EVALGRIHDF  VRQHQQRRVK
       TaACS2pep    KLNVSPGTSF  HCQEPGNFRV  CHANMDDETM  GVALGRIRDF  VRQHQQGKAK
       AtACS1pep    KINVSPGSSF  HCSEPGWFRV  CFANMSEDTL  QIALERIKDF  VVGDRANKNK
       AtACS2pep    KLNVSPGSSF  RCTEPGNFRI  CFANMDDDTL  EVALGRIQDF  V...SKNKNK
       LeACS2pep    klnvspgssf  ecqepgwfrv  cfanmddgtv  dialarirrf  vgvek.....
       LeACS4pep    klnvspgssf  ncssvgwfrv  cfaniddgta  eialarirmf  sdayn.....
       NaACS1pep    KLNISPGSSF  HCSEPGNFRV  SFANMDDDTAM  KIALSRIESF  VYREN.....
       NaACS5pep    KLNISPGSSF  HCSEPGNFRV  CFANMDDTAM  KIALRRIEHF  VYREN.....
      LeACS1Apep    klnvspgcsf  hcsepgwfrv  cfanmddeta  rialkrisyf  v.........
      LeACS1Bpep    klnvspgcsf  hcsepgwfrv  cfanmddeta  rialkrirnf  v.........
       LeACS6pep    KLNVSPGCSF  HCSEPGNFRV  CFANMDDATM  KIALDRIRHF  V.........
       AtACS6pep    KLNVSPGGSF  HCSEPGNFRV  CFANMDRETM  STALERIKVF  TSQLE.....
       Consensus    KLNVSPG-SF  -C-E-GWFPV  -FAN-D-----  --AL-RI---F  ----------
```

Fig. 12 (cont.)

```
              451                                                      500
     A47pep   AERNAATRPM  RLSLPRRGGA  TASHLDISSP  M.ALLSPQSP  MVHAS-----
     A56pep   AERNAATRPL  RLSLPRRGAT  TASRLAISSP  L.ALLSPQSP  MVHAG-----
 osiacs1pep   AERNAANRQL  RLSLPHHHL.  .SPAH.LSSP  L.ALLSPQSP  MVRATS----
 osjacs1pep   AERNAANRQL  RLSLPHHHL.  .SPAH.LSSP  L.ALLSPQSP  MVRATS----
   TaACS2pep  AQRNAARSHL  RLSLQRRGPM  ASQYHALSSP  MAALLSPQSP  LVHAAG----
   AtACS1pep  NCNCICNNKR  ..ENKKRKSF  ...QKNLKLS  LSSMR..YEE  HVRSPR.LKS
   AtACS2pep  IVEKASENDQ  VIQNKSARRL  KWTQTNLRLS  FRRL...YED  GLSSPG.INS
   LeACS2pep  ..sgdkss..  ....smekkq  qwkknnlrls  fs..krmyde  svlspisspi
   LeACS4pep  ..nvnksq..  ....vmknhh  ngrgttydlt  pq..mgstmk  mlla------
   MaACS1pep  ..DAA.....  ...VQAKNKR  RWDEA.LRLS  LPR.RRFEDP  TIHTP.HLKS
   MaACS5pep  ..DAA.....  ...VQAKNKR  KWDET.LRLS  LP..RRFEDP  TIHTP.HLKS
  LeACS1Apep  ....lgp.kg  lsnlaaikkq  c.srrklqis  ls.frrldhe  fmnspahspm
  LeACS1Bpep  ....lgt.kg  lsnlaaikkq  c.srsklqis  ls.frrld.d  f.nspahspm
   LeACS6pep  ...YLQPNKG  V.EVATRRQY  CRTPSKLEIS  LS.FRRLD.S  FWNSP.HSPM
   AtACS6pep  ..EETKPMAA  TTMMANKKKK  CM.QSNLRLS  PSDTRRFDDS  FF.SP.RSPV
   Consensus  ----------  ----------  ------?---  ----------  ----------

501
     A47pep   ----------
     A56pep   ----------
 osiacs1pep   ----------
 osjacs1pep   ----------
   TaACS2pep  ----------
   AtACS1pep  PRSPLLRA--
   AtACS2pep  PRSPLLRA--
   LeACS2pep  ppsplvr---
   LeACS4pep  ----------
   MaACS1pep  PRSPLVQAAT
   MaACS5pep  PRSPLVQAAT
  LeACS1Apep  .nsplvrt--
  LeACS1Bpep  .nsplvrt--
   LeACS6pep  .SSPMVQARN
   AtACS6pep  PPSPLVRAQT
   Consensus  ----------
```

Fig. 12 (cont.)

Consensus Sequence (identical amino acid residues)

```
1                                                                   50
      A6Spep  --------MIAD ERPQPQLLSK KAACNSHGQD SSYFLGWEEY EKNFYDPVAN
 osiacs2pep  --MVSQVVAE EK..PQLLSK KAGCNSHGQD SSYFLGWQEY EKNPFDPVGN
   AtACS5pep  ------------ ----MKQLST KVTSNGHGQD SSYFLGWEEY EKNPYDEIKN
      AtACS9  ------------ ----MKQLSR KVTSNAHGQD SSYFLGWEEY EKNPYDEIKN
   AtACS4pep  ------------ ----MVQLSR KATCNSHGQV SSYFLGWEEY EKNPYDVTKN
      AtACS8  ------------ ----NGLLSR KASCNTHGQD SSYFWGWEEY EKNPYDEIKN
    MaACS2pep ------------ ------------ ------------ ------------ ------------
    MaACS3pep ------------ ------------ ------------ ------------ ------------
   LeACS3pep  ------------ ----MKLLSK KATCNSHGQD SSYFLGWQEY EKNPYDEIQN
   LeACS7pep  ------------ ----MKLLSK KAMCNSHGQD SSYFLGWEEY QKNPYDEIRN
  OsjACS2pep  MGGKLLPAAA FGSSAPPLSQ VATSAAHGES SPYFAGWKAY DEDPYHAVDN
      OsjACS3  MGGKLLPAAA FGSSAPPLSQ VATSAAHGED SPYFAGWKAY DEDPYHAVDN
   OsiACS3pep MGGKLLPAAA FGSSAPPLSQ VATSAAHGED SPYFAGWKAY DEDPYHAVDN
      AtACS7  MGLPLMMERS GSNNNVELSR VAVSDTHGED SPYFAGWKAY DENPYDESNN
   Consensus  ------------ ---------LS- ---------HG-- S-YF-GW---Y ----P------N 51                                                  100
      A6Spep  PSGIIQMGLA ENQLSFDLLE AWLEA.NPDA LGLRR..GGA SVFRELALFQ
 osiacs2pep  PSGIIQMGLA ENQLSFDLLE SNLEK.NPHA LGLRRSGGGA SVFRELALFQ
   AtACS5pep  PNGMIQMGLA ENQLCFDLIE SWLTK.NPDA ASLKRN..GQ SIFRELALFQ
      AtACS9  PNGIIQMGLA ENQLCFDLIE TWLAK.NPDA AGLKKD..GQ SIFRELALFQ
   AtACS4pep  PQGIIQMGLA ENQLCFDLLE SWLAQ.NTDA ACFKRD..GQ SVFRELALFQ
      AtACS8  PDGIIQMGLA ENQLSFDLIE SNLAK.NPDA ANFQRE..GQ SIFRELALFQ
    MaACS2pep ------MGFT ENQLCFDLIE SWLEN.HPDP AAFKKD..GA LLFRELALFQ
    MaACS3pep ------MGFA ENRVSFDLIE SWLED.HPDL TGFKKD..GG LVFRELALFQ
   LeACS3pep  PKGIIQMGLA ENQLSFDLLE SWLAQ.NPDA AGFKRN..GE SIFRELALFQ
   LeACS7pep  PKGIIQMGLA ENQLSFDLLE SWLTL.NPDA SAFKRN..GH SIFRELSLFQ
  OsjACS2pep  PDGVIQMGLA ENQVSFDLLE AYL.RDHPEA AGWSTGGAGA GSFRDNALFQ
      OsjACS3  PDGVIQMGLA ENQVSFDLLE AYL.RDHPEA AGWSTGGAGA GSFRDNALFQ
   OsiACS3pep PDGVIQMGLA ENQVSFDLLE AYL.RDHPEA AGWSTGGAGA GSFRDNALFQ
      AtACS7  PSGVIQMGLA ENQVSFDLLE TYLEKNPEG SMW..GSKGA PGFRENALFQ
   Consensus  PSGIIQMG-- EN---FDL-E --L---------- --------------G-- ---F------LFQ 101                                                 150
      A6Spep  DYHGMPAFKN ALARFMSEQR GYRVTFDPSN IVLTAGATSA NEALMFCLAD
 osiacs2pep  DYHGLPAFKQ ALARFMSEQR GYKVVFDPSN IVLTAGATSA NEALMFCLAD
   AtACS5pep  DYHGMPEFKK AMASFMEEIR GNRVTFDPKK IVLAAGSTSA NETLMFCLAE
      AtACS9  DYHGLPSFKK ALAEFMEEIR GNRVTFDPSK IVLAAGSTSA NETLMFCLAE
   AtACS4pep  DYHGLSSFKN AFADFMSENR GNRVSFDSNK LVLTAGATSA NETLMFCLAD
      AtACS8  DYHGLPSFKN AMADFMSENR GNRVSFNPNK LVLTAGATPA NETLMFCLAD
    MaACS2pep DYHGLPAFKR ALTKYMGEVR GNKVAFDPNR LVLTAGATSA NETLMFCLAE
    MaACS3pep DYHGLPAFKN ALARYMGEVR GNKVSFEPSK LVLTAGATSA NETLMFCLAD
   LeACS3pep  DYHGLPAFKN AMTKFMSEIR GNRVSFDSNK LVLTAGATSA NETLMFCLAN
   LeACS7pep  DYHGLPAFKD ALVQFMSEIR GNKVSFDCNK LVLTAGATSA NETLMFCLAD
  OsjACS2pep  DYHGLKSFRK AMASFMGKIR GGKARFDPDK IVLTAGATAA NELLTFILAN
      OsjACS3  DYHGLKSFRK AMASFMGKIR GGKARFDPDK IVLTAGATAA NELLTFILAN
   OsiACS3pep DYHGLKSFRK AMASFMGKIR GGKARFDPDK IVLTAGATAA NELLTFILAN
      AtACS7  DYHGLKTFRQ AMASFMEQIR GGKARFDPDR IVLTAGATAA NELLTFILAD
   Consensus  DYHG----F-- A-------M-----R G------P------ --VL-AG-T-A NE-L-F-LA- 151                                                 200
```

Fig. 13

```
      A65pep  HGDAFLIPTP  YYPGFDRDLK  WRTGAEIVPV  HCTSGNGFRL  TRAALDDAYR
 osiacs2pep  HGDAFLIPTP  YYPGFDRDLK  WRTGAEIVPV  HCASANGFRV  TRAALDDAYR
   AtACS5pep  PGDAFLLPTP  YYPGFDRDLK  WRTGAEIVPI  HCSSSNGFQI  TESALQQAYQ
       AtACS9  PGDAFLLPTP  YYPGFDRDLK  WRTGAEIVPI  HCSSSNGFQI  TESALQQAYQ
   AtACS4pep  PGDAFLLPTP  YYPGFDRDLK  WRTGVEIVPI  QSSSTNGFRI  TKLALEEAYE
       AtACS8  PGDAFLLPTP  YYPGFDRDLK  WRTGAEIVPI  QCNSANGFRI  TKVALEEAYE
   MaACS2pep  PGEAFLLPTP  YYPGFDRDLK  WRTGAEIVPI  HCSSSNGFRI  TKPALEAAYQ
   MaACS3pep  PGEAFLLPTP  YYPGFDRDLK  WRTGVEIVPI  HCSSSNGFRI  TRAALEAALR
   LeACS3pep  QGDAFLLPTP  YYPGFDRDLK  WRTGAEIVPI  HCSSSNGFRI  TESALEEAYL
   LeACS7pep  PGEAFLLPTP  YYPGFDRDLK  WRTGAEIVPI  QCTSSNGFRI  TESALEEAYT
  OsjACS2pep  PGDALLIPTP  YYPGFDRDLR  WRTGVNIVPV  RCDSANGFQV  TVAALQAAYD
      OsjACS3  PGDALLIPTP  YYPGFDRDLR  WRTGVNIVPV  RCDSANGFQV  TVAALQAAYD
  OsiACS3pep  PGDALLIPTP  YYPGFDRDLR  WRTGVNIVPV  RCSSANGFQV  TVAALQAAYD
       AtACS7  PNDALLVPTP  YYPGFDRDLR  WRTGVKIVPI  RCDSSNRFQI  TPEALESAYQ
   Consensus  ----A-L-PTP  YYPGFDRDL-  WRTG---IVP-  ----S-N-F---  T--AL---A--

201                                                    250
      A65pep  RAQKLRLRVK  GVLITNPSNP  LGTTSPRADL  EMLVDFVA.A  KGIHLVSDEI
 osiacs2pep  RAQKRRLRVK  GVLITNPSNP  LGTASPRADL  ETIVDFVA.A  KGIHLISDEI
   AtACS5pep  QAQKLDLKVK  GVLVTNPSNP  LGTALTRREL  NLLVDFIT.S  KNIHLISDEI
       AtACS9  QAQKLDLKVK  GVLVTNPSNP  LGTMLTRREL  NLLVDFIT.S  KNIHLISDEI
   AtACS4pep  QAKKLDLRVK  GILITNPSNP  LGTTTTQTEL  NILFDFITKN  KNIRLVSDEI
       AtACS8  QAQKLNLKVK  GVLITNPSNP  LGTTTTRTEL  NHLLDFISR.  KRIHLISDEI
   MaACS2pep  DAQKRSLRVK  GVLVTNPSNP  LGTTLTRHEL  DILVDFVV.S  KDIHLISDEI
   MaACS3pep  RAQKRRLRVK  GVLVTNPSNP  LGTTLTRQEL  DTLVDFAV.A  NDIHLISDEI
   LeACS3pep  DARKRNLKVK  GVLVTNPSNP  LGTTLRRNEL  ELLLTFID.E  KGIHLISDEI
   LeACS7pep  EAERRNLRVK  GVLVTNPSNP  LGTTLTKKEL  QLLLTFVS.T  KQIHLISDEI
  OsjACS2pep  EAAAVGMRAR  AVLITNPSNP  LGTTVRRKML  DDILDFVGR.  NDIHLISDEI
      OsjACS3  EAAAVGMRAR  AVLITNPSNP  LGTTVRRKML  DDILDFVGR.  NDIHLISDEI
  OsiACS3pep  EAAAAGMRAR  AVLITNPSNP  LGTTVRAKVL  DDILDFVGR.  NDIHLISDEI
       AtACS7  TARDANIRVR  GVLITNPSNP  LGATVQKKVL  RDLLDFCVR.  KNIRLVSDEI
   Consensus  -A---------  ---L-TNPSNP  LG--------L  ------F-----  --IHL-SDEI 251                                                    300
      A65pep  YSGTVFADP.  .GFVSVLEVV  AARAATDDGV  VGVGPLSDRV  HVVYSLSKDL
 osiacs2pep  YAGTAFAEPP  AGFVSALEVV  AGR....DG.  .GGAPYSDRV  HVVYSLSKDL
   AtACS5pep  YGGTMFQFE.  .QFISVMDVL  KDKKLED...  ...TEVSKRV  HVVYSLSKDL
       AtACS9  YSGTVFCFE.  .QFVSVMDVL  KDKHLEN...  ...SEVSKRV  HIVYSLSKDL
   AtACS4pep  YSGTVFNSS.  .EFISVMEIL  KNNQLEN...  ...TDVLNRV  HIVCSLSKDL
       AtACS8  YSGTVFTNP.  .GPISVMEVL  KDRELEN...  ...TDVFDRV  HIVYSLSKDL
   MaACS2pep  YGGTNFDSP.  .GFISIAEAT  KDRN......  ....NVSHRI  HIVCSLSKDL
   MaACS3pep  YSGTTFGSP.  .GFVSIAEAT  KGRD......  ....DVSHRI  HIVCSLSKDL
   LeACS3pep  YGGTVFNSP.  .GLVSVMEVL  IEKNYMK...  ...TRVWERV  HIVYSLSKDL
   LeACS7pep  YSGTVFNSP.  .KFVSVMEVL  IENNYMY...  ...TDVWDRV  HIVYSLSKDL
  OsjACS2pep  YSGSVFAAPD  ..LVSVAELV  EAR.......  .GGDGIAGRV  HIVYSLSKDL
      OsjACS3  YSGSVFAAPD  ..LVSVAELV  EAR.......  .GGDGIAGRV  HIVYSLSKDL
  OsiACS3pep  YSGSVFAAPD  ..LVSVAELV  EAR.......  .DGDGIAGRV  HIVYSLSKDL
       AtACS7  YSGSVFNASE  ..FTSVAEIV  ENI.......  .DDVSVKERV  HIVYSLSKDL
   Consensus  Y-G--F----  ----S------  ----------  ---------R-  H-V-SLSKDL 301                                                    350
      A65pep  GLPGFRVGAI  YSSNAGVVSA  ATKMSSFGLV  SSQTQHLLAS  LLGDRDFTRR
 osiacs2pep  GLPGFRVGAI  YSANAAVVSA  ATKMSSFGLV  SSQTQYLLAA  LLGDRDFTRS
   AtACS5pep  GLPGFRVGAI  YSNDENIVSA  ATKMSSFGLV  SSQTQYLLSA  LLSDRRFTSQ
       AtACS9  GLPGFRVGAI  YSNDEMVVSA  ATKMSSFGLV  SSQTQYLLSA  LLSDKKFTST
```

```
MaACS3pep   ------------  ------------  ------------  ------------  ------------
LeACS3pep   IKDFVESTAP    NATNHQNQQQ    SNANSKKKSF    ...SKNVFRL    ...SFNDRQR
LeACS7pep   LKAFVDSRVN    NKDDIQNQQQ    ..CSNKKKSF    ...SKNVFRL    ...SFNERQR
OsjACS2pep  ISRFMDTWNG    TKQQASCQQQ    EQQ---------  ------------  ------------
OsjACS3     ISRFMDTWNG    TKQQASCQQQ    EQQ---------  ------------  ------------
OsiACS3pep  ISRFMDTWNG    TKQQASCQQQ    EQQ---------  ------------  ------------
AtACS7      IHEFMDRRRR    R-----------  ------------  ------------  ------------
Consensus   ------------  ------------  ------------  ------------  ------------

501
A65pep      ER-
osiacs2pep  ER-
AtACS5pep   DER
AtACS9      DER
AtACS4pep   EER
AtACS8      EER
MaACS2pep   ---
MaACS3pep   ---
LeACS3pep   ER-
LeACS7pep   ER-
OsjACS2pep  ---
OsjACS3     ---
OsiACS3pep  ---
AtACS7      ---
Consensus   ---
```

```
              151                                                           200
    A65pep    HGDAFLIPTP YYPGFDRDLK WRTGAEIVPV HCTSNGFRL  TRAALDDAYR
 osiacs2pep   HGDAFLIPTP YYPGFDRDLK WRTGAEIVPV HCASANGFRV TRAALDDAYR
   AtACS5pep  PGDAFLLPTP YYPGFDRDLK WRTGAEIVPI HCSSSNGFQI TESALQQAYQ
      AtACS9  PGDAFLLPTP YYPGFDRDLK WRTGAEIVPI HCSSSNGFQI TESALQQAYQ
   AtACS4pep  PGDAFLLPTP YYPGFDRDLK WRTGVEIVPI QSSGTNGFRI TKLALEEAYE
      AtACS8  PGDAFLLPTP YYPGFDRDLK WRTGAEIVPI QCKSANGFRI TKVALEEAYE
   MaACS2pep  PGEAFLLPTP YYPGFDRDLK WRTGAEIVPI HCSSSNGFRI TKPALEAAYQ
   MaACS3pep  PGEAFLLPTP YYPGFDRDLK WRTGVEIVPI HCSSSNGFRI TRAALEAALE
   LeACS3pep  QGDAFLLPTP YYPGFDRDLK WRTGAEIVPI RCSSSNGFRI TESALEEAYL
   LeACS7pep  PGHAFLLPTP YYPGFDRDLK WRTGAEIVPI QCTSSNGFRI TESALEEAYT
   OsjACS2pep PGDALLIPTP YYPGFDRDLR WRTGVNIVPV RCDSANGFQV TVAALQAAYD
      OsjACS3 PGDALLIPTP YYPGFDRDLR WRTGVNIVPV RCDSANGFQV TVAALQAAYD
   OsiACS3pep PGDALLIPTP YYPGFDRDLR WRTGVNIVPV RCDSANGFQV TVAALQAAYD
       AtACS7 PNDALLVPTP YYPGFDRDLR WRTGVEIVPI HCDSSNHFQI TPEALESAYQ
    Consensus ----A-LLPTP YYPGFDRDLK WRTG--IVPI ---S-N-F-I T--ALE-A---

201                                                           250
    A65pep    RAQKLRLRVK GVLITNPSNP LGTTSPRADL EMLVDFVA.A KGIHLVSDEI
 osiacs2pep   RAQKRRLRVK GVLITNPSNP LGTASPRADL ETIVDFVA.A KGIHLISDEI
   AtACS5pep  QAQKLDLKVK GVLVTNPSNP LGTALTRREL NLLVDFIT.S KNIHLISDEI
      AtACS9  QAQKLDLKVK GVLVTNPSNP LGTNLTRREL NLLVDFIT.S KNIHLISDEI
   AtACS4pep  QAKKLDLNVK GILITNPSNP LGTTTQTEL  NILFDFITKN KNIHLVSDEI
      AtACS8  QAQKLNLKVK GVLITNPSNP LGTTTRTEL  NHLLDFIGR. KKIHLISDEI
   MaACS2pep  DAQKRSLRVK GVLVTNPSNP LGTTLTRHEL DILVDFVV.S KDIHLISDEI
   MaACS3pep  RAQKRRLRVK GVLVTNPSNP LGTTLTRQEL DTLVDFAV.A NGIHLISDEI
   LeACS3pep  DAKKRNLRVK GVLVTNPSNP LGTTLNRHEL ELLLTFID.E KGIHLISDEI
   LeACS7pep  KAERRNLRVK GVLVTNPSNP LGTTLIKKEL QLLLTFVS.T KQIHLISDEI
   OsjACS2pep EAAAVGMRAR AVLITNPSNP LGTTVRRSML DDILDFVSR. NDIHLISDEI
      OsjACS3 EAAAVGMRAR AVLITNPSNP LGTTVRRKNL DDILDFVSR. NDIHLISDEI
   OsiACS3pep EAAAAGMRAR AVLITNPSNP LGTTVRRKVL DDILDFVSR. NDIHLISDEI
       AtACS7 TARDANIRVR GVLITNPSNP LGATVQRKVL EDILDFCVR. KNIHLVSDEI
    Consensus -A-----L--K -VLITNPSNP LG--------L ---L--F---- ---IHLISDEI 251                                                           300
    A65pep    YSGTVFADP. .QPVSVLEVV AARAATDGGV VQVGFLSDRV HVVYSLSKDL
 osiacs2pep   YAGTAFAEPP AGFVSALEVV AGR....DG. .GSADVSDRV HVVYSLSKDL
   AtACS5pep  YSGTMFGFE. .QFISVMDVL KDKKLED... ...TEVSKRV HVVYSLSKDL
   AtACS9     YSGTVFGFE. .QFVSVMDVL KDKNLEN... ...SEVSKRV HIVYSLSKDL
   AtACS4pep  YSGTVFNSS. .EFISVMEIL KNHQLEN... ...TDVLNRV HIVCSLSKDL
      AtACS8  YSGTVFTNP. .GFISVMEVL KDRKLEN... ...TDVFDRV HIVYSLSKDL
   MaACS2pep  YSGTNFDSP. .GFISIAEAT KDRN...... ....NVSHRI HIVCSLSKDL
   MaACS3pep  YSGTTFGSP. .GFVSIAEAT KGRD...... ....DVSHRI HIVCSLSKDL
   LeACS3pep  YSGTVFNSP. .GLVSVMEVL IEKNYMK... ...TRVWERV HIVYSLSKDL
   LeACS7pep  YSGTVFNSP. .KPVSVMEVL IENNYMY... ...TDVWDRV HIVYSLSKDL
   OsjACS2pep YSGSVFAAPD ..LVSVAELV EAR....... .GDDGIAGRV HIVYSLSKDL
      OsjACS3 YSGSVFAAPD ..LVSVAELV EAR....... .GDDGIAGRV HIVYSLSKDL
   OsiACS3pep YSGSVFAAPD ..LVSVAELV EAR....... .DGDGIAGRV HIVYSLSKDL
       AtACS7 YSGSVFRASE ..FTSVAEIV ENI....... .DDVSVKERV HIVYSLSKDL
    Consensus Y-G--F---- -----S--E-- ----------- ------V---RV HIV-SLSKDL 301                                                           350
    A65pep    GLPGFRVGAI YSNAGVVSA  ATKMSSFGLV SSQTQHLLAS LLGDRDFTKR
 osiacs2pep   GLPGFRVGAI YSANAAVVSA ATKMSSFGLV SSQTQYLLAA LLGIRDFTRS
   AtACS5pep  GLPGFRVGAI YSNDEMIVSA ATKMSSFGLV SSQTQYLLSA LLSDKKFTSQ
```

```
MaACS2pep   ----------  ----------  ----------  ----------  ----------
MaACS3pep   ----------  ----------  ----------  ----------  ----------
LeACS3pep   IKDFVESTAP  NATNHQNQQQ  SNANSKKKSF  ...SKNVFRL  ...SFNDRQR
LeACS7pep   LKAFVDSRVN  NKDDIQNQQQ  ..CSNKKKSF  ...SKNVFRL  ...SFNERQR
OsjACS2pep  ISRFMDTWNG  TKQQASCQQQ  EQQ-------  ----------  ----------
OsjACS3     ISRFMDTWNG  TKQQASCQQQ  EQQ-------  ----------  ----------
OsiACS3pep  ISRFMDTWNG  TKQQASCQQQ  EQQ-------  ----------  ----------
AtACS7      IHSFMDRRRR  F---------  ----------  ----------  ----------
Consensus   L----D----  ----------  ----------  ----------  ----------

501
A6pep       ER-
osiacs2pep  ER-
AtACS5pep   DER
AtACS9      DER
AtACS4pep   EER
AtACS8      EER
MaACS2pep   ---
MaACS3pep   ---
LeACS3pep   ER-
LeACS7pep   ER-
OsjACS2pep  ---
OsjACS3     ---
OsiACS3pep  ---
AtACS7      ---
Consensus   ---
```

Fig. 14 (cont.)

Consensus Sequence (identical amino acid residues)

```
1                                                          50
   A47pep  -MAGSSASQ  LLSRIASGDG  HGENSSYFDG  NKAYDMDPFD  LRHNRDGVIQ
   A50pep  --MAGSSAEQ  LLSRIAAGDS  HGENSSYFDG  NKAYDMNPFD  LRHNRDGVIQ
   A65pep  MIADEKPQPQ  LLSKKAACNS  HGQDSSYFLG  NEEYEKNPYD  PVANPGGIIQ
Consensus  ---------Q  LLS--A----  HG--SSYF-G  N--Y---P-D  ---N--G-IQ 51                                                 100
   A47pep  MGLAENQLSL  DLIEQWSMEH  PEASICTAQG  ASQFRRIANF  QDYHGLPEFR
   A50pep  MGLAENQLSL  DLIEQWSVDH  PEASICTAQG  APQFRRIANF  QDYHGLPEFR
   A65pep  MGLAENQLSF  DLLEAWLEAN  PDALGLRRGG  ASVFRELALF  QDYSGNPAFK
Consensus  MGLAENQLS-  DL-E-W----  P-A------G  A--FR--A-F  QDYHG-P-F-

101                                                150
   A47pep  EAMAKFMGQV  RAGKVTFDPD  RVVMCGGATG  AQSTLAPCLA  DPGDAYLVPT
   A50pep  EAMAKFMGQV  RGSKVTFDPD  RVVMCGGATG  AQDTLAPCLA  DPGDAYLVPT
   A65pep  NALARFMSEQ  RGYRVTFDPS  NIVLTAGATS  ANEALMPCLA  DWGDAFLIPT
Consensus  -A-A-FM---  R----VTFDP-  --V---GAT-  A----L-PCLA  D-GDA-L-PT 151                                                200
   A47pep  PYYPAPDRDC  CWRGGVKLLP  IECHSSNNFT  LTREALVSAY  DGARRQGVRV
   A50pep  PYYPAPDRDC  CWRSGVKLLP  IECRSSNNFT  LTREALVSAY  DGARRQGVRV
   A65pep  PYYPGPDRDL  NWRTGAEIVP  VHCTSGNGFR  LTRAALSDAY  RRAQKLRLRV
Consensus  PYYP-PDRD-  -WR-G----P  --C-S-N-F-  LTR-AL--AY  --A-----RV 201                                                250
   A47pep  KGVLITNPSN  PLGTTMDRAT  LAMLARFATE  RRVHLICDEI  YAGSVFAKPD
   A50pep  RGILITNPSN  PLGTTMDSGT  LAMLAAFATE  RRVHLICDEI  YAGSVFAKPG
   A65pep  KGVLITNPSN  PLGTTSPRAD  LEMLVDFVAA  KGIHLVSDEI  YSGTVFADPG
Consensus  -G-LITNPSN  PLGTT--R--  L-ML--F---  ---HL--DEI  Y-G-VFA-P-

251                                                300
   A47pep  FVSIAEVIER  .DVP......  .GCNRDLIHI  AYSLSKDFGL  PGFRVGIVYS
   A50pep  FVSIAEVIER  GDAP......  .GCNRDLVHI  AYSLSKDFGL  PGFRVGIVYS
   A65pep  FVSVLEVVAA  RAATDGSVVG  VGPLSDKVRV  VYSLSKDLGL  PGFRVGAIYS
Consensus  FVS--EV---  ----------  -G---D--H-  -YSLSKD-GL  PGFRVG--YS 301                                                350
   A47pep  YNDDVVACAR  KMSSFGLVSS  QTQHFLAKML  SDAEFMARFL  AESARRLAAR
   A50pep  YNDDVVACAR  KMSSFGLVSS  QTQHFLAMML  ADAEFMARFL  AESARRLAAR
   A65pep  SNAGVVSAAT  KMSSFGLVSS  QTQHLLASLL  GDRDFTRRYI  AENTRRIRER
Consensus  -N--VV--A-  KMSSFGLVSS  QTQH-LA--L  -D--F--R--  AE--RR---R 351                                                400
   A47pep  SDRFVAGLRE  VGIACLPGNA  GLFSWMDLRG  MLRQKTHDAE  LELWRVIVRK
   A50pep  SDRFVAGLRE  VGIACLPGNA  GLFSWMDLRG  MLREKTSDAE  LELWRVIVRR
   A65pep  REQLAEGLAA  VGIECLESNA  GLFCWVNMRR  LMKSRSFEGE  MELWKKVFE
Consensus  -------GL--  VGI-CL--NA  GLF-W---R-  --R------E  -ELW---V--

401                                                450
   A47pep  VKLNVSPGTS  FHCNEPGWFR  VCHANMDDET  MEVALDRIRR  FVRQHQ..K
   A50pep  VKLNVSPGTS  FHCNEPGWFR  VCYANMDDDT  MEVALDRIRR  FVRQHQS.K
   A65pep  VGLNISPGSS  CHCREPGWFR  VCFADMGART  LDVALQRLGA  FEEAATAGRR
```

Fig. 15

```
Consensus  V-LN-SPG-S  -HC-SPGNFR  VC-AMM---?  --VAL-R---  F---------

451                                                      498
A47pep  AKAERWAATR  PMRLSLPRR.  .GGATASHLP  ISSPMALLSP  QSPMVRAS
A50pep  AKAERWAATR  PLRLSLPRR.  .GATTASHLA  ISSPLALLSP  QSPMVRAS
A65pep  VLAPARSISL  PVRFSWANRL  TPGSAAORKA  ER--------  --------
Consensus  --A-------  P-R-S---R-  -----A----  ----------  --------
```

Fig. 15 (cont.)

Consensus Sequence (similar amino acid residues)

```
1                                                           50
    A47pep  -MAGSSAEQ LLSRIASGDG HGENSSYFDG WKAYDMDPFD LRHNRDGVIQ
    A50pep  --MAGSSAEQ LLSRIAAGDG HGENSSYFDG WKAYDMNPFD LRHNRDSVIQ
    A65pep  NIADEKPQPQ LLSKKAACNS HGQDSSYFLG NEETEKNPYD FVANPGGIIQ
 Consensus  ---------Q LLSR-A---- HGE-SSYF-G N--YD--PFD ---N--GVIQ 51                                                         100
    A47pep  NGLAENQLSL DLIEQNSMEH PEASICTAQG ASQFRRIANF QDYHGLPEFR
    A50pep  NGLAENQLSL DLIEQNSVDH PEASICTAQG APQFRRIANF QDYHGLPEFR
    A65pep  NGLAENQLSF DLLEAWLEAN PDALGLSSGG ASVFRELALF QDYSSMPAFK
 Consensus  NGLAENQLS- DLIE-N---- PEA------G A--FR-IA-F QDYHGLP-FR 101                                                        150
    A47pep  EAMAKFMGQV RAGKVTFDPD RVVMCGGATG AQDTLAFCLA DPGDAYLVPT
    A50pep  EAMAKFMGQV RGSKVTFDPD RVVMCGGATG AQDTLAFCLA DPGDAYLVPT
    A65pep  NALAKFMSEQ RGYRVTFDPS NIVLTAGATS ANEALMFCLA DMGDAFLIPT
 Consensus  -AMAKFM-Q- R--KVTFDP- -VVM--GAT- A-D-L-FCLA D-GDAYLVPT 151                                                        200
    A47pep  PYYPAFDRDC CWRSGVKLLP IECHSSNNFT LTREALVSAY SGARRQGVRV
    A50pep  PYYPAFDRDC CWRSGVKLLP IECHSSNNFT LTREALVSAY SGARRQGVRV
    A65pep  PYYPGFDRDL KNRTGAEIVP VHCTSGNGFR LTRAALDDAY PPAQKLRLPV
 Consensus  PYYP-FDRD- -WR-G--L-P I-C-S-N-F- LTR-AL--AY --A-R---RV 201                                                        250
    A47pep  KGVLITNPSN PLGTTMDRAT LAMLARFATE SRVHLICDEI YAGSVFAKPD
    A50pep  KGILITNPSN PLGTTMDRGT LAMLAAFATE SRVHLICDEI YAGSVFAKPG
    A65pep  KGVLITNPSN PLGTTSPRAD LEMLVDFVAA KGISLVSDEI YSGTVFADPG
 Consensus  KGVLITNPSN PLGTT--R-- L-ML--F--- --VHLI-DEI Y-G-VFA-P-

251                                                        300
    A47pep  FVSIAEVIER .DVP...... .GCNRDLIHI AYSLSKDFGL PGFRVGIVYS
    A50pep  FVSIAEVIER GDAP...... .GCNRDLVHI AYSLSKDFGL PGFRVGIVYS
    A65pep  FVSVLEVVAA RAATDDGVVG VGPLSDRVHV VYSLSKDLGL PGFRVGAIYS
 Consensus  FVSI-EVI-- ---------- -G----D-V-I -YSLSKD-GL PGFRVG-VYS 301                                                        350
    A47pep  YNDDVVACAR KMSSFGLVSS QTQHFLAKML SDAEFMARFL AESARRLAAR
    A50pep  YNDDVVACAR KMSSFGLVSS QTQHFLAMML ADAEFMARFL AESARRLAAR
    A65pep  SNAGVVSAAT KMSSFGLVSS QTQHLLASLL GDRDFTRRYI ASNTRRIRER
 Consensus  -N--VV--A- KMSSFGLVSS QTQH-LA-ML -D-EF--RFL AE--RRL--R 351                                                        400
    A47pep  HDRFVAGLRE VGIACLPGNA GLFSNMDLRG MLRDKTHDAE LELNRVIVRK
    A50pep  HDRFVAGLRE VGIACLPGNA GLFSNMDLRG MLREKTHDAE LELNRVIVHR
    A65pep  REQLAEGLAA VGISCLESNA GLFCNVNMRR LDRSRSFEGE MELNKKVVFE
 Consensus  -D----GL-- VGI-CL--NA GLF-N--LR- MLR-K--D-E LELNR-IV--

401                                                        450
    A47pep  VKLNVSPGTS FHCNEPGWFR VCHANMDDET MEVALDRIRR FVRQHQH..K
    A50pep  VKLNVSPGTS FHCNEPGWFR VCYANMDDDT MEVALDRIRR FVRQHQS..K
    A65pep  VGLNISPGSS CHCREPGWFR VCFANMSAKT LDVALQRLGA FAKAATAGRR
```

Fig. 16

```
Consensus  V-LNVSPG-S -HC-EPGWFR VC-ANM---T MEVAL-RI-- F--------K 451                                              498
    A47pep AKAERWAATR PNRLSLPRR. .GGATASHLP ISSPMALLSP QSPMVHAS
    A50pep AKAERWAATR PLRLSLPRR. .GATTASHLA ISSPLALLSP QSPMVHAS
    A65pep VLAPARSISL PVRFSWNNRL TPGSAADRKA ER-------- --------
  Consensus --A------- P-R-S----R- -----A---- ---------- --------
```

Fig. 16 (cont.)

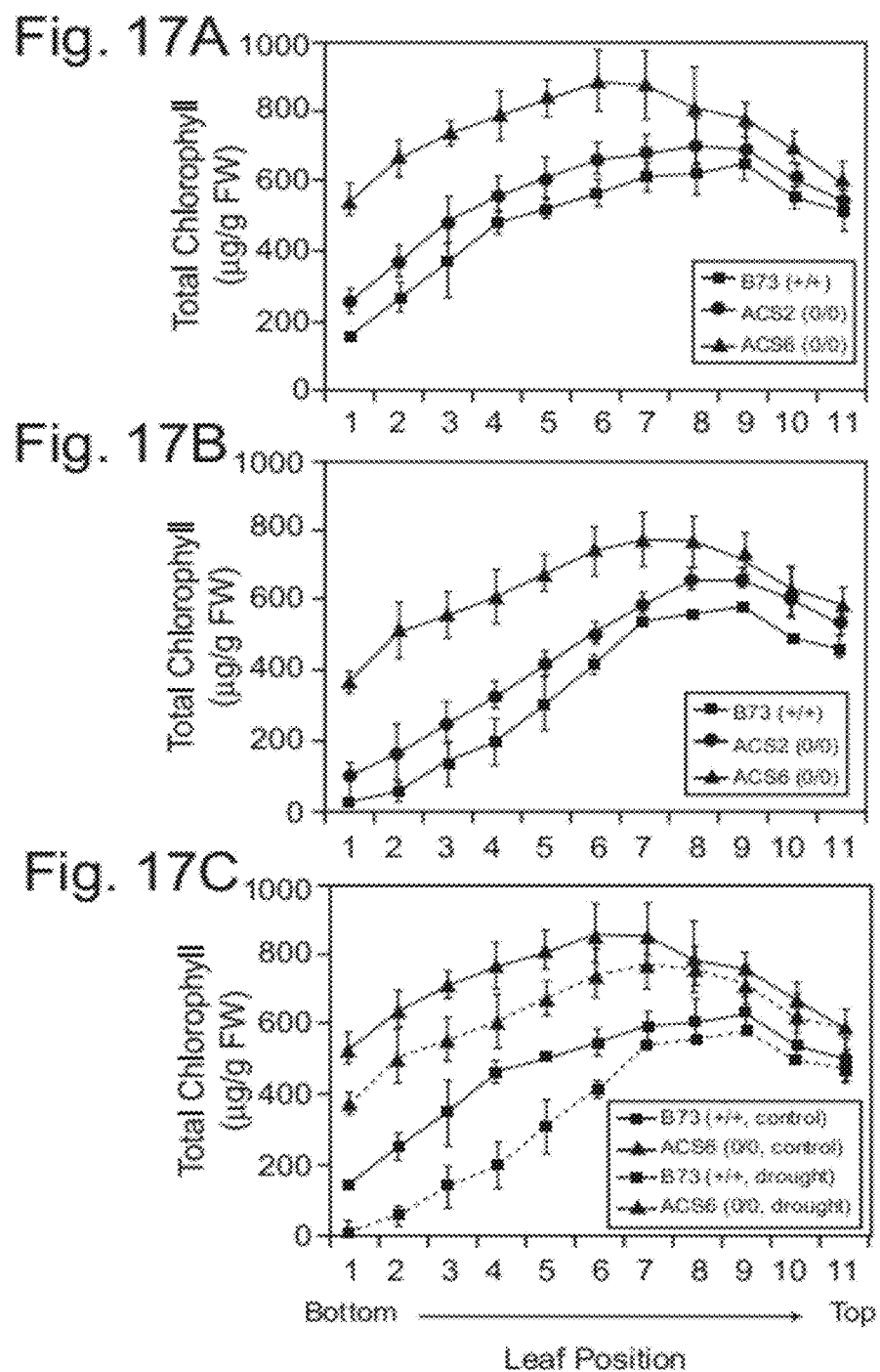

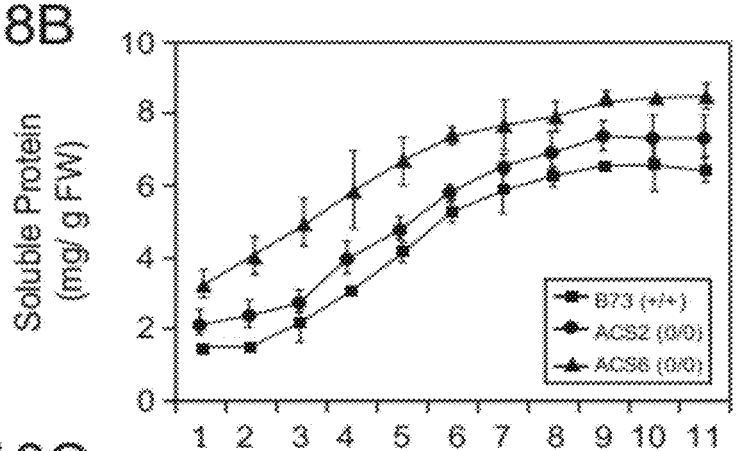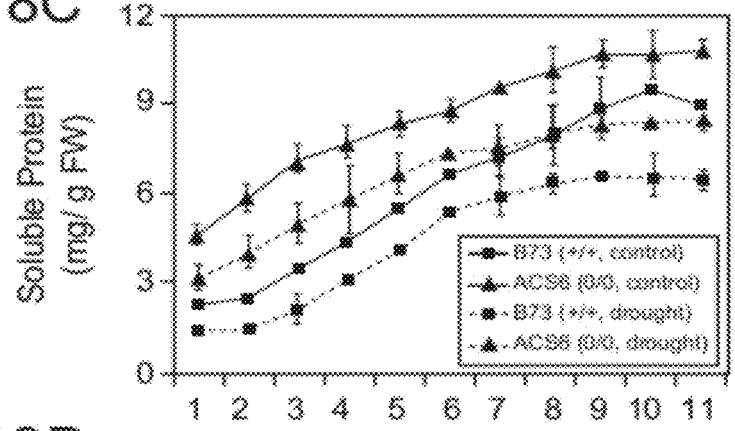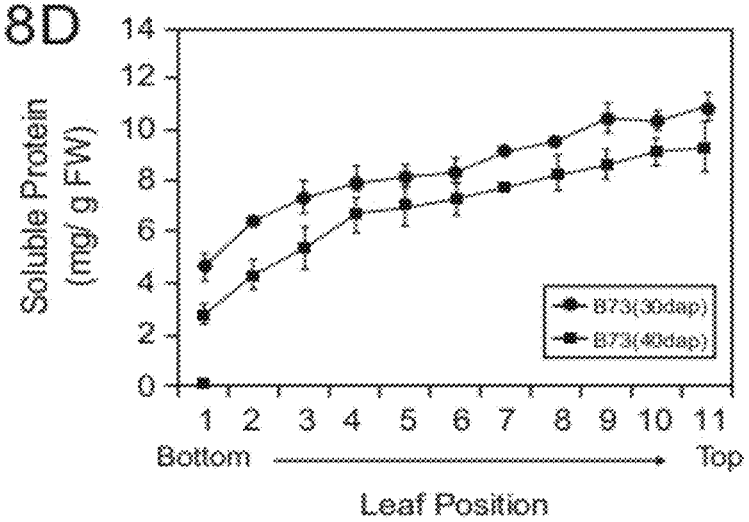

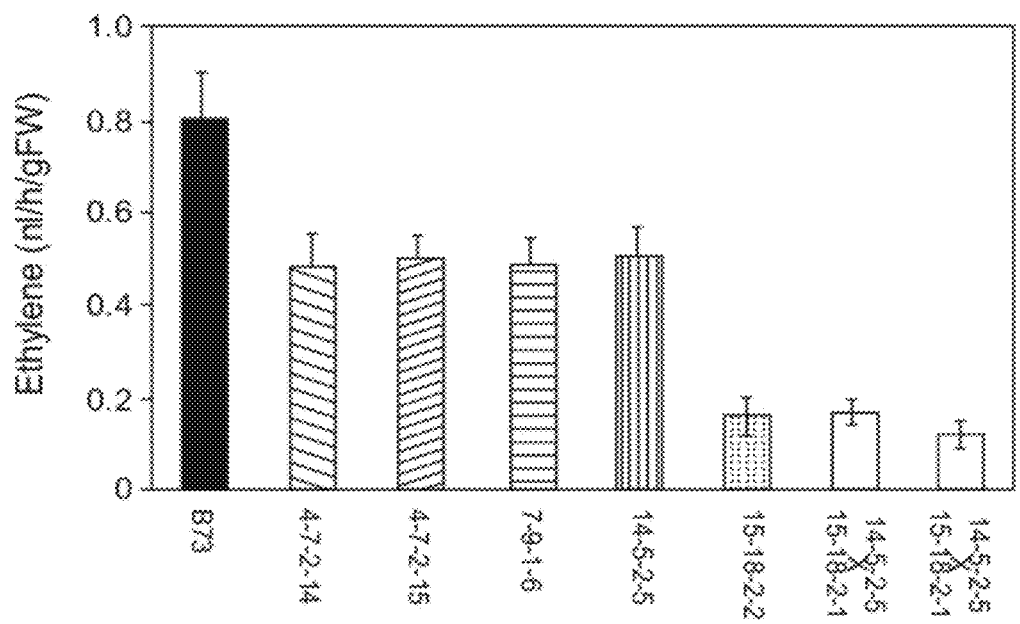
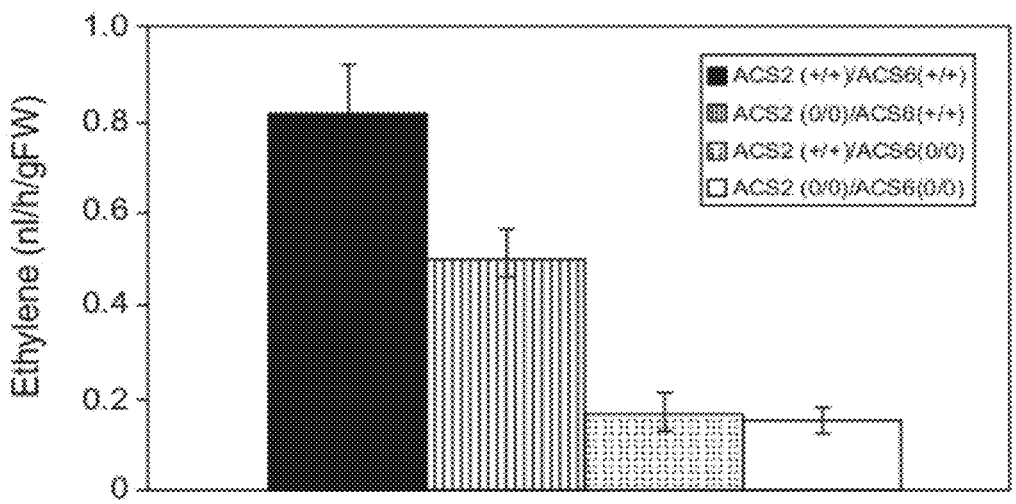

GATCCGCCGCTTCGTGCGGCCAGCACCAGCACAGCAAGGCCAAGGCCGAGCCGCTGGCGGCCCACGC
GGGCCCTCCCGCCTCAGCTTGCCGGCGCCGGCGGAGCAACCACCGCTTCGCACCTCGCCATCCCCAGCC
CCTTGGCGTTGCTGTCGCCCGCAGTCCCCGATGGTCCACGGCCAGCTAGCTAGTCACCGAGCCGTTCGG
TAAGACTGGCTGTAGGGGTGTGCCCCTCACATAACTGCAAACAAGTGGACAAAAAATATTAGACAAG
ACTAATAAAGGGCATTAGTAGCTAGCTTGACATTACACAGAGACGTTGCACAGGCGTCAGCAGGC
GTCGGCCGGTAAGCAGCTAGTCAAGCAGGACGCATTGTCCTCGATTTTTTCGTGTATATATGTTCTT
TTTTCTGTTTTGCCAAATCGCATGTATGGTTTGGTTTAACGTTAGTACACGGTAGAATAACGATCGG
GTATGGTAATTTAGACCTCCCGATCAATTGTTGTTGAAAACCTGTCACGTAACTTCAGGACACAGA
AGGCGTAGCTCAAGGGGTGAATAAAAGACCAGTTTACATATCAAAAAAAAAAAAAAAAAAAAAAA
AAAAAGGCC

Fig. 21C

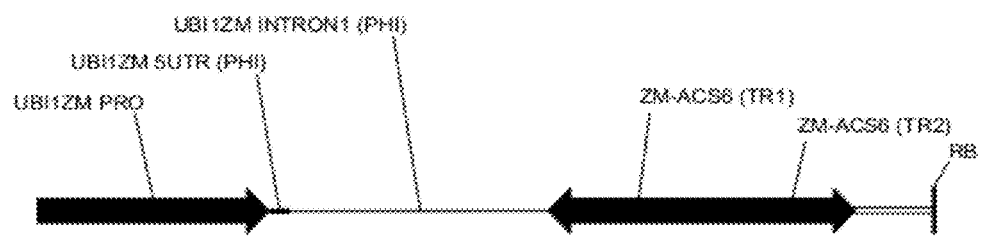

Fig. 22A

```
TAGCAGACGCGGAACCAGCCGGGCTCCCCGGCAGTGGCAGGACGGAGCCCGGCGGAGATGTTGAGCC
CCACCCTCGAAGACCACCTTCTTCCACAGCTCCATCTCGCCCTCGAACGACCGGCTCCGCATCAGGC
GCCGGCATGTTGACCCAGCAGAAGAGCCCCGCGTTGCTCTCCAGGCACTCGATGCCCACCGCCGCC
AGGCCCTCCGCCAGCTGCTCGCGCCGCTCCCTGATCCGCCGCGTGTTCTCCGCGATGTACCTCCGC
GTGAAGTCCCTGTCGCCCAGGAGCGACGCCACGACGTGCTGCGTCTGGGACGACACCAGGCCGAA
GCTCGACATCTTGGTGGCCGCGGAGACCACGCCCGGCGTTGGACGAGTAGATGGCGCCCACGCGGA
ACCCCGGGAGGCCCAGGTCCTTGGACAGGCTGTACACCACGTGCACGCGGTCCGACAGCGGCCCA
ACGCCGACGACGCCCGTCGTCCGTGGCGGCGCGCGCGGCCACCACCTCGAGGACGGCTCACGAACCC
CGGGTCCGCGAAGACCGTGCCCGAGTATATCTCGTCGCTCACCAGGTGGATGCCCTTGGCGGCCAC
GAAGTCCACCAGCATCTCCAGGTCGGCGGCGGCGGACGTGGTGCCCAGCCGGGTTGGAAGGGTTGG
TGATGAGCACGCCCTTGACGCCGCAGCCGCAGCTTCTGCGGCGGCCGGTA
```

Fig. 22B

```
CGCGCCGGCCACGGACGACGGCGTCGTCGGCCGTTGGCCGCTGTCGGACCGCGTGCACGTGGTGTA
CAGCCTGTCCAAGGACCTGGGCCCTCCCCGGCGGTTCCGCGTGGGCGCCATCTACTCGTCCAACGCCGG
CGTGGTCTCCGCGGCCACCAAGAGATGTCGAGCTTCGGCCTGGTGTCGTCCCAGAGACGCAGCACCTCCT
GGCGTCGCTCCTGGGCGGACAGCGGACTTCACGCCGGAGGTACATCGCCGGAGAACACGCGGCCGATCA
GGGAGCCGGCGCCAGCAGCCTGGCCGGAGCGGCCTCGCCGGCCGTGGGCATCGAGTGCCTCGAGAGCAA
CGCCGGCGCTCTTTCTGCTGGCGTCAACATGCCGGCCGCCTGATGCCGAGCCCGGTCGTTCGAGCGCGAGA
TGGAGCTGTCGGAAGAAGGTGGTCTTCGAGGTGGGGCTCAACATCTCCCCCGGGCTCCTCCTGCCACT
GCCCGGGAGCCCGGCTGGTTCCGCGTCTGCTAA
```

Fig. 22C

ENGINEERING SINGLE-GENE-CONTROLLED STAYGREEN POTENTIAL INTO PLANTS

CROSS-REFERENCE TO RELATED APPLICATIONS

This application is a continuation of U.S. Patent application Ser. No. 12/800,466, filed May 14, 2010, entitled "Engineering single-gene-controlled staygreen potential into plants" by Gallie et al., which issued on Mar. 6, 2012 as U.S. Pat. No. 8,129,587, entitled "*Zea mays* seeds and plants with reduced expression of the ACS2 gene," and which is a divisional of U.S. patent application Ser. No. 11/698,310, filed Jan. 24, 2007, entitled "Engineering single-gene-controlled staygreen potential into plants" by Gallie et al., which issued on Jul. 27, 2010 as U.S. Pat. No. 7,763,773, entitled "Engineering single-gene-controlled staygreen potential into plants," and which is a continuation of U.S. patent application Ser. No. 10/875,127, filed Jun. 22, 2004, entitled "Engineering single-gene-controlled staygreen potential into plants" by Gallie et al., which issued on Jun. 12, 2007 as U.S. Pat. No. 7,230,161, entitled "Engineering single-gene-controlled staygreen potential into plants utilizing ACC synthase from maize," and which claims priority to and benefit of the following prior provisional patent application: U.S. Ser. No. 60/480,861, filed Jun. 23, 2003, entitled "Engineering single-gene-controlled staygreen potential into plants" by Gallie et al. Each of these applications is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under grants 97-35304-4657 and 98-35100-6150 awarded by the United States Department of Agriculture and grant 0076434 awarded by the National Science Foundation. The government has certain rights in the invention.

FIELD OF THE INVENTION

This invention relates to modulating staygreen potential in plants, inhibiting ethylene production in plants, and modulating sterility in plants. The invention also provides knockout plant cells, e.g., where the knockout plant cells are disrupted in ACC synthase expression and/or activity, or knockout plants, e.g., which display a staygreen phenotype or a male sterility phenotype. Nucleic acid sequences and amino acid sequences encoding various ACC synthases are also included.

BACKGROUND OF THE INVENTION

Stay-green is a term used to describe a plant phenotype, e.g., whereby leaf senescence (most easily distinguished by yellowing of the leaf associated with chlorophyll degradation) is delayed compared to a standard reference. See, Thomas H and Howarth C J (2000) "*Five ways to stay green*" *Journal of Experimental Botany* 51: 329-337. In sorghum, several stay-green genotypes have been identified which exhibit a delay in leaf senescence during grain filling and maturation. See, Duncan R R, et al. (1981) "*Descriptive comparison of senescent and non-senescent sorghum genotypes.*" *Agronomy Journal* 73: 849-853. Moreover, under conditions of limited water availability, which normally hastens leaf senescence (see, e.g., Rosenow D T, and Clark L E (1981) *Drought tolerance in sorghum*. In: Loden H D, Wilkinson D, eds. *Proceedings of the 36th annual corn and sorghum industry research conference*, 18-31), these genotypes retain more green leaf area and continue to fill grain normally (see, e.g., McBee G G, Waskom R M, Miller F R, Creelman R A (1983) *Effect of senescence and non-senescence on carbohydrates in sorghum during late kernel maturity states. Crop Science* 23: 372-377; Rosenow D T, Quisenberry J E, Wendt C W, Clark L E (1983) *Drought-tolerant sorghum and cotton germplasm. Agricultural Water Management* 7: 207-222; and, Borrell A K, Douglas A C L (1996) *Maintaining green leaf area in grain sorghum increases yield in a water-limited environment*. In: Foale M A, Henzell R G, Kneipp J F, eds. *Proceedings of the third Australian sorghum conference. Melbourne: Australian Institute of Agricultural Science, Occasional Publication No.* 93). The stay-green phenotype has also been used as a selection criterion for the development of improved varieties of corn, particularly with regard to the development of drought-tolerance. See, e.g., Russell W A (1991) *Genetic improvement of maize yields. Advances in Agronomy* 46: 245-298; and, Bruce et al. (2002), "*Molecular and physiological approaches to maize improvement for drought tolerance*" *Journal of Experimental Botany*, 53 (366): 13-25.

Five fundamentally distinct types of stay-green have been described, which are Types A, B, C, D and E (see e.g., Thomas H, Smart C M (1993) *Crops that stay green. Annals of Applied Biology* 123: 193-219; and, Thomas and Howarth, supra). In Type A stay-green, initiation of the senescence program is delayed, but then proceeds at a normal rate. In Type B stay-green, while initiation of the senescence program is unchanged, the progression is comparatively slower. In Type C stay-green, chlorophyll is retained even though senescence (as determined through measurements of physiological function such as photosynthetic capacity) proceeds at a normal rate. Type D stay-green is more artificial in that killing of the leaf (i.e. by freezing, boiling or drying) prevents initiation of the senescence program, thereby stopping the degradation of chlorophyll. In Type E stay-green, initial levels of chlorophyll are higher, while initiation and progression of leaf senescence are unchanged, thereby giving the illusion of a relatively slower progression rate. Type A and B are functional stay-greens, as photosynthetic capacity is maintained along with chlorophyll content, and these are the types associated with increased yield and drought tolerance in sorghum. Despite the potential importance of this trait, in particular the benefits associated with increasing yield and drought tolerance, very little progress has been made in understanding the biochemical, physiological or molecular basis for genetically determined stay-green (Thomas and Howarth, supra).

This invention solves these and other problems. The invention relates to the identification of ACC synthase genes associated with staygreen potential phenotype in plants and modulation of staygreen potential and/or ethylene production. Polypeptides encoded by these genes, methods for modulating staygreen potential in plants, methods for inhibiting ethylene production in plants, methods for modulating sterility in plants, and knockout plant cells and plants, as well as other features, will become apparent upon review of the following materials.

SUMMARY OF THE INVENTION

This invention provides methods and compositions for modulating staygreen potential and sterility in plants and modulating (e.g., inhibiting) ethylene synthesis and/or production in plants. This invention also relates to ACC synthase nucleic acid sequences in plants, exemplified by, e.g., SEQ ID NO:1 through SEQ ID NO:6 and SEQ ID NO:10, and a set of polypeptide sequences, e.g., SEQ ID NO:7 through SEQ ID NO:9 and SEQ ID NO:11, which can modulate these activities.

In a first aspect, the invention provides for an isolated or recombinant knockout plant cell comprising at least one disruption in at least one endogenous ACC synthase gene (e.g., a nucleic acid sequence, or complement thereof, comprising, e.g., at least about 70%, at least about 75%, at least about 80%, at least about 85%, at least about 90%, at least about 95%, at least about 99%, about 99.5% or more sequence identity to SEQ ID NO:1 (gACS2), SEQ ID NO:2 (gACS6), or SEQ ID NO:3 (gACS7)). The disruption inhibits expression or activity of at least one ACC synthase protein compared to a corresponding control plant cell lacking the disruption. In one embodiment, the at least one endogenous ACC synthase gene comprises two or more endogenous ACC synthase genes (e.g., any two or more of ACS2, ACS6, and ACS7, e.g., ACS2 and ACS6). Similarly, in another embodiment, the at least one endogenous ACC synthase gene comprises three or more endogenous ACC synthase genes. In certain embodiments, the disruption results in reduced ethylene production by the knockout plant cell as compared to the control plant cell.

In one embodiment, the at least one disruption in the knockout plant cell is produced by introducing at least one polynucleotide sequence comprising an ACC synthase nucleic acid sequence, or subsequence thereof, into a plant cell, such that the at least one polynucleotide sequence is linked to a promoter in a sense or antisense orientation, and where the at least one polynucleotide sequence comprises, e.g., at least about 70%, at least about 75%, at least about 80%, at least about 85%, at least about 90%, at least about 95%, at least about 99%, about 99.5% or more sequence identity to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cACS7), or SEQ ID NO:10 (CCRA178R) or a subsequence thereof, or a complement thereof. In another embodiment, the disruption is introduced into the plant cell by introducing at least one polynucleotide sequence comprising one or more subsequences of an ACC synthase nucleic acid sequence configured for RNA silencing or interference.

In another embodiment, the disruption comprises insertion of one or more transposons, where the one or more transposons are in the at least one endogenous ACC synthase gene. In yet another embodiment, the disruption comprises one or more point mutations in the at least one endogenous ACC synthase gene. The disruption can be a homozygous disruption in the at least one ACC synthase gene. Alternatively, the disruption is a heterozygous disruption in the at least one ACC synthase gene. In certain embodiments, when more than one ACC synthase gene is involved, there is more than one disruption, which can include homozygous disruptions, heterozygous disruptions or a combination of homozygous disruptions and heterozygous disruptions.

In certain embodiments, a plant cell of the invention is from a dicot or monocot. In one aspect, the plant cell is in a hybrid plant comprising a staygreen potential phenotype. In another aspect, the plant cell is in a plant comprising a sterility phenotype, e.g., a male sterility phenotype. Plants regenerated from the plant cells of the invention are also a feature of the invention.

The invention also provides for knockout plants that comprise a staygreen potential phenotype. For example, the invention provides for a knockout plant that comprises a staygreen potential phenotype results from a disruption in at least one endogenous ACC synthase gene. In one embodiment, the disruption includes one or more transposons, and inhibits expression or activity of at least one ACC synthase protein compared to a corresponding control plant. In another embodiment, the disruption includes one or more point mutations in the endogenous ACC synthase gene and inhibits expression or activity of at least one ACC synthase protein compared to a corresponding control plant. In certain embodiments, the at least one endogenous ACC synthase gene comprises a nucleic acid sequence comprising, e.g., at least about 70%, at least about 75%, at least about 80%, at least about 85%, at least about 90%, at least about 95%, at least about 99%, about 99.5% or more, sequence identity to SEQ ID NO:1 (gACS2), SEQ ID NO:2 (gACS6), or SEQ ID NO:3 (gACS7), or a complement thereof. In certain embodiments, the knockout plant is a hybrid plant. Essentially all of the features noted above apply to this embodiment as well, as relevant.

In another embodiment, a knockout plant includes a transgenic plant that comprises a staygreen potential phenotype. For example, a transgenic plant of the invention includes a staygreen potential phenotype resulting from at least one introduced transgene that inhibits ethylene synthesis. The introduced transgene includes a nucleic acid sequence encoding at least one ACC synthase or subsequence thereof, which nucleic acid sequence comprises, e.g., at least about 70%, at least about 75%, at least about 80%, at least about 85%, at least about 90%, at least about 95%, at least about 99%, about 99.5% or more sequence identity to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cACS7) or SEQ ID NO:10 (CCRA178R), or a subsequence thereof, or a complement thereof, and is in a configuration that modifies a level of expression or activity of the at least one ACC synthase (e.g., a sense, antisense, RNA silencing or interference configuration). Essentially all of the features noted above apply to this embodiment as well, as relevant.

A transgenic plant of the invention can also include a staygreen potential phenotype resulting from at least one introduced transgene which inhibits ethylene synthesis, where said at least one introduced transgene comprises a nucleic acid sequence encoding a subsequence(s) of at least one ACC synthase, which at least one ACC synthase comprises, e.g., at least about 70%, at least about 75%, at least about 80%, at least about 85%, at least about 90%, at least about 95%, at least about 99%, about 99.5% or more sequence identity to SEQ ID NO:7 (pACS2), SEQ ID NO:8 (pACS6), SEQ ID NO.:9 (pACS7), or SEQ ID NO.:11 (pCCRA178R), or a conservative variation thereof. The nucleic acid sequence is typically in an RNA silencing or interference configuration (or, e.g., a sense or antisense configuration), and modifies a level of expression or activity of the at least one ACC synthase. Essentially all of the features noted above apply to this embodiment as well, as relevant.

The staygreen potential of a plant of the invention includes, but is not limited to, e.g., (a) a reduction in the production of at least one ACC synthase specific mRNA; (b) a reduction in the production of an ACC synthase; (c) a reduction in the production of ethylene; (d) a delay in leaf senescence; (e) an increase of drought resistance; (f) an increased time in maintaining photosynthetic activity; (g) an increased transpiration; (h) an increased stomatal conductance; (i) an increased $CO_2$ assimilation; (j) an increased maintenance of $CO_2$ assimilation; or (k) any combination of (a)-(j); compared to a corresponding control plant, and the like.

One aspect of the invention provides knockout or transgenic plants including sterility phenotypes, e.g., a male or female sterility phenotype. Thus, one class of embodiments provides a knockout plant comprising a male sterility phenotype (e.g., reduced pollen shedding) which results from at least one disruption in at least one endogenous ACC synthase gene. The disruption inhibits expression or activity of at least one ACC synthase protein compared to a corresponding control plant. In one embodiment, the at least one disruption results in reduced ethylene production by the knockout plant as compared to the control plant. In one embodiment, the at least one disruption includes one or more transposons, wherein the one or more transposons are in the at least one endogenous ACC synthase gene. In another embodiment, the at least one disruption comprises one or more point mutations, wherein the one or more point mutations are in the at least one endogenous ACC synthase gene. In yet another embodiment, the at least one disruption is introduced into the knockout plant by introducing at least one polynucleotide sequence comprising one or more subsequences of an ACC synthase nucleic acid sequence configured for RNA silencing or interference. In certain embodiments, the at least one endogenous ACC synthase gene comprises a nucleic acid sequence comprising, e.g., at least about 70%, at least about 75%, at least about 80%, at least about 85%, at least about 90%, at least about 95%, at least about 99%, about 99.5% or more, sequence identity to SEQ ID NO:1 (gACS2), SEQ ID NO:2 (gACS6), or SEQ ID NO:3 (gACS7), or a complement thereof. Essentially all of the features noted above apply to this embodiment as well, as relevant.

Another class of embodiments provides a transgenic knockout plant comprising a male sterility phenotype resulting from at least one introduced transgene which inhibits ethylene synthesis. The at least one introduced transgene comprises a nucleic acid sequence encoding at least one ACC synthase, which nucleic acid sequence comprises at least about 85% sequence identity to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cACS7) or SEQ ID NO:10 (CCRA178R), or a subsequence thereof, or a complement thereof, and is in a configuration that modifies a level of expression or activity of the at least one ACC synthase (e.g., an antisense, sense or RNA silencing or interference configuration). In certain embodiments, the transgene includes a tissue-specific promoter or an inducible promoter. Essentially all of the features noted above apply to this embodiment as well, as relevant.

Polynucleotides are also a feature of the invention. In certain embodiments, an isolated or recombinant polynucleotide comprises a member selected from the group consisting of: (a) a polynucleotide, or a complement thereof, comprising, e.g., at least about 70%, at least about 75%, at least about 80%, at least about 85%, at least about 90%, at least about 95%, at least about 99%, about 99.5% or more sequence identity to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cACS7) or SEQ ID NO:10 (CCRA178R), or a subsequence thereof, or a conservative variation thereof; (b) a polynucleotide, or a complement thereof, encoding a polypeptide sequence of SEQ ID NO:7 (pACS2), SEQ ID NO:8 (pACS6), SEQ ID NO.:9 (pACS7), or SEQ ID NO:11 (pCCRA178R), or a subsequence thereof, or a conservative variation thereof; (c) a polynucleotide, or a complement thereof, that hybridizes under stringent conditions over substantially the entire length of a polynucleotide subsequence comprising at least 100 contiguous nucleotides of SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cACS7), or SEQ ID NO:10 (CCRA178R), or that hybridizes to a polynucleotide sequence of (a) or (b); and, (d) a polynucleotide that is at least about 85% identical to a polynucleotide sequence of (a), (b) or (c). In certain embodiments, the polynucleotide inhibits ethylene production when expressed in a plant.

The polynucleotides of the invention can comprise or be contained within an expression cassette or a vector (e.g., a viral vector). The vector or expression cassette can comprise a promoter (e.g., a constitutive, tissue-specific, or inducible promoter) operably linked to the polynucleotide. A polynucleotide of the invention can be linked to the promoter in an antisense orientation or a sense orientation, be configured for RNA silencing or interference, or the like.

The invention also provides methods for inhibiting ethylene production in a plant (and plants produced by such methods). For example, a method of inhibiting ethylene production comprises inactivating one or more ACC synthase genes in the plant, wherein the one or more ACC synthase genes encode one or more ACC synthases, wherein at least one of the one or more ACC synthases comprises, e.g., at least about 70%, at least about 75%, at least about 80%, at least about 85%, at least about 90%, at least about 95%, at least about 99%, about 99.5% or more identity to SEQ ID NO:7 (pACS2), SEQ ID NO:8 (pACS6), SEQ ID NO:9 (pAC7) or SEQ ID NO:11 (pCCRA178R).

In one embodiment, the inactivating step comprises introducing one or more mutations into an ACC synthase gene sequence, wherein the one or more mutations in the ACC synthase gene sequence comprise one or more transposons, thereby inactivating the one or more ACC synthase genes compared to a corresponding control plant. In another embodiment, the inactivating step comprises introducing one or more mutations into an ACC synthase gene sequence, wherein the one or more mutations in the ACC synthase gene sequence comprise one or more point mutations, thereby inactivating the one or more ACC synthase genes compared to a corresponding control plant. The one or more mutations can comprise, for example, a homozygous disruption in the one or more ACC synthase genes, a heterozygous disruption in the one or more ACC synthase genes, or a combination of both homozygous disruptions and heterozygous disruptions if more than one ACC synthase gene is disrupted. In certain embodiments, the one or more mutations are introduced by a sexual cross. In certain embodiments, at least one of the one or more ACC synthase genes is, e.g., at least about 70%, at least about 75%, at least about 80%, at least about 85%, at least about 90%, at least about 95%, at least about 99%, about 99.5% or more, identical to SEQ ID NO:1 (gACS2), SEQ ID NO:2 (gACS6) or SEQ ID NO:3 (gAC7), or a complement thereof).

In another embodiment, the inactivating step comprises: (a) introducing into the plant at least one polynucleotide sequence, wherein the at least one polynucleotide sequence comprises a nucleic acid encoding one or more ACC synthases, or a subsequence thereof, and a promoter, which promoter functions in plants to produce an RNA sequence; and, (b) expressing the at least one polynucleotide sequence, thereby inactivating the one or more ACC synthase genes compared to a corresponding control plant (e.g., its non-transgenic parent or a non-transgenic plant of the same species). For example, the at least one polynucleotide sequence can be introduced by techniques including, but not limited to, electroporation, micro-projectile bombardment, *Agrobacterium*-mediated transfer, and the like. In certain aspects of the invention, the polynucleotide is linked to the promoter in a sense orientation or an antisense orientation, or is configured for RNA silencing or interference. Essentially all of the features noted above apply to this embodiment as well, as relevant.

Methods for modulating staygreen potential in plants are also a feature of the invention (as are plants produced by such methods). For example, a method of modulating staygreen potential comprises: a) selecting at least one ACC synthase gene (e.g., encoding an ACC synthase, for example, SEQ ID NO:7 (pACS2), SEQ ID NO:8 (pACS6), SEQ ID NO:9 (pAC7) or SEQ ID NO:11 (pCCRA178R)) to mutate, thereby providing at least one desired ACC synthase gene; b) introducing a mutant form (e.g., an antisense or sense configuration of at least one ACC synthase gene or subsequence thereof, an RNA silencing configuration of at least one ACC synthase gene or subsequence thereof, a heterozygous mutation in the at least one ACC synthase gene, a homozygous mutation in the at least one ACC synthase gene or a combination of homozygous mutation and heterozygous mutation if more than one ACC synthase gene is selected, and the like) of the at least one desired ACC synthase gene into the plant; and, c) expressing the mutant form, thereby modulating staygreen potential in the plant. In one embodiment, selecting the at least one ACC synthase gene comprises determining a degree (e.g., weak, moderate or strong) of staygreen potential desired. In certain embodiments, the mutant gene is introduced by *Agrobacterium*-mediated transfer, electroporation, micro-projectile bombardment, a sexual cross, or the like. Essentially all of the features noted above apply to this embodiment as well, as relevant.

Detection of expression products is performed either qualitatively (by detecting presence or absence of one or more product of interest) or quantitatively (by monitoring the level of expression of one or more product of interest). In one embodiment, the expression product is an RNA expression product. Aspects of the invention optionally include monitoring an expression level of a nucleic acid, polypeptide or chemical (e.g., ACC, ethylene, etc.) as noted herein for detection of ACC synthase, ethylene production, staygreen potential, etc. in a plant or in a population of plants.

The compositions and methods of the invention can include a variety of plants, e.g., a plant of the Poaceae (Gramineae) family. Examples of members of the Poaceae family include, by are not limited to, Acamptoclados, Achnatherum, Achnella, Acroceras, Aegilops, Aegopogon, Agroelymus, Agrohordeum, Agropogon, Agropyron, Agrositanion, Agrostis, Aira, Allolepis, Alloteropsis, Alopecurus, Amblyopyrum, Ammophila, Ampelodesmos, Amphibromus, Amphicarpum, Amphilophis, Anastrophus, Anatherum, Andropogron, Anemathele, Aneurolepidium, Anisantha, Anthaenantia, Anthephora, Anthochloa, Anthoxanthum, Apera, Apluda, Archtagrostis, Arctophila, Argillochloa, Aristida, Arrhenatherum, Arthraxon, Arthrostylidium, Arundinaria, Arundinella, Arundo, Aspris, Atheropogon, Avena, Avenella, Avenochloa, Avenula, Axonopus, Bambusa, Beckmannia, Blepharidachne, Blepharoneuron, Bothriochloa, Bouteloua, Brachiaria, Brachyelytrum, Brachypodium, Briza, Brizopyrum, Bromelica, Bromopsis, Bromus, Buchloe, Bulbilis, Calamagrostis, Calamovilfa, Campulosus, Capriola, Catabrosa, Catapodium, Cathestecum, Cenchropsis, Cenchrus, Centotheca, Ceratochloa, Chaetochloa, Chasmanthium, Chimonobambusa, Chionochloa, Chloris, Chondrosum, Chrysopon, Chusquea, Cinna, Cladoraphis, Coelorachis, Coix, Coleanthus, Colpodium, Coridochloa, Cornucopiae, Cortaderia, Corynephorus, Cottea, Critesion, Crypsis, Ctenium, Cutandia, Cylindropyrum, Cymbopogon, Cynodon, Cynosurus, Cytrococcum, Dactylis, Dactyloctenium, Danthonia, Dasyochloa, Dasyprum, Davyella, Dendrocalamus, Deschampsia, Desmazeria, Deyeuxia, Diarina, Diarrhena, Dichanthelium, Dichanthium, Dichelachne, Diectomus, Digitaria, Dimeria, Dimorpostachys, Dinebra, Diplachne, Dissanthelium, Dissochondrus, Distichlis, Drepanostachyum, Dupoa, Dupontia, Echinochloa, Ectosperma, Ehrharta, Eleusine, Elyhordeum, Elyleymus, Elymordeum, Elymus, Elyonurus, Elysitanion, Elytesion, Elytrigia, Enneapogon, Enteropogon, Epicampes, Eragrostis, Eremochloa, Eremopoa, Eremopyrum, Erianthus, Ericoma, Erichloa, Eriochrysis, Erioneuron, Euchlaena, Euclasta, Eulalia, Eulaliopsis, Eustachys, Fargesia, Festuca, Festulolium, Fingerhuthia, Fluminia, Garnotia, Gastridium, Gaudinia, Gigantochloa, Glyceria, Graphephorum, Gymnopogon, Gynerium, Hackelochloa, Hainardia, Hakonechloa, Haynaldia, Heleochloa, Helictotrichon, Hemarthria, Hesperochloa, Hesperostipa, Heteropogon, Hibanobambusa, Hierochloe, Hilaria, Holcus, Homalocenchrus, Hordeum, Hydrochloa, Hymenachne, Hyparrhenia, Hypogynium, Hystrix, Ichnanthus, Imperata, Indocalamus, Isachne, Ischaemum, Ixophorus, Koeleria, Korycarpus, Lagurus, Lamarckia, Lasiacis, Leersia, Leptochloa, Leptochloopsis, Leptocoryphium, Leptoloma, Leptogon, Lepturus, Lerchenfeldia, Leucopoa, Leymostachys, Leymus, Limnodea, Lithachne, Lolium, Lophochlaena, Lophochloa, Lophopyrum, Ludolfia, Luziola, Lycurus, Lygeum, Maltea, Manisuris, Megastachya, Melica, Melinis, Mibora, Microchloa, Microlaena, Microstegium, Milium, Miscanthus, Mnesithea, Molinia, Monanthochloe, Monerma, Monroa, Muhlenbergia, Nardus, Nassella, Nazia, Neeragrostis, Neoschischkinia, Neostapfia, Neyraudia, Notholcus, Olyra, Opizia, Oplismenus, Orcuttia, Oryza, Oryzopsis, Otatea, Oxytenanthera, Particularia, Panicum, Pappophorum, Parapholis, Pascopyrum, Paspalidium, Paspalum, Pennisetum, Phalaris, Phalaroides, Phanopyrum, Pharus, Phippsia, Phleum, Pholiurus, Phragmites, Phyllostachys, Piptatherum, Piptochaetium, Pleioblastus, Pleopogon, Pleuraphis, Pleuropogon, Poa, Podagrostis, Polypogon, Polytrias, Psathyrostachys, Pseudelymus, Pseudoroegneria, Pseudosasa, Ptilagrostis, Puccinellia, Pucciphippsia, Redfieldia, Reimaria, Reimarochloa, Rhaphis, Rhombolytrum, Rhynchelytrum, Roegneria, Rostraria, Rottboellia, Rytilix, Saccharum, Sacciolepis, Sasa, Sasaella, Sasamorpha, Savastana, Schedonnardus, Schismus, Schizachne, Schizachyrium, Schizostachyum, Sclerochloa, Scleropoa, Scleropogon, Scolochloa, Scribneria, Secale, Semiarundinaria, Sesleria, Setaria, Shibataea, Sieglingia, Sinarundinaria, Sinobambusa, Sinocalamus, Sitanion, Sorghastrum, Sorghum, Spartina, Sphenopholis, Spodiopogon, Sporobolus, Stapfia, Steinchisma, Stenotaphrum, Stipa, Stipagrostis, Stiporyzopsis, Swallenia, Syntherisma, Taeniatherum, Terrellia, Terrelymus, Thamnocalamus, Themeda, Thinopyrum, Thuarea, Thysanolaena, Torresia, Torreyochloa, Trachynia, Trachypogon, Tragus, Trichachne, Trichloris, Tricholaena, Trichoneura, Tridens, Triodia, Triplasis, Tripogon, Tripsacum, Trisetobromus, Trisetum, Triticosecale, Triticum, Tuctoria, Uniola, Urachne, Uralepis, Urochloa, Vahlodea, Valota, Vaseyochloa, Ventenata, Vetiveria, Vilfa, Vulpia, Willkommia, Yushania, Zea, Zizania, Zizaniopsis, and Zoysia. In one embodiment, the plant is *Zea mays*, wheat, rice, sorghum, barley, oat, lawn grass, rye, soybean, tomato, potato, pepper, broccoli, cabbage, a commercial corn line, or the like.

Kits which incorporate one or more of the nucleic acids or polypeptides noted above are also a feature of the invention. Such kits can include any of the above noted components and further include, e.g., instructions for use of the components in any of the methods noted herein, packaging materials, containers for holding the components, and/or the like. For example, a kit for modulating staygreen potential in a plant includes a container containing at least one polynucleotide sequence comprising a nucleic acid sequence, where the nucleic acid sequence is, e.g., at least about 70%, at least about 75%, at least about 80%, at least about 85%, at least about 90%, at least about 95%, at least about 99%, about 99.5% or more, identical to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cAC7) or SEQ ID NO:10 (CCRA178R), or a subsequence thereof, or a complement thereof. In a further embodiment, the kit includes instructional materials for the use of the at least one polynucleotide sequence to control staygreen potential in a plant. Essentially all of the features noted above apply to this embodiment as well, as relevant.

As another example, a kit for modulating sterility, e.g., male sterility, in a plant includes a container containing at least one polynucleotide sequence comprising a nucleic acid sequence, wherein the nucleic acid sequence is, e.g., at least about 70%, at least about 75%, at least about 80%, at least about 85%, at least about 90%, at least about 95%, at least about 99%, about 99.5% or more, identical to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cAC7) or SEQ ID NO:10 (CCRA178R), or a subsequence thereof, or a complement thereof. The kit optionally also includes instructional materials for the use of the at least one polynucleotide sequence to control sterility, e.g., male sterility, in a plant. Essentially all of the features noted above apply to this embodiment as well, as relevant.

DEFINITIONS

Before describing the invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

Unless defined otherwise, all technical and scientific terms used herein have the same meaning as commonly understood by one of ordinary skill in the art to which the invention pertains. In describing and claiming the present invention, the following terminology will be used in accordance with the definitions set out below.

The term "plant" refers generically to any of: whole plants, plant parts or organs (e.g., leaves, stems, roots, etc.), shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat), fruit (the mature ovary), plant tissue (e.g. vascular tissue, ground tissue, and the like), tissue culture callus, and plant cells (e.g. guard cells, egg cells, trichomes and the like), and progeny of same. Plant cell, as used herein, further includes, without limitation, cells obtained from or found in: seeds, cultures, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues.

The term "dicot" refers to a dicotyledonous plant. Dicotyledonous plants belong to large subclass of Angiosperms that have two seed-leaves (cotyledon).

The term "monocot" refers to a monocotyledonous plant, which in the developing plant has only one cotyledon.

The term "knockout plant cell" refers to a plant cell having a disruption in at least one ACC synthase gene in the cell, where the disruption results in a reduced expression or activity of the ACC synthase encoded by that gene compared to a control cell. The knockout can be the result of, e.g., antisense constructs, sense constructs, RNA silencing constructs, RNA interference, genomic disruptions (e.g., transposons, tilling, homologous recombination, etc.), and the like. The term "knockout plant" refers to a plant that has a disruption in at least one of its ACC synthase genes in at least one cell.

The term "transgenic" refers to a plant that has incorporated nucleic acid sequences, including but not limited to genes, polynucleotides, DNA, RNA, etc., which have been introduced into a plant compared to a non-introduced plant.

The term "endogenous" relates to any gene or nucleic acid sequence that is already present in a cell.

A "transposable element" (TE) or "transposable genetic element" is a DNA sequence that can move from one location to another in a cell. Movement of a transposable element can occur from episome to episome, from episome to chromosome, from chromosome to chromosome, or from chromosome to episome. Transposable elements are characterized by the presence of inverted repeat sequences at their termini. Mobilization is mediated enzymatically by a "transposase." Structurally, a transposable element is categorized as a "transposon," ("TN") or an "insertion sequence element," (IS element) based on the presence or absence, respectively, of genetic sequences in addition to those necessary for mobilization of the element. A mini-transposon or mini-IS element typically lacks sequences encoding a transposase.

The term "nucleic acid" or "polynucleotide" is generally used in its art-recognized meaning to refer to a ribose nucleic acid (RNA) or deoxyribose nucleic acid (DNA) polymer, or analog thereof, e.g., a nucleotide polymer comprising modifications of the nucleotides, a peptide nucleic acid, or the like. In certain applications, the nucleic acid can be a polymer that includes multiple monomer types, e.g., both RNA and DNA subunits. A nucleic acid can be, e.g., a chromosome or chromosomal segment, a vector (e.g., an expression vector), an expression cassette, a naked DNA or RNA polymer, the product of a polymerase chain reaction (PCR), an oligonucleotide, a probe, etc. A nucleic acid can be e.g., single-stranded and/or double-stranded. Unless otherwise indicated, a particular nucleic acid sequence of this invention optionally comprises or encodes complementary sequences, in addition to any sequence explicitly indicated.

The term "polynucleotide sequence" or "nucleotide sequence" refers to a contiguous sequence of nucleotides in a single nucleic acid or to a representation, e.g., a character string, thereof. That is, a "polynucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

The term "subsequence" or "fragment" is any portion of an entire sequence.

A "phenotype" is the display of a trait in an individual plant resulting from the interaction of gene expression and the environment.

An "expression cassette" is a nucleic acid construct, e.g., vector, such as a plasmid, a viral vector, etc., capable of producing transcripts and, potentially, polypeptides encoded by a polynucleotide sequence. An expression vector is capable of producing transcripts in an exogenous cell, e.g., a bacterial cell, or a plant cell, in vivo or in vitro, e.g., a cultured plant protoplast. Expression of a product can be either constitutive or inducible depending, e.g., on the promoter selected. Antisense, sense or RNA interference or silencing configurations that are not or cannot be translated are expressly included by this definition. In the context of an expression vector, a promoter is said to be "operably linked" to a polynucleotide sequence if it is capable of regulating expression of the associated polynucleotide sequence. The term also applies to alternative exogenous gene constructs, such as expressed or integrated transgenes. Similarly, the term operably linked applies equally to alternative or additional transcriptional regulatory sequences such as enhancers, associated with a polynucleotide sequence.

A polynucleotide sequence is said to "encode" a sense or antisense RNA molecule, or RNA silencing or interference molecule or a polypeptide, if the polynucleotide sequence can be transcribed (in spliced or unspliced form) and/or translated into the RNA or polypeptide, or a subsequence thereof.

"Expression of a gene" or "expression of a nucleic acid" means transcription of DNA into RNA (optionally including modification of the RNA, e.g., splicing), translation of RNA into a polypeptide (possibly including subsequent modification of the polypeptide, e.g., posttranslational modification), or both transcription and translation, as indicated by the context.

The term "gene" is used broadly to refer to any nucleic acid associated with a biological function. Genes typically include coding sequences and/or the regulatory sequences required for expression of such coding sequences. The term "gene" applies to a specific genomic sequence, as well as to a cDNA or an mRNA encoded by that genomic sequence. Genes also include non-expressed nucleic acid segments that, for example, form recognition sequences for other proteins. Non-expressed regulatory sequences include promoters and enhancers, to which regulatory proteins such as transcription factors bind, resulting in transcription of adjacent or nearby sequences.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

The term "recombinant" indicates that the material (e.g., a cell, a nucleic acid, or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures; a "recombinant polypeptide" or "recombinant protein" is a polypeptide or protein which is produced by expression of a recombinant nucleic acid. Examples of recombinant cells include cells containing recombinant nucleic acids and/or recombinant polypeptides.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating.

In the context of the invention, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. An isolated plant cell, for example, can be in an environment (e.g., a cell culture system, or purified from cell culture) other than the native environment of wild-type plant cells (e.g., a whole plant).

The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described below.

A "host cell", as used herein, is a cell which has been transformed or transfected, or is capable of transformation or transfection, by an exogenous polynucleotide sequence. "Exogenous polynucleotide sequence" is defined to mean a sequence not naturally in the cell, or which is naturally present in the cell but at a different genetic locus, in different copy number, or under direction of a different regulatory element.

A "promoter", as used herein, includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells, such as *Agrobacterium* or *Rhizobium*. Examples of promoters under developmental control include promoters that preferentially initiate transcription in certain tissues, such as leaves, roots, or seeds or spatially in regions such as endosperm, embryo, or meristematic regions. Such promoters are referred to as "tissue-preferred" or "tissue-specific". A temporally regulated promoter drives expression at particular times, such as between 0-25 days after pollination. A "cell-type-preferred" promoter primarily drives expression in certain cell types in one or more organs, for example, vascular cells in roots or leaves. An "inducible" promoter is a promoter that is under environmental control and may be inducible or de-repressible. Examples of environmental conditions that may effect transcription by inducible promoters include anaerobic conditions or the presence of light. Tissue-specific, cell-type-specific, and inducible promoters constitute the class of "non-constitutive" promoters. A "constitutive" promoter is a promoter that is active under most environmental conditions and in all or nearly all tissues, at all or nearly all stages of development.

"Transformation", as used herein, is the process by which a cell is "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to higher eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6, Panels A, B and C illustrate leaf transpiration (Panel A), stomatal conductance (Panel B) and $CO_2$ assimilation (Panel C) for wild-type (B73, +/+), ACS2 null (7, O/O) and ACS6 null (15, O/O) mutant leaves. Plants were grown under limited water conditions and each leaf on a plant was measured at forty days after pollination. Values represent a mean of six determinations.

Figure 8:
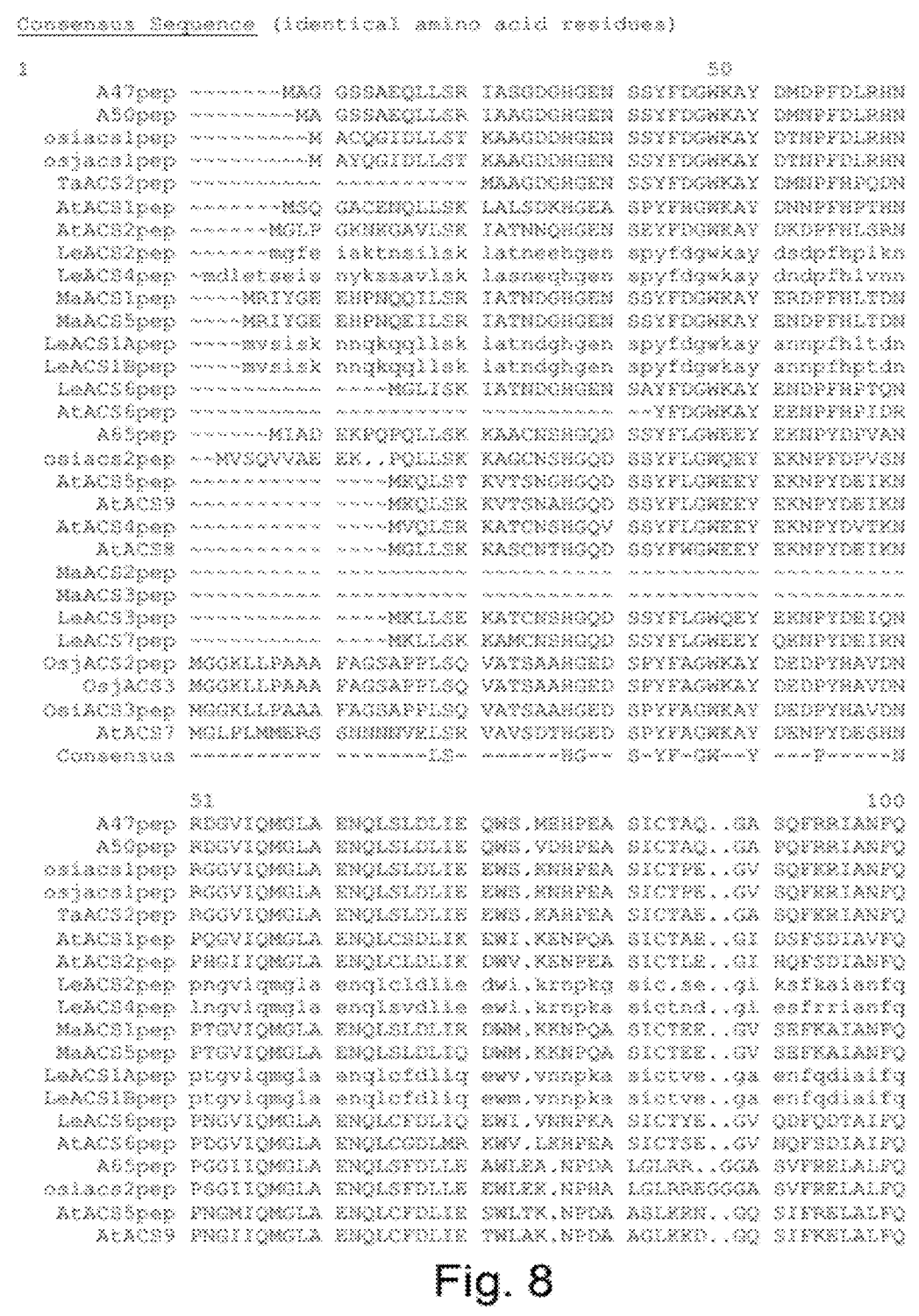

FIG. 8 illustrates a peptide consensus sequence alignment with ACC synthase sequences of A47 (also known as ACS2 or ACC2), A50 (also known as ACS7 or ACC7), and A65 (also known as ACS6 or ACC6) with both dicot (AtACS, LeACS) and monocot (OsiACS, OsjACS, TaACS, and MaACS) species. The alignment is done with a most stringent criteria (identical amino acids) and the plurality is 26.00, the threshold is 4, the AveWeight is 1.00, the AveMatch is 2.78 and the AvMisMatch is −2.25. SEQ ID NOs are as follows: A47pep SEQ ID NO:25; A50pep SEQ ID NO:26; osiacs1pep SEQ ID NO:27; osjacs1pep SEQ ID NO:28; TaACS2pep SEQ ID NO:29; AtACS1pep SEQ ID NO:30; AtACS2pep SEQ ID NO:31; LeACS2pep SEQ ID NO:32; LeACS4pep SEQ ID NO:33; MaACS1pep SEQ ID NO:34; MaACS5pep SEQ ID NO:35; LeACS1Apep SEQ ID NO:36; LeACS1Bpep SEQ ID NO:37; LeACS6pep SEQ ID NO:38; AtACS6pep SEQ ID NO:39; A65pep SEQ ID NO:40; osiacs2pep SEQ ID NO:41; AtACS5pep SEQ ID NO:42; AtACS9 SEQ ID NO:43; AtACS4pep SEQ ID NO:44; AtACS8 SEQ ID NO:45; MaACS2pep SEQ ID NO:46; MaACS3pep SEQ ID NO:47; LeACS3pep SEQ ID NO:48; LeACS7pep SEQ ID NO:49; OsjACS2pep SEQ ID NO:50; OsjACS3 SEQ ID NO:51; OsiACS3pep SEQ ID NO:52; AtACS7 SEQ ID NO:53; and the peptide consensus sequence SEQ ID NO:58.

Figure 9:
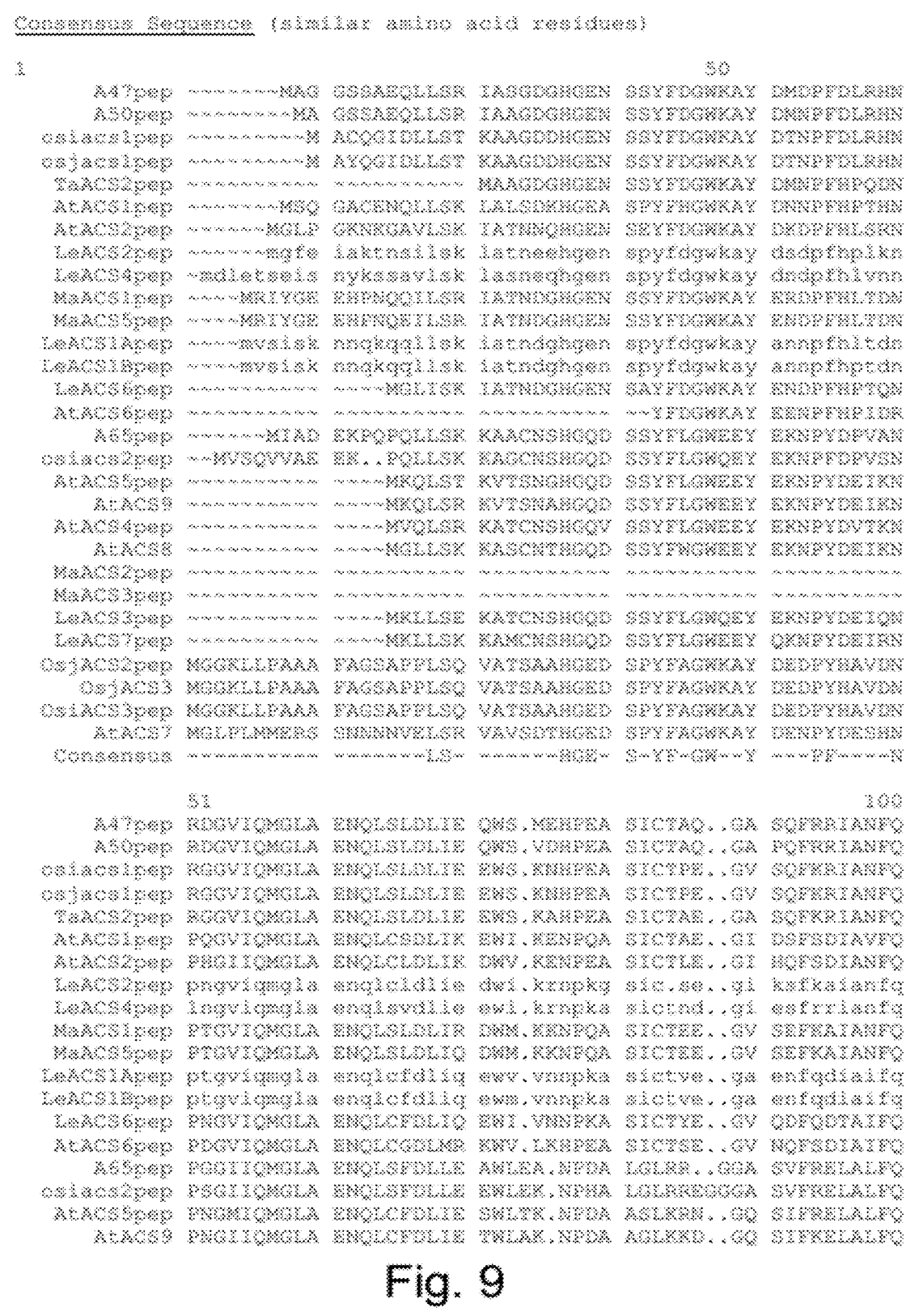
Figure 9:
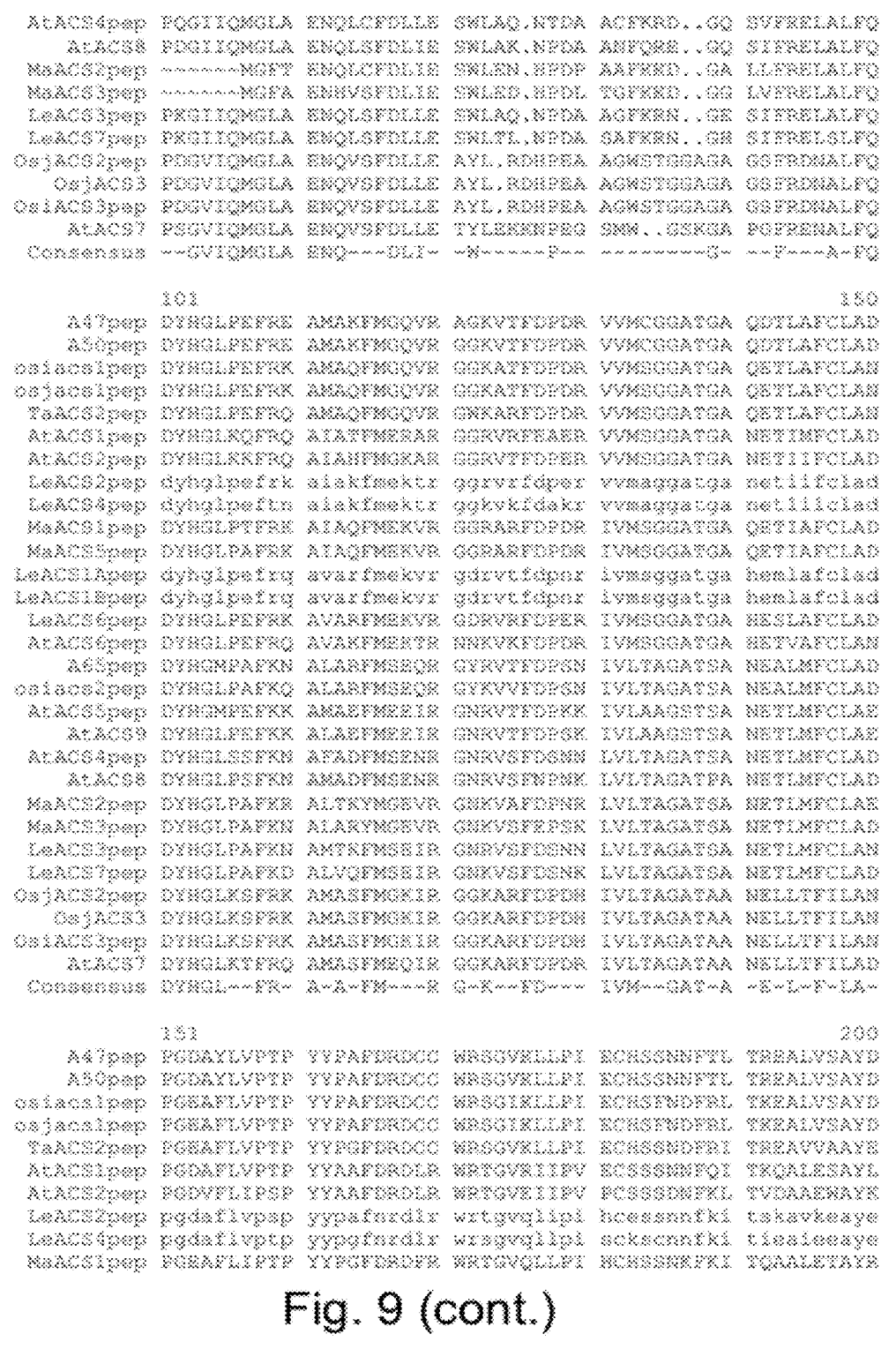
Figure 9:
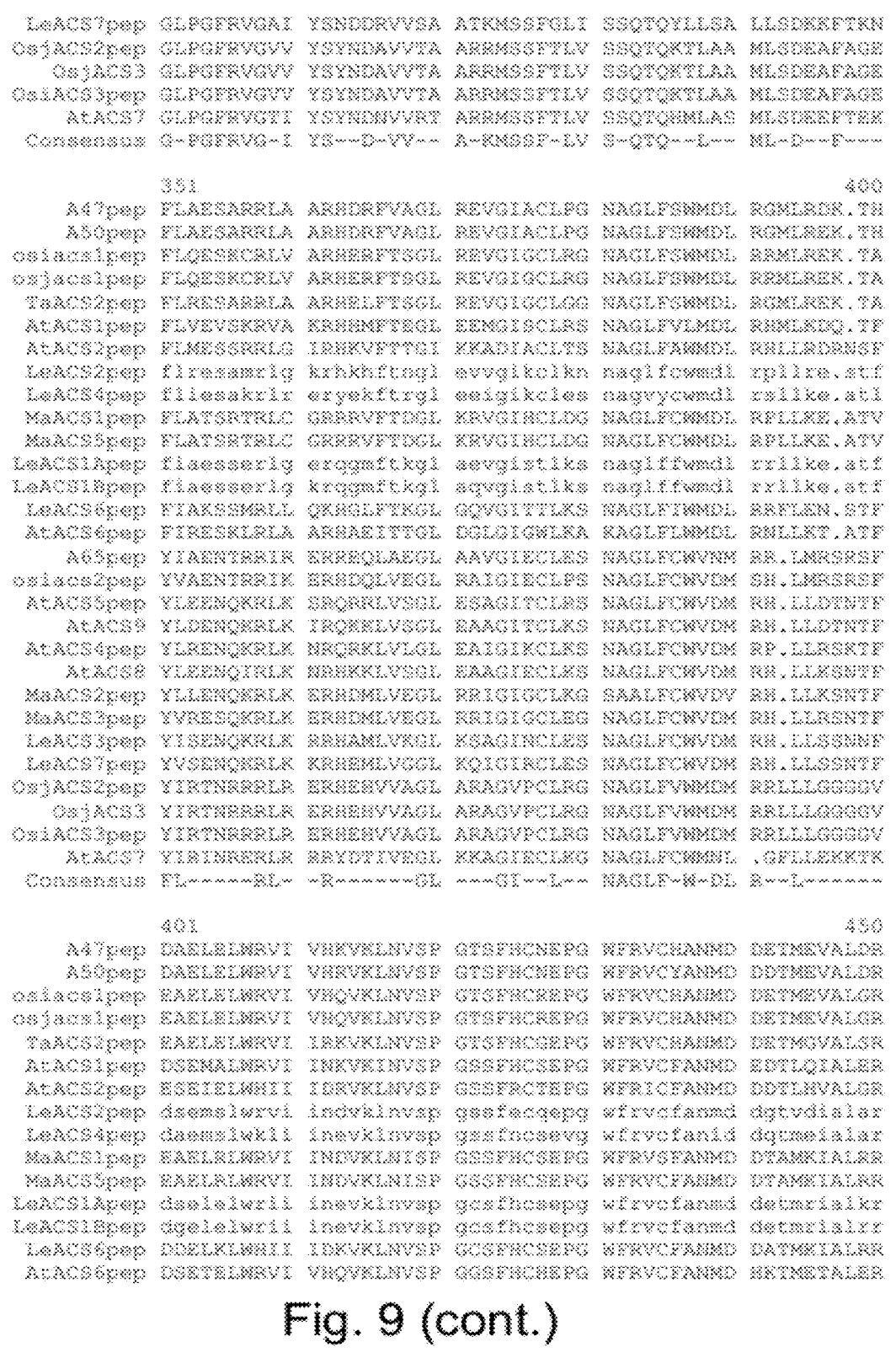
Figure 9:
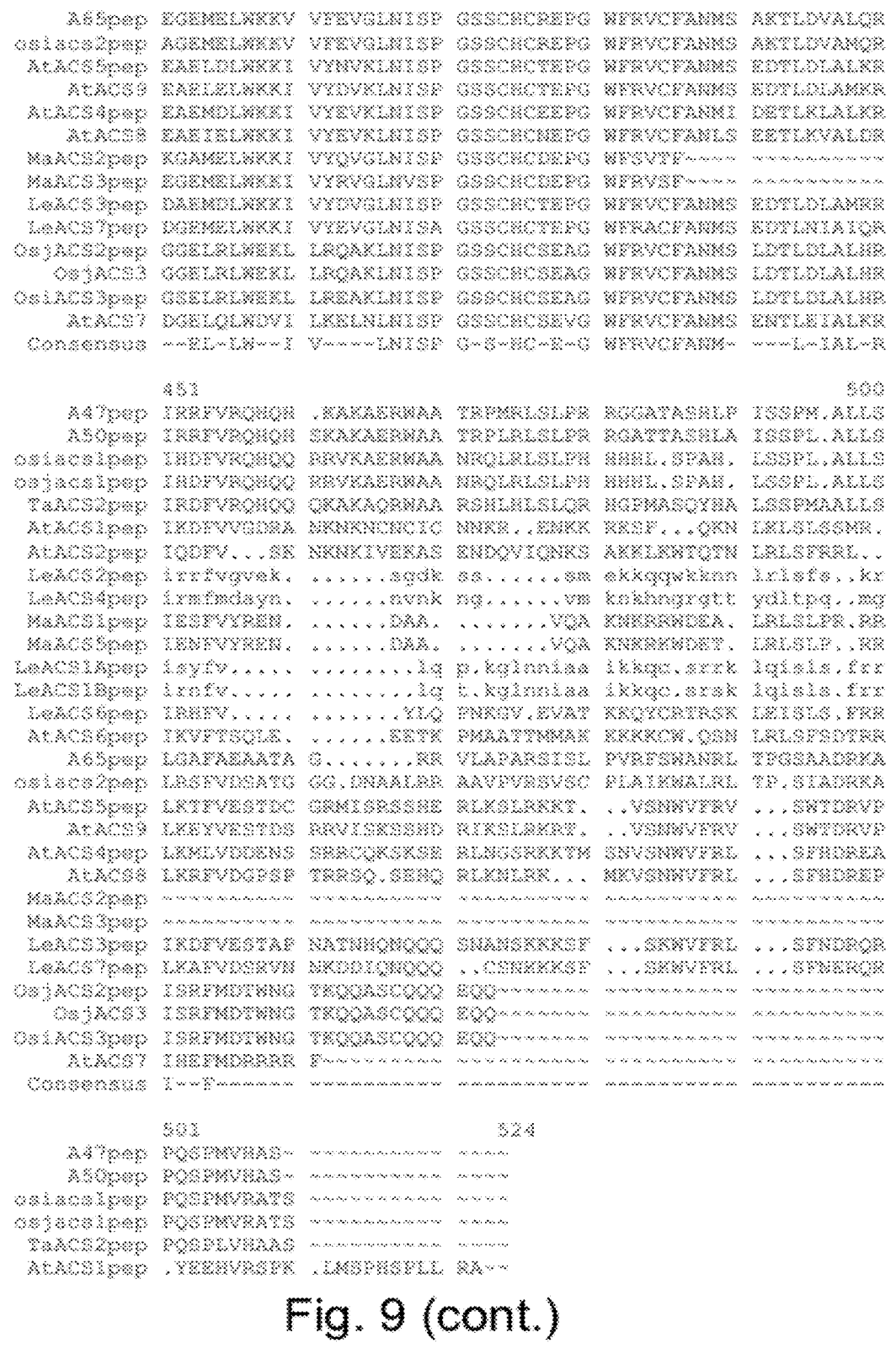

FIG. 9 illustrates a peptide consensus sequence alignment with ACC synthase sequences of A47 (also known as ACS2 or ACC2), A50 (also known as ACS7 or ACC7), and A65 (also known as ACS6 or ACC6) with both dicot (AtACS, LeACS) and monocot (OsiACS, OsjACS, TaACS, MaACS) species (SEQ ID NOs:25-53). The alignment is done with a stringent criteria (similar amino acid residues) and the plurality is 26.00, the threshold is 2, the AveWeight is 1.00, the AveMatch is 2.78 and the AvMisMatch is −2.25. The peptide consensus sequence is set forth in SEQ ID NO:59.

Figure 10:
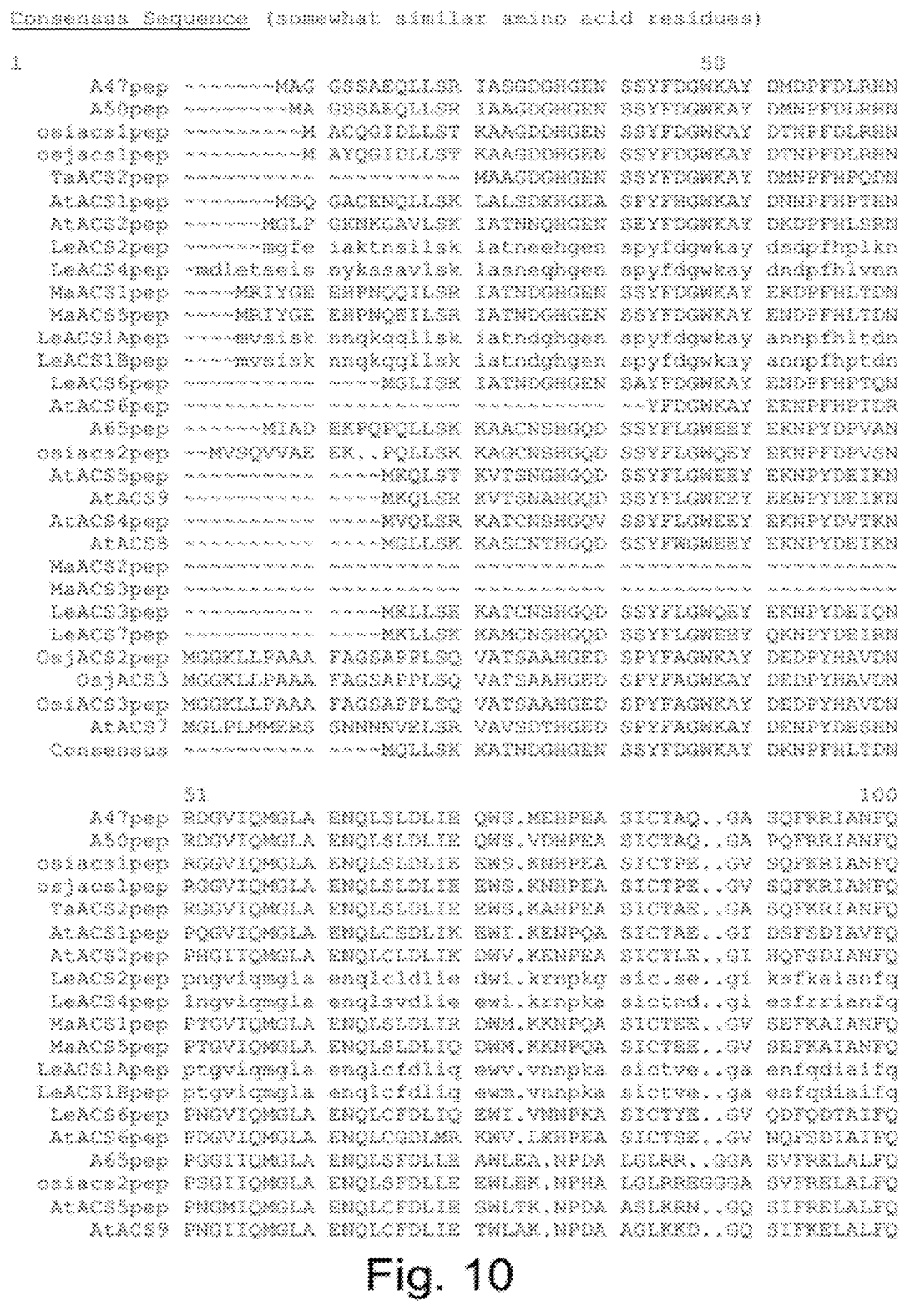
Figure 10:
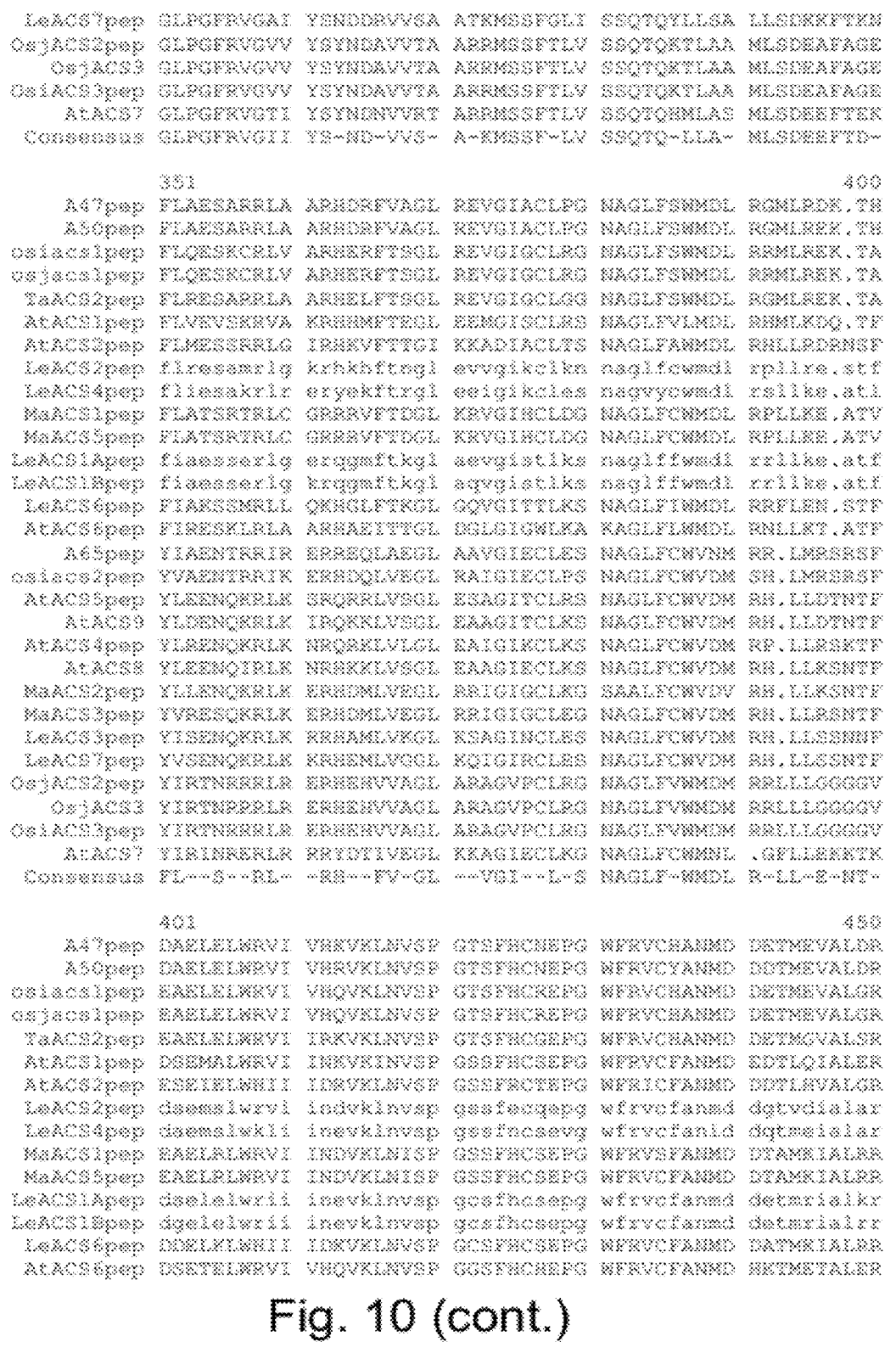
Figure 10:
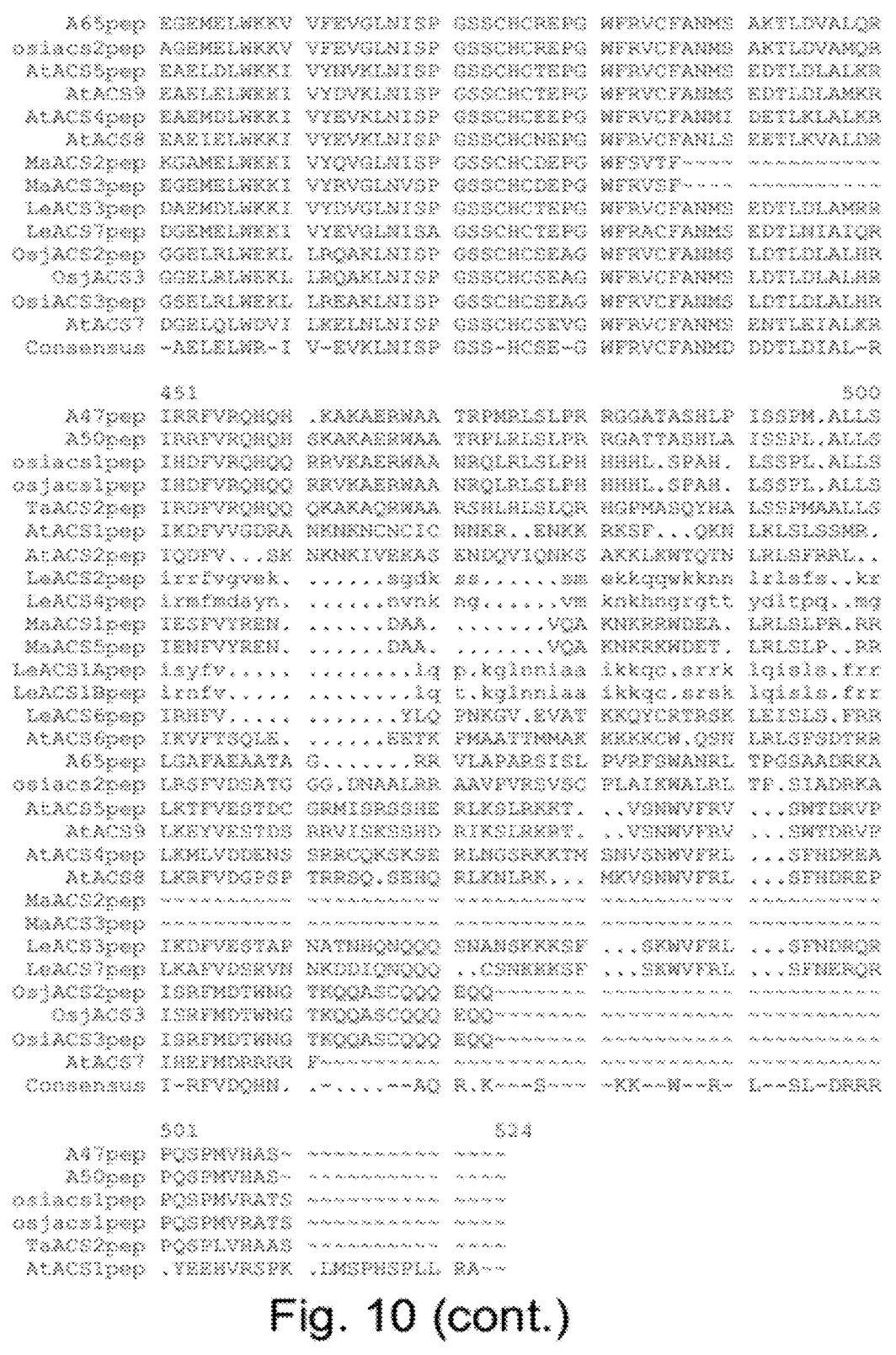

FIG. 10 illustrates a peptide consensus sequence alignment with ACC synthase sequences of A47 (also known as ACS2 or ACC2), A50 (also known as ACS7 or ACC7), and A65 (also known as ACS6 or ACC6) with both dicot (AtACS, LeACS) and monocot (OsiACS, OsjACS, TaACS, MaACS) species (SEQ ID NOs:25-53). The alignment is done with a less stringent criteria (somewhat similar amino acid residues) and the plurality is 26.00, the threshold is 0, the AveWeight is 1.00, the AveMatch is 2.78 and the AvMisMatch is −2.25. The peptide consensus sequence is set forth in SEQ ID NO:60.

FIG. 11 illustrates a peptide consensus sequence alignment with ACC synthase sequences of A47 (also known as ACS2 or ACC2), and A50 (also known as ACS7 or ACC7) with sequences that are most similar to ACS2 and ACS7 (SEQ ID NOs:25-39). The alignment is done with most stringent criteria (identical amino acids) and the plurality is 15.00, the threshold is 4, the AveWeight is 1.00, the AveMatch is 2.78 and the AvMisMatch is −2.25. The peptide consensus sequence is set forth in SEQ ID NO:61.

FIG. 12 illustrates a peptide consensus sequence alignment with ACC synthase sequences of A47 (also known as ACS2 or ACC2), and A50 (also known as ACS7 or ACC7) with sequences that are most similar to ACS2 and ACS7 (SEQ ID NOs:25-39). The alignment is done with stringent criteria (similar amino acid residues) and the plurality is 15.00, the threshold is 2, the AveWeight is 1.00, the AveMatch is 2.78 and the AvMisMatch is −2.25. The peptide consensus sequence is set forth in SEQ ID NO:62.

FIG. 13 illustrates a peptide consensus sequence alignment with ACC synthase sequences of A65 (also known as ACS6 or ACC6) with sequences that are most similar to ACS6 (SEQ ID NOs:40-53). The alignment is done with most stringent criteria (identical amino acids) and the plurality is 14.00, the threshold is 4, the AveWeight is 1.00, the AveMatch is 2.78 and the AvMisMatch is −2.25. The peptide consensus sequence is set forth in SEQ ID NO:63.

Figure 14:
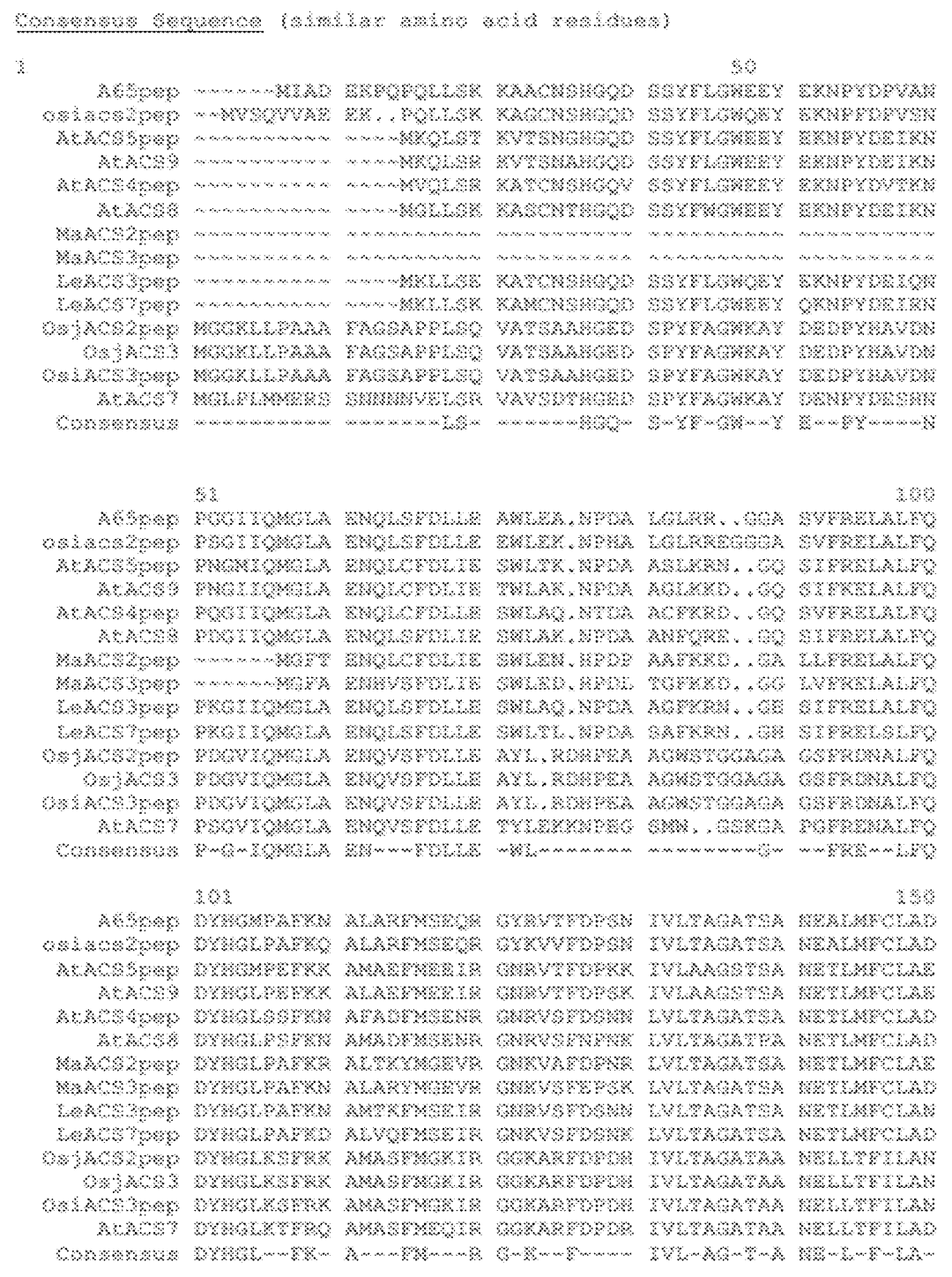
Figure 14:
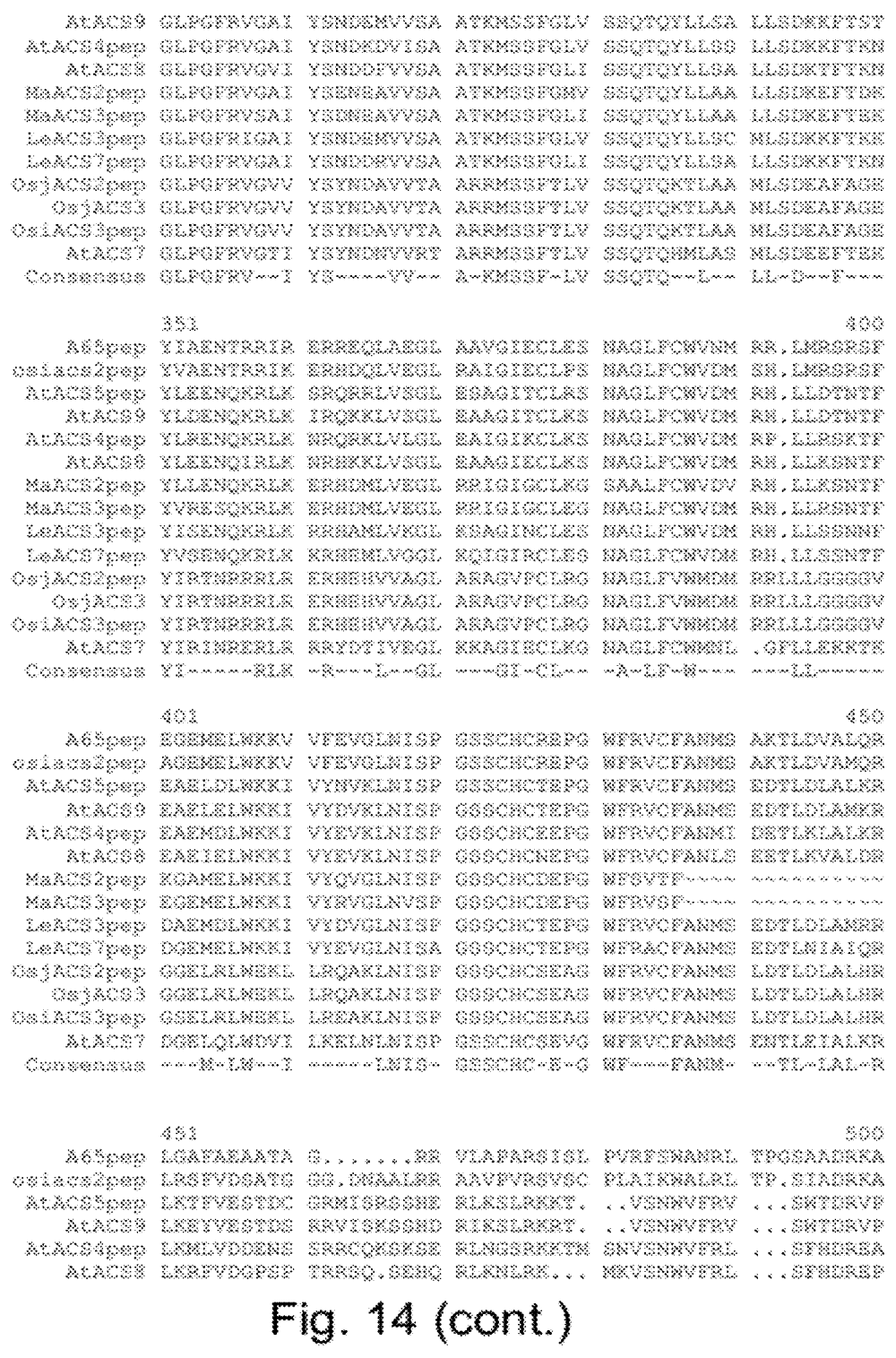

FIG. 14 illustrates a peptide consensus sequence alignment with ACC synthase sequences of A65 (also known as ACS6 or ACC6) with sequences that are most similar to ACS6 (SEQ ID NOs:40-53). The alignment is done with stringent criteria (similar amino acid residues) and the plurality is 14.00, the threshold is 2, the AveWeight is 1.00, the AveMatch is 2.78 and the AvMisMatch is −2.25. The peptide consensus sequence is set forth in SEQ ID NO:64.

FIG. 15 illustrates a peptide consensus sequence alignment with ACC synthase sequences of A47 (also known as ACS2 or ACC2), A50 (also known as ACS7 or ACC7), and A65 (also known as ACS6 or ACC6) (SEQ ID NOs:25-26 and 40). The alignment is done with most stringent criteria (identical amino acids) and the plurality is 3.00, the threshold is 4, the AveWeight is 1.00, the AveMatch is 2.78 and the AvMisMatch is −2.25. The peptide consensus sequence is set forth in SEQ ID NO:65.

FIG. 16 illustrates a peptide consensus sequence alignment with ACC synthase sequences of A47 (also known as ACS2 or ACC2), A50 (also known as ACS7 or ACC7), and A65 (also known as ACS6 or ACC6) (SEQ ID NOs:25-26 and 40). The alignment is done with stringent criteria (similar amino acid residues) and the plurality is 3.00, the threshold is 2, the AveWeight is 1.00, the AveMatch is 2.78 and the AvMisMatch is −2.25. The peptide consensus sequence is set forth in SEQ ID NO:66.

FIG. 22 Panels A-C illustrate the ACS6 hairpin construct. Panel A is a schematic diagram of PHP20323 containing a ubiquitin promoter (UBI1ZM PRO) driving expression of the ACS6 hairpin (a terminal repeat consisting of TR1 and TR2). RB represents the *Agrobacterium* right border sequence. A 3564 bp fragment of the 49108 bp cassette is illustrated. Panel B presents the sequence of ZM-ACS6 TR1 (SEQ ID NO:56), and Panel C presents the sequence of ZM-ACS6 TR2 (SEQ ID NO:57).

DETAILED DESCRIPTION

Figure 1:
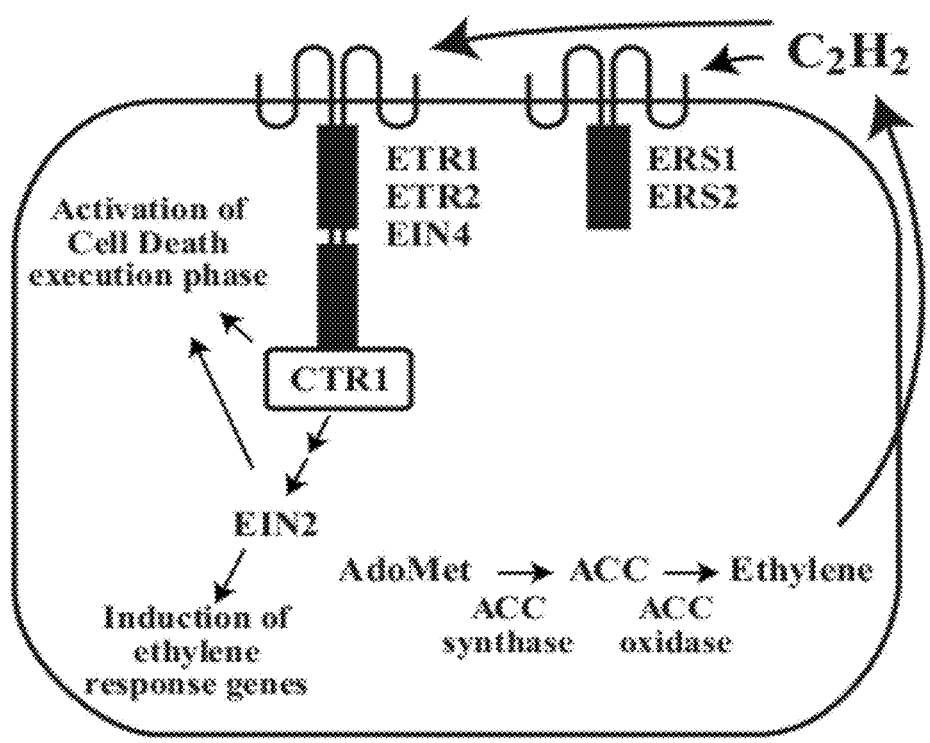
FIG. 1 schematically illustrates ethylene biosynthetic and signaling genes in plants, e.g., *Arabidopsis*.

"Stay-green" is a term commonly used to describe a plant phenotype. Staygreen is a desirable trait in commercial agriculture, e.g., a desirable trait associated with grain filling. As described herein, five fundamentally distinct types of stay-green have been described, including Types A, B, C, D, and E (see, e.g., Thomas H and Smart C M (1993) *Crops that stay green. Annals of Applied Biology* 123: 193-219; and Thomas H and Howarth C J (2000) *Five ways to stay green. Journal of Experimental Botany* 51: 329-337). However, there is very little description of the biochemical, physiological or molecular basis for genetically determined stay-green. See, e.g., Thomas and Howarth, supra. This invention provides a molecular/biochemical basis for staygreen potential.

A number of environmental and physiological conditions have been shown to significantly alter the timing and progression of leaf senescence and can provide some insight into the basis for this trait. Among environmental factors, light is probably the most significant, and it has long been established that leaf senescence can be induced in many plant species by placing detached leaves in darkness. See, e.g., Weaver L M and Amasino R M (2001) *Senescence is induced in individually darkened Arabidopsis leaves, but inhibited in whole* darkened plants. *Plant Physiology* 127: 876-886. Limited nutrient and water availability have also been shown to induce leaf senescence prematurely. See, e.g., Rosenow D T, et al. (1983) *Drought-tolerant sorghum and cotton germplasm. Agricultural Water Management* 7: 207-222. Among physiological determinants, growth regulators play a key role in directing the leaf senescence program. Modification of cytokinin levels can significantly delay leaf senescence. For example, plants transformed with isopentenyl transferase (ipt), an *Agrobacterium* gene encoding a rate-limiting step in cytokinin biosynthesis, when placed under the control of a senescence inducible promoter, resulted in autoregulated cytokinin production and a strong stay-green phenotype. See, e.g., Gan S and Amasino R M (1995) *Inhibition of leaf senescence by autoregulated production of cytokinin. Science* 270: 1986-1988. However, there are other factors that are involved with this trait.

For example, ethylene has also been implicated in controlling leaf senescence (see, e.g., Davis K M and Grierson D (1989) *Identification of cDNA clones for tomato (Lycopersicon esculentum* Mill.) *mRNAs that accumulate during fruit ripening and leaf senescence in response to ethylene. Planta* 179: 73-80) and some dicot plants impaired in ethylene production or perception also show a delay in leaf senescence (see, e.g., Picton S, et al. (1993) *Altered fruit ripening and leaf senescence in tomatoes expressing an antisense ethylene forming enzyme transgene. The Plant Journal* 3: 469-481; Grbic V and Bleeker A B (1995) *Ethylene regulates the timing of leaf senescence in Arabidopsis. The Plant Journal* 8: 95-102; and, John I, et al. (1995) *Delayed leaf senescence in ethylene-deficient ACC-oxidase antisense tomato plants: molecular and physiological analysis. The Plant Journal* 7: 483-490), which can be phenocopied by exogenous application of inhibitors of ethylene biosynthesis and action (see, e.g., Abeles F B, et al. (1992) *Ethylene in Plant Biology*. Academic Press, San Diego, Calif.).

Ethylene perception involves membrane-localized receptors that, e.g., in *Arabidopsis* include ETR1, ERS1, ETR2, ERS2, and EIN4 (see FIG. 1). ETR1, ETR2, and EIN4 are composed of three domains, an N-terminal ethylene binding domain, a putative histidine protein kinase domain, and a C-terminal receiver domain, whereas ERS1 and ERS2 lack the receiver domain. These genes have been grouped into two subfamilies based on homology, where ETR1 and ERS1 comprise one subfamily and ETR2, ERS2 and EIN4 comprise the other. In *Arabidopsis*, analysis of loss-of-function mutants has revealed that ethylene inhibits the signaling activity of these receptors and subsequently their ability to activate CTR1, a negative regulator of ethylene responses that is related to mammalian RAF-type serine/threonine kinases. Ethylene signal transduction pathway suggests that ethylene binding to the receptor inhibits its own kinase activity, resulting in decreased activity of CTR1, and consequently, an increase in EIN2 activity (which acts downstream of CTR1) ultimately leads to increases in ethylene responsiveness. Differential expression of members of the ethylene receptor family has been observed, both developmentally and in response to ethylene.

The identification and analysis of mutants in *Arabidopsis* and tomato that are deficient in ethylene biosynthesis and perception are valuable in establishing the role that ethylene plays in plant growth and development. Mutant analysis has also been instrumental in identifying and characterizing the ethylene signal transduction pathway. While many ethylene mutants have been identified in dicot plants (e.g., *Arabidopsis* and tomato), no such mutants have been identified in monocots (e.g., rice, wheat, and corn). Herein are described, e.g., ethylene mutants (e.g., in a monocot) deficient in ACC synthase, the first enzyme in the ethylene biosynthetic pathway.

This invention provides ACC synthase polynucleotide sequences from plants, which modulate staygreen potential in plants and ethylene production, exemplified by, e.g., SEQ ID NO:1 through SEQ ID NO:6 and SEQ ID NO:10 and, e.g., a set of polypeptide sequences which modulate staygreen potential in plants and/or ethylene production, e.g., SEQ ID NO:7 through SEQ ID NO:9 and SEQ ID NO:11. The invention also provides knockout plant cells deficient in ACC synthase and knockout plants having a staygreen potential phenotype, as well as knockout plants having a male sterility phenotype. The plants of the invention can have the characteristic of regulating responses to environmental stress better than control plants, e.g., higher tolerance to drought stress. Plants of the invention can also have a higher tolerance for other stresses (e.g., crowding in, e.g., maize) compared to a control plants. Thus, plants of the invention can be planted at higher densities than currently practiced by farmers. In addition, plants of the invention are critical in elucidating the regulatory roles that ethylene plays throughout plant development as well as its role in regulating responses to stress, e.g., drought, crowding, etc.

Ethylene in Plants

Ethylene ($C_2H_4$) is a gaseous plant hormone. It has a varied spectrum of effects that can be tissue and/or species specific. For example, physiological activities include, but are not limited to, promotion of food ripening, abscission of leaves and fruit of dicotyledonous species, flower senescence, stem extension of aquatic plants, gas space (aerenchyma) development in roots, leaf epinastic curvatures, stem and shoot swelling (in association with stunting), femaleness in curcubits, fruit growth in certain species, apical hook closure in etiolated shoots, root hair formation, flowering in the Bromeliaceae, diageotropism of etiolated shoots, and increased gene expression (e.g., of polygalacturonase, cellulase, chitinases, $\beta$-1,3-glucanases, etc.). Ethylene is released naturally by ripening fruit and is also produced by most plant tissues, e.g., in response to stress (e.g., drought, crowding, disease or pathogen attack, temperature (cold or heat) stress, wounding, etc.), and in maturing and senescing organs.

Ethylene is generated from methionine by a well-defined pathway involving the conversion of S-adenosyl-L-methionine (SAM or Ado Met) to the cyclic amino acid 1-aminocyclopropane-1-carboxylic acid (ACC) which is facilitated by ACC synthase (see, e.g., FIG. 1). Sulphur is conserved in the process by recycling 5'-methylhioadenosine.

ACC synthase is an aminotransferase which catalyzes the rate limiting step in the formation of ethylene by converting S-adenosylmethionine to ACC. Typically, the enzyme requires pyridoxal phosphate as a cofactor. ACC synthase is typically encoded in multigene families. Examples include SEQ ID NOs:1-3, described herein. Individual members can exhibit tissue-specific regulation and/or are induced in response to environmental and chemical stimuli. Features of the invention include ACC synthase sequences and subsequences. See the section herein entitled "Polynucleotides and Polypeptides of the Invention."

Ethylene is then produced from the oxidation of ACC through the action of ACC oxidase (also known as the ethylene forming enzyme) with hydrogen cyanide as a secondary product that is detoxified by $\beta$-cyanoalanine synthase. ACC oxidase is encoded by multigene families in which individual members exhibit tissue-specific regulation and/or are induced in response to environmental and chemical stimuli. Activity of ACC oxidase can be inhibited by anoxia and cobalt ions. The ACC oxidase enzyme is stereospecific and uses cofactors, e.g., $Fe^{+2}$, $O_2$, ascorbate, etc. Finally, ethylene is metabolized by oxidation to $CO_2$ or to ethylene oxide and ethylene glycol.

Polynucleotides and Polypeptides of the Invention

The invention features the identification of gene sequences, coding nucleic acid sequences, and amino acid sequences of ACC synthase, which are associated, e.g., with staygreen potential in plants and/or ethylene production. The sequences of the invention can influence staygreen potential in plants by modulating the production of ethylene.

Polynucleotide sequences of the invention include, e.g., the polynucleotide sequences represented by SEQ ID NO:1 through SEQ ID NO:6 and SEQ ID NO:10, and subsequences thereof. In addition to the sequences expressly provided in the accompanying sequence listing, the invention includes polynucleotide sequences that are highly related structurally and/or functionally. For example, polynucleotides encoding polypeptide sequences represented by SEQ ID NO:7 through SEQ ID NO:9 and SEQ ID NO:11, or subsequences thereof, are one embodiment of the invention. In addition, polynucleotide sequences of the invention include polynucleotide sequences that hybridize under stringent conditions to a polynucleotide sequence comprising any of SEQ ID NO:1-SEQ ID NO:6 and SEQ ID NO:10, or a subsequence thereof (e.g., a subsequence comprising at least 100 contiguous nucleotides). Polynucleotides of the invention also include ACC synthase sequences and/or subsequences configured for RNA production, e.g., mRNA, antisense RNA, sense RNA, RNA silencing and interference configurations, etc.

In addition to the polynucleotide sequences of the invention, e.g., enumerated in SEQ ID NO:1 to SEQ ID NO:6 and SEQ ID NO:10, polynucleotide sequences that are substantially identical to a polynucleotide of the invention can be used in the compositions and methods of the invention. Substantially identical or substantially similar polynucleotide sequences are defined as polynucleotide sequences that are identical, on a nucleotide by nucleotide bases, with at least a subsequence of a reference polynucleotide, e.g., selected from SEQ ID NOs:1-6 and 10. Such polynucleotides can include, e.g., insertions, deletions, and substitutions relative to any of SEQ ID NOs:1-6 and 10. For example, such polynucleotides are typically at least about 70% identical to a reference polynucleotide selected from among SEQ ID NO:1 through SEQ ID NO:6 and SEQ ID NO:10, or subsequence thereof. For example, at least 7 out of 10 nucleotides within a window of comparison are identical to the reference sequence selected, e.g., from SEQ ID NO:1-6 and 10. Frequently, such sequences are at least about 70%, at least about 75%, at least about 80%, at least about 85%, at least about 90%, at least about 95%, at least about 98%, at least about 99%, or at least about 99.5%, identical to the reference sequence, e.g., at least one of SEQ ID NO:1 to SEQ ID NO:6 or SEQ ID NO:10. Subsequences of the polynucleotides of the invention described above, e.g., SEQ ID NOs: 1-6 and 10, including, e.g., at least about 5, at least about 10, at least about 15, at least about 20, at least about 25, at least about 50, at least about 75, at least about 100, at least about 500, about 1000 or more, contiguous nucleotides or complementary subsequences thereof are also a feature of the invention. Such subsequences can be, e.g., oligonucleotides, such as synthetic oligonucleotides, isolated oligonucleotides, or full-length genes or cDNAs.

In addition, polynucleotide sequences complementary to any of the above described sequences are included among the polynucleotides of the invention.

Polypeptide sequences of the invention include, e.g., the amino acid sequences represented by SEQ ID NO:7 through SEQ ID NO:9 and SEQ ID NO:11, and subsequences thereof. In addition to the sequences expressly provided in the accompanying sequence listing, the invention includes amino acid sequences that are highly related structurally and/or functionally. For example, in addition to the amino acid sequences of the invention, e.g., enumerated in SEQ ID NO:7 to SEQ ID NO:9 and SEQ ID NO:11, amino acid sequences that are substantially identical to a polypeptide of the invention can be used in the compositions and methods of the invention. Substantially identical or substantially similar amino acid sequences are defined as amino acid sequences that are identical, on an amino acid by amino acid bases, with at least a subsequence of a reference polypeptide, e.g., selected from SEQ ID NOs:7-9 and 11. Such polypeptides can include, e.g., insertions, deletions, and substitutions relative to any of SEQ ID NOs:7-9 and 11. For example, such polypeptides are typically at least about 70% identical to a reference polypeptide selected from among SEQ ID NO:7 through SEQ ID NO:9 and SEQ ID NO:11, or a subsequence thereof. For example, at least 7 out of 10 amino acids within a window of comparison are identical to the reference sequence selected, e.g., from SEQ ID NO:7-9 and 11. Frequently, such sequences are at least about 70%, at least about 75%, at least about 80%, at least about 85%, at least about 90%, at least about 95%, at least about 98%, at least about 99%, or at least about 99.5%, identical to the reference sequence, e.g., at least one of SEQ ID NO:7 to SEQ ID NO:9 or SEQ ID NO:11. Subsequences of the polypeptides of the invention described above, e.g., SEQ ID NOs:7-9 and 11, including, e.g., at least about 5, at least about 10, at least about 15, at least about 20, at least about 25, at least about 50, at least about 75, at least about 100, at least about 500, about 1000 or more, contiguous amino acids are also a feature of the invention. Conservative variants of amino acid sequences or subsequences of the invention are also amino acid sequences of the invention. Polypeptides of the invention are optionally immunogenic, enzymatically active, enzymatically inactive, and the like.

Where the polynucleotide sequences of the invention are translated to form a polypeptide or subsequence of a polypeptide, nucleotide changes can result in either conservative or non-conservative amino acid substitutions. Conservative amino acid substitutions refer to the interchangeability of residues having functionally similar side chains. Conservative substitution tables providing functionally similar amino acids are well known in the art. Table 1 sets forth six groups which contain amino acids that are "conservative substitutions" for one another. Other conservative substitution charts are available in the art, and can be used in a similar manner.

TABLE 1

Conservative Substitution Group

| | | | |
|---|---|---|---|
| 1 Alanine (A) | Serine (S) | Threonine (T) | |
| 2 Aspartic acid (D) | Glutamic acid (E) | | |
| 3 Asparagine (N) | Glutamine (Q) | | |
| 4 Arginine (R) | Lysine (K) | | |
| 5 Isoleucine (I) | Leucine (L) | Methionine (M) | Valine (V) |
| 6 Phenylalanine (F) | Tyrosine (Y) | Tryptophan (W) | |

One of skill in the art will appreciate that many conservative substitutions of the nucleic acid constructs which are disclosed yield functionally identical constructs. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence (e.g., about 1%, 2%, 3%, 4%, 5%, 6%, 7%, 8%, 9%, 10% or more) are substituted with different amino acids with highly similar properties, are also readily identified as being highly similar to a disclosed construct. Such conservative variations of each disclosed sequence are a feature of the invention.

Methods for obtaining conservative variants, as well as more divergent versions of the nucleic acids and polypeptides of the invention, are widely known in the art. In addition to naturally occurring homologues which can be obtained, e.g., by screening genomic or expression libraries according to any of a variety of well-established protocols, see, e.g., Ausubel et al. *Current Protocols in Molecular Biology* (supplemented through 2004) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel Guide to *Molecular Cloning Techniques, Methods in Enzymology* volume 152 Academic Press, Inc., San Diego, Calif. ("Berger"), additional variants can be produced by any of a variety of mutagenesis procedures. Many such procedures are known in the art, including site directed mutagenesis, oligonucleotide-directed mutagenesis, and many others. For example, site directed mutagenesis is described, e.g., in Smith (1985) "*In vitro mutagenesis*" *Ann. Rev. Genet.* 19:423-462, and references therein, Botstein & Shortie (1985) "*Strategies and applications of in vitro mutagenesis*" *Science* 229:1193-1201; and Carter (1986) "*Site-directed mutagenesis*" *Biochem. J.* 237:1-7. Oligonucleotide-directed mutagenesis is described, e.g., in Zoller & Smith (1982) "*Oligonucleotide-directed mutagenesis using M13-derived vectors: an efficient and general procedure for the production of point mutations in any DNA fragment*" *Nucleic Acids Res.* 10:6487-6500). Mutagenesis using modified bases is described e.g., in Kunkel (1985) "*Rapid and efficient site-specific mutagenesis without phenotypic selection*" *Proc. Natl. Acad. Sci. USA* 82:488-492, and Taylor et al. (1985) "*The rapid generation of oligonucleotide-directed mutations at high frequency using phosphorothioate-modified DNA*" *Nucl. Acids Res.* 13: 8765-8787. Mutagenesis using gapped duplex DNA is described, e.g., in Kramer et al. (1984) "*The gapped duplex DNA approach to oligonucleotide-directed mutation construction*" *Nucl. Acids Res.* 12: 9441-9460). Point mismatch mutagenesis is described, e.g., by Kramer et al. (1984) "*Point Mismatch Repair*" *Cell* 38:879-887). Double-strand break mutagenesis is described, e.g., in Mandecki (1986) "*Oligonucleotide-directed double-strand break repair in plasmids of Escherichia coli: a method for site-specific mutagenesis*" *Proc. Natl. Acad. Sci. USA*, 83:7177-7181, and in Arnold (1993) "*Protein engineering for unusual environments*" *Current Opinion in Biotechnology* 4:450-455). Mutagenesis using repair-deficient host strains is described, e.g., in Carter et al. (1985) "*Improved oligonucleotide site-directed mutagenesis using M13 vectors*" *Nucl. Acids Res.* 13: 4431-4443. Mutagenesis by total gene synthesis is described e.g., by Nambiar et al. (1984) "*Total synthesis and cloning of a gene coding for the ribonuclease S protein*" *Science* 223: 1299-1301. DNA shuffling is described, e.g., by Stemmer (1994) "*Rapid evolution of a protein in vitro by DNA shuffling*" *Nature* 370:389-391, and Stemmer (1994) "*DNA shuffling by random fragmentation and reassembly: In vitro recombination for molecular evolution.*" *Proc. Natl. Acad. Sci. USA* 91:10747-10751.

Many of the above methods are further described in *Methods in Enzymology* Volume 154, which also describes useful controls for trouble-shooting problems with various mutagenesis methods. Kits for mutagenesis, library construction and other diversity generation methods are also commercially available. For example, kits are available from, e.g., Amersham International plc (Piscataway, N.J.) (e.g., using the Eckstein method above), Bio/Can Scientific (Mississauga, Ontario, CANADA), Bio-Rad (Hercules, Calif.) (e.g., using the Kunkel method described above), Boehringer Mannheim Corp. (Ridgefield, Conn.), Clonetech Laboratories of BD Biosciences (Palo Alto, Calif.), DNA Technologies (Gaithersburg, Md.), Epicentre Technologies (Madison, Wis.) (e.g., the 5 prime 3 prime kit); Genpak Inc. (Stony Brook, N.Y.), Lemargo Inc (Toronto, CANADA), Invitrogen Life Technologies (Carlsbad, Calif.), New England Biolabs (Beverly, Mass.), Pharmacia Biotech (Peapack, N.J.), Promega Corp. (Madison, Wis.), QBiogene (Carlsbad, Calif.), and Stratagene (La Jolla, Calif.) (e.g., QuickChange™ site-directed mutagenesis kit and Chameleon™ double-stranded, site-directed mutagenesis kit).

Determining Sequence Relationships

The nucleic acid and amino acid sequences of the invention include, e.g., those provided in SEQ ID NO:1 to SEQ ID NO:11 and subsequences thereof, as well as similar sequences. Similar sequences are objectively determined by any number of methods, e.g., percent identity, hybridization, immunologically, and the like. A variety of methods for determining relationships between two or more sequences (e.g., identity, similarity and/or homology) are available and well known in the art. The methods include manual alignment, computer assisted sequence alignment and combinations thereof, for example. A number of algorithms (which are generally computer implemented) for performing sequence alignment are widely available or can be produced by one of skill These methods include, e.g., the local homology algorithm of Smith and Waterman (1981) *Adv. Appl. Math.* 2:482; the homology alignment algorithm of Needleman and Wunsch (1970) *J. Mol. Biol.* 48:443; the search for similarity method of Pearson and Lipman (1988) *Proc. Natl. Acad. Sci.* (USA) 85:2444; and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.).

For example, software for performing sequence identity (and sequence similarity) analysis using the BLAST algorithm is described in Altschul et al. (1990) *J. Mol. Biol.* 215:403-410. This software is publicly available, e.g., through the National Center for Biotechnology Information on the world wide web at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP (BLAST Protein) program uses as defaults a wordlength (W) of 3, an expectation (E) of 10, and the BLOSUM62 scoring matrix (see, Henikoff & Henikoff (1989) *Proc. Natl. Acad. Sci. USA* 89:10915).

Additionally, the BLAST algorithm performs a statistical analysis of the similarity between two sequences (see, e.g., Karlin & Altschul (1993) *Proc. Nat'l. Acad. Sci. USA* 90:5873-5787). One measure of similarity provided by the BLAST algorithm is the smallest sum probability (p(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple DNA, or amino acid, sequence alignments is the CLUSTALW program (Thompson, J. D. et al. (1994) *Nucl. Acids. Res.* 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) *Proc. Natl. Acad. Sci. USA* 89: 10915-10919.

Nucleic Acid Hybridization

Similarity between ACC synthase nucleic acids of the invention can also be evaluated by "hybridization" between single stranded (or single stranded regions of) nucleic acids with complementary or partially complementary polynucleotide sequences.

Hybridization is a measure of the physical association between nucleic acids, typically, in solution, or with one of the nucleic acid strands immobilized on a solid support, e.g., a membrane, a bead, a chip, a filter, etc. Nucleic acid hybridization occurs based on a variety of well characterized physico-chemical forces, such as hydrogen bonding, solvent exclusion, base stacking, and the like. Numerous protocols for nucleic acid hybridization are well known in the art. An extensive guide to the hybridization of nucleic acids is found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," (Elsevier, New York), as well as in Ausubel et al. *Current Protocols in Molecular Biology* (supplemented through 2004) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger"). Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

Conditions suitable for obtaining hybridization, including differential hybridization, are selected according to the theoretical melting temperature ($T_m$) between complementary and partially complementary nucleic acids. Under a given set of conditions, e.g., solvent composition, ionic strength, etc., the $T_m$ is the temperature at which the duplex between the hybridizing nucleic acid strands is 50% denatured. That is, the $T_m$ corresponds to the temperature corresponding to the midpoint in transition from helix to random coil; it depends on the length of the polynucleotides, nucleotide composition, and ionic strength, for long stretches of nucleotides.

After hybridization, unhybridized nucleic acids can be removed by a series of washes, the stringency of which can be adjusted depending upon the desired results. Low stringency washing conditions (e.g., using higher salt and lower temperature) increase sensitivity, but can product nonspecific hybridization signals and high background signals. Higher stringency conditions (e.g., using lower salt and higher temperature that is closer to the $T_m$) lower the background signal, typically with primarily the specific signal remaining. See, also, Rapley, R. and Walker, J. M. eds., *Molecular Biomethods Handbook* (Humana Press, Inc. 1998).

"Stringent hybridization wash conditions" or "stringent conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

An example of stringent hybridization conditions for hybridization of complementary nucleic acids which have more than 100 complementary residues on a filter in a Southern or northern blot is 2×SSC, 50% formamide at 42° C., with the hybridization being carried out overnight (e.g., for approximately 20 hours). An example of stringent wash conditions is a 0.2×SSC wash at 65° C. for 15 minutes (see Sambrook, supra for a description of SSC buffer). Often, the wash determining the stringency is preceded by a low stringency wash to remove signal due to residual unhybridized probe. An example low stringency wash is 2×SSC at room temperature (e.g., 20° C. for 15 minutes).

In general, a signal to noise ratio of at least 2.5×-5× (and typically higher) than that observed for an unrelated probe in the particular hybridization assay indicates detection of a specific hybridization. Detection of at least stringent hybridization between two sequences in the context of the invention indicates relatively strong structural similarity to, e.g., the nucleic acids of ACC synthases provided in the sequence listings herein.

For purposes of the invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

For example, in determining stringent or highly stringent hybridization (or even more stringent hybridization) and wash conditions, the stringency of the hybridization and wash conditions is gradually increased (e.g., by increasing temperature, decreasing salt concentration, increasing detergent concentration, and/or increasing the concentration of organic solvents, such as formamide, in the hybridization or wash), until a selected set of criteria are met. For example, the stringency of the hybridization and wash conditions is gradually increased until a probe comprising one or more polynucleotide sequences of the invention, e.g., selected from SEQ ID NO:1 to SEQ ID NO:6 and SEQ ID NO:10, or a subsequence thereof, and/or complementary polynucleotide sequences thereof, binds to a perfectly matched complementary target (again, a nucleic acid comprising one or more nucleic acid sequences or subsequences selected from SEQ ID NO:1 to SEQ ID NO:6 and SEQ ID NO:10, and complementary polynucleotide sequences thereof), with a signal to noise ratio that is at least 2.5×, and optionally 5×, or 10×, or 100× or more, as high as that observed for hybridization of the probe to an unmatched target, as desired.

Using subsequences derived from the nucleic acids encoding the ACC synthase polypeptides of the invention, novel target nucleic acids can be obtained; such target nucleic acids are also a feature of the invention. For example, such target nucleic acids include sequences that hybridize under stringent conditions to an oligonucleotide probe that corresponds to a unique subsequence of any of the polynucleotides of the invention, e.g., SEQ ID NOs: 1-6, 10, or a complementary sequence thereof; the probe optionally encodes a unique subsequence in any of the polypeptides of the invention, e.g., SEQ ID NOs: 7-9 and 11.

For example, hybridization conditions are chosen under which a target oligonucleotide that is perfectly complementary to the oligonucleotide probe hybridizes to the probe with at least about a 5-10× higher signal to noise ratio than for hybridization of the target oligonucleotide to a negative control non-complimentary nucleic acid.

Higher ratios of signal to noise can be achieved by increasing the stringency of the hybridization conditions such that ratios of about 15×, 20×, 30×, 50× or more are obtained. The particular signal will depend on the label used in the relevant assay, e.g., a fluorescent label, a colorimetric label, a radioactive label, or the like.

Vectors, Promoters and Expression Systems

Nucleic acids of the invention can be in any of a variety of forms, e.g., expression cassettes, vectors, plasmids, or linear nucleic acid sequences. For example, vectors, plasmids, cosmids, bacterial artificial chromosomes (BACs), YACs (yeast artificial chromosomes), phage, viruses and nucleic acid segments can comprise an ACC synthase nucleic acid sequence or subsequence thereof which one desires to introduce into cells. These nucleic acid constructs can further include promoters, enhancers, polylinkers, regulatory genes, etc.

Thus, the present invention also relates, e.g., to vectors comprising the polynucleotides of the present invention, host cells that incorporate the vectors of the invention, and the production of polypeptides of the invention by recombinant techniques.

In accordance with this aspect of the invention, the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors, also may be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host, operably linked to the polynucleotide to be expressed. Appropriate trans-acting factors are supplied by the host, supplied by a complementing vector or supplied by the vector itself upon introduction into the host.

In certain preferred embodiments in this regard, the vectors provide for preferred expression. Such preferred expression may be inducible expression, temporally limited expression, or expression restricted to predominantly certain types of cells, or any combination of the above. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids and binaries used for *Agrobacterium*-mediated transformations. All may be used for expression in accordance with this aspect of the present invention.

Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene (or other polynucleotide sequence of the present invention) to be expressed, typically under control of regulatory elements. In one embodiment, a selectable marker and a reporter gene are also included. For ease of obtaining sufficient quantities of vector, a bacterial origin that allows replication in *E. coli* can be used.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Useful plant binary vectors include BIN19 and its derivatives available from Clontech. These vectors are listed solely by way of illustration of the many commercially available and well-known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention, several of which are disclosed in more detail below.

In general, expression constructs will contain sites for transcription initiation and termination, and, in the transcribed region, a ribosome-binding site for translation when the construct encodes a polypeptide. The coding portion of the mature transcripts expressed by the constructs will include a translation-initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination signals, among others. For secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Transcription of the DNA (e.g., encoding the polypeptides) of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers. Additional enhancers useful in the invention to increase transcription of the introduced DNA segment, include, inter alia, viral enhancers like those within the 35S promoter, as shown by Odell et al., *Plant Mol. Biol.* 10:263-72 (1988), and an enhancer from an opine gene as described by Fromm et al., *Plant Cell* 1:977 (1989). The enhancer may affect the tissue-specificity and/or temporal specificity of expression of sequences included in the vector.

Termination regions also facilitate effective expression by ending transcription at appropriate points. Useful terminators for practicing this invention include, but are not limited to, pinII (see An et al., Plant Cell 1(1):115-122 (1989)), glb1 (see Genbank Accession #L22345), gz (see gzw64a terminator, Genbank Accession #S78780), and the nos terminator from *Agrobacterium*. The termination region can be native with the promoter nucleotide sequence, can be native with the DNA sequence of interest, or can be derived from another source. For example, other convenient termination regions are available from the Ti-plasmid of *A. tumefaciens*, such as the octopine synthase and nopaline synthase termination regions. See also: Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) Gene 91:151-158; Ballas et al. 1989) *Nucleic Acids Res.* 17:7891-7903; and Joshi et al. (1987) *Nucleic Acid Res.* 15:9627-9639.

Among known eukaryotic promoters suitable for generalized expression are the CMV immediate early promoter, the HSV thymidine kinase promoter, the early and late SV40 promoters, the promoters of retroviral LTRs, such as those of the Rous sarcoma virus ("RSV"), metallothionein promoters, such as the mouse metallothionein-I promoter and various plant promoters, such as globulin-1. When available, the native promoters of the ACC synthase genes may be used. Representatives of prokaryotic promoters include the phage lambda PL promoter, the *E. coli* lac, trp and tac promoters to name just a few of the well-known promoters.

Isolated or recombinant plants, or plant cells, incorporating the ACC synthase nucleic acids are a feature of the invention. The transformation of plant cells and protoplasts can be carried out in essentially any of the various ways known to those skilled in the art of plant molecular biology, including, but not limited to, the methods described herein. See, in general, *Methods in Enzymology*, Vol. 153 (Recombinant DNA Part D) Wu and Grossman (eds.) 1987, Academic Press, incorporated herein by reference. As used herein, the term "transformation" means alteration of the genotype of a host plant by the introduction of a nucleic acid sequence, e.g., a "heterologous", "exogenous" or "foreign" nucleic acid sequence. The heterologous nucleic acid sequence need not necessarily originate from a different source but it will, at some point, have been external to the cell into which is introduced.

In addition to Berger, Ausubel and Sambrook, useful general references for plant cell cloning, culture and regeneration include Jones (ed) (1995) *Plant Gene Transfer and Expression Protocols—Methods in Molecular Biology*, Volume 49 Humana Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of cell culture media are described in Atlas and Parks (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS). Additional details regarding plant cell culture are found in Croy, (ed.) (1993) *Plant Molecular Biology* Bios Scientific Publishers, Oxford, U.K. See also the section herein entitled "Plant transformations."

In an embodiment of this invention, recombinant vectors including one or more of the ACC synthase nucleic acids or a subsequence thereof, e.g., selected from SEQ ID NO:1 to SEQ ID NO:6, or SEQ ID NO:10, suitable for the transformation of plant cells are prepared. In another embodiment, a nucleic acid sequence encoding for the desired ACC synthase RNA or protein or subsequence thereof, e.g., selected from among SEQ ID NO:7 to SEQ ID NO:9, or SEQ ID NO:11, is conveniently used to construct a recombinant expression cassette which can be introduced into the desired plant. In the context of the invention, an expression cassette will typically comprise a selected ACC synthase nucleic acid sequence or subsequence in an RNA configuration (e.g., antisense, sense, RNA silencing or interference configuration, and/or the like) operably linked to a promoter sequence and other transcriptional and translational initiation regulatory sequences which are sufficient to direct the transcription of the ACC synthase RNA configuration sequence in the intended tissues (e.g., entire plant, leaves, anthers, roots, etc.) of the transformed plant.

In general, the particular promoter used in the expression cassette in plants depends on the intended application. Any of a number of promoters can be suitable. For example, the nucleic acids can be combined with constitutive, inducible, tissue-specific (tissue-preferred), or other promoters for expression in plants. For example, a strongly or weakly constitutive plant promoter that directs expression of an ACC synthase RNA configuration sequence in all tissues of a plant can be favorably employed. Such promoters are active under most environmental conditions and states of development or cell differentiation. Examples of constitutive promoters include the 1'- or 2'-promoter of *Agrobacterium tumefaciens* (see, e.g., O'Grady (1995) *Plant Mol. Biol.* 29:99-108). Other plant promoters include the ribulose-1,3-bisphosphate carboxylase small subunit promoter, the phaseolin promoter, alcohol dehydrogenase (Adh) gene promoters (see, e.g., Millar (1996) *Plant Mol. Biol.* 31:897-904), sucrose synthase promoters, c'-tubulin promoters, actin promoters, such as the *Arabidopsis* actin gene promoter (see, e.g., Huang (1997) *Plant Mol. Biol.* 1997 33:125-139), cab, PEPCase, R gene complex, ACT11 from *Arabidopsis* (Huang et al. *Plant Mol. Biol.* 33:125-139 (1996)), Cat3 from *Arabidopsis* (Zhong et al., *Mol. Gen. Genet.* 251:196-203 (1996)), the gene encoding stearoyl-acyl carrier protein desaturase from *Brassica napus* (Solocombe et al. (1994) *Plant Physiol.* 104:1167-1176), GPc1 from maize (Martinez et al. (1989) *J. Mol. Biol.* 208: 551-565), Gpc2 from maize (Manjunath et al. (1997), Plant Mol. Biol. 33:97-112), and other transcription initiation regions from various plant genes known to those of skill. See also Holtorf (1995) *"Comparison of different constitutive and inducible promoters for the overexpression of transgenes in Arabidopsis thaliana,"* Plant Mol. Biol. 29:637-646. The promoter sequence from the E8 gene (see, Deikman and Fischer (1988) *EMBO J.* 7:3315) and other genes can also be used, along with promoters specific for monocotyledonous species (e.g., McElroy D., et al. (1994.) *Foreign gene expression in transgenic cereals. Trends Biotech.*, 12:62-68). Other constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Yet, other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

In addition to the promoters noted herein, promoters of bacterial origin which operate in plants can be used in the invention. They include, e.g., the octopine synthase promoter, the nopaline synthase promoter and other promoters derived from Ti plasmids. See, Herrera-Estrella et al. (1983) *Nature* 303:209. Viral promoters can also be used. Examples of viral promoters include the 35S and 19S RNA promoters of cauliflower mosaic virus (CaMV). See, Odell et al., (1985) *Nature* 313:810; and, Dagless (1997) *Arch. Virol.* 142:183-191. Other examples of constitutive promoters from viruses which infect plants include the promoter of the tobacco mosaic virus; cauliflower mosaic virus (CaMV) 19S and 35S promoters or the promoter of Figwort mosaic virus, e.g., the figwort mosaic virus 35S promoter (see, e.g., Maiti (1997) Transgenic Res. 6:143-156), etc. Alternatively, novel promoters with useful characteristics can be identified from any viral, bacterial, or plant source by methods, including sequence analysis, enhancer or promoter trapping, and the like, known in the art.

Tissue-preferred (tissue-specific) promoters and enhancers can be utilized to target enhanced gene expression within a particular plant tissue. Tissue-preferred (tissue-specific) promoters include, e.g., those described in Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

In certain embodiments, leaf specific promoters can be used, e.g., pyruvate, orthophosphate dikinase (PPDK) promoter from C4 plant (maize), cab-m1 Ca+2 promoter from maize, the *Arabidopsis thaliana* myb-related gene promoter (Atmyb5), the ribulose biphosphate carboxylase (RBCS) promoters (e.g., the tomato RBCS1, RBCS2 and RBCS3A genes, which are expressed in leaves and light-grown seedlings, while RBCS1 and RBCS2 are expressed in developing tomato fruits, and/or a ribulose bisphosphate carboxylase promoter which is expressed almost exclusively in mesophyll cells in leaf blades and leaf sheaths at high levels, etc.), and the like. See, e.g., Matsuoka et al., (1993) *Tissue-specific light-regulated expression directed by the promoter of a C4 gene, maize pyruvate, orthophosphate dikinase, in a C3 plant, rice, PNAS USA* 90(20):9586-90; (2000) *Plant Cell Physiol.* 41(1):42-48; (2001) *Plant Mol. Biol.* 45(1):1-15; Shiina, T. et al., (1997) *Identification of Promoter Elements involved in the cytosolic Ca+2 mediated photoregulation of maize cab-m1 expression, Plant Physiol.* 115:477-483; Casal (1998) *Plant Physiol.* 116:1533-1538; Li (1996) *FEBS Lett.* 379:117-121; Busk (1997) *Plant J.* 11:1285-1295; and, Meier (1997) *FEBS Lett.* 415:91-95; and, Matsuoka (1994) *Plant J.* 6:311-319. Other leaf-specific promoters include, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20): 9586-9590.

In certain embodiments, senescence specific promoters can be used (e.g., a tomato promoter active during fruit ripening, senescence and abscission of leaves, a maize promoter of gene encoding a cysteine protease, and the like). See, e.g., Blume (1997) *Plant J.* 12:731-746; Griffiths et al., (1997) *Sequencing, expression pattern and RFLP mapping of a senescence-enhanced cDNA from Zea Mays with high homology to oryzain gamma and aleurain, Plant Mol. Biol.* 34(5): 815-21; *Zea mays* partial see1 gene for cysteine protease, promoter region and 5' coding region, Genbank AJ494982; Kleber-Janke, T. and Krupinska, K. (1997) *Isolation of cDNA clones for genes showing enhanced expression in barley leaves during dark-induced senescence as well as during senescence under field conditions, Planta* 203(3): 332-40;

and, Lee, R H et al., (2001) *Leaf senescence in rice plants: cloning and characterization of senescence up-regulated genes, J. Exp. Bot.* 52(358):1117-21.

In other embodiments, anther-specific promoters can be used. Such promoters are known in the art or can be discovered by known techniques; see, e.g., Bhalla and Singh (1999) *Molecular control of male fertility in Brassica Proc. 10th Annual Rapeseed Congress, Canberra, Australia*; van Tunen et al. (1990) *Pollen-and anther-specific chi promoters from petunia: tandem promoter regulation of the chiA gene. Plant Cell* 2:393-40; Jeon et al. (1999) *Isolation and characterization of an anther-specific gene, RA8, from rice (Oryza sativa L). Plant Molecular Biology* 39:35-44; and Twell et al. (1993) *Activation and developmental regulation of an Arabidopsis anther-specific promoter in microspores and pollen of Nicotiana tabacum. Sex. Plant Reprod.* 6:217-224.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed ro1C and ro1D root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue (see, e.g., *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and ro1B promoter (Capana et al. (1994) *Plant Mol. Biol.* 25(4): 681-691. See also, U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See, e.g., Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40 (U.S. Pat. No. 6,403,862); nuc1c (U.S. Pat. No. 6,407,315); and ce1A (cellulose synthase) (see WO 00/11177). Gama-zein is an endosperm-specific promoter. Glob-1 is an embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kD γ-zein promoter (such as gzw64A promoter, see Genbank Accession #S78780), a waxy promoter, a shrunken 1 promoter, a shrunken 2 promoter, a globulin 1 promoter (see Genbank Accession # L22344), an ltp2 promoter (Kalla, et al., Plant Journal 6:849-860 (1994); U.S. Pat. No. 5,525,716); cim1 promoter (see U.S. Pat. No. 6,225,529) maize end1 and end2 promoters (See U.S. Pat. No. 6,528,704 and application Ser. No. 10/310,191, filed Dec. 4, 2002); nuc1 promoter (U.S. Pat. No. 6,407,315); Zm40 promoter (U.S. Pat. No. 6,403, 862); eep1 and eep2; lec1 (U.S. patent application Ser. No. 09/718,754); thioredoxinH promoter (U.S. provisional patent application 60/514,123); mlip15 promoter (U.S. Pat. No. 6,479,734); PCNA2 promoter; and the shrunken-2 promoter. (Shaw et al., Plant Phys 98:1214-1216, 1992; Zhong Chen et al., PNAS USA 100:3525-3530, 2003) However, other promoters useful in the practice of the invention are known to those of skill in the art such as nucellain promoter (See C. Linnestad, et al., *Nucellain, A Barley Homolog of the Dicot Vacuolar—Processing Proteasem Is Localized in Nucellar Cell Walls, Plant Physiol.* 118:1169-80 (1998), kn1 promoter (See S. Hake and N. Ori, *The Role of knotted1 in Meristem Functions*, B8: INTERACTIONS AND INTERSECTIONS IN PLANT PATHWAYS, COEUR D' ALENE, IDAHO, KEYSTONE SYMPOSIA, Feb. 8-14, 1999, at 27.), and F3.7 promoter (Baszczynski et al., Maydica 42:189-201 (1997)), etc. In certain embodiments, spatially acting promoters such as glb1, an embryo-preferred promoter; or gamma zein, an endosperm-preferred promoter; or a promoter active in the embryo-surrounding region (see U.S. patent application Ser. No. 10/786,679, filed Feb. 25, 2004), or BETL1 (See G. Hueros, et al., Plant Physiology 121:1143-1152 (1999) and Plant Cell 7:747-57 (June 1995)), are useful, including promoters preferentially active in female reproductive tissues, and those active in meristematic tissues, particularly in meristematic female reproductive tissues. See also, WO 00/12733, where seed-preferred promoters from end1 and end2 genes are disclosed.

A tissue-specific promoter can drive expression of operably linked sequences in tissues other than the target tissue. Thus, as used herein, a tissue-specific promoter is one that drives expression preferentially in the target tissue, but can also lead to some expression in other tissues as well.

The use of temporally-acting promoters is also contemplated by this invention. For example, promoters that act from 0-25 days after pollination (DAP), 4-21, 4-12, or 8-12 DAP can be selected, e.g., promoters such as cim1 and Itp2. Promoters that act from −14 to 0 days after pollination can also be used, such as SAG12 (See WO 96/29858, Richard M. Amasino, published 3 Oct. 1996) and ZAG1 or ZAG2 (See R. J. Schmidt, et al., *Identification and Molecular Characterization of ZAG1, the Maize Homolog of the Arabidopsis Floral Homeotic Gene AGAMOUS, Plant-Cell* 5(7): 729-37 (July 1993)). Other useful promoters include maize zag2.1, Zap (also known as ZmMADS; U.S. patent application Ser. No. 10/387,937; WO 03/078590); and the maize tbl promoter (see also Hubbarda et al., Genetics 162:1927-1935, 2002).

Where overexpression of an ACC synthase RNA configuration nucleic acid is detrimental to the plant, one of skill will recognize that weak constitutive promoters can be used for low-levels of expression (or, in certain embodiments, inducible or tissue-specific promoters can be used). In those cases where high levels of expression are not harmful to the plant, a strong promoter, e.g., a t-RNA, or other pol III promoter, or a strong pol II promoter (e.g., the cauliflower mosaic virus promoter, CaMV, 35S promoter), can be used.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompass promoters that drive expression in only a few cells and not in others to give a total low level of expression. Where a promoter drives expression at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072, 050), the core 35S CaMV promoter, and the like.

In certain embodiments of the invention, an inducible promoter can be used. For example, a plant promoter can be under environmental control. Such promoters are referred to as "inducible" promoters. Examples of environmental conditions that can alter transcription by inducible promoters include pathogen attack, anaerobic conditions, elevated temperature, and the presence of light. For example, the invention incorporates the drought-inducible promoter of maize (Busk (1997) *Plant J.* 11:1285-1295); the cold, drought, high salt inducible promoter from potato (Kirch (1997) *Plant Mol. Biol.* 33:897-909), and the like.

Pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also the application entitled "Inducible Maize Promoters", U.S. patent application Ser. No. 09/257,583, filed Feb. 25, 1999.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci.* 83:2427-2430; Somsisch et al. (1988) *Mol. Gen. Genet.* 2:93-98; and Yang (1996) *Proc. Natl. Acad. Sci.* 93:14972-14977. See also, Chen et al. (1996) *Plant J.* 10:955-966; Zhang et al. (1994) *Proc. Natl. Acad. Sci.* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) Ann. Rev. Phytopath. 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like.

Alternatively, plant promoters which are inducible upon exposure to plant hormones, such as auxins, are used to express the polynucleotides of the invention. For example, the invention can use the auxin-response elements E1 promoter subsequence (AuxREs) from the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco; a plant biotin response element (Streit (1997) *Mol. Plant. Microbe Interact.* 10:933-937); and the promoter responsive to the stress hormone abscisic acid (Sheen (1996) *Science* 274:1900-1902).

Plant promoters which are inducible upon exposure to chemical reagents which can be applied to the plant, such as herbicides or antibiotics, are also used to express the polynucleotides of the invention. Depending upon the objective, the promoter can be a chemical-inducible promoter, where application of the chemical induces gene expression, or a chemical-repressible promoter, where application of the chemical represses gene expression. For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. An ACC synthase coding sequence or RNA configuration can also be under the control of, e.g., tetracycline-inducible and tetracycline-repressible promoters (see, e.g., Gatz et al. (1991) *Mol. Gen. Genet.* 227:229-237; U.S. Pat. Nos. 5,814, 618 and 5,789,156; and, Masgrau (1997) *Plant J.* 11:465-473 (describing transgenic tobacco plants containing the *Avena sativa* L. (oat) arginine decarboxylase gene with a tetracycline-inducible promoter); or, a salicylic acid-responsive element (Stange (1997) *Plant J.* 11:1315-1324. Other chemical-inducible promoters are known in the art and include, but are not limited to, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257).

Endogenous promoters of genes related to herbicide tolerance and related phenotypes are also useful for driving expression of ACC synthase RNA configuration nucleic acids, e.g., P450 monooxygenases, glutathione-S-transferases, homoglutathione-S-transferases, glyphosate oxidases and 5-enolpyruvylshikimate-2-phosphate synthases. For example, a plant promoter attached to a polynucleotide of the invention can be useful when one wants to turn on expression in the presence of a particular condition, e.g., drought conditions, short growing conditions, density, etc.

Tissue specific promoters can also be used to direct expression of polynucleotides of the invention, including the ACC synthase RNA configuration nucleic acids, such that a polynucleotide of the invention is expressed only in certain tissues or stages of development, e.g., leaves, anthers, roots, shoots, etc. Tissue specific expression can be advantageous, for example, when expression of the polynucleotide in certain tissues is desirable while expression in other tissues is undesirable. Tissue specific promoters are transcriptional control elements that are only active in particular cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue. Reproductive tissue-specific promoters may be, e.g., anther-specific, ovule-specific, embryo-specific, endosperm-specific, integument-specific, seed and seed coat-specific, pollen-specific, petal-specific, sepal-specific, or some combination thereof.

It will be understood that numerous promoters not mentioned are suitable for use in this aspect of the invention, are well known and readily may be employed by those of skill in the manner illustrated by the discussion and the examples herein. For example, this invention contemplates using, when appropriate, the native ACC synthase promoters to drive the expression of the enzyme (or of ACC synthase polynucleotide sequences or subsequences) in a recombinant environment.

In preparing expression vectors of the invention, sequences other than those associated with the endogenous ACC synthase gene, mRNA or polypeptide sequence, or subsequence thereof, can optionally be used. For example, other regulatory elements such as introns, leader sequences, polyadenylation regions, signal/localization peptides, etc. can also be included.

The vector comprising a polynucleotide of the invention can also include a marker gene which confers a selectable phenotype on plant cells. For example, the marker can encode biocide tolerance, particularly antibiotic tolerance, such as tolerance to kanamycin, G418, bleomycin, hygromycin, or herbicide tolerance, such as tolerance to chlorosulfuron, or phosphinothricin. Reporter genes which are used to monitor gene expression and protein localization via visualizable reaction products (e.g., beta-glucuronidase, beta-galactosidase, and chloramphenicol acetyltransferase) or by direct visualization of the gene product itself (e.g., green fluorescent protein, GFP; Sheen et al. (1995) *The Plant Journal* 8:777) can be used for, e.g., monitoring transient gene expression in plant cells.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other prokaryotes. Kanamycin and herbicide resistance genes (PAT and BAR) are generally useful in plant systems.

Selectable marker genes, in physical proximity to the introduced DNA segment, are used to allow transformed cells to be recovered by either positive genetic selection or screening. The selectable marker genes also allow for maintaining selection pressure on a transgenic plant population, to ensure that the introduced DNA segment, and its controlling promoters and enhancers, are retained by the transgenic plant.

Many of the commonly used positive selectable marker genes for plant transformation have been isolated from bacteria and code for enzymes that metabolically detoxify a selective chemical agent which may be an antibiotic or a herbicide. Other positive selection marker genes encode an altered target which is insensitive to the inhibitor.

An example of a selection marker gene for plant transformation is the BAR or PAT gene, which is used with the selecting agent bialaphos (Spencer et al., *J. Theor. Appl'd Genetics* 79:625-631 (1990)). Another useful selection marker gene is the neomycin phosphotransferase II (val) gene, isolated from Tn5, which confers resistance to kanamycin when placed under the control of plant regulatory signals (Fraley et al., *Proc. Nat'l Acad. Sci. (USA)* 80:4803 (1983)). The hygromycin phosphotransferase gene, which confers resistance to the antibiotic hygromycin, is a further example of a useful selectable marker (Vanden Elzen et al., *Plant Mol. Biol.* 5:299 (1985)). Additional positive selectable marker genes of bacterial origin that confer resistance to antibiotics include gentamicin acetyl transferase, streptomycin phosphotransferase, aminoglycoside-3'-adenyl transferase and the bleomycin resistance determinant (Hayford et al., *Plant Physiol.* 86:1216 (1988); Jones et al., *Mol. Gen. Genet.* 210:86 (1987); Svab et al., *Plant Mol. Biol.* 14:197 (1990); Hille et al., *Plant Mol. Biol.* 7:171 (1986)).

Other positive selectable marker genes for plant transformation are not of bacterial origin. These genes include mouse dihydrofolate reductase, plant 5-enolpyruvylshikimate-3-phosphate synthase and plant acetolactate synthase (Eichholtz et al., *Somatic Cell Mol. Genet.* 13:67 (1987); Shah et al., *Science* 233:478 (1986); Charest et al., *Plant Cell Rep.* 8:643 (1990)). Other examples of suitable selectable marker genes include, but are not limited to: genes encoding resistance to chloramphenicol, Herrera Estrella et al. (1983) *EMBO J.* 2:987-992; methotrexate, Herrera Estrella et al. (1983) *Nature* 303:209-213; Meijer et al. (1991) *Plant Mol. Biol.* 16:807-820; hygromycin, Waldron et al. (1985) *Plant Mol. Biol.* 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419-423; glyphosate, Shaw et al. (1986) *Science* 233:478-481; phosphinothricin, DeBlock et al. (1987) *EMBO J.* 6:2513-2518.

Another class of useful marker genes for plant transformation with the DNA sequence requires screening of presumptively transformed plant cells rather than direct genetic selection of transformed cells for resistance to a toxic substance such as an antibiotic. These genes are particularly useful to quantitate or visualize the spatial pattern of expression of the DNA sequence in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, *Plant Mol. Biol. Rep.* 5:387 (1987); Teeri et al., *EMBO J.* 8:343 (1989); Koncz et al., *Proc. Nat'l Acad. Sci. (USA)* 84:131 (1987); De Block et al., *EMBO J.* 3:1681 (1984)). Examples of other suitable reporter genes known in the art can be found in, for example: Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330. Another approach to the identification of relatively rare transformation events has been use of a gene that encodes a dominant constitutive regulator of the *Zea mays* anthocyanin pigmentation pathway (Ludwig et al., *Science* 247:449 (1990)).

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. The sequence may be inserted in a forward or reverse orientation. Procedures for restriction and ligation that can be used to this end are well known and routine to those of skill Suitable procedures in this regard, and for constructing expression vectors using alternative techniques, which also are well known and routine to those of skill, are set forth in great detail in Sambrook et al., *MOLECULAR CLONING, A LABORATORY MANUAL*, 2nd Ed.; Cold Spring Harbor Laboratory Press, Cold Spring Harbor, N.Y. (1989).

A polynucleotide of the invention, optionally encoding the heterologous structural sequence of a polypeptide of the invention, generally will be inserted into the vector using standard techniques so that it is operably linked to the promoter for expression. (Operably linked, as used herein, includes reference to a functional linkage between a promoter and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.) When the polynucleotide is intended for expression of a polypeptide, the polynucleotide will be positioned so that the transcription start site is located appropriately 5' to a ribosome binding site. The ribosome-binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signals appropriately disposed at the 3' end of the transcribed region may also be included in the polynucleotide construct.

For nucleic acid constructs designed to express a polypeptide, the expression cassettes can additionally contain 5' leader sequences. Such leader sequences can act to enhance translation. Translation leaders are known in the art and include: picornavirus leaders, for example: EMCV leader (Encephalomyocarditis 5' noncoding region), Elroy-Stein et al. (1989) *Proc. Nat. Acad. Sci. USA* 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al. (1989) *Molecular Biology of RNA, pages* 237-256; and maize chlorotic mottle virus leader (MCMV) Lommel et al. (1991) *Virology* 81:382-385. See also Della-Cioppa et al. (1987) *Plant Physiology* 84:965-968. The cassette can also contain sequences that enhance translation and/or mRNA stability such as introns. The expression cassette also typically includes, at the 3' terminus of the isolated nucleotide sequence of interest, a translational termination region, e.g., one functional in plants.

In those instances where it is desirable to have the expressed product of the isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements. In general, the vectors should be functional in plant cells. At times, it may be preferable to have vectors that are functional in other host cells, e.g., in *E. coli* (e.g., for production of protein for raising antibodies, DNA sequence analysis, construction of inserts, or obtaining quantities of nucleic acids). Vectors and procedures for cloning and expression in *E. coli* are discussed in Sambrook et al. (supra).

The transformation vector, comprising the promoter of the present invention operably linked to an isolated nucleotide sequence in an expression cassette, can also contain at least one additional nucleotide sequence for a gene to be co-transformed into the organism. Alternatively, the additional sequence(s) can be provided on another transformation vector.

The vector containing the appropriate DNA sequence as described elsewhere herein, as well as an appropriate promoter, and other appropriate control sequences, may be introduced into an appropriate host using a variety of well-known techniques suitable to expression therein of a desired RNA and/or polypeptide. The present invention also relates to host cells containing the above-described constructs. The host cell can be a higher eukaryotic cell, such as a plant cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, microinjection, cationic lipid-mediated transfection, electroporation, transduction, scrape loading, ballistic introduction, infection or other methods. Such methods are described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989).

Representative examples of appropriate hosts include bacterial cells, such as streptococci, staphylococci, *E. coli, streptomyces* and *Salmonella typhimurium* cells; fungal cells, such as yeast cells and *Aspergillus* cells; insect cells such as *Drosophila* S2 and *Spodoptera* Sf9 cells; animal cells such as CHO, COS and Bowes melanoma cells; and plant cells. The plant cells may be derived from a broad range of plant types, particularly monocots such as the species of the Family Graminiae including *Sorghum bicolor* and *Zea mays*, as well as dicots such as soybean (*Glycine max*) and canola (*Brassica napus, Brassica rapa* ssp.). Preferably, plants include maize, soybean, sunflower, safflower, canola, wheat, barley, rye, alfalfa, rice, oat, lawn grass, and sorghum; however, the isolated nucleic acid and proteins of the present invention can be used in species from the genera: *Ananas, Antirrhinum, Arabidopsis, Arachis, Asparagus, Atropa, Avena, Brassica, Bromus, Browaalia, Camellia, Capsicum, Ciahorium, Citrus, Cocos, Cofea, Cucumis, Cucurbita, Datura, Daucus, Digitalis, Ficus, Fragaria, Geranium, Glycine, Gossypium, Helianthus, Heterocallis, Hordeum, Hyoscyamus, Ipomoea, Juglans, Lactuca, Linum, Lolium, Lotus, Lycopersicon, Majorana, Mangifera, Manihot, Medicago, Musa, Nemesis, Nicotiana, Olea, Onobrychis, Oryza, Panieum, Pelargonium,*

*Pennisetum, Persea, Petunia, Phaseolus, Pisum, Psidium, Ranunculus, Raphanus, Rosa, Salpiglossis, Secale, Senecio, Solanum, Sinapis, Sorghum, Theobroma, Triticum, Trifolium, Trigonella, Vigna, Vitis,* and *Zea,* among many other examples (e.g., other genera noted herein).

The promoter regions of the invention may be isolated from any plant, including, but not limited to, maize (corn; *Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably, plants include maize, soybean, sunflower, safflower, canola, wheat, barley, rye, alfalfa, rice, oat, lawn grass, and sorghum.

Hosts for a great variety of expression constructs are well known, and those of skill will be enabled by the present disclosure readily to select a host for expressing a polypeptide in accordance with this aspect of the present invention.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of nucleic acids and/or polypeptides of the present invention, as will be apparent to those of skill in the art.

Mature proteins can be expressed in mammalian cells, yeast, bacteria, or other cells under the control of appropriate promoters. Cell-free translation systems can also be employed to produce such proteins using RNAs derived from the DNA constructs of the present invention.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well known to those skilled in the art.

Methods of Inhibiting Ethylene Production

The invention also provides methods for inhibiting ethylene production in a plant (and plants produced by such methods). For example, a method of inhibiting ethylene production comprises inactivating one or more ACC synthase genes in the plant, wherein the one or more ACC synthase genes encodes one or more ACC synthases. Typically, at least one of the one or more ACC synthases comprises, e.g., at least about 70%, at least about 75%, at least about 80%, at least about 85%, at least about 90%, at least about 95%, at least about 99%, about 99.5% or more identity to SEQ ID NO:7 (pACS2), SEQ ID NO:8 (pACS6), SEQ ID NO:9 (pAC7) or SEQ ID NO:11 (pCCRA178R).

Antisense, Sense, RNA Silencing or Interference Configurations

The one or more ACC synthase gene can be inactivated by introducing and expressing transgenic sequences, e.g., antisense or sense configurations, or RNA silencing or interference configurations, etc, encoding one or more ACC synthases, or a subsequence thereof, and a promoter, thereby inactivating the one or more ACC synthase genes compared to a corresponding control plant (e.g., its non-transgenic parent or a non-transgenic plant of the same species). See also the section entitled "Polynucleotides of the Invention." The at least one polynucleotide sequence can be introduced by techniques including, but not limited to, e.g., electroporation, micro-projectile bombardment, *Agrobacterium*-mediated transfer, or other available methods. See also, the section entitled "Plant Transformation," herein. In certain aspects of the invention, the polynucleotide is linked to the promoter in a sense orientation or in an antisense orientation or is configured for RNA silencing or interference.

In certain situations it may be preferable to silence or down-regulate certain genes, such as ACC synthase genes. Relevant literature describing the application of homology-dependent gene silencing includes: Jorgensen, *Trends Biotechnol.* 8 (12):340-344 (1990); Flavell, *Proc. Nat'l. Acad. Sci. (USA)* 91:3490-3496 (1994); Finnegan et al., *Bio/Technology* 12: 883-888 (1994); Neuhuber et al., *Mol. Gen. Genet.* 244:230-241 (1994); Flavell et al. (1994) *Proc. Natl. Acad. Sci. USA* 91:3490-3496; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al. (2002) *Plant Physiol.* 129:1723-1731; Yu et al. (2003) *Phytochemistry* 63:753-763; and U.S. Pat. Nos. 5,034,323, 5,283,184, and 5,942,657. Alternatively, another approach to gene silencing can be with the use of antisense technology (Rothstein et al. in *Plant Mol. Cell. Biol.* 6:221-246 (1989); Liu et al. (2002) *Plant Physiol.* 129:1732-1743 and U.S. Pat. Nos. 5,759,829 and 5,942,657.

Use of antisense nucleic acids is well known in the art. An antisense nucleic acid has a region of complementarity to a target nucleic acid, e.g., an ACC synthase gene, mRNA, or cDNA. The antisense nucleic acid can be RNA, DNA, a PNA or any other appropriate molecule. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced, e.g., for an ACC synthase gene by a number of well-established techniques (e.g., chemical synthesis of an antisense RNA or oligonucleotide (optionally including modified nucleotides and/or linkages that increase resistance to degradation or improve cellular uptake) or in vitro transcription). Antisense nucleic acids and their use are described, e.g., in U.S. Pat. No. 6,242,258 to Haselton and Alexander (Jun. 5, 2001) entitled "Methods for the selective regulation of DNA and RNA transcription and translation by photoactivation"; U.S. Pat. Nos. 6,500,615; 6,498,035; 6,395, 544; 5,563,050; E. Schuch et al (1991) *Symp Soc. Exp Biol* 45:117-127; de Lange et al., (1995) *Curr Top Microbiol Immunol* 197:57-75; Hamilton et al. (1995) *Curr Top Microbiol Immunol* 197:77-89; Finnegan et al., (1996) *Proc Natl Acad Sci USA* 93:8449-8454; Uhlmann and A. Pepan (1990), *Chem. Rev.* 90:543; P. D. Cook (1991), *Anti-Cancer Drug Design* 6:585; J. Goodchild, Bioconjugate Chem. 1 (1990) 165; and, S. L. Beaucage and R. P. Iyer (1993), Tetrahedron 49:6123; and F. Eckstein, Ed. (1991), *Oligonucleotides and Analogues—A Practical Approach*, IRL Press.

Catalytic RNA molecules or ribozymes can also be used to inhibit expression of ACC synthase genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the constructs.

A number of classes of ribozymes have been identified. For example, one class of ribozymes is derived from a number of small circular RNAs that are capable of self-cleavage and replication in plants. The RNAs can replicate either alone (viroid RNAs) or with a helper virus (satellite RNAs). Examples of RNAs include RNAs from avocado sunblotch viroid and the satellite RNAs from tobacco ringspot virus, lucerne transient streak virus, velvet tobacco mottle virus, *solanum* nodiflorum mottle virus and subterranean clover mottle virus. The design and use of target RNA-specific ribozymes has been described. See, e.g., Haseloff et al. (1988) *Nature*, 334:585-591.

Another method to inactivate an ACC synthase gene by inhibiting expression is by sense suppression. Introduction of expression cassettes in which a nucleic acid is configured in the sense orientation with respect to the promoter has been shown to be an effective means by which to block the transcription of a desired target gene. See, e.g., Napoli et al. (1990), *The Plant Cell* 2:279-289, and U.S. Pat. Nos. 5,034,323, 5,231,020, and 5,283,184.

Isolated or recombinant plants which include one or more inactivated ACC synthase gene can also be produced by using RNA silencing or interference (RNAi), which can also be termed post-transcriptional gene silencing (PTGS) or cosuppression. In the context of this invention, "RNA silencing" (also called RNAi or RNA-mediated interference) refers to any mechanism through which the presence of a single-stranded or, typically, a double-stranded RNA in a cell results in inhibition of expression of a target gene comprising a sequence identical or nearly identical to that of the RNA, including, but not limited to, RNA interference, repression of translation of a target mRNA transcribed from the target gene without alteration of the mRNA's stability, and transcriptional silencing (e.g., histone acetylation and heterochromatin formation leading to inhibition of transcription of the target mRNA). In "RNA interference," the presence of the single-stranded or double-stranded RNA in the cell leads to endonucleolytic cleavage and then degradation of the target mRNA.

In one embodiment, a transgene (e.g., a sequence and/or subsequence of an ACC synthase gene or coding sequence) is introduced into a plant cell to inactivate one or more ACC synthase genes by RNA silencing or interference (RNAi). For example, a sequence or subsequence includes a small subsequence, e.g., about 21-25 bases in length (with, e.g., at least 80%, at least 90%, or about 100% identity to one or more of the ACC synthase gene subsequences), a larger subsequence, e.g., about 25-100 or about 100-2000 (or about 200-1500, about 250-1000, etc.) bases in length (with at least one region of about 21-25 bases of at least 80%, at least 90%, or 100% identity to one or more ACC synthase gene subsequences), and/or the entire coding sequence or gene. In one embodiment, a transgene includes a region in the sequence or subsequence that is about 21-25 bases in length with at least 80%, at least 90%, or about 100% identity to the ACC synthase gene or coding sequence.

Use of RNAi for inhibiting gene expression in a number of cell types (including, e.g., plant cells) and organisms, e.g., by expression of a hairpin (stem-loop) RNA or of the two strands of an interfering RNA, for example, is well described in the literature, as are methods for determining appropriate interfering RNA(s) to target a desired gene, e.g., an ACC synthase gene, and for generating such interfering RNAs. For example, RNA interference is described e.g., in US patent application publications 20020173478, 20020162126, and 20020182223 and in Cogoni and Macino (2000) "*Post-transcriptionnal gene silencing across kingdoms*" Genes Dev., 10:638-643; Guru T. (2000), "*A silence that speaks volumes*" Nature 404: 804-808; Hammond et al., (2001), "*Post-transcriptional Gene Silencing by Double-stranded RNA*" Nature Rev. Gen. 2: 110-119; Napoli et al., (1990) "*Introduction of a chalcone synthase gene into Petunia results in reversible co-suppression of homologous genes in trans.*" Plant Cell 2:279-289; Jorgensen et al., (1996), "*Chalcone synthase cosuppression phenotypes in petunia flowers: comparison of sense vs. antisense constructs and single-copy vs. complex T-DNA sequences*" Plant Mol. Biol., 31:957-973; Hannon G. J. (2002) "*RNA interference*" Nature., July 11; 418(6894):244-51; Ueda R. (2001) "*RNAi: a new technology in the post-genomic sequencing era*" J. Neurogenet.; 15(3-4):193-204; Ullu et al (2002) "*RNA interference: advances and questions*" Philos Trans R Soc Lond B Biol Sci. January 29; 357(1417):65-70; Waterhouse et al., (1998) Proc Natl Acad Sci USA 95:133959-13964; Schmid et al (2002) "*Combinatorial RNAi: a method for evaluating the functions of gene families in Drosophila*" Trends Neurosci. February; 25(2): 71-4; Zeng et al. (2003) "*MicroRNAs and small interfering RNAs can inhibit mRNA expression by similar mechanisms*" Proc. Natl. Acad. Sci. USA 100:9779-9784; Doench et al. (2003) "*siRNAs can function as miRNAs*" Genes & Dev. 17:438-442; Bartel and Bartel (2003) "*MicroRNAs: At the root of plant development?*" Plant Physiology 132:709-717; Schwarz and Zamore (2002) "*Why do miRNAs live in the miRNP?*" Genes & Dev. 16:1025-1031; Tang et al. (2003) "*A biochemical framework for RNA silencing in plants*" Genes & Dev. 17:49-63; Meister et al. (2004) "*Sequence-specific inhibition of microRNA- and siRNA-induced RNA silencing*" RNA 10:544-550; Nelson et al. (2003) "*The microRNA world: Small is mighty*" Trends Biochem. Sci. 28:534-540; Dykxhoorn et al. (2003) "*Killing the messenger: Short RNAs that silence gene expression*" Nature Reviews Molec. and Cell Biol. 4:457-467; McManus and Sharp (2002) "*Gene silencing in mammals by small interfering RNAs*" Nature Reviews Genetics 3:737-747; Hutvagner and Zamore (2002) "*RNAi: Nature abhors a double strand*" Curr Opin Genet & Dev 200:225-232; and Agami (2002) "*RNAi and related mechanisms and their potential use for therapy*" Curr Opin Chem Biol 6:829-834.

The ACC synthase polynucleotide sequence(s) or subsequence(s) expressed to induce RNAi can be expressed, e.g., under control of a constitutive promoter, an inducible promoter, or a tissue specific promoter. Expression from a tissue-specific promoter can be advantageous in certain embodiments. For example, expression from a leaf-specific promoter can inactivate one or more ACC synthase genes in the leaf, producing a staygreen phenotype, without inactivating ACC synthase genes in the root (which can decrease flood tolerance). Similarly, expression from an anther-specific promoter can inactivate one or more ACC synthase genes in the anther, producing a male sterility phenotype, without inactivating ACC synthase genes in the remainder of the plant. Such approaches are optionally combined, e.g., to inactivate one or more ACC synthase genes in both leaves and anthers.

Transposons

The one or more ACC synthase genes can also be inactivated by, e.g., transposon based gene inactivation. In one embodiment, the inactivating step comprises producing one or more mutations in an ACC synthase gene sequence, where the one or more mutations in the ACC synthase gene sequence comprise one or more transposon insertions, thereby inactivating the one or more ACC synthase gene compared to a corresponding control plant. For example, the one or more mutations comprise a homozygous disruption in the one or more ACC synthase gene or the one or more mutations comprise a heterozygous disruption in the one or more ACC synthase gene or a combination of both homozygous disruptions and heterozygous disruptions if more than one ACC synthase gene is disrupted.

Transposons were first identified in maize by Barbara McClintock in the late 1940s. The Mutator family of transposable elements, e.g., Robertson's Mutator (Mu) transposable elements, are typically used in plant, e.g., maize, gene mutagenesis, because they are present in high copy number (10-100) and insert preferentially within and around genes.

Transposable elements can be categorized into two broad classes based on their mode of transposition. These are designated Class I and Class II; both have applications as mutagens and as delivery vectors. Class I transposable elements transpose by an RNA intermediate and use reverse transcriptases, i.e., they are retroelements. There are at least three types of Class I transposable elements, e.g., retrotransposons, retroposons, SINE-like elements.

Retrotransposons typically contain LTRs, and genes encoding viral coat proteins (gag) and reverse transcriptase, RnaseH, integrase and polymerase (pol) genes. Numerous retrotransposons have been described in plant species. Such retrotransposons mobilize and translocate via a RNA intermediate in a reaction catalyzed by reverse transcriptase and RNase H encoded by the transposon. Examples fall into the Ty1-copia and Ty3-gypsy groups as well as into the SINE-like and LINE-like classifications. A more detailed discussion can be found in Kumar and Bennetzen (1999) *Plant Retrotransposons* in *Annual Review of Genetics* 33:479. In addition, DNA transposable elements such as Ac, Tam1 and En/Spm are also found in a wide variety of plant species, and can be utilized in the invention.

Transposons (and IS elements) are common tools for introducing mutations in plant cells. These mobile genetic elements are delivered to cells, e.g., through a sexual cross, transposition is selected for and the resulting insertion mutants are screened, e.g., for a phenotype of interest. Plants comprising disrupted ACC synthase genes can be introduced into other plants by crossing the isolated or recombinant plants with a non-disrupted plant, e.g., by a sexual cross. Any of a number of standard breeding techniques can be used, depending upon the species to be crossed. The location of a TN within a genome of an isolated or recombinant plant can be determined by known methods, e.g., sequencing of flanking regions as described herein. For example, a PCR reaction from the plant can be used to amplify the sequence, which can then be diagnostically sequenced to confirm its origin. Optionally, the insertion mutants are screened for a desired phenotype, such as the inhibition of expression or activity of ACC synthase, inhibition or reduced production of ethylene, staygreen potential, etc. compared to a control plant.

TILLING

TILLING can also be used to inactivate one or more ACC synthase gene. TILLING is Targeting Induced Local Lesions INGenomics. See, e.g., McCallum et al., (2000), "*Targeting Induced Local Lesions IN Genomics* (TILLING) for Plant Functional Genomics" Plant Physiology 123:439-442; McCallum et al., (2000) "*Targeted screening for induced mutations*" Nature Biotechnology 18:455-457; and, Colbert et al., (2001) "*High-Throughput Screening for Induced Point Mutations*" Plant Physiology 126:480-484.

TILLING combines high density point mutations with rapid sensitive detection of the mutations. Typically, ethylmethanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes.

For example, DNA from M2 plants is pooled and mutations in an ACC synthase gene are detected by detection of heteroduplex formation. Typically, DNA is prepared from each M2 plant and pooled. The desired ACC synthase gene is amplified by PCR. The pooled sample is then denatured and annealed to allow formation of heteroduplexes. If a mutation is present in one of the plants; the PCR products will be of two types: wild-type and mutant. Pools that include the heteroduplexes are identified by separating the PCR reaction, e.g., by Denaturing High Performance Liquid Chromatography (DPHPLC). DPHPLC detects mismatches in heteroduplexes created by melting and annealing of heteroallelic DNA. Chromatography is performed while heating the DNA. Heteroduplexes have lower thermal stability and form melting bubbles resulting in faster movement in the chromatography column. When heteroduplexes are present in addition to the expected homoduplexes, a double peak is seen. As a result, the pools that carry the mutation in an ACC synthase gene are identified. Individual DNA from plants that make up the selected pooled population can then be identified and sequenced. Optionally, the plant possessing a desired mutation in an ACC synthase can be crossed with other plants to remove background mutations.

Other mutagenic methods can also be employed to introduce mutations in an ACC synthase gene. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

Other detection methods for detecting mutations in an ACC synthase gene can be employed, e.g., capillary electrophoresis (e.g., constant denaturant capillary electrophoresis and single-stranded conformational polymorphism). In another example, heteroduplexes can be detected by using mismatch repair enzymology (e.g., CEL I endonuclease from celery). CEL I recognizes a mismatch and cleaves exactly at the 3' side of the mismatch. The precise base position of the mismatch can be determined by cutting with the mismatch repair enzyme followed by, e.g., denaturing gel electrophoresis. See, e.g., Oleykowski et al., (1998) "*Mutation detection using a novel plant endonuclease*" Nucleic Acid Res. 26:4597-4602; and, Colbert et al., (2001) "*High-Throughput Screening for Induced Point Mutations*" Plant Physiology 126:480-484.

The plant containing the mutated ACC synthase gene can be crossed with other plants to introduce the mutation into another plant. This can be done using standard breeding techniques.

Homologous Recombination

Homologous recombination can also be used to inactivate one or more ACC synthase genes. Homologous recombination has been demonstrated in plants. See, e.g., Puchta et al. (1994), *Experientia* 50: 277-284; Swoboda et al. (1994), *EMBO J.* 13: 484-489; Offring a et al. (1993), *Proc. Natl. Acad. Sci. USA* 90: 7346-7350; Kempin et al. (1997) *Nature* 389:802-803; and, Terada et al., (2002) "Efficient gene targeting by homologous recombination in rice" *Nature Biotechnology,* 20(10):1030-1034.

Homologous recombination can be used to induce targeted gene modifications by specifically targeting an ACC synthase gene in vivo. Mutations in selected portions of an ACC synthase gene sequence (including 5' upstream, 3' downstream, and intragenic regions) such as those provided herein are made in vitro and introduced into the desired plant using standard techniques. The mutated gene will interact with the target ACC synthase wild-type gene in such a way that homologous recombination and targeted replacement of the wild-type gene will occur in transgenic plants, resulting in suppression of ACC synthase activity.

Methods for Modulating Staygreen Potential in a Plant

Methods for modulating staygreen potential in plants are also features of the invention. The ability to introduce different degrees of staygreen potential into plants offers a flexible and simple approach to introduce this trait in a purpose-specific manner: for example, introduction of a strong staygreen trait for improved grain-filling or for silage in areas with longer or dryer growing seasons versus the introduction of a moderate staygreen trait for silage in areas with shorter growing seasons. In addition, the staygreen potential of a plant of the invention can include, e.g., (a) a reduction in the production of at least one ACC synthase specific mRNA; (b) a reduction in the production of an ACC synthase; (c) a reduction in the production of ethylene; (d) a delay in leaf senescence; (e) an increase of drought resistance; (f) an increased time in maintaining photosynthetic activity; (g) an increased transpiration; (h) an increased stomatal conductance; (i) an increased $CO_2$ assimilation; (j) an increased maintenance of $CO_2$ assimilation; or (k) any combination of (a)-(j); compared to a corresponding control plant, and the like.

For example, a method of the invention can include: a) selecting at least one ACC synthase gene to mutate, thereby providing at least one desired ACC synthase gene; b) introducing a mutant form of the at least one desired ACC synthase gene into the plant; and, c) expressing the mutant form, thereby modulating staygreen potential in the plant. Plants produced by such methods are also a feature of the invention.

The degree of staygreen potential introduced into a plant can be determined by a number of factors, e.g., which ACC synthase gene is selected, whether the mutant gene member is present in a heterozygous or homozygous state, or by the number of members of this family which are inactivated, or by a combination of two or more such factors. In one embodiment, selecting the at least one ACC synthase gene comprises determining a degree (e.g., weak (e.g., ACS2), moderate or strong (e.g., ACS6)) of staygreen potential desired. For example, ACS2 lines show a weak staygreen phenotype, with a delay in senescence of about 1 week. The ACS6 lines show a strong staygreen phenotype (e.g., leaf senescence is delayed about 2-3 weeks or more). The ACS7 lines can also show a strong staygreen phenotype (e.g., leaf senescence is delayed about 2-3 weeks or more). For example, the ACC synthase gene is selected for encoding a specific ACC synthase, such as, SEQ ID NO:7 (pACS2), SEQ ID NO:8 (pACS6), SEQ ID NO:9 (pAC7), or SEQ ID NO:11 (pCCRA178R). In one embodiment, two or more ACC synthase genes are disrupted (e.g., ACS2 and ACS6), e.g., to produce a strong staygreen phenotype. In other embodiments, three or more ACC synthase genes are disrupted.

Once the desired ACC synthase gene is selected, a mutant form of the ACC synthase gene is introduced into a plant. In certain embodiments, the mutant form is introduced by *Agrobacterium*-mediated transfer, electroporation, micro-projectile bombardment, homologous recombination or a sexual cross. In certain embodiments, the mutant form includes, e.g., a heterozygous mutation in the at least one ACC synthase gene, a homozygous mutation in the at least one ACC synthase gene or a combination of homozygous mutation and heterozygous mutation if more than one ACC synthase gene is selected. In another embodiment, the mutant form includes a subsequence of the at least one desired ACC synthase gene in an antisense, sense or RNA silencing or interference configuration.

Expression of the mutant form of the ACC synthase gene or result of expression of the mutant form can be determined in a number of ways. For example, detection of expression products is performed either qualitatively (presence or absence of one or more product of interest) or quantitatively (by monitoring the level of expression of one or more product of interest). In one embodiment, the expression product is an RNA expression product. The invention optionally includes monitoring an expression level of a nucleic acid or polypeptide as noted herein for detection of ACC synthase in a plant or in a population of plants. Monitoring levels of ethylene or ACC can also be used for detection of inhibition of expression or activity of a mutant form of the ACC synthase gene.

In addition to increasing tolerance to drought stress in plants of the invention compared to a control plant, another important aspect of the invention is that higher density planting of plants of the invention can be possible, leading to increased yield per acre of corn. Most of the increase yield per acre of corn over the last century has come from increasing tolerance to crowding, which is a stress in, e.g., maize. Methods for modulating stress, e.g., increasing tolerance for crowding, in a plant are also a feature of the invention. For example, a method of the invention can include: a) selecting at least one ACC synthase gene to mutate, thereby providing at least one desired ACC synthase gene; b) introducing a mutant form of the at least one desired ACC synthase gene into the plant; and, c) expressing the mutant form, thereby modulating stress in the plant. Plants produced by such methods are also a feature of the invention. When the ethylene production is reduced in a plant by a mutant form of a desired ACC synthase gene, the plant does not perceive crowding. Thus, plants of the invention can be planted at higher density than currently practiced by farmers.

In another aspect, inactivation of one or more ACC synthase genes as described herein can influence response to disease or pathogen attack.

Methods for Modulating Sterility in a Plant

Methods for modulating sterility, e.g., female or male sterility, in plants are also features of the invention. The ability to introduce female or male sterility into plants permits rapid production of female or male sterile lines, e.g., for use in commercial breeding programs, e.g., for production of hybrid seed, where cross-pollination is desired.

ACC synthase knockout plants, particularly ACS6 knockouts and ACS2/ACS6 double knockouts, have been observed to shed less pollen than wild-type plants, suggesting disruption of ethylene production as a novel means of modulating plant sterility.

For example, a method of the invention can include: a) selecting at least one ACC synthase gene to mutate, thereby providing at least one desired ACC synthase gene; b) introducing a mutant form of the at least one desired ACC synthase gene into the plant; and, c) expressing the mutant form, thereby modulating sterility in the plant. Plants produced by such methods are also a feature of the invention.

Essentially all of the features noted above apply to this embodiment as well, as relevant, for example, with respect to the number of ACC synthase genes disrupted, techniques for introducing the mutant form of the ACC synthase gene into the plant, polynucleotide constructs, and the like.

In one class of embodiments, the at least one ACC synthase gene is disrupted by insertion of a transposon, by a point mutation, or by constitutive expression of a transgene comprising an ACC synthase polynucleotide in an antisense, sense, or RNA silencing or interference configuration. Such lines can be propagated by exogenously providing ethylene, for example, by spraying the plants at an appropriate developmental stage with 2-chloroethylphosphonic acid (CEPA), which breaks down in water to produce ethylene.

In another class of embodiments, the at least one ACC synthase gene is disrupted by expression of a transgene comprising an ACC synthase polynucleotide in an antisense, sense, or RNA silencing or interference configuration under the control of an inducible promoter, such that sterility can be induced and/or repressed as desired. In yet another class of embodiments, the at least one ACC synthase gene is disrupted by expression of a transgene comprising an ACC synthase polynucleotide in an antisense, sense, or RNA silencing or interference configuration under the control of a tissue-specific promoter, e.g., an anther-specific promoter to produce male sterile plants. Again, if necessary, such lines can be propagated by exogenously providing ethylene (e.g., by spraying with CEPA.

Screening/Characterization of Plants or Plant Cells of the Invention

The plants of this invention can be screened and/or characterized either genotypically, biochemically, phenotypically or a combination of two or more of the these to determine the presence, absence, and/or expression (e.g., amount, modulation, such as a decrease or increase compared to a control cell, and the like) of a polynucleotide of the invention, the presence, absence, expression, and/or enzymatic activity of a polypeptide of the invention, modulation of staygreen potential, modulation of crowding, and/or modulation of ethylene production. See, e.g., FIG. 19.

Genotypic analysis can be performed by any of a number of well-known techniques, including PCR amplification of genomic nucleic acid sequences and hybridization of genomic nucleic acid sequences or expressed nucleic acid sequences with specific labeled probes (e.g., Southern blotting, northern blotting, dot or slot blots, etc.).

For example, the Trait Utility System for Corn (TUSC), developed by Pioneer Hybrid Int., is a powerful PCR-based screening strategy to identify Mu transposon insertions in specific genes without the need for an observable phenotype. The system utilizes, e.g., TIR-PCR in which one PCR primer is derived from the target gene and the other (Mu-TIR) from the terminal-inverted-repeat (TIR) region of Mu. Using these primers in PCR reactions of DNA pooled from a large population of Mu containing plants, successful amplification is identified by Southern hybridization using the target gene as the probe. Screening the individuals within a positive pool is then performed to identify the candidate line containing insertion of a Mu element in the target gene. In order to determine whether an insertion event is limited to somatic cells or is present in the germ line (and therefore represents a heritable change), progeny from a candidate are optionally subjected to the same PCR/Southern hybridization analysis used in the original screen.

Biochemical analysis can also be performed for detecting, e.g., the presence, the absence or modulation (e.g., decrease or increase) of protein production (e.g., by ELISAs, western blots, etc.), the presence and/or amount of ethylene produced, and the like. For example, expressed polypeptides can be recovered and purified from isolated or recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art, including, e.g., those set forth in Sandana (1997) *Bioseparation of Proteins*, Academic Press, Inc.; and Bollag et al. (1996) *Protein Methods, 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

Chemicals, e.g., ethylene, ACC, etc., can be recovered and assayed from the cell extracts. For example, internal concentrations of ACC can be assayed by gas chromatography-mass spectroscopy, in acidic plant extracts as ethylene after decomposition in alkaline hypochlorite solution, etc. The concentration of ethylene can be determined by, e.g., gas chromatography-mass spectroscopy, etc. See, e.g., Nagahama, K., Ogawa, T., Fujii, T., Tazaki, M., Tanase, S., Morino, Y. and Fukuda, H. (1991) "*Purification and properties of an ethyleneforming enzyme from Pseudomonas syringae*" *J. Gen. Microbiol.* 137: 2281-2286. For example, ethylene can be measured with a gas chromatograph equipped with, e.g., an alumina based column (such as an HP-PLOT A1203 capillary column) and a flame ionization detector.

Phenotypic analysis includes, e.g., analyzing changes in chemical composition (e.g., as described under biochemical analysis), morphology, or physiological properties of the plant. For example, morphological changes can include, but are not limited to, increased staygreen potential, a delay in leaf senescence, an increase in drought resistance, an increase in crowding resistance, etc. Physiological properties can include, e.g., increased sustained photosynthesis, increased transpiration, increased stomatal conductance, increased $CO_2$ assimilation, longer maintenance of $CO_2$ assimilation, etc.

A variety of assays can be used for monitoring staygreen potential. For example, assays include, but are not limited to, visual inspection, monitoring photosynthesis measurements, and measuring levels of chlorophyll, DNA, RNA and/or protein content of, e.g., the leaves.

Plants of the Invention

Plant cells of the invention include, but are not limited to, meristem cells, Type I, Type II, and Type III callus, immature embryos, and gametic cells such as microspores, pollen, sperm and egg. In certain embodiments, the plant cell of the invention is from a dicot or monocot. A plant regenerated from the plant cell(s) of the invention is also a feature of the invention.

In one embodiment, the plant cell is in a plant, e.g., a hybrid plant, comprising a staygreen potential phenotype. In another embodiment, the plant cell is in a plant comprising a sterility phenotype, e.g., a male sterility phenotype. Through a series of breeding manipulations, the disrupted ACC synthase gene can be moved from one plant line to another plant line. For example, the hybrid plant can be produced by sexual cross of a plant comprising a disruption in one or more ACC synthase genes and a control plant.

Knockout plant cells are also a feature of the invention. In a first aspect, the invention provides for an isolated or recombinant knockout plant cell comprising at least one disruption in at least one endogenous ACC synthase gene (e.g., a nucleic acid sequence, or complement thereof, comprising, e.g., at least about 70%, at least about 75%, at least about 80%, at least about 85%, at least about 90%, at least about 95%, at least about 99%, about 99.5% or more, sequence identity to SEQ ID NO:1 (gACS2), SEQ ID NO:2 (gACS6), or SEQ ID NO:3 (gACS7)). The disruption inhibits expression or activity of at least one ACC synthase protein compared to a corresponding control plant cell lacking the disruption.

In one embodiment, the at least one endogenous ACC synthase gene comprises two or more endogenous ACC synthase genes. In another embodiment, the at least one endogenous ACC synthase gene comprises three or more endogenous ACC synthase genes. In certain embodiments, the at least one disruption results in reduced ethylene production by the knockout plant cell as compared to the control plant cell. In one aspect of the invention, the disruption of an ACC synthase gene in a plant cell comprises one or more transposons, wherein the one or more transposons are in the at least one endogenous ACC synthase gene. In another aspect, the disruption includes one or more point mutations in at least one endogenous ACC synthase gene. Optionally, the disruption is a homozygous disruption in the at least one ACC synthase gene. Alternatively, the disruption is a heterozygous disruption in the at least one ACC synthase gene. In certain embodiments, more than one ACC synthase gene is involved and there is more than one disruption, which can include homozygous disruptions, heterozygous disruptions or a combination of homozygous disruptions and heterozygous disruptions. See also sections herein entitled "Transposons and TILLING."

In another embodiment, the disruption of an ACC synthase gene is produced by inhibiting expression of the ACC synthase gene. For example, a knockout plant cell is produced by introducing at least one polynucleotide sequence comprising an ACC synthase nucleic acid sequence, or subsequence thereof, into a plant cell, such that the at least one polynucleotide sequence is linked to a promoter in a sense or antisense orientation. The polynucleotide sequence comprises, e.g., at least about 70%, at least about 75%, at least about 80%, at least about 85%, at least about 90%, at least about 95%, at least about 99%, about 99.5% or more sequence identity to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cACS7), or SEQ ID NO.:10 (CCRA178R), or a subsequence thereof, or a complement thereof. For example, the knockout plant cell can be produced by introducing at least one polynucleotide sequence comprising one or more subsequences of an ACC synthase nucleic acid sequence configured for RNA silencing or interference. The polynucleotide optionally comprises a vector, expression cassette, or the like. In another aspect, the knockout plant cell is produced by homologous recombination. See also sections herein entitled "Antisense, Sense, RNA Silencing or Interference Configurations" and "Homologous Recombination."

Knockout plants that comprise a staygreen potential phenotype are a feature of the invention. Typically, the staygreen potential phenotype in the knockout plant results from a disruption in at least one endogenous ACC synthase gene. In one embodiment, the disruption comprises one or more transposons, and the disruption inhibits expression or activity of at least one ACC synthase protein compared to a corresponding control plant. In another embodiment, the disruption comprises one or more point mutations and inhibits expression or activity of the at least one ACC synthase protein compared to a corresponding control. In certain embodiments, the at least one endogenous ACC synthase gene comprises a nucleic acid sequence, or complement thereof, comprising, e.g., at least about 70%, at least about 75%, at least about 80%, at least about 85%, at least about 90%, at least about 95%, at least about 99%, about 99.5% or more, sequence identity to SEQ ID NO:1 (gACS2), SEQ ID NO:2 (gACS6), or SEQ ID NO:3 (gACS7), or a complement thereof. In certain embodiments, the knockout plant is a hybrid plant.

The invention also features knockout plants that comprise a transgenic plant with a staygreen potential phenotype. For example, a transgenic plant of the invention includes a staygreen potential phenotype resulting from at least one introduced transgene which inhibits ethylene synthesis, wherein said at least one introduced transgene comprises a nucleic acid sequence encoding at least one ACC synthase or subsequence thereof, which nucleic acid sequence comprises, e.g., at least about 70%, at least about 75%, at least about 80%, at least about 85%, at least about 90%, at least about 95%, at least about 99%, about 99.5% or more, sequence identity to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cACS7) or SEQ ID NO:10 (CCRA178R), or a subsequence thereof, or a complement thereof, and modifies a level of expression or activity of the at least one ACC synthase. Typically, the configuration is a sense, antisense, or RNA silencing or interference configuration. A transgenic plant of the invention can also include a staygreen potential phenotype resulting from at least one introduced transgene which inhibits ethylene synthesis, wherein said at least one introduced transgene comprises a nucleic acid sequence encoding subsequences of at least one ACC synthase, which at least one ACC synthase comprises, e.g., at least about 70%, at least about 75%, at least about 80%, at least about 85%, at least about 90%, at least about 95%, at least about 99%, about 99.5% or more, sequence identity to SEQ ID NO:7 (pACS2), SEQ ID NO:8 (pACS6), SEQ ID NO.:9 (pACS7), or SEQ ID NO:11(pCCRA178R), or a conservative variation thereof, and is in an RNA silencing or interference configuration, and modifies a level of expression or activity of the at least one ACC synthase. In one aspect, the transgene optionally comprises a tissue-specific promoter or an inducible promoter (e.g., a leaf-specific promoter, a drought-inducible promoter, or the like).

The invention also features knockout plants that have a sterility phenotype, e.g., a male or female sterility phenotype. Thus, one class of embodiments provides a knockout plant comprising a male sterility phenotype which results from at least one disruption in at least one endogenous ACC synthase gene. The disruption inhibits expression or activity of at least one ACC synthase protein compared to a corresponding control plant. For example, ACS2, ACS6, and ACS7 can be disrupted, singly or in any combination (e.g., ACS6, or ACS2 and ACS6). Typically, the at least one disruption results in reduced ethylene production by the knockout plant as compared to the control plant.

In one embodiment, the at least one disruption comprises one or more transposons in the at least one endogenous ACC synthase gene. In another embodiment, the at least one disruption comprises one or more point mutations in the at least one endogenous ACC synthase gene. In other embodiments, the at least one disruption is introduced into the knockout plant by introducing at least one polynucleotide sequence comprising one or more subsequences of an ACC synthase nucleic acid sequence configured for RNA silencing or interference (or, alternatively, in a sense or antisense configuration). As noted, the polynucleotide sequence is optionally under the control of an inducible or tissue-specific (e.g., anther-specific) promoter.

In one embodiment, the male sterility phenotype comprises reduced pollen shedding by the knockout plant as compared to the control plant. For example, the knockout plant can shed at most 50%, 25%, 10%, 5%, or 1% as much pollen as the control plant, or it can shed no detectable pollen.

The invention also features knockout plants that comprise a transgenic plant with a male sterility phenotype. For example, a transgenic plant of the invention includes a male sterility phenotype resulting from at least one introduced transgene which inhibits ethylene synthesis, wherein said at least one introduced transgene comprises a nucleic acid sequence encoding at least one ACC synthase or subsequence thereof, which nucleic acid sequence comprises, e.g., at least about 70%, at least about 75%, at least about 80%, at least about 85%, at least about 90%, at least about 95%, at least about 99%, about 99.5% or more, sequence identity to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cACS7) or SEQ ID NO:10 (CCRA178R), or a subsequence thereof, or a complement thereof, and modifies a level of expression or activity of the at least one ACC synthase. Typically, the configuration is a sense, antisense, or RNA silencing or interference configuration. As noted, the transgene optionally comprises a tissue-specific promoter (e.g., an anther-specific promoter) or an inducible promoter.

Essentially any plant can be used in the methods and compositions of the invention. Such species include, but are not restricted to members of the families: Poaceae (formerly Graminae, including *Zea mays* (corn), rye, triticale, barley, millet, rice, wheat, oats, etc.); Leguminosae (including pea, beans, lentil, peanut, yam bean, cowpeas, velvet beans, soybean, clover, alfalfa, lupine, vetch, lotus, sweet clover, wisteria, sweetpea, etc.); Compositae (the largest family of vascular plants, including at least 1,000 genera, including important commercial crops such as sunflower) and Rosaciae (including raspberry, apricot, almond, peach, rose, etc.), as well as nut plants (including, walnut, pecan, hazelnut, etc.), forest trees (including *Pinus, Quercus, Pseutotsuga, Sequoia, Populus*, etc.), and other common crop plants (e.g., cotton, sorghum, lawn grasses, tomato, potato, pepper, broccoli, cabbage, etc.)

Additional plants, as well as those specified above, include plants from the genera: *Acamptoclados, Achnatherum, Achnella, Acroceras, Aegilops, Aegopgon, Agroelymus, Agrohordeum, Agropogon, Agropyron, Agrositanion, Agrostis, Aira, Allolepis, Alloteropsis, Alopecurus, Amblyopyrum, Ammophila, Ampelodesmos, Amphibromus, Amphicarpum, Amphilophis, Anastrophus, Anatherum, Andropogon, Anemathele, Aneurolepidium, Anisantha, Anthaenantia, Anthephora, Anthochloa, Anthoxanthum, Apera, Apluda, Archtagrostis, Arctophila, Argillochloa, Aristida, Arrhenatherum, Arthraxon, Arthrostylidium, Arundinaria, Arundinella, Arundo, Aspris, Atheropogon, Avena (e.g., oats), Avenella, Avenochloa, Avenula, Axonopus, Bambusa, Beckmannia, Blepharidachne, Blepharoneuron, Bothriochloa, Bouteloua, Brachiaria, Brachyelytrum, Brachypodium, Briza, Brizopyrum, Bromelica, Bromopsis, Bromus, Buchloe, Bulbilis, Calamagrostis, Calamovilfa, Campulosus, Capriola, Catabrosa, Catapodium, Cathestecum, Cenchropsis, Cenchrus, Centotheca, Ceratochloa, Chaetochloa, Chasmanthium, Chimonobambusa, Chionochloa, Chloris, Chondrosum, Chrysopon, Chusquea, Cinna, Cladoraphis, Coelorachis, Coix, Coleanthus, Colpodium, Coridochloa, Cornucopiae, Cortaderia, Corynephorus, Cottea, Critesion, Crypsis, Ctenium, Cutandia, Cylindropyrum, Cymbopogon, Cynodon, Cynosurus, Cytrococcum, Dactylis, Dactyloctenium, Danthonia, Dasyochloa, Dasyprum, Davyella, Dendrocalamus, Deschampsia, Desmazeria, Deyeuxia, Diarina, Diarrhena, Dichanthelium, Dichanthium, Dichelachne, Diectomus, Digitaria, Dimeria, Dimorpostachys, Dinebra, Diplachne, Dissanthelium, Dissochondrus, Distichlis, Drepanostachyum, Dupoa, Dupontia, Echinochloa, Ectosperma, Ehrharta, Eleusine, Elyhordeum, Elyleymus, Elymordeum, Elymus, Elyonurus, Elysitanion, Elytesion, Elytrigia, Enneapogon, Enteropogon, Epicampes, Eragrostis, Eremochloa, Eremopoa, Eremopyrum, Erianthus, Ericoma, Erichloa, Eriochrysis, Erioneuron, Euchlaena, Euclasta, Eulalia, Eulaliopsis, Eustachys, Fargesia, Festuca, Festulolium, Fingerhuthia, Fluminia, Garnotia, Gastridium, Gaudinia, Gigantochloa, Glyceria, Graphephorum, Gymnopogon, Gynerium, Hackelochloa, Hainardia, Hakonechloa, Haynaldia, Heleochloa, Helictotrichon, Hemarthria, Hesperochloa, Hesperostipa, Heteropogon, Hibanobambusa, Hierochloe, Hilaria, Holcus, Homalocenchrus, Hordeum* (e.g., barley), *Hydrochloa, Hymenachne, Hyparrhenia, Hypogynium, Hystrix, Ichnanthus, Imperata, Indocalamus, Isachne, Ischaemum, Ixophorus, Koeleria, Korycarpus, Lagurus, Lamarckia, Lasiacis, Leersia, Leptochloa, Leptochloopsis, Leptocoryphium, Leptoloma, Leptogon, Lepturus, Lerchenfeldia, Leucopoa, Leymostachys, Leymus, Limnodea, Lithachne, Lolium, Lophochlaena, Lophochloa, Lophopyrum, Ludolfia, Luziola, Lycurus, Lygeum, Maltea, Manisuris, Megastachya, Melica, Melinis, Mibora, Microchloa, Microlaena, Microstegium, Milium, Miscanthus, Mnesithea, Molinia, Monanthochloe, Monerma, Monroa, Muhlenbergia, Nardus, Nassella, Nazia, Neeragrostis, Neoschischkinia, Neostapfia, Neyraudia, Nothoholcus, Olyra, Opizia, Oplismenus, Orcuttia, Oryza* (e.g., rice), *Oryzopsis, Otatea, Oxytenanthera, Particularia, Panicum, Pappophorum, Parapholis, Pascopyrum, Paspalidium, Paspalum, Pennisetum* (e.g., millet), *Phalaris, Phalaroides, Phanopyrum, Pharus, Phippsia, Phleum, Pholiurus, Phragmites, Phyllostachys, Piptatherum, Piptochaetium, Pleioblastus, Pleopogon, Pleuraphis, Pleuropogon, Poa, Podagrostis, Polypogon, Polytrias, Psathyrostachys, Pseudelymus, Pseudoroegneria, Pseudosasa, Ptilagrostis, Puccinellia, Pucciphippsia, Redfieldia, Reimaria, Reimarochloa, Rhaphis, Rhombolytrum, Rhynchelytrum, Roegneria, Rostraria, Rottboellia, Rytilix, Saccharum, Sacciolepis, Sasa, Sasaella, Sasamorpha, Savastana, Schedonnardus, Schismus, Schizachne, Schizachyrium, Schizostachyum, Sclerochloa, Scleropoa, Scleropogon, Scolochloa, Scribneria, Secale* (e.g., rye), *Semiarundinaria,*

*Sesleria, Setaria, Shibataea, Sieglingia, Sinarundinaria, Sinobambusa, Sinocalamus, Sitanion, Sorghastrum, Sorghum, Spartina, Sphenopholis, Spodiopogon, Sporobolus, Stapfia, Steinchisma, Stenotaphrum, Stipa, Stipagrostis, Stiporyzopsis, Swallenia, Syntherisma, Taeniatherum, Terrellia, Terrelymus, Thamnocalamus, Themeda, Thinopyrum, Thuarea, Thysanolaena, Torresia, Torreyochloa, Trachynia, Trachypogon, Tragus, Trichachne, Trichloris, Tricholaena, Trichoneura, Tridens, Triodia, Triplasis, Tripogon, Tripsacum, Trisetobromus, Trisetum, Triticosecale, Triticum* (e.g., wheat), *Tuctoria, Uniola, Urachne, Uralepis, Urochloa, Vahlodea, Valota, Vaseyochloa, Ventenata, Vetiveria, Vilfa, Vulpia, Willkommia, Yushania, Zea* (e.g., corn), *Zizania, Zizaniopsis,* and *Zoysia.*

Plant Transformation

Nucleic acid sequence constructs of the invention (e.g., isolated nucleic acids, recombinant expression cassettes, etc.) can be introduced into plant cells, either in culture or in the organs of plants, by a variety of conventional techniques. For example, techniques include, but are not limited to, infection, transduction, transfection, transvection and transformation. The nucleic acid sequence constructs can be introduced alone or with other polynucleotides. Such other polynucleotides can be introduced independently, co-introduced, or introduced joined to polynucleotides of the invention.

Techniques for transforming a wide variety of higher plant species are well known and described in the technical and scientific literature. See, e.g., Payne et al. (1992) *Plant Cell and Tissue Culture in Liquid Systems* John Wiley & Sons, Inc. New York, N.Y. (Payne); Gamborg and Phillips (eds) (1995) *Plant Cell, Tissue and Organ Culture; Fundamental Methods* Springer Lab Manual, Springer-Verlag (Berlin Heidelberg New York) (Gamborg); Croy, (ed.) (1993) *Plant Molecular Biology* Bios Scientific Publishers, Oxford, U.K; Jones (ed) (1995) *Plant Gene Transfer and Expression Protocols—Methods in Molecular Biology*, Volume 49 Humana Press Towata N J, and as well as others, etc., as well as, e.g., Weising et al. (1988) *Ann. Rev. Genet.* 22:421. See, also, WO 95/06128 entitled "Fertile, Transgenic Maize Plants and Methods for Their Production" published on 2 Mar. 1995. Numerous protocols for establishment of transformable protoplasts from a variety of plant types and subsequent transformation of the cultured protoplasts are available in the art and are incorporated herein by reference. For example, see, Hashimoto et al. (1990) *Plant Physiol.* 93:857; Fowke and Constabel (eds) (1994) *Plant Protoplasts*; Saunders et al. (1993) *Applications of Plant In Vitro Technology Symposium*, UPM 16-18; and Lyznik et al. (1991) *BioTechniques* 10:295, each of which is incorporated herein by reference. Numerous methods are available in the art to accomplish chloroplast transformation and expression (e.g., Daniell et al. (1998) *Nature Biotechnology* 16:346; O'Neill et al. (1993) *The Plant Journal* 3:729; Maliga (1993) *TIBTECH* 11:1).

For example, nucleic acid sequences can be introduced directly into the genomic DNA of a plant cell using techniques such as electroporation, PEG poration, particle bombardment, silicon fiber delivery, or microinjection of plant cell protoplasts or embryogenic callus, or the nucleic acid sequence constructs can be introduced directly to plant tissue using ballistic methods, such as particle bombardment. Exemplary particles include, but are not limited to, tungsten, gold, platinum, and the like. Alternatively, the nucleic acid sequence constructs can be introduced by infection of cells with viral vectors, or by combining the nucleic acid sequence constructs with suitable T-DNA flanking regions and introduced into a conventional *Agrobacterium tumefaciens* host vector. The virulence functions of the *Agrobacterium* host will direct the insertion of the construct and adjacent marker into the plant cell DNA when the plant cell is infected by the bacteria. See, U.S. Pat. No. 5,591,616.

Microinjection techniques are known in the art and well described in the scientific and patent literature (see, e.g., Jones (ed) (1995) *Plant Gene Transfer and Expression Protocols—Methods in Molecular Biology*, Volume 49 Humana Press Towata N.J., and as well as others). The introduction of nucleic acid sequence constructs using polyethylene glycol precipitation is described in Paszkowski et al (1984) *EMBO J.* 3:2717. Electroporation techniques are described in Fromm et al. (1985) *Proc Nat'l Acad Sci USA* 82:5824. Ballistic transformation techniques are described in Klein et al. (1987) *Nature* 327:70; and Weeks et al. *Plant Physiol* 102:1077 and by Tomes, D. et al., IN: Plant Cell, Tissue and Organ Culture: Fundamental Methods, Eds. O. L. Gamborg and G. C. Phillips, Chapter 8, pgs. 197-213 (1995). (See also Tomes et al., U.S. Pat. Nos. 5,886,244; 6,258,999; 6,570,067; 5,879,918).

Viral vectors which are plant viruses can also be used to introduce polynucleotides of the invention into plants. Viruses are typically useful as vectors for expressing exogenous DNA sequences in a transient manner in plant hosts. In contrast to *agrobacterium* mediated transformation which results in the stable integration of DNA sequences in the plant genome, viral vectors are generally replicated and expressed without the need for chromosomal integration. Plant virus vectors offer a number of advantages, specifically: a) DNA copies of viral genomes can be readily manipulated in *E. coli*, and transcribed in vitro, where necessary, to produce infectious RNA copies; b) naked DNA, RNA, or virus particles can be easily introduced into mechanically wounded leaves of intact plants; c) high copy numbers of viral genomes per cell results in high expression levels of introduced genes; d) common laboratory plant species as well as monocot and dicot crop species are readily infected by various virus strains; e) infection of whole plants permits repeated tissue sampling of single library clones; f) recovery and purification of recombinant virus particles is simple and rapid; and g) because replication occurs without chromosomal insertion, expression is not subject to position effects. See, e.g., Scholthof, Scholthof and Jackson, (1996) *"Plant virus gene vectors for transient expression of foreign proteins in plants," Annu. Rev. of Phytopathol.* 34:299-323.

Plant viruses cause a range of diseases, most commonly mottled damage to leaves, so-called mosaics. Other symptoms include necrosis, deformation, outgrowths, and generalized yellowing or reddening of leaves. Plant viruses are known which infect every major food-crop, as well as most species of horticultural interest. The host range varies between viruses, with some viruses infecting a broad host range (e.g., alfalfa mosaic virus infects more than 400 species in 50 plant families) while others have a narrow host range, sometimes limited to a single species (e.g. barley yellow mosaic virus). Appropriate vectors can be selected based on the host used in the methods and compositions of the invention.

In certain embodiments of the invention, a vector includes a plant virus, e.g., either RNA (single or double stranded) or DNA (single-stranded or doubled-stranded) virus. Examples of such viruses include, but are not limited to, e.g., an alfamovirus, a bromovirus, a capillovirus, a carlavirus, a carmovirus, a caulimovirus, a closterovirus, a comovirus, a cryptovirus, a cucumovirus, a dianthovirus, a fabavirus, a fijivirus, a furovirus, a geminivirus, a hordeivirus, a ilarvirus, a luteovirus, a machlovirus, a maize chlorotic dwarf virus, a marafivirus, a necrovirus, a nepovirus, a parsnip yellow fleck virus, a pea enation mosaic virus, a potexvirus, a potyvirus, a reovirus, a rhabdovirus, a sobemovirus, a tenuivirus, a tobamovirus, a tobravirus, a tomato spotted wilt virus, a tombusvirus, a tymovirus, or the like.

Typically, plant viruses encode multiple proteins required for initial infection, replication and systemic spread, e.g. coat proteins, helper factors, replicases, and movement proteins. The nucleotide sequences encoding many of these proteins are matters of public knowledge, and accessible through any of a number of databases, e.g. (Genbank: available on the World Wide Web at ncbi.nlm.nih.gov/genbank/ or EMBL: available on the World Wide Web at ebi.ac.uk.embl/).

Methods for the transformation of plants and plant cells using sequences derived from plant viruses include the direct transformation techniques described above relating to DNA molecules, see e.g., Jones, ed. (1995) *Plant Gene Transfer and Expression Protocols*, Humana Press, Totowa, N.J. In addition, viral sequences can be cloned adjacent T-DNA border sequences and introduced via *Agrobacterium* mediated transformation or Agroinfection.

Viral particles comprising the plant virus vectors including polynucleotides of the invention can also be introduced by mechanical inoculation using techniques well known in the art; see, e.g., Cunningham and Porter, eds. (1997) *Methods in Biotechnology, Vol. 3. Recombinant Proteins from Plants: Production and Isolation of Clinically Useful Compounds*, for detailed protocols. Briefly, for experimental purposes, young plant leaves are dusted with silicon carbide (carborundum), then inoculated with a solution of viral transcript or encapsidated virus and gently rubbed. Large scale adaptations for infecting crop plants are also well known in the art, and typically involve mechanical maceration of leaves using a mower or other mechanical implement, followed by localized spraying of viral suspensions, or spraying leaves with a buffered virus/carborundum suspension at high pressure. Any of these above mentioned techniques can be adapted to the vectors of the invention, and are useful for alternative applications depending on the choice of plant virus and host species, as well as the scale of the specific transformation application.

In some embodiments, *Agrobacterium* mediated transformation techniques are used to transfer the ACC synthase sequences or subsequences of the invention to transgenic plants. *Agrobacterium*-mediated transformation is widely used for the transformation of dicots; however, certain monocots can also be transformed by *Agrobacterium*. For example, *Agrobacterium* transformation of rice is described by Hiei et al. (1994) *Plant J.* 6:271; U.S. Pat. Nos. 5,187,073; 5,591, 616; Li et al. (1991) *Science in China* 34:54; and Raineri et al. (1990) *Bio/Technology* 8:33. Transformed maize, barley, triticale and asparagus by *Agrobacterium* mediated transformation have also been described (Xu et al. (1990) *Chinese J Bot* 2:81).

*Agrobacterium* mediated transformation techniques take advantage of the ability of the tumor-inducing (Ti) plasmid of *A. tumefaciens* to integrate into a plant cell genome to co-transfer a nucleic acid of interest into a plant cell. Typically, an expression vector is produced wherein the nucleic acid of interest, such as an ACC synthase RNA configuration nucleic acid of the invention, is ligated into an autonomously replicating plasmid which also contains T-DNA sequences. T-DNA sequences typically flank the expression cassette nucleic acid of interest and comprise the integration sequences of the plasmid. In addition to the expression cassette, T-DNA also typically includes a marker sequence, e.g., antibiotic resistance genes. The plasmid with the T-DNA and the expression cassette are then transfected into *Agrobacterium* cells. Typically, for effective transformation of plant cells, the *A. tumefaciens* bacterium also possesses the necessary vir regions on a plasmid, or integrated into its chromosome. For a discussion of *Agrobacterium* mediated transformation, see, Firoozabady and Kuehnle, (1995) *Plant Cell Tissue and Organ Culture Fundamental Methods*, Gamborg and Phillips (eds.).

*Agrobacterium tumefaciens-mediated* transformation techniques are well described in the scientific literature. See, for example Horsch et al., *Science* 233: 496-498 (1984), and Fraley et al., *Proc. Natl. Acad. Sci* (*USA*) 80: 4803 (1983). Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include: (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J., In: DNA Cloning, Vol. II, D. M. Glover, Ed., Oxford, IRI Press, 1985); Application PCT/US87/02512 (WO 88/02405 published Apr. 7, 1988) describes the use of *A. rhizogenes* strain A4 and its Ri plasmid along with *A. tumefaciens* vectors pARC8 or pARC16, (2) liposome-mediated DNA uptake (see, e.g., Freeman et al., *Plant Cell Physiol.* 25: 1353, 1984), and (3) the vortexing method (see, e.g., Kindle, *Proc. Nat'l. Acad. Sci.* (*USA*) 87: 1228, (1990).

DNA can also be introduced into plants by direct DNA transfer into pollen as described by Zhou et al., *Methods in Enzymology*, 101:433 (1983); D. Hess, *Intern. Rev. Cytol.*, 107:367 (1987); Luo et al., *Plant Mol. Biol. Reporter,* 6:165 (1988). Expression of polypeptide coding genes can be obtained by injection of the DNA into reproductive organs of a plant as described by Pena et al., *Nature* 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo.* 1986, Butterworth, Stoneham, Mass., pp. 27-54 (1986). A variety of plant viruses that can be employed as vectors are known in the art and include cauliflower mosaic virus (CaMV), geminivirus, brome mosaic virus, and tobacco mosaic virus.

Other references describing suitable methods of transforming plant cells include microinjection, Crossway et al. (1986) *Biotechniques* 4:320-334; electroporation, Riggs et al. (1986) *Proc. Natl. Acad. Sci. USA* 83:5602-5606; *Agrobacterium*-mediated transformation, see for example, Townsend et al. U.S. Pat. No. 5,563,055; direct gene transfer, Paszkowski et al. (1984) *EMBO J.* 3:2717-2722; and ballistic particle acceleration, see for example, Sanford et al. U.S. Pat. No. 4,945, 050; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926. Also see Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) Bio/Technology 6:923-926 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) *Nature* (London) 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. G. P. Chapman et al. (Longman, New York), pp. 197-209

(pollen); Kaeppler et al. (1990) *Plant Cell Reports* 9:415-418; and Kaeppler et al. (1992) *Theor. Appl. Genet.* 84:560-566 (whisker-mediated transformation); D. Halluin et al. (1992) *Plant Cell* 4:1495-1505 (electroporation); Li et al. (1993) *Plant Cell Reports* 12:250-255 and Christou et al. (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Regeneration of Isolated, Recombinant or Trangenic Plants

Transformed plant cells which are derived by plant transformation techniques and isolated or recombinant plant cells, including those discussed above, can be cultured to regenerate a whole plant which possesses the desired genotype (i.e., a knockout ACC synthase nucleic acid), and/or thus the desired phenotype, e.g., staygreen phenotype, sterility phenotype, crowding resistant phenotype, etc. The desired cells, which can be identified, e.g., by selection or screening, are cultured in medium that supports regeneration. The cells can then be allowed to mature into plants. For example, such regeneration techniques can rely on manipulation of certain phytohormones in a tissue culture growth medium, typically relying on a biocide and/or herbicide marker which has been introduced together with the desired nucleotide sequences. Alternatively, screening can be performed to screen for inhibition of expression and/or activity of ACC synthase, reduction in ethylene production conferred by the knockout ACC synthase nucleic acid sequence, etc. Plant regeneration from cultured protoplasts is described in Evans et al. (1983) *Protoplasts Isolation and Culture, Handbook of Plant Cell Culture*, pp 124-176, Macmillan Publishing Company, New York; Davey, (1983) *Protoplasts*, pp. 12-29, Birkhauser, Basal 1983; Dale, *Protoplasts* (1983) pp. 31-41, Birkhauser, Basel; and, Binding (1985) *Regeneration of Plants, Plant Protoplasts* pp 21-73, CRC Press, Boca Raton. Regeneration can also be obtained from plant callus, explants, organs, or parts thereof. Such regeneration techniques are described generally in Klee et al. (1987) *Ann Rev of Plant Phys* 38:467. See also, e.g., Payne and Gamborg. For transformation and regeneration of maize see, for example, U.S. Pat. No. 5,736,369.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillilan Publishing Company, New York, pp. 124-176 (1983); and Binding, *Regeneration of Plants, Plant Protoplasts*, CRC Press, Boca Raton, pp. 21-73 (1985).

The regeneration of plants containing the foreign gene introduced by *Agrobacterium* from leaf explants can be achieved as described by Horsch et al., *Science*, 227:1229-1231 (1985). After transformation with *Agrobacterium*, the explants typically are transferred to selection medium. One of skill will realize that the selection medium depends on the selectable marker that is co-transfected into the explants. In this procedure, transformants are grown in the presence of a selection agent and in a medium that induces the regeneration of shoots in the plant species being transformed as described by Fraley et al., *Proc. Nat'l. Acad. Sci. (U.S.A)*., 80:4803 (1983). This procedure typically produces shoots, e.g., within two to four weeks, and these transformant shoots (which are typically, e.g., about 1-2 cm in length) are then transferred to an appropriate root-inducing medium containing the selective agent and an antibiotic to prevent bacterial growth. Selective pressure is typically maintained in the root and shoot medium.

Typically, the transformants will develop roots in about 1-2 weeks and form plantlets. After the plantlets are about 3-5 cm in height, they are placed in sterile soil in fiber pots. Those of skill in the art will realize that different acclimation procedures are used to obtain transformed plants of different species. For example, after developing a root and shoot, cuttings, as well as somatic embryos of transformed plants, are transferred to medium for establishment of plantlets. For a description of selection and regeneration of transformed plants, see, e.g., Dodds and Roberts (1995) *Experiments in Plant Tissue Culture*, $3^{rd}$ Ed., Cambridge University Press. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys*. 38: 467-486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed-propagated crops, mature transgenic plants can be self-crossed to produce a homozygous inbred plant. The inbred plant produces seed containing the newly introduced heterologous nucleic acid. These seeds can be grown to produce plants that would produce the selected phenotype. Mature transgenic plants can also be crossed with other appropriate plants, generally another inbred or hybrid, including, for example, an isogenic untransformed inbred.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these plants comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Some embodiments comprise a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous (aka hemizygous) transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant, or with a plant transgenic for the same or another trait or traits, are also contemplated.

It is also expected that the transformed plants will be used in traditional breeding programs, including TOPCROSS pollination systems as disclosed in U.S. Pat. Nos. 5,706,603 and 5,704,160, the disclosure of each of which is incorporated herein by reference.

In addition to Berger, Ausubel and Sambrook, useful general references for plant cell cloning, culture and regeneration include Jones (ed) (1995) *Plant Gene Transfer and Expression Protocols—Methods in Molecular Biology*, Volume 49 Humana Press Towata N J; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of cell culture media are described in Atlas and Parks (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS). Additional details regarding plant cell culture are found in Croy, (ed.) (1993) *Plant Molecular Biology* Bios Scientific Publishers, Oxford, U.K.

"Stacking" of Constructs and Traits

In certain embodiments, the nucleic acid sequences of the present invention can be used in combination ("stacked") with other polynucleotide sequences of interest in order to create plants with a desired phenotype. The polynucleotides of the present invention may be stacked with any gene or combination of genes, and the combinations generated can include multiple copies of any one or more of the polynucleotides of interest. The desired combination may affect one or more traits; that is, certain combinations may be created for modulation of gene expression affecting ACC synthase activity and/or ethylene production. Other combinations may be designed to produce plants with a variety of desired traits, including but not limited to traits desirable for animal feed such as high oil genes (e.g., U.S. Pat. No. 6,232,529); balanced amino acids (e.g. hordothionins (U.S. Pat. Nos. 5,990, 389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005, 429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737, 514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method, including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or over-expression cassettes to generate the desired combination of traits in the plant.

Use in Breeding Methods

The transformed plants of the invention may be used in a plant breeding program. The goal of plant breeding is to combine, in a single variety or hybrid, various desirable traits.

For field crops, these traits may include, for example, resistance to diseases and insects, tolerance to heat and drought, reduced time to crop maturity, greater yield, and better agronomic quality. With mechanical harvesting of many crops, uniformity of plant characteristics such as germination and stand establishment, growth rate, maturity, and plant and ear height is desirable. Traditional plant breeding is an important tool in developing new and improved commercial crops. This invention encompasses methods for producing a maize plant by crossing a first parent maize plant with a second parent maize plant wherein one or both of the parent maize plants is a transformed plant displaying a staygreen phenotype, a sterility phenotype, a crowding resistance phenotype, or the like, as described herein.

Plant breeding techniques known in the art and used in a maize plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids, and transformation. Often combinations of these techniques are used.

The development of maize hybrids in a maize plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular maize plant using transformation techniques can be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation, then the transgenic plants could be crossed to a different inbred in order to produce a transgenic hybrid maize plant. As used herein, "crossing" can refer to a simple X by Y cross, or the process of backcrossing, depending on the context.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly uniform; and (3) crossing the selected inbred lines with different inbred lines to produce the hybrids. During the inbreeding process in maize, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×zB)×C. Much of the hybrid vigor and uniformity exhibited by F1 hybrids is lost in the next generation (F2). Consequently, seed produced by hybrids is consumed rather than planted.

Antibodies

The polypeptides of the invention can be used to produce antibodies specific for the polypeptides of SEQ ID NO:7-SEQ ID NO:9 and SEQ ID NO.:11, and conservative variants thereof. Antibodies specific for, e.g., SEQ ID NOs: 7-9 and 11, and related variant polypeptides are useful, e.g., for screening and identification purposes, e.g., related to the activity, distribution, and expression of ACC synthase.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production. The full length polypeptide, subsequences, fragments or oligopeptides can be antigenic. Peptides used to induce specific antibodies typically have an amino acid sequence of at least about 10 amino acids, and often at least 15 or 20 amino acids. Short stretches of a polypeptide, e.g., selected from among SEQ ID NO:7-SEQ ID NO:9 and SEQ ID NO:11, can be fused with another protein, such as keyhole limpet hemocyanin, and antibody produced against the chimeric molecule.

Numerous methods for producing polyclonal and monoclonal antibodies are known to those of skill in the art and can be adapted to produce antibodies specific for the polypeptides of the invention, e.g., corresponding to SEQ ID NO:7-SEQ ID NO:9 and SEQ ID NO:11. See, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; *Fundamental Immunology*, e.g., $4^{th}$ Edition (or later) W. E. Paul (ed.), Raven Press, N.Y. (1998); and Kohler and Milstein (1975) Nature 256: 495-497. Other suitable techniques for antibody preparation include selection of libraries of recombinant antibodies in phage or similar vectors. See, Huse et al. (1989) *Science* 246: 1275-1281; and Ward, et al. (1989) Nature 341: 544-546. Specific monoclonal and polyclonal antibodies and antisera will usually bind with a $K_D$ of at least about 0.1 µM, preferably at least about 0.01 µM or better, and most typically and preferably, 0.001 µM or better.

Kits for Modulating Staygreen Potential or Sterility

Certain embodiments of the invention can optionally be provided to a user as a kit. For example, a kit of the invention can contain one or more nucleic acid, polypeptide, antibody, diagnostic nucleic acid or polypeptide, e.g., antibody, probe set, e.g., as a cDNA microarray, one or more vector and/or cell line described herein. Most often, the kit is packaged in a suitable container. The kit typically further comprises one or more additional reagents, e.g., substrates, labels, primers, or the like for labeling expression products, tubes and/or other accessories, reagents for collecting samples, buffers, hybridization chambers, cover slips, etc. The kit optionally further comprises an instruction set or user manual detailing preferred methods of using the kit components for discovery or application of gene sets. When used according to the instructions, the kit can be used, e.g., for evaluating expression or polymorphisms in a plant sample, e.g., for evaluating ACC synthase, ethylene production, staygreen potential, crowding resistance potential, sterility, etc. Alternatively, the kit can be used according to instructions for using at least one ACC synthase polynucleotide sequence to control staygreen potential in a plant.

As another example, a kit for modulating sterility, e.g., male sterility, in a plant includes a container containing at least one polynucleotide sequence comprising a nucleic acid sequence, wherein the nucleic acid sequence is, e.g., at least about 70%, at least about 75%, at least about 80%, at least about 85%, at least about 90%, at least about 95%, at least about 99%, about 99.5% or more, identical to SEQ ID NO:1 (gACS2), SEQ ID NO:2 (gACS6), SEQ ID NO:3 (gACS7), SEQ ID NO:4 (cACS2), SEQ ID NO:5 (cACS6), SEQ ID NO:6 (cAC7) or SEQ ID NO:10 (CCRA178R), or a subsequence thereof, or a complement thereof. The kit optionally also includes instructional materials for the use of the at least one polynucleotide sequence to control sterility, e.g., male sterility, in a plant.

Other Nucleic Acid and Protein Assays

In the context of the invention, nucleic acids and/or proteins are manipulated according to well known molecular biology methods. Detailed protocols for numerous such procedures are described in, e.g., in Ausubel et al. *Current Protocols in Molecular Biology* (supplemented through 2004) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying polynucleotides of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3. In lieu of synthesizing the desired sequences, essentially any nucleic acid can be custom ordered from any of a variety of commercial sources, such as The Midland Certified Reagent Company (mcrc@oligos.com) (Midland, Tex.), The Great American Gene Company (available on the World Wide Web at genco.com) (Ramona, Calif.), ExpressGen, Inc. (available on the World Wide Web at expressgen.com) (Chicago Ill.), Operon Technologies, Inc. (available on the World Wide Web at operon.com) (Alameda Calif.), and many others.

EXAMPLES

The following examples are offered to illustrate, but not to limit the claimed invention.

Example 1

Isolation of Maize ACC Synthase Knockouts

Figure 2:
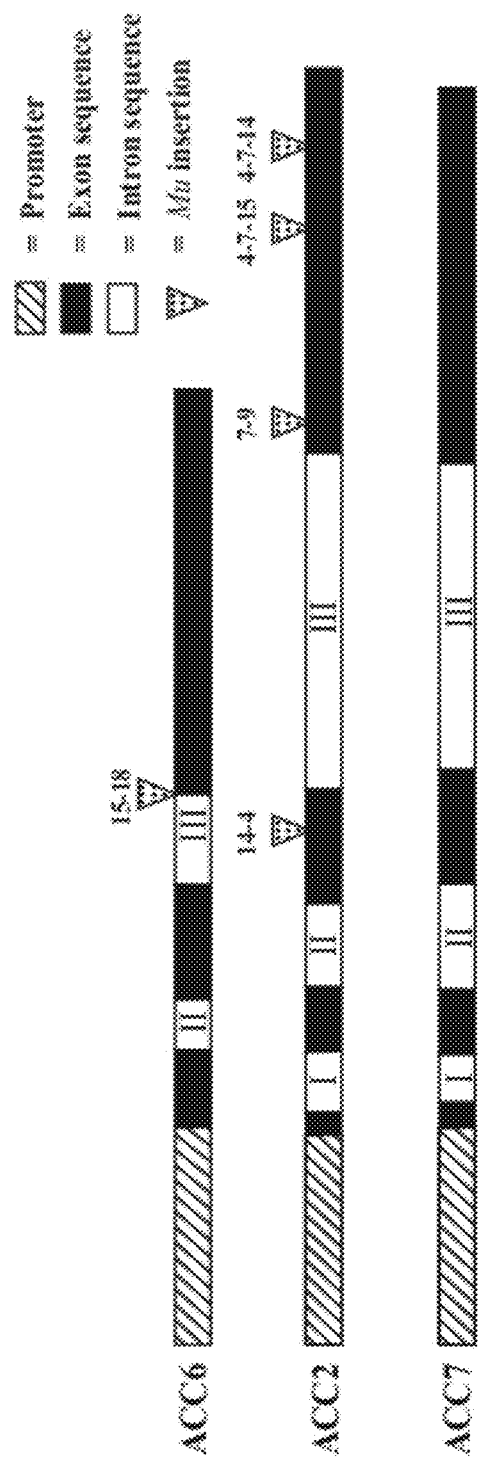
FIG. 2 schematically illustrates isolated and mapped ACC synthase genes and Mu insertion mutations. ACC6 is also known as ACS6, ACC2 is also known as ACS2, and ACCT is also known as ACS7.
Figure 3A:
FIG. 3, Panels A, B, C, and D illustrate heterozygous ACC synthase knockouts in plants, e.g., maize. Panel A and Panel B illustrate heterozygous ACC synthase knockout plants in a field of wild-type plants. Panel C and Panel D illustrate leaves from a heterozygous ACC synthase knockout plant, left side of panel, compared to leaves from an ACC synthase wild-type plant, right side of panel.
Figure 3B:
Figure 3C:
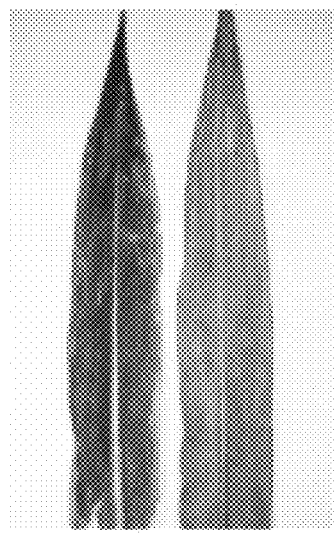
Figure 3D:
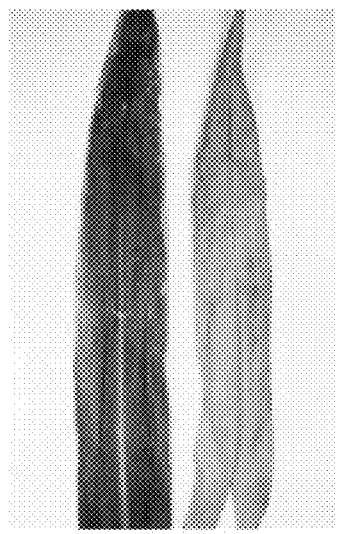

Because ethylene has been associated with promoting leaf senescence in some species, to introduce staygreen potential into, e.g., maize, we undertook to reduce ethylene biosynthesis in maize leaves through the inactivation of ACC synthase genes. The maize ACC synthase gene family is composed of three members: ACS2, ACS6, and ACS7. In order to isolate ethylene mutants, we screened for disruptions of each member of the ACC synthase gene family using the Trait Utility System for Corn (TUSC). To date, we have determined the exact Mu insertion site for 8 mutant lines (three ACS6 and five ACS2) by sequencing across the Mu/ACC synthase junction. Five insertions were stably inherited; their positions are indicated in FIG. 2, which also schematically depicts ACS7.

Figure 4:
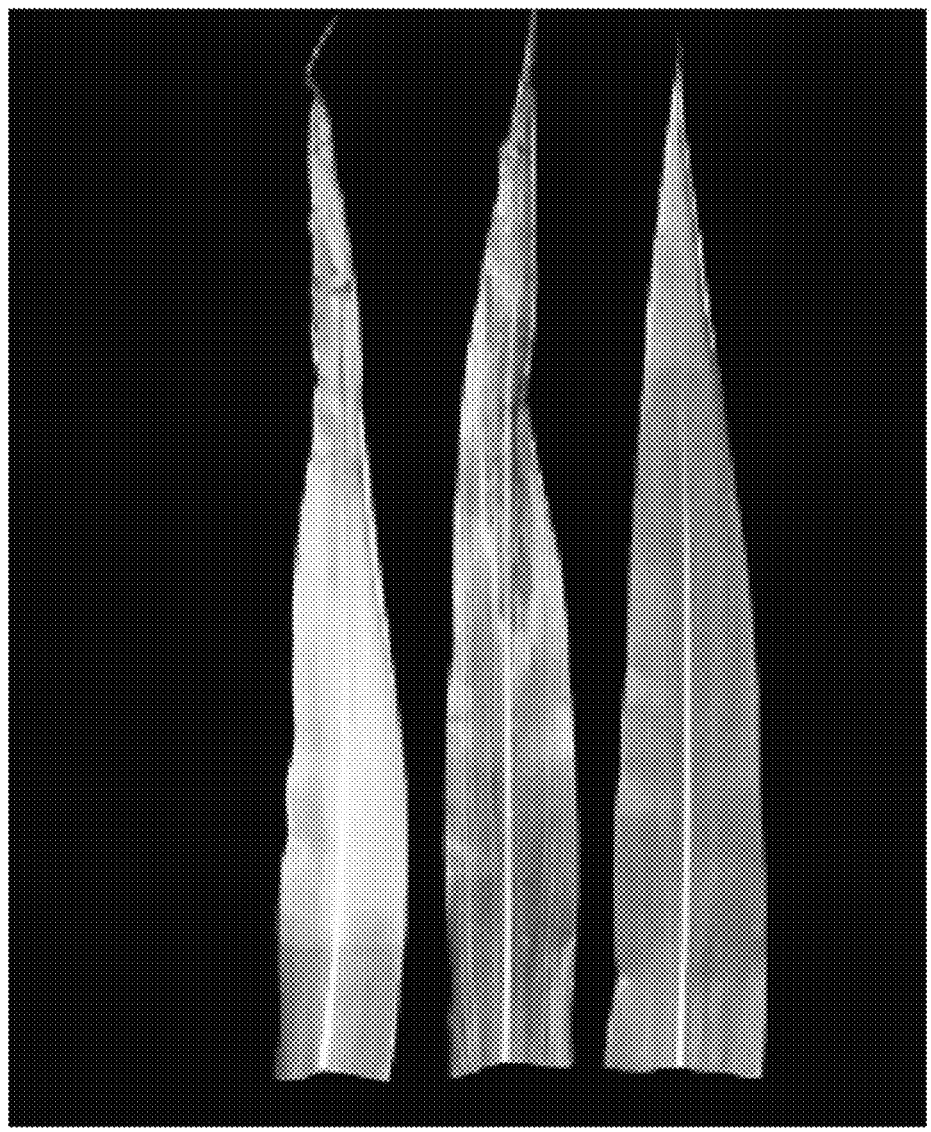
FIG. 4 illustrates an enhanced staygreen trait observed in leaves of plants that are homozygous ACC synthase knockouts (right) compared to wild type leaves (left) and heterozygous knockout leaves (middle).

A pronounced staygreen phenotype was observed in leaves of those plants in which a single gene member of the ACS family was present in a heterozygous mutant state (see FIG. 3, Panels A, B, C, and D). When present in a homozygous mutant state, an even more pronounced staygreen phenotype was observed (see FIG. 4). In FIG. 4, a leaf from the wild-type (left), heterozygous ACC synthase knockout (middle), and homozygous ACC synthase knockout (right) was sheathed for seven (7) days in the dark. Leaves from homozygous ACC synthase knockout plants exhibited a greater staygreen trait than leaves of the heterozygous ACC synthase knockout and exhibited a substantially greater staygreen trait than leaves of wild type plants.

The degree of staygreen potential introduced was gene member specific. Consequently, a strong staygreen trait was introduced with the mutation of one member (e.g., ACS6), while a less pronounced staygreen phenotype was introduced with the mutation of another member (e.g., ACS2). Therefore, the degree of staygreen potential introduced into a line can be controlled by which mutant gene member is introduced, whether the mutant gene member is present in a heterozygous or homozygous state, and by the number of members of this family which are inactivated (e.g., ACS2/ACS6 double mutants have a strong staygreen phenotype). Traits associated with improved hybrid standability include resistance to stalk rot and leaf blights, genetic stalk strength, short plant height and ear placement, and high staygreen potential.

Typically, leaves follow a typical progression from initiation through expansion ultimately ending in senescence. The carbon fixation capacity also increases during expansion and ultimately declines to low levels throughout senescence. See, e.g., Gay A P, and Thomas H (1995) *Leaf development in Lolium temulentum: photosynthesis in relation to growth and senescence. New Phytologist* 130: 159-168. This is of particular relevance to cereal species where yield potential is largely dependent upon the ability of the plant to fix carbon and store this carbon in the seed, mainly in the form of starch. Both the timing at which senescence is initiated and the rate at which it progresses can have a significant impact on the overall carbon a particular leaf can ultimately contribute to a plant. See, e.g., Thomas H, and Howarth C J (2000) *Five ways to stay green. Journal of Experimental Botany* 51: 329-337. This is of particular relevance to those crops where yield potential is reduced by adverse environmental conditions that induce premature leaf senescence. Stay-green is a general term used to describe a phenotype whereby leaf senescence (most easily distinguished by yellowing of the leaf associated with chlorophyll degradation) is delayed compared to a standard reference. See, e.g., Thomas and Howarth, supra. In sorghum, several stay-green genotypes have been identified which exhibit a delay in leaf senescence during grain filling and maturation. See, e.g., Duncan R R, et al. (1981) *Descriptive comparison of senescent and non-senescent sorghum genotypes. Agronomy Journal* 73: 849-853. Moreover, under conditions of limited water availability, which normally hastens leaf senescence (e.g., Rosenow D T, and Clark L E (1981) *Drought tolerance in sorghum*. In: Loden H D, Wilkinson D, eds. *Proceedings of the 36th annual corn and sorghum industry research conference,* 18-31), these genotypes retain more green leaf area and continue to fill grain normally (e.g., McBee G G, et al. (1983) *Effect of senescence and non-senescence on carbohydrates in sorghum during late kernel maturity states. Crop Science* 23: 372-377; Rosenow D T, et al. (1983) *Drought-tolerant sorghum and cotton germplasm. Agricultural Water Management* 7: 207-222; and, Borrell A K, Douglas A C L (1996) *Maintaining green leaf area in grain sorghum increases yield in a water-limited environment*. In: Foale M A, Henzell R G, Kneipp J F, eds. *Proceedings of the third Australian sorghum conference. Melbourne: Australian Institute of Agricultural Science, Occasional Publication No.* 93). The stay-green phenotype has also been used as a selection criterion for the development of improved varieties of corn, particularly with regard to the development of drought-tolerance. See, e.g., Russell W A (1991) *Genetic improvement of maize yields. Advances in Agronomy* 46: 245-298; and, Bruce et al., (2002), *Molecular and physiological approaches to maize improvement for drought tolerance, Journal of Experimental Botany,* 53 (366):13-25.

Five fundamentally distinct types of stay-green have been described. See, e.g., Thomas H, and Smart C M (1993) *Crops that stay green. Annals of Applied Biology* 123: 193-219; and, Thomas and Howarth, supra. In Type A stay-green, initiation of the senescence program is delayed, but then proceeds at a normal rate. In Type B stay-green, while initiation of the senescence program is unchanged, the progression is comparatively slower. In Type C stay-green, chlorophyll is retained even though senescence (as determined through measurements of physiological function such as photosynthetic capacity) proceeds at a normal rate. Type D stay-green is more artificial in that killing of the leaf (i.e. by freezing, boiling or drying) prevents initiation of the senescence program thereby stopping the degradation of chlorophyll. In Type E stay-green, initial levels of chlorophyll are higher while initiation and progression of leaf senescence are unchanged, thereby giving the illusion of a relatively slower progression rate. Type A and B are functional stay-greens as photosynthetic capacity is maintained along with chlorophyll content and are the types associated with increased yield and drought tolerance in sorghum. Despite the potential importance of this trait, in particular the benefits associated with increasing yield and drought tolerance, very little progress has been made in understanding the biochemical, physiological or molecular basis for genetically-determined stay-green. See, e.g., Thomas and Howarth, supra.

A number of environmental and physiological conditions have been shown to significantly alter the timing and progression of leaf senescence and can provide some insight into the basis for this trait. Among environmental factors, light is probably the most significant and it has long been established that leaf senescence can be induced in many plant species by placing detached leaves in darkness. See, e.g., Weaver L M, Amasino R M (2001) *Senescence is induced in individually darkened Arabidopsis leaves, but inhibited in whole darkened plants. Plant Physiology* 127: 876-886. Limited nutrient and water availability have also been shown to induce leaf senescence prematurely (e.g., Rosenow D T, Quisenberry J E, Wendt C W, Clark L E (1983) *Drought-tolerant sorghum and cotton germplasm. Agricultural Water Management* 7: 207-222). Among physiological determinants, growth regulators play a key role in directing the leaf senescence program. Of particular relevance is the observation that modification of cytokinin levels can significantly delay leaf senescence. For example, plants transformed with isopentenyl transferase (ipt), an *Agrobacterium* gene encoding a rate-limiting step in cytokinin biosynthesis, when placed under the control of a senescence inducible promoter, resulted in autoregulated cytokinin production and a strong stay-green phenotype. See, e.g., Gan S, Amasino R M (1995) *Inhibition of leaf senescence by autoregulated production of cytokinin. Science* 270: 1986-1988. Ethylene has also been implicated in controlling leaf senescence (e.g., Davis K M, and Grierson D (1989) *Identification of cDNA clones for tomato (Lycopersicon esculentum Mill.) mRNAs that accumulate during fruit ripening and leaf senescence in response to ethylene. Planta* 179: 73-80) and plants impaired in ethylene production or perception also show a delay in leaf senescence (e.g., Picton S, et al., (1993) *Altered fruit ripening and leaf senescence in tomatoes expressing an antisense ethylene-forming enzyme transgene. The Plant Journal* 3: 469-481; Grbic V, and Bleeker A B (1995) *Ethylene regulates the timing of leaf senescence in Arabidopsis. The Plant Journal* 8: 95-102; and, John I, et al., (1995) *Delayed leaf senescence in ethylene-deficient ACC-oxidase antisense tomato plants: molecular and physiological analysis. The Plant Journal* 7: 483-490), which can be phenocopied by exogenous application of inhibitors of ethylene biosynthesis and action (e.g., Abeles F B, et al., (1992) *Ethylene in Plant Biology*. Academic Press, San Diego, Calif.).

The identification and analysis of mutants in *Arabidopsis* and tomato that are deficient in ethylene biosynthesis and perception are valuable in establishing the important role that ethylene plays in plant growth and development. Mutant analysis has also been instrumental in identifying and characterizing the ethylene signal transduction pathway. While many ethylene mutants have been identified in dicot plants (e.g., *Arabidopsis* and tomato), no such mutants have been identified in monocots (e.g., rice, wheat, and corn). Here the identification of maize mutants deficient in ACC synthase, the first enzyme in the ethylene biosynthetic pathway, are described. These mutants are critical in elucidating the regulatory roles that ethylene plays throughout cereal development as well as its role in regulating responses to environmental stress. Knowledge obtained from such mutant analysis will increase the understanding of the role of ethylene in maize development and will be pertinent to other cereal crop species.

Mutants were deficient in ethylene production and exhibited a staygreen phenotype. Staygreen was observed under normal growth conditions and following prolonged conditions of drought that induced premature onset of leaf senescence in wild-type plants. In addition to the maintenance of chlorophyll during water stress, ACC synthase-deficient leaves maintained photosynthetic function and continued to assimilate $CO_2$. Surprisingly, reducing ethylene production improved leaf function in all leaves under normal growth conditions and maintained a high level of function in drought-stressed plants even for those leaves in which senescence had not been induced in similar age leaves of wild-type plants. These findings indicate that ethylene may serve to regulate leaf function under normal growth conditions as well as in response to conditions of drought.

Materials and Methods

Cloning of ACC Synthase Genes from *Zea mays*

To facilitate cloning of ACC synthase gene(s) from maize, primers were designed to regions highly conserved between multiple monocot and dicot species using sequence information currently available in GenBank. Initial PCR reactions were carried out on maize genomic DNA using primers ACCF1 (ccagatgggcctcgccgagaac; SEQ ID NO:12) and ACC1 (gttggcgtagcagacgcggaacca; SEQ ID NO:13) and revealed the presence of three fragments of different sizes. All three fragments were sequenced and confirmed to be highly similar in sequence to other known ACC synthase genes.

To obtain the entire genomic sequences for each of these genes, all three fragments were radiolabeled with dCTP using the Prime-a-Gene™ labeling system (Promega) and used to screen an EMBL3 maize (B73) genomic library (Stratagene) according to methods described in Sambrook, supra. Hybridization was carried out overnight at 30° C. in buffer containing 5×SSPE, 5×Denhardt's, 50% Formamide and 1% SDS. Blots were washed sequentially at 45° C. in 1×SSPE and 0.1×SSPE containing 0.1% SDS and exposed to film at −80° C. with an intensifier screen. A total of 36 confluent plates (150 mm diameter) were screened. Putative positives plaques were subsequently screened directly by PCR using the above primers to identify which clones contained fragments corresponding to the three fragments initially identified. PCR screening was accomplished using HotStarTaq™ (a hot start Taq DNA polymerase, Qiagen). Reactions contained 1× buffer, 200 μM of each dNTP, 3 μM MgCl$_2$, 0.25 μM forward and reverse primer, 1.25 U HotStarTaq™ and 1 μl primary phage dilution (1/600 total in SM buffer) as a template in a total reaction volume of 25 μl. Reaction conditions were as follows: 95° C./15 min. (1 cycle); 95° C./1 min, 62° C./1 min, 72° C./2 min (35 cycles); 72° C./5 min (1 cycle). Samples were separated on a 1% agarose gel and the products were visualized following staining with ethidium bromide. All fragments amplified were also subjected to restriction analysis to identify other potential sequence specific differences independent of subsequence size.

To facilitate sequencing the remaining portions of these genes, primers ACCF1 and ACC1 were used in conjunction with primers specific to either the left (gacaaactgcgcaactcgtgaaaggt; SEQ ID NO:14) or right (ctcgtccgagaataacgagtggatct; SEQ ID NO:15) arm of the EMBL3 vector to amplify each half of the gene. Takara LA Taq (a thermostable DNA polymerase having proof reading activity, Panvera) was used to amplify the fragments due to the large size. Reactions contained 1 μl phage dilution (1/600 total in SM buffer) and 2 μM each primer (final concentration), 1× buffer (final concentration), 400 μM dNTP mix (final concentration) and 1.25 U LA Taq in 25 μltotal volume. Reactions were carried out under the following conditions: 98° C./1 min. (1 cycle); 98° C./30 sec, 69° C./15 min. (35 cycles); 72° C./10 min (1 cycle). Amplified products were purified using the StrataPrep™ PCR purification kit (Stratagene) and sent to the sequencing facility at the University of Florida, Gainesville for direct sequencing.

Identification of ACC Synthase Knock Out Mutants

Maize has proven to be a rich source of mutants, in part due to the presence of active or previously active transposable element systems within its genome. Depending precisely on the location of the insertion site in a gene, a transposon can partially or completely inactivate expression of a gene. Gene inactivation may or may not have an observable phenotype depending upon the amount of redundancy (i.e. presence of multiple family members and the tissue specificity of the family members). Trait Utility System for Corn (TUSC), developed by Pioneer Hybrid Int., is a powerful PCR-based screening strategy to identify Mu transposon insertions in specific genes without the need for an observable phenotype. This screening approach is best suited to target genes that have been previously isolated from maize. The system utilizes TIR-PCR in which one PCR primer is derived from the target gene and the other (Mu-TIR) from the terminal-inverted-repeat (TIR) region of Mu. Using these primers in PCR reactions of DNA pooled from a large population of Mu containing plants, successful amplification is identified by Southern hybridization using the target gene as the probe. Screening the individuals within a positive pool is then performed to identify the candidate line containing insertion of a Mu element in the target gene. In order to determine whether an insertion event is limited to somatic cells or is present in the germ line (and therefore represents a heritable change), progeny from a candidate are subjected to the same PCR/Southern hybridization analysis used in the original screen.

A research effort was established to identify knockout mutants in ethylene biosynthesis. To accomplish this, four primers (ACCF1, ccagatgggcctcgccgagaac, SEQ ID NO:12; ACC-1, gttggcgtagcagacgcggaacca, SEQ ID NO:13; ACC-C, cagttatgtgagggcacaccctacagcca, SEQ ID NO:16; ACC-D, catcgaatgccacagctcgaacaacttc, SEQ ID NO:17) specific to the maize ACC synthase genes discussed above were used to screen for Mu insertions in combination with the Mu-TIR primer (aagccaacgcca(a/t)cgcctc(c/t)atttcgt; SEQ ID NO:18). The initial screening resulted in the putative identification of 19 separate lines carrying Mu insertions in the maize ACC synthase multigene family. Seed from each of these lines was planted and DNA was extracted from the leaf of each individual. For DNA isolation, 1 cm$^2$ of seedling leaf was isolated from each plant and placed into a 1.5 ml centrifuge tube containing some sand. Samples were quick-frozen in liquid nitrogen and ground to a fine powder using a disposable pestle (Fisher Scientific). 600 μl of extraction buffer (100 mM Tris (pH 8.0), 50 mM EDTA, 200 mM NaCl, 1% SDS, 10 μl/ml β-mercaptoethanol) was added immediately and mixed thoroughly. 700 μl Phenol/Chloroform (1:1) was added and samples were centrifuged 10 min at 12,000 rpm. 500 μl supernatant was removed to a new tube and the nucleic acid precipitated at −20° C. following addition of 1/10 vol 3M sodium acetate and 1 vol isopropanol. Total nucleic acid was pelleted by centrifugation at 12,000 rpm, washed 3× with 75% ethanol and resuspended in 600 μl H$_2$O. PCR screening was accomplished using HotStarTaq™ (Qiagen). Reactions contained 1× buffer, 200 μM of each dNTP, 3 mM MgCl$_2$, 0.25 μM ACC synthase specific primer (ACCF1, ACC-1, ACC-C or ACC-D), 0.25 μM Mu specific primer (MuTIR), 0.25 μl HotStarTaq™ and 1.5 μl total nucleic acid as a template in a total reaction volume of 25 μl. Reaction conditions were as follows: 95° C./15 min. (1 cycle); 95° C./1 min, 62° C./1 min, 72° C./2 min (35 cycles); 72° C./5 min (1 cycle). PCR products were separated on a 1% agarose gel, visualized following staining with ethidium bromide and transferred to nylon membranes according to methods described in Sambrook et al. (1989). Southern blot analysis was performed as described above for library screening except the hybridization temperature was increased to 45° C. BC1 (backcross 1) seed was planted from each of the 13 putative mutant lines and screened by PCR/Southern analysis (as just described). Of these lines, only 5 were found to be stably inherited. These five lines were backcrossed an additional 4 times to minimize the effects of unrelated Mu insertions.

BC5 seed was self-pollinated to generate homozygous null individuals. Homozygous null individual lines were identified by PCR using Takara LA Taq and the ACCF1 and ACC-1 primers. Reactions contained 1 µl leaf DNA, 2 µM each primer (final concentration), 1× buffer (final concentration), 400 µM dNTP mix (final concentration) and 1.25 U LA Taq in 25 µl total volume. Reactions were carried out under the following conditions: 98° C./1 min. (1 cycle); 98° C./30 sec, 69° C./15 min. (35 cycles); 72° C./10 min (1 cycle). PCR of wild-type B73 DNA using these primers and conditions results in the amplification of three different sized fragments corresponding to the three genes identified. Individuals which are either wild-type or heterozygous for one of the null insertion-alleles display this characteristic pattern while those which are homozygous for one of the null insertion-alleles are missing the subsequence corresponding to the gene in which the insertion is located.

To determine the exact location of the Mu insertion site, PCR products from each of the lines were amplified using either the ACCF1 or ACC-1 primer in combination with the MuTIR primer. These fragments were then sequenced across the Mu/target gene junction using the Mu-TIR primer. The location of these Mu elements within each of the ACC synthase genes is shown in FIG. 2.

Protein Extraction

For total protein isolation, leaves of B73 or mutant plants were collected at the indicated times, quick-frozen in liquid nitrogen and ground to a fine powder. One ml of extraction buffer (20 mM HEPES (pH 7.6), 100 mM KCl, 10% Glycerol) was added to approximately 0.1 g frozen powder and mixed thoroughly. Samples were centrifuged 10 min at 10,000 rpm, the supernatant removed to a new tube and the concentration determined spectrophotometrically according to the methods of Bradford (1976). See, Bradford M M (1976) *A rapid and sensitive method for the quantitation of microgram quantities of protein utilizing the principle of protein-dye binding. Anal. Biochem.* 72: 248-254. (See FIG. 18).

Chlorophyll Extraction

Leaves were frozen in liquid nitrogen and ground to a fine powder. Samples of approximately 0.1 g were removed to a 1.5 ml tube and weighed. Chlorophyll was extracted 5× with 1 ml (or 0.8 ml) of 80% acetone. Individual extractions were combined and the final volume adjusted to 10 ml (or 15 ml) with additional 80% acetone. Chlorophyll content (a+b) was determined spectrophotometrically according to the methods of Wellburn (1994). See, Wellburn, A. R. (1994) *The spectral determination of chlorophylls a and b, as well as total caretenoids, using various solvents with spectrophotometers of different resolution. J. Plant Physiol.* 144: 307-313. (See FIG. 17).

Measurement of Photosynthesis

Plants were grown in the field under normal and drought-stress conditions. Normal plants were watered for eight hours twice a week. For drought-stressed plants, water was limited to approximately four hours per week for a period starting approximately one week before pollination and continuing through three weeks after pollination. During the period of limited water availability, drought-stressed plants showed visible signs of wilting and leaf rolling. Transpiration, stomatal conductance and $CO_2$ assimilation were determined with a portable TPS-1 Photosynthesis System (PP Systems). Each leaf on a plant was measured at forty days after pollination. Values represent a mean of six determinations. See FIGS. 5 and 6.

DNA and RNA Purification

For total nucleic acid isolation, leaves of B73 are collected at desired times, quick-frozen in liquid nitrogen and ground to a fine powder. Ten ml of extraction buffer (100 mM Tris (pH 8.0), 50 mM EDTA, 200 mM NaCl, 1% SDS, 10 µml β-mercaptoethanol) is added and mixed thoroughly until thawed. Ten ml of Phenol/Chloroform (1:1, vol:vol) is added and mixed thoroughly. Samples are centrifuged 10 min at 8,000 rpm, the supernatant is removed to a new tube and the nucleic acid is precipitated at −20° C. following addition of 1/10 vol 3M sodium acetate and 1 vol isopropanol. Total nucleic acid is pelleted by centrifugation at 8,000 rpm and resuspended in 1 ml TE. One half of the prep is used for DNA purification and the remaining half is used for RNA purification. (Alternatively, DNA or total nucleic acids can be extracted from 1 $cm^2$ of seedling leaf, quick-frozen in liquid nitrogen, and ground to a fine powder. 600 µl of extraction buffer [100 mM Tris (pH 8.0), 50 mM EDTA, 200 mM NaCl, 1% SDS, 10 µl/ml β-mercaptoethanol] is added and the sample mixed. The sample is extracted with 700 µl phenol/chloroform (1:1) and centrifuged for 10 min at 12,000 rpm. DNA is precipitated and resuspended in 600 µl H2O.)

For DNA purification, 500 µg DNase-free RNase is added to the tube and incubated at 37° C. for 1 hr. Following RNase digestion, an equal volume of Phenol/Chloroform (1:1, vol:vol) is added and mixed thoroughly. Samples are centrifuged 10 min at 10,000 rpm, the supernatant is removed to a new tube and the DNA precipitated at −20° C. following addition of 1/10 vol 3M sodium acetate and 1 vol isopropanol. DNA is resuspended in sterile water and the concentration is determined spectrophotometrically. To determine DNA integrity, 20 mg of DNA is separated on a 1.8% agarose gel and visualized following staining with ethidium bromide. RNA is purified by 2 rounds of $LiCl_2$ precipitation according to methods described by Sambrook et al, supra.

Real-Time RT-PCR Analysis

Fifty µg total RNA is treated with RQ1™ DNase (Promega) to ensure that no contaminating DNA is present. Two µg total RNA is used directly for cDNA synthesis using the Omniscript RT™ reverse transcription kit (Qiagen) with oligo-dT(20) as the primer.

Analysis of transcript abundance is accomplished using the QuantiTect™ SYBR Green PCR kit (Qiagen). Reactions contain 1× buffer, 0.5 µl of the reverse transcription reaction (equivalent to 50 ng total RNA) and 0.25 µM (final concentration) forward and reverse primers (see table 2 below) in a total reaction volume of 25 µl.

TABLE 2

| Gene | Forward Primer (5'-3') | Reverse Primer (5'-3') |
|---|---|---|
| ZmACS47 | atcgcgtacagcctctccaagga<br>SEQ ID NO: 19 | gatagtcttttgtcaaccatcccataga<br>SEQ ID NO: 20 |
| ZmACS50 | atcgcgtacagcctctccaagga<br>SEQ ID NO: 21 | caacgtctctgtcactctgtgtaatgt<br>SEQ ID NO: 22 |

TABLE 2-continued

| Gene | Forward Primer (5'-3') | Reverse Primer (5'-3') |
|---|---|---|
| ZmACS65 | agctgtggaagaaggtggtcttcgaggt SEQ ID NO: 23 | agtacgtgaccgtggtttctatga SEQ ID NO: 24 |

Reactions are carried out using an ABI PRISM 7700 sequence detection system under the following conditions: 95° C./15 min. (1 cycle); 95° C./30 sec, 62° C./30 sec, 72° C./2 min (50 cycles); 72° C./5 min (1 cycle). Each gene is analyzed a minimum of four times.

All the primer combinations are initially run and visualized on an agarose gel to confirm the presence single product of the correct size. All amplification products are subcloned into the pGEM-T Easy vector system (Promega) to use for generation of standard curves to facilitate conversion of expression data to a copy/µg RNA basis.

Ethylene Determination

Ethylene was measured from the second fully-expanded leaf of seedlings leaves at the 4-leaf stage or from the terminal 15 cm of leaves of plants 20, 30, or 40 days after pollination (DAP). Leaves were harvested at the indicated times and allowed to recover for 2 hr prior to collecting ethylene, between moist paper towels. Leaves were placed into glass vials and capped with a rubber septum. Following a 3-4 hour incubation, 0.9 mL of headspace was sampled from each vial and the ethylene content measured using a 6850 series gas chromatography system (Hewlett-Packard, Palo Alto, Calif.) equipped with a HP Plot alumina-based capillary column (Agilent Technologies, Palo Alto, Calif.). Tissue fresh weight was measured for each sample. Three replicates were measured and the average and standard deviation reported.

Western Blot Analysis

B73 leaves were collected at the indicated times and ground in liquid nitrogen to a fine powder. One ml of extraction buffer [20 mM HEPES (pH 7.6), 100 mM KCl, 10% glycerol, 1 mM PMSF] was added to approximately 0.1 g frozen powder and mixed thoroughly. Cell debris was pelleted by centrifugation at 10,000 rpm for 10 min and the protein concentration determined as described (Bradford, 1976). Antiserum raised against the large subunit of rice Rubisco was obtained from Dr. Tadahiko Mae (Tohoku University, Sendai, Japan). Protein extracts were resolved using standard SDS-PAGE and the protein transferred to 0.22 µm nitrocellulose membrane by electroblotting. Following transfer, the membranes were blocked in 5% milk, 0.01% thimerosal in TPBS (0.1% TWEEN 20, 13.7 mM NaCl, 0.27 mM KCl, 1 mM Na2HPO4, 0.14 mM KH2PO4) followed by incubation with primary antibodies diluted typically 1:1000 to 1:2000 in TPBS with 1% milk for 1.5 hrs. The blots were then washed twice with TPBS and incubated with goat anti-rabbit horseradish peroxidase-conjugated antibodies (Southern Biotechnology Associates, Inc.) diluted to 1:5000 to 1:10,000 for 1 hr. The blots were washed twice with TPBS and the signal detected typically between 1 to 15 min using chemiluminescence (Amersham Corp).

Results

Identification of ACC Synthase Knockout Mutants

Three genes encoding ACC synthase were isolated from the inbred B73 and sequenced (see, e.g., SEQ ID NOs:1-11). Two members of the family (i.e., ACS2 and ACS7) are closely related (97% amino acid identity) whereas the third gene (i.e., ACS6) is considerably more divergent (54% and 53% amino acid identity with ACS2 and ACS7, respectively). A reverse genetic approach was used to screen for transposon insertions in ACC synthase gene family members (Bensen et al. (1995) *Cloning and characterization of the maize An1 gene. Plant Cell* 7:75-84). 19 candidate lines were identified, 13 of which were confirmed by terminal-inverted-repeat (TIR)-PCR to harbor a Mu insertion in one of the three ACC synthase genes. Of these, 5 lines stably inherited the transposon in the first backcross to B73 which were backcrossed an additional 4 times to reduce unwanted Mu insertions. Plants were then self-pollinated to generate homozygous null individuals which were identified by PCR using the ACCF1 and ACC-1 primers (see Methods). PCR amplification of wild-type lines or heterozygous null mutants with these primers resulted in three different sized fragments corresponding to the three ACC synthase genes whereas the products of PCR amplification of homozygous null mutants lack the fragment corresponding to the mutant gene. The Mu insertion site for each mutant line was determined by sequencing across the Mu/ACC synthase junction using the Mu-TIR primer (FIG. 2). Four of the five insertion lines contained a Mu in ACS2: one mutant contained an insertion in the third exon whereas the other three contained insertions in the fourth exon at unique positions (FIG. 2). The fifth insertion line contained a Mu in ACS6 in the second intron near the 3' splice site. Quantitative real time RT-PCR revealed that all three genes are expressed during maize leaf development and confirmed that the Mu insertions resulted in the loss of or a decrease in ACS expression. Insertions in ACS7 were identified in the first generation but were not inherited, suggesting that they were somatic mutants or that expression of ACS7 is required for germ line development.

For a description of ACC synthase expression patterns during endosperm and embryo development, see Gallie and Young (2004) *The ethylene biosynthetic and perception machinery is differentially expressed during endosperm and embryo development Mol Gen Genomics* 271:267-281.

ACS6 or ACS2 Gene Disruption Reduces Ethylene Synthesis

Figure 19C:
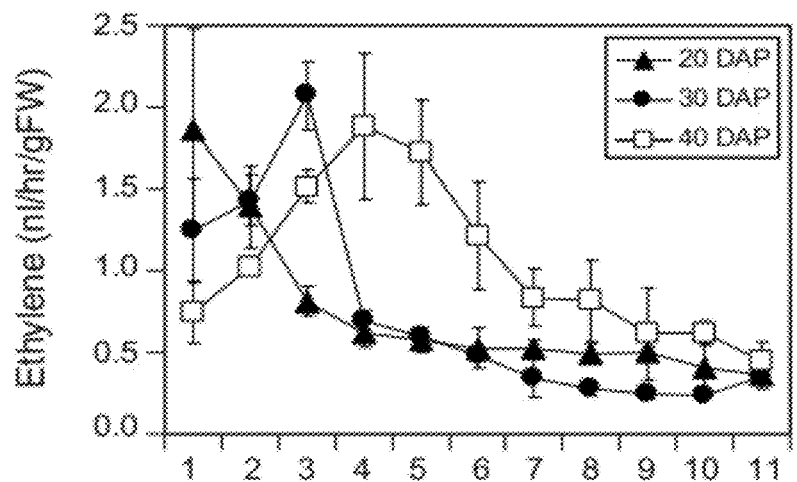
FIG. 19, Panels A and B illustrate ethylene production in seedling leaves. Panel A illustrates various lines. In Panel B, the seedling leaves are averaged by genotype. In Panel C, ethylene production was determined for every leaf of wild-type (i.e., B73) plants at 20, 30, and 40 DAP. Leaf 1 represents the oldest surviving leaf and leaf 11 the youngest. Three replicates were measured and the average and standard deviation reported.

The level of ethylene evolution in maize leaves increased as a function of leaf age (FIG. 19 Panel C). At 20 DAP, the highest level of ethylene was observed in leaf 1 (the oldest surviving leaf) which by 30 DAP had progressed to leaf 3 and by 40 DAP (i.e., kernel maturity) to leaves 4-5. To determine whether Mu disruptions of ACS6 or ACS2 described above reduced ethylene evolution, ethylene was measured from leaf 4 of wild-type and mutant plants. Ethylene evolution from acs2 plants was approximately 55% of wild-type plants, a level that was similar for all acs2 mutant alleles (FIG. 19 Panels A-B). Ethylene evolution from acs6 plants was only 10% of that from wild-type plants (FIG. 19 Panel B). Ethylene evolution from acs2\acs6 double mutant plants was similar to that from acs6 plants. These data suggest that loss of ACS6 expression results in a greater reduction in the ability of maize leaves to produce ethylene than does the loss of ACS2 expression.

Disruption of ACS6 Confers a Staygreen Phenotype

A substantial increase in ethylene evolution correlated with the appearance of visible signs of senescence in wild-type leaves, suggesting that ethylene may promote the entry of leaves into the senescence program. If so, a delay in the senescence of acs6 leaves, which produce significantly less ethylene, would be expected. To test this possibility, homozygous (i.e., acs6/acs6), heterozygous (i.e., ACS6/acs6), and wild-type (i.e., ACS6/ACS6) plants were field-grown until 50 days after pollination. At this stage, the oldest wild-type leaves had senesced, whereas the corresponding ACS6/acs6 leaves were just beginning to senesce and acs6/acs6 leaves remained fully green. These observations suggest that the level of ethylene evolution may determine the timing of leaf senescence.

Senescence can also be induced following prolonged exposure to darkness. To determine whether a reduction in ethylene evolution can delay dark-induced senescence, leaves from adult plants were covered with sheaths to exclude light for two weeks. The leaves from younger plants (i.e., 20 DAP) were used to ensure that age-related senescence would not occur during the course of the experiment and they remained attached to the plant. Greenhouse grown maize was also employed to avoid any heating that might occur in the field as a consequence of the sheathing. Following the two-week dark-treatment, senescence was observed for virtually the entire region of wild-type leaves that was covered (the region covered by the sheath is indicated by the distinct transition from yellow to green, FIG. 4 on left). The tip of ACS6/acs6 leaves had undergone dark-induced senescence but the rest of the covered region showed significantly less senescence (FIG. 4 in center). In contrast, acs6/acs6 leaves remained fully green (FIG. 4 on right). The degree of senescence correlated with the amount of ethylene produced by each, in which ACS6/acs6 leaves produced just 70% of wild-type ethylene and acs6/acs6 leaves produced only 14.6% of wild-type ethylene. These results suggest that ethylene mediates the onset of dark-induced senescence as it does natural senescence. They also indicate that the ACS6/acs6 heterozygous mutant with a loss of one copy of ACS6 produces less ethylene and exhibits a weak staygreen phenotype similar to that observed for the acs2 mutant which also exhibited a moderate (i.e., 40%) reduction in ethylene evolution.

To examine if exogenous ACC could complement the acs6 mutant and reverse its staygreen phenotype, the third oldest, sixth, and ninth leaf from ACS6/ACS6, acs2/acs2, and acs6/acs6 plants were subject to dark-induced senescence at 20 DAP by covering them with sheaths for 7 days. All leaves were fully green at the onset of the experiment and remained attached to the plant. acs6/acs6 plants were watered daily with water or 100 µM ACC for 7 days. Following 7 days, dark-induced senescence had initiated in wild-type (i.e., ASC6/ASC6) leaves although it had not progressed to the extent observed following a 2 week dark treatment. The extent of dark-induced senescence increased as a function of leaf age such that leaf 3 exhibited more senescence than did leaf 6 or leaf 9 (which were younger), suggesting that competency for senescence increases with leaf age. Dark-induced senescence was also observed in leaf 3 of the acs2 homozygous mutant although it was less pronounced than that observed in the corresponding wild-type leaves. Although no acs6 homozygous leaves exhibited dark-induced senescence consistent with the observations made in FIG. 4, dark-induced senescence similar to that of wild-type leaves was observed when acs6 leaves were watered with 100 µM ACC for 7 days. The ACC treatment did not affect acs6 leaves that were not sheathed, demonstrating that the senescence observed for sheathed acs6 leaves was specific to the dark-treatment.

Figure 20A:
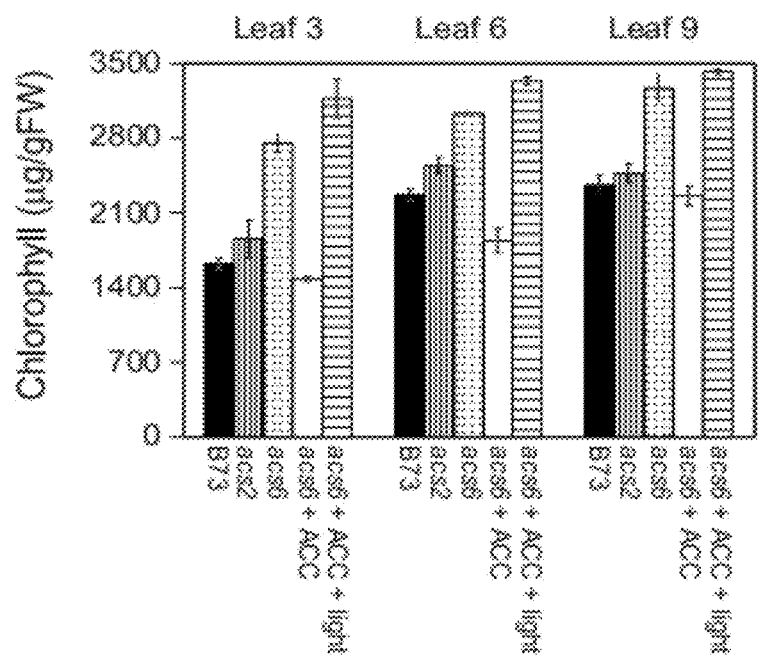
FIG. 20 Panel A illustrates chlorophyll data, Panel B soluble protein, and Panel C Rubisco expression. The level of chlorophyll a+b (Panel A) and soluble protein (Panel B) was measured in the third oldest leaf (Leaf 3), sixth oldest leaf (Leaf 6), and ninth oldest leaf (Leaf 9) of adult wild-type (i.e., ACS6/ACS6), acs21acs2, and acs61acs6 plants following dark treatment for 7 days. Plants were watered daily. Additional acs61acs6 plants were watered daily with 100 µM ACC during the treatment. acs61acs6 leaves watered with 100 µM ACC but kept unsheathed are also shown. The average and standard deviation of leaves from three individual plants is shown. (Panel C) Western analysis of the same leaves was performed using rice anti-Rubisco antiserum. Soluble protein from leaf samples of equal fresh weight was used.
Figure 20B:
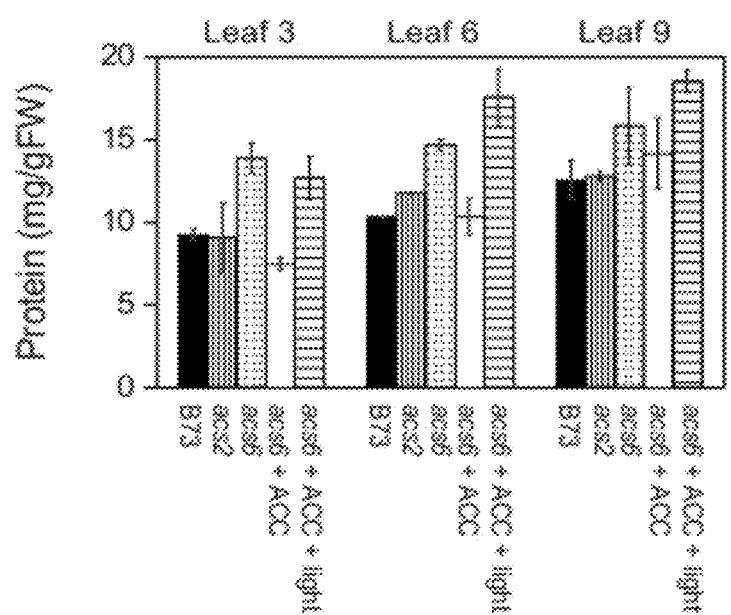
Figure 20C:
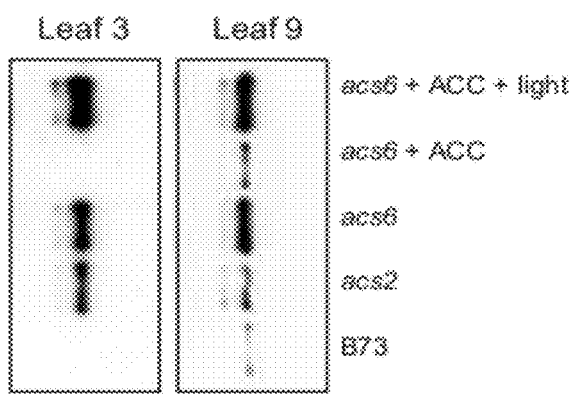

Determination of the level of chlorophyll a+b from leaf 3 confirmed the visual results in that acs6 leaves retained substantially more chlorophyll after the 7 day dark treatment than did wild-type leaves but did not do so when watered with 100 µM ACC (FIG. 20 Panel A). The treatment with ACC in itself did not induce premature loss of chlorophyll as chlorophyll was not lost from unsheathed leaves of acs6 mutants watered with ACC. acs2 leaves retained only moderately greater amount of chlorophyll did wildtype leaves. Similar results were observed for leaf 6 and leaf 9 although the level of chlorophyll in these younger leaves was higher than in the older leaf 3 samples as was expected (FIG. 20 Panel A). Similar trends were observed for total soluble leaf protein: acs6 leaves retained substantially more protein following the dark treatment than did wild-type leaves but did not do so when watered with 100 µM ACC (FIG. 20 Panel B).

Western analysis for ribulose biscarboxylase (Rubisco) demonstrated a substantial loss of Rubisco from dark-treated B73 leaves that was greater with the oldest leaves (leaf 3) than the youngest (leaf 9) (FIG. 20 Panel C). Dark-treated acs6 leaves retained substantially more Rubisco than did dark-treated wild-type leaves and acs2 leaves retained a moderate level of Rubisco (FIG. 20 Panel C). Dark-treated acs6 leaves watered with 100 µM ACC lost an amount of Rubisco similar to that of dark-treated B73 leaves suggesting that ACC complemented the loss of ACC synthase expression. No loss of Rubisco was observed in ACC-treated acs6 leaves when they remained in the light demonstrating that treatment with ACC alone did not reduce the level of Rubisco. These data demonstrate that the staygreen phenotype, which involves retention of chlorophyll and leaf protein such as Rubisco, can be complemented by exogenous ACC, suggesting that the delay in senescence in these plants is a consequence of the reduction in loss of ACC synthase expression in the acs6 mutant.

Reducing Ethylene Delays Natural Leaf Senescence and Reduces Loss of Chlorophyll and Protein Drought is known to induce premature onset of leaf senescence. To investigate whether the drought response is mediated by ethylene and to determine whether reducing ethylene evolution may increase drought tolerance in maize, homozygous acs6 and acs2 mutant plants and wild-type plants were field-grown under well-watered (eight hours twice a week) and water-stressed conditions (four hours per week for a one month period that initiated approximately one week before pollination and continued for 3 weeks after pollination). During the period of limited water availability, drought-stressed plants exhibited leaf wilting and rolling, visible confirmation of drought stress. Following the water stress treatment, the extent of leaf senescence and function was measured.

Senescence of the oldest leaves was evident in wild-type plants under well-watered conditions and even more significantly during drought conditions. Similar results were observed for acs2 plants. In contrast, no visible sign of senescence was observed in acs6 leaves under well-watered or drought conditions. Interestingly, anthocyanin production was also reduced in acs6 leaves.

Figure 17D:
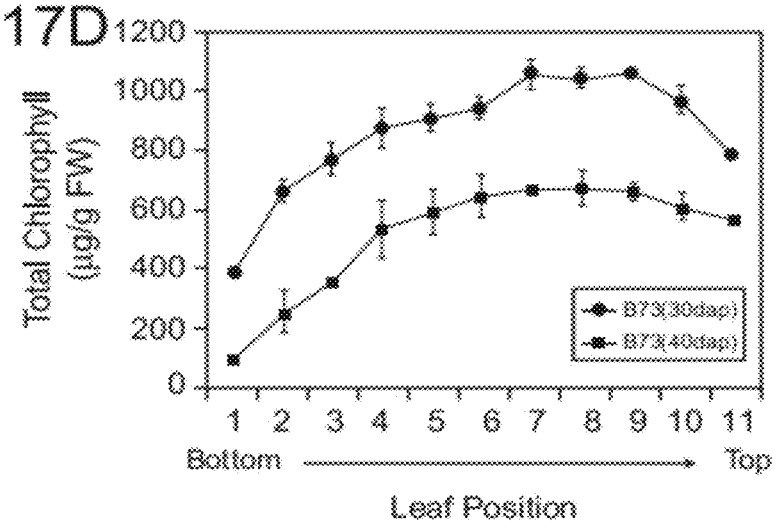
FIG. 17 Panels A, B, C, and D illustrate total chlorophyll data for wild-type and ACC synthase knockout plants. Panels A and B illustrate total chlorophyll data for wild-type (B73, +/+), ACS2 null (0/0), and ACS6 null (0/0) plants 40 days after pollination for plants grown under normal conditions (Panel A) or drought conditions (Panel B). Panel C compares total chlorophyll for wild-type (B73, +/+) and ACS6 null (0/0) plants 40 days after pollination under normal and drought conditions. Panel D illustrates a comparison of total chlorophyll for B73 (wild-type) plants collected at 30 and 40 days after pollination.

To confirm that the staygreen phenotype correlates with enhanced levels of chlorophyll, the level of chlorophyll a and b was measured. Chlorophyll decreased with leaf age as well as with the age of the plants (FIG. 17 Panels A and D). As expected, the greatest decrease in chlorophyll correlated with the visible onset of senescence. Under well-watered conditions, the level of chlorophyll in acs6 (ACS6 0/0) leaves was up to 8-fold higher than in the corresponding leaves of wild-type plants that had initiated senescence. Surprisingly, the level of chlorophyll in all acs6 leaves, including the youngest, was substantially higher than in wild-type plants (FIG. 17 Panel A). The level of chlorophyll in acs2 (ACS2 0/0) leaves was moderately higher than in wild-type plants. These results indicate that the increase in chlorophyll content inversely correlates with the level of ethylene production: the moderate reduction in ethylene in acs2 plants correlated with a moderate increase in chlorophyll content whereas the large reduction in ethylene in acs6 plants correlated with a substantial increase in chlorophyll content. These results also demonstrate that reducing ethylene increases the level of chlorophyll even in young leaves that are exhibiting maximum leaf function (see below).

Under drought conditions, the level of chlorophyll was reduced in mutant and wild-type plants but decreased to an even greater extent in wild-type plants (FIG. 17 Panels B-C). For example, the level of chlorophyll in leaf 5 of water-stressed wild-type plants decreased 2.5-fold relative to non-drought plants whereas it decreased by only 20% in leaf 5 of water-stressed acs6 plants (FIG. 17 Panel C). Consequently, reducing ethylene evolution resulted in a level of chlorophyll in the oldest leaves of acs6 plants that was up to 20-fold higher than in the corresponding leaves of wild-type plants. As observed for non-drought plants, the level of chlorophyll was higher in all acs6 leaves, including the youngest. Chlorophyll content in acs2 leaves also remained moderately higher under drought conditions than in wild-type plants. Thus, loss of ACS6 expression reduced responsiveness to water stress in that chlorophyll content was substantially maintained under those stress conditions that had elicited a significant loss of chlorophyll in wild-type plants.

Figure 18A:
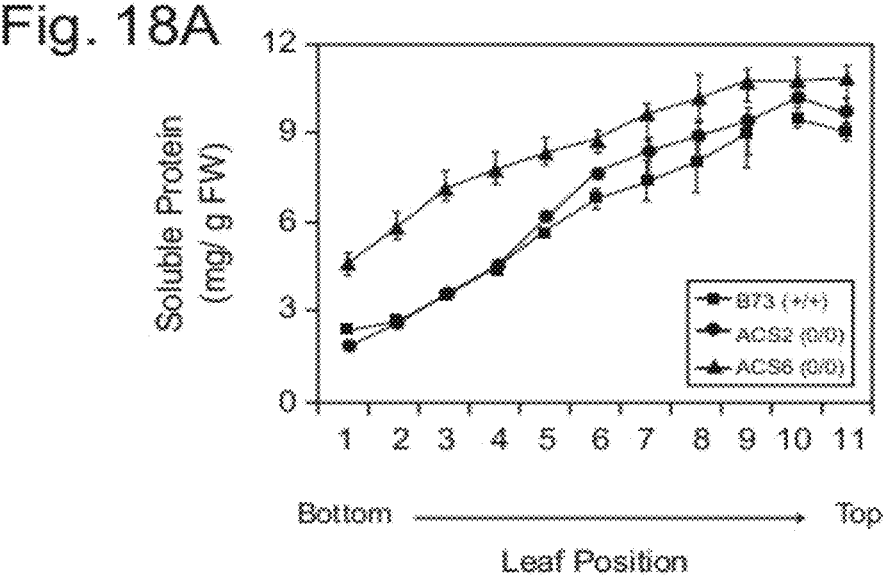
FIG. 18 Panels A, B, C, and D illustrate soluble protein data for wild-type and ACC synthase knockout plants. Panels A and B illustrate soluble protein data for wild-type (B73, +/+), ACS2 null (0/0), and ACS6 null (0/0) plants 40 days after pollination for plants grown under normal conditions (Panel A) or drought conditions (Panel B). Panel C compares soluble protein for wild-type (B73, +/+) and ACS6 null (0/0) plants 40 days after pollination under normal and drought conditions. Panel D illustrates a comparison of soluble protein for B73 (wild-type) plants collected at 30 and 40 days after pollination.

Leaf protein also declined with leaf age and with plant age (FIG. 18 Panel D). As observed for chlorophyll, the most substantial decrease in protein correlated with the visible onset of senescence (FIG. 18 Panel D). Under non-drought conditions, the level of protein in acs6 leaves was up to 2-fold higher than in the corresponding leaves of wild-type plants that had initiated senescence (FIG. 18 Panel A). As observed for chlorophyll, the level of protein in all acs6 leaves, including the youngest, was substantially higher than in wild-type plants and the level of protein in acs2 leaves was moderately higher than in wild-type plants (FIG. 18 Panel A). Exposure to conditions of drought resulted in a greater decrease of protein in the oldest wildtype leaves than was observed in acs6 leaves (FIG. 18 Panels B-C). As observed for non-drought plants, the level of protein was higher in all acs6 leaves, including the youngest. These results parallel those for chlorophyll and indicate that protein content inversely correlates with the level of ethylene evolution. They also demonstrate that loss of ACC synthase expression in the acs6 mutant reduced responsiveness to water stress in that protein levels were substantially maintained under those stress conditions that had elicited a significant reduction of protein in wild-type plants.

Figure 5D:
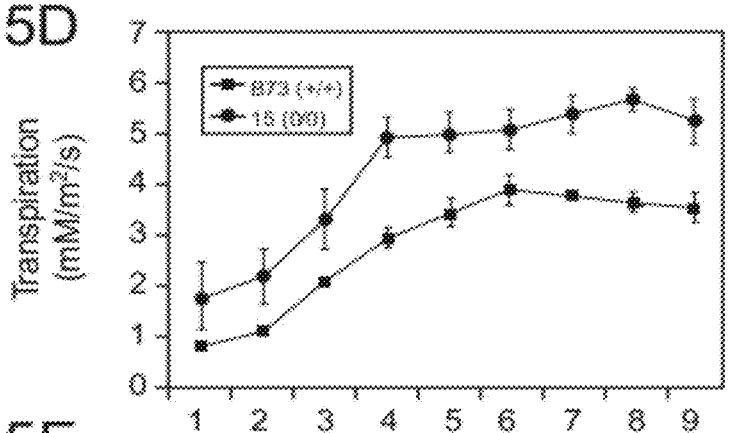
FIG. 5, Panels A, B, C, D, E, and F illustrate leaf transpiration (Panels A and D), stomatal conductance (Panels B and E) and $CO_2$ assimilation (Panels C and F) for wild-type (B73, +/+) and ACS6 null (15, O/O) mutant leaves under control conditions (Panels A, B, and C) or drought conditions (Panels D, E, and F). For control conditions, plants were grown under well-watered conditions and each leaf on a plant was measured at forty days after pollination (dap). For drought conditions, plants were grown under limited water conditions and each leaf on a plant was measured at forty days after pollination. Values represent a mean of six determinations.
Figure 5E:
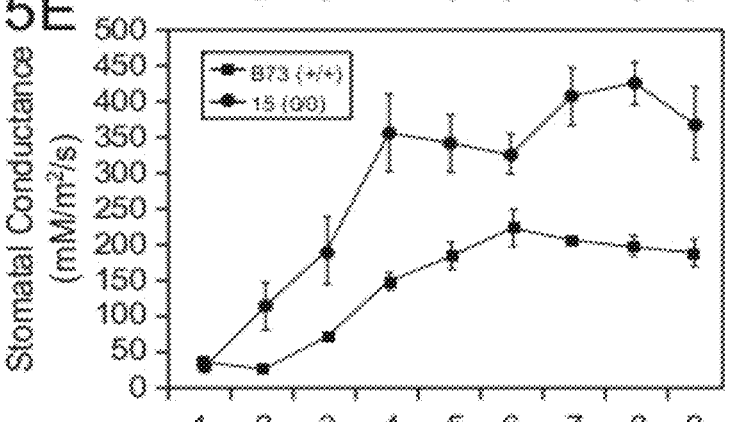
Figure 5F:
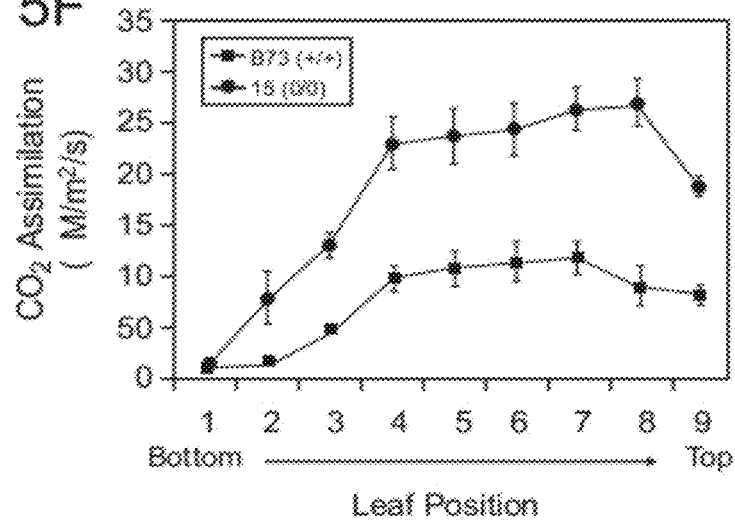

Reducing Ethylene Maintains Leaf Function During Well-watered and Drought Conditions The maintenance of chlorophyll and protein in acs6 leaves suggests that leaf function, e.g., the ability to transpire and assimilate $CO_2$, may also be maintained. To investigate this, the rate of transpiration, stomatal conductance, and rate of $CO_2$ assimilation were measured in every leaf of well watered acs6 and wild-type plants at 40 DAP when the lower leaves of wild-type plants had begun to senesce. The youngest leaves of acs6 plants exhibited a higher rate of transpiration (FIG. 5 Panel A) and stomatal conductance (FIG. 5 Panel B) than control plants whereas no significant difference was observed in older leaves. In contrast, the rate of $CO_2$ assimilation was substantially higher in all leaves of acs6 plants than in control plants (FIG. 5 Panel C). Specifically, older leaves of acs6 plants exhibited more than a 2-fold higher rate of $CO_2$ assimilation than wild-type plants and the rate of $CO_2$ assimilation in younger leaves increased from 50 to 100% (FIG. 5 Panel C).

The effect of reducing ethylene on the maintenance of leaf function under drought conditions was also investigated. The rate of transpiration (FIG. 5 Panel D) and stomatal conductance (FIG. 5 Panel E) were significantly reduced in wild-type leaves when subjected to conditions of drought (i.e., four hours per week for a one month period starting approximately one week before pollination and continuing through three weeks after pollination) whereas they remained largely unaffected in acs6 leaves, resulting in a substantially higher rate of transpiration (FIG. 5 Panel D) and increased stomatal conductance (FIG. 5 Panel E) for the mutant. In addition, drought treatment resulted in a significant decrease in the rate of $CO_2$ assimilation in wild-type leaves but not in acs6 leaves, resulting in up to a 2.5-fold increase in $CO_2$ assimilation in younger acs6 leaves and up to a 6-fold increase in older acs6 leaves than in the control (FIG. 5 Panel F). These results indicate that ethylene controls leaf function during conditions of drought and a reduction in its production results in a delay of leaf senescence in older leaves while maintaining leaf function in all leaves thus providing greater tolerance to drought. Similar, though less pronounced, results were obtained for ACS2 (FIG. 6 Panels A-C).

Discussion

In summary, ACC synthase mutants affecting the first step in ethylene biosynthesis were isolated in maize. These mutants exhibited a delay in natural, dark-induced, and drought-induced leaf senescence and a staygreen phenotype. The delay in senescence was reversible following exposure to ethylene. ACC synthase mutant leaves exhibited a substantially higher rate of $CO_2$ assimilation during growth under normal or drought conditions. Surprisingly, improved leaf function was observed in all ACC synthase mutant leaves, including the youngest which had not entered either natural or drought-induced senescence programs. These observations suggest that ethylene mediates the response of maize to water stress and that decreasing ethylene production serves as a means to maintain leaf performance during water stress and thereby increase its tolerance to drought conditions. As noted, ACC synthase mutants can have other advantageous phenotypes, e.g., male sterility phenotypes, crowding resistance phenotypes, altered pathogen resistance, and the like.

The above examples show that ethylene plays a significant role in regulating the onset of leaf senescence in maize whether during growth under well-watered conditions or during conditions of drought which normally induces premature leaf senescence. The reduction in ethylene evolution resulting from loss of ACS6 expression is largely responsible for directing natural and drought-induced leaf senescence. While not intending to be limited by any particular theory, loss of ACS6 expression may directly delay entry into the senescence program or may affect total ACC synthase expression from all gene members. Knockout of ACS2 alone reduced ethylene production by approximately 40% and did result in a small increase in chlorophyll and protein. In contrast, ethylene production in acs6 leaves was reduced up to 90% and acs6 leaves contained substantially higher levels of chlorophyll and protein. These observations suggests that entry into the senescence program may be controlled by more than one gene family member.

The level of chlorophyll and protein in wild-type leaves was reduced substantially following water-stress but remained unaffected in acs6 leaves. These results indicate two roles for ethylene in maize leaves: under normal growth conditions, ethylene may help to maintain the correct level of chlorophyll and protein in a leaf, whereas during water stress, ethylene may serve to reduce the level of both. The observation that a 40% reduction in ethylene resulted in a moderate increase in chlorophyll and protein whereas a 90% reduction resulted in a substantially larger increase in chlorophyll and protein suggests that these leaf components may be quantitatively controlled by the level of ethylene produced in leaves. Greater increases in leaf chlorophyll and protein might be expected if ethylene production were reduced even further.

Loss of chlorophyll and protein in wild-type maize subjected to drought conditions was accompanied by decreased rates of transpiration, stomatal conductance, and $CO_2$ assimilation. In contrast, maintenance of chlorophyll and protein levels in leaves of acs6 plants subjected to drought conditions was accompanied by the maintenance of transpiration, stomatal conductance, and $CO_2$ assimilation. These results suggest that reducing ethylene not only confers a staygreen phenotype but actually maintains leaf function under stress conditions. The observation that ethylene controls the onset of leaf senescence is consistent with the role of this hormone in other species such as *Arabidopsis* and tomato (Davis and Grierson (1989) *Identification of cDNA clones for tomato (Lycopersicon esculentum Mill.) mRNAs that accumulate during fruit ripening and leaf senescence in response to ethylene*. Planta 179:73-80; Abeles et al. (1992). Ethylene in Plant Biology. (San Diego: Academic Press); Picton et al. (1993). *Altered fruit ripening and leaf senescence in tomatoes expressing an antisense ethylene forming enzyme transgene* Plant J. 3:469-481; Grbic and Bleecker (1995) *Ethylene regulates the timing of leaf senescence in Arabidopsis* Plant J. 8:95-102; John et al. (1995) *Delayed leaf senescence in ethylene-deficient ACC-oxidase antisense tomato plants: molecular and physiological analysis* Plant J. 7:483-490). The observation that a reduction in ethylene evolution would increase the level of chlorophyll and protein and increase the rate of $CO_2$ assimilation in all leaves, including the youngest, was unexpected. This suggests that ethylene plays an active role in controlling aspects of leaf function well before a leaf enters a senescence program. Equally unexpected was the observation that a reduction in ethylene would affect the water-stress response of all leaves. These findings suggest that increased tolerance to conditions of drought can be easily introduced into maize, and optionally other grain species, through a reduction in the level of ethylene produced in leaves.

Example 2

Sequence Alignments and Phylogenetic Analysis

Figure 7:
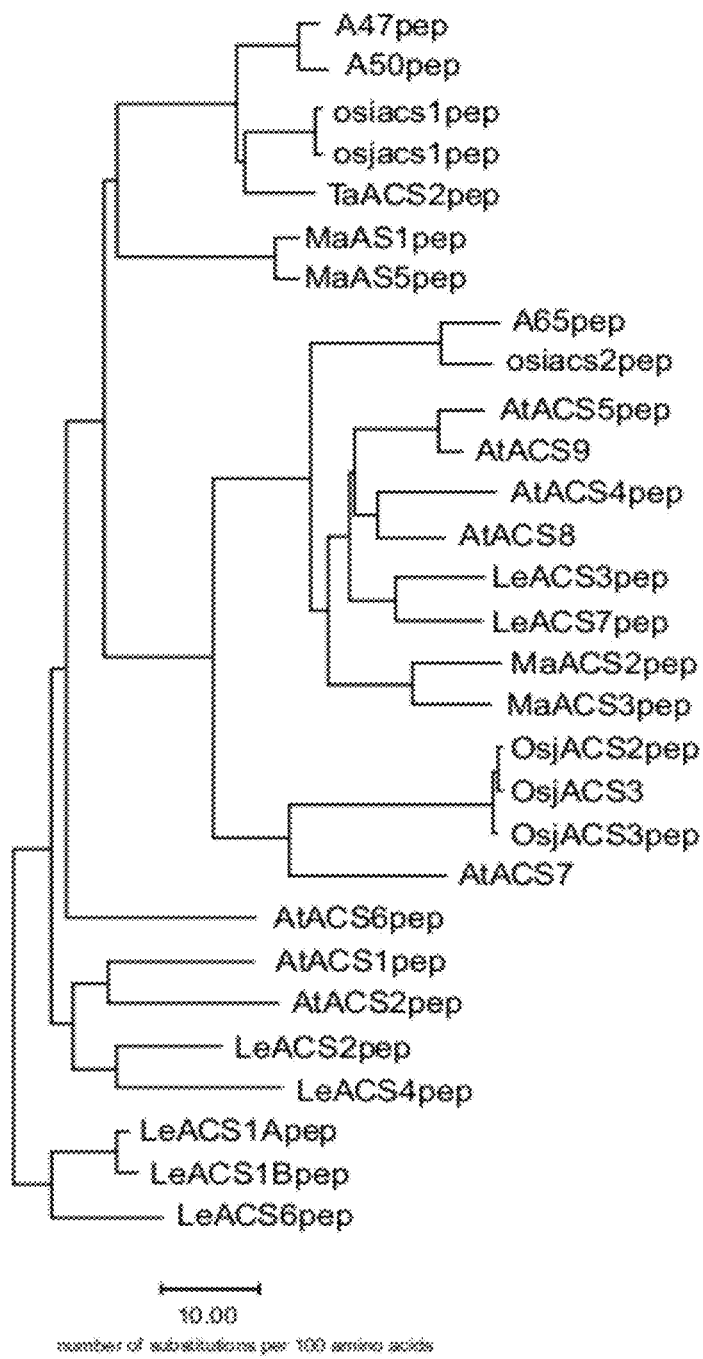
FIG. 7 schematically illustrates phylogenetic analysis of ACC synthase gene sequences, where maize sequences are indicated by (A47 (also known as ACS2 or ACC2 herein), A50 (also known as ACS7 or ACC7 herein), A65 (also known as ACS6 or ACC6 herein)), *Arabidopsis* sequences are indicated by (AtACS . . . ), tomato sequences are indicated by (LeACS . . . ), rice sequences are indicated by (indica (OsiACS . . . ), & japonica (OsjACS . . . )), wheat sequences are indicated by (TaACS . . . ), and banana sequences are indicated by (MaACS . . . ).

A phylogenetic analysis of ACC synthase sequences described herein, e.g., (A47 (also known as ACS2 or ACC2 herein), A50 (also known as ACS7 or ACC7 herein), A65 (also known as ACS6 or ACC6 herein)) from maize, with ACC synthase sequences from other species, is shown in FIG. 7 (ACSgrowtree2), where *Arabidopsis* sequences are indicated by (AtACS . . . ), tomato sequences are indicated by (LeACS . . . ), rice sequences are indicated by (indica (OsiACS . . . ), and japonica (OsjACS . . . )), wheat sequences are indicated by (TaACS . . . ), and banana sequences are indicated by (MaACS . . . ). In the analysis, the indicated ACC synthases fall into two subfamilies. One of the subfamilies is further subdivided into monocot (Zm (maize), Osi, Osj, Ta, Ma) ACS genes and dicot (At, Le) ACS genes.

Various peptide consensus sequences alignments of ACC synthase sequences described herein, e.g., (A47 (also known as ACS2 or ACC2 herein), A50 (also known as ACS7 or ACC7 herein), A65 (also known as ACS6 or ACC6 herein)) from maize (Zm), with ACC synthase sequences from other species are shown in FIGS. 8-16. A Pretty program is used (e.g., available on the SeqWeb (GCG) web page) to determine the consensus sequence with different stringencies (e.g., most stringent (identical), stringent (similar amino acids), or least stringent (somewhat similar amino acids). The stringency is indicated in each figure after "consensus sequence." The GapWeight is 8 and the GapLengthWeight is 2.

Example 3

ACC Synthase Knockouts by Hairpin RNA Expression

As noted previously, knockout plant cells and plants can be produced, for example, by introduction of an ACC synthase polynucleotide sequence configured for RNA silencing or interference. This example describes hairpin RNA expression cassettes for modifying ethylene production and staygreen phenotype, e.g., in maize. As noted previously, knockout of ACC synthase(s), e.g., by hpRNA expression, can result in plants or plant cells having reduced expression (up to and including no detectable expression) of one or more ACC synthases.

Figures 21A, 21B:
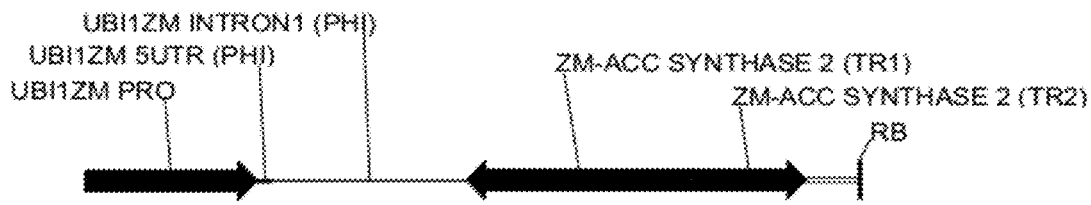
FIG. 21 Panels A-C illustrate the ACS2 hairpin construct. Panel A is a schematic diagram of PHP20600 containing a ubiquitin promoter (UBI1ZM PRO) driving expression of the ACS2 hairpin (a terminal repeat consisting of TR1 and TR2). RB represents the *Agrobacterium* right border sequence. A 4126 bp fragment of the 49682 bp cassette is illustrated. Panel B presents the sequence of ZM-ACS2 TR1 (SEQ ID NO:54), and Panel C presents the sequence of ZM-ACS2 TR2 (SEQ ID NO:55).

Expression of hairpin RNA (hpRNA) molecules specific for ACC synthase genes (e.g., promoters, other untranslated regions, or coding regions) that encode ACC synthases in plants can alter ethylene production and staygreen potential, sterility, crowding resistance, etc. of the plants, e.g., through RNA interference and/or silencing.

hpRNA constructs of ACS2 (PHP20600) and ACS6 (PHP20323) were generated by linking a ubiquitin promoter to an inverted repeat of a portion of the coding sequence of either the ACS2 or ACS6 gene (see FIGS. 21 and 22, Panels A-C). Each construct was transformed into maize using *Agrobacterium*-mediated transformation techniques. Nucleic acid molecules and methods for preparing the constructs and transforming maize were as previously described and known in the art; see, e.g., the sections herein entitled "Vectors, Promoters, and Expression Systems," "Plant Transformation," "Other Nucleic Acid and Protein Assays," and the following example "Transformation of Maize".

Figure 23A:
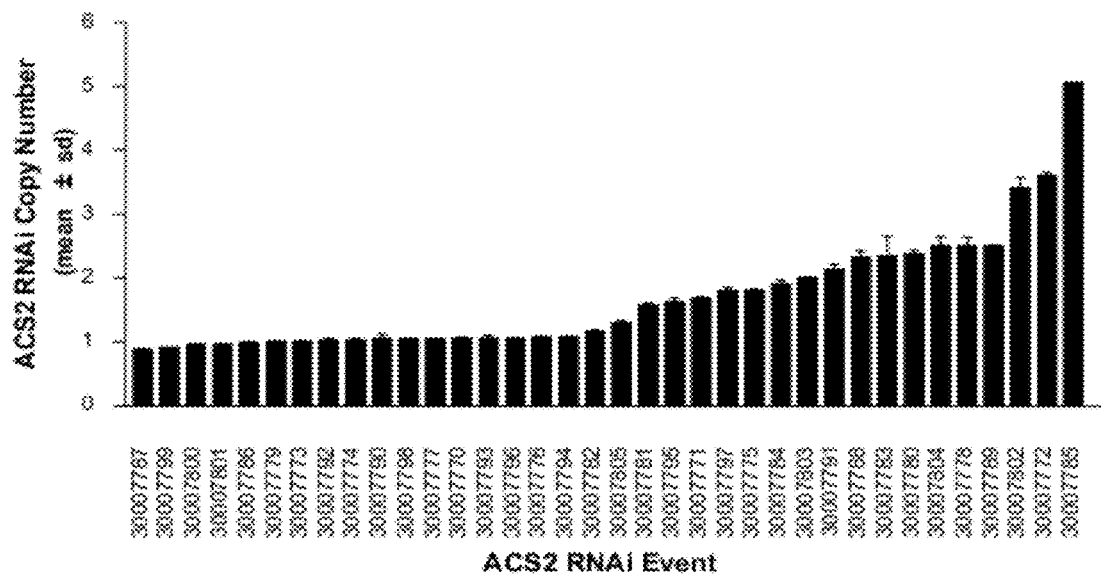
FIG. 23 Panels A and B illustrate events generated for ACS2- and ACS6-hairpin constructs. Panel A presents a diagram showing the number of individual events for ACS2 hairpin (PHP20600) and the associated transgene copy number per event. Panel B presents a diagram showing the number of individual events for ACS6 hairpin (PHP20323) and the associated transgene copy number per event.
Figure 23B:
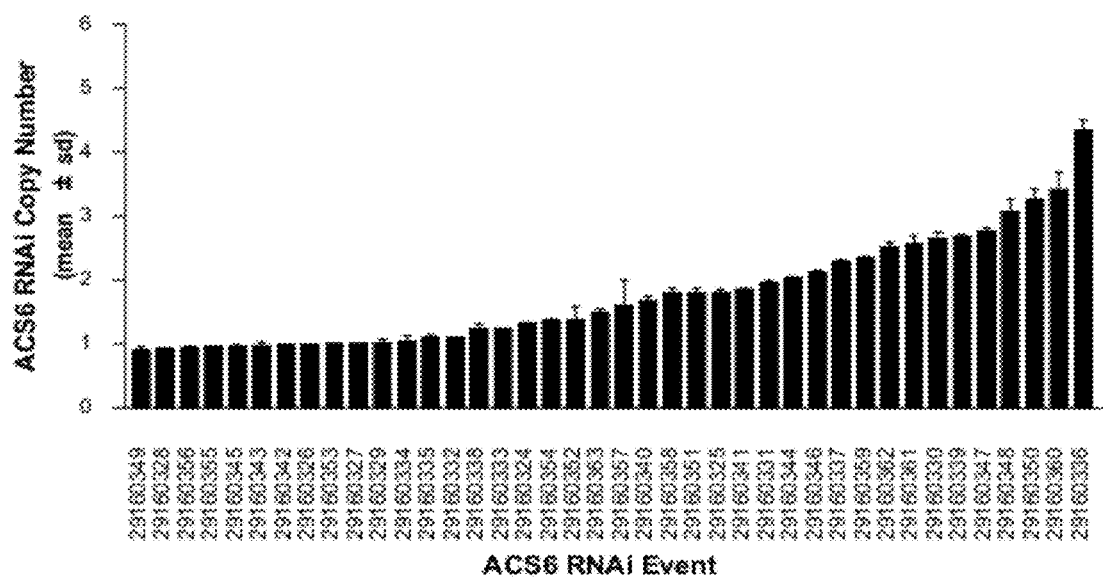

Expression of hpRNA specific for either ACS2 or ACS6 coding sequences resulted in maize plants that displayed no abnormalities in vegetative and reproductive growth. A total of 36 and 40 individual maize transgenic events were generated for ACS2- and ACS6-hairpin constructs, respectively (FIG. 23, Panels A and B).

Approximately 10 low copy number events per hpRNA construct were selected for additional backcrossing and transgene evaluation. Staygreen potential phenotype is evaluated for the backcrossed lines comprising the hpRNA transgene(s), e.g., as described herein (for example, by visual inspection, measurements of photosynthetic activity, determination of chlorophyll or protein content, or the like, under normal and drought or other stress conditions).

Example 4

Transformation of Maize

Biolistics

The inventive polynucleotides contained within a vector are transformed into embryogenic maize callus by particle bombardment, generally as described by Tomes, D. et al., IN: Plant Cell, Tissue and Organ Culture: Fundamental Methods, Eds. O. L. Gamborg and G. C. Phillips, Chapter 8, pgs. 197-213 (1995) and as briefly outlined below. Transgenic maize plants are produced by bombardment of embryogenically responsive immature embryos with tungsten particles associated with DNA plasmids. The plasmids typically comprise or consist of a selectable marker and an unselected structural gene, or a selectable marker and an ACC synthase polynucleotide sequence or subsequence, or the like.

Preparation of Particles:

Fifteen mg of tungsten particles (General Electric), 0.5 to 1.8 preferably 1 to 1.8µ, and most preferably 1 are added to 2 ml of concentrated nitric acid. This suspension is sonicated at 0° C. for 20 minutes (Branson Sonifier Model 450, 40% output, constant duty cycle). Tungsten particles are pelleted by centrifugation at 10000 rpm (Biofuge) for one minute, and the supernatant is removed. Two milliliters of sterile distilled water are added to the pellet, and brief sonication is used to resuspend the particles. The suspension is pelleted, one milliliter of absolute ethanol is added to the pellet, and brief sonication is used to resuspend the particles. Rinsing, pelleting, and resuspending of the particles is performed two more times with sterile distilled water, and finally the particles are resuspended in two milliliters of sterile distilled water. The particles are subdivided into 250-1 µl aliquots and stored frozen.

Preparation of Particle-Plasmid DNA Association:

The stock of tungsten particles are sonicated briefly in a water bath sonicator (Branson Sonifier Model 450, 20% output, constant duty cycle) and 50 µl is transferred to a microfuge tube. The vectors are typically cis: that is, the selectable marker and the gene (or other polynucleotide sequence) of interest are on the same plasmid.

Plasmid DNA is added to the particles for a final DNA amount of 0.1 to 10 µg in 10 µL total volume, and briefly sonicated. Preferably, 10 µg (1 µg/µL in TE buffer) total DNA is used to mix DNA and particles for bombardment. Fifty microliters (50 µL) of sterile aqueous 2.5 M $CaCl_2$ are added, and the mixture is briefly sonicated and vortexed. Twenty microliters (20 µL) of sterile aqueous 0.1 M spermidine are added and the mixture is briefly sonicated and vortexed. The mixture is incubated at room temperature for 20 minutes with intermittent brief sonication. The particle suspension is centrifuged, and the supernatant is removed. Two hundred fifty microliters (250 µL) of absolute ethanol are added to the pellet, followed by brief sonication. The suspension is pelleted, the supernatant is removed, and 60 µl of absolute ethanol are added. The suspension is sonicated briefly before loading the particle-DNA agglomeration onto macrocarriers.

Preparation of Tissue

Immature embryos of maize variety High Type II are the target for particle bombardment-mediated transformation. This genotype is the $F_1$ of two purebred genetic lines, parents A and B, derived from the cross of two known maize inbreds, A188 and B73. Both parents are selected for high competence of somatic embryogenesis, according to Armstrong et al., *Maize Genetics Coop. News* 65:92 (1991).

Ears from $F_1$ plants are selfed or sibbed, and embryos are aseptically dissected from developing caryopses when the scutellum first becomes opaque. This stage occurs about 9-13 days post-pollination, and most generally about 10 days post-pollination, depending on growth conditions. The embryos are about 0.75 to 1.5 millimeters long. Ears are surface sterilized with 20-50% Clorox for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite, and 8.5 mg/l $AgNO_3$. Chu et al., *Sci. Sin.* 18:659 (1975); Eriksson, *Physiol. Plant* 18:976 (1965). The medium is sterilized by autoclaving at 121° C. for 15 minutes and dispensed into 100×25 mm Petri dishes. $AgNO_3$ is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per Petri dish are located in the center of a Petri dish in an area about 2 cm in diameter. The embryos are maintained on this medium for 3-16 hour, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 µl are deposited on macrocarriers and the ethanol is allowed to evaporate. The macrocarrier is accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi are used, with 650 to 1100 psi being preferred, and about 900 psi being most highly preferred. Multiple disks are used to effect a range of rupture pressures.

The shelf containing the plate with embryos is placed 5.1 cm below the bottom of the macrocarrier platform (shelf #3). To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum chamber and located in the projected path of accelerated particles. A vacuum is created in the chamber, preferably about 28 in Hg. After operation of the device, the vacuum is released and the Petri dish is removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite, 0.85 mg/l Ag $NO_3$ and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselected marker genes, proliferates from about 7% of the bombarded embryos. Putative transgenic tissue is rescued, and that tissue derived from individual embryos is considered to be an event and is propagated independently on selection medium. Two cycles of clonal propagation are achieved by visual selection for the smallest contiguous fragments of organized embryogenic tissue.

A sample of tissue from each event is processed to recover DNA. The DNA is restricted with a restriction endonuclease and probed with primer sequences designed to amplify DNA sequences overlapping the ACC synthase and non-ACC synthase portion of the plasmid. Embryogenic tissue with amplifiable sequence is advanced to plant regeneration.

For regeneration of transgenic plants, embryogenic tissue is subcultured to a medium comprising MS salts and vitamins (Murashige & Skoog, *Physiol. Plant* 15: 473 (1962)), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm Petri dishes, and is incubated in darkness at 28° C. until the development of well-formed, matured somatic embryos can be seen. This requires about 14 days. Well-formed somatic embryos are opaque and cream-colored, and are comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite in 100×25 mm Petri dishes and incubated under a 16 hour light:8 hour dark photoperiod and 40 meinsteinsm$^{-2}$ sec$^{-1}$ from cool-white fluorescent tubes. After about 7 days, the somatic embryos have germinated and produced a well-defined shoot and root. The individual plants are subcultured to germination medium in 125×25 mm glass tubes to allow further plant development. The plants are maintained under a 16 hour light:8 hour dark photoperiod and 40 meinsteinsm$^{-2}$ sec$^{-1}$ from cool-white fluorescent tubes. After about 7 days, the plants are well-established and are transplanted to horticultural soil, hardened off, and potted into commercial greenhouse soil mixture and grown to sexual maturity in a greenhouse. An elite inbred line is used as a male to pollinate regenerated transgenic plants.

*Agrobacterium*-Mediated

When *Agrobacterium*-mediated transformation is used, the method of Zhao is employed as in PCT patent publication WO98/32326, the contents of which are hereby incorporated by reference. Briefly, immature embryos are isolated from maize and the embryos contacted with a suspension of *Agrobacterium* (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step) and preferably calli grown on selective medium are cultured on solid medium to regenerate the plants.

Example 5

Expression of Transgenes in Monocots

A plasmid vector is constructed comprising a preferred promoter operably linked to an isolated polynucleotide comprising an ACC synthase polynucleotide sequence or subsequence (e.g., selected from SEQ ID NOs:1-6 and 10). This construct can then be introduced into maize cells by the following procedure.

Immature maize embryos are dissected from developing caryopses derived from crosses of maize lines. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus, consisting of undifferentiated masses of cells with somatic proembryoids and embryoids borne on suspensor structures, proliferates from the scutellum of these immature embryos. The embryogenic callus isolated from the primary explant can be cultured on N6 medium and sub-cultured on this medium every 2 to 3 weeks.

The plasmid p35S/Ac (Hoechst Ag, Frankfurt, Germany) or equivalent may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and comprises the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton flying disc (Bio-Rad Labs). The particles are then accelerated into the corn tissue with a Biolistic™ PDS-1000/He biolistic particle delivery system (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 6

Expression of Transgenes in Dicots

Soybean embryos are bombarded with a plasmid comprising a preferred promoter operably linked to a heterologous nucleotide sequence comprising an ACC synthase polynucleotide sequence or subsequence (e.g., selected from SEQ ID NOs:1-6 and 10), as follows. To induce somatic embryos, cotyledons of 3-5 mm in length are dissected from surface-sterilized, immature seeds of the soybean cultivar A2872, then cultured in the light or dark at 26° C. on an appropriate agar medium for six to ten weeks. Somatic embryos producing secondary embryos are then excised and placed into a suitable liquid medium. After repeated selection for clusters of somatic embryos that multiply as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are sub-cultured every two weeks by inoculating approximately 35 mg of tissue into 35 ml of liquid medium.

Soybean embryogenic suspension cultures may then be transformed by the method of particle gun bombardment (Klein et al. (1987) Nature (London) 327:70-73, U.S. Pat. No. 4,945,050). A DuPont Biolistic™ PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette of interest, comprising the preferred promoter and a heterologous ACC synthase polynucleotide, can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

| SEQ ID: | TYPE | SEQUENCE |
|---|---|---|
| SEQ ID: 1 | Gene ACS2 (ACC2) ACC Synthase gene sequence (A47) from *Zea mays* (Zm) inbred 'B73' (= ACC2 pcr fragment originally isolated from inbred 'Oh43') | AAACTTCATA CCGGTCGGTG CCTTACGTTC TCTGGCGTTC TTATCCTTTC<br>CTCCGCTTTT AGTCGATGAT TATAGTAGTT TCTACAACAA GCTTTCAACG<br>CCATTGACTA TTTTTTCCCC CATTGAAAAC GAACACCACC ATTGACACTG<br>ATAAATGTAG TACAGCATTT GACAACATAC TTTCCTAGAA AGTAACCAGC<br>AGAGACTGGA CGCTACGTAC TACCACACCA TTGGAGCAGC CAATTTAATC<br>GTGTATAGAA CTCCGTATCG AAATTTGTCT GTGAATGGAC CTTCATTTGC<br>ATCTAGGTCT AGTACAATGG ATTTCGAACA GGACAGCGCC GATCTGGCAA<br>TACACACACG CACGACGTAG CACAGCTGTT CTTCGTTCCA CGCGTTAATT<br>GAAGGCAAAG CGACTGTAGT TGCTGTTGGT GGCCAAGTTG TTTAATGCTA<br>TAGTAGCAGC CAGTCACTCC TAGGGCAAAT TTTAGGACTT TTGCATTGCA<br>TTGCCGCCAT GTAGAGGTTG ACTGCACACC GAGAATATCG AGCATTCATT<br>AGGCTCCTTG ACTTGTTGCT GTGAACTCCG GCCATCTGTC ACAGTACGTA<br>TATGACCAGA TCGGCACCAT TTGTCTCGGC CTGACAATCT CGCGCGCCAT<br>TGGCCATGCA AAGCTGTCCT GCCGTTCGGA GAGACTAGAG AGCCAGTTGG |

| SEQ ID: | TYPE | SEQUENCE |
|---|---|---|
| | | CAAATTGACA TTTGCGATAG GTGGGGCGGC TTTGACTATG ACATGATGAC |
| | | AGATCCAGAT GGTCCTCCGC TAGTCCCCCC GAGCCCGAGG ACAGCACACT |
| | | AGCTCACACG AACTGACAGC GCGGAGGAGG ACACGTACCG GGATGACACC |
| | | GCCACCCATT TGCTGGCAAG CCGGGGTGCG CCGGCGGTTC AGGTTGAATC |
| | | CTTCCTAATG GTCGTGCTAG CAAACCCCGC AAGCTCAGTG CGGGTCCAAA |
| | | ACCCATTAAT TATCCCACAA AGCCGCCGTT AGACGTAGAA TCGACGCCGC |
| | | GCGCCACGGC CGGCGGCGGC TACCTGGCTC TTACCACCAT CATTCGCTTG |
| | | TCCGTTCCGT CGCCCCCGCC ACCCTCTCAG AGATGGAGGC GGTTAAGTGC |
| | | CTGTCGACTA TTGCAGAACG TCGTCAGGCT CGCTAGTTCG ACCGAGCATC |
| | | CTAGATACAT AATCCAAATT CCGCTCGGCG ATTATAGGAG GGTGATAGTA |
| | | CTGAGTACAG GGCGAAAAAC GTTGAAAAGG TCAGCGAGGC CCCCACATGT |
| | | CTCCCCCGGT CGCGTTCGCA TTCAACACCC TCTGCGCTGC GTTTCATGGA |
| | | AGTTTCCAGC AGCCACGCCC ACGCGCATGG ACGCGGCTGA TCTTATAAAG |
| | | GTGGCGCGCG TCCCAACCTC GGGAGCCATC ATTTCACCAG AAGCTGCAAA |
| | | TTGCAAGCTC TCCTCCCTAG CTAGCCTCTC CAGCAGCCCA ACCACAGCCT |
| | | GCAGCTGCAG CTCGCGTTGG CACAGCGCCG CCTGAACGCG TGCTAATTTA |
| | | AGCTCTGTCG TAGCTCAACG CGGCCGCCGG GCTTTCGCCG ACGACGTCAA |
| | | AATGGCCGGT GGTAGCAGTG CCGAGCAGCT CCTATCCAGG ATCGCCTCCG |
| | | GCGATGGCCA CGGCGAGAAC TCGTCCTACT TCGACGGGTG GAAGGCCTAC |
| | | GACATGACC CTTTCGACCT GCGCCACAAC CGCGACGGCG TCATCCAGAT |
| | | GGGCCTCGCC GAGAACCAAG TACGTGACGT AGCCCTGCCG CATGCAGCTA |
| | | CAGCTACACC CTTTCGACCT GCGCAACAAC CGCGACGGCG TCATCCAGAT |
| | | GGGCCTGCTG TCGATGGAAT GCTCATGTAA TTAAACCACC GGCCGGGGCG |
| | | TGTTTTGCAG CTGTCCCTGG ACCTGATCGA GCAATGGAGC ATGGAGCACC |
| | | CGGAGGCGTC CATCTGCACG GCGCAGGGAG CGTCGCAGTT CAGGAGGATA |
| | | GCCAACTTCC AGGACTACCA CGGCCTGCCG GAGTTCAGAG AGGTATTAAT |
| | | TAAGTTAACT AACAGCTCGG CTAAGGAAAC GCCAGAATCA TTGATTAGGT |
| | | TTGCTGCTCT CTAATGGCGA CTGCGAAAAC GACGGAGCAG CTACCGGCCA |
| | | GCCGGCCGGC GGTTAGCTAG CACTAGCAGC CGCCTTCCTG ACAGATCATC |
| | | CATGACGTTT TGATTGTTGC AGGCGATGGC CAAGTTCATG GGCCAGGTGA |
| | | GGGCCGGGAA GGTGACGTTC GACCCCGACC GCGTCGTCAT GTGCGGAGGC |
| | | GCCACCGGCG CGCAGGACAC TCTCGCCTTC TGCCTCGCTG ACCCGGGCGA |
| | | CGCCTACCTC GTGCCGACGC CATACTACCC AGCGTATGTC TCGACCAACG |
| | | TCATCCTTGT ACTTGTACCA AAATTAGTCA CCCGTTGACA CGAAAGTTGG |
| | | TAAGAGGGTA AGAGCAGGGA AAGGCAGAGC TAAGGCCCTG TTTGGTTTGA |
| | | GGTGACTAAA GTTTAGTGAC TAATATTTAG TCACTTTTAG TCTCTAAAGA |
| | | AGTAAACATG GTGACTAAAG TGAAGTGACT AAATTTTAGT TCTTTAGTCA |
| | | CTAAGAGGCT GACTAAAAGG GACTAAAGTA GTATTTTTAC CTTATTTGTC |
| | | CTCTCCACTT TCTTCTTATA GCAAACATCT ATTAATTAAT AGGGATAAAA |
| | | TAATCATTAT TCACAGCAAT TAATGCCCTT TAGTCCGGTT TAGTCACTGG |
| | | AACCAAACGG GATACTTTAG CGACTAAACT TTAGTCACTA AAATTTAGTC |
| | | TAGTGACTAA GGGAACCAAA CAGGACCTAA TTCGAGTGTG ATGTCAACAA |
| | | GACAACAAAT AATAGCCAAT TGTAGCCCCT CGCCATCTTT CCTTGTTTGG |
| | | GTAACGTTTC AAAATTTAGG GGGTGTTTGG TTTCTAGGGA CTAATGTTTA |
| | | GTCCCTTCAT TTTATTCCAT TTTAGTATAT AAATTGTCAA ATATAAAAAC |
| | | CAAAATAGAG TTTTAGTTTC TATATTTGAC AATTTTAGAA CTAAAATGAA |
| | | ATAAAATGTA GGGACTAAAG TATAAACTAA ACACCCCCTT ACCTCGATCA |
| | | CGAACCTCTA AAAGTAAGTA GCACCCTCCT CCCCCACAGT CAAATCAACA |
| | | TAATACAGTA CAATAGACCT TGTTAGTCGC ATGGATGATT GTCGTCAAGT |
| | | GGGCAACGCA ATCTAGTCAC GTAAGGAAAA CCATGCACGT TGTTCATACA |
| | | CGGTCTGTTT CCATGCGACT TTAATTTCCA CGCACGTTTG CATCGTTGAC |
| | | CAACCAACTG AACGTGCCTG TAGGTCCCGC ACAGCAACGT AAGCATATGC |
| | | ATGCACGTAC GACGTACGGC ACGGGAAAAA AATTCTGCAC ACCGTATTTT |
| | | ACAGCTCTTC ATATCCACCA CATGTAGCGG CCCCACAAAA AACAGATTAA |
| | | AATTTGCAAC TTAATCCTTA AGTAATTTGT TTTTCTTCTA TTTATATAGA |
| | | TTATCAGTTG ATGGATGTGT GAAGTTGTAA AAGAGATTAT TTGTATCCAG |
| | | GATTAAAATA ATTTTCCGTA CGGCACGCCT GCAGTACTCA TTCTCGCCAG |
| | | CCCTGAGCCC CTGATATATG ACACGCTTTT CATTGTTCAC ACAGTTTCGA |
| | | CCGTGACTGT TGCTGGAGGT CAGGCGTGAA GCTGCTGCCC ATCGAATGCC |
| | | ACAGCTCAAA CAACTTCACC CTCACACGGG AGGCGCTCGT GTCGGCCTAC |
| | | GACGGCGCGC GGAGGCAGGG CGTCCGCGTC AAGGGCGTCC TCATCCACCA |
| | | CCCCTCCAAC CCGCTGGGCA CCACCATGGA CCGCGCCACG CTGGCGATGC |
| | | TCGCCAGGTT CGCCACGGAG CACCGTGTCC ACCTCATCTG CGACGAGATC |
| | | TACGCGGGCT CCGTCTTCGC CAAGCCGGAC TTCGTGAGCA TCGCCGAGGT |
| | | CATCGAGCGC GACGTCCCGG GCTGCAACAG GGACCTCATC CACATCGCGT |
| | | ACAGCCTCTC CAAGGACTTC GGCCTCCCGG GCTTCCGCGT CGGCATCGTC |
| | | TACTCGTACA ACGACGACGT CGTGGCCTGC GCGCGCAAGA TGTCCAGCTT |
| | | CGGCCTCGTC TCCTCGCAGA CGCAGCACTT CCTGGCGAAG ATGCTGTCGG |
| | | ACGCGGAGTT CATGGCCCGC TTCCTCGCGG AGAGCGCGCG GCGGCTGGCG |
| | | GCGCGCCACG ACCGCTTCGT CGCGGGACTC CGCGAGGTCG GCATCGCGTG |
| | | CCTGCCCGGC AACGCGGGGC TCTTCTCGTG GATGGACCTG CGGGGCATGC |
| | | TCCGGGACAA GACGCACGAC GCGGAGCTGG AGCTGTGGCG GGTCATCGTA |
| | | CACAAGGTGA AGCTCAACGT GTCGCCCGGC ACGTCGTTCC ACTGCAACGA |
| | | GCCCGGCTGG TTCCGCGTCT GCCACGCTAA CATGGACGAC GAGACCATGG |
| | | AGGTCGCGCT CGACAGGATC CGCCGCTTCG TGCGCCAGCA CCAGCACAAG |
| | | GCCAAGGCCG AGCGCTGGGC GGCCACGCGG CCCATGCGCC TCAGCTTGCC |
| | | GCGCCGGGGA GGCGCCACCG CTTCGCACCT CCCCATCTCC AGCCCCATGG |

| SEQ ID: | TYPE | SEQUENCE |
|---|---|---|
| | | CGTTGCTGTC GCCGCAGTCC CCGATGGTTC ACGCCAGCTA GTCACCGAGC |
| | | ATCCGGCAAG ACTGGCTGTA GGGTGTGCCC GTACATCCGT ACGTACACCT |
| | | TTTTTTCCCA TTCACGTGAC TGCAATCAAG TCTATGGGAT GGTTGACAAA |
| | | AGACTATCTA GACAAGAGTG GGCGTAGTAC GTAACTAGTT TGACGTTGTA |
| | | CAGGCGTCAG CAGGTATCGG TAAGCAGCTA GTCAAAAGCA CGCAAGCAGG |
| | | ACGCATTTGT CCTCGATACT TTCGTGTAAA TCTCTCTCTA TTTTTTTTTG |
| | | CGAAATTCGC GTGTATGGTT TGTTTTGACG TTGGTATAAA GTATGGTAGA |
| | | ATAACGATGG GAAATGGCAA TTTAGTCCTC CCGATCAATT GTTATTGTAA |
| | | ACCACTGACG AAAGTTAAGA ACAGAAGCTG TACCAGAAGG GTGAATAAAA |
| | | ATACCACATA GGTATTGAAT AATAATCTA TGTATTTCGA GTTACTCCTG |
| | | CAAGATATCT ATTTTTTCAT GCTGTGCTGG CCACATTTGC CTCTTCTTCA |
| | | AACTAGTTTC TCGCA |
| SEQ ID: 2 | Gene ACS6 (ACC6) ACC Synthase gene sequence (A65) from Zea mays (Zm) inbred 'B73' (= ACC6 pcr fragment originally isolated from inbred 'Oh43') | CGGCTAGTTT TGATAGTTAG ACGATGTTCT GACAGCGCAC CAGACAGTAA |
| | | CCAGTGACAG TCCGGTGCCT GGCTAAATAT CGAGCCAGCG AACAGCGCGC |
| | | TCTCGGGTTT CTACGGGGGC AGAGGGTTGC TCTCGGGGCA TTCTTGTGCT |
| | | CACTGTCAGG GGGAGCACCA GACAGTCCGG TGCACAGCGA ACAGTCTGAT |
| | | GCCCCTAGGT CAGCAAGTCA AAGTTCTCTT CCTTAGATTT TTCTAAACCG |
| | | TTTTCGTTTT AACTTGTGAG TGAGTTATCG AGTGACACCT AGCACTAGTT |
| | | GTGAGTATGA ACACCAACAC TATATTAGAT TTCTCTTGGT CAAACTACTC |
| | | ATCCACAACC ACTCTTTATA GTACGGCTAA AATAAAAATA GAAGTCCTAA |
| | | CTTTATACCA AGTGTCAACA ACTCCTTCGG ACACTTAGAA TATAAAGTCC |
| | | TTCATCTTTT GTTTCGCCTT TTTCCGCCGT CGCTTCAAGT TCTCATCCGA |
| | | GGGATTGTTT TATCGTTGTA GTGCAACTTC ATGCAATGTG ACCTAACTTG |
| | | CCATTTGCTC TTCAAAACAC ACGTTAGTCA TATAATATTA CGTTGTCATT |
| | | AATCTCTATC GATATTTTTC ACCCATTACG TTGTCACTAG ATGCTTTCAC |
| | | CCATTTCGAT TTCAGACGAT GTCTTCGGAC GTTGCGGGCC ATGTGTCCAA |
| | | ACGTGGTTAA GTGTGGTCGG GAAATACCCG ATCGAGGTTG AGTTCGGCCT |
| | | TCGCTCCGAC ACCCAGCCGT GTCATTACTG TCATATATAT TGTAGCAATG |
| | | TCAAAAAAAA TCAAAACATT GAGTATGACG TATAGGGCAC ATATGTCATT |
| | | AAACTTATTC AGTGTAATGA TATATTATCA TCACGGGACT TTTTTTTAAT |
| | | GTATGTATTA GATTACCTCT GCCATGCACT ATACAAACAG CTACGCCGCA |
| | | GTCGCAAGCA AACAGGCTCT AAAAGGCTTC AGTCGGAGAA GGATATGAGA |
| | | GCGGTGAGTA CCAAACGGGT ATCTTCCCCT TCCAAATGAT ATAAGCCTAC |
| | | TTGTTTGACC CCAGCCCGCA GGCAGTCATC TGCTATAATA GGCTAATACA |
| | | ACTTGTGTAC TCTAGTCTGC TCTCGCCGCG TTGTCCGCAT GCTGAACCCG |
| | | CGATGTTAAC ACCTCCCTGA ACGAGTCCTC TGTTCCTCAA CTGAAATTCA |
| | | GCAATAAAAG GAAAAATCCG CGGTCCCTGT CCCTGTCCAG CACCGCACTC |
| | | TCGCACTTGT GCTGCAGGCT TCTGAGCTCG GCACCTGCTG CTAGCTGCTG |
| | | CTATATATAG ACGCGTTTTG GGGTCACCAA AACCACCAGC TGATCAACAG |
| | | CTAGCTTCAT TCCTCTGCCT CTCTCTCCCT CCTTCGCCAA CTGGCCATCT |
| | | CTGTTGTCTC TCGCTAGCTA GCTCGCTCGC TCGCTCGCCA GTCACCACAC |
| | | ACACACACAC ACACTGTGTG TCTGTGCCTG ACGCCGCCCC CCAGTTTCAA |
| | | ACGAACGACC CAGCCAGAAA CGCGCGCGCG CCAAAGCTAC GTGAGTGACG |
| | | TGGCAGCATG GTGAGCATGA TCGCCGACGA GAAGCCGCAG CCGCAGCTGC |
| | | TGTCCAAGAA GGCCGCCTGC AACAGCCACG GCCAGGACTG GTCCTACTTC |
| | | CTGGGGTGG AGGAGTATGA GAAAAACCCA TACGACCCCG TCGCCAACCC |
| | | CGGCGGCATC ATCCAGATGG GCCTCGCCGA GAACCAGCTG TCCTTCGACC |
| | | TGCTGGAGGC GTGGCTGGAG GCCAACCCGG ACGCGCTCGG CCTCCGCCGG |
| | | GGAGGCGCCT CTGTATTCCG CGAGCTCGCG CTCTTCCAGG ACTACCACGG |
| | | CATGCCGGCC TTCAAGAATG TGAGTGCCTG CTAGCTTACT CATTCCCAGG |
| | | CAGGCAGGCA GCCAGCCACG GCATGCCGAA CCAGTCTGAC CTCTCTCGCG |
| | | CACATGAATG CGTGATTCCC GCAGGCATTG GCGAGGTTCA TGTCGGAGCA |
| | | ACGTGGGTAC CGGGTGACCT TCGACCCCAG CAACATCGTG CTCACCGCCG |
| | | GAGCCACCTC GGCCAACGAG GCCCTCATGT TCTGCCTCGC CGACCACGGA |
| | | GACGCCTTTC TCATCCCCAC GCCATACTAC CCAGGGTATG TGTGTGTGTT |
| | | GCCTTGTACT TACTCGTCGC CGCAAGTACT TGCAGTAGGG AACGTGCAAG |
| | | TGGCGGCGGG GCGGCGTCTG GGTGTCGCCG CGATGCACGT TACTGCTATT |
| | | AAAGTAGTAG TAGTACACTA ATAGCTAGGC CCACCACAGC ACACGATGAC |
| | | ATGACGAACG ATGGATGGGA ACGGCTGCTG ACTGGGCCTG CTTGCTCTTG |
| | | TCTGCAGGTT CGACCGTGAC CTCAAGTGGC GCACCGGCGC GGAGATCGTC |
| | | CCCGTGCACT GCACGAGCGG CAACGGCTTC CGGCTGACGC GCGCCGCGCT |
| | | GGACGACGCG TACCGGCGCG CGCAGAAGCT GCGGCTGCGC GTCAAGGGCG |
| | | TGCTCATCAC CAACCCTTCC AACCCGCTGG GCACCACGTC GCCGCGCGCC |
| | | GACCTGGAGA TGCTGGTGGA CTTCGTGGCC GCCAAGGGCA TCCACCTGGT |
| | | GAGCGACGAG ATATACTCGG GCACGTTCTT CGCGGACCCG GGCTTCGTGA |
| | | GCGTCCTCGA GGTGGTGGCC GCGCGCGCCG CCACGGACGA CGGCGTCGTC |
| | | GGCGTTGGGC CGCTGTCGGA CCGCGTGCAC GTGGTGTACA GCCTGTCCAA |
| | | GGACCTGGGC CTCCCGGGGT TCCGCGTGGG CGCCATCTAC TCGTCCAACG |
| | | CCGGCGTGGT CTCCGCGGCC ACCAAGATGT CGAGCTTCGG CCTGGTGTCG |
| | | TCCCAGACGC AGCACCTCCT GGCGTCGCTC CTGGGCACAA GGGACTTCAC |
| | | GCGGAGGTAC ATCGCGGAGA ACACGCGGCG GATCAGGGAG CGGCGCGAGC |
| | | AGCTGGCGGA GGGCCTGGCG GCCGTGGGCA TCGAGTGCCT GGAGAGCAAC |
| | | GCGGGGCTCT TCTGCTGGGT CAACATGCGG CGCCTGATGC GGAGCCGGTC |
| | | GTTCGAGGGC GAGATGGAGC TGTGGAAGAA GGTGGTCTTC GAGGTGGGGC |
| | | TCAACATCTC CCCGGGCTCC TCCTGCCACT GCCGGAGCC CGGCTGGTTC |
| | | CGCGTCTGCT TCGCCAACAT GTCCGCCAAG ACGCTCGACG TCGCGCTCCA |

| SEQ ID: | TYPE | SEQUENCE |
|---|---|---|
| | | GCGCCTGGGC GCCTTCGCGG AGGCCGCCAC CGCGGGGCGC CGCGTGCTTG |
| | | CCCCCGCCAG GAGCATCAGC CTCCCGGTCC GCTTCAGCTG GGCTAACCGC |
| | | CTCACCCCGG GCTCCGCCGC CGACCGGAAG GCCGAGCGGT AGCCGGTCCC |
| | | CGTCCGCGCC GACCGCACGT GCTCAGCTCA GCAGCTTCAC AGCTCACCAC |
| | | CAGTCACCAC CACCACCACC ACCACCACCT GGGGTGGAGG CGTGGAGCAA |
| | | GCAATGTTCA TAGAAACCAC GGTCACGTAC TATACAATAC TACTACCGTA |
| | | CCACACCACA CGGCAGCATC ATTAGCAGTA GGAGATTAGT AGTAATCATT |
| | | AATTCCTTAT TGGGTTCTTG TAATTTCGTA TATACCACGC CGCCATTTTT |
| | | CCTTGGGGCC AGGCCAGCCG ATAGGTGCCC GAGGGCCACT GCACTGCACT |
| | | GCTGTATTAG GTAGGAGCAG GAGTGGTGGG TAGCGAATCC ACCTTCCAGC |
| | | AGCAGGCATC ACATTTGTGT ATTTTTCGAC TGGGTCTCCC GGTTGTTTT |
| SEQ ID: 3 | Gene ACS7 (ACC7) ACC Synthase gene sequence (A50) from *Zea mays* (Zm) inbred 'B73' (= ACC7 pcr fragment originally isolated from inbred 'Oh43') | GCTGGTAGCT TCTTTAACTG ATCTCAATGG GGCATTTCGG TGGCTAGCAA |
| | | TTCACATTAA TAATTTAAAA GTGAATTTCA GGTGTACATT TGATGGCCTC |
| | | CGATATGGTG CAGCCTTCAA TCCTCTACAA TGTGCGAGAA TGTTGCTCCG |
| | | GAGGGTAGAG GCGATTAACG GCTGAACACA GATGACCTCC TCGGAGTCAT |
| | | GTTTCTAATT ATCTACACTA CGATTCTCTT TCCGTTGATA AAATATTTGT |
| | | TTTATTGTCC TGTGAGCTAA TGATAACATT GATGGTAAGT AAATATAGTC |
| | | CATGCATATT CTCATCACAG ATGGCTGAAA AACTCCCGGT GCTGCTACAC |
| | | TACTAGAGTC TTCATGTGCA TACTTACTTC AAGAACTCAA GGTACACAAA |
| | | GTTTTCTCAA CAGAAGAATG TGTATCTGTT TGATTCCAGC TGAAATGCTT |
| | | ACTAAACTCA GTGTGTCGCT TTAGATGATA TGAGATGAAG TTGGGCAAGA |
| | | CCAAAGTGAA AGGGAGAGAA TAACGGAAGA ACTTGTTCGC CAACTTGGAG |
| | | AAACCAATAC TAAAACTCAG TGAATATATG TGTGGATTTG GAAGCAAGTG |
| | | AATTTTACAG AAAAGTTTTT TGAGAGTGTT TATATGAATC GTACTCATCT |
| | | GTTTATTTTG ATGACTGCAA TATAACTACT TGTATTTATA GTTTGAGATC |
| | | AAGAAAATAA GTTATTATTT AGAAATAATA AAAAATTATA GTGATGTTTG |
| | | TTGTTCCGTA TCAATGTTTC ATACAAATGT TTTACTTCCG TCGCAACACA |
| | | CGGGAATATA CCTATAATAT ATATTGTTAT CATGTTATTA TACGGTTCCG |
| | | TTGCAACGCA CGGGCACATA CCTAGTACAA AAATAATTAC GCATCCCGCA |
| | | GTTGACATCT GGGAGCGCTA CAAATAATGA AGGCAGCTGG TCCACCACAC |
| | | GAACTGACAG CGCGGAGAAG GGAGTGCACC GGCCCACCGG GATGGCACCG |
| | | CGAATCAGCC TCGGCAGCGC CATACTGCCC ACCCATTTTT TCTGGCGAAT |
| | | CCGGGTGCGG CGGGCGGTTG AGGATGAATT GAATAATACT CTACTTCCTA |
| | | ATGGTCGTGC TAGCAGACCC TGGAAGCTCA GTGTGGCTCC AAAACCCATT |
| | | AATTAATTAA ACCACAAAGC CGCCGCCGTT AGACCTAGAA CCACCGCTGC |
| | | GCTCGCCGGG CGCCGGCTAC CCGGCGTAAC TGCCGTCACC ATCCACCACC |
| | | TGGCCGCTCC GTTCTTTCCT CCACCCCAAG ATGGAGCCGG TTAACCTGTC |
| | | CAATCTTACC TCATATGCGT AATCAACTAT TTTAACTTTC ACTATATATA |
| | | TATGTTAATA TTTATAATAT ATAATTTGTA GTATAAGATA AATATTTGAA |
| | | TTTGTTTTTA TAATAAACGT ATTTTGACAT ATAAATATTG GTAATATTTT |
| | | TTTTTTACAA ATCTGACTAG ATTTTAAATC TGTAACGAGG AGTACATAGT |
| | | ACGAAATGTT GAAAAGTCAG CGTGTCTTTG GTCGCGTTCG CATTCATTCT |
| | | TTCTTTACCT CAGCCACCCA CCTGCCACAC CCTGTGGGCC GTGGCGCCTT |
| | | CACGGAAGGT TCGCCGGCCA CGCATGGAGG CGGCTCTTTA TAAAGCTGGT |
| | | GCGCGGGCGG GAGGGGAGAG GGCACCAGAA GCAGCCAGCA AGCTCATGCC |
| | | CTTCAAAAGC CTCCGGCAGC CCAGCGCCCC AGCCAGCTAG TGGTGATCTC |
| | | TCATCTCAGC AGCGCGCCTG AACGTGTGCT CCCTGCTAAG CTCTGCGCCT |
| | | CGATAGGCAA AGGAAAATCA AACCGATCGT CGTCAGATTA AATGGCCGGT |
| | | AGCAGCGCGG AGCAGCTCCT CTCCAGGATC GCCGCCGGCG ACGGCCACGG |
| | | CGAGAACTCG TCCTACTTCG ACGGGTGGAA GGCCTACGAC ATGAACCCTT |
| | | TCGACCTGCG CCACAACCGC GACGGCGTCA TCCAGATGGG CCTCGCCGAG |
| | | AACCAAGTAC GTACCTATAG CGTGTACCTA CCCTTCCGAT CTGTAGTACT |
| | | GCCCACACTT GCTGCATGCT GCTGCCGATC CAAGTCCAAT GCTCATGTAA |
| | | ACTGGCGTGC TGCAGCTGTC GTTGGACCTG ATCGAGCAAT GGAGCGTGGA |
| | | CCACCCGGAG GCGTCCATCT GCACGGCGCA GGGCGCGCCG CAGTTCCGGA |
| | | GGATAGCCAA CTTCCAGGAC TACCACGGCC TGCCGGAGTT CAGAGAGGTA |
| | | ACTAACTAGT AGTGATTAAC AAGCAAATAA ACGCCAGGAT CACTGCATCG |
| | | ATTAGCTAGG TTTGCTGCTG CTGCTGCTGC TGTCTAATAT AATGGCGACT |
| | | GCACGCGAAA AGCGACGGAG CAGCTACCGG CCGGCGGCTA GCTAGCTAGC |
| | | TGGCACTGGC AGCGCAGTCG CCTTCATGAG TCCACGCACG CGCGGCTACG |
| | | TCTTAATGAT CGATCGGCTC GTCGTTTGTT GCAGGCGATG GCCAAGTTCA |
| | | TGGGGCAGGT GAGGGGCGGC AAGGTGACGT TCGACCCCGA CCGCGTCGTC |
| | | ATGTGCGAG GAGCCACCGG CGCGCAGGAC ACTCGCCT TCTGCCTCGC |
| | | TGACCCGGGC GACGCCTACC TCGTGCCGAC GCCTTATTAC CCAGCGTATG |
| | | TTCTGACGTC ACCCTTGTAC TGCCAAACTA CTACTCAGGT CCTAGTCATA |
| | | TCCGTAGACA CGAAAGGGTG GGTGGGTCTG GTTGTTGGT TGGTCAAGAG |
| | | CACGCAAAAT TGAGCTAATT CGACTACGTA CGTGTCAATG TCAACTAGCC |
| | | ACTTATCTTT CCTTGTTTGG GTAAAGTTTC AAAACTTATT AACTCGATCA |
| | | GGAACCTCTC TAAAAAGCAT TCACCTATTT TTCCCCCGTA AGGCGGTAAC |
| | | CAAATCTAAA CGATATACCC TTGTTAGTCG CACTGATGAC TGCATTGTGG |
| | | TCAAGTGGAC AACGCAATCT AGTCACGCGA CCTCTAAGGA AAACCACGCA |
| | | CGTATACGCA CTTCGTGCAC GGTCTGTTCC ACGCGACTTT AGTTTCCATG |
| | | CACGTTTACA TCGTTGACCA TCCGCAGTCC GCACAGCAAC GTAAGCATAA |
| | | ACATGCACGC ACGACGTACG GCACACCGTA CCTGTTCCTC TCGAGGGCTG |
| | | AGACCCTGAC ACGTTTTTTT CGTTGTGTGG TGATCACAGT TTCGACCGCG |
| | | ACTGTTGCTG GAGGTCAGGA GTGAAGCTGC TGCCCATCGA ATGCCACAGC |

| SEQ ID: | TYPE | SEQUENCE |
|---|---|---|
| | | TCGAACAACT TCACCCTCAC CAGGGAGGCG CTCGTGTCGG CCTACGACGG
CGCGCGGAGG CAGGGCGTCC GCGTCAGGGG CATCCTCATC ACCAACCCCT
CCAACCCGCT GGGCACCACC ATGGACCGCG GCACGCTGGC GATGCTCGCC
GCGTTCGCCA CAGAGCGCCG CGTCCACCTC ATCTGCGACG AGATCTACGC
GGGCTCCGTC TTCGCCAAGC CGGGCTTCGT GAGCATCGCC GAGGTCATCG
AGCGCGGCGA CGCCCCGGGC TGCAACAGGG ACCTCGTCCA CATCGCGTAC
AGCCTCTCCA AGGACTTCGG CCTCCCGGGC TTCCGCGTCG GCATCGTCTA
CTCCTACAAC GACGACGTGG TGGCCTGCGC GCGCAAGATG TCCAGCTTCG
GCCTCGTCTC GTCGCAGACG CAGCACTTCC TGGCGATGAT GCTCGCCGAC
GCGGAGTTCA TGGCACGCTT CCTCGCGGAG AGCGCGCGGC GGCTGGCGGC
GCGCCACGAC CGCTTCGTCG CGGGCCTCCG CGAGGTCGGC ATCGCGTGCC
TGCCGGGCAA CGCGGGCCTC TTCTCGTGGA TGGACCTGCG GGGCATGCTC
CGGGAGAAGA CGCACGACGC GGAGCTCGAG CTGTGGCGGG TCATCGTACA
CAGGGTGAAG CTCAACGTGT CGCCCGGCAC GTCGTTCCAC TGCAACGAGC
CCGGCTGGTT CCGCGTCTGC TACGCCAACA TGGACGACGA CACCATGGAG
GTCGCGCTCG ACCGGATCCG CCGCTTCGTG CGCCAGCACC AGCACAGCAA
GGCCAAGGCC GAGCGCTGGG CGGCCACGCG GCCCCTTCGC CTCAGCTTGC
CGCGCCGGGG AGCAACCACC GCTTCGCATC TCGCCATCTC CAGCCCCTTG
GCGTTGCTGT CGCCGCAGTC CCCGATGGTC CACGCCAGCT AGGTAGTCAC
CGAGCGTTCG GTAAGACTGG CTGTAGGTTG TGCCCTCACA TGACTGCAAA
CAAGTGGACA AAAAAAAAGA CAAGACTAAT AAAGGGCGTA CGTAGCTAGC
TTGACATTAC ACAGAGTGAC AGAGACGTTG CACAGGCGTC AGCAGGCGTC
GGCGGTAAGC AGCTAGTCAA GTAGGACGCA TTTGTCCTCG ATTTTTTCGT
GTTTTTTTTT TGACGAAGGG GCGAAGCCCC CTATTTCATT AAGAAATAGG
AAAGTATGAA ACAACCGCAC CCACGCGGTA GGACCTCCAA AAAGAACAGC
CACGGCCAGA AAGTAATCTA GACTCTAAAC ACTATCGCTA GATCAGTGAA
GAGACTATGA TAACAGGGAA AGTTTTGGCC TACGAAGAGC TACATAAGAC
TTTCTTATAT ACAACCAACC AAGACAGGCA GAAGCCACAA AAGACCTGAA
CAGAATGGCC AACAAAAGAC AGACAACTAT CCCAACAAGG TTTCACAGCT
TCAGCATCTT TGTCATCCAG AAATCCGCCT GTCAAGAGGA CACCACCCCA
AGGCCCTCCC GAAAGCTTCA CTTGCCGTCT TTCGGATTAA CCTGCTTCCT
AGCACCACCA TTCTTTGCTC CTTCTTTTTC TGACGAATCG CCCAAGAATC
CAACCAGAAG CAGCAAAGAA AAATGATGTT AGATGGGTCA AGTAAATGAC
TATTCCCAAA ACACCAATCA TTCCTAGTGC GCCAAATAGC CCAGAATAAA
GCACCACAAC CAAATAACAC CAACTGAGCC ATCGTGTCTT TTGGTTTACA
AAACCAATTG TCATACAAAT CTTTGATATT TTTTGGAATA GATCTCAAAT
TCAGGGCCAC TTGAATAACT CTCCACATGT ATTGAGCAAT GGGGCAATAG
AAAAA |
| SEQ ID: 4 | cDNA ACS2 (ACC2) ACC Synthase cDNA sequence (A47) from Zea mays (Zm) inbred 'B73' (= ACC2 pcr fragment originally isolated from inbred 'Oh43') | ATGGCCGGTGGTAGCAGTGCCGAGCAGCTCCTATCCAGGATCGCCTCCGGCGATGGCCAC
GGCGAGAACTCGTCCTACTTCGACGGGTGGAAGGCCTACGACATGGACCCTTTCGACCTG
CGCCACAACCGCGACGGCGTCATCCAGATGGGCCTCGCCGAGAACCAACTGTCCCTGGAC
CTGATCGAGCAATGGAGCATGGAGCACCCGGAGGCGTCCATCTGCACGGCGCAGGGAGCG
TCGCAGTTCAGGAGGATAGCCAACTTCCAGGACTACCACGGCCTGCCGGAGTTCAGAGAG
GCGATGGCCAAGTTCATGGGCCAGGTGAGGGCCGGGAAGGTGACGTTCGACCCCGACCGC
GTCGTCATGTGCGGAGGCGCCACCGGCGCGCAGGACACTCTCGCCTTCTGCCTCGCTGAC
CCGGGCGACGCCTACCTCGTGCCGACGCCATACTACCCAGCGTTCGACCGTGACTGTTGC
TGGAGGTCAGGCGTGAAGCTGCTGCCCATCGAATGCCACAGCTCAAACAACTTCACCCTC
ACACGGGAGGCGCTCGTGTCGGCCTACGACGGCGCGCGGAGGCAGGGCGTCCGCGTCAAG
GGCGTCCTCATCACCAACCCCTCCAACCCGCTGGGCACCACCATGGACCGCGCCACGCTG
GCGATGCTCGCCAGGTTCGCCACGGAGCACCGTGTCCACCTCATCTGCGACGAGATCTAC
GCGGGCTCCGTCTTCGCCAAGCCGGACTTCGTGAGCATCGCCGAGGTCATCGAGCGCGAC
GTCCCGGGCTGCAACAGGGACCTCATCCACATCGCGTACAGCCTCTCCAAGGACTTCGGC
CTCCCGGGCTTCCGCGTCGGCATCGTCTACTCGTACAACGACGACGTCTGGCCTGCGCA
CGCAAGATGTCCAGCTTCGGCCTCGTCCTCGCAGACGCAGCACTTCCTGGCGAAGATG
CTGTCGGACGCGGAGTTCATGGCCCGCTTCCTCGCGGAGAGCGCGCGGCGGCTGGCGGCG
CGCCACGACCGCTTCGTCGCGGGACTCCGCGAGGTCGGCATCGCGTGCCTGCCCGGCAAC
GCGGGGCTCTTCTCGTGGATGGACCTGCGGGGCATGCTCCGGGACAAGACGCACGACGCG
GAGCTGGAGCTGTGGCGGGTCATCGTACACAAGGTGAAGCTCAACGTGTCGCCCGGCACG
TCGTTCCACTGCAACGAGCCCGGCTGGTTCCGCGTCTGCCACGCTAACATGGACGACGAG
ACCATGGAGGTCGCGCTCGACAGGATCCGCCGCTTCGTGCGCCAGCACCAGCACAAGGCC
AAGGCCGAGCGCTGGGCGGCCACGCGGCCCATGCGCCTCAGCTTGCCGCGCCGGGGAGGC
GCCACCGCTTCGCACCTCCCCATCTCCAGCCCCATGGCGTTGCTGTCGCCGCAGTCCCCG
ATGGTTCACGCCAGC |
| SEQ ID: 5 | cDNA ACS6 (ACC6) ACC Synthase cDNA sequence (A65) from Zea mays (Zm) inbred 'B73' (= ACC6 pcr fragment originally isolated from inbred 'Oh43') | ATGATCGCCGACGAGAAGCCGCAGCCGCAGCTGCTGTCCAAGAAGGCCGCCTGCAACAGC
CACGGCCAGGACTCGTCCTACTTCCTGGGGTGGGAGGAGTATGAGAAAAACCCATACGAC
CCCGTCGCCAACCCCGGCGGCATCATCCAGATGGGCCTCGCCGAGAACCAGCTGTCCTTC
GACCTGCTGGAGGCGTGGCTGGAGGCCAACCCGGACGCGCTCGGCCTCCGCCGGGGAGGC
GCCTCTGTATTCCGCGAGCTCGCGCTCTTCCAGGACTACCACGGCATGCCGGCCTTCAAG
AATGCATTGGCGAGGTTCATGTCGGAGCAACGTGGGTACCGGGTGACCTTCGACCCCAGC
AACATCGTGCTCACCGCCGGAGCCACCTCGGCCAACGAGGCCCTCATGTTCTGCCTCGCC
GACCACGGAGACGCCTTTCTCATCCCCACGCCATACTACCCAGGGTTCGACCGTGACCTC
AAGTGGCGCACCGGCGCGGAGATCGTCCCCGTGCACTGCACGAGCGGCAACGGCTTCCGG
CTGACGCGCGCCGCGCTGGACGACGCGTACCGGCGCGCGCAGAAGCTGCGGCTGCGCGTC
AAGGGCGTGCTCATCACCAACCCTTCCAACCCGCTGGGCACCACGTCGCCGCGCGCCGAC
CTGGAGATGCTGGTGGACTTCGTGGCCGCCAAGGGCATCCACCTGGTGAGCGACGAGATA

| SEQ ID: | TYPE | SEQUENCE |
|---|---|---|
| | | TACTCGGGCACGGTCTTCGCGGACCCGGGCTTCGTGAGCGTCCTCGAGGTGGTGGCCGCG |
| | | CGCGCCGCCACGGACGACGGCGTCGTCGGCGTTGGGCCGCTGTCGGACCGCGTGCACGTG |
| | | GTGTACAGCCTGTCCAAGGACCTGGGCCTCCCGGGGTTCCGCGTGGGCGCCATCTACTCG |
| | | TCCAACGCCGGCGTGGTCTCCGCGGCCACCAAGATGTCCGAGCTTCGGCCTGGTGTCGTCC |
| | | CAGACGCAGCACCTCCTGGCGTCGCTCCTGGGCGACAGGGACTTCACGCGGAGGTACATC |
| | | GCGGAGAACACGCGGCGGATCAGGGAGCGGCGCGAGCAGCTGGCGGAGGGCCTGGCGGCC |
| | | GTGGGCATCGAGTGCCTGGAGAGCAACGCGGGGCTCTTCTGCTGGGTCAACATGCGGCGC |
| | | CTGATGCGGAGCCGGTCGTTCGAGGGCGAGATGGAGCTGTGGAAGAAGGTGGTCTTCGAG |
| | | GTGGGGCTCAACATCTCCCCGGGCTCCTCCTGCCACTGCCGGGAGCCCGGCTGGTTCCGC |
| | | GTCTGCTTCGCCAACATGTCCGCCAAGACGCTCGACGTCGCGCTCCAGCGCCTGGGCGCC |
| | | TTCGCGGAGGCCGCCACCGCGGGGCGCCGCGTGCTTGCCCCCGCCAGGAGCATCAGCCTC |
| | | CCGGTCCGCTTCAGCTGGGCTAACCGCCTCACCCCGGGCTCCGCCGCCGACCGGAAGGCC |
| | | GAGCGG |
| SEQ ID: 6 | cDNA ACS7 (ACC7) ACC Synthase cDNA sequence (A50) from Zea mays (Zm) inbred 'B73' (= ACC7 pcr fragment originally isolated from inbred 'Oh43') | ATGGCCGGTAGCAGCGCGGAGCAGCTCCTCTCCAGGATCGCCGCCGGCGACGGCCACGGC |
| | | GAGAACTCGTCCTACTTCGACGGGTGGAAGGCCTACGACATGAACCCTTTCGACCTGCGC |
| | | CACAACCGCGACGGCGTCATCCAGATGGGCCTCGCCGAGAACCAACTGTCGTTGGACCTG |
| | | ATCGAGCAATGGAGCGTGGACCACCCGGAGGCGTCCATCTGCACGGCGCAGGGCGCGCCG |
| | | CAGTTCCGGAGGATAGCCAACTTCCAGGACTACCACGGCCTGCCGGAGTTCAGAGAGGCG |
| | | ATGGCCAAGTTCATGGGGCAGGTGAGGGGCGGCAAGGTGACGTTCGACCCCGACGCGTC |
| | | GTCATGTGCGGAGGAGCCACCGGCGCGCAGGACACTCGCCTTCTGCCTCGCTGACCCG |
| | | GGCGACGCCTACCTCGTGCCGACGCCTTATTACCCAGCGTTCGACCGCGACTGTTGCTGG |
| | | AGGTCAGGAGTGAAGCTGCTGCCCATCGAATGCCACAGCTCGAACAACTTCACCCTCACC |
| | | AGGGAGGCGCTCGTGTCGGCCTACGACGGCGCGGAGGCAGGGCGTCCGCGTCAGGGGC |
| | | ATCCTCATCACCAACCCCTCCAACCCGCTGGGCACCACCATGGACCGCGCACGCTGGCG |
| | | ATGCTCGCCGCGTTCGCCACAGAGCGCCGCGTCCACCTCATCTGCGACGAGATCTACGCG |
| | | GGCTCCGTCTTCGCCAAGCCGGGCTTCGTGAGCATCGCCGAGGTCATCGAGCGCGGCGAC |
| | | GCCCCGGGCTGCAACAGGGACCTCGTCCACATCGCGTACAGCCTCTCCAAGGACTTCGGC |
| | | CTCCCGGGCTTCCGCGTCGGCATCGTCTACTCCTACAACGACGACGTGGTGGCCTGCGCG |
| | | CGCAAGATGTCCAGCTTCGGCCTCGTCTCGTCGCAGACGCAGCACTTCCTGGCGATGATG |
| | | CTCGCCGACGCGGAGTTCATGGCACGCTTCCTCGCGGAGAGCGCGCGGCGGCTGGCGGCG |
| | | CGCCACGACCGCTTCGTCGCGGGCCTCCGCGAGGTCGGCATCGCGTGCCTGCCGGGCAAC |
| | | GCGGGCCTCTTCTCGTGGATGGACCTGCGGGGCATGCTCCGGGAGAAGACGCACGACGCG |
| | | GAGCTCGAGCTGTGGCGGGTCATCGTACACAGGGTGAAGCTCAACGTGTCGCCCGGCACG |
| | | TCGTTCCACTGCAACGAGCCCGGCTGGTTCCGCGTCTGCTACGCCAACATGGACGACGAC |
| | | ACCATGGAGGTCGCGCTCGACCGGATCCGCCGCTTCGTGCGCCAGCACCAGCACAGCAAG |
| | | GCCAAGGCCGAGCGCTGGGCGGCCACGCGGCCCCTTCGCCTCAGCTTGCCGCGCCGGGGA |
| | | GCAACCACCGCTTCGCATCTCGCCATCTCCAGCCCCTTGGCGTTGCTGTCGCCGCAGTCC |
| | | CCGATGGTCCACGCCAGC |
| SEQ ID: 7 | Synthase aa ACS2 (ACC2) ACC Synthase amino acid sequence (A47) from Zea mays (Zm) inbred 'B73' (= ACC2 pcr fragment originally isolated from inbred 'Oh43') | MAGGSSAEQL LSRIASGDGH GENSSYFDGW KAYDMDPFDL RHNRDGVIQM |
| | | GLAENQLSLD LIEQWSMEHP EASICTAQGA SQFRRIANFQ DYHGLPEFRE |
| | | AMAKFMGQVR AGKVTFDPDR VVMCGGATGA QDTLAFCLAD PGDAYLVPTP |
| | | YYPAFDRDCC WRSGVKLLPI ECHSSNNFTL TREALVSAYD GARRQGVRVK |
| | | GVLITNPSNP LGTTMDRATL AMLARFATEH RVHLICDEIY AGSVFAKPDF |
| | | VSIAEVIERD VPGCNRDLIH IAYSLSKDFG LPGFRVGIVY SYNDDVVACA |
| | | RKMSSFGLVS SQTQHFLAKM LSDAEFMARF LAESARRLAA RHDRFVAGLR |
| | | EVGIACLPGN AGLFSWMDLR GMLRDKTHDA ELELWRVIVH KVKLNVSPGT |
| | | SFHCNEPGWF RVCHANMDDE TMEVALDRIR RFVRQHQHKA KAERWAATRP |
| | | MRLSLPRRGG ATASHLPISS PMALLSPQSP MVHAS |
| SEQ ID: 8 | Synthase aa ACS6 (ACC6) ACC Synthase amino acid sequence (A65) from Zea mays (Zm) inbred 'B73' (= ACC6 pcr fragment originally isolated from inbred 'Oh43') | MIADEKPQPQ LLSKKAACNS HGQDSSYFLG WEEYEKNPYD PVANPGGIIQ |
| | | MGLAENQLSF DLLEAWLEAN PDALGLRRGG ASVFRELALF QDYHGMPAFK |
| | | NALARFMSEQ RGYRVTFDPS NIVLTAGATS ANEALMFCLA DHGDAFLIPT |
| | | PYYPGFDRDL KWRTGAEIVP VHCTSGNGFR LTRAALDDAY RRAQKLRLRV |
| | | KGVLITNPSN PLGTTSPRAD LEMLVDFVAA KGIHLVSDEI YSGTVFADPG |
| | | FVSVLEVVAA RAATDDGVVG VGPLSDRVHV VYSLSKDLGL PGFRVGAIYS |
| | | SNAGVVSAAT KMSSFGLVSS QTQHLLASLL GDRDFTRRYI AENTRRIRER |
| | | REQLAEGLAA VGIECLESNA GLFCWVNMRR LMRSRSFEGE MELWKKVVFE |
| | | VGLNISPGSS CHCREPGWFR VCFANMSAKT LDVALQRLGA FAEAATAGRR |
| | | VLAPARSISL PVRFSWANRL TPGSAADRKA ER |
| SEQ ID: 9 | Synthase aa ACS7 (ACCT) ACC Synthase amino acid sequence (A50) from Zea mays (Zm) inbred 'B73' (= ACC7 pcr fragment | MAGSSAEQLL SRIAAGDGHG ENSSYFDGWK AYDMNPFDLR HNRDGVIQMG |
| | | LAENQLSLDL IEQWSVDHPE ASICTAQGAP QFRRIANFQD YHGLPEFREA |
| | | MAKFMGQVRG GKVTFDPDRV VMCGGATGAQ DTLAFCLADP GDAYLVPTPY |
| | | YPAFDRDCCW RSGVKLLPIE CHSSNNFTLT REALVSAYDG ARRQGVRVRG |
| | | ILITNPSNPL GTTMDRGTLA MLAAFATERR VHLICDEIYA GSVFAKPGFV |
| | | SIAEVIERGD APGCNRDLVH IAYSLSKDFG LPGFRVGIVY SYNDDVVACA |
| | | RKMSSFGLVS SQTQHFLAMM LADAEFMARF LAESARRLAA RHDRFVAGLR |
| | | EVGIACLPGN AGLFSWMDLR GMLREKTHDA ELELWRVIVH RVKLNVSPGT |
| | | SFHCNEPGWF RVCYANMDDD TMEVALDRIR RFVRQHQHSK AKAERWAATR |

| SEQ ID: | TYPE | SEQUENCE |
|---|---|---|
| | originally isolated from inbred 'Oh43') | PLRLSLPRRG ATTASHLAIS SPLALLSPQS PMVHAS |
| SEQ ID: 10 | CCRA178R | ATGACCATGA TTACGCCAAG CTCTAATACG ACTCACTATA GGGAAAGCTG<br>GTACGCCTGC AGGTACCGGT CCGGAATTCC CGGGTCGACC CACGCGTCCG<br>CAGCAAGCTC ATCCCCTTCA AAACCCTCCG GCAGCCCAGC CAGCTAGTGG<br>TGATCTCTCA GCAGCGCGCC TGAACGTGTG CTCCCTGCTA AACTCTGCGC<br>CTCGGTAGGC AAGGAAAATT AAACCGGTCG TCGTCAGATT AAATGGCCGG<br>TAGCAGCGCG GAGCAGCTCC TCTCCAGGAT CGCCGCCGGC GATGGCCACG<br>GCGAGAACTC GTCCTACTTC GACGGGTGGA AGGCCTACGA CACGAACCCT<br>TTCGACCTGC GCCACAACCG CGACGGCGTC ATCCAGATGG GACTCGCCGA<br>GAACCAACTG TCGCTGGACC TGATCGAGCA ATGGAGCGTG GACCACCCGG<br>AGGCGTCCAT CTGCACGGCG CAGGGCGCGC CGCAGTTCCG GAGGATAGCC<br>AACTTCCAGG ACTACCACGG CCTGCCGGAG TTCAGAGAGG CGATGGCCAA<br>GTTCATGGGG CAGGTGAGGG GCGGCAAGGT GACGTTCGAC CCCGACCGCG<br>TCGTCATGTG CGGGGGAGCC ACCGGCGCGC AGGACACTCT CGCCTTCTGC<br>CTCGCTGACC CGGGCGACGC CTACCTCGTG CCGACGCCTT ATTACCCAGC<br>TTTCGACCGC GACTGTTGCT GGAGGTCAGG AGTGAAGCTG CTGCCCATCG<br>AATGCCACAG CTCGAACAAC TTCACCCTCA CCAGGGAGGC GCTCGTGTCG<br>GCCTACGACG GCGCGCGGAG GCAGGGCGTC CGCGTCAGGG GCATCCTCAT<br>CACCAACCCC TCCAACCCGC TGGGCACCAC AATGGACCGC GGCACGCTGG<br>CGATGCTCGC CGCGTTCGCC ACAGAGCGCC GCGTCCACCT CATCTGCGAC<br>GAGATCTACG CGGGCTCCGT CTTCGCCAAG CCGGGCTTCG TGAGCATCGC<br>CGAGGTCATC GAGCGCGGCG ACGCCCCGGG CTGCAACAGG GACCTCGTCC<br>ACATCGCGTA CAGCCTCTCC AAGGACTTCG GCCTCCCGGG CTTCCGCGTC<br>GGCATCGTCT ACTCCTACAA CGACGACGTG GTGGCCTGCG CGCGCAAGAT<br>GTCCAGCTTC GGCCTCGTCT CGTCGCAGAC GCAGCACTTC CTGGCGATGA<br>TGCTCGCCGA CGCGGAGTTC ATGGCACGCT TCCTCGCGGA GAGCGCGCGG<br>CGGCTGGCGG CGCGCCACGA CCGCTTCGTC GCGGGCCTCC GCGAGGTCGG<br>CATCGCGTGC CTGCCGGGCA ACGCGGGCCT CTTCTCGTGG ATGGACCTGC<br>GGGGCATGCT CCGGGAGAGG ACGCACGACG CGGAGCTGGA GCTGTGGCGG<br>GTCATCGTAC ACGGGTGAA GCTCAACGTG TCGCCCGGCA CGTCGTTCCA<br>CTGCAACGAG CCCGGCTGGT TCCGCGTCTG CTACGCCAAC ATGGACGACG<br>ACACCATGGA GGTCGCGCTC GACCGGATCC GCCGCTTCGT GCGCCAGCAC<br>CAGCACAGCA AGGCCAAGGC CGAGCGCTGG GCGGCCACGC GGCCCCTCCG<br>CCTCAGCTTG CCGCGCCGGG GAGCAACCAC CGCTTCGCAC CTCGCCATCC<br>CCAGCCCCTT GGCGTTGCTG TCGCCGCAGT CCCCGATGGT CCACGCCAGC<br>TAGCTAGTCA CCGAGCGTTC GGTAAGACTG GCTGTAGGGT GTGCCCTCAC<br>ATAACTGCAA ACAAGTGGAC AAAAAATATT AGACAAGACT AATAAAGGGC<br>ATTAGTAGCT AGCTTGACAT TACACAGAGA CGTTGCACAG GCGTCAGCAG<br>GCGTCGGCGG TAAGCAGCTA GTCAAGCAGG ACGCATTTGT CCTCGATTTT<br>TTCGTGTATA TATGTTCTTT TTTCTGTTTT GCCAAATCGC ATGTATGGTT<br>TGGTTTAACG TTAGTACACG GTAGAATAAC GATCGGGTAT GGTAATTTAG<br>ACCTCCCGAT CAATTGTTGT TGAAAACCTG TCACGTAACT TCAGGACACA<br>GAAGGCGTAG CTCAAGGGTG AATAAAAGAC CAGTTTACAT ATCAAAAAAA<br>AAAAAAAAAA AAAAAAAAAA |
| SEQ ID: 11 | CCRA178R aa | MAGSSAEQLL SRIAAGDGHG ENSSYFDGWK AYDTNPFDLR HNRDGVIQMG<br>LAENQLSLDL IEQWSVDHPE ASICTAQGAP QFRRIANFQD YHGLPEFREA<br>MAKFMGQVRG GKVTFDPDRV VMCGGATGAQ DTLAFCLADP GDAYLVPTPY<br>YPAFDRDCCW RSGVKLLPIE CHSSNNFTLT REALVSAYDG ARRQGVRVRG<br>ILITNPSNPL GTTMDRGTLA MLAAFATERR VHLICDEIYA GSVFAKPGFV<br>SIAEVIERGD APGCNRDLVH IAYSLSKDFG LPGFRVGIVY SYNDDVVACA<br>RKMSSFGLVS SQTQHFLAMM LADAEFMARF LAESARRLAA RHDRFVAGLR<br>EVGIACLPGN AGLFSWMDLR GMLRERTHDA ELELWRVIVH RVKLNVSPGT<br>SFHCNEPGWF RVCYANMDDD TMEVALDRIR RFVRQHQHSK AKAERWAATR<br>PLRLSLPRRG ATTASHLAIP SPLALLSPQS PMVHAS |
| SEQ ID: 12 | ACCF1 (forward primer | ccagatgggcctcgccgagaac |
| SEQ ID: 13 | ACC1 (reverse primer) | gttggcgtagcagacgcggaacca |

What is claimed is:

1. An expression cassette comprising an isolated or recombinant nucleic acid operably linked to a heterologous promoter, wherein expression of the nucleic acid inhibits ethylene production in a *Poaceae* plant, and wherein the nucleic acid comprises:
   a. a polynucleotide comprising the polynucleotide sequence of SEQ ID NO: 3 or SEQ ID NO: 6, or a complete complement thereof;
   b. a polynucleotide comprising at least 95% sequence identity to the full length of SEQ ID NO: 3 or SEQ ID NO: 6, or a complete complement thereof; or
   c. a polynucleotide comprising at least 100 contiguous nucleotides of SEQ ID NO: 3 or SEQ ID NO: 6 and the complement of said polynucleotide.

2. The expression cassette of claim 1, wherein the nucleic acid is linked in an antisense orientation to the promoter.

3. A *Poaceae* plant cell transformed with a construct effective for inhibiting expression of at least one endogenous ACC synthase gene in a *Poaceae* plant, wherein said construct comprises a nucleic acid operably linked to a heterologous promoter, said promoter functional in plants operably linked to a nucleic acid selected from the group consisting of:
   a. a nucleic acid comprising at least 90% sequence identity to the full length of SEQ ID NO: 3 or SEQ ID NO: 6 linked in sense orientation relative to the promoter, wherein said construct inhibits expression of the at least one endogenous ACC synthase gene by cosuppression;
   b. a nucleic acid comprising at least 90% sequence identity to the full length of SEQ ID NO: 3 or SEQ ID NO: 6 linked in antisense orientation relative to the promoter;
   c. a nucleic acid comprising at least 95% sequence identity to a fragment comprising at least 100 contiguous nucleotides of SEQ ID NO: 3 or SEQ ID NO: 6 linked in sense orientation relative to the promoter, wherein said construct inhibits expression of the at least one endogenous ACC synthase gene by cosuppression;
   d. a nucleic acid comprising at least 95% sequence identity to a fragment comprising at least 100 contiguous nucleotides of SEQ ID NO: 3 or SEQ ID NO: 6 linked in antisense orientation relative to the promoter: and
   e. a nucleic acid configured for RNA silencing or interference, wherein said nucleic acid comprises a polynucleotide of at least 100 contiguous nucleotides of SEQ ID NO: 3 or SEQ ID NO: 6 and further comprises the complement of said polynucleotide;
   wherein said construct inhibits expression of the at least one endogenous ACC synthase gene.

4. A plant regenerated from the plant cell of claim 3.

5. The plant of claim 4, wherein the plant comprises a phenotype of increased drought resistance, increased time for maintaining a photosynthetically active plant, or delayed leaf senescence, compared to a control plant.

6. The plant of claim 4, wherein the plant is *Zea mays*, wheat, rice, sorghum, barley, oat, lawn grass, or rye.

7. A method of inhibiting ethylene production in a *Poaceae* plant, the method comprising inhibiting the expression of one or more ACC synthase genes in the plant by introducing into the plant the expression cassette of claim 1.

8. The expression cassette of claim 1, wherein said promoter is a constitutive, inducible, or tissue-preferred promoter.

* * * * *

SEQUENCE LISTING

<160> NUMBER OF SEQ ID NOS: 66

<210> SEQ ID NO 1
<211> LENGTH: 5115

```
<212> TYPE: DNA
<213> ORGANISM: Zea mays

<400> SEQUENCE: 1
aaacttcata ccggtcggtg ccttacgttc tctggcgttc ttatcctttc ctccgctttt      60
agtcgatgat tatagtagtt tctacaacaa gcttttcaacg ccattgacta tttttttcccc    120
cattgaaaac gaacaccacc attgacactg ataaatgtag tacagcattt gacaacatac     180
tttcctagaa agtaaccagc agagactgga cgctacgtac taccacacca ttggagcagc     240
caatttaatc gtgtatagaa ctccgtatcg aaatttgtct gtgaatggac cttcatttgc     300
atctaggtct agtacaatgg atttcgaaca ggacagcgcc gatctggcaa tacacacacg     360
cacgacgtag cacagctgtt cttcgttcca cgcgttaatt gaaggcaaag cgactgtagt     420
tgctgttggt ggccaagttg tttaatgcta tagtagcagc cagtcactcc tagggcaaat     480
tttaggactt ttgcattgca ttgccgccat gtagaggttg actgcacacc gagaatatcg     540
agcattcatt aggctccttg acttgttgct gtgaactccg gccatctgtc acagtacgta     600
tatgaccaga tcggcaccat ttgtctcggc ctgacaatct cgcgcgccat ggccatgca      660
aagctgtcct gccgttcgga gagactgag agccagttgg caaattgaca tttgcgatag     720
gtggggcggc tttgactatg acatgatgac agatccagat ggtcctccgc tagtccccc     780
gagcccgagg acagcacact agctcacacg aactgacagc gcggaggagg acacgtaccg    840
ggatgacacc gccacccatt tgctggcaag ccggggtgcg ccggcggttc aggttgaatc     900
cttcctaatg gtcgtgctag caaaccccgc aagctcagtg cgggtccaaa acccattaat     960
tatcccacaa agccgccgtt agacgtagaa tcgacgccgc gcgccacggc cggcggcggc    1020
tacctggctc ttaccaccat cattcgcttg tccgttccgt cgcccccgcc accctctcag    1080
agatggaggc ggttaagtgc ctgtcgacta ttgcagaacg tcgtcaggct cgctagttcg    1140
accgagcatc ctagatacat aatccaaatt ccgctcggcg attataggag ggtgatagta    1200
ctgagtacag ggcgaaaaac gttgaaaagg tcagcgaggc ccccacatgt ctccccggt     1260
cgcgttcgca ttcaacaccc tctgcgctgc gtttcatgga agtttccagc agccacgccc    1320
acgcgcatgg acgcggctga tcttataaag gtggcgcgcg tcccaacctc gggagccatc    1380
atttcaccag aagctgcaaa ttgcaagctc tcctccctag ctagcctctc cagcagccca    1440
accacagcct gcagctgcag ctcgcgttgg cacagcgccg cctgaacgcg tgctaattta    1500
agctctgtcg tagctcaacg cggccgccgg gctttcgccg acgacgtcaa aatggccggt    1560
ggtagcagtg ccgagcagct cctatccagg atcgcctccg gcgatggcca cggcgagaac    1620
tcgtcctact cgacgggtg gaaggcctac gacatggacc ctttcgacct gcgccacaac    1680
cgcgacggcg tcatccagat gggcctcgcc gagaaccaag tacgtgacgt agccctgccg    1740
catgcagcta cagctacacc ctttcgacct gcgcaacaac cgcgacggcg tcatccagat    1800
gggcctgctg tcgatggaat gctcatgtaa ttaaaccacc ggccggggcg tgttttgcag    1860
ctgtccctgg acctgatcga gcaatggagc atggagcacc cggaggcgtc catctgcacg    1920
gcgcagggag cgtcgcagtt caggaggata gccaacttcc aggactacca cggcctgccg    1980
gagttcagag aggtattaat taagttaact aacagctcgg ctaaggaaac gccagaatca    2040
ttgattaggt ttgctgctct ctaatggcga ctgcgaaaac gacggagcag ctaccggcca    2100
gccgccggc ggttagctag cactagcagc cgccttcctg acagatcatc catgacgttt     2160
tgattgttgc aggcgatggc caagttcatg ggccaggtga gggccgggaa ggtgacgttc    2220
```

```
gaccccgacc gcgtcgtcat gtgcggaggc gccaccggcg cgcaggacac tctcgccttc    2280
tgcctcgctg acccgggcga cgcctacctc gtgccgacgc catactaccc agcgtatgtc    2340
tcgaccaacg tcatccttgt acttgtacca aaattagtca cccgttgaca cgaaagttgg    2400
taagagggta agagcaggga aaggcagagc taaggccctg tttggtttga ggtgactaaa    2460
gtttagtgac taatatttag tcacttttag tctctaaaga agtaaacatg gtgactaaag    2520
tgaagtgact aaattttagt tctttagtca ctaagaggct gactaaaagg gactaaagta    2580 gtattttttac cttatttgtc ctctccactt tcttcttata gcaaacatct attaattaat    2640
agggataaaa taatcattat tcacagcaat aatgcccctt tagtccggtt tagtcactgg    2700
aaccaaacgg gatactttag cgactaaact ttagtcacta aaatttagtc tagtgactaa    2760
gggaaccaaa caggacctaa ttcgagtgtg atgtcaacaa gacaacaaat aatagccaat    2820
tgtagcccct cgccatcttt ccttgtttgg gtaacgtttc aaaatttagg gggtgtttgg    2880
tttctaggga ctaatgttta gtcccttcat tttattccat tttagtatat aaattgtcaa    2940
atataaaaac caaaatagag ttttagtttc tatatttgac aattttagaa ctaaaatgaa    3000
ataaaatgta gggactaaag tataaactaa acaccccctt acctcgatca cgaacctcta    3060
aaagtaagta gcaccctcct cccccacagt caaatcaaca taatacagta caatagacct    3120
tgttagtcgc atggatgatt gtcgtcaagt gggcaacgca atctagtcac gtaaggaaaa    3180
ccatgcacgt tgttcataca cggtctgttt ccatgcgact ttaatttcca cgcacgtttg    3240
catcgttgac caaccaactg aacgtgcctg taggtcccgc acagcaacgt aagcatatgc    3300
atgcacgtac gacgtacggc acgggaaaaa aattctgcac accgtatttt acagctcttc    3360
atatccacca catgtagcgg ccccacaaaa aacagattaa aatttgcaac ttaatcctta    3420
agtaatttgt ttttcttcta tttatataga ttatcagttg atggatgtgt gaagttgtaa    3480
aagagattat ttgtatccag gattaaaata attttccgta cggcacgcct gcagtactca    3540
ttctcgccag ccctgagccc ctgatatatg acacgctttt cattgttcac acagtttcga    3600
ccgtgactgt tgctggaggt caggcgtgaa gctgctgccc atcgaatgcc acagctcaaa    3660
caacttcacc ctcacacggg aggcgctcgt gtcggcctac gacggcgcgc ggaggcaggg    3720
cgtccgcgtc aagggcgtcc tcatcaccaa cccctccaac ccgctgggca ccaccatgga    3780
ccgcgccacg ctggcgatgc tcgccaggtt cgccacggag caccgtgtcc acctcatctg    3840
cgacgagatc tacgcgggct ccgtcttcgc caagccggac ttcgtgagca tcgccgaggt    3900
catcgagcgc gacgtcccgg gctgcaacag ggacctcatc cacatcgcgt acagcctctc    3960
caaggacttc ggcctcccgg gcttccgcgt cggcatcgtc tactcgtaca acgacgacgt    4020
cgtggcctgc gcgcgcaaga tgtccagctt cggcctcgtc tcctcgcaga cgcagcactt    4080
cctggcgaag atgctgtcgg acgcggagtt catggcccgc ttcctcgcgg agagcgcgcg    4140
gcggctggcg cgcgccacg accgcttcgt cgcgggactc cgcgaggtcg gcatcgcgtg    4200
cctgcccggc aacgcggggc tcttctcgtg gatggacctg cggggcatgc tccgggacaa    4260
gacgcacgac gcggagctgg agctgtggcg ggtcatcgta cacaaggtga agctcaacgt    4320
gtcgcccggc acgtcgttcc actgcaacga gccggctgg ttccgcgtct gccacgctaa    4380
catggacgac gagaccatgg aggtcgcgct cgacaggatc cgccgcttcg tgcgccagca    4440
ccagcacaag gccaaggccg agcgctgggc ggccacgcgg cccatgcgcc tcagcttgcc    4500 gcgccggggga ggcgccaccg cttcgcacct ccccatctcc agcccatgg cgttgctgtc    4560 gccgcagtcc ccgatggttc acgccagcta gtcaccgagc atccggcaag actggctgta    4620
```

```
gggtgtgccc gtacatccgt acgtacacct ttttttccca ttcacgtgac tgcaatcaag    4680
tctatgggat ggttgacaaa agactatcta gacaagagtg ggcgtagtac gtaactagtt    4740
tgacgttgta caggcgtcag caggtatcgg taagcagcta gtcaaaagca cgcaagcagg    4800
acgcatttgt cctcgatact ttcgtgtaaa tctctctcta ttttttttg cgaaattcgc     4860 gtgtatggtt tgttttgacg ttggtataaa gtatggtaga ataacgatgg gaaatggcaa    4920
tttagtcctc ccgatcaatt gttattgtaa accactgacg aaagttaaga acagaagctg    4980
taccagaagg gtgaataaaa ataccacata ggtattgaat aataatcta tgtatttcga     5040 gttactcctg caagatatct atttttttcat gctgtgctgg ccacatttgc ctcttcttca   5100
aactagtttc tcgca                                                     5115

<210> SEQ ID NO 2
<211> LENGTH: 3749
<212> TYPE: DNA
<213> ORGANISM: Zea mays

<400> SEQUENCE: 2
cggctagttt tgatagttag acgatgttct gacagcgcac cagacagtaa ccagtgacag      60
tccggtgcct ggctaaatat cgagccagcg aacagcgcgc tctcgggttt ctacgggggc    120
agagggttgc tctcggggca ttcttgtgct cactgtcagg gggagcacca gacagtccgg    180
tgcacagcga acagtctgat gccctaggt cagcaagtca aagttctctt ccttagattt     240
ttctaaaccg ttttcgtttt aacttgtgag tgagttatcg agtgcaccct agcactagtt    300
gtgagtatga acaccaacac tatattagat ttctcttggt caaactactc atccacaacc    360
actctttata gtacggctaa aataaaaata gaagtcctaa ctttataccca agtgtcaaca   420 actccttcgg acacttagaa tataaagtcc ttcatctttt gtttcgcctt tttccgccgt    480
cgcttcaagt tctcatccga gggattgttt tatcgttgta gtgcaacttc atgcaatgtg    540
acctaacttg ccatttgctc ttcaaaacac acgttagtca tataatatta cgttgtcatt    600
aatctctatc gatatttttc acccattacg ttgtcactag atgctttcac ccatttcgat    660
ttcagacgat gtcttcggac gttgcgggcc atgtgtccaa acgtggttaa gtgtggtcgg    720
gaaatacccg atcgaggttg agttcggcct tcgctccgac acccagccgt gtcattactg    780
tcatatatat tgtagcaatg tcaaaaaaaa tcaaaacatt gagtatgacg tataggggcac    840 atatgtcatt aaacttattc agtgtaatga tatattatca tcacgggact tttttttaat    900
gtatgtatta gattacctct gccatgcact atacaaacag ctacgccgca gtcgcaagca    960
aacaggctct aaaaggcttc agtcggagaa ggatatgaga gcggtgagta ccaaacgggt   1020
atcttcccct tccaaatgat ataagcctac ttgtttgacc ccagcccgca ggcagtcatc   1080
tgctataata ggctaataca acttgtgtac tctagtctgc tctcgccgcg ttgtccgcat   1140
gctgaacccg cgatgttaac acctccctga acgagtcctc tgttcctcaa ctgaaattca   1200
gcaataaaag gaaaaatccg cggtccctgt ccctgtccag caccgcactc tcgcacttgt   1260
gctgcaggct tctgagctcg gcacctgctg ctagctgctg ctatatatag acgcgttttg   1320
gggtcaccaa aaccaccagc tgatcaacag ctagcttcat tcctctgcct ctctctcccct   1380 ccttcgccaa ctggccatct ctgttgtctc tcgctagcta gctcgctcgc tcgctcgcca   1440
gtcaccacac acacacacac acactgtgtg tctgtgcctg acgccgcccc ccagtttcaa   1500
acgaacgacc cagccagaaa cgcgcgcgcg ccaaagctac gtgagtgacg tggcagcatg   1560
```

```
gtgagcatga tcgccgacga gaagccgcag ccgcagctgc tgtccaagaa ggccgcctgc    1620
aacagccacg gccaggactc gtcctacttc ctggggtggg aggagtatga gaaaaaccca    1680
tacgaccccg tcgccaaccc cggcggcatc atccagatgg gcctcgccga gaaccagctg    1740
tccttcgacc tgctggaggc gtggctggag gccaacccgg acgcgctcgg cctccgccgg    1800
ggaggcgcct ctgtattccg cgagctcgcg ctcttccagg actaccacgg catgccggcc    1860
ttcaagaatg tgagtgcctg ctagcttact cattcccagg caggcaggca gccagccacg    1920
gcatgccgaa ccagtctgac ctctctcgcg cacatgaatg cgtgattccc gcaggcattg    1980
gcgaggttca tgtcggagca acgtgggtac cgggtgacct tcgacccag caacatcgtg     2040
ctcaccgccg gagccacctc ggccaacgag gccctcatgt tctgcctcgc cgaccacgga    2100
gacgcctttc tcatccccac gccatactac ccagggtatg tgtgtgtgtt gccttgtact    2160
tactcgtcgc cgcaagtact tgcagtaggg aacgtgcaag tggcggcggg gcggcgtctg    2220
ggtgtcgccg cgatgcacgt tactgctatt aaagtagtag tagtacacta atagctaggc    2280
ccaccacagc acacgatgac atgacgaacg atggatggga acggctgctg actgggcctg    2340
cttgctcttg tctgcaggtt cgaccgtgac ctcaagtggc gcaccggcgc ggagatcgtc    2400
cccgtgcact gcacgagcgg caacggcttc cggctgacgc gcgccgcgct ggacgacgcg    2460
taccggcgcg cgcagaagct gcggctgcgc gtcaagggcg tgctcatcac caacccttcc    2520
aacccgctgg gcaccacgtc gccgcgcgcc gacctggaga tgctggtgga cttcgtggcc    2580
gccaagggca tccacctggt gagcgacgag atatactcgg gcacggtctt cgcggacccg    2640
ggcttcgtga gcgtcctcga ggtggtggcc gcgcgcgccg ccacgacga cggcgtcgtc    2700
ggcgttgggc cgctgtcgga ccgcgtgcac gtggtgtaca gcctgtccaa ggacctgggc    2760
ctcccggggt tccgcgtggg cgccatctac tcgtccaacg ccggcgtggt ctccgcggcc    2820
accaagatgt cgagcttcgg cctggtgtcg tcccagacgc agcacctcct ggcgtcgctc    2880
ctgggcgaca gggacttcac gcggaggtac atcgcgagga cacgcggcg gatcagggag    2940
cggcgcgagc agctggcgga gggcctggcg gccgtgggca tcgagtgcct ggagagcaac    3000
gcggggctct tctgctgggt caacatgcgg cgcctgatgc ggagccggtc gttcgagggc    3060
gagatggagc tgtggaagaa ggtggtcttc gaggtgggc tcaacatctc cccgggctcc    3120
tcctgccact gccgggagcc cggctggttc cgcgtctgct cgccaacat gtccgccaag    3180
acgctcgacg tcgcgctcca gcgcctgggc gccttcgcgg aggccgccac cgcggggcgc    3240
cgcgtgcttg cccccgccag gagcatcagc ctcccggtcc gcttcagctg ggctaaccgc    3300
ctcaccccgg gctccgccgc cgaccggaag gccgagcggt agccggtccc cgtccgcgcc    3360
gaccgcacgt gctcagctca gcagcttcac agctcaccac cagtcaccac caccaccacc    3420
accaccacct ggggtggagg cgtggagcaa gcaatgttca tagaaaccac ggtcacgtac    3480
tatacaatac tactaccgta ccacaccaca cggcagcatc attagcagta ggagattagt    3540
agtaatcatt aattccttat tgggttcttg taatttcgta tataccacgc cgccatttt    3600
ccttggggcc aggccagccg ataggtgccc gagggccact gcactgcact gctgtattag    3660
gtaggagcag gagtggtggg tagcgaatcc accttccagc agcaggcatc acatttgtgt    3720
attttcgac tgggtctccc ggttgttttt                                     3749
```

<210> SEQ ID NO 3
<211> LENGTH: 5105
<212> TYPE: DNA
<213> ORGANISM: Zea mays

<400> SEQUENCE: 3

```
gctggtagct tctttaactg atctcaatgg ggcatttcgg tggctagcaa ttcacattaa     60
taatttaaaa gtgaatttca ggtgtacatt tgatggcctc cgatatggtg cagccttcaa    120
tcctctacaa tgtgcgagaa tgttgctccg gagggtagag gcgattaacg gctgaacaca    180
gatgacctcc tcggagtcat gtttctaatt atctacacta cgattctctt tccgttgata    240
aaatatttgt tttattgtcc tgtgagctaa tgataacatt gatggtaagt aaatatagtc    300
catgcatatt ctcatcacag atggctgaaa actcccggt gctgctacac tactagagtc     360
ttcatgtgca tacttacttc aagaactcaa ggtacacaaa gttttctcaa cagaagaatg    420
tgtatctgtt tgattccagc tgaaatgctt actaaactca gtgtgtcgct ttagatgata    480
tgagatgaag ttgggcaaga ccaaagtgaa agggagagaa taacggaaga acttgttcgc    540
caacttggag aaaccaatac taaaactcag tgaatatatg tgtggatttg aagcaagtg     600
aattttacag aaaagttttt tgagagtgtt tatatgaatc gtactcatct gtttattttg    660
atgactgcaa tataactact tgtatttata gtttgagatc aagaaaataa gttattattt    720
agaaataata aaaattata gtgatgtttg ttgttccgta tcaatgtttc atacaaatgt     780
tttacttccg tcgcaacaca cgggaatata cctataatat atattgttat catgttatta    840
tacggttccg ttgcaacgca cgggcacata cctagtacaa aaataattac gcatcccgca    900
gttgacatct gggagcgcta caaataatga aggcagctgg tccaccacac gaactgacag    960
cgcggagaag ggagtgcacc ggcccaccgg gatggcaccg cgaatcagcc tcggcagcgc   1020
catactgccc acccatttt tctggcgaat ccgggtgcgg cgggcggttg aggatgaatt    1080
gaataatact ctacttccta atggtcgtgc tagcagaccc tggaagctca gtgtggctcc   1140
aaaacccatt aattaattaa accacaaagc cgccgccgtt agacctagaa ccaccgctgc   1200
gctcgccggg cgccggctac ccggcgtaac tgccgtcacc atccaccacc tggccgctcc   1260
gttctttcct ccacccccaag atggagccgg ttaacctgtc caatcttacc tcatatgcgt   1320
aatcaactat tttaactttc actatatata tatgttaata tttataatat ataatttgta   1380
gtataagata aatatttgaa tttgttttta taataaacgt attttgacat ataaatattg   1440
gtaatatttt tttttttacaa atctgactag attttaaatc tgtaacgagg agtacatagt   1500
acgaaatgtt gaaagtcag cgtgtctttg gtcgcgttcg cattcattct ttctttacct    1560
cagccaccca cctgccacac cctgtgggcc gtggcgcctt cacggaaggt tcgccggcca   1620
cgcatggagg cggctcttta taaagctggt gcgcgggcgg gaggggagag ggcaccagaa   1680
gcagccagca agctcatgcc cttcaaaagc ctccggcagc ccagcgcccc agccagctag   1740
tggtgatctc tcatctcagc agcgcgcctg aacgtgtgct ccctgctaag ctctgcgcct   1800
cgataggcaa aggaaaatca aaccgatcgt cgtcagatta aatggccggt agcagcgcgg   1860
agcagctcct ctccaggatc gccgccgcg acggccacgg cgagaactcg tcctacttcg    1920
acgggtggaa ggcctacgac atgaaccctt tcgacctgcg ccacaaccgc gacggcgtca   1980
tccagatggg cctcgccgag aaccaagtac gtacctatag cgtgtaccta cccttccgat   2040
ctgtagtact gcccacactt gctgcatgct gctgccgatc caagtccaat gctcatgtaa   2100
actggcgtgc tgcagctgtc gttggacctg atcgagcaat ggagcgtgga ccacccggag   2160
gcgtccatct gcacgcgca gggcgcgccg cagttccgga ggatagccaa cttccaggac   2220
taccacggcc tgccggagtt cagagaggta actaactagt agtgattaac aagcaaataa   2280
```

```
acgccaggat cactgcatcg attagctagg tttgctgctg ctgctgctgc tgtctaatat    2340
aatggcgact gcacgcgaaa agcgacggag cagctaccgg ccggcggcta gctagctagc    2400
tggcactggc agcgcagtcg ccttcatgag tccacgcacg cgcggctacg tcttaatgat    2460
cgatcggctc gtcgtttgtt gcaggcgatg gccaagttca tggggcaggt gaggggcggc    2520
aaggtgacgt tcgaccccga ccgcgtcgtc atgtgcggag gagccaccgg cgcgcaggac    2580
actctcgcct tctgcctcgc tgacccgggc gacgcctacc tcgtgccgac gccttattac    2640
ccagcgtatg ttctgacgtc acccttgtac tgccaaacta ctactcaggt cctagtcata    2700
tccgtagaca cgaaagggtg ggtgggtctg ggttgttggt tggtcaagag cacgcaaaat    2760
tgagctaatt cgactacgta cgtgtcaatg tcaactagcc acttatcttt ccttgtttgg    2820
gtaaagtttc aaaacttatt aactcgatca ggaacctctc taaaaagcat tcacctattt    2880
ttcccccgta aggcggtaac caaatctaaa cgatatacac ttgttagtcg cactgatgac    2940
tgcattgtcg tcaagtggac aacgcaatct agtcacgcga cctctaagga aaaccacgca    3000
cgtatacgca cttcgtgcac ggtctgttcc acgcgacttt agtttccatg cacgtttaca    3060
tcgttgacca tccgcagtcc gcacagcaac gtaagcataa acatgcacgc acgacgtacg    3120
gcacaccgta cctgttcctc tcgagggctg agaccctgac acgttttttt cgttgtgtgg    3180
tgatcacagt ttcgaccgcg actgttgctg gaggtcagga gtgaagctgc tgcccatcga    3240
atgccacagc tcgaacaact tcaccctcac caggaggcg ctcgtgtcgg cctacgacgg    3300
cgcgcggagg cagggcgtcc gcgtcagggg catcctcatc accaaccccct ccaacccgct    3360 gggcaccacc atgaccgcg gcacgctggc gatgctcgcc gcgttcgcca cagagcgccg    3420
cgtccacctc atctgcgacg agatctacgc gggctccgtc ttcgccaagc cgggcttcgt    3480
gagcatcgcc gaggtcatcg agcgcggcga cgccccgggc tgcaacaggg acctcgtcca    3540
catcgcgtac agcctctcca aggacttcgg cctcccgggc ttccgcgtcg gcatcgtcta    3600
ctcctacaac gacgacgtgg tggcctgcgc gcgcaagatg tccagcttcg gcctcgtctc    3660
gtcgcagacg cagcacttcc tggcgatgat gctcgccgac gcggagttca tggcacgctt    3720
cctcgcggag agcgcgcggc ggctggcggc gcgccgac cgcttcgtcg cgggcctccg    3780
cgaggtcggc atcgcgtgcc tgccgggcaa cgcgggcctc ttctcgtgga tggacctgcg    3840
gggcatgctc cgggagaaga cgcacgacgc ggagctcgag ctgtggcggg tcatcgtaca    3900
cagggtgaag ctcaacgtgt cgcccggcac gtcgttccac tgcaacgagc ccggctggtt    3960
ccgcgtctgc tacgccaaca tggacgacga caccatggag gtcgcgctcg accggatccg    4020
ccgcttcgtg cgccagcacc agcacagcaa ggccaaggcc gagcgctggg cggccacgcg    4080 gcccttcgc ctcagcttgc cgcgccgggg agcaaccacc gcttcgcatc tcgccatctc    4140
cagccccttg gcgttgctgt cgccgcagtc cccgatggtc cacgccagct aggtagtcac    4200
cgagcgttcg gtaagactgg ctgtaggttg tgccctcaca tgactgcaaa caagtggaca    4260 aaaaaaaga caagactaat aaagggcgta cgtagctagc ttgacattac acagagtgac    4320
agagacgttg cacaggcgtc agcaggcgtc ggcggtaagc agctagtcaa gtaggacgca    4380
tttgtcctcg attttttcgt gttttttttt tgacgaaggg gcgaagcccc ctatttcatt    4440
aagaaatagg aaagtatgaa acaaccgcac ccacgcggta ggacctccaa aaagaacagc    4500
cacggccaga aagtaatcta gactctaaac actatcgcta gatcagtgaa gagactatga    4560
taacagggaa agttttggcc tacgaagagc tacataagac tttcttatat acaaccaacc    4620
aagacaggca gaagccacaa aagacctgaa cagaatggcc aacaaaagac agacaactat    4680
```

```
cccaacaagg tttcacagct tcagcatctt tgtcatccag aaatccgcct gtcaagagga    4740
caccacccca aggccctccc gaaagcttca cttgccgtct ttcggattaa cctgcttcct    4800
agcaccacca ttctttgctc cttcttttc tgacgaatcg cccaagaatc caaccagaag     4860
cagcaaagaa aaatgatgtt agatgggtca agtaaatgac tattcccaaa acaccaatca    4920
ttcctagtgc gccaaatagc ccagaataaa gcaccacaac caaataacac caactgagcc    4980
atcgtgtctt ttggtttaca aaaccaattg tcatacaaat ctttgatatt ttttggaata    5040
gatctcaaat tcagggccac ttgaataact ctccacatgt attgagcaat ggggcaatag    5100
aaaaa                                                                5105

<210> SEQ ID NO 4
<211> LENGTH: 1455
<212> TYPE: DNA
<213> ORGANISM: Zea mays

<400> SEQUENCE: 4
atggccggtg gtagcagtgc cgagcagctc ctatccagga tcgcctccgg cgatggccac      60
ggcgagaact cgtcctactt cgacgggtgg aaggcctacg acatggaccc tttcgacctg     120
cgccacaacc gcgacggcgt catccagatg ggcctcgccg agaaccaact gtccctggac     180
ctgatcgagc aatggagcat ggagcacccg gaggcgtcca tctgcacggc gcagggagcg     240
tcgcagttca ggaggatagc caacttccag gactaccacg gcctgccgga gttcagagag     300
gcgatggcca agttcatggg ccaggtgagg gccgggaagg tgacgttcga ccccgaccgc     360
gtcgtcatgt gcggaggcgc caccggcgcg caggacactc tcgccttctg cctcgctgac     420
ccgggcgacg cctacctcgt gccgacgcca tactacccag cgttcgaccg tgactgttgc     480
tggaggtcag gcgtgaagct gctgcccatc gaatgccaca gctcaaacaa cttcaccctc     540
acacgggagg cgctcgtgtc ggcctacgac ggcgcgcgga ggcagggcgt ccgcgtcaag     600
ggcgtcctca tcaccaaccc ctccaacccg ctgggcacca ccatggaccg cgccacgctg     660
gcgatgctcg ccaggttcgc cacggagcac cgtgtccacc tcatctgcga cgagatctac     720
gcgggctccg tcttcgccaa gccggacttc gtgagcatcg ccgaggtcat cgagcgcgac     780
gtcccgggct gcaacaggga cctcatccac atcgcgtaca gcctctccaa ggacttcggc     840
ctcccgggct ccgcgtcgg catcgtctac tcgtacaacg acgacgtcgt ggcctgcgcg      900
cgcaagatgt ccagcttcgg cctcgtctcc tcgcagacgc agcacttcct ggcgaagatg     960 ctgtcgacg cggagttcat ggcccgcttc ctcgcggaga gcgcgcggcg gctggcggcg     1020
cgccacgacc gcttcgtcgc gggactccgc gaggtcggca tcgcgtgcct gcccggcaac    1080
gcggggctct ctcgtggat ggacctgcgg ggcatgctcc gggacaagac gcacgacgcg     1140
gagctggagc tgtggcgggt catcgtacac aaggtgaagc tcaacgtgtc gcccggcacg    1200
tcgttccact gcaacgagcc cggctggttc cgcgtctgcc acgctaacat ggacgacgag    1260
accatggagg tcgcgctcga caggatccgc cgcttcgtgc gccagcacca gcacaaggcc    1320
aaggccgagc gctgggcggc cacgcggccc atgcgcctca gcttccgcg ccggggaggc    1380 gccaccgctt cgcacctccc catctccagc cccatggcgt tgctgtcgcc gcagtccccg    1440
atggttcacg ccagc                                                     1455

<210> SEQ ID NO 5
<211> LENGTH: 1446
<212> TYPE: DNA
```

<213> ORGANISM: Zea mays

<400> SEQUENCE: 5

```
atgatcgccg acgagaagcc gcagccgcag ctgctgtcca agaaggccgc ctgcaacagc      60
cacggccagg actcgtccta cttcctgggg tgggaggagt atgagaaaaa cccatacgac     120
cccgtcgcca accccggcgg catcatccag atgggcctcg ccgagaacca gctgtccttc     180
gacctgctgg aggcgtggct ggaggccaac ccggacgcgc tcggcctccg ccggggaggc     240
gcctctgtat tccgcgagct cgcgctcttc caggactacc acggcatgcc ggccttcaag     300
aatgcattgg cgaggttcat gtcggagcaa cgtgggtacc gggtgacctt cgaccccagc     360
aacatcgtgc tcaccgccgg agccacctcg gccaacgagg ccctcatgtt ctgcctcgcc     420
gaccacggag acgcctttct catccccacg ccatactacc agggttcga ccgtgacctc      480
aagtggcgca ccggcgcgga gatcgtcccc gtgcactgca cgagcggcaa cggcttccgg     540
ctgacgcgcg ccgcgctgga cgacgcgtac cggcgcgcgc agaagctgcg gctgcgcgtc     600
aagggcgtgc tcatcaccaa cccttccaac ccgctgggca ccacgtcgcc gcgcgccgac     660
ctggagatgc tggtggactt cgtggccgcc aagggcatcc acctggtgag cgacgagata     720
tactcgggca cggtcttcgc ggacccgggc ttcgtgagcg tcctcgaggt ggtggccgcg     780
cgcgccgcca cggacgacgg cgtcgtcggc gttgggccgc tgtcggaccg cgtgcacgtg     840
gtgtacagcc tgtccaagga cctgggcctc ccggggttcc gcgtgggcgc catctactcg     900
tccaacgccg gcgtggtctc cgcggccacc aagatgtcga gcttcggcct ggtgtcgtcc     960
cagacgcagc acctcctggc gtcgctcctg ggcgacaggg acttcacgcg gaggtacatc    1020
gcggagaaca cgcggcggat cagggagcgg cgcgagcagc tggcggaggg cctggcggcc    1080
gtgggcatcg agtgcctgga gagcaacgcg gggctcttct gctgggtcaa catgcggcgc    1140
ctgatgcgga gccggtcgtt cgagggcgag atggagctgt ggaagaaggt ggtcttcgag    1200
gtggggctca acatctcccc gggctcctcc tgccactgcc gggagcccgg ctggttccgc    1260
gtctgcttcg ccaacatgtc cgccaagacg ctcgacgtcg cgctccagcg cctgggcgcc    1320
ttcgcggagg ccgccaccgc ggggcgccgc gtgcttgccc cgccaggag catcagcctc    1380
ccggtccgct tcagctgggc taaccgcctc accccgggct ccgccgccga ccggaaggcc    1440
gagcgg                                                                1446
```

<210> SEQ ID NO 6
<211> LENGTH: 1458
<212> TYPE: DNA
<213> ORGANISM: Zea mays

<400> SEQUENCE: 6

```
atggccggta gcagcgcgga gcagctcctc tccaggatcg ccgccggcga cggccacggc      60
gagaactcgt cctacttcga cgggtggaag gcctacgaca tgaacccttt cgacctgcgc     120
cacaaccgcg acgcgtcat ccagatgggc ctcgccgaga accaactgtc gttggacctg      180
atcgagcaat ggagcgtgga ccaccccgga gcgtccatct gcacggcgca gggcgcgccg     240
cagttccgga ggatagccaa cttccaggac taccacggcc tgccggagtt cagagaggcg     300
atggccaagt tcatggggca ggtgaggggc ggcaaggtga cgttcgaccc cgaccgcgtc     360
gtcatgtgcg gaggagccac cggcgcgcag gacactctcg ccttctgcct cgctgacccg     420
ggcgacgcct acctcgtgcc gacgccttat taccagcgt cgaccgcga ctgttgctgg       480
aggtcaggag tgaagctgct gcccatcgaa tgccacagct cgaacaactt caccctcacc     540
```

```
agggaggcgc tcgtgtcggc ctacgacggc gcgcggaggc agggcgtccg cgtcagggc      600
atcctcatca ccaaccctc caacccgctg ggcaccacca tggaccgcgg cacgctggcg      660
atgctcgccg cgttcgccac agagcgccgc gtccacctca tctgcgacga gatctacgcg      720
ggctccgtct tcgccaagcc gggcttcgtg agcatcgccg aggtcatcga gcgcggcgac      780
gccccgggct gcaacaggga cctcgtccac atcgcgtaca gcctctccaa ggacttcggc      840
ctcccgggct tccgcgtcgg catcgtctac tcctacaacg acgacgtggt ggcctgcgcg      900
cgcaagatgt ccagcttcgg cctcgtctcg tcgcagacgc agcacttcct ggcgatgatg      960
ctcgccgacg cggagttcat ggcacgcttc tcgcgcgaga gcgcgcggcg gctggcggcg     1020
cgccacgacc gcttcgtcgc gggcctccgc gaggtcggca tcgcgtgcct gccgggcaac     1080
gcgggcctct tctcgtggat ggacctgcgg ggcatgctcc gggagaagac gcacgacgcg     1140
gagctcgagc tgtggcgggt catcgtacac agggtgaagc tcaacgtgtc gcccggcacg     1200
tcgttccact gcaacgagcc cggctggttc cgcgtctgct acgccaacat ggacgacgac     1260
accatggagg tcgcgctcga ccggatccgc cgcttcgtgc gccagcacca gcacagcaag     1320
gccaaggccg agcgctgggc ggccacgcgg ccccttcgcc tcagcttgcc gcgccggga      1380
gcaaccaccg cttcgcatct cgccatctcc agccccttgg cgttgctgtc gccgcagtcc     1440
ccgatggtcc acgccagc                                                    1458
```

<210> SEQ ID NO 7
<211> LENGTH: 485
<212> TYPE: PRT
<213> ORGANISM: Zea mays

<400> SEQUENCE: 7

```
Met Ala Gly Gly Ser Ser Ala Glu Gln Leu Leu Ser Arg Ile Ala Ser
1               5                   10                  15

Gly Asp Gly His Gly Glu Asn Ser Ser Tyr Phe Asp Gly Trp Lys Ala
            20                  25                  30

Tyr Asp Met Asp Pro Phe Asp Leu Arg His Asn Arg Asp Gly Val Ile
        35                  40                  45

Gln Met Gly Leu Ala Glu Asn Gln Leu Ser Leu Asp Leu Ile Glu Gln
    50                  55                  60

Trp Ser Met Glu His Pro Glu Ala Ser Ile Cys Thr Ala Gln Gly Ala
65                  70                  75                  80

Ser Gln Phe Arg Arg Ile Ala Asn Phe Gln Asp Tyr His Gly Leu Pro
                85                  90                  95

Glu Phe Arg Glu Ala Met Ala Lys Phe Met Gly Gln Val Arg Ala Gly
            100                 105                 110

Lys Val Thr Phe Asp Pro Asp Arg Val Val Met Cys Gly Gly Ala Thr
        115                 120                 125

Gly Ala Gln Asp Thr Leu Ala Phe Cys Leu Ala Asp Pro Gly Asp Ala
    130                 135                 140

Tyr Leu Val Pro Thr Pro Tyr Tyr Pro Ala Phe Asp Arg Asp Cys Cys
145                 150                 155                 160

Trp Arg Ser Gly Val Lys Leu Leu Pro Ile Glu Cys His Ser Ser Asn
                165                 170                 175

Asn Phe Thr Leu Thr Arg Glu Ala Leu Val Ser Ala Tyr Asp Gly Ala
            180                 185                 190

Arg Arg Gln Gly Val Arg Val Lys Gly Val Leu Ile Thr Asn Pro Ser
        195                 200                 205
```

Asn Pro Leu Gly Thr Thr Met Asp Arg Ala Thr Leu Ala Met Leu Ala
    210                 215                 220

Arg Phe Ala Thr Glu His Arg Val His Leu Ile Cys Asp Glu Ile Tyr
225                 230                 235                 240

Ala Gly Ser Val Phe Ala Lys Pro Asp Phe Val Ser Ile Ala Glu Val
            245                 250                 255

Ile Glu Arg Asp Val Pro Gly Cys Asn Arg Asp Leu Ile His Ile Ala
        260                 265                 270

Tyr Ser Leu Ser Lys Asp Phe Gly Leu Pro Gly Phe Arg Val Gly Ile
    275                 280                 285

Val Tyr Ser Tyr Asn Asp Val Val Ala Cys Ala Arg Lys Met Ser
290                 295                 300

Ser Phe Gly Leu Val Ser Ser Gln Thr Gln His Phe Leu Ala Lys Met
305                 310                 315                 320

Leu Ser Asp Ala Glu Phe Met Ala Arg Phe Leu Ala Glu Ser Ala Arg
            325                 330                 335

Arg Leu Ala Ala Arg His Asp Arg Phe Val Ala Gly Leu Arg Glu Val
        340                 345                 350

Gly Ile Ala Cys Leu Pro Gly Asn Ala Gly Leu Phe Ser Trp Met Asp
    355                 360                 365

Leu Arg Gly Met Leu Arg Asp Lys Thr His Asp Ala Glu Leu Glu Leu
370                 375                 380

Trp Arg Val Ile Val His Lys Val Lys Leu Asn Val Ser Pro Gly Thr
385                 390                 395                 400

Ser Phe His Cys Asn Glu Pro Gly Trp Phe Arg Val Cys His Ala Asn
            405                 410                 415

Met Asp Asp Glu Thr Met Glu Val Ala Leu Asp Arg Ile Arg Arg Phe
        420                 425                 430

Val Arg Gln His Gln His Lys Ala Lys Ala Glu Arg Trp Ala Ala Thr
    435                 440                 445

Arg Pro Met Arg Leu Ser Leu Pro Arg Arg Gly Gly Ala Thr Ala Ser
450                 455                 460

His Leu Pro Ile Ser Ser Pro Met Ala Leu Leu Ser Pro Gln Ser Pro
465                 470                 475                 480

Met Val His Ala Ser
            485

<210> SEQ ID NO 8
<211> LENGTH: 482
<212> TYPE: PRT
<213> ORGANISM: Zea mays

<400> SEQUENCE: 8

Met Ile Ala Asp Glu Lys Pro Gln Pro Gln Leu Leu Ser Lys Lys Ala
1               5                   10                  15

Ala Cys Asn Ser His Gly Gln Asp Ser Ser Tyr Phe Leu Gly Trp Glu
            20                  25                  30

Glu Tyr Glu Lys Asn Pro Tyr Asp Pro Val Ala Asn Pro Gly Gly Ile
        35                  40                  45

Ile Gln Met Gly Leu Ala Glu Asn Gln Leu Ser Phe Asp Leu Leu Glu
    50                  55                  60

Ala Trp Leu Glu Ala Asn Pro Asp Ala Leu Gly Leu Arg Arg Gly Gly
65                  70                  75                  80

Ala Ser Val Phe Arg Glu Leu Ala Leu Phe Gln Asp Tyr His Gly Met

```
                    85                  90                  95
Pro Ala Phe Lys Asn Ala Leu Ala Arg Phe Met Ser Glu Gln Arg Gly
            100                 105                 110

Tyr Arg Val Thr Phe Asp Pro Ser Asn Ile Val Leu Thr Ala Gly Ala
            115                 120                 125

Thr Ser Ala Asn Glu Ala Leu Met Phe Cys Leu Ala Asp His Gly Asp
        130                 135                 140

Ala Phe Leu Ile Pro Thr Pro Tyr Tyr Pro Gly Phe Asp Arg Asp Leu
145                 150                 155                 160

Lys Trp Arg Thr Gly Ala Glu Ile Val Pro Val His Cys Thr Ser Gly
                165                 170                 175

Asn Gly Phe Arg Leu Thr Arg Ala Ala Leu Asp Asp Ala Tyr Arg Arg
            180                 185                 190

Ala Gln Lys Leu Arg Leu Arg Val Lys Gly Val Leu Ile Thr Asn Pro
        195                 200                 205

Ser Asn Pro Leu Gly Thr Thr Ser Pro Arg Ala Asp Leu Glu Met Leu
    210                 215                 220

Val Asp Phe Val Ala Ala Lys Gly Ile His Leu Val Ser Asp Glu Ile
225                 230                 235                 240

Tyr Ser Gly Thr Val Phe Ala Asp Pro Gly Phe Val Ser Val Leu Glu
                245                 250                 255

Val Val Ala Ala Arg Ala Ala Thr Asp Asp Gly Val Val Gly Val Gly
            260                 265                 270

Pro Leu Ser Asp Arg Val His Val Val Tyr Ser Leu Ser Lys Asp Leu
        275                 280                 285

Gly Leu Pro Gly Phe Arg Val Gly Ala Ile Tyr Ser Ser Asn Ala Gly
    290                 295                 300

Val Val Ser Ala Ala Thr Lys Met Ser Ser Phe Gly Leu Val Ser Ser
305                 310                 315                 320

Gln Thr Gln His Leu Leu Ala Ser Leu Leu Gly Asp Arg Asp Phe Thr
                325                 330                 335

Arg Arg Tyr Ile Ala Glu Asn Thr Arg Arg Ile Arg Glu Arg Glu
            340                 345                 350

Gln Leu Ala Glu Gly Leu Ala Ala Val Gly Ile Glu Cys Leu Glu Ser
        355                 360                 365

Asn Ala Gly Leu Phe Cys Trp Val Asn Met Arg Arg Leu Met Arg Ser
    370                 375                 380

Arg Ser Phe Glu Gly Glu Met Glu Leu Trp Lys Lys Val Val Phe Glu
385                 390                 395                 400

Val Gly Leu Asn Ile Ser Pro Gly Ser Ser Cys His Cys Arg Glu Pro
                405                 410                 415

Gly Trp Phe Arg Val Cys Phe Ala Asn Met Ser Ala Lys Thr Leu Asp
            420                 425                 430

Val Ala Leu Gln Arg Leu Gly Ala Phe Ala Glu Ala Thr Ala Gly
        435                 440                 445

Arg Arg Val Leu Ala Pro Ala Arg Ser Ile Ser Leu Pro Val Arg Phe
    450                 455                 460

Ser Trp Ala Asn Arg Leu Thr Pro Gly Ser Ala Ala Asp Arg Lys Ala
465                 470                 475                 480

Glu Arg

<210> SEQ ID NO 9
<211> LENGTH: 486
```

<212> TYPE: PRT
<213> ORGANISM: Zea mays

<400> SEQUENCE: 9

```
Met Ala Gly Ser Ser Ala Glu Gln Leu Leu Ser Arg Ile Ala Ala Gly
1               5                   10                  15

Asp Gly His Gly Glu Asn Ser Ser Tyr Phe Asp Gly Trp Lys Ala Tyr
            20                  25                  30

Asp Met Asn Pro Phe Asp Leu Arg His Asn Arg Asp Gly Val Ile Gln
        35                  40                  45

Met Gly Leu Ala Glu Asn Gln Leu Ser Leu Asp Leu Ile Glu Gln Trp
    50                  55                  60

Ser Val Asp His Pro Glu Ala Ser Ile Cys Thr Ala Gln Gly Ala Pro
65                  70                  75                  80

Gln Phe Arg Arg Ile Ala Asn Phe Gln Asp Tyr His Gly Leu Pro Glu
                85                  90                  95

Phe Arg Glu Ala Met Ala Lys Phe Met Gly Gln Val Arg Gly Gly Lys
            100                 105                 110

Val Thr Phe Asp Pro Asp Arg Val Val Met Cys Gly Gly Ala Thr Gly
        115                 120                 125

Ala Gln Asp Thr Leu Ala Phe Cys Leu Ala Asp Pro Gly Asp Ala Tyr
    130                 135                 140

Leu Val Pro Thr Pro Tyr Tyr Pro Ala Phe Asp Arg Asp Cys Cys Trp
145                 150                 155                 160

Arg Ser Gly Val Lys Leu Leu Pro Ile Glu Cys His Ser Ser Asn Asn
                165                 170                 175

Phe Thr Leu Thr Arg Glu Ala Leu Val Ser Ala Tyr Asp Gly Ala Arg
            180                 185                 190

Arg Gln Gly Val Arg Val Arg Gly Ile Leu Ile Thr Asn Pro Ser Asn
        195                 200                 205

Pro Leu Gly Thr Thr Met Asp Arg Gly Thr Leu Ala Met Leu Ala Ala
    210                 215                 220

Phe Ala Thr Glu Arg Arg Val His Leu Ile Cys Asp Glu Ile Tyr Ala
225                 230                 235                 240

Gly Ser Val Phe Ala Lys Pro Gly Phe Val Ser Ile Ala Glu Val Ile
                245                 250                 255

Glu Arg Gly Asp Ala Pro Gly Cys Asn Arg Asp Leu Val His Ile Ala
            260                 265                 270

Tyr Ser Leu Ser Lys Asp Phe Gly Leu Pro Gly Phe Arg Val Gly Ile
        275                 280                 285

Val Tyr Ser Tyr Asn Asp Asp Val Val Ala Cys Ala Arg Lys Met Ser
    290                 295                 300

Ser Phe Gly Leu Val Ser Ser Gln Thr Gln His Phe Leu Ala Met Met
305                 310                 315                 320

Leu Ala Asp Ala Glu Phe Met Ala Arg Phe Leu Ala Glu Ser Ala Arg
                325                 330                 335

Arg Leu Ala Ala Arg His Asp Arg Phe Val Ala Gly Leu Arg Glu Val
            340                 345                 350

Gly Ile Ala Cys Leu Pro Gly Asn Ala Gly Leu Phe Ser Trp Met Asp
        355                 360                 365

Leu Arg Gly Met Leu Arg Glu Lys Thr His Asp Ala Glu Leu Glu Leu
    370                 375                 380

Trp Arg Val Ile Val His Arg Val Lys Leu Asn Val Ser Pro Gly Thr
385                 390                 395                 400
```

```
Ser Phe His Cys Asn Glu Pro Gly Trp Phe Arg Val Cys Tyr Ala Asn
            405                 410                 415

Met Asp Asp Asp Thr Met Glu Val Ala Leu Asp Arg Ile Arg Arg Phe
        420                 425                 430

Val Arg Gln His Gln His Ser Lys Ala Lys Ala Glu Arg Trp Ala Ala
    435                 440                 445

Thr Arg Pro Leu Arg Leu Ser Leu Pro Arg Arg Gly Ala Thr Thr Ala
    450                 455                 460

Ser His Leu Ala Ile Ser Ser Pro Leu Ala Leu Leu Ser Pro Gln Ser
465                 470                 475                 480

Pro Met Val His Ala Ser
            485

<210> SEQ ID NO 10
<211> LENGTH: 2120
<212> TYPE: DNA
<213> ORGANISM: Zea mays

<400> SEQUENCE: 10
```

| | | |
|---|---|---|
| atgaccatga ttacgccaag ctctaatacg actcactata gggaaagctg gtacgcctgc | 60 |
| aggtaccggt ccggaattcc cgggtcgacc cacgcgtccg cagcaagctc atccccttca | 120 |
| aaaccctccg gcagcccagc cagctagtgg tgatctctca gcagcgcgcc tgaacgtgtg | 180 |
| ctccctgcta aactctgcgc tcggtaggc aaggaaaatt aaaccggtcg tcgtcagatt | 240 |
| aaatggccgg tagcagcgcg gagcagctcc tctccaggat cgccgccggc gatggccacg | 300 |
| gcgagaactc gtcctacttc gacgggtgga aggcctacga cacgaaccct ttcgacctgc | 360 |
| gccacaaccg cgacggcgtc atccagatgg gactcgccga gaaccaactg tcgctggacc | 420 |
| tgatcgagca atggagcgtg gaccacccgg aggcgtccat ctgcacggcg cagggcgcgc | 480 |
| cgcagttccg gaggatagcc aacttccagg actaccacgg cctgccggag ttcagagagg | 540 |
| cgatggccaa gttcatgggg caggtgaggg gcggcaaggt gacgttcgac cccgaccgcg | 600 |
| tcgtcatgtg cgggggagcc accggcgcgc aggacactct cgccttctgc ctcgctgacc | 660 |
| cgggcgacgc ctacctcgtg ccgacgcctt attcccagc tttcgaccgc gactgttgct | 720 |
| ggaggtcagg agtgaagctg ctgcccatcg aatgccacag ctcgaacaac ttcaccctca | 780 |
| ccagggaggc gctcgtgtcg gcctacgacg gcgcgcggag gcagggcgtc cgcgtcaggg | 840 |
| gcatcctcat caccaacccc tccaacccgc tgggcaccac aatggaccgc ggcacgctgg | 900 |
| cgatgctcgc cgcgttcgcc acagagcgcc gcgtccacct catctgcgac gagatctacg | 960 |
| cgggctccgt cttcgccaag ccgggcttcg tgagcatcgc cgaggtcatc gagcgcggcg | 1020 |
| acgccccggg ctgcaacagg gacctcgtcc acatcgcgta cagcctctcc aaggacttcg | 1080 |
| gcctcccggg cttccgcgtc ggcatcgtct actcctacaa cgacgacgtg gtggcctgcg | 1140 |
| cgcgcaagat gtccagcttc ggcctcgtct cgtcgcagac gcagcacttc ctggcgatga | 1200 |
| tgctcgccga cgcggagttc atggcacgct tcctcgcgga gagcgcgcgg cggctggcgg | 1260 |
| cgcgccacga ccgcttcgtc gcgggcctcc gcgaggtcgg catcgcgtgc ctgccgggca | 1320 |
| acgcgggcct cttctcgtgg atggacctgc ggggcatgct ccgggagagg acgcacgacg | 1380 |
| cggagctgga gctgtggcgg gtcatcgtac acagggtgaa gctcaacgtg tcgcccggca | 1440 |
| cgtcgttcca ctgcaacgag cccggctggt tccgcgtctg ctacgccaac atggacgacg | 1500 |
| acaccatgga ggtcgcgctc gaccggatcc gccgcttcgt gcgccagcac cagcacagca | 1560 |

-continued

```
aggccaaggc cgagcgctgg gcggccacgc ggcccctccg cctcagcttg ccgcgccggg    1620
gagcaaccac cgcttcgcac ctcgccatcc ccagccccct tggcgttgct gtcgccgcagt   1680 ccccgatggt ccacgccagc tagctagtca ccgagcgttc ggtaagactg gctgtagggt    1740
gtgccctcac ataactgcaa acaagtggac aaaaaatatt agacaagact aataaagggc    1800
attagtagct agcttgacat tacacagaga cgttgcacag gcgtcagcag cgtcggcgg     1860 taagcagcta gtcaagcagg acgcatttgt cctcgatttt ttcgtgtata tatgttcttt    1920
tttctgtttt gccaaatcgc atgtatggtt tggtttaacg ttagtacacg gtagaataac    1980
gatcgggtat ggtaatttag acctcccgat caattgttgt tgaaaacctg tcacgtaact    2040
tcaggacaca gaaggcgtag ctcaagggtg aataaaagac cagtttacat atcaaaaaaa    2100
aaaaaaaaaa aaaaaaaaa                                                 2120
```

<210> SEQ ID NO 11
<211> LENGTH: 486
<212> TYPE: PRT
<213> ORGANISM: Zea mays

<400> SEQUENCE: 11

```
Met Ala Gly Ser Ser Ala Glu Gln Leu Leu Ser Arg Ile Ala Ala Gly
1               5                   10                  15

Asp Gly His Gly Glu Asn Ser Ser Tyr Phe Asp Gly Trp Lys Ala Tyr
                20                  25                  30

Asp Thr Asn Pro Phe Asp Leu Arg His Asn Arg Asp Gly Val Ile Gln
            35                  40                  45

Met Gly Leu Ala Glu Asn Gln Leu Ser Leu Asp Leu Ile Glu Gln Trp
        50                  55                  60

Ser Val Asp His Pro Glu Ala Ser Ile Cys Thr Ala Gln Gly Ala Pro
65                  70                  75                  80

Gln Phe Arg Arg Ile Ala Asn Phe Gln Asp Tyr His Gly Leu Pro Glu
                85                  90                  95

Phe Arg Glu Ala Met Ala Lys Phe Met Gly Gln Val Arg Gly Gly Lys
            100                 105                 110

Val Thr Phe Asp Pro Asp Arg Val Val Met Cys Gly Gly Ala Thr Gly
        115                 120                 125

Ala Gln Asp Thr Leu Ala Phe Cys Leu Ala Asp Pro Gly Asp Ala Tyr
    130                 135                 140

Leu Val Pro Thr Pro Tyr Tyr Pro Ala Phe Asp Arg Asp Cys Cys Trp
145                 150                 155                 160

Arg Ser Gly Val Lys Leu Leu Pro Ile Glu Cys His Ser Ser Asn Asn
                165                 170                 175

Phe Thr Leu Thr Arg Glu Ala Leu Val Ser Ala Tyr Asp Gly Ala Arg
            180                 185                 190

Arg Gln Gly Val Arg Val Arg Gly Ile Leu Ile Thr Asn Pro Ser Asn
        195                 200                 205

Pro Leu Gly Thr Thr Met Asp Arg Gly Thr Leu Ala Met Leu Ala Ala
    210                 215                 220

Phe Ala Thr Glu Arg Arg Val His Leu Ile Cys Asp Glu Ile Tyr Ala
225                 230                 235                 240

Gly Ser Val Phe Ala Lys Pro Gly Phe Val Ser Ile Ala Glu Val Ile
                245                 250                 255

Glu Arg Gly Asp Ala Pro Gly Cys Asn Arg Asp Leu Val His Ile Ala
            260                 265                 270
```

```
Tyr Ser Leu Ser Lys Asp Phe Gly Leu Pro Gly Phe Arg Val Gly Ile
            275                 280                 285

Val Tyr Ser Tyr Asn Asp Val Val Ala Cys Ala Arg Lys Met Ser
        290                 295                 300

Ser Phe Gly Leu Val Ser Ser Gln Thr Gln His Phe Leu Ala Met Met
305                 310                 315                 320

Leu Ala Asp Ala Glu Phe Met Ala Arg Phe Leu Ala Glu Ser Ala Arg
                325                 330                 335

Arg Leu Ala Ala Arg His Asp Arg Phe Val Ala Gly Leu Arg Glu Val
                340                 345                 350

Gly Ile Ala Cys Leu Pro Gly Asn Ala Gly Leu Phe Ser Trp Met Asp
            355                 360                 365

Leu Arg Gly Met Leu Arg Glu Arg Thr His Asp Ala Glu Leu Glu Leu
        370                 375                 380

Trp Arg Val Ile Val His Arg Val Lys Leu Asn Val Ser Pro Gly Thr
385                 390                 395                 400

Ser Phe His Cys Asn Glu Pro Gly Trp Phe Arg Val Cys Tyr Ala Asn
                405                 410                 415

Met Asp Asp Asp Thr Met Glu Val Ala Leu Asp Arg Ile Arg Arg Phe
                420                 425                 430

Val Arg Gln His Gln His Ser Lys Ala Lys Ala Glu Arg Trp Ala Ala
            435                 440                 445

Thr Arg Pro Leu Arg Leu Ser Leu Pro Arg Arg Gly Ala Thr Thr Ala
        450                 455                 460

Ser His Leu Ala Ile Pro Ser Pro Leu Ala Leu Leu Ser Pro Gln Ser
465                 470                 475                 480

Pro Met Val His Ala Ser
                485

<210> SEQ ID NO 12
<211> LENGTH: 22
<212> TYPE: DNA
<213> ORGANISM: Artificial
<220> FEATURE:
<223> OTHER INFORMATION: oligonucleotide primer

<400> SEQUENCE: 12
ccagatgggc ctcgccgaga ac                                              22

<210> SEQ ID NO 13
<211> LENGTH: 24
<212> TYPE: DNA
<213> ORGANISM: Artificial
<220> FEATURE:
<223> OTHER INFORMATION: oligonucleotide primer

<400> SEQUENCE: 13
gttggcgtag cagacgcgga acca                                            24

<210> SEQ ID NO 14
<211> LENGTH: 26
<212> TYPE: DNA
<213> ORGANISM: Artificial
<220> FEATURE:
<223> OTHER INFORMATION: oligonucleotide primer

<400> SEQUENCE: 14
gacaaactgc gcaactcgtg aaaggt                                          26
```

-continued

```
<210> SEQ ID NO 15
<211> LENGTH: 26
<212> TYPE: DNA
<213> ORGANISM: Artificial
<220> FEATURE:
<223> OTHER INFORMATION: oligonucleotide primer

<400> SEQUENCE: 15
ctcgtccgag aataacgagt ggatct                                          26

<210> SEQ ID NO 16
<211> LENGTH: 29
<212> TYPE: DNA
<213> ORGANISM: Artificial
<220> FEATURE:
<223> OTHER INFORMATION: oligonucleotide primer

<400> SEQUENCE: 16
cagttatgtg agggcacacc ctacagcca                                       29

<210> SEQ ID NO 17
<211> LENGTH: 28
<212> TYPE: DNA
<213> ORGANISM: Artificial
<220> FEATURE:
<223> OTHER INFORMATION: oligonucleotide primer

<400> SEQUENCE: 17
catcgaatgc cacagctcga acaacttc                                        28

<210> SEQ ID NO 18
<211> LENGTH: 27
<212> TYPE: DNA
<213> ORGANISM: Artificial
<220> FEATURE:
<223> OTHER INFORMATION: oligonucleotide primer
<220> FEATURE:
<221> NAME/KEY: misc_feature
<222> LOCATION: (13)..(13)
<223> OTHER INFORMATION: n is A or T
<220> FEATURE:
<221> NAME/KEY: misc_feature
<222> LOCATION: (20)..(20)
<223> OTHER INFORMATION: n is C or T

<400> SEQUENCE: 18
aagccaacgc cancgcctcn atttcgt                                         27

<210> SEQ ID NO 19
<211> LENGTH: 23
<212> TYPE: DNA
<213> ORGANISM: Artificial
<220> FEATURE:
<223> OTHER INFORMATION: oligonucleotide primer

<400> SEQUENCE: 19
atcgcgtaca gcctctccaa gga                                             23

<210> SEQ ID NO 20
<211> LENGTH: 28
<212> TYPE: DNA
<213> ORGANISM: Artificial
<220> FEATURE:
<223> OTHER INFORMATION: oligonucleotide primer

<400> SEQUENCE: 20
gatagtcttt tgtcaaccat cccataga                                        28
```

<210> SEQ ID NO 21
<211> LENGTH: 23
<212> TYPE: DNA
<213> ORGANISM: Artificial
<220> FEATURE:
<223> OTHER INFORMATION: oligonucleotide primer

<400> SEQUENCE: 21
atcgcgtaca gcctctccaa gga                                           23

<210> SEQ ID NO 22
<211> LENGTH: 27
<212> TYPE: DNA
<213> ORGANISM: Artificial
<220> FEATURE:
<223> OTHER INFORMATION: oligonucleotide primer

<400> SEQUENCE: 22
caacgtctct gtcactctgt gtaatgt                                       27

<210> SEQ ID NO 23
<211> LENGTH: 28
<212> TYPE: DNA
<213> ORGANISM: Artificial
<220> FEATURE:
<223> OTHER INFORMATION: oligonucleotide primer

<400> SEQUENCE: 23
agctgtggaa gaaggtggtc ttcgaggt                                      28

<210> SEQ ID NO 24
<211> LENGTH: 24
<212> TYPE: DNA
<213> ORGANISM: Artificial
<220> FEATURE:
<223> OTHER INFORMATION: oligonucleotide primer

<400> SEQUENCE: 24
agtacgtgac cgtggtttct atga                                          24

<210> SEQ ID NO 25
<211> LENGTH: 485
<212> TYPE: PRT
<213> ORGANISM: Zea mays

<400> SEQUENCE: 25

Met Ala Gly Gly Ser Ser Ala Glu Gln Leu Leu Ser Arg Ile Ala Ser
1               5                   10                  15

Gly Asp Gly His Gly Glu Asn Ser Ser Tyr Phe Asp Gly Trp Lys Ala
            20                  25                  30

Tyr Asp Met Asp Pro Phe Asp Leu Arg His Asn Arg Asp Gly Val Ile
        35                  40                  45

Gln Met Gly Leu Ala Glu Asn Gln Leu Ser Leu Asp Leu Ile Glu Gln
    50                  55                  60

Trp Ser Met Glu His Pro Glu Ala Ser Ile Cys Thr Ala Gln Gly Ala
65                  70                  75                  80

Ser Gln Phe Arg Arg Ile Ala Asn Phe Gln Asp Tyr His Gly Leu Pro
                85                  90                  95

Glu Phe Arg Glu Ala Met Ala Lys Phe Met Gly Gln Val Arg Ala Gly
            100                 105                 110

Lys Val Thr Phe Asp Pro Asp Arg Val Val Met Cys Gly Gly Ala Thr
        115                 120                 125

```
Gly Ala Gln Asp Thr Leu Ala Phe Cys Leu Ala Asp Pro Gly Asp Ala
        130                 135                 140
Tyr Leu Val Pro Thr Pro Tyr Pro Ala Phe Asp Arg Asp Cys Cys
145                 150                 155                 160
Trp Arg Ser Gly Val Lys Leu Leu Pro Ile Glu Cys His Ser Ser Asn
                    165                 170                 175
Asn Phe Thr Leu Thr Arg Glu Ala Leu Val Ser Ala Tyr Asp Gly Ala
                180                 185                 190
Arg Arg Gln Gly Val Arg Val Lys Gly Val Leu Ile Thr Asn Pro Ser
            195                 200                 205
Asn Pro Leu Gly Thr Thr Met Asp Arg Ala Thr Leu Ala Met Leu Ala
210                 215                 220
Arg Phe Ala Thr Glu His Arg Val His Leu Ile Cys Asp Glu Ile Tyr
225                 230                 235                 240
Ala Gly Ser Val Phe Ala Lys Pro Asp Phe Val Ser Ile Ala Glu Val
                    245                 250                 255
Ile Glu Arg Asp Val Pro Gly Cys Asn Arg Asp Leu Ile His Ile Ala
                260                 265                 270
Tyr Ser Leu Ser Lys Asp Phe Gly Leu Pro Gly Phe Arg Val Gly Ile
            275                 280                 285
Val Tyr Ser Tyr Asn Asp Asp Val Val Ala Cys Ala Arg Lys Met Ser
290                 295                 300
Ser Phe Gly Leu Val Ser Ser Gln Thr Gln His Phe Leu Ala Lys Met
305                 310                 315                 320
Leu Ser Asp Ala Glu Phe Met Ala Arg Phe Leu Ala Glu Ser Ala Arg
                    325                 330                 335
Arg Leu Ala Ala Arg His Asp Arg Phe Val Ala Gly Leu Arg Glu Val
                340                 345                 350
Gly Ile Ala Cys Leu Pro Gly Asn Ala Gly Leu Phe Ser Trp Met Asp
            355                 360                 365
Leu Arg Gly Met Leu Arg Asp Lys Thr His Asp Ala Glu Leu Glu Leu
370                 375                 380
Trp Arg Val Ile Val His Lys Val Lys Leu Asn Val Ser Pro Gly Thr
385                 390                 395                 400
Ser Phe His Cys Asn Glu Pro Gly Trp Phe Arg Val Cys His Ala Asn
                    405                 410                 415
Met Asp Asp Glu Thr Met Glu Val Ala Leu Asp Arg Ile Arg Arg Phe
                420                 425                 430
Val Arg Gln His Gln His Lys Ala Lys Ala Glu Arg Trp Ala Ala Thr
            435                 440                 445
Arg Pro Met Arg Leu Ser Leu Pro Arg Arg Gly Gly Ala Thr Ala Ser
450                 455                 460
His Leu Pro Ile Ser Ser Pro Met Ala Leu Leu Ser Pro Gln Ser Pro
465                 470                 475                 480
Met Val His Ala Ser
                485

<210> SEQ ID NO 26
<211> LENGTH: 486
<212> TYPE: PRT
<213> ORGANISM: Zea mays

<400> SEQUENCE: 26

Met Ala Gly Ser Ser Ala Glu Gln Leu Leu Ser Arg Ile Ala Ala Gly
```

-continued

```
1               5                   10                  15
Asp Gly His Gly Glu Asn Ser Ser Tyr Phe Asp Gly Trp Lys Ala Tyr
                20                  25                  30
Asp Met Asn Pro Phe Asp Leu Arg His Asn Arg Asp Gly Val Ile Gln
                35                  40                  45
Met Gly Leu Ala Glu Asn Gln Leu Ser Leu Asp Leu Ile Glu Gln Trp
            50                  55                  60
Ser Val Asp His Pro Glu Ala Ser Ile Cys Thr Ala Gln Gly Ala Pro
65                  70                  75                  80
Gln Phe Arg Arg Ile Ala Asn Phe Gln Asp Tyr His Gly Leu Pro Glu
                85                  90                  95
Phe Arg Glu Ala Met Ala Lys Phe Met Gly Gln Val Arg Gly Gly Lys
                100                 105                 110
Val Thr Phe Asp Pro Asp Arg Val Val Met Cys Gly Gly Ala Thr Gly
                115                 120                 125
Ala Gln Asp Thr Leu Ala Phe Cys Leu Ala Asp Pro Gly Asp Ala Tyr
            130                 135                 140
Leu Val Pro Thr Pro Tyr Tyr Pro Ala Phe Asp Arg Asp Cys Cys Trp
145                 150                 155                 160
Arg Ser Gly Val Lys Leu Leu Pro Ile Glu Cys His Ser Ser Asn Asn
                165                 170                 175
Phe Thr Leu Thr Arg Glu Ala Leu Val Ser Ala Tyr Asp Gly Ala Arg
                180                 185                 190
Arg Gln Gly Val Arg Val Arg Gly Ile Leu Ile Thr Asn Pro Ser Asn
                195                 200                 205
Pro Leu Gly Thr Thr Met Asp Arg Gly Thr Leu Ala Met Leu Ala Ala
            210                 215                 220
Phe Ala Thr Glu Arg Arg Val His Leu Ile Cys Asp Glu Ile Tyr Ala
225                 230                 235                 240
Gly Ser Val Phe Ala Lys Pro Gly Phe Val Ser Ile Ala Glu Val Ile
                245                 250                 255
Glu Arg Gly Asp Ala Pro Gly Cys Asn Arg Asp Leu Val His Ile Ala
                260                 265                 270
Tyr Ser Leu Ser Lys Asp Phe Gly Leu Pro Gly Phe Arg Val Gly Ile
            275                 280                 285
Val Tyr Ser Tyr Asn Asp Asp Val Val Ala Cys Ala Arg Lys Met Ser
            290                 295                 300
Ser Phe Gly Leu Val Ser Ser Gln Thr Gln His Phe Leu Ala Met Met
305                 310                 315                 320
Leu Ala Asp Ala Glu Phe Met Ala Arg Phe Leu Ala Glu Ser Ala Arg
                325                 330                 335
Arg Leu Ala Ala Arg His Asp Arg Phe Val Ala Gly Leu Arg Glu Val
                340                 345                 350
Gly Ile Ala Cys Leu Pro Gly Asn Ala Gly Leu Phe Ser Trp Met Asp
                355                 360                 365
Leu Arg Gly Met Leu Arg Glu Lys Thr His Asp Ala Glu Leu Glu Leu
            370                 375                 380
Trp Arg Val Ile Val His Arg Val Lys Leu Asn Val Ser Pro Gly Thr
385                 390                 395                 400
Ser Phe His Cys Asn Glu Pro Gly Trp Phe Arg Val Cys Tyr Ala Asn
                405                 410                 415
Met Asp Asp Thr Met Glu Val Ala Leu Asp Arg Ile Arg Arg Phe
                420                 425                 430
```

```
Val Arg Gln His Gln His Ser Lys Ala Lys Ala Glu Arg Trp Ala Ala
        435                 440                 445

Thr Arg Pro Leu Arg Leu Ser Leu Pro Arg Arg Gly Ala Thr Thr Ala
450                 455                 460

Ser His Leu Ala Ile Ser Ser Pro Leu Ala Leu Leu Ser Pro Gln Ser
465                 470                 475                 480

Pro Met Val His Ala Ser
                485

<210> SEQ ID NO 27
<211> LENGTH: 483
<212> TYPE: PRT
<213> ORGANISM: Oryza sativa indica

<400> SEQUENCE: 27

Met Ala Cys Gln Gly Ile Asp Leu Leu Ser Thr Lys Ala Ala Gly Asp
1               5                   10                  15

Asp His Gly Glu Asn Ser Ser Tyr Phe Asp Gly Trp Lys Ala Tyr Asp
            20                  25                  30

Thr Asn Pro Phe Asp Leu Arg His Asn Arg Gly Gly Val Ile Gln Met
        35                  40                  45

Gly Leu Ala Glu Asn Gln Leu Ser Leu Asp Leu Ile Glu Glu Trp Ser
50                  55                  60

Lys Asn His Pro Glu Ala Ser Ile Cys Thr Pro Glu Gly Val Ser Gln
65                  70                  75                  80

Phe Lys Arg Ile Ala Asn Phe Gln Asp Tyr His Gly Leu Pro Glu Phe
                85                  90                  95

Arg Lys Ala Met Ala Gln Phe Met Gly Gln Val Arg Gly Gly Lys Ala
            100                 105                 110

Thr Phe Asp Pro Asp Arg Val Val Met Ser Gly Gly Ala Thr Gly Ala
        115                 120                 125

Gln Glu Thr Leu Ala Phe Cys Leu Ala Asn Pro Gly Glu Ala Phe Leu
130                 135                 140

Val Pro Thr Pro Tyr Tyr Pro Ala Phe Asp Arg Asp Cys Cys Trp Arg
145                 150                 155                 160

Ser Gly Ile Lys Leu Leu Pro Ile Glu Cys His Ser Phe Asn Asp Phe
                165                 170                 175

Arg Leu Thr Lys Glu Ala Leu Val Ser Ala Tyr Asp Gly Ala Arg Arg
            180                 185                 190

Gln Gly Ile Ser Val Lys Gly Ile Leu Ile Thr Asn Pro Ser Asn Pro
        195                 200                 205

Leu Gly Thr Ile Thr Asp Arg Asp Thr Leu Ala Met Leu Ala Thr Phe
210                 215                 220

Ala Thr Glu His Arg Val His Leu Val Cys Asp Glu Ile Tyr Ala Gly
225                 230                 235                 240

Ser Val Phe Ala Thr Pro Glu Tyr Val Ser Ile Ala Glu Val Ile Glu
                245                 250                 255

Arg Asp Val Pro Trp Cys Asn Arg Asp Leu Ile His Val Val Tyr Ser
            260                 265                 270

Leu Ser Lys Asp Phe Gly Leu Pro Gly Phe Arg Val Gly Ile Ile Tyr
        275                 280                 285

Ser Tyr Asn Asp Ala Val Val Ala Ala Ala Arg Arg Met Ser Ser Phe
290                 295                 300

Gly Leu Val Ser Ser Gln Thr Gln Tyr Phe Leu Ala Arg Met Leu Ser
```

```
305                 310                 315                 320
Asp Glu Glu Phe Ile Gly Arg Phe Leu Gln Glu Ser Lys Cys Arg Leu
                325                 330                 335
Val Ala Arg His Glu Arg Phe Thr Ser Gly Leu Arg Glu Val Gly Ile
            340                 345                 350
Gly Cys Leu Arg Gly Asn Ala Gly Leu Phe Ser Trp Met Asp Leu Arg
        355                 360                 365
Arg Met Leu Arg Glu Lys Thr Ala Glu Ala Glu Leu Glu Leu Trp Arg
    370                 375                 380
Val Ile Val His Gln Val Lys Leu Asn Val Ser Pro Gly Thr Ser Phe
385                 390                 395                 400
His Cys Arg Glu Pro Gly Trp Phe Arg Val Cys His Ala Asn Met Asp
                405                 410                 415
Asp Glu Thr Met Glu Val Ala Leu Gly Arg Ile His Asp Phe Val Arg
            420                 425                 430
Gln His Gln Gln Arg Arg Val Lys Ala Glu Arg Trp Ala Ala Asn Arg
        435                 440                 445
Gln Leu Arg Leu Ser Leu Pro His His His Leu Ser Pro Ala His
    450                 455                 460
Leu Ser Ser Pro Leu Ala Leu Leu Ser Pro Gln Ser Pro Met Val Arg
465                 470                 475                 480
Ala Thr Ser

<210> SEQ ID NO 28
<211> LENGTH: 483
<212> TYPE: PRT
<213> ORGANISM: Oryza sativa japonica

<400> SEQUENCE: 28

Met Ala Tyr Gln Gly Ile Asp Leu Leu Ser Thr Lys Ala Ala Gly Asp
1               5                   10                  15
Asp His Gly Glu Asn Ser Ser Tyr Phe Asp Gly Trp Lys Ala Tyr Asp
                20                  25                  30
Thr Asn Pro Phe Asp Leu Arg His Asn Arg Gly Gly Val Ile Gln Met
            35                  40                  45
Gly Leu Ala Glu Asn Gln Leu Ser Leu Asp Leu Ile Glu Glu Trp Ser
        50                  55                  60
Lys Asn His Pro Glu Ala Ser Ile Cys Thr Pro Glu Gly Val Ser Gln
65                  70                  75                  80
Phe Lys Arg Ile Ala Asn Phe Gln Asp Tyr His Gly Leu Pro Glu Phe
                85                  90                  95
Arg Lys Ala Met Ala Gln Phe Met Gly Gln Val Arg Gly Gly Lys Ala
            100                 105                 110
Thr Phe Asp Pro Asp Arg Val Val Met Ser Gly Gly Ala Thr Gly Ala
        115                 120                 125
Gln Glu Thr Leu Ala Phe Cys Leu Ala Asn Pro Gly Glu Ala Phe Leu
    130                 135                 140
Val Pro Thr Pro Tyr Tyr Pro Ala Phe Asp Arg Asp Cys Cys Trp Arg
145                 150                 155                 160
Ser Gly Ile Lys Leu Leu Pro Ile Glu Cys His Ser Phe Asn Asp Phe
                165                 170                 175
Arg Leu Thr Lys Glu Ala Leu Val Ser Ala Tyr Asp Gly Ala Arg Arg
            180                 185                 190
Gln Gly Ile Ser Val Lys Gly Ile Leu Ile Thr Asn Pro Ser Asn Pro
```

```
                195                 200                 205
Leu Gly Thr Ile Thr Asp Arg Asp Thr Leu Ala Met Leu Ala Thr Phe
            210                 215                 220
Ala Thr Glu His Arg Val His Leu Val Cys Asp Glu Ile Tyr Ala Gly
225                 230                 235                 240
Ser Val Phe Ala Thr Pro Glu Tyr Val Ser Ile Ala Glu Val Ile Glu
            245                 250                 255
Arg Asp Val Pro Trp Cys Asn Arg Asp Leu Ile His Val Val Tyr Ser
                260                 265                 270
Leu Ser Lys Asp Phe Gly Leu Pro Gly Phe Arg Val Gly Ile Ile Tyr
            275                 280                 285
Ser Tyr Asn Asp Ala Val Val Ala Ala Arg Arg Met Ser Ser Phe
290                 295                 300
Gly Leu Val Ser Ser Gln Thr Gln Tyr Phe Leu Ala Arg Met Leu Ser
305                 310                 315                 320
Asp Glu Glu Phe Ile Gly Arg Phe Leu Gln Glu Ser Lys Cys Arg Leu
                325                 330                 335
Val Ala Arg His Glu Arg Phe Thr Ser Gly Leu Arg Glu Val Gly Ile
            340                 345                 350
Gly Cys Leu Arg Gly Asn Ala Gly Leu Phe Ser Trp Met Asp Leu Arg
            355                 360                 365
Arg Met Leu Arg Glu Lys Thr Ala Glu Ala Glu Leu Glu Leu Trp Arg
370                 375                 380
Val Ile Val His Gln Val Lys Leu Asn Val Ser Pro Gly Thr Ser Phe
385                 390                 395                 400
His Cys Arg Glu Pro Gly Trp Phe Arg Val Cys His Ala Asn Met Asp
                405                 410                 415
Asp Glu Thr Met Glu Val Ala Leu Gly Arg Ile His Asp Phe Val Arg
                420                 425                 430
Gln His Gln Gln Arg Arg Val Lys Ala Glu Arg Trp Ala Ala Asn Arg
            435                 440                 445
Gln Leu Arg Leu Ser Leu Pro His His His Leu Ser Pro Ala His
450                 455                 460
Leu Ser Ser Pro Leu Ala Leu Leu Ser Pro Gln Ser Pro Met Val Arg
465                 470                 475                 480
Ala Thr Ser

<210> SEQ ID NO 29
<211> LENGTH: 475
<212> TYPE: PRT
<213> ORGANISM: Triticum aestivum

<400> SEQUENCE: 29

Met Ala Ala Gly Asp Gly His Gly Glu Asn Ser Ser Tyr Phe Asp Gly
1               5                   10                  15
Trp Lys Ala Tyr Asp Met Asn Pro Phe His Pro Gln Asp Asn Arg Gly
            20                  25                  30
Gly Val Ile Gln Met Gly Leu Ala Glu Asn Gln Leu Ser Leu Asp Leu
        35                  40                  45
Ile Glu Glu Trp Ser Lys Ala His Pro Glu Ala Ser Ile Cys Thr Ala
    50                  55                  60
Glu Gly Ala Ser Gln Phe Lys Arg Ile Ala Asn Phe Gln Asp Tyr His
65                  70                  75                  80
Gly Leu Pro Glu Phe Arg Gln Ala Met Ala Gln Phe Met Gly Gln Val
```

```
                    85                  90                  95
Arg Gly Trp Lys Ala Arg Phe Asp Pro Asp Arg Val Val Met Ser Gly
                100                 105                 110
Gly Ala Thr Gly Ala Gln Glu Thr Leu Ala Phe Cys Leu Ala Asn Pro
                115                 120                 125
Gly Glu Ala Phe Leu Val Pro Thr Pro Tyr Tyr Pro Gly Phe Asp Arg
                130                 135                 140
Asp Cys Cys Trp Arg Ser Gly Val Lys Leu Leu Pro Ile Glu Cys His
145                 150                 155                 160
Ser Ser Asn Asp Phe Arg Ile Thr Arg Glu Ala Val Val Ala Ala Tyr
                165                 170                 175
Glu Gly Ala Arg Ser Ser Gly Val Arg Val Lys Gly Ile Leu Ile Thr
                180                 185                 190
Asn Pro Ser Asn Pro Leu Gly Thr Thr Ala Asp Arg Ala Thr Leu Ala
                195                 200                 205
Met Leu Ala Thr Phe Ala Thr Glu His Arg Val His Leu Ile Cys Asp
                210                 215                 220
Glu Ile Tyr Ala Gly Ser Val Phe Ala Lys Pro Glu Tyr Val Ser Ile
225                 230                 235                 240
Ala Glu Val Ile Glu His Asp Ala Pro Gly Ala Asp Arg Asp Leu Ile
                245                 250                 255
His Ile Ala Tyr Ser Leu Ser Lys Asp Phe Gly Leu Pro Gly Phe Arg
                260                 265                 270
Val Gly Ile Val Tyr Ser Tyr Asn Asp Ala Val Val Ala Cys Ala Arg
                275                 280                 285
Lys Met Ser Ser Phe Gly Leu Val Ser Ser Gln Thr Gln Leu Phe Leu
290                 295                 300
Ala Lys Met Leu Gly Asp Glu Glu Phe Met Ser Arg Phe Leu Arg Glu
305                 310                 315                 320
Ser Ala Arg Arg Leu Ala Ala Arg His Glu Leu Phe Thr Ser Gly Leu
                325                 330                 335
Arg Glu Val Gly Ile Gly Cys Leu Gly Gly Asn Ala Gly Leu Phe Ser
                340                 345                 350
Trp Met Asp Leu Arg Gly Met Leu Arg Glu Lys Thr Ala Glu Ala Glu
                355                 360                 365
Leu Glu Leu Trp Arg Val Ile Ile Arg Lys Val Lys Leu Asn Val Ser
                370                 375                 380
Pro Gly Thr Ser Phe His Cys Gly Glu Pro Gly Trp Phe Arg Val Cys
385                 390                 395                 400
His Ala Asn Met Asp Asp Glu Thr Met Gly Val Ala Leu Ser Arg Ile
                405                 410                 415
Arg Asp Phe Val Arg Gln His Gln Gln Lys Ala Lys Ala Gln Arg
                420                 425                 430
Trp Ala Ala Arg Ser His Leu His Leu Ser Leu Gln Arg His Gly Pro
                435                 440                 445
Met Ala Ser Gln Tyr His Ala Leu Ser Ser Pro Met Ala Ala Leu Leu
                450                 455                 460
Ser Pro Gln Ser Pro Leu Val His Ala Ala Ser
465                 470                 475

<210> SEQ ID NO 30
<211> LENGTH: 488
<212> TYPE: PRT
<213> ORGANISM: Arabidopsis thaliana
```

<400> SEQUENCE: 30

```
Met Ser Gln Gly Ala Cys Glu Asn Gln Leu Leu Ser Lys Leu Ala Leu
1               5                   10                  15

Ser Asp Lys His Gly Glu Ala Ser Pro Tyr Phe His Gly Trp Lys Ala
            20                  25                  30

Tyr Asp Asn Asn Pro Phe His Pro Thr His Asn Pro Gln Gly Val Ile
        35                  40                  45

Gln Met Gly Leu Ala Glu Asn Gln Leu Cys Ser Asp Leu Ile Lys Glu
    50                  55                  60

Trp Ile Lys Glu Asn Pro Gln Ala Ser Ile Cys Thr Ala Glu Gly Ile
65              70                  75                  80

Asp Ser Phe Ser Asp Ile Ala Val Phe Gln Asp Tyr His Gly Leu Lys
                85                  90                  95

Gln Phe Arg Gln Ala Ile Ala Thr Phe Met Glu Arg Ala Arg Gly Gly
            100                 105                 110

Arg Val Arg Phe Glu Ala Glu Arg Val Val Met Ser Gly Gly Ala Thr
        115                 120                 125

Gly Ala Asn Glu Thr Ile Met Phe Cys Leu Ala Asp Pro Gly Asp Ala
    130                 135                 140

Phe Leu Val Pro Thr Pro Tyr Tyr Ala Ala Phe Asp Arg Asp Leu Arg
145                 150                 155                 160

Trp Arg Thr Gly Val Arg Ile Ile Pro Val Glu Cys Ser Ser Ser Asn
                165                 170                 175

Asn Phe Gln Ile Thr Lys Gln Ala Leu Glu Ser Ala Tyr Leu Lys Ala
            180                 185                 190

Gln Glu Thr Gly Ile Lys Ile Lys Gly Leu Ile Ile Ser Asn Pro Leu
        195                 200                 205

Gly Thr Ser Leu Asp Arg Glu Thr Leu Glu Ser Leu Val Ser Phe Ile
    210                 215                 220

Asn Asp Lys Gln Ile His Leu Val Cys Asp Glu Ile Tyr Ala Ala Thr
225                 230                 235                 240

Val Phe Ala Glu Pro Gly Phe Ile Ser Val Ala Glu Ile Ile Gln Glu
                245                 250                 255

Met Tyr Tyr Val Asn Arg Asp Leu Ile His Ile Val Tyr Ser Leu Ser
            260                 265                 270

Lys Asp Met Gly Leu Pro Gly Phe Arg Val Gly Val Val Tyr Ser Tyr
        275                 280                 285

Asn Asp Val Val Val Ser Cys Ala Arg Arg Met Ser Ser Phe Gly Leu
    290                 295                 300

Val Ser Ser Gln Thr Gln Ser Phe Leu Ala Ala Met Leu Ser Asp Gln
305                 310                 315                 320

Ser Phe Val Asp Asn Phe Leu Val Glu Val Ser Lys Arg Val Ala Lys
                325                 330                 335

Arg His His Met Phe Thr Glu Gly Leu Glu Met Gly Ile Ser Cys
            340                 345                 350

Leu Arg Ser Asn Ala Gly Leu Phe Val Leu Met Asp Leu Arg His Met
        355                 360                 365

Leu Lys Asp Gln Thr Phe Asp Ser Glu Met Ala Leu Trp Arg Val Ile
    370                 375                 380

Ile Asn Lys Val Lys Ile Asn Val Ser Pro Gly Ser Ser Phe His Cys
385                 390                 395                 400

Ser Glu Pro Gly Trp Phe Arg Val Cys Phe Ala Asn Met Asp Glu Asp
```

```
                     405                 410                 415
Thr Leu Gln Ile Ala Leu Glu Arg Ile Lys Asp Phe Val Val Gly Asp
                420                 425                 430

Arg Ala Asn Lys Asn Lys Asn Cys Asn Cys Ile Cys Asn Asn Lys Arg
            435                 440                 445

Glu Asn Lys Lys Arg Lys Ser Phe Gln Lys Asn Leu Lys Leu Ser Leu
        450                 455                 460

Ser Ser Met Arg Tyr Glu Glu His Val Arg Ser Pro Lys Leu Met Ser
465                 470                 475                 480

Pro His Ser Pro Leu Leu Arg Ala
                485

<210> SEQ ID NO 31
<211> LENGTH: 496
<212> TYPE: PRT
<213> ORGANISM: Arabidopsis thaliana

<400> SEQUENCE: 31

Met Gly Leu Pro Gly Lys Asn Lys Gly Ala Val Leu Ser Lys Ile Ala
1               5                   10                  15

Thr Asn Asn Gln His Gly Glu Asn Ser Glu Tyr Phe Asp Gly Trp Lys
            20                  25                  30

Ala Tyr Asp Lys Asp Pro Phe His Leu Ser Arg Asn Pro His Gly Ile
        35                  40                  45

Ile Gln Met Gly Leu Ala Glu Asn Gln Leu Cys Leu Asp Leu Ile Lys
    50                  55                  60

Asp Trp Val Lys Glu Asn Pro Glu Ala Ser Ile Cys Thr Leu Glu Gly
65                  70                  75                  80

Ile His Gln Phe Ser Asp Ile Ala Asn Phe Gln Asp Tyr His Gly Leu
                85                  90                  95

Lys Lys Phe Arg Gln Ala Ile Ala His Phe Met Gly Lys Ala Arg Gly
            100                 105                 110

Gly Arg Val Thr Phe Asp Pro Glu Arg Val Val Met Ser Gly Gly Ala
        115                 120                 125

Thr Gly Ala Asn Glu Thr Ile Ile Phe Cys Leu Ala Asp Pro Gly Asp
    130                 135                 140

Val Phe Leu Ile Pro Ser Pro Tyr Tyr Ala Ala Phe Asp Arg Asp Leu
145                 150                 155                 160

Arg Trp Arg Thr Gly Val Glu Ile Ile Pro Val Pro Cys Ser Ser Ser
                165                 170                 175

Asp Asn Phe Lys Leu Thr Val Asp Ala Ala Glu Trp Ala Tyr Lys Lys
            180                 185                 190

Ala Gln Glu Ser Asn Lys Lys Val Lys Gly Leu Ile Leu Thr Asn Pro
        195                 200                 205

Ser Asn Pro Leu Gly Thr Met Leu Asp Lys Asp Thr Leu Thr Asn Leu
    210                 215                 220

Val Arg Phe Val Thr Arg Lys Asn Ile His Leu Val Val Asp Glu Ile
225                 230                 235                 240

Tyr Ala Ala Thr Val Phe Ala Gly Gly Asp Phe Val Ser Val Ala Glu
                245                 250                 255

Val Val Asn Asp Val Asp Ile Ser Glu Val Asn Val Asp Leu Ile His
            260                 265                 270

Ile Val Tyr Ser Leu Ser Lys Asp Met Gly Leu Pro Gly Phe Arg Val
        275                 280                 285
```

```
Gly Ile Val Tyr Ser Phe Asn Asp Ser Val Val Ser Cys Ala Arg Lys
            290                 295                 300

Met Ser Ser Phe Gly Leu Val Ser Ser Gln Thr Gln Leu Met Leu Ala
305                 310                 315                 320

Ser Met Leu Ser Asp Asp Gln Phe Val Asp Asn Phe Leu Met Glu Ser
                325                 330                 335

Ser Arg Arg Leu Gly Ile Arg His Lys Val Phe Thr Thr Gly Ile Lys
                340                 345                 350

Lys Ala Asp Ile Ala Cys Leu Thr Ser Asn Ala Gly Leu Phe Ala Trp
                355                 360                 365

Met Asp Leu Arg His Leu Leu Arg Asp Arg Asn Ser Phe Glu Ser Glu
370                 375                 380

Ile Glu Leu Trp His Ile Ile Asp Arg Val Lys Leu Asn Val Ser
385                 390                 395                 400

Pro Gly Ser Ser Phe Arg Cys Thr Glu Pro Gly Trp Phe Arg Ile Cys
                405                 410                 415

Phe Ala Asn Met Asp Asp Asp Thr Leu His Val Ala Leu Gly Arg Ile
                420                 425                 430

Gln Asp Phe Val Ser Lys Asn Lys Asn Lys Ile Val Glu Lys Ala Ser
                435                 440                 445

Glu Asn Asp Gln Val Ile Gln Asn Lys Ser Ala Lys Lys Leu Lys Trp
450                 455                 460

Thr Gln Thr Asn Leu Arg Leu Ser Phe Arg Arg Leu Tyr Glu Asp Gly
465                 470                 475                 480

Leu Ser Ser Pro Gly Ile Met Ser Pro His Ser Pro Leu Leu Arg Ala
                485                 490                 495

<210> SEQ ID NO 32
<211> LENGTH: 485
<212> TYPE: PRT
<213> ORGANISM: Lycopersicon esculentum

<400> SEQUENCE: 32

Met Gly Phe Glu Ile Ala Lys Thr Asn Ser Ile Leu Ser Lys Leu Ala
1               5                   10                  15

Thr Asn Glu Glu His Gly Glu Asn Ser Pro Tyr Phe Asp Gly Trp Lys
                20                  25                  30

Ala Tyr Asp Ser Asp Pro Phe His Pro Leu Lys Asn Pro Asn Gly Val
                35                  40                  45

Ile Gln Met Gly Leu Ala Glu Asn Gln Leu Cys Leu Asp Leu Ile Glu
            50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Gly
                100                 105                 110

Arg Val Arg Phe Asp Pro Glu Arg Val Val Met Ala Gly Gly Ala Thr
            115                 120                 125

Gly Ala Asn Glu Thr Ile Ile Phe Cys Leu Ala Asp Pro Gly Asp Ala
        130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175
```

```
Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
        195                 200                 205

Asn Pro Leu Gly Thr Thr Leu Asp Lys Asp Thr Leu Lys Ser Val Leu
    210                 215                 220

Ser Phe Thr Asn Gln His Asn Ile His Leu Val Cys Asp Glu Ile Tyr
225                 230                 235                 240

Ala Ala Thr Val Phe Asp Thr Pro Gln Phe Val Ser Ile Ala Glu Ile
                245                 250                 255

Leu Asp Glu Gln Glu Met Thr Tyr Cys Asn Lys Asp Leu Val His Ile
            260                 265                 270

Val Tyr Ser Leu Ser Lys Asp Met Gly Leu Pro Gly Phe Arg Val Gly
        275                 280                 285

Ile Ile Tyr Ser Phe Asn Asp Val Val Asn Cys Ala Arg Lys Met
    290                 295                 300

Ser Ser Phe Gly Leu Val Ser Thr Gln Thr Gln Tyr Phe Leu Ala Ala
305                 310                 315                 320

Met Leu Ser Asp Glu Lys Phe Val Asp Asn Phe Leu Arg Glu Ser Ala
                325                 330                 335

Met Arg Leu Gly Lys Arg His Lys His Phe Thr Asn Gly Leu Glu Val
            340                 345                 350

Val Gly Ile Lys Cys Leu Lys Asn Asn Ala Gly Leu Phe Cys Trp Met
        355                 360                 365

Asp Leu Arg Pro Leu Leu Arg Glu Ser Thr Phe Asp Ser Glu Met Ser
    370                 375                 380

Leu Trp Arg Val Ile Ile Asn Asp Val Lys Leu Asn Val Ser Pro Gly
385                 390                 395                 400

Ser Ser Phe Glu Cys Gln Glu Pro Gly Trp Phe Arg Val Cys Phe Ala
                405                 410                 415

Asn Met Asp Asp Gly Thr Val Asp Ile Ala Leu Ala Arg Ile Arg Arg
            420                 425                 430

Phe Val Gly Val Glu Lys Ser Gly Asp Lys Ser Ser Met Glu Lys
        435                 440                 445

Lys Gln Gln Trp Lys Lys Asn Asn Leu Arg Leu Ser Phe Ser Lys Arg
    450                 455                 460

Met Tyr Asp Glu Ser Val Leu Ser Pro Leu Ser Ser Pro Ile Pro Pro
465                 470                 475                 480

Ser Pro Leu Val Arg
                485

<210> SEQ ID NO 33
<211> LENGTH: 476
<212> TYPE: PRT
<213> ORGANISM: Lycopersicon esculentum

<400> SEQUENCE: 33

Met Asp Leu Glu Thr Ser Glu Ile Ser Asn Tyr Lys Ser Ser Ala Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
```

```
             50                  55                  60
Val Asp Leu Ile Glu Glu Trp Ile Lys Arg Asn Pro Lys Ala Ser Ile
 65                  70                  75                  80

Cys Thr Asn Asp Gly Ile Glu Ser Phe Arg Arg Ile Ala Asn Phe Gln
                     85                  90                  95

Asp Tyr His Gly Leu Pro Glu Phe Thr Asn Ala Ile Ala Lys Phe Met
                100                 105                 110

Glu Lys Thr Arg Gly Gly Lys Val Lys Phe Asp Ala Lys Arg Val Val
                115                 120                 125

Met Ala Gly Gly Ala Thr Gly Ala Asn Glu Thr Leu Ile Leu Cys Leu
130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
                180                 185                 190

Glu Ala Tyr Glu Lys Gly Gln Gln Ala Asn Val Lys Ile Lys Gly Leu
                195                 200                 205

Ile Leu Thr Asn Pro Cys Asn Pro Leu Gly Thr Ile Leu Asp Arg Asp
210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Val Phe Asn Pro Pro Lys Phe
                245                 250                 255

Val Ser Ile Ala Glu Ile Ile Asn Glu Asp Asn Cys Ile Asn Lys Asp
                260                 265                 270

Leu Val His Ile Val Ser Leu Ser Lys Asp Leu Gly Phe Pro Gly
                275                 280                 285

Phe Arg Val Gly Ile Val Tyr Ser Phe Asn Asp Asp Val Val Asn Cys
290                 295                 300

Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
                340                 345                 350

Gly Leu Glu Glu Ile Gly Ile Lys Cys Leu Glu Ser Asn Ala Gly Val
                355                 360                 365

Tyr Cys Trp Met Asp Leu Arg Ser Leu Leu Lys Glu Ala Thr Leu Asp
370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
                420                 425                 430

Arg Ile Arg Met Phe Met Asp Ala Tyr Asn Asn Val Asn Lys Asn Gly
                435                 440                 445

Val Met Lys Asn Lys His Asn Gly Arg Gly Thr Thr Tyr Asp Leu Thr
                450                 455                 460

Pro Gln Met Gly Ser Thr Met Lys Met Leu Leu Ala
465                 470                 475
```

<210> SEQ ID NO 34
<211> LENGTH: 486
<212> TYPE: PRT
<213> ORGANISM: Musa acuminata

<400> SEQUENCE: 34

| | | | | | | | | | | | | | | |
|---|---|---|---|---|---|---|---|---|---|---|---|---|---|---|
| Met | Arg | Ile | Tyr | Gly | Glu | Glu | His | Pro | Asn | Gln | Gln | Ile | Leu | Ser | Arg |
| 1 | | | | 5 | | | | | 10 | | | | | 15 | |
| Ile | Ala | Thr | Asn | Asp | Gly | His | Gly | Glu | Asn | Ser | Ser | Tyr | Phe | Asp | Gly |
| | | | 20 | | | | | 25 | | | | | 30 | | |
| Trp | Lys | Ala | Tyr | Glu | Arg | Asp | Pro | Phe | His | Leu | Thr | Asp | Asn | Pro | Thr |
| | | 35 | | | | | 40 | | | | | 45 | | | |
| Gly | Val | Ile | Gln | Met | Gly | Leu | Ala | Glu | Asn | Gln | Leu | Ser | Leu | Asp | Leu |
| | 50 | | | | | 55 | | | | | 60 | | | | |
| Ile | Arg | Asp | Trp | Met | Lys | Lys | Asn | Pro | Gln | Ala | Ser | Ile | Cys | Thr | Glu |
| 65 | | | | | 70 | | | | | 75 | | | | | 80 |
| Glu | Gly | Val | Ser | Glu | Phe | Lys | Ala | Ile | Ala | Asn | Phe | Gln | Asp | Tyr | His |
| | | | | 85 | | | | | 90 | | | | | 95 | |
| Gly | Leu | Pro | Thr | Phe | Arg | Lys | Ala | Ile | Ala | Gln | Phe | Met | Glu | Lys | Val |
| | | | 100 | | | | | 105 | | | | | 110 | | |
| Arg | Gly | Gly | Arg | Ala | Arg | Phe | Asp | Pro | Asp | Arg | Ile | Val | Met | Ser | Gly |
| | | 115 | | | | | 120 | | | | | 125 | | | |
| Gly | Ala | Thr | Gly | Ala | Gln | Glu | Thr | Ile | Ala | Phe | Cys | Leu | Ala | Asp | Pro |
| | 130 | | | | | 135 | | | | | 140 | | | | |
| Gly | Glu | Ala | Phe | Leu | Ile | Pro | Thr | Pro | Tyr | Tyr | Pro | Gly | Phe | Asp | Arg |
| 145 | | | | | 150 | | | | | 155 | | | | | 160 |
| Asp | Phe | Arg | Trp | Arg | Thr | Gly | Val | Gln | Leu | Leu | Pro | Ile | His | Cys | His |
| | | | | 165 | | | | | 170 | | | | | 175 | |
| Ser | Ser | Asn | Lys | Phe | Lys | Ile | Thr | Gln | Ala | Ala | Leu | Glu | Thr | Ala | Tyr |
| | | | 180 | | | | | 185 | | | | | 190 | | |
| Arg | Lys | Ala | Arg | Asn | Ser | His | Ile | Arg | Val | Lys | Gly | Ile | Leu | Val | Thr |
| | | 195 | | | | | 200 | | | | | 205 | | | |
| Asn | Pro | Ser | Lys | Pro | Leu | Gly | Thr | Thr | Met | Asp | Arg | Glu | Thr | Leu | Arg |
| | 210 | | | | | 215 | | | | | 220 | | | | |
| Thr | Leu | Val | Ser | Phe | Val | Asn | Glu | Lys | Arg | Met | His | Leu | Val | Cys | Asp |
| 225 | | | | | 230 | | | | | 235 | | | | | 240 |
| Glu | Ile | Phe | Ser | Gly | Thr | Val | Phe | Asp | Lys | Pro | Ser | Tyr | Val | Ser | Val |
| | | | | 245 | | | | | 250 | | | | | 255 | |
| Ser | Glu | Val | Ile | Glu | Asp | Asp | Pro | Tyr | Cys | Asp | Arg | Asp | Leu | Ile | His |
| | | | 260 | | | | | 265 | | | | | 270 | | |
| Ile | Ala | Tyr | Ser | Leu | Ser | Lys | Asp | Leu | Gly | Val | Pro | Gly | Phe | Arg | Val |
| | | 275 | | | | | 280 | | | | | 285 | | | |
| Gly | Val | Ile | Tyr | Ser | Tyr | Asn | Asp | Ala | Val | Val | Thr | Cys | Ala | Arg | Lys |
| | 290 | | | | | 295 | | | | | 300 | | | | |
| Met | Ser | Ser | Phe | Gly | Leu | Val | Ser | Ser | Gln | Thr | Gln | His | Leu | Leu | Ala |
| 305 | | | | | 310 | | | | | 315 | | | | | 320 |
| Ser | Met | Leu | Gly | Asp | Glu | Glu | Phe | Thr | Thr | Ser | Phe | Leu | Ala | Thr | Ser |
| | | | | 325 | | | | | 330 | | | | | 335 | |
| Arg | Thr | Arg | Leu | Cys | Gly | Arg | Arg | Val | Phe | Thr | Asp | Gly | Leu | Lys |
| | | | 340 | | | | | 345 | | | | | 350 | | |
| Arg | Val | Gly | Ile | His | Cys | Leu | Asp | Gly | Asn | Ala | Gly | Leu | Phe | Cys | Trp |
| | | 355 | | | | | 360 | | | | | 365 | | | |
| Met | Asp | Leu | Arg | Pro | Leu | Leu | Lys | Glu | Ala | Thr | Val | Glu | Ala | Glu | Leu |

```
                370                 375                 380
Arg Leu Trp Arg Val Ile Ile Asn Asp Val Lys Leu Asn Ile Ser Pro
385                 390                 395                 400

Gly Ser Ser Phe His Cys Ser Glu Pro Gly Trp Phe Arg Val Ser Phe
                405                 410                 415

Ala Asn Met Asp Asp Thr Ala Met Lys Ile Ala Leu Arg Arg Ile Glu
            420                 425                 430

Ser Phe Val Tyr Arg Glu Asn Asp Ala Ala Val Gln Ala Lys Asn Lys
        435                 440                 445

Arg Arg Trp Asp Glu Ala Leu Arg Leu Ser Leu Pro Arg Arg Arg Phe
    450                 455                 460

Glu Asp Pro Thr Ile Met Thr Pro His Leu Met Ser Pro His Ser Pro
465                 470                 475                 480

Leu Val Gln Ala Ala Thr
                485

<210> SEQ ID NO 35
<211> LENGTH: 485
<212> TYPE: PRT
<213> ORGANISM: Musa acuminata

<400> SEQUENCE: 35

Met Arg Ile Tyr Gly Glu Glu His Pro Asn Gln Glu Ile Leu Ser Arg
1               5                   10                  15

Ile Ala Thr Asn Asp Gly His Gly Glu Asn Ser Ser Tyr Phe Asp Gly
            20                  25                  30

Trp Lys Ala Tyr Glu Asn Asp Pro Phe His Leu Thr Asp Asn Pro Thr
        35                  40                  45

Gly Val Ile Gln Met Gly Leu Ala Glu Asn Gln Leu Ser Leu Asp Leu
    50                  55                  60

Ile Gln Asp Trp Met Lys Lys Asn Pro Gln Ala Ser Ile Cys Thr Glu
65                  70                  75                  80

Glu Gly Val Ser Glu Phe Lys Ala Ile Ala Asn Phe Gln Asp Tyr His
                85                  90                  95

Gly Leu Pro Ala Phe Arg Lys Ala Ile Ala Gln Phe Met Glu Lys Val
            100                 105                 110

Arg Gly Gly Arg Ala Arg Phe Asp Pro Asp Arg Ile Val Met Ser Gly
        115                 120                 125

Gly Ala Thr Gly Ala Gln Glu Thr Ile Ala Phe Cys Leu Ala Asp Pro
    130                 135                 140

Gly Glu Ala Phe Leu Ile Pro Thr Pro Tyr Tyr Pro Gly Phe Asp Arg
145                 150                 155                 160

Asp Phe Arg Trp Arg Thr Gly Val Gln Leu Leu Pro Ile His Cys His
                165                 170                 175

Ser Ser Asn Lys Phe Lys Ile Thr Gln Ala Ala Leu Glu Thr Ala Tyr
            180                 185                 190

Arg Lys Ala Arg Asn Ser His Ile Arg Val Lys Gly Ile Val Val Thr
        195                 200                 205

Lys Pro Ser Asn Pro Leu Gly Thr Thr Met Asp Arg Asp Thr Leu Arg
    210                 215                 220

Thr Leu Val Ser Phe Val Asn Glu Lys Arg Met His Leu Val Cys Asp
225                 230                 235                 240

Glu Val Phe Ser Gly Thr Val Phe Asp Lys Pro Ser Tyr Val Ser Val
                245                 250                 255
```

```
Ala Glu Val Ile Gln Asp Asp Pro Tyr Cys Asp Arg Asp Leu Ile His
            260                 265                 270

Ile Ala Tyr Ser Leu Ser Lys Asp Leu Gly Val Pro Gly Phe Arg Val
        275                 280                 285

Gly Val Ile Tyr Ser Tyr Asn Asp Ala Val Val Ser Cys Ala Arg Lys
    290                 295                 300

Met Ser Ser Phe Gly Leu Val Ser Ser Gln Thr Gln His Leu Leu Ala
305                 310                 315                 320

Ser Met Leu Gly Asp Glu Glu Phe Thr Thr Ser Phe Leu Ala Thr Ser
                325                 330                 335

Arg Thr Arg Leu Cys Gly Arg Arg Val Phe Thr Asp Gly Leu Lys
            340                 345                 350

Arg Val Gly Ile His Cys Leu Asp Gly Asn Ala Gly Leu Phe Cys Trp
        355                 360                 365

Met Asp Leu Arg Pro Leu Leu Lys Glu Ala Thr Val Glu Ala Glu Leu
    370                 375                 380

Arg Leu Trp Arg Val Ile Ile Asn Asp Val Lys Leu Asn Ile Ser Pro
385                 390                 395                 400

Gly Ser Ser Phe His Cys Ser Glu Pro Gly Trp Phe Arg Val Cys Phe
                405                 410                 415

Ala Asn Met Asp Asp Thr Ala Met Lys Ile Ala Leu Arg Arg Ile Glu
            420                 425                 430

Asn Phe Val Tyr Arg Glu Asn Asp Ala Ala Val Gln Ala Lys Asn Lys
        435                 440                 445

Arg Lys Trp Asp Glu Thr Leu Arg Leu Ser Leu Pro Arg Arg Phe Glu
    450                 455                 460

Asp Pro Thr Ile Met Thr Pro His Leu Met Ser Pro His Ser Pro Leu
465                 470                 475                 480

Val Gln Ala Ala Thr
                485

<210> SEQ ID NO 36
<211> LENGTH: 485
<212> TYPE: PRT
<213> ORGANISM: Lycopersicon esculentum

<400> SEQUENCE: 36

Met Val Ser Ile Ser Lys Asn Asn Gln Lys Gln Leu Leu Ser Lys
1               5                   10                  15

Ile Ala Thr Asn Asp Gly His Gly Glu Asn Ser Pro Tyr Phe Asp Gly
            20                  25                  30

Trp Lys Ala Tyr Ala Asn Asn Pro Phe His Leu Thr Asp Asn Pro Thr
        35                  40                  45

Gly Val Ile Gln Met Gly Leu Ala Glu Asn Gln Leu Cys Phe Asp Leu
    50                  55                  60

Ile Gln Glu Trp Val Val Asn Asn Pro Lys Ala Ser Ile Cys Thr Val
65                  70                  75                  80

Glu Gly Ala Glu Asn Phe Gln Asp Ile Ala Ile Phe Gln Asp Tyr His
                85                  90                  95

Gly Leu Pro Glu Phe Arg Gln Ala Val Ala Arg Phe Met Glu Lys Val
            100                 105                 110

Arg Gly Asp Arg Val Thr Phe Asp Pro Asn Arg Ile Val Met Ser Gly
        115                 120                 125

Gly Ala Thr Gly Ala His Glu Met Leu Ala Phe Cys Leu Ala Asp Pro
    130                 135                 140
```

Gly Asp Ala Phe Leu Val Pro Thr Pro Tyr Tyr Pro Gly Phe Asp Arg
145                 150                 155                 160

Asp Leu Arg Trp Arg Thr Gly Val Gln Leu Phe Pro Val Val Cys Glu
            165                 170                 175

Ser Cys Asn Asp Phe Lys Val Thr Thr Lys Ala Leu Glu Glu Ala Tyr
            180                 185                 190

Glu Lys Ala Gln Gln Ser Asn Ile Lys Ile Lys Gly Leu Leu Ile Asn
        195                 200                 205

Asn Pro Ser Asn Pro Leu Gly Thr Leu Leu Asp Lys Asp Thr Leu Arg
210                 215                 220

Asp Ile Val Thr Phe Ile Asn Ser Lys Asn Ile His Leu Val Cys Asp
225                 230                 235                 240

Glu Ile Tyr Ala Ala Thr Val Phe Asp Gln Pro Arg Phe Ile Ser Val
                245                 250                 255

Ser Glu Ile Val Glu Asp Met Ile Glu Cys Asn Lys Asp Leu Ile His
            260                 265                 270

Ile Val Tyr Ser Leu Ser Lys Asp Leu Gly Phe Pro Gly Phe Arg Val
        275                 280                 285

Gly Ile Val Tyr Ser Tyr Asn Asp Thr Val Val Asn Ile Ala Arg Lys
290                 295                 300

Met Ser Ser Phe Gly Leu Val Ser Ala Gln Thr Gln His Leu Leu Ala
305                 310                 315                 320

Ser Met Leu Ser Asp Glu Val Phe Ile Asp Lys Phe Ile Ala Glu Ser
                325                 330                 335

Ser Glu Arg Leu Gly Glu Arg Gln Gly Met Phe Thr Lys Gly Leu Ala
            340                 345                 350

Glu Val Gly Ile Ser Thr Leu Lys Ser Asn Ala Gly Leu Phe Phe Trp
        355                 360                 365

Met Asp Leu Arg Arg Leu Leu Lys Glu Ala Thr Phe Asp Ser Glu Leu
370                 375                 380

Glu Leu Trp Arg Ile Ile Asn Glu Val Lys Leu Asn Val Ser Pro
385                 390                 395                 400

Gly Cys Ser Phe His Cys Ser Glu Pro Gly Trp Phe Arg Val Cys Phe
                405                 410                 415

Ala Asn Met Asp Asp Glu Thr Met Arg Ile Ala Leu Lys Arg Ile Ser
            420                 425                 430

Tyr Phe Val Leu Gln Pro Lys Gly Leu Asn Asn Ile Ala Ala Ile Lys
        435                 440                 445

Lys Gln Cys Ser Arg Arg Lys Leu Gln Ile Ser Leu Ser Phe Arg Arg
450                 455                 460

Leu Asp His Glu Phe Met Asn Ser Pro Ala His Ser Pro Met Asn Ser
465                 470                 475                 480

Pro Leu Val Arg Thr
            485

<210> SEQ ID NO 37
<211> LENGTH: 483
<212> TYPE: PRT
<213> ORGANISM: Lycopersicon esculentum

<400> SEQUENCE: 37

Met Val Ser Ile Ser Lys Asn Asn Gln Lys Gln Gln Leu Leu Ser Lys
1               5                   10                  15

Ile Ala Thr Asn Asp Gly His Gly Glu Asn Ser Pro Tyr Phe Asp Gly

```
                20                  25                  30
Trp Lys Ala Tyr Ala Asn Asn Pro Phe His Pro Thr Asp Asn Pro Thr
             35                  40                  45
Gly Val Ile Gln Met Gly Leu Ala Glu Asn Gln Leu Cys Phe Asp Leu
 50                  55                  60
Ile Gln Glu Trp Met Val Asn Asn Pro Lys Ala Ser Ile Cys Thr Val
 65                  70                  75                  80
Glu Gly Ala Glu Asn Phe Gln Asp Ile Ala Ile Phe Gln Asp Tyr His
                 85                  90                  95
Gly Leu Pro Glu Phe Arg Gln Ala Val Ala Arg Phe Met Glu Lys Val
            100                 105                 110
Arg Gly Asp Arg Val Thr Phe Asp Pro Asn Arg Ile Val Met Ser Gly
            115                 120                 125
Gly Ala Thr Gly Ala His Glu Met Leu Ala Phe Cys Leu Ala Asp Pro
130                 135                 140
Gly Asp Ala Phe Leu Val Pro Thr Pro Tyr Tyr Pro Gly Phe Asp Arg
145                 150                 155                 160
Asp Leu Arg Trp Arg Thr Gly Val Gln Leu Phe Pro Val Val Cys Glu
                165                 170                 175
Ser Cys Asn Asp Phe Lys Val Thr Thr Lys Ala Leu Glu Glu Ala Tyr
            180                 185                 190
Glu Lys Ala Gln Gln Ser Asn Ile Lys Ile Lys Gly Leu Leu Ile Asn
            195                 200                 205
Asn Pro Ser Asn Pro Leu Gly Thr Leu Leu Asp Lys Asp Thr Leu Arg
            210                 215                 220
Asp Ile Val Thr Phe Ile Asn Ser Lys Asn Ile His Leu Val Cys Asp
225                 230                 235                 240
Glu Ile Tyr Ala Ala Thr Val Phe Asp Gln Pro Arg Phe Ile Ser Val
                245                 250                 255
Ser Glu Met Val Glu Glu Met Ile Glu Cys Asn Thr Asp Leu Ile His
            260                 265                 270
Ile Val Tyr Ser Leu Ser Lys Asp Leu Gly Phe Pro Gly Phe Arg Val
            275                 280                 285
Gly Ile Val Tyr Ser Tyr Asn Asp Thr Val Val Asn Ile Ser Arg Lys
290                 295                 300
Met Ser Ser Phe Gly Leu Val Ser Thr Gln Thr Gln His Met Leu Ala
305                 310                 315                 320
Ser Met Leu Ser Asp Glu Ile Phe Val Glu Lys Phe Ile Ala Glu Ser
                325                 330                 335
Ser Glu Arg Leu Gly Lys Arg Gln Gly Met Phe Thr Lys Gly Leu Ala
            340                 345                 350
Gln Val Gly Ile Ser Thr Leu Lys Ser Asn Ala Gly Leu Phe Phe Trp
            355                 360                 365
Met Asp Leu Arg Arg Leu Leu Lys Glu Ala Thr Phe Asp Gly Glu Leu
            370                 375                 380
Glu Leu Trp Arg Ile Ile Asn Glu Val Lys Leu Asn Val Ser Pro
385                 390                 395                 400
Gly Cys Ser Phe His Cys Ser Glu Pro Gly Trp Phe Arg Val Cys Phe
                405                 410                 415
Ala Asn Met Asp Asp Glu Thr Met Arg Ile Ala Leu Arg Arg Ile Arg
            420                 425                 430
Asn Phe Val Leu Gln Thr Lys Gly Leu Asn Asn Ile Ala Ala Ile Lys
            435                 440                 445
```

```
Lys Gln Cys Ser Arg Ser Lys Leu Gln Ile Ser Leu Ser Phe Arg Arg
            450                 455                 460

Leu Asp Asp Phe Asn Ser Pro Ala His Ser Pro Met Asn Ser Pro Leu
465                 470                 475                 480

Val Arg Thr

<210> SEQ ID NO 38
<211> LENGTH: 477
<212> TYPE: PRT
<213> ORGANISM: Lycopersicon esculentum

<400> SEQUENCE: 38

Met Gly Leu Ile Ser Lys Ile Ala Thr Asn Asp Gly His Gly Glu Asn
1               5                   10                  15

Ser Ala Tyr Phe Asp Gly Trp Lys Ala Tyr Glu Asn Asp Pro Phe His
            20                  25                  30

Pro Thr Gln Asn Pro Asn Gly Val Ile Gln Met Gly Leu Ala Glu Asn
        35                  40                  45

Gln Leu Cys Phe Asp Leu Ile Gln Glu Trp Ile Val Asn Asn Pro Lys
50                  55                  60

Ala Ser Ile Cys Thr Tyr Glu Gly Val Gln Asp Phe Gln Asp Thr Ala
65                  70                  75                  80

Ile Phe Gln Asp Tyr His Gly Leu Pro Glu Phe Arg Lys Ala Val Ala
                85                  90                  95

Arg Phe Met Glu Lys Val Arg Gly Asp Arg Val Arg Phe Asp Pro Glu
            100                 105                 110

Arg Ile Val Met Ser Gly Gly Ala Thr Gly Ala His Glu Ser Leu Ala
        115                 120                 125

Phe Cys Leu Ala Asp Pro Gly Asp Ala Phe Leu Val Pro Thr Pro Tyr
130                 135                 140

Tyr Pro Gly Phe Asp Arg Asp Leu Arg Trp Arg Thr Gly Val Gln Leu
145                 150                 155                 160

Phe Pro Val Val Cys Glu Ser Ser Asn Asn Phe Lys Val Thr Lys Glu
                165                 170                 175

Ala Leu Glu Glu Ala Tyr Ser Lys Ala Gln Glu Ser Asn Ile Lys Val
            180                 185                 190

Lys Gly Leu Leu Ile Asn Asn Pro Ser Asn Pro Leu Gly Thr Ile Leu
        195                 200                 205

Asp Lys Glu Thr Leu Lys Asp Ile Leu Arg Phe Ile Asn Asp Lys Asn
210                 215                 220

Ile His Leu Val Cys Asp Glu Ile Tyr Ala Ala Thr Ala Phe Ser Gln
225                 230                 235                 240

Pro Ser Phe Ile Ser Ile Ser Glu Val Lys Ser Glu Val Val Gly Cys
                245                 250                 255

Asn Asp Asp Leu Val His Ile Val Tyr Ser Leu Ser Lys Asp Leu Gly
            260                 265                 270

Phe Pro Gly Phe Arg Val Gly Ile Ile Tyr Ser Tyr Asn Asp Ala Val
        275                 280                 285

Val Asn Ile Ala Arg Lys Met Ser Ser Phe Gly Leu Val Ser Thr Gln
290                 295                 300

Thr Gln Arg Leu Ile Ala Ser Met Leu Leu Asp Thr Ile Phe Val Glu
305                 310                 315                 320

Asp Phe Ile Ala Lys Ser Ser Met Arg Leu Leu Gln Lys His Gly Leu
                325                 330                 335
```

```
Phe Thr Lys Gly Leu Gly Gln Val Gly Ile Thr Thr Leu Lys Ser Asn
            340                 345                 350

Ala Gly Leu Phe Ile Trp Met Asp Leu Arg Arg Phe Leu Glu Asn Ser
            355                 360                 365

Thr Phe Asp Asp Glu Leu Lys Leu Trp His Ile Ile Asp Lys Val
            370                 375                 380

Lys Leu Asn Val Ser Pro Gly Cys Ser Phe His Cys Ser Glu Pro Gly
385                 390                 395                 400

Trp Phe Arg Val Cys Phe Ala Asn Met Asp Asp Ala Thr Met Lys Ile
                405                 410                 415

Ala Leu Arg Arg Ile Arg His Phe Val Tyr Leu Gln Pro Asn Lys Gly
            420                 425                 430

Val Glu Val Ala Thr Lys Lys Gln Tyr Cys Arg Thr Arg Ser Lys Leu
            435                 440                 445

Glu Ile Ser Leu Ser Phe Arg Arg Leu Asp Asp Phe Met Asn Ser Pro
            450                 455                 460

His Ser Pro Met Ser Ser Pro Met Val Gln Ala Arg Asn
465                 470                 475

<210> SEQ ID NO 39
<211> LENGTH: 466
<212> TYPE: PRT
<213> ORGANISM: Arabidopsis thaliana

<400> SEQUENCE: 39

Tyr Phe Asp Gly Trp Lys Ala Tyr Glu Glu Asn Pro Phe His Pro Ile
1               5                   10                  15

Asp Arg Pro Asp Gly Val Ile Gln Met Gly Leu Ala Glu Asn Gln Leu
            20                  25                  30

Cys Gly Asp Leu Met Arg Lys Trp Val Leu Lys His Pro Glu Ala Ser
        35                  40                  45

Ile Cys Thr Ser Glu Gly Val Asn Gln Phe Ser Asp Ile Ala Ile Phe
    50                  55                  60

Gln Asp Tyr His Gly Leu Pro Glu Phe Arg Gln Ala Val Ala Lys Phe
65                  70                  75                  80

Met Glu Lys Thr Arg Asn Asn Lys Val Lys Phe Asp Pro Asp Arg Ile
                85                  90                  95

Val Met Ser Gly Gly Ala Thr Gly Ala His Glu Thr Val Ala Phe Cys
            100                 105                 110

Leu Ala Asn Pro Gly Asp Gly Phe Leu Val Pro Thr Pro Tyr Tyr Pro
            115                 120                 125

Gly Phe Asp Arg Asp Leu Arg Trp Arg Thr Gly Val Asn Leu Val Pro
        130                 135                 140

Val Thr Cys His Ser Ser Asn Gly Phe Lys Ile Thr Val Glu Ala Leu
145                 150                 155                 160

Glu Ala Ala Tyr Glu Asn Ala Arg Lys Ser Asn Ile Pro Val Lys Gly
                165                 170                 175

Leu Leu Val Thr Asn Pro Ser Asn Pro Leu Gly Thr Thr Leu Asp Arg
            180                 185                 190

Glu Cys Leu Lys Ser Leu Val Asn Phe Thr Asn Asp Lys Gly Ile His
        195                 200                 205

Leu Ile Ala Asp Glu Ile Tyr Ala Ala Thr Thr Phe Gly Gln Ser Glu
    210                 215                 220

Phe Ile Ser Val Ala Glu Val Ile Glu Glu Ile Glu Asp Cys Asn Arg
```

```
              225                 230                 235                 240
Asp Leu Ile His Ile Val Tyr Ser Leu Ser Lys Asp Met Gly Leu Pro
                245                 250                 255
Gly Leu Arg Val Gly Ile Val Tyr Ser Tyr Asn Asp Arg Val Val Gln
                260                 265                 270
Ile Ala Arg Lys Met Ser Ser Phe Gly Leu Val Ser Ser Gln Thr Gln
                275                 280                 285
His Leu Ile Ala Lys Met Leu Ser Asp Glu Glu Phe Val Asp Glu Phe
                290                 295                 300
Ile Arg Glu Ser Lys Leu Arg Leu Ala Ala Arg His Ala Glu Ile Thr
305                 310                 315                 320
Thr Gly Leu Asp Gly Leu Gly Ile Gly Trp Leu Lys Ala Lys Ala Gly
                325                 330                 335
Leu Phe Leu Trp Met Asp Leu Arg Asn Leu Leu Lys Thr Ala Thr Phe
                340                 345                 350
Asp Ser Glu Thr Glu Leu Trp Arg Val Ile Val His Gln Val Lys Leu
                355                 360                 365
Asn Val Ser Pro Gly Gly Ser Phe His Cys His Glu Pro Gly Trp Phe
                370                 375                 380
Arg Val Cys Phe Ala Asn Met Asp His Lys Thr Met Glu Thr Ala Leu
385                 390                 395                 400
Glu Arg Ile Lys Val Phe Thr Ser Gln Leu Glu Glu Glu Thr Lys Pro
                405                 410                 415
Met Ala Ala Thr Thr Met Met Ala Lys Lys Lys Lys Cys Trp Gln
                420                 425                 430
Ser Asn Leu Arg Leu Ser Phe Ser Asp Thr Arg Arg Phe Asp Asp Gly
                435                 440                 445
Phe Phe Ser Pro His Ser Pro Val Pro Pro Ser Pro Leu Val Arg Ala
                450                 455                 460
Gln Thr
465

<210> SEQ ID NO 40
<211> LENGTH: 482
<212> TYPE: PRT
<213> ORGANISM: Zea mays

<400> SEQUENCE: 40

Met Ile Ala Asp Glu Lys Pro Gln Pro Gln Leu Leu Ser Lys Lys Ala
1               5                   10                  15
Ala Cys Asn Ser His Gly Gln Asp Ser Ser Tyr Phe Leu Gly Trp Glu
                20                  25                  30
Glu Tyr Glu Lys Asn Pro Tyr Asp Pro Val Ala Asn Pro Gly Gly Ile
                35                  40                  45
Ile Gln Met Gly Leu Ala Glu Asn Gln Leu Ser Phe Asp Leu Leu Glu
                50                  55                  60
Ala Trp Leu Glu Ala Asn Pro Asp Ala Leu Gly Leu Arg Arg Gly Gly
65                  70                  75                  80
Ala Ser Val Phe Arg Glu Leu Ala Leu Phe Gln Asp Tyr His Gly Met
                85                  90                  95
Pro Ala Phe Lys Asn Ala Leu Ala Arg Phe Met Ser Glu Gln Arg Gly
                100                 105                 110
Tyr Arg Val Thr Phe Asp Pro Ser Asn Ile Val Leu Thr Ala Gly Ala
                115                 120                 125
```

```
Thr Ser Ala Asn Glu Ala Leu Met Phe Cys Leu Ala Asp His Gly Asp
    130                 135                 140

Ala Phe Leu Ile Pro Thr Pro Tyr Tyr Pro Gly Phe Asp Arg Asp Leu
145                 150                 155                 160

Lys Trp Arg Thr Gly Ala Glu Ile Val Pro Val His Cys Thr Ser Gly
                165                 170                 175

Asn Gly Phe Arg Leu Thr Arg Ala Ala Leu Asp Asp Ala Tyr Arg Arg
            180                 185                 190

Ala Gln Lys Leu Arg Leu Arg Val Lys Gly Val Leu Ile Thr Asn Pro
        195                 200                 205

Ser Asn Pro Leu Gly Thr Thr Ser Pro Arg Ala Asp Leu Glu Met Leu
210                 215                 220

Val Asp Phe Val Ala Ala Lys Gly Ile His Leu Val Ser Asp Glu Ile
225                 230                 235                 240

Tyr Ser Gly Thr Val Phe Ala Asp Pro Gly Phe Val Ser Val Leu Glu
                245                 250                 255

Val Val Ala Ala Arg Ala Ala Thr Asp Asp Gly Val Val Gly Val Gly
            260                 265                 270

Pro Leu Ser Asp Arg Val His Val Val Tyr Ser Leu Ser Lys Asp Leu
        275                 280                 285

Gly Leu Pro Gly Phe Arg Val Gly Ala Ile Tyr Ser Ser Asn Ala Gly
290                 295                 300

Val Val Ser Ala Ala Thr Lys Met Ser Ser Phe Gly Leu Val Ser Ser
305                 310                 315                 320

Gln Thr Gln His Leu Leu Ala Ser Leu Leu Gly Asp Arg Asp Phe Thr
                325                 330                 335

Arg Arg Tyr Ile Ala Glu Asn Thr Arg Arg Ile Arg Glu Arg Glu
            340                 345                 350

Gln Leu Ala Glu Gly Leu Ala Ala Val Gly Ile Glu Cys Leu Glu Ser
        355                 360                 365

Asn Ala Gly Leu Phe Cys Trp Val Asn Met Arg Arg Leu Met Arg Ser
370                 375                 380

Arg Ser Phe Glu Gly Glu Met Glu Leu Trp Lys Lys Val Val Phe Glu
385                 390                 395                 400

Val Gly Leu Asn Ile Ser Pro Gly Ser Ser Cys His Cys Arg Glu Pro
                405                 410                 415

Gly Trp Phe Arg Val Cys Phe Ala Asn Met Ser Ala Lys Thr Leu Asp
            420                 425                 430

Val Ala Leu Gln Arg Leu Gly Ala Phe Ala Glu Ala Thr Ala Gly
        435                 440                 445

Arg Arg Val Leu Ala Pro Ala Arg Ser Ile Ser Leu Pro Val Arg Phe
450                 455                 460

Ser Trp Ala Asn Arg Leu Thr Pro Gly Ser Ala Ala Asp Arg Lys Ala
465                 470                 475                 480

Glu Arg

<210> SEQ ID NO 41
<211> LENGTH: 487
<212> TYPE: PRT
<213> ORGANISM: Oryza sativa indica

<400> SEQUENCE: 41

Met Val Ser Gln Val Val Ala Glu Glu Lys Pro Gln Leu Leu Ser Lys
1               5                   10                  15
```

-continued

```
Lys Ala Gly Cys Asn Ser His Gly Gln Asp Ser Ser Tyr Phe Leu Gly
                20                  25                  30
Trp Gln Glu Tyr Glu Lys Asn Pro Phe Asp Pro Val Ser Asn Pro Ser
        35                  40                  45
Gly Ile Ile Gln Met Gly Leu Ala Glu Asn Gln Leu Ser Phe Asp Leu
    50                  55                  60
Leu Glu Glu Trp Leu Glu Lys Asn Pro His Ala Leu Gly Leu Arg Arg
65                  70                  75                  80
Glu Gly Gly Ala Ser Val Phe Arg Glu Leu Ala Leu Phe Gln Asp
                85                  90                  95
Tyr His Gly Leu Pro Ala Phe Lys Gln Ala Leu Ala Arg Phe Met Ser
                100                 105                 110
Glu Gln Arg Gly Tyr Lys Val Val Phe Asp Pro Ser Asn Ile Val Leu
            115                 120                 125
Thr Ala Gly Ala Thr Ser Ala Asn Glu Ala Leu Met Phe Cys Leu Ala
    130                 135                 140
Asp His Gly Asp Ala Phe Leu Ile Pro Thr Pro Tyr Tyr Pro Gly Phe
145                 150                 155                 160
Asp Arg Asp Leu Lys Trp Arg Thr Gly Ala Glu Ile Val Pro Val His
                165                 170                 175
Cys Ala Ser Ala Asn Gly Phe Arg Val Thr Arg Ala Ala Leu Asp Asp
            180                 185                 190
Ala Tyr Arg Arg Ala Gln Lys Arg Leu Arg Val Lys Gly Val Leu
                195                 200                 205
Ile Thr Asn Pro Ser Asn Pro Leu Gly Thr Ala Ser Pro Arg Ala Asp
    210                 215                 220
Leu Glu Thr Ile Val Asp Phe Val Ala Ala Lys Gly Ile His Leu Ile
225                 230                 235                 240
Ser Asp Glu Ile Tyr Ala Gly Thr Ala Phe Ala Glu Pro Pro Ala Gly
                245                 250                 255
Phe Val Ser Ala Leu Glu Val Val Ala Gly Arg Asp Gly Gly Ala
            260                 265                 270
Asp Val Ser Asp Arg Val His Val Val Tyr Ser Leu Ser Lys Asp Leu
    275                 280                 285
Gly Leu Pro Gly Phe Arg Val Gly Ala Ile Tyr Ser Ala Asn Ala Ala
290                 295                 300
Val Val Ser Ala Ala Thr Lys Met Ser Ser Phe Gly Leu Val Ser Ser
305                 310                 315                 320
Gln Thr Gln Tyr Leu Leu Ala Ala Leu Leu Gly Asp Arg Asp Phe Thr
            325                 330                 335
Arg Ser Tyr Val Ala Glu Asn Thr Arg Arg Ile Lys Glu Arg His Asp
        340                 345                 350
Gln Leu Val Glu Gly Leu Arg Ala Ile Gly Ile Glu Cys Leu Pro Ser
    355                 360                 365
Asn Ala Gly Leu Phe Cys Trp Val Asp Met Ser His Leu Met Arg Ser
370                 375                 380
Arg Ser Phe Ala Gly Glu Met Glu Leu Trp Lys Lys Val Val Phe Glu
385                 390                 395                 400
Val Gly Leu Asn Ile Ser Pro Gly Ser Ser Cys His Cys Arg Glu Pro
                405                 410                 415
Gly Trp Phe Arg Val Cys Phe Ala Asn Met Ser Ala Lys Thr Leu Asp
            420                 425                 430
Val Ala Met Gln Arg Leu Arg Ser Phe Val Asp Ser Ala Thr Gly Gly
```

```
            435                 440                 445
Gly Asp Asn Ala Ala Leu Arg Arg Ala Ala Val Pro Val Arg Ser Val
450                 455                 460

Ser Cys Pro Leu Ala Ile Lys Trp Ala Leu Arg Leu Thr Pro Ser Ile
465                 470                 475                 480

Ala Asp Arg Lys Ala Glu Arg
                485

<210> SEQ ID NO 42
<211> LENGTH: 470
<212> TYPE: PRT
<213> ORGANISM: Arabidopsis thaliana

<400> SEQUENCE: 42

Met Lys Gln Leu Ser Thr Lys Val Thr Ser Asn Gly His Gly Gln Asp
1                5                  10                  15

Ser Ser Tyr Phe Leu Gly Trp Glu Glu Tyr Glu Lys Asn Pro Tyr Asp
                20                  25                  30

Glu Ile Lys Asn Pro Asn Gly Met Ile Gln Met Gly Leu Ala Glu Asn
            35                  40                  45

Gln Leu Cys Phe Asp Leu Ile Glu Ser Trp Leu Thr Lys Asn Pro Asp
50                  55                  60

Ala Ala Ser Leu Lys Arg Asn Gly Gln Ser Ile Phe Arg Glu Leu Ala
65                  70                  75                  80

Leu Phe Gln Asp Tyr His Gly Met Pro Glu Phe Lys Lys Ala Met Ala
                85                  90                  95

Glu Phe Met Glu Glu Ile Arg Gly Asn Arg Val Thr Phe Asp Pro Lys
            100                 105                 110

Lys Ile Val Leu Ala Ala Gly Ser Thr Ser Ala Asn Glu Thr Leu Met
        115                 120                 125

Phe Cys Leu Ala Glu Pro Gly Asp Ala Phe Leu Leu Pro Thr Pro Tyr
130                 135                 140

Tyr Pro Gly Phe Asp Arg Asp Leu Lys Trp Arg Thr Gly Ala Glu Ile
145                 150                 155                 160

Val Pro Ile His Cys Ser Ser Ser Asn Gly Phe Gln Ile Thr Glu Ser
                165                 170                 175

Ala Leu Gln Gln Ala Tyr Gln Gln Ala Gln Lys Leu Asp Leu Lys Val
            180                 185                 190

Lys Gly Val Leu Val Thr Asn Pro Ser Asn Pro Leu Gly Thr Ala Leu
        195                 200                 205

Thr Arg Arg Glu Leu Asn Leu Leu Val Asp Phe Ile Thr Ser Lys Asn
210                 215                 220

Ile His Leu Ile Ser Asp Glu Ile Tyr Ser Gly Thr Met Phe Gly Phe
225                 230                 235                 240

Glu Gln Phe Ile Ser Val Met Asp Val Leu Lys Asp Lys Lys Leu Glu
                245                 250                 255

Asp Thr Glu Val Ser Lys Arg Val His Val Val Tyr Ser Leu Ser Lys
            260                 265                 270

Asp Leu Gly Leu Pro Gly Phe Arg Val Gly Ala Ile Tyr Ser Asn Asp
        275                 280                 285

Glu Met Ile Val Ser Ala Ala Thr Lys Met Ser Ser Phe Gly Leu Val
290                 295                 300

Ser Ser Gln Thr Gln Tyr Leu Leu Ser Ala Leu Leu Ser Asp Lys Lys
305                 310                 315                 320
```

```
Phe Thr Ser Gln Tyr Leu Glu Glu Asn Gln Lys Arg Leu Lys Ser Arg
            325                 330                 335

Gln Arg Arg Leu Val Ser Gly Leu Glu Ser Ala Gly Ile Thr Cys Leu
        340                 345                 350

Arg Ser Asn Ala Gly Leu Phe Cys Trp Val Asp Met Arg His Leu Leu
        355                 360                 365

Asp Thr Asn Thr Phe Glu Ala Glu Leu Asp Leu Trp Lys Lys Ile Val
370                 375                 380

Tyr Asn Val Lys Leu Asn Ile Ser Pro Gly Ser Ser Cys His Cys Thr
385                 390                 395                 400

Glu Pro Gly Trp Phe Arg Val Cys Phe Ala Asn Met Ser Glu Asp Thr
                405                 410                 415

Leu Asp Leu Ala Leu Lys Arg Leu Lys Thr Phe Val Glu Ser Thr Asp
            420                 425                 430

Cys Gly Arg Met Ile Ser Arg Ser His Glu Arg Leu Lys Ser Leu
            435                 440                 445

Arg Lys Lys Thr Val Ser Asn Trp Val Phe Arg Val Ser Trp Thr Asp
        450                 455                 460

Arg Val Pro Asp Glu Arg
465                 470

<210> SEQ ID NO 43
<211> LENGTH: 470
<212> TYPE: PRT
<213> ORGANISM: Arabidopsis thaliana

<400> SEQUENCE: 43

Met Lys Gln Leu Ser Arg Lys Val Thr Ser Asn Ala His Gly Gln Asp
1               5                   10                  15

Ser Ser Tyr Phe Leu Gly Trp Glu Glu Tyr Lys Asn Pro Tyr Asp
            20                  25                  30

Glu Ile Lys Asn Pro Asn Gly Ile Ile Gln Met Gly Leu Ala Glu Asn
            35                  40                  45

Gln Leu Cys Phe Asp Leu Ile Glu Thr Trp Leu Ala Lys Asn Pro Asp
        50                  55                  60

Ala Ala Gly Leu Lys Lys Asp Gly Gln Ser Ile Phe Lys Glu Leu Ala
65                  70                  75                  80

Leu Phe Gln Asp Tyr His Gly Leu Pro Glu Phe Lys Lys Ala Leu Ala
                85                  90                  95

Glu Phe Met Glu Glu Ile Arg Gly Asn Arg Val Thr Phe Asp Pro Ser
            100                 105                 110

Lys Ile Val Leu Ala Ala Gly Ser Thr Ser Ala Asn Glu Thr Leu Met
        115                 120                 125

Phe Cys Leu Ala Glu Pro Gly Asp Ala Phe Leu Leu Pro Thr Pro Tyr
    130                 135                 140

Tyr Pro Gly Phe Asp Arg Asp Leu Lys Trp Arg Thr Gly Ala Glu Ile
145                 150                 155                 160

Val Pro Ile His Cys Ser Ser Asn Gly Phe Gln Ile Thr Glu Ser
                165                 170                 175

Ala Leu Gln Gln Ala Tyr Gln Gln Ala Gln Lys Leu Asp Leu Lys Val
            180                 185                 190

Lys Gly Val Leu Val Thr Asn Pro Ser Asn Pro Leu Gly Thr Met Leu
        195                 200                 205

Thr Arg Arg Glu Leu Asn Leu Leu Val Asp Phe Ile Thr Ser Lys Asn
    210                 215                 220
```

Ile His Leu Ile Ser Asp Glu Ile Tyr Ser Gly Thr Val Phe Gly Phe
225                 230                 235                 240

Glu Gln Phe Val Ser Val Met Asp Val Leu Lys Asp Lys Asn Leu Glu
            245                 250                 255

Asn Ser Glu Val Ser Lys Arg Val His Ile Val Tyr Ser Leu Ser Lys
        260                 265                 270

Asp Leu Gly Leu Pro Gly Phe Arg Val Gly Ala Ile Tyr Ser Asn Asp
    275                 280                 285

Glu Met Val Val Ser Ala Ala Thr Lys Met Ser Ser Phe Gly Leu Val
290                 295                 300

Ser Ser Gln Thr Gln Tyr Leu Leu Ser Ala Leu Leu Ser Asp Lys Lys
305                 310                 315                 320

Phe Thr Ser Thr Tyr Leu Asp Glu Asn Gln Lys Arg Leu Lys Ile Arg
            325                 330                 335

Gln Lys Lys Leu Val Ser Gly Leu Glu Ala Ala Gly Ile Thr Cys Leu
        340                 345                 350

Lys Ser Asn Ala Gly Leu Phe Cys Trp Val Asp Met Arg His Leu Leu
    355                 360                 365

Asp Thr Asn Thr Phe Glu Ala Glu Leu Glu Leu Trp Lys Lys Ile Val
370                 375                 380

Tyr Asp Val Lys Leu Asn Ile Ser Pro Gly Ser Ser Cys His Cys Thr
385                 390                 395                 400

Glu Pro Gly Trp Phe Arg Val Cys Phe Ala Asn Met Ser Glu Asp Thr
            405                 410                 415

Leu Asp Leu Ala Met Lys Arg Leu Lys Glu Tyr Val Glu Ser Thr Asp
        420                 425                 430

Ser Arg Arg Val Ile Ser Lys Ser Ser His Asp Arg Ile Lys Ser Leu
    435                 440                 445

Arg Lys Arg Thr Val Ser Asn Trp Val Phe Arg Val Ser Trp Thr Asp
450                 455                 460

Arg Val Pro Asp Glu Arg
465                 470

<210> SEQ ID NO 44
<211> LENGTH: 474
<212> TYPE: PRT
<213> ORGANISM: Arabidopsis thaliana

<400> SEQUENCE: 44

Met Val Gln Leu Ser Arg Lys Ala Thr Cys Asn Ser His Gly Gln Val
1               5                   10                  15

Ser Ser Tyr Phe Leu Gly Trp Glu Glu Tyr Glu Lys Asn Pro Tyr Asp
            20                  25                  30

Val Thr Lys Asn Pro Gln Gly Ile Ile Gln Met Gly Leu Ala Glu Asn
        35                  40                  45

Gln Leu Cys Phe Asp Leu Leu Glu Ser Trp Leu Ala Gln Asn Thr Asp
    50                  55                  60

Ala Ala Cys Phe Lys Arg Asp Gly Gln Ser Val Phe Arg Glu Leu Ala
65                  70                  75                  80

Leu Phe Gln Asp Tyr His Gly Leu Ser Ser Phe Lys Asn Ala Phe Ala
                85                  90                  95

Asp Phe Met Ser Glu Asn Arg Gly Asn Arg Val Ser Phe Asp Ser Asn
            100                 105                 110

Asn Leu Val Leu Thr Ala Gly Ala Thr Ser Ala Asn Glu Thr Leu Met 115                 120                 125
Phe Cys Leu Ala Asp Pro Gly Asp Ala Phe Leu Leu Pro Thr Pro Tyr
    130                 135                 140

Tyr Pro Gly Phe Asp Arg Asp Leu Lys Trp Arg Thr Gly Val Glu Ile
145                 150                 155                 160

Val Pro Ile Gln Ser Ser Thr Asn Gly Phe Arg Ile Thr Lys Leu
                165                 170                 175

Ala Leu Glu Glu Ala Tyr Glu Gln Ala Lys Lys Leu Asp Leu Asn Val
                180                 185                 190

Lys Gly Ile Leu Ile Thr Asn Pro Ser Asn Pro Leu Gly Thr Thr Thr
                195                 200                 205

Thr Gln Thr Glu Leu Asn Ile Leu Phe Asp Phe Ile Thr Lys Asn Lys
    210                 215                 220

Asn Ile His Leu Val Ser Asp Glu Ile Tyr Ser Gly Thr Val Phe Asn
225                 230                 235                 240

Ser Ser Glu Phe Ile Ser Val Met Glu Ile Leu Lys Asn Asn Gln Leu
                245                 250                 255

Glu Asn Thr Asp Val Leu Asn Arg Val His Ile Val Cys Ser Leu Ser
                260                 265                 270

Lys Asp Leu Gly Leu Pro Gly Phe Arg Val Gly Ala Ile Tyr Ser Asn
                275                 280                 285

Asp Lys Asp Val Ile Ser Ala Ala Thr Lys Met Ser Ser Phe Gly Leu
    290                 295                 300

Val Ser Ser Gln Thr Gln Tyr Leu Leu Ser Ser Leu Leu Ser Asp Lys
305                 310                 315                 320

Lys Phe Thr Lys Asn Tyr Leu Arg Glu Asn Gln Lys Arg Leu Lys Asn
                325                 330                 335

Arg Gln Arg Lys Leu Val Leu Gly Leu Glu Ala Ile Gly Ile Lys Cys
                340                 345                 350

Leu Lys Ser Asn Ala Gly Leu Phe Cys Trp Val Asp Met Arg Pro Leu
    355                 360                 365

Leu Arg Ser Lys Thr Phe Glu Ala Glu Met Asp Leu Trp Lys Lys Ile
370                 375                 380

Val Tyr Glu Val Lys Leu Asn Ile Ser Pro Gly Ser Ser Cys His Cys
385                 390                 395                 400

Glu Glu Pro Gly Trp Phe Arg Val Cys Phe Ala Asn Met Ile Asp Glu
                405                 410                 415

Thr Leu Lys Leu Ala Leu Lys Arg Leu Lys Met Leu Val Asp Asp Glu
                420                 425                 430

Asn Ser Ser Arg Arg Cys Gln Lys Ser Lys Ser Glu Arg Leu Asn Gly
                435                 440                 445

Ser Arg Lys Thr Met Ser Asn Val Ser Asn Trp Val Phe Arg Leu
    450                 455                 460

Ser Phe His Asp Arg Glu Ala Glu Glu Arg
465                 470

<210> SEQ ID NO 45
<211> LENGTH: 469
<212> TYPE: PRT
<213> ORGANISM: Arabidopsis thaliana

<400> SEQUENCE: 45

Met Gly Leu Leu Ser Lys Lys Ala Ser Cys Asn Thr His Gly Gln Asp
1               5                   10                  15

-continued

Ser Ser Tyr Phe Trp Gly Trp Glu Glu Tyr Glu Lys Asn Pro Tyr Asp
            20                  25                  30

Glu Ile Lys Asn Pro Asp Gly Ile Ile Gln Met Gly Leu Ala Glu Asn
            35                  40                  45

Gln Leu Ser Phe Asp Leu Ile Glu Ser Trp Leu Ala Lys Asn Pro Asp
50                  55                  60

Ala Ala Asn Phe Gln Arg Glu Gly Gln Ser Ile Phe Arg Glu Leu Ala
65                  70                  75                  80

Leu Phe Gln Asp Tyr His Gly Leu Pro Ser Phe Lys Asn Ala Met Ala
                85                  90                  95

Asp Phe Met Ser Glu Asn Arg Gly Asn Arg Val Ser Phe Asn Pro Asn
            100                 105                 110

Lys Leu Val Leu Thr Ala Gly Ala Thr Pro Ala Asn Glu Thr Leu Met
            115                 120                 125

Phe Cys Leu Ala Asp Pro Gly Asp Ala Phe Leu Leu Pro Thr Pro Tyr
            130                 135                 140

Tyr Pro Gly Phe Asp Arg Asp Leu Lys Trp Arg Thr Gly Ala Glu Ile
145                 150                 155                 160

Val Pro Ile Gln Cys Lys Ser Ala Asn Gly Phe Arg Ile Thr Lys Val
                165                 170                 175

Ala Leu Glu Glu Ala Tyr Gln Ala Gln Lys Leu Asn Leu Lys Val
            180                 185                 190

Lys Gly Val Leu Ile Thr Asn Pro Ser Asn Pro Leu Gly Thr Thr Thr
            195                 200                 205

Thr Arg Thr Glu Leu Asn His Leu Leu Asp Phe Ile Ser Arg Lys Lys
210                 215                 220

Ile His Leu Ile Ser Asp Glu Ile Tyr Ser Gly Thr Val Phe Thr Asn
225                 230                 235                 240

Pro Gly Phe Ile Ser Val Met Glu Val Leu Lys Asp Arg Lys Leu Glu
                245                 250                 255

Asn Thr Asp Val Phe Asp Arg Val His Ile Val Tyr Ser Leu Ser Lys
            260                 265                 270

Asp Leu Gly Leu Pro Gly Phe Arg Val Gly Val Ile Tyr Ser Asn Asp
            275                 280                 285

Asp Phe Val Val Ser Ala Ala Thr Lys Met Ser Ser Phe Gly Leu Ile
            290                 295                 300

Ser Ser Gln Thr Gln Tyr Leu Leu Ser Ala Leu Leu Ser Asp Lys Thr
305                 310                 315                 320

Phe Thr Lys Asn Tyr Leu Glu Glu Asn Gln Ile Arg Leu Lys Asn Arg
                325                 330                 335

His Lys Lys Leu Val Ser Gly Leu Glu Ala Ala Gly Ile Glu Cys Leu
            340                 345                 350

Lys Ser Asn Ala Gly Leu Phe Cys Trp Val Asp Met Arg His Leu Leu
            355                 360                 365

Lys Ser Asn Thr Phe Glu Ala Glu Gly Ile Glu Leu Trp Lys Lys Ile Val
            370                 375                 380

Tyr Glu Val Lys Leu Asn Ile Ser Pro Gly Ser Ser Cys His Cys Asn
385                 390                 395                 400

Glu Pro Gly Trp Phe Arg Val Cys Phe Ala Asn Leu Ser Glu Glu Thr
                405                 410                 415

Leu Lys Val Ala Leu Asp Arg Leu Lys Arg Phe Val Asp Gly Pro Ser
            420                 425                 430

Pro Thr Arg Arg Ser Gln Ser Glu His Gln Arg Leu Lys Asn Leu Arg

```
              435                 440                 445
Lys Met Lys Val Ser Asn Trp Val Phe Arg Leu Ser Phe His Asp Arg
    450                 455                 460

Glu Pro Glu Glu Arg
465

<210> SEQ ID NO 46
<211> LENGTH: 363
<212> TYPE: PRT
<213> ORGANISM: Musa acuminata

<400> SEQUENCE: 46

Met Gly Phe Thr Glu Asn Gln Leu Cys Phe Asp Leu Ile Glu Ser Trp
1               5                  10                  15

Leu Glu Asn His Pro Asp Pro Ala Ala Phe Lys Lys Asp Gly Ala Leu
            20                  25                  30

Leu Phe Arg Glu Leu Ala Leu Phe Gln Asp Tyr His Gly Leu Pro Ala
        35                  40                  45

Phe Lys Arg Ala Leu Thr Lys Tyr Met Gly Glu Val Arg Gly Asn Lys
    50                  55                  60

Val Ala Phe Asp Pro Asn Arg Leu Val Leu Thr Ala Gly Ala Thr Ser
65                  70                  75                  80

Ala Asn Glu Thr Leu Met Phe Cys Leu Ala Glu Pro Gly Glu Ala Phe
                85                  90                  95

Leu Leu Pro Thr Pro Tyr Tyr Pro Gly Phe Asp Arg Asp Leu Lys Trp
            100                 105                 110

Arg Thr Gly Ala Glu Ile Val Pro Ile His Cys Ser Ser Ser Asn Gly
        115                 120                 125

Phe Arg Ile Thr Lys Pro Ala Leu Glu Ala Ala Tyr Gln Asp Ala Gln
    130                 135                 140

Lys Arg Ser Leu Arg Val Lys Gly Val Leu Val Thr Asn Pro Ser Asn
145                 150                 155                 160

Pro Leu Gly Thr Thr Leu Thr Arg His Glu Leu Asp Ile Leu Val Asp
                165                 170                 175

Phe Val Val Ser Lys Asp Ile His Leu Ile Ser Asp Glu Ile Tyr Ser
            180                 185                 190

Gly Thr Asn Phe Asp Ser Pro Gly Phe Ile Ser Ile Ala Glu Ala Thr
        195                 200                 205

Lys Asp Arg Asn Asn Val Ser His Arg Ile His Ile Val Cys Ser Leu
    210                 215                 220

Ser Lys Asp Leu Gly Leu Pro Gly Phe Arg Val Gly Ala Ile Tyr Ser
225                 230                 235                 240

Glu Asn Glu Ala Val Val Ser Ala Ala Thr Lys Met Ser Ser Phe Gly
                245                 250                 255

Met Val Ser Ser Gln Thr Gln Tyr Leu Leu Ala Ala Leu Leu Ser Asp
            260                 265                 270

Lys Glu Phe Thr Asp Lys Tyr Leu Leu Glu Asn Gln Lys Arg Leu Lys
        275                 280                 285

Glu Arg His Asp Met Leu Val Glu Gly Leu Arg Arg Ile Gly Ile Gly
    290                 295                 300

Cys Leu Lys Gly Ser Ala Ala Leu Phe Cys Trp Val Asp Val Arg His
305                 310                 315                 320

Leu Leu Lys Ser Asn Thr Phe Lys Gly Ala Met Glu Leu Trp Lys Lys
                325                 330                 335
```

Ile Val Tyr Gln Val Gly Leu Asn Ile Ser Pro Gly Ser Ser Cys His
              340                 345                 350

Cys Asp Glu Pro Gly Trp Phe Ser Val Thr Phe
        355                 360

<210> SEQ ID NO 47
<211> LENGTH: 363
<212> TYPE: PRT
<213> ORGANISM: Musa acuminata

<400> SEQUENCE: 47

Met Gly Phe Ala Glu Asn His Val Ser Phe Asp Leu Ile Glu Ser Trp
1               5                   10                  15

Leu Glu Asp His Pro Asp Leu Thr Gly Phe Lys Lys Asp Gly Gly Leu
            20                  25                  30

Val Phe Arg Glu Leu Ala Leu Phe Gln Asp Tyr His Gly Leu Pro Ala
        35                  40                  45

Phe Lys Asn Ala Leu Ala Arg Tyr Met Gly Glu Val Arg Gly Asn Lys
    50                  55                  60

Val Ser Phe Glu Pro Ser Lys Leu Val Leu Thr Ala Gly Ala Thr Ser
65                  70                  75                  80

Ala Asn Glu Thr Leu Met Phe Cys Leu Ala Asp Pro Gly Glu Ala Phe
                85                  90                  95

Leu Leu Pro Thr Pro Tyr Tyr Pro Gly Phe Asp Arg Asp Leu Lys Trp
            100                 105                 110

Arg Thr Gly Val Glu Ile Val Pro Ile His Cys Ser Ser Ser Asn Gly
        115                 120                 125

Phe Arg Ile Thr Arg Ala Ala Leu Glu Ala Ala Leu Arg Arg Ala Gln
    130                 135                 140

Lys Arg Arg Leu Arg Val Lys Gly Val Leu Val Thr Asn Pro Ser Asn
145                 150                 155                 160

Pro Leu Gly Thr Thr Leu Thr Arg Gln Glu Leu Asp Thr Leu Val Asp
                165                 170                 175

Phe Ala Val Ala Asn Asp Ile His Leu Ile Ser Asp Glu Ile Tyr Ser
            180                 185                 190

Gly Thr Thr Phe Gly Ser Pro Gly Phe Val Ser Ile Ala Glu Ala Thr
        195                 200                 205

Lys Gly Arg Asp Asp Val Ser Arg Ile His Ile Val Cys Ser Leu
    210                 215                 220

Ser Lys Asp Leu Gly Leu Pro Gly Phe Arg Val Ser Ala Ile Tyr Ser
225                 230                 235                 240

Asp Asn Glu Ala Val Val Ser Ala Ala Thr Lys Met Ser Ser Phe Gly
                245                 250                 255

Leu Ile Ser Ser Gln Thr Gln Tyr Leu Ala Ala Leu Leu Ser Asp
            260                 265                 270

Lys Glu Phe Thr Glu Lys Tyr Val Arg Glu Ser Gln Lys Arg Leu Lys
        275                 280                 285

Glu Arg His Asp Met Leu Val Glu Gly Leu Arg Ile Gly Ile Gly
    290                 295                 300

Cys Leu Glu Gly Asn Ala Gly Leu Phe Cys Trp Val Asp Met Arg His
305                 310                 315                 320

Leu Leu Arg Ser Asn Thr Phe Glu Gly Glu Met Glu Leu Trp Lys Lys
                325                 330                 335

Ile Val Tyr Arg Val Gly Leu Asn Val Ser Pro Gly Ser Ser Cys His
            340                 345                 350

```
Cys Asp Glu Pro Gly Trp Phe Arg Val Ser Phe
        355                 360

<210> SEQ ID NO 48
<211> LENGTH: 469
<212> TYPE: PRT
<213> ORGANISM: Lycopersicon esculentum

<400> SEQUENCE: 48

Met Lys Leu Leu Ser Glu Lys Ala Thr Cys Asn Ser His Gly Gln Asp
1               5                   10                  15

Ser Ser Tyr Phe Leu Gly Trp Gln Glu Tyr Glu Lys Asn Pro Tyr Asp
            20                  25                  30

Glu Ile Gln Asn Pro Lys Gly Ile Ile Gln Met Gly Leu Ala Glu Asn
        35                  40                  45

Gln Leu Ser Phe Asp Leu Leu Glu Ser Trp Leu Ala Gln Asn Pro Asp
    50                  55                  60

Ala Ala Gly Phe Lys Arg Asn Gly Glu Ser Ile Phe Arg Glu Leu Ala
65                  70                  75                  80

Leu Phe Gln Asp Tyr His Gly Leu Pro Ala Phe Lys Asn Ala Met Thr
                85                  90                  95

Lys Phe Met Ser Glu Ile Arg Gly Asn Arg Val Ser Phe Asp Ser Asn
            100                 105                 110

Asn Leu Val Leu Thr Ala Gly Ala Thr Ser Ala Asn Glu Thr Leu Met
        115                 120                 125

Phe Cys Leu Ala Asn Gln Gly Asp Ala Phe Leu Leu Pro Thr Pro Tyr
    130                 135                 140

Tyr Pro Gly Phe Asp Arg Asp Leu Lys Trp Arg Thr Gly Ala Glu Ile
145                 150                 155                 160

Val Pro Ile His Cys Ser Ser Asn Gly Phe Arg Ile Thr Glu Ser
                165                 170                 175

Ala Leu Glu Glu Ala Tyr Leu Asp Ala Lys Lys Arg Asn Leu Lys Val
            180                 185                 190

Lys Gly Val Leu Val Thr Asn Pro Ser Asn Pro Leu Gly Thr Thr Leu
        195                 200                 205

Asn Arg Asn Glu Leu Glu Leu Leu Thr Phe Ile Asp Glu Lys Gly
    210                 215                 220

Ile His Leu Ile Ser Asp Glu Ile Tyr Ser Gly Thr Val Phe Asn Ser
225                 230                 235                 240

Pro Gly Leu Val Ser Val Met Glu Val Leu Ile Glu Lys Asn Tyr Met
                245                 250                 255

Lys Thr Arg Val Trp Glu Arg Val His Ile Val Tyr Ser Leu Ser Lys
            260                 265                 270

Asp Leu Gly Leu Pro Gly Phe Arg Ile Gly Ala Ile Tyr Ser Asn Asp
        275                 280                 285

Glu Met Val Val Ser Ala Ala Thr Lys Met Ser Ser Phe Gly Leu Val
    290                 295                 300

Ser Ser Gln Thr Gln Tyr Leu Leu Ser Cys Met Leu Ser Asp Lys Lys
305                 310                 315                 320

Phe Thr Lys Lys Tyr Ile Ser Glu Asn Gln Lys Arg Leu Lys Arg Arg
                325                 330                 335

His Ala Met Leu Val Lys Gly Leu Lys Ser Ala Gly Ile Asn Cys Leu
            340                 345                 350

Glu Ser Asn Ala Gly Leu Phe Cys Trp Val Asp Met Arg His Leu Leu
```

```
            355                 360                 365
Ser Ser Asn Asn Phe Asp Ala Glu Met Asp Leu Trp Lys Lys Ile Val
        370                 375                 380

Tyr Asp Val Gly Leu Asn Ile Ser Pro Gly Ser Ser Cys His Cys Thr
385                 390                 395                 400

Glu Pro Gly Trp Phe Arg Val Cys Phe Ala Asn Met Ser Glu Asp Thr
                    405                 410                 415

Leu Asp Leu Ala Met Arg Arg Ile Lys Asp Phe Val Glu Ser Thr Ala
                420                 425                 430

Pro Asn Ala Thr Asn His Gln Asn Gln Gln Gln Ser Asn Ala Asn Ser
            435                 440                 445

Lys Lys Lys Ser Phe Ser Lys Trp Val Phe Arg Leu Ser Phe Asn Asp
        450                 455                 460

Arg Gln Arg Glu Arg
465

<210> SEQ ID NO 49
<211> LENGTH: 467
<212> TYPE: PRT
<213> ORGANISM: Lycopersicon esculentum

<400> SEQUENCE: 49

Met Lys Leu Leu Ser Lys Lys Ala Met Cys Asn Ser His Gly Gln Asp
1               5                   10                  15

Ser Ser Tyr Phe Leu Gly Trp Glu Glu Tyr Gln Lys Asn Pro Tyr Asp
                20                  25                  30

Glu Ile Arg Asn Pro Lys Gly Ile Ile Gln Met Gly Leu Ala Glu Asn
            35                  40                  45

Gln Leu Ser Phe Asp Leu Leu Glu Ser Trp Leu Thr Leu Asn Pro Asp
    50                  55                  60

Ala Ser Ala Phe Lys Arg Asn Gly His Ser Ile Phe Arg Glu Leu Ser
65                  70                  75                  80

Leu Phe Gln Asp Tyr His Gly Leu Pro Ala Phe Lys Asp Ala Leu Val
                85                  90                  95

Gln Phe Met Ser Glu Ile Arg Gly Asn Lys Val Ser Phe Asp Ser Asn
                100                 105                 110

Lys Leu Val Leu Thr Ala Gly Ala Thr Ser Ala Asn Glu Thr Leu Met
            115                 120                 125

Phe Cys Leu Ala Asp Pro Gly His Ala Phe Leu Leu Pro Thr Pro Tyr
    130                 135                 140

Tyr Pro Gly Phe Asp Arg Asp Leu Lys Trp Arg Thr Gly Ala Glu Ile
145                 150                 155                 160

Val Pro Ile Gln Cys Thr Ser Ser Asn Gly Phe Arg Ile Thr Glu Ser
                165                 170                 175

Ala Leu Glu Glu Ala Tyr Thr Glu Ala Glu Arg Arg Asn Leu Arg Val
                180                 185                 190

Lys Gly Val Leu Val Thr Asn Pro Ser Asn Pro Leu Gly Thr Thr Leu
            195                 200                 205

Thr Lys Lys Glu Leu Gln Leu Leu Leu Thr Phe Val Ser Thr Lys Gln
    210                 215                 220

Ile His Leu Ile Ser Asp Glu Ile Tyr Ser Gly Thr Val Phe Asn Ser
225                 230                 235                 240

Pro Lys Phe Val Ser Val Met Glu Val Leu Ile Glu Asn Asn Tyr Met
                245                 250                 255
```

Tyr Thr Asp Val Trp Asp Arg Val His Ile Val Tyr Ser Leu Ser Lys
                260                 265                 270

Asp Leu Gly Leu Pro Gly Phe Arg Val Gly Ala Ile Tyr Ser Asn Asp
            275                 280                 285

Asp Arg Val Val Ser Ala Ala Thr Lys Met Ser Ser Phe Gly Leu Ile
        290                 295                 300

Ser Ser Gln Thr Gln Tyr Leu Leu Ser Ala Leu Leu Ser Asp Lys Lys
305                 310                 315                 320

Phe Thr Lys Asn Tyr Val Ser Glu Asn Gln Lys Arg Leu Lys Lys Arg
                325                 330                 335

His Glu Met Leu Val Gly Gly Leu Lys Gln Ile Gly Ile Arg Cys Leu
            340                 345                 350

Glu Ser Asn Ala Gly Leu Phe Cys Trp Val Asp Met Arg His Leu Leu
        355                 360                 365

Ser Ser Asn Thr Phe Asp Gly Glu Met Glu Leu Trp Lys Lys Ile Val
370                 375                 380

Tyr Glu Val Gly Leu Asn Ile Ser Ala Gly Ser Ser Cys His Cys Thr
385                 390                 395                 400

Glu Pro Gly Trp Phe Arg Ala Cys Phe Ala Asn Met Ser Glu Asp Thr
            405                 410                 415

Leu Asn Ile Ala Ile Gln Arg Leu Lys Ala Phe Val Asp Ser Arg Val
        420                 425                 430

Asn Asn Lys Asp Asp Ile Gln Asn Gln Gln Cys Ser Asn Lys Lys
            435                 440                 445

Lys Ser Phe Ser Lys Trp Val Phe Arg Leu Ser Phe Asn Glu Arg Gln
450                 455                 460

Arg Glu Arg
465

<210> SEQ ID NO 50
<211> LENGTH: 461
<212> TYPE: PRT
<213> ORGANISM: Oryza sativa japonica

<400> SEQUENCE: 50

Met Gly Gly Lys Leu Leu Pro Ala Ala Phe Ala Gly Ser Ala Pro
1               5                   10                  15

Pro Leu Ser Gln Val Ala Thr Ser Ala Ala His Gly Glu Asp Ser Pro
            20                  25                  30

Tyr Phe Ala Gly Trp Lys Ala Tyr Asp Glu Asp Pro Tyr His Ala Val
        35                  40                  45

Asp Asn Pro Asp Gly Val Ile Gln Met Gly Leu Ala Glu Asn Gln Val
    50                  55                  60

Ser Phe Asp Leu Leu Glu Ala Tyr Leu Arg Asp His Pro Glu Ala Ala
65                  70                  75                  80

Gly Trp Ser Thr Gly Gly Ala Gly Ala Gly Ser Phe Arg Asp Asn Ala
                85                  90                  95

Leu Phe Gln Asp Tyr His Gly Leu Lys Ser Phe Arg Lys Ala Met Ala
            100                 105                 110

Ser Phe Met Gly Lys Ile Arg Gly Gly Lys Ala Arg Phe Asp Pro Asp
        115                 120                 125

His Ile Val Leu Thr Ala Gly Ala Thr Ala Ala Asn Glu Leu Leu Thr
    130                 135                 140

Phe Ile Leu Ala Asn Pro Gly Asp Ala Leu Leu Ile Pro Thr Pro Tyr
145                 150                 155                 160

```
Tyr Pro Gly Phe Asp Arg Asp Leu Arg Trp Arg Thr Gly Val Asn Ile
            165                 170                 175

Val Pro Val Arg Cys Asp Ser Ala Asn Gly Phe Gln Val Thr Val Ala
            180                 185                 190

Ala Leu Gln Ala Ala Tyr Asp Glu Ala Ala Val Gly Met Arg Ala
            195                 200                 205

Arg Ala Val Leu Ile Thr Asn Pro Ser Asn Pro Leu Gly Thr Thr Val
210                 215                 220

Arg Arg Lys Met Leu Asp Asp Ile Leu Asp Phe Val Ser Arg Asn Asp
225                 230                 235                 240

Ile His Leu Ile Ser Asp Glu Ile Tyr Ser Gly Ser Val Phe Ala Ala
            245                 250                 255

Pro Asp Leu Val Ser Val Ala Glu Leu Val Glu Ala Arg Gly Gly Asp
            260                 265                 270

Gly Ile Ala Gly Arg Val His Ile Val Tyr Ser Leu Ser Lys Asp Leu
            275                 280                 285

Gly Leu Pro Gly Phe Arg Val Gly Val Val Tyr Ser Tyr Asn Asp Ala
            290                 295                 300

Val Val Thr Ala Ala Arg Arg Met Ser Ser Phe Thr Leu Val Ser Ser
305                 310                 315                 320

Gln Thr Gln Lys Thr Leu Ala Ala Met Leu Ser Asp Glu Ala Phe Ala
            325                 330                 335

Gly Glu Tyr Ile Arg Thr Asn Arg Arg Leu Arg Glu Arg His Glu
            340                 345                 350

His Val Val Ala Gly Leu Ala Arg Ala Gly Val Pro Cys Leu Arg Gly
            355                 360                 365

Asn Ala Gly Leu Phe Val Trp Met Asp Met Arg Leu Leu Gly
            370                 375                 380

Gly Gly Gly Val Gly Gly Glu Leu Arg Leu Trp Glu Lys Leu Leu Arg
385                 390                 395                 400

Gln Ala Lys Leu Asn Ile Ser Pro Gly Ser Ser Cys His Cys Ser Glu
            405                 410                 415

Ala Gly Trp Phe Arg Val Cys Phe Ala Asn Met Ser Leu Asp Thr Leu
            420                 425                 430

Asp Leu Ala Leu His Arg Ile Ser Arg Phe Met Asp Thr Trp Asn Gly
            435                 440                 445

Thr Lys Gln Gln Ala Ser Cys Gln Gln Gln Glu Gln
            450                 455                 460

<210> SEQ ID NO 51
<211> LENGTH: 461
<212> TYPE: PRT
<213> ORGANISM: Oryza sativa japonica

<400> SEQUENCE: 51

Met Gly Gly Lys Leu Leu Pro Ala Ala Phe Ala Gly Ser Ala Pro
1               5                   10                  15

Pro Leu Ser Gln Val Ala Thr Ser Ala Ala His Gly Glu Asp Ser Pro
            20                  25                  30

Tyr Phe Ala Gly Trp Lys Ala Tyr Asp Glu Asp Pro His Ala Val
            35                  40                  45

Asp Asn Pro Asp Gly Val Ile Gln Met Gly Leu Ala Glu Asn Gln Val
50                  55                  60

Ser Phe Asp Leu Leu Glu Ala Tyr Leu Arg Asp His Pro Glu Ala Ala
```

```
            65                  70                  75                  80
        Gly Trp Ser Thr Gly Gly Ala Gly Ala Gly Ser Phe Arg Asp Asn Ala
                            85                  90                  95

Leu Phe Gln Asp Tyr His Gly Leu Lys Ser Phe Arg Lys Ala Met Ala
                        100                 105                 110

Ser Phe Met Gly Lys Ile Arg Gly Lys Ala Arg Phe Asp Pro Asp
                    115                 120                 125

His Ile Val Leu Thr Ala Gly Ala Thr Ala Ala Asn Glu Leu Leu Thr
                130                 135                 140

Phe Ile Leu Ala Asn Pro Gly Asp Ala Leu Leu Ile Pro Thr Pro Tyr
        145                 150                 155                 160

Tyr Pro Gly Phe Asp Arg Asp Leu Arg Trp Arg Thr Gly Val Asn Ile
                        165                 170                 175

Val Pro Val Arg Cys Asp Ser Ala Asn Gly Phe Gln Val Thr Val Ala
                    180                 185                 190

Ala Leu Gln Ala Ala Tyr Asp Glu Ala Ala Val Gly Met Arg Ala
                195                 200                 205

Arg Ala Val Leu Ile Thr Asn Pro Ser Asn Pro Leu Gly Thr Thr Val
        210                 215                 220

Arg Arg Lys Met Leu Asp Asp Ile Leu Asp Phe Val Ser Arg Asn Asp
        225                 230                 235                 240

Ile His Leu Ile Ser Asp Glu Ile Tyr Ser Gly Ser Val Phe Ala Ala
                        245                 250                 255

Pro Asp Leu Val Ser Val Ala Glu Leu Val Glu Ala Arg Gly Gly Asp
                    260                 265                 270

Gly Ile Ala Gly Arg Val His Ile Val Tyr Ser Leu Ser Lys Asp Leu
                275                 280                 285

Gly Leu Pro Gly Phe Arg Val Gly Val Val Tyr Ser Tyr Asn Asp Ala
                290                 295                 300

Val Val Thr Ala Ala Arg Arg Met Ser Ser Phe Thr Leu Val Ser Ser
        305                 310                 315                 320

Gln Thr Gln Lys Thr Leu Ala Ala Met Leu Ser Asp Glu Ala Phe Ala
                        325                 330                 335

Gly Glu Tyr Ile Arg Thr Asn Arg Arg Leu Arg Glu Arg His Glu
                    340                 345                 350

His Val Val Ala Gly Leu Ala Arg Ala Gly Val Pro Cys Leu Arg Gly
                355                 360                 365

Asn Ala Gly Leu Phe Val Trp Met Asp Met Arg Arg Leu Leu Leu Gly
                370                 375                 380

Gly Gly Gly Val Gly Gly Glu Leu Arg Leu Trp Glu Lys Leu Leu Arg
        385                 390                 395                 400

Gln Ala Lys Leu Asn Ile Ser Pro Gly Ser Ser Cys His Cys Ser Glu
                        405                 410                 415

Ala Gly Trp Phe Arg Val Cys Phe Ala Asn Met Ser Leu Asp Thr Leu
                    420                 425                 430

Asp Leu Ala Leu His Arg Ile Ser Arg Phe Met Asp Thr Trp Asn Gly
                435                 440                 445

Thr Lys Gln Gln Ala Ser Cys Gln Gln Glu Gln Gln
                450                 455                 460

<210> SEQ ID NO 52
<211> LENGTH: 461
<212> TYPE: PRT
<213> ORGANISM: Oryza sativa indica
```

<400> SEQUENCE: 52

```
Met Gly Gly Lys Leu Leu Pro Ala Ala Ala Phe Ala Gly Ser Ala Pro
1               5                   10                  15

Pro Leu Ser Gln Val Ala Thr Ser Ala Ala His Gly Glu Asp Ser Pro
            20                  25                  30

Tyr Phe Ala Gly Trp Lys Ala Tyr Asp Glu Asp Pro Tyr His Ala Val
        35                  40                  45

Asp Asn Pro Asp Gly Val Ile Gln Met Gly Leu Ala Glu Asn Gln Val
    50                  55                  60

Ser Phe Asp Leu Leu Glu Ala Tyr Leu Arg Asp His Pro Glu Ala Ala
65                  70                  75                  80

Gly Trp Ser Thr Gly Ala Gly Ala Gly Ser Phe Arg Asp Asn Ala
                85                  90                  95

Leu Phe Gln Asp Tyr His Gly Leu Lys Ser Phe Arg Lys Ala Met Ala
                100                 105                 110

Ser Phe Met Gly Lys Ile Arg Gly Gly Lys Ala Arg Phe Asp Pro Asp
                115                 120                 125

His Ile Val Leu Thr Ala Gly Ala Thr Ala Ala Asn Glu Leu Leu Thr
                130                 135                 140

Phe Ile Leu Ala Asn Pro Gly Asp Ala Leu Leu Ile Pro Thr Pro Tyr
145                 150                 155                 160

Tyr Pro Gly Phe Asp Arg Asp Leu Arg Trp Arg Thr Gly Val Asn Ile
                165                 170                 175

Val Pro Val Arg Cys Asp Ser Ala Asn Gly Phe Gln Val Thr Val Ala
                180                 185                 190

Ala Leu Gln Ala Ala Tyr Asp Glu Ala Ala Ala Gly Met Arg Ala
                195                 200                 205

Arg Ala Val Leu Ile Thr Asn Pro Ser Asn Pro Leu Gly Thr Thr Val
                210                 215                 220

Arg Arg Lys Val Leu Asp Asp Ile Leu Asp Phe Val Ser Arg Asn Asp
225                 230                 235                 240

Ile His Leu Ile Ser Asp Glu Ile Tyr Ser Gly Ser Val Phe Ala Ala
                245                 250                 255

Pro Asp Leu Val Ser Val Ala Glu Leu Val Glu Ala Arg Asp Gly Asp
                260                 265                 270

Gly Ile Ala Gly Arg Val His Ile Val Tyr Ser Leu Ser Lys Asp Leu
                275                 280                 285

Gly Leu Pro Gly Phe Arg Val Gly Val Val Tyr Ser Tyr Asn Asp Ala
                290                 295                 300

Val Val Thr Ala Ala Arg Arg Met Ser Ser Phe Thr Leu Val Ser Ser
305                 310                 315                 320

Gln Thr Gln Lys Thr Leu Ala Ala Met Leu Ser Asp Glu Ala Phe Ala
                325                 330                 335

Gly Glu Tyr Ile Arg Thr Asn Arg Arg Leu Arg Glu Arg His Glu
                340                 345                 350

His Val Val Ala Gly Leu Ala Arg Ala Gly Val Pro Cys Leu Arg Gly
                355                 360                 365

Asn Ala Gly Leu Phe Val Trp Met Asp Met Arg Arg Leu Leu Leu Gly
                370                 375                 380

Gly Gly Gly Val Gly Ser Glu Leu Arg Leu Trp Glu Lys Leu Leu Arg
385                 390                 395                 400

Glu Ala Lys Leu Asn Ile Ser Pro Gly Ser Ser Cys His Cys Ser Glu
```

```
            405                 410                 415
Ala Gly Trp Phe Arg Val Cys Phe Ala Asn Met Ser Leu Asp Thr Leu
            420                 425                 430

Asp Leu Ala Leu His Arg Ile Ser Arg Phe Met Asp Thr Trp Asn Gly
            435                 440                 445

Thr Lys Gln Gln Ala Ser Cys Gln Gln Gln Glu Gln Gln
            450                 455                 460

<210> SEQ ID NO 53
<211> LENGTH: 447
<212> TYPE: PRT
<213> ORGANISM: Arabidopsis thaliana

<400> SEQUENCE: 53

Met Gly Leu Pro Leu Met Met Glu Arg Ser Ser Asn Asn Asn Asn Val
1               5                   10                  15

Glu Leu Ser Arg Val Ala Val Ser Asp Thr His Gly Glu Asp Ser Pro
            20                  25                  30

Tyr Phe Ala Gly Trp Lys Ala Tyr Asp Glu Asn Pro Tyr Asp Glu Ser
        35                  40                  45

His Asn Pro Ser Gly Val Ile Gln Met Gly Leu Ala Glu Asn Gln Val
    50                  55                  60

Ser Phe Asp Leu Leu Glu Thr Tyr Leu Glu Lys Lys Asn Pro Glu Gly
65                  70                  75                  80

Ser Met Trp Gly Ser Lys Gly Ala Pro Gly Phe Arg Glu Asn Ala Leu
                85                  90                  95

Phe Gln Asp Tyr His Gly Leu Lys Thr Phe Arg Gln Ala Met Ala Ser
            100                 105                 110

Phe Met Glu Gln Ile Arg Gly Gly Lys Ala Arg Phe Asp Pro Asp Arg
        115                 120                 125

Ile Val Leu Thr Ala Gly Ala Thr Ala Ala Asn Glu Leu Leu Thr Phe
    130                 135                 140

Ile Leu Ala Asp Pro Asn Asp Ala Leu Leu Val Pro Thr Pro Tyr Tyr
145                 150                 155                 160

Pro Gly Phe Asp Arg Asp Leu Arg Trp Arg Thr Gly Val Lys Ile Val
                165                 170                 175

Pro Ile His Cys Asp Ser Ser Asn His Phe Gln Ile Thr Pro Glu Ala
            180                 185                 190

Leu Glu Ser Ala Tyr Gln Thr Ala Arg Asp Ala Asn Ile Arg Val Arg
        195                 200                 205

Gly Val Leu Ile Thr Asn Pro Ser Asn Pro Leu Gly Ala Thr Val Gln
    210                 215                 220

Lys Lys Val Leu Glu Asp Leu Leu Asp Phe Cys Val Arg Lys Asn Ile
225                 230                 235                 240

His Leu Val Ser Asp Glu Ile Tyr Ser Gly Ser Val Phe His Ala Ser
                245                 250                 255

Glu Phe Thr Ser Val Ala Glu Ile Val Glu Asn Ile Asp Asp Val Ser
            260                 265                 270

Val Lys Glu Arg Val His Ile Val Tyr Ser Leu Ser Lys Asp Leu Gly
        275                 280                 285

Leu Pro Gly Phe Arg Val Gly Thr Ile Tyr Ser Tyr Asn Asp Asn Val
    290                 295                 300

Val Arg Thr Ala Arg Arg Met Ser Ser Phe Thr Leu Val Ser Ser Gln
305                 310                 315                 320
```

```
Thr Gln His Met Leu Ala Ser Met Leu Ser Asp Glu Glu Phe Thr Glu
            325                 330                 335

Lys Tyr Ile Arg Ile Asn Arg Glu Arg Leu Arg Arg Tyr Asp Thr
        340                 345                 350

Ile Val Glu Gly Leu Lys Lys Ala Gly Ile Glu Cys Leu Lys Gly Asn
            355                 360                 365

Ala Gly Leu Phe Cys Trp Met Asn Leu Gly Phe Leu Leu Glu Lys Lys
        370                 375                 380

Thr Lys Asp Gly Glu Leu Gln Leu Trp Asp Val Ile Leu Lys Glu Leu
385                 390                 395                 400

Asn Leu Asn Ile Ser Pro Gly Ser Ser Cys His Cys Ser Glu Val Gly
            405                 410                 415

Trp Phe Arg Val Cys Phe Ala Asn Met Ser Glu Asn Thr Leu Glu Ile
        420                 425                 430

Ala Leu Lys Arg Ile His Glu Phe Met Asp Arg Arg Arg Phe
        435                 440                 445

<210> SEQ ID NO 54
<211> LENGTH: 1173
<212> TYPE: DNA
<213> ORGANISM: Zea mays

<400> SEQUENCE: 54 ggccgcccctt tttttttttt tttttttttt tttttttgata tgtaaactgg tcttttattc      60
acccttgagc tacgccttct gtgtcctgaa gttacgtgac aggttttcaa caacaattga     120
tcgggaggtc taaattacca tacccgatcg ttattctacc gtgtactaac gttaaaccaa     180
accatacatg cgatttggca aaacagaaaa aagaacatat atacacgaaa aaatcgagga     240
caaatgcgtc ctgcttgact agctgcttac cgccgacgcc tgctgacgcc tgtgcaacgt     300
ctctgtgtaa tgtcaagcta gctactaatg ccctttatta gtcttgtcta atatttttg      360 tccacttgtt tgcagttatg tgagggcaca ccctacagcc agtcttaccg aacgctcggt     420
gactagctag ctggcgtgga ccatcgggga ctgcggcgac agcaacgcca aggggctggg     480
gatggcgagg tgcgaagcgg tggttgctcc ccggcgcggc aagctgaggc ggaggggccg     540
cgtggccgcc cagcgctcgg ccttggcctt gctgtgctgg tgctggcgca cgaagcggcg     600
gatccggtcg agcgcgacct ccatggtgtc gtcgtccatg ttggcgtagc agacgcggaa     660
ccagccgggc tcgttgcagt ggaacgacgt gccgggcgac acgttgagct tcaccctgtg     720
tacgatgacc cgcccacagct ccagctccgc gtcgtgcgtc ctctcccgga gcatgccccg     780
caggtccatc cacgagaaga ggcccgcgtt gcccggcagg cacgcgatgc cgacctcgcg     840
gaggcccgcg acgaagcggt cgtggcgcgc gccagccgc cgcgcgctct ccgcgaggaa     900
gcgtgccatg aactccgcgt cggcgagcat catcgccagg aagtgctgcg tctgcgacga     960
gacgaggccg aagctggaca tcttgcgcgc gcaggccacc acgtcgtcgt tgtaggagta    1020
gacgatgccg acgcggaagc ccgggaggcc gaagtccttg gagaggctgt acgcgatgtg    1080
gacgaggtcc ctgttgcagc ccggggcgtc gccgcgctcg atgacctcgg cgatgctcac    1140
gaagcccggc ttggcgaaga cggagcccgc gta                                 1173

<210> SEQ ID NO 55
<211> LENGTH: 600
<212> TYPE: DNA
<213> ORGANISM: Zea mays

<400> SEQUENCE: 55
```

```
gatccgccgc ttcgtgcgcc agcaccagca cagcaaggcc aaggccgagc gctgggcggc      60
cacgcggccc ctccgcctca gcttgccgcg ccggggagca accaccgctt cgcacctcgc     120
catccccagc cccttggcgt tgctgtcgcc gcagtccccg atggtccacg ccagctagct     180
agtcaccgag cgttcggtaa gactggctgt agggtgtgcc ctcacataac tgcaaacaag     240
tggacaaaaa atattagaca agactaataa agggcattag tagctagctt gacattacac     300
agagacgttg cacaggcgtc agcaggcgtc ggcggtaagc agctagtcaa gcaggacgca     360
tttgtcctcg atttttttcgt gtatatatgt tcttttttct gttttgccaa atcgcatgta    420
tggtttggtt taacgttagt acacggtaga ataacgatcg ggtatggtaa tttagacctc     480
ccgatcaatt gttgttgaaa acctgtcacg taacttcagg acacagaagg cgtagctcaa     540
gggtgaataa aagaccagtt tacatatcaa aaaaaaaaa aaaaaaaaa aaaaagggc         600
```

<210> SEQ ID NO 56
<211> LENGTH: 701
<212> TYPE: DNA
<213> ORGANISM: Zea mays

<400> SEQUENCE: 56

```
tagcagacgc ggaaccagcc gggctcccgg cagtggcagg aggagcccgg ggagatgttg      60
agccccacct cgaagaccac cttcttccac agctccatct cgccctcgaa cgaccggctc     120
cgcatcaggc gccgcatgtt gacccagcag aagagcccg cgttgctctc caggcactcg      180
atgcccacgg ccgccaggcc ctcgccagc tgctcgcgcc gctccctgat ccgccgcgtg       240
ttctccgcga tgtacctccg cgtgaagtcc ctgtcgccca ggagcgacgc caggaggtgc     300
tgcgtctggg acgacaccag gccgaagctc gacatcttgg tggccgcgga gaccacgccg     360
gcgttggacg agtagatggc gccccacgcgg aaccccggga ggcccaggtc cttggacagg   420
ctgtacacca cgtgcacgcg gtccgacagc ggcccaacgc cgacgacgcc gtcgtccgtg     480
gcggcgcgcg cggccaccac ctcgaggacg ctcacgaagc ccgggtccgc gaagaccgtg     540
cccgagtata tctcgtcgct caccaggtgg atgcccttgg cggccacgaa gtccaccagc     600
atctccaggt cggcgcgcgg cgacgtggtg cccagcgggt tggaagggtt ggtgatgagc     660
acgcccttga cgcgcagccg cagcttctgc gcgcgccggt a                          701
```

<210> SEQ ID NO 57
<211> LENGTH: 489
<212> TYPE: DNA
<213> ORGANISM: Zea mays

<400> SEQUENCE: 57

```
cgcgccgcca cggacgacgg cgtcgtcggc gttgggccgc tgtcggaccg cgtgcacgtg      60
gtgtacagcc tgtccaagga cctgggcctc ccggggttcc gcgtgggcgc catctactcg     120
tccaacgccg cgtggtctc cgcggccacc aagatgtcga gcttcggcct ggtgtcgtcc      180
cagacgcagc acctcctggc gtcgctcctg ggcgacaggg acttcacgcg gaggtacatc     240
gcggagaaca cgcggcggat cagggagcgg cgcgagcagc tggcggaggg cctggcggcc     300
gtgggcatcg agtgcctgga gagcaacgcg ggctcttct gctgggtcaa catgcggcgc      360
ctgatgcgga gccggtcgtt cgagggcgag atggagctgt ggaagaaggt ggtcttcgag     420
gtggggctca acatctcccc gggctcctcc tgccactgcc gggagccggg ctggttccgc     480
gtctgctaa                                                             489
```

```
<210> SEQ ID NO 58
<211> LENGTH: 524
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE
<222> LOCATION: (1)..(17)
<223> OTHER INFORMATION: Xaa is non-conserved residue
<220> FEATURE:
<221> NAME/KEY: MISC_FEATURE
<222> LOCATION: (20)..(26)
<223> OTHER INFORMATION: Xaa is non-conserved residue
<220> FEATURE:
<221> NAME/KEY: MISC_FEATURE
<222> LOCATION: (29)..(30)
<223> OTHER INFORMATION: Xaa is non-conserved residue
<220> FEATURE:
<221> NAME/KEY: MISC_FEATURE
<222> LOCATION: (32)..(32)
<223> OTHER INFORMATION: Xaa is non-conserved residue
<220> FEATURE:
<221> NAME/KEY: MISC_FEATURE
<222> LOCATION: (35)..(35)
<223> OTHER INFORMATION: Xaa is non-conserved residue
<220> FEATURE:
<221> NAME/KEY: MISC_FEATURE
<222> LOCATION: (38)..(39)
<223> OTHER INFORMATION: Xaa is non-conserved residue
<220> FEATURE:
<221> NAME/KEY: MISC_FEATURE
<222> LOCATION: (41)..(43)
<223> OTHER INFORMATION: Xaa is non-conserved residue
<220> FEATURE:
<221> NAME/KEY: MISC_FEATURE
<222> LOCATION: (45)..(49)
<223> OTHER INFORMATION: Xaa is non-conserved residue
<220> FEATURE:
<221> NAME/KEY: MISC_FEATURE
<222> LOCATION: (51)..(52)
<223> OTHER INFORMATION: Xaa is non-conserved residue
<220> FEATURE:
<221> NAME/KEY: MISC_FEATURE
<222> LOCATION: (54)..(54)
<223> OTHER INFORMATION: Xaa is non-conserved residue
<220> FEATURE:
<221> NAME/KEY: MISC_FEATURE
<222> LOCATION: (64)..(66)
<223> OTHER INFORMATION: Xaa is non-conserved residue
<220> FEATURE:
<221> NAME/KEY: MISC_FEATURE
<222> LOCATION: (69)..(77)
<223> OTHER INFORMATION: Xaa is non-conserved residue
<220> FEATURE:
<221> NAME/KEY: MISC_FEATURE
<222> LOCATION: (79)..(88)
<223> OTHER INFORMATION: Xaa is non-conserved residue
<220> FEATURE:
<221> NAME/KEY: MISC_FEATURE
<222> LOCATION: (90)..(92)
<223> OTHER INFORMATION: Xaa is non-conserved residue
<220> FEATURE:
<221> NAME/KEY: MISC_FEATURE
<222> LOCATION: (94)..(96)
<223> OTHER INFORMATION: Xaa is non-conserved residue
<220> FEATURE:
<221> NAME/KEY: MISC_FEATURE
<222> LOCATION: (98)..(98)
<223> OTHER INFORMATION: Xaa is non-conserved residue
<220> FEATURE:
<221> NAME/KEY: MISC_FEATURE
<222> LOCATION: (106)..(107)
<223> OTHER INFORMATION: Xaa is non-conserved residue
<220> FEATURE:
<221> NAME/KEY: MISC_FEATURE
<222> LOCATION: (109)..(110)
<223> OTHER INFORMATION: Xaa is non-conserved residue
```

```
<220> FEATURE:
<221> NAME/KEY: MISC_FEATURE
<222> LOCATION: (112)..(112)
<223> OTHER INFORMATION: Xaa is non-conserved residue
<220> FEATURE:
<221> NAME/KEY: MISC_FEATURE
<222> LOCATION: (114)..(114)
<223> OTHER INFORMATION: Xaa is non-conserved residue
<220> FEATURE:
<221> NAME/KEY: MISC_FEATURE
<222> LOCATION: (117)..(119)
<223> OTHER INFORMATION: Xaa is non-conserved residue
<220> FEATURE:
<221> NAME/KEY: MISC_FEATURE
<222> LOCATION: (122)..(125)
<223> OTHER INFORMATION: Xaa is non-conserved residue
<220> FEATURE:
<221> NAME/KEY: MISC_FEATURE
<222> LOCATION: (128)..(131)
<223> OTHER INFORMATION: Xaa is non-conserved residue
<220> FEATURE:
<221> NAME/KEY: MISC_FEATURE
<222> LOCATION: (133)..(135)
<223> OTHER INFORMATION: Xaa is non-conserved residue
<220> FEATURE:
<221> NAME/KEY: MISC_FEATURE
<222> LOCATION: (139)..(139)
<223> OTHER INFORMATION: Xaa is non-conserved residue
<220> FEATURE:
<221> NAME/KEY: MISC_FEATURE
<222> LOCATION: (141)..(141)
<223> OTHER INFORMATION: Xaa is non-conserved residue
<220> FEATURE:
<221> NAME/KEY: MISC_FEATURE
<222> LOCATION: (143)..(145)
<223> OTHER INFORMATION: Xaa is non-conserved residue
<220> FEATURE:
<221> NAME/KEY: MISC_FEATURE
<222> LOCATION: (147)..(147)
<223> OTHER INFORMATION: Xaa is non-conserved residue
<220> FEATURE:
<221> NAME/KEY: MISC_FEATURE
<222> LOCATION: (150)..(150)
<223> OTHER INFORMATION: Xaa is non-conserved residue
<220> FEATURE:
<221> NAME/KEY: MISC_FEATURE
<222> LOCATION: (153)..(153)
<223> OTHER INFORMATION: Xaa is non-conserved residue
<220> FEATURE:
<221> NAME/KEY: MISC_FEATURE
<222> LOCATION: (155)..(155)
<223> OTHER INFORMATION: Xaa is non-conserved residue
<220> FEATURE:
<221> NAME/KEY: MISC_FEATURE
<222> LOCATION: (157)..(157)
<223> OTHER INFORMATION: Xaa is non-conserved residue
<220> FEATURE:
<221> NAME/KEY: MISC_FEATURE
<222> LOCATION: (164)..(164)
<223> OTHER INFORMATION: Xaa is non-conserved residue
<220> FEATURE:
<221> NAME/KEY: MISC_FEATURE
<222> LOCATION: (169)..(170)
<223> OTHER INFORMATION: Xaa is non-conserved residue
<220> FEATURE:
<221> NAME/KEY: MISC_FEATURE
<222> LOCATION: (173)..(173)
<223> OTHER INFORMATION: Xaa is non-conserved residue
<220> FEATURE:
<221> NAME/KEY: MISC_FEATURE
<222> LOCATION: (175)..(178)
<223> OTHER INFORMATION: Xaa is non-conserved residue
<220> FEATURE:
<221> NAME/KEY: MISC_FEATURE
<222> LOCATION: (180)..(181)
<223> OTHER INFORMATION: Xaa is non-conserved residue
<220> FEATURE:
<221> NAME/KEY: MISC_FEATURE
<222> LOCATION: (183)..(183)
```

```
<223> OTHER INFORMATION: Xaa is non-conserved residue
<220> FEATURE:
<221> NAME/KEY: MISC_FEATURE
<222> LOCATION: (185)..(185)
<223> OTHER INFORMATION: Xaa is non-conserved residue
<220> FEATURE:
<221> NAME/KEY: MISC_FEATURE
<222> LOCATION: (187)..(187)
<223> OTHER INFORMATION: Xaa is non-conserved residue
<220> FEATURE:
<221> NAME/KEY: MISC_FEATURE
<222> LOCATION: (189)..(190)
<223> OTHER INFORMATION: Xaa is non-conserved residue
<220> FEATURE:
<221> NAME/KEY: MISC_FEATURE
<222> LOCATION: (192)..(193)
<223> OTHER INFORMATION: Xaa is non-conserved residue
<220> FEATURE:
<221> NAME/KEY: MISC_FEATURE
<222> LOCATION: (195)..(197)
<223> OTHER INFORMATION: Xaa is non-conserved residue
<220> FEATURE:
<221> NAME/KEY: MISC_FEATURE
<222> LOCATION: (200)..(201)
<223> OTHER INFORMATION: Xaa is non-conserved residue
<220> FEATURE:
<221> NAME/KEY: MISC_FEATURE
<222> LOCATION: (203)..(210)
<223> OTHER INFORMATION: Xaa is non-conserved residue
<220> FEATURE:
<221> NAME/KEY: MISC_FEATURE
<222> LOCATION: (212)..(215)
<223> OTHER INFORMATION: Xaa is non-conserved residue
<220> FEATURE:
<221> NAME/KEY: MISC_FEATURE
<222> LOCATION: (224)..(229)
<223> OTHER INFORMATION: Xaa is non-conserved residue
<220> FEATURE:
<221> NAME/KEY: MISC_FEATURE
<222> LOCATION: (231)..(235)
<223> OTHER INFORMATION: Xaa is non-conserved residue
<220> FEATURE:
<221> NAME/KEY: MISC_FEATURE
<222> LOCATION: (237)..(243)
<223> OTHER INFORMATION: Xaa is non-conserved residue
<220> FEATURE:
<221> NAME/KEY: MISC_FEATURE
<222> LOCATION: (246)..(247)
<223> OTHER INFORMATION: Xaa is non-conserved residue
<220> FEATURE:
<221> NAME/KEY: MISC_FEATURE
<222> LOCATION: (252)..(255)
<223> OTHER INFORMATION: Xaa is non-conserved residue
<220> FEATURE:
<221> NAME/KEY: MISC_FEATURE
<222> LOCATION: (257)..(264)
<223> OTHER INFORMATION: Xaa is non-conserved residue
<220> FEATURE:
<221> NAME/KEY: MISC_FEATURE
<222> LOCATION: (266)..(267)
<223> OTHER INFORMATION: Xaa is non-conserved residue
<220> FEATURE:
<221> NAME/KEY: MISC_FEATURE
<222> LOCATION: (269)..(290)
<223> OTHER INFORMATION: Xaa is non-conserved residue
<220> FEATURE:
<221> NAME/KEY: MISC_FEATURE
<222> LOCATION: (292)..(294)
<223> OTHER INFORMATION: Xaa is non-conserved residue
<220> FEATURE:
<221> NAME/KEY: MISC_FEATURE
<222> LOCATION: (300)..(300)
<223> OTHER INFORMATION: Xaa is non-conserved residue
<220> FEATURE:
<221> NAME/KEY: MISC_FEATURE
<222> LOCATION: (302)..(302)
<223> OTHER INFORMATION: Xaa is non-conserved residue
<220> FEATURE:
<221> NAME/KEY: MISC_FEATURE
```

-continued

```
<222> LOCATION: (309)..(310)
<223> OTHER INFORMATION: Xaa is non-conserved residue
<220> FEATURE:
<221> NAME/KEY: MISC_FEATURE
<222> LOCATION: (313)..(316)
<223> OTHER INFORMATION: Xaa is non-conserved residue
<220> FEATURE:
<221> NAME/KEY: MISC_FEATURE
<222> LOCATION: (319)..(320)
<223> OTHER INFORMATION: Xaa is non-conserved residue
<220> FEATURE:
<221> NAME/KEY: MISC_FEATURE
<222> LOCATION: (322)..(323)
<223> OTHER INFORMATION: Xaa is non-conserved residue
<220> FEATURE:
<221> NAME/KEY: MISC_FEATURE
<222> LOCATION: (328)..(328)
<223> OTHER INFORMATION: Xaa is non-conserved residue
<220> FEATURE:
<221> NAME/KEY: MISC_FEATURE
<222> LOCATION: (332)..(332)
<223> OTHER INFORMATION: Xaa is non-conserved residue
<220> FEATURE:
<221> NAME/KEY: MISC_FEATURE
<222> LOCATION: (336)..(337)
<223> OTHER INFORMATION: Xaa is non-conserved residue
<220> FEATURE:
<221> NAME/KEY: MISC_FEATURE
<222> LOCATION: (339)..(341)
<223> OTHER INFORMATION: Xaa is non-conserved residue
<220> FEATURE:
<221> NAME/KEY: MISC_FEATURE
<222> LOCATION: (343)..(343)
<223> OTHER INFORMATION: Xaa is non-conserved residue
<220> FEATURE:
<221> NAME/KEY: MISC_FEATURE
<222> LOCATION: (345)..(346)
<223> OTHER INFORMATION: Xaa is non-conserved residue
<220> FEATURE:
<221> NAME/KEY: MISC_FEATURE
<222> LOCATION: (348)..(357)
<223> OTHER INFORMATION: Xaa is non-conserved residue
<220> FEATURE:
<221> NAME/KEY: MISC_FEATURE
<222> LOCATION: (360)..(361)
<223> OTHER INFORMATION: Xaa is non-conserved residue
<220> FEATURE:
<221> NAME/KEY: MISC_FEATURE
<222> LOCATION: (363)..(368)
<223> OTHER INFORMATION: Xaa is non-conserved residue
<220> FEATURE:
<221> NAME/KEY: MISC_FEATURE
<222> LOCATION: (371)..(373)
<223> OTHER INFORMATION: Xaa is non-conserved residue
<220> FEATURE:
<221> NAME/KEY: MISC_FEATURE
<222> LOCATION: (376)..(377)
<223> OTHER INFORMATION: Xaa is non-conserved residue
<220> FEATURE:
<221> NAME/KEY: MISC_FEATURE
<222> LOCATION: (379)..(380)
<223> OTHER INFORMATION: Xaa is non-conserved residue
<220> FEATURE:
<221> NAME/KEY: MISC_FEATURE
<222> LOCATION: (386)..(386)
<223> OTHER INFORMATION: Xaa is non-conserved residue
<220> FEATURE:
<221> NAME/KEY: MISC_FEATURE
<222> LOCATION: (388)..(388)
<223> OTHER INFORMATION: Xaa is non-conserved residue
<220> FEATURE:
<221> NAME/KEY: MISC_FEATURE
<222> LOCATION: (390)..(390)
<223> OTHER INFORMATION: Xaa is non-conserved residue
<220> FEATURE:
<221> NAME/KEY: MISC_FEATURE
<222> LOCATION: (392)..(393)
<223> OTHER INFORMATION: Xaa is non-conserved residue
<220> FEATURE:
```

```
<221> NAME/KEY: MISC_FEATURE
<222> LOCATION: (395)..(402)
<223> OTHER INFORMATION: Xaa is non-conserved residue
<220> FEATURE:
<221> NAME/KEY: MISC_FEATURE
<222> LOCATION: (404)..(405)
<223> OTHER INFORMATION: Xaa is non-conserved residue
<220> FEATURE:
<221> NAME/KEY: MISC_FEATURE
<222> LOCATION: (408)..(415)
<223> OTHER INFORMATION: Xaa is non-conserved residue
<220> FEATURE:
<221> NAME/KEY: MISC_FEATURE
<222> LOCATION: (418)..(418)
<223> OTHER INFORMATION: Xaa is non-conserved residue
<220> FEATURE:
<221> NAME/KEY: MISC_FEATURE
<222> LOCATION: (422)..(422)
<223> OTHER INFORMATION: Xaa is non-conserved residue
<220> FEATURE:
<221> NAME/KEY: MISC_FEATURE
<222> LOCATION: (424)..(424)
<223> OTHER INFORMATION: Xaa is non-conserved residue
<220> FEATURE:
<221> NAME/KEY: MISC_FEATURE
<222> LOCATION: (427)..(427)
<223> OTHER INFORMATION: Xaa is non-conserved residue
<220> FEATURE:
<221> NAME/KEY: MISC_FEATURE
<222> LOCATION: (429)..(429)
<223> OTHER INFORMATION: Xaa is non-conserved residue
<220> FEATURE:
<221> NAME/KEY: MISC_FEATURE
<222> LOCATION: (436)..(436)
<223> OTHER INFORMATION: Xaa is non-conserved residue
<220> FEATURE:
<221> NAME/KEY: MISC_FEATURE
<222> LOCATION: (439)..(446)
<223> OTHER INFORMATION: Xaa is non-conserved residue
<220> FEATURE:
<221> NAME/KEY: MISC_FEATURE
<222> LOCATION: (448)..(449)
<223> OTHER INFORMATION: Xaa is non-conserved residue
<220> FEATURE:
<221> NAME/KEY: MISC_FEATURE
<222> LOCATION: (451)..(524)
<223> OTHER INFORMATION: X is non-conserved residue

<400> SEQUENCE: 58

Xaa Xaa Xaa Xaa Xaa Xaa Xaa Xaa Xaa Xaa Xaa Xaa Xaa Xaa Xaa
1               5                   10                  15

Xaa Leu Ser Xaa Xaa Xaa Xaa Xaa Xaa His Gly Xaa Xaa Ser Xaa
            20                  25                  30

Tyr Phe Xaa Gly Trp Xaa Xaa Tyr Xaa Xaa Pro Xaa Xaa Xaa Xaa
            35                  40                  45

Xaa Asn Xaa Xaa Gly Xaa Ile Gln Met Gly Leu Ala Glu Asn Gln Xaa
        50                  55                  60

Xaa Xaa Asp Leu Xaa Xaa Xaa Xaa Xaa Xaa Xaa Xaa Pro Xaa
65                  70                  75                  80

Xaa Xaa Xaa Xaa Xaa Xaa Xaa Xaa Gly Xaa Xaa Xaa Phe Xaa Xaa Xaa
                85                  90                  95

Ala Xaa Phe Gln Asp Tyr His Gly Leu Xaa Xaa Phe Xaa Xaa Ala Xaa
            100                 105                 110

Ala Xaa Phe Met Xaa Xaa Xaa Arg Gly Xaa Xaa Xaa Xaa Phe Asp Xaa
            115                 120                 125

Xaa Xaa Xaa Val Xaa Xaa Xaa Gly Ala Thr Xaa Ala Xaa Glu Xaa Xaa
            130                 135                 140

Xaa Phe Xaa Leu Ala Xaa Pro Gly Xaa Ala Xaa Leu Xaa Pro Thr Pro
145                 150                 155                 160
```

Tyr Tyr Pro Xaa Phe Asp Arg Asp Xaa Xaa Trp Arg Xaa Gly Xaa Xaa
                165                 170                 175

Xaa Xaa Pro Xaa Xaa Cys Xaa Ser Xaa Asn Xaa Phe Xaa Xaa Thr Xaa
            180                 185                 190

Xaa Ala Xaa Xaa Xaa Ala Tyr Xaa Xaa Ala Xaa Xaa Xaa Xaa Xaa Xaa
        195                 200                 205

Xaa Xaa Gly Xaa Xaa Xaa Xaa Asn Pro Ser Asn Pro Leu Gly Thr Xaa
    210                 215                 220

Xaa Xaa Xaa Xaa Xaa Leu Xaa Xaa Xaa Xaa Phe Xaa Xaa Xaa Xaa
225                 230                 235                 240

Xaa Xaa Xaa His Leu Xaa Xaa Asp Glu Ile Tyr Xaa Xaa Xaa Xaa Phe
            245                 250                 255

Xaa Xaa Xaa Xaa Xaa Xaa Xaa Ser Xaa Xaa Glu Xaa Xaa Xaa Xaa
            260                 265                 270

Xaa Xaa Xaa Xaa Xaa Xaa Xaa Xaa Xaa Xaa Xaa Xaa Xaa Xaa Xaa
            275                 280                 285

Xaa Xaa His Xaa Xaa Xaa Ser Leu Ser Lys Asp Xaa Gly Xaa Pro Gly
        290                 295                 300

Phe Arg Val Gly Xaa Xaa Tyr Ser Xaa Xaa Xaa Xaa Val Val Xaa Xaa
305                 310                 315                 320

Ala Xaa Xaa Met Ser Ser Phe Xaa Leu Val Ser Xaa Gln Thr Gln Xaa
                325                 330                 335

Xaa Leu Xaa Xaa Xaa Leu Xaa Asp Xaa Xaa Phe Xaa Xaa Xaa Xaa
            340                 345                 350

Xaa Xaa Xaa Xaa Xaa Arg Leu Xaa Xaa Arg Xaa Xaa Xaa Xaa Xaa Xaa
            355                 360                 365

Gly Leu Xaa Xaa Xaa Gly Ile Xaa Xaa Leu Xaa Xaa Asn Ala Gly Leu
    370                 375                 380

Phe Xaa Trp Xaa Asp Xaa Arg Xaa Xaa Leu Xaa Xaa Xaa Xaa Xaa Xaa
385                 390                 395                 400

Xaa Xaa Glu Xaa Xaa Leu Trp Xaa Xaa Xaa Xaa Xaa Xaa Xaa Xaa Leu
            405                 410                 415

Asn Xaa Ser Pro Gly Xaa Ser Xaa His Cys Xaa Glu Xaa Gly Trp Phe
            420                 425                 430

Arg Val Cys Xaa Ala Asn Xaa Xaa Xaa Xaa Xaa Xaa Xaa Ala Xaa
            435                 440                 445

Xaa Arg Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa
            515                 520

<210> SEQ ID NO 59
<211> LENGTH: 524
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE

```
<222> LOCATION: (1)..(17)
<223> OTHER INFORMATION: Xaa is non-conserved residue
<220> FEATURE:
<221> NAME/KEY: MISC_FEATURE
<222> LOCATION: (20)..(26)
<223> OTHER INFORMATION: Xaa is non-conserved residue
<220> FEATURE:
<221> NAME/KEY: MISC_FEATURE
<222> LOCATION: (30)..(30)
<223> OTHER INFORMATION: Xaa is non-conserved residue
<220> FEATURE:
<221> NAME/KEY: MISC_FEATURE
<222> LOCATION: (32)..(32)
<223> OTHER INFORMATION: Xaa is non-conserved residue
<220> FEATURE:
<221> NAME/KEY: MISC_FEATURE
<222> LOCATION: (35)..(35)
<223> OTHER INFORMATION: Xaa is non-conserved residue
<220> FEATURE:
<221> NAME/KEY: MISC_FEATURE
<222> LOCATION: (38)..(39)
<223> OTHER INFORMATION: Xaa is non-conserved residue
<220> FEATURE:
<221> NAME/KEY: MISC_FEATURE
<222> LOCATION: (41)..(43)
<223> OTHER INFORMATION: Xaa is non-conserved residue
<220> FEATURE:
<221> NAME/KEY: MISC_FEATURE
<222> LOCATION: (46)..(49)
<223> OTHER INFORMATION: Xaa is non-conserved residue
<220> FEATURE:
<221> NAME/KEY: MISC_FEATURE
<222> LOCATION: (51)..(52)
<223> OTHER INFORMATION: Xaa is non-conserved residue
<220> FEATURE:
<221> NAME/KEY: MISC_FEATURE
<222> LOCATION: (64)..(66)
<223> OTHER INFORMATION: Xaa is non-conserved residue
<220> FEATURE:
<221> NAME/KEY: MISC_FEATURE
<222> LOCATION: (70)..(71)
<223> OTHER INFORMATION: Xaa is non-conserved residue
<220> FEATURE:
<221> NAME/KEY: MISC_FEATURE
<222> LOCATION: (73)..(77)
<223> OTHER INFORMATION: Xaa is non-conserved residue
<220> FEATURE:
<221> NAME/KEY: MISC_FEATURE
<222> LOCATION: (79)..(88)
<223> OTHER INFORMATION: Xaa is non-conserved residue
<220> FEATURE:
<221> NAME/KEY: MISC_FEATURE
<222> LOCATION: (90)..(92)
<223> OTHER INFORMATION: Xaa is non-conserved residue
<220> FEATURE:
<221> NAME/KEY: MISC_FEATURE
<222> LOCATION: (94)..(96)
<223> OTHER INFORMATION: Xaa is non-conserved residue
<220> FEATURE:
<221> NAME/KEY: MISC_FEATURE
<222> LOCATION: (98)..(98)
<223> OTHER INFORMATION: Xaa is non-conserved residue
<220> FEATURE:
<221> NAME/KEY: MISC_FEATURE
<222> LOCATION: (106)..(107)
<223> OTHER INFORMATION: Xaa is non-conserved residue
<220> FEATURE:
<221> NAME/KEY: MISC_FEATURE
<222> LOCATION: (110)..(110)
<223> OTHER INFORMATION: Xaa is non-conserved residue
<220> FEATURE:
<221> NAME/KEY: MISC_FEATURE
<222> LOCATION: (112)..(112)
<223> OTHER INFORMATION: Xaa is non-conserved residue
<220> FEATURE:
<221> NAME/KEY: MISC_FEATURE
<222> LOCATION: (114)..(114)
<223> OTHER INFORMATION: Xaa is non-conserved residue
<220> FEATURE:
```

```
<221> NAME/KEY: MISC_FEATURE
<222> LOCATION: (117)..(119)
<223> OTHER INFORMATION: Xaa is non-conserved residue
<220> FEATURE:
<221> NAME/KEY: MISC_FEATURE
<222> LOCATION: (122)..(122)
<223> OTHER INFORMATION: Xaa is non-conserved residue
<220> FEATURE:
<221> NAME/KEY: MISC_FEATURE
<222> LOCATION: (124)..(125)
<223> OTHER INFORMATION: Xaa is non-conserved residue
<220> FEATURE:
<221> NAME/KEY: MISC_FEATURE
<222> LOCATION: (128)..(130)
<223> OTHER INFORMATION: Xaa is non-conserved residue
<220> FEATURE:
<221> NAME/KEY: MISC_FEATURE
<222> LOCATION: (134)..(135)
<223> OTHER INFORMATION: Xaa is non-conserved residue
<220> FEATURE:
<221> NAME/KEY: MISC_FEATURE
<222> LOCATION: (139)..(139)
<223> OTHER INFORMATION: Xaa is non-conserved residue
<220> FEATURE:
<221> NAME/KEY: MISC_FEATURE
<222> LOCATION: (141)..(141)
<223> OTHER INFORMATION: Xaa is non-conserved residue
<220> FEATURE:
<221> NAME/KEY: MISC_FEATURE
<222> LOCATION: (143)..(143)
<223> OTHER INFORMATION: Xaa is non-conserved residue
<220> FEATURE:
<221> NAME/KEY: MISC_FEATURE
<222> LOCATION: (145)..(145)
<223> OTHER INFORMATION: Xaa is non-conserved residue
<220> FEATURE:
<221> NAME/KEY: MISC_FEATURE
<222> LOCATION: (147)..(147)
<223> OTHER INFORMATION: Xaa is non-conserved residue
<220> FEATURE:
<221> NAME/KEY: MISC_FEATURE
<222> LOCATION: (150)..(150)
<223> OTHER INFORMATION: Xaa is non-conserved residue
<220> FEATURE:
<221> NAME/KEY: MISC_FEATURE
<222> LOCATION: (155)..(155)
<223> OTHER INFORMATION: Xaa is non-conserved residue
<220> FEATURE:
<221> NAME/KEY: MISC_FEATURE
<222> LOCATION: (164)..(164)
<223> OTHER INFORMATION: Xaa is non-conserved residue
<220> FEATURE:
<221> NAME/KEY: MISC_FEATURE
<222> LOCATION: (169)..(170)
<223> OTHER INFORMATION: Xaa is non-conserved residue
<220> FEATURE:
<221> NAME/KEY: MISC_FEATURE
<222> LOCATION: (173)..(173)
<223> OTHER INFORMATION: Xaa is non-conserved residue
<220> FEATURE:
<221> NAME/KEY: MISC_FEATURE
<222> LOCATION: (175)..(176)
<223> OTHER INFORMATION: Xaa is non-conserved residue
<220> FEATURE:
<221> NAME/KEY: MISC_FEATURE
<222> LOCATION: (181)..(181)
<223> OTHER INFORMATION: Xaa is non-conserved residue
<220> FEATURE:
<221> NAME/KEY: MISC_FEATURE
<222> LOCATION: (183)..(183)
<223> OTHER INFORMATION: Xaa is non-conserved residue
<220> FEATURE:
<221> NAME/KEY: MISC_FEATURE
<222> LOCATION: (185)..(185)
<223> OTHER INFORMATION: Xaa is non-conserved residue
<220> FEATURE:
<221> NAME/KEY: MISC_FEATURE
<222> LOCATION: (187)..(187)
<223> OTHER INFORMATION: Xaa is non-conserved residue
```

```
<220> FEATURE:
<221> NAME/KEY: MISC_FEATURE
<222> LOCATION: (189)..(189)
<223> OTHER INFORMATION: Xaa is non-conserved residue
<220> FEATURE:
<221> NAME/KEY: MISC_FEATURE
<222> LOCATION: (192)..(193)
<223> OTHER INFORMATION: Xaa is non-conserved residue
<220> FEATURE:
<221> NAME/KEY: MISC_FEATURE
<222> LOCATION: (196)..(197)
<223> OTHER INFORMATION: Xaa is non-conserved residue
<220> FEATURE:
<221> NAME/KEY: MISC_FEATURE
<222> LOCATION: (200)..(201)
<223> OTHER INFORMATION: Xaa is non-conserved residue
<220> FEATURE:
<221> NAME/KEY: MISC_FEATURE
<222> LOCATION: (203)..(208)
<223> OTHER INFORMATION: Xaa is non-conserved residue
<220> FEATURE:
<221> NAME/KEY: MISC_FEATURE
<222> LOCATION: (215)..(215)
<223> OTHER INFORMATION: Xaa is non-conserved residue
<220> FEATURE:
<221> NAME/KEY: MISC_FEATURE
<222> LOCATION: (224)..(226)
<223> OTHER INFORMATION: Xaa is non-conserved residue
<220> FEATURE:
<221> NAME/KEY: MISC_FEATURE
<222> LOCATION: (228)..(229)
<223> OTHER INFORMATION: Xaa is non-conserved residue
<220> FEATURE:
<221> NAME/KEY: MISC_FEATURE
<222> LOCATION: (231)..(232)
<223> OTHER INFORMATION: Xaa is non-conserved residue
<220> FEATURE:
<221> NAME/KEY: MISC_FEATURE
<222> LOCATION: (234)..(235)
<223> OTHER INFORMATION: Xaa is non-conserved residue
<220> FEATURE:
<221> NAME/KEY: MISC_FEATURE
<222> LOCATION: (237)..(242)
<223> OTHER INFORMATION: Xaa is non-conserved residue
<220> FEATURE:
<221> NAME/KEY: MISC_FEATURE
<222> LOCATION: (247)..(247)
<223> OTHER INFORMATION: Xaa is non-conserved residue
<220> FEATURE:
<221> NAME/KEY: MISC_FEATURE
<222> LOCATION: (252)..(255)
<223> OTHER INFORMATION: Xaa is non-conserved residue
<220> FEATURE:
<221> NAME/KEY: MISC_FEATURE
<222> LOCATION: (257)..(263)
<223> OTHER INFORMATION: Xaa is non-conserved residue
<220> FEATURE:
<221> NAME/KEY: MISC_FEATURE
<222> LOCATION: (267)..(267)
<223> OTHER INFORMATION: Xaa is non-conserved residue
<220> FEATURE:
<221> NAME/KEY: MISC_FEATURE
<222> LOCATION: (271)..(289)
<223> OTHER INFORMATION: Xaa is non-conserved residue
<220> FEATURE:
<221> NAME/KEY: MISC_FEATURE
<222> LOCATION: (293)..(294)
<223> OTHER INFORMATION: Xaa is non-conserved residue
<220> FEATURE:
<221> NAME/KEY: MISC_FEATURE
<222> LOCATION: (300)..(300)
<223> OTHER INFORMATION: Xaa is non-conserved residue
<220> FEATURE:
<221> NAME/KEY: MISC_FEATURE
<222> LOCATION: (302)..(302)
<223> OTHER INFORMATION: Xaa is non-conserved residue
<220> FEATURE:
<221> NAME/KEY: MISC_FEATURE
<222> LOCATION: (309)..(309)
```

```
<223> OTHER INFORMATION: Xaa is non-conserved residue
<220> FEATURE:
<221> NAME/KEY: MISC_FEATURE
<222> LOCATION: (313)..(314)
<223> OTHER INFORMATION: Xaa is non-conserved residue
<220> FEATURE:
<221> NAME/KEY: MISC_FEATURE
<222> LOCATION: (316)..(316)
<223> OTHER INFORMATION: Xaa is non-conserved residue
<220> FEATURE:
<221> NAME/KEY: MISC_FEATURE
<222> LOCATION: (319)..(320)
<223> OTHER INFORMATION: Xaa is non-conserved residue
<220> FEATURE:
<221> NAME/KEY: MISC_FEATURE
<222> LOCATION: (322)..(322)
<223> OTHER INFORMATION: Xaa is non-conserved residue
<220> FEATURE:
<221> NAME/KEY: MISC_FEATURE
<222> LOCATION: (328)..(328)
<223> OTHER INFORMATION: Xaa is non-conserved residue
<220> FEATURE:
<221> NAME/KEY: MISC_FEATURE
<222> LOCATION: (332)..(332)
<223> OTHER INFORMATION: Xaa is non-conserved residue
<220> FEATURE:
<221> NAME/KEY: MISC_FEATURE
<222> LOCATION: (336)..(337)
<223> OTHER INFORMATION: Xaa is non-conserved residue
<220> FEATURE:
<221> NAME/KEY: MISC_FEATURE
<222> LOCATION: (339)..(340)
<223> OTHER INFORMATION: Xaa is non-conserved residue
<220> FEATURE:
<221> NAME/KEY: MISC_FEATURE
<222> LOCATION: (343)..(343)
<223> OTHER INFORMATION: Xaa is non-conserved residue
<220> FEATURE:
<221> NAME/KEY: MISC_FEATURE
<222> LOCATION: (345)..(346)
<223> OTHER INFORMATION: Xaa is non-conserved residue
<220> FEATURE:
<221> NAME/KEY: MISC_FEATURE
<222> LOCATION: (348)..(350)
<223> OTHER INFORMATION: Xaa is non-conserved residue
<220> FEATURE:
<221> NAME/KEY: MISC_FEATURE
<222> LOCATION: (353)..(357)
<223> OTHER INFORMATION: Xaa is non-conserved residue
<220> FEATURE:
<221> NAME/KEY: MISC_FEATURE
<222> LOCATION: (360)..(361)
<223> OTHER INFORMATION: Xaa is non-conserved residue
<220> FEATURE:
<221> NAME/KEY: MISC_FEATURE
<222> LOCATION: (363)..(368)
<223> OTHER INFORMATION: Xaa is non-conserved residue
<220> FEATURE:
<221> NAME/KEY: MISC_FEATURE
<222> LOCATION: (371)..(373)
<223> OTHER INFORMATION: Xaa is non-conserved residue
<220> FEATURE:
<221> NAME/KEY: MISC_FEATURE
<222> LOCATION: (376)..(377)
<223> OTHER INFORMATION: Xaa is non-conserved residue
<220> FEATURE:
<221> NAME/KEY: MISC_FEATURE
<222> LOCATION: (379)..(380)
<223> OTHER INFORMATION: Xaa is non-conserved residue
<220> FEATURE:
<221> NAME/KEY: MISC_FEATURE
<222> LOCATION: (386)..(386)
<223> OTHER INFORMATION: Xaa is non-conserved residue
<220> FEATURE:
<221> NAME/KEY: MISC_FEATURE
<222> LOCATION: (388)..(388)
<223> OTHER INFORMATION: Xaa is non-conserved residue
<220> FEATURE:
<221> NAME/KEY: MISC_FEATURE
```

```
<222> LOCATION: (392)..(393)
<223> OTHER INFORMATION: Xaa is non-conserved residue
<220> FEATURE:
<221> NAME/KEY: MISC_FEATURE
<222> LOCATION: (395)..(402)
<223> OTHER INFORMATION: Xaa is non-conserved residue
<220> FEATURE:
<221> NAME/KEY: MISC_FEATURE
<222> LOCATION: (405)..(405)
<223> OTHER INFORMATION: Xaa is non-conserved residue
<220> FEATURE:
<221> NAME/KEY: MISC_FEATURE
<222> LOCATION: (408)..(409)
<223> OTHER INFORMATION: Xaa is non-conserved residue
<220> FEATURE:
<221> NAME/KEY: MISC_FEATURE
<222> LOCATION: (412)..(415)
<223> OTHER INFORMATION: Xaa is non-conserved residue
<220> FEATURE:
<221> NAME/KEY: MISC_FEATURE
<222> LOCATION: (422)..(422)
<223> OTHER INFORMATION: Xaa is non-conserved residue
<220> FEATURE:
<221> NAME/KEY: MISC_FEATURE
<222> LOCATION: (424)..(424)
<223> OTHER INFORMATION: Xaa is non-conserved residue
<220> FEATURE:
<221> NAME/KEY: MISC_FEATURE
<222> LOCATION: (427)..(427)
<223> OTHER INFORMATION: Xaa is non-conserved residue
<220> FEATURE:
<221> NAME/KEY: MISC_FEATURE
<222> LOCATION: (429)..(429)
<223> OTHER INFORMATION: Xaa is non-conserved residue
<220> FEATURE:
<221> NAME/KEY: MISC_FEATURE
<222> LOCATION: (440)..(443)
<223> OTHER INFORMATION: Xaa is non-conserved residue
<220> FEATURE:
<221> NAME/KEY: MISC_FEATURE
<222> LOCATION: (445)..(445)
<223> OTHER INFORMATION: Xaa is non-conserved residue
<220> FEATURE:
<221> NAME/KEY: MISC_FEATURE
<222> LOCATION: (449)..(449)
<223> OTHER INFORMATION: Xaa is non-conserved residue
<220> FEATURE:
<221> NAME/KEY: MISC_FEATURE
<222> LOCATION: (452)..(453)
<223> OTHER INFORMATION: Xaa is non-conserved residue
<220> FEATURE:
<221> NAME/KEY: MISC_FEATURE
<222> LOCATION: (455)..(524)
<223> OTHER INFORMATION: Xaa is non-conserved residue

<400> SEQUENCE: 59

Xaa Xaa Xaa Xaa Xaa Xaa Xaa Xaa Xaa Xaa Xaa Xaa Xaa Xaa Xaa Xaa
1               5                   10                  15

Xaa Leu Ser Xaa Xaa Xaa Xaa Xaa Xaa Xaa His Gly Glu Xaa Ser Xaa
            20                  25                  30

Tyr Phe Xaa Gly Trp Xaa Xaa Tyr Xaa Xaa Xaa Pro Phe Xaa Xaa Xaa
        35                  40                  45

Xaa Asn Xaa Xaa Gly Val Ile Gln Met Gly Leu Ala Glu Asn Gln Xaa
    50                  55                  60

Xaa Xaa Asp Leu Ile Xaa Xaa Trp Xaa Xaa Xaa Xaa Pro Xaa Xaa
65                  70                  75                  80

Xaa Xaa Xaa Xaa Xaa Xaa Xaa Gly Xaa Xaa Xaa Phe Xaa Xaa Xaa
                85                  90                  95

Ala Xaa Phe Gln Asp Tyr His Gly Leu Xaa Xaa Phe Arg Xaa Ala Xaa
            100                 105                 110

Ala Xaa Phe Met Xaa Xaa Xaa Arg Gly Xaa Lys Xaa Xaa Phe Asp Xaa
```

```
                115                 120                 125
Xaa Xaa Ile Val Met Xaa Xaa Gly Ala Thr Xaa Ala Xaa Glu Xaa Leu
            130                 135                 140

Xaa Phe Xaa Leu Ala Xaa Pro Gly Asp Ala Xaa Leu Val Pro Thr Pro
145                 150                 155                 160

Tyr Tyr Pro Xaa Phe Asp Arg Asp Xaa Xaa Trp Arg Xaa Gly Xaa Xaa
                165                 170                 175

Ile Val Pro Ile Xaa Cys Xaa Ser Xaa Asn Xaa Phe Xaa Ile Thr Xaa
            180                 185                 190

Xaa Ala Leu Xaa Xaa Ala Tyr Xaa Xaa Ala Xaa Xaa Xaa Xaa Xaa Xaa
                195                 200                 205

Val Lys Gly Val Leu Ile Xaa Asn Pro Ser Asn Pro Leu Gly Thr Xaa
            210                 215                 220

Xaa Xaa Arg Xaa Xaa Leu Xaa Xaa Leu Xaa Xaa Phe Xaa Xaa Xaa Xaa
225                 230                 235                 240

Xaa Xaa Ile His Leu Ile Xaa Asp Glu Ile Tyr Xaa Xaa Xaa Xaa Phe
                245                 250                 255

Xaa Xaa Xaa Xaa Xaa Xaa Xaa Val Ser Val Xaa Glu Val Ile Xaa Xaa
            260                 265                 270

Xaa Xaa Xaa Xaa Xaa Xaa Xaa Xaa Xaa Xaa Xaa Xaa Xaa Xaa Xaa Xaa
            275                 280                 285

Xaa Val His Ile Xaa Xaa Ser Leu Ser Lys Asp Xaa Gly Xaa Pro Gly
290                 295                 300

Phe Arg Val Gly Xaa Ile Tyr Ser Xaa Xaa Asp Xaa Val Val Xaa Xaa
305                 310                 315                 320

Ala Xaa Lys Met Ser Ser Phe Xaa Leu Val Ser Xaa Gln Thr Gln Xaa
                325                 330                 335

Xaa Leu Xaa Xaa Met Leu Xaa Asp Xaa Xaa Phe Xaa Xaa Xaa Phe Leu
            340                 345                 350

Xaa Xaa Xaa Xaa Xaa Arg Leu Xaa Xaa Arg Xaa Xaa Xaa Xaa Xaa Xaa
            355                 360                 365

Gly Leu Xaa Xaa Xaa Gly Ile Xaa Xaa Leu Xaa Xaa Asn Ala Gly Leu
            370                 375                 380

Phe Xaa Trp Xaa Asp Leu Arg Xaa Xaa Leu Xaa Xaa Xaa Xaa Xaa Xaa
385                 390                 395                 400

Xaa Xaa Glu Leu Xaa Leu Trp Xaa Xaa Ile Val Xaa Xaa Xaa Xaa Leu
                405                 410                 415

Asn Ile Ser Pro Gly Xaa Ser Xaa His Cys Xaa Glu Xaa Gly Trp Phe
            420                 425                 430

Arg Val Cys Phe Ala Asn Met Xaa Xaa Xaa Xaa Leu Xaa Ile Ala Leu
            435                 440                 445

Xaa Arg Ile Xaa Xaa Phe Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa
            515                 520

<210> SEQ ID NO 60
```

```
<211> LENGTH: 524
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE
<222> LOCATION: (1)..(14)
<223> OTHER INFORMATION: Xaa is non-conserved residue
<220> FEATURE:
<221> NAME/KEY: MISC_FEATURE
<222> LOCATION: (65)..(65)
<223> OTHER INFORMATION: Xaa is non-conserved residue
<220> FEATURE:
<221> NAME/KEY: MISC_FEATURE
<222> LOCATION: (73)..(76)
<223> OTHER INFORMATION: Xaa is non-conserved residue
<220> FEATURE:
<221> NAME/KEY: MISC_FEATURE
<222> LOCATION: (82)..(83)
<223> OTHER INFORMATION: Xaa is non-conserved residue
<220> FEATURE:
<221> NAME/KEY: MISC_FEATURE
<222> LOCATION: (87)..(88)
<223> OTHER INFORMATION: Xaa is non-conserved residue
<220> FEATURE:
<221> NAME/KEY: MISC_FEATURE
<222> LOCATION: (90)..(92)
<223> OTHER INFORMATION: Xaa is non-conserved residue
<220> FEATURE:
<221> NAME/KEY: MISC_FEATURE
<222> LOCATION: (96)..(96)
<223> OTHER INFORMATION: Xaa is non-conserved residue
<220> FEATURE:
<221> NAME/KEY: MISC_FEATURE
<222> LOCATION: (98)..(98)
<223> OTHER INFORMATION: Xaa is non-conserved residue
<220> FEATURE:
<221> NAME/KEY: MISC_FEATURE
<222> LOCATION: (106)..(106)
<223> OTHER INFORMATION: Xaa is non-conserved residue
<220> FEATURE:
<221> NAME/KEY: MISC_FEATURE
<222> LOCATION: (119)..(119)
<223> OTHER INFORMATION: Xaa is non-conserved residue
<220> FEATURE:
<221> NAME/KEY: MISC_FEATURE
<222> LOCATION: (125)..(125)
<223> OTHER INFORMATION: Xaa is non-conserved residue
<220> FEATURE:
<221> NAME/KEY: MISC_FEATURE
<222> LOCATION: (128)..(128)
<223> OTHER INFORMATION: Xaa is non-conserved residue
<220> FEATURE:
<221> NAME/KEY: MISC_FEATURE
<222> LOCATION: (143)..(143)
<223> OTHER INFORMATION: Xaa is non-conserved residue
<220> FEATURE:
<221> NAME/KEY: MISC_FEATURE
<222> LOCATION: (145)..(145)
<223> OTHER INFORMATION: Xaa is non-conserved residue
<220> FEATURE:
<221> NAME/KEY: MISC_FEATURE
<222> LOCATION: (147)..(147)
<223> OTHER INFORMATION: Xaa is non-conserved residue
<220> FEATURE:
<221> NAME/KEY: MISC_FEATURE
<222> LOCATION: (169)..(170)
<223> OTHER INFORMATION: Xaa is non-conserved residue
<220> FEATURE:
<221> NAME/KEY: MISC_FEATURE
<222> LOCATION: (181)..(181)
<223> OTHER INFORMATION: Xaa is non-conserved residue
<220> FEATURE:
<221> NAME/KEY: MISC_FEATURE
<222> LOCATION: (183)..(183)
<223> OTHER INFORMATION: Xaa is non-conserved residue
<220> FEATURE:
<221> NAME/KEY: MISC_FEATURE
```

```
<222> LOCATION: (192)..(192)
<223> OTHER INFORMATION: Xaa is non-conserved residue
<220> FEATURE:
<221> NAME/KEY: MISC_FEATURE
<222> LOCATION: (196)..(196)
<223> OTHER INFORMATION: Xaa is non-conserved residue
<220> FEATURE:
<221> NAME/KEY: MISC_FEATURE
<222> LOCATION: (205)..(205)
<223> OTHER INFORMATION: Xaa is non-conserved residue
<220> FEATURE:
<221> NAME/KEY: MISC_FEATURE
<222> LOCATION: (224)..(224)
<223> OTHER INFORMATION: Xaa is non-conserved residue
<220> FEATURE:
<221> NAME/KEY: MISC_FEATURE
<222> LOCATION: (228)..(229)
<223> OTHER INFORMATION: Xaa is non-conserved residue
<220> FEATURE:
<221> NAME/KEY: MISC_FEATURE
<222> LOCATION: (231)..(232)
<223> OTHER INFORMATION: Xaa is non-conserved residue
<220> FEATURE:
<221> NAME/KEY: MISC_FEATURE
<222> LOCATION: (238)..(239)
<223> OTHER INFORMATION: Xaa is non-conserved residue
<220> FEATURE:
<221> NAME/KEY: MISC_FEATURE
<222> LOCATION: (258)..(262)
<223> OTHER INFORMATION: Xaa is non-conserved residue
<220> FEATURE:
<221> NAME/KEY: MISC_FEATURE
<222> LOCATION: (267)..(267)
<223> OTHER INFORMATION: Xaa is non-conserved residue
<220> FEATURE:
<221> NAME/KEY: MISC_FEATURE
<222> LOCATION: (273)..(287)
<223> OTHER INFORMATION: Xaa is non-conserved residue
<220> FEATURE:
<221> NAME/KEY: MISC_FEATURE
<222> LOCATION: (289)..(289)
<223> OTHER INFORMATION: Xaa is non-conserved residue
<220> FEATURE:
<221> NAME/KEY: MISC_FEATURE
<222> LOCATION: (294)..(294)
<223> OTHER INFORMATION: Xaa is non-conserved residue
<220> FEATURE:
<221> NAME/KEY: MISC_FEATURE
<222> LOCATION: (313)..(313)
<223> OTHER INFORMATION: Xaa is non-conserved residue
<220> FEATURE:
<221> NAME/KEY: MISC_FEATURE
<222> LOCATION: (316)..(316)
<223> OTHER INFORMATION: Xaa is non-conserved residue
<220> FEATURE:
<221> NAME/KEY: MISC_FEATURE
<222> LOCATION: (320)..(320)
<223> OTHER INFORMATION: Xaa is non-conserved residue
<220> FEATURE:
<221> NAME/KEY: MISC_FEATURE
<222> LOCATION: (322)..(322)
<223> OTHER INFORMATION: Xaa is non-conserved residue
<220> FEATURE:
<221> NAME/KEY: MISC_FEATURE
<222> LOCATION: (328)..(328)
<223> OTHER INFORMATION: Xaa is non-conserved residue
<220> FEATURE:
<221> NAME/KEY: MISC_FEATURE
<222> LOCATION: (336)..(336)
<223> OTHER INFORMATION: Xaa is non-conserved residue
<220> FEATURE:
<221> NAME/KEY: MISC_FEATURE
<222> LOCATION: (340)..(340)
<223> OTHER INFORMATION: Xaa is non-conserved residue
<220> FEATURE:
<221> NAME/KEY: MISC_FEATURE
<222> LOCATION: (350)..(350)
<223> OTHER INFORMATION: Xaa is non-conserved residue
<220> FEATURE:
```

-continued

```
<221> NAME/KEY: MISC_FEATURE
<222> LOCATION: (353)..(354)
<223> OTHER INFORMATION: Xaa is non-conserved residue
<220> FEATURE:
<221> NAME/KEY: MISC_FEATURE
<222> LOCATION: (356)..(357)
<223> OTHER INFORMATION: Xaa is non-conserved residue
<220> FEATURE:
<221> NAME/KEY: MISC_FEATURE
<222> LOCATION: (360)..(361)
<223> OTHER INFORMATION: Xaa is non-conserved residue
<220> FEATURE:
<221> NAME/KEY: MISC_FEATURE
<222> LOCATION: (364)..(365)
<223> OTHER INFORMATION: Xaa is non-conserved residue
<220> FEATURE:
<221> NAME/KEY: MISC_FEATURE
<222> LOCATION: (368)..(368)
<223> OTHER INFORMATION: Xaa is non-conserved residue
<220> FEATURE:
<221> NAME/KEY: MISC_FEATURE
<222> LOCATION: (371)..(372)
<223> OTHER INFORMATION: Xaa is non-conserved residue
<220> FEATURE:
<221> NAME/KEY: MISC_FEATURE
<222> LOCATION: (376)..(377)
<223> OTHER INFORMATION: Xaa is non-conserved residue
<220> FEATURE:
<221> NAME/KEY: MISC_FEATURE
<222> LOCATION: (379)..(379)
<223> OTHER INFORMATION: Xaa is non-conserved residue
<220> FEATURE:
<221> NAME/KEY: MISC_FEATURE
<222> LOCATION: (386)..(386)
<223> OTHER INFORMATION: Xaa is non-conserved residue
<220> FEATURE:
<221> NAME/KEY: MISC_FEATURE
<222> LOCATION: (392)..(392)
<223> OTHER INFORMATION: Xaa is non-conserved residue
<220> FEATURE:
<221> NAME/KEY: MISC_FEATURE
<222> LOCATION: (395)..(395)
<223> OTHER INFORMATION: Xaa is non-conserved residue
<220> FEATURE:
<221> NAME/KEY: MISC_FEATURE
<222> LOCATION: (397)..(397)
<223> OTHER INFORMATION: Xaa is non-conserved residue
<220> FEATURE:
<221> NAME/KEY: MISC_FEATURE
<222> LOCATION: (400)..(401)
<223> OTHER INFORMATION: Xaa is non-conserved residue
<220> FEATURE:
<221> NAME/KEY: MISC_FEATURE
<222> LOCATION: (409)..(409)
<223> OTHER INFORMATION: Xaa is non-conserved residue
<220> FEATURE:
<221> NAME/KEY: MISC_FEATURE
<222> LOCATION: (412)..(412)
<223> OTHER INFORMATION: Xaa is non-conserved residue
<220> FEATURE:
<221> NAME/KEY: MISC_FEATURE
<222> LOCATION: (424)..(424)
<223> OTHER INFORMATION: Xaa is non-conserved residue
<220> FEATURE:
<221> NAME/KEY: MISC_FEATURE
<222> LOCATION: (429)..(429)
<223> OTHER INFORMATION: Xaa is non-conserved residue
<220> FEATURE:
<221> NAME/KEY: MISC_FEATURE
<222> LOCATION: (449)..(449)
<223> OTHER INFORMATION: Xaa is non-conserved residue
<220> FEATURE:
<221> NAME/KEY: MISC_FEATURE
<222> LOCATION: (452)..(452)
<223> OTHER INFORMATION: Xaa is non-conserved residue
<220> FEATURE:
<221> NAME/KEY: MISC_FEATURE
<222> LOCATION: (460)..(468)
<223> OTHER INFORMATION: Xaa is non-conserved residue
```

```
<220> FEATURE:
<221> NAME/KEY: MISC_FEATURE
<222> LOCATION: (472)..(472)
<223> OTHER INFORMATION: Xaa is non-conserved residue
<220> FEATURE:
<221> NAME/KEY: MISC_FEATURE
<222> LOCATION: (474)..(476)
<223> OTHER INFORMATION: Xaa is non-conserved residue
<220> FEATURE:
<221> NAME/KEY: MISC_FEATURE
<222> LOCATION: (478)..(481)
<223> OTHER INFORMATION: Xaa is non-conserved residue
<220> FEATURE:
<221> NAME/KEY: MISC_FEATURE
<222> LOCATION: (484)..(485)
<223> OTHER INFORMATION: Xaa is non-conserved residue
<220> FEATURE:
<221> NAME/KEY: MISC_FEATURE
<222> LOCATION: (487)..(488)
<223> OTHER INFORMATION: Xaa is non-conserved residue
<220> FEATURE:
<221> NAME/KEY: MISC_FEATURE
<222> LOCATION: (490)..(490)
<223> OTHER INFORMATION: Xaa is non-conserved residue
<220> FEATURE:
<221> NAME/KEY: MISC_FEATURE
<222> LOCATION: (492)..(493)
<223> OTHER INFORMATION: Xaa is non-conserved residue
<220> FEATURE:
<221> NAME/KEY: MISC_FEATURE
<222> LOCATION: (496)..(496)
<223> OTHER INFORMATION: Xaa is non-conserved residue
<220> FEATURE:
<221> NAME/KEY: MISC_FEATURE
<222> LOCATION: (501)..(524)
<223> OTHER INFORMATION: Xaa is non-conserved residue

<400> SEQUENCE: 60

Xaa Xaa Xaa Xaa Xaa Xaa Xaa Xaa Xaa Xaa Xaa Xaa Xaa Xaa Met Gln
1               5                   10                  15

Leu Leu Ser Lys Lys Ala Thr Asn Asp Gly His Gly Glu Asn Ser Ser
            20                  25                  30

Tyr Phe Asp Gly Trp Lys Ala Tyr Asp Lys Asn Pro Phe His Leu Thr
        35                  40                  45

Asp Asn Pro Asp Gly Val Ile Gln Met Gly Leu Ala Glu Asn Gln Leu
50                  55                  60

Xaa Phe Asp Leu Ile Glu Glu Trp Xaa Xaa Xaa Xaa Asn Pro Glu Ala
65                  70                  75                  80

Ser Xaa Xaa Thr Arg Glu Xaa Gly Xaa Xaa Phe Arg Glu Xaa
                85                  90                  95

Ala Xaa Phe Gln Asp Tyr His Gly Leu Xaa Glu Phe Arg Lys Ala Met
        100                 105                 110

Ala Lys Phe Met Glu Lys Xaa Arg Gly Gly Lys Val Xaa Phe Asp Xaa
        115                 120                 125

Asp Arg Ile Val Met Thr Gly Gly Ala Thr Gly Ala Asn Glu Xaa Leu
130                 135                 140

Xaa Phe Xaa Leu Ala Asp Pro Gly Asp Ala Phe Leu Val Pro Thr Pro
145                 150                 155                 160

Tyr Tyr Pro Gly Phe Asp Arg Asp Xaa Xaa Trp Arg Thr Gly Val Glu
                165                 170                 175

Ile Val Pro Ile Xaa Cys Xaa Ser Ser Asn Gly Phe Arg Ile Thr Xaa
            180                 185                 190

Glu Ala Leu Xaa Glu Ala Tyr Glu Lys Ala Gln Lys Xaa Asn Ile Arg
        195                 200                 205

Val Lys Gly Val Leu Ile Thr Asn Pro Ser Asn Pro Leu Gly Thr Xaa
```

```
                  210                 215                 220
Leu Asp Arg Xaa Xaa Leu Xaa Xaa Leu Val Asp Phe Val Xaa Xaa Glu
225                 230                 235                 240

Lys Asn Ile His Leu Ile Ser Asp Glu Ile Tyr Ser Gly Thr Val Phe
                245                 250                 255

Ala Xaa Xaa Xaa Xaa Phe Val Ser Val Xaa Glu Val Ile Glu Asp
                260                 265                 270

Xaa Xaa Xaa Xaa Xaa Xaa Xaa Xaa Xaa Xaa Xaa Xaa Xaa Asp
            275                 280                 285

Xaa Val His Ile Val Xaa Ser Leu Ser Lys Asp Leu Gly Leu Pro Gly
            290                 295                 300

Phe Arg Val Gly Ile Ile Tyr Ser Xaa Asn Asp Xaa Val Val Ser Xaa
305                 310                 315                 320

Ala Xaa Lys Met Ser Ser Phe Xaa Leu Val Ser Ser Gln Thr Gln Xaa
                325                 330                 335

Leu Leu Ala Xaa Met Leu Ser Asp Glu Glu Phe Thr Asp Xaa Phe Leu
                340                 345                 350

Xaa Xaa Ser Xaa Xaa Arg Leu Xaa Xaa Arg His Xaa Xaa Phe Val Xaa
            355                 360                 365

Gly Leu Xaa Xaa Val Gly Ile Xaa Leu Xaa Ser Asn Ala Gly Leu
            370                 375                 380

Phe Xaa Trp Met Asp Leu Arg Xaa Leu Leu Xaa Glu Xaa Asn Thr Xaa
385                 390                 395                 400

Xaa Ala Glu Leu Glu Leu Trp Arg Xaa Ile Val Xaa Glu Val Lys Leu
                405                 410                 415

Asn Ile Ser Pro Gly Ser Ser Xaa His Cys Ser Glu Xaa Gly Trp Phe
                420                 425                 430

Arg Val Cys Phe Ala Asn Met Asp Asp Thr Leu Asp Ile Ala Leu
            435                 440                 445

Xaa Arg Ile Xaa Arg Phe Val Asp Gln His Asn Xaa Xaa Xaa Xaa Xaa
450                 455                 460

Xaa Xaa Xaa Xaa Ala Gln Arg Xaa Lys Xaa Xaa Xaa Ser Xaa Xaa Xaa
465                 470                 475                 480

Xaa Lys Lys Xaa Xaa Trp Xaa Xaa Arg Xaa Leu Xaa Xaa Ser Leu Xaa
                485                 490                 495

Asp Arg Arg Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa
            515                 520

<210> SEQ ID NO 61
<211> LENGTH: 510
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE
<222> LOCATION: (1)..(20)
<223> OTHER INFORMATION: Xaa is non-conserved residue
<220> FEATURE:
<221> NAME/KEY: MISC_FEATURE
<222> LOCATION: (22)..(25)
<223> OTHER INFORMATION: Xaa is non-conserved residue
<220> FEATURE:
<221> NAME/KEY: MISC_FEATURE
<222> LOCATION: (29)..(29)
<223> OTHER INFORMATION: Xaa is non-conserved residue
<220> FEATURE:
```

```
<221> NAME/KEY: MISC_FEATURE
<222> LOCATION: (31)..(31)
<223> OTHER INFORMATION: Xaa is non-conserved residue
<220> FEATURE:
<221> NAME/KEY: MISC_FEATURE
<222> LOCATION: (40)..(42)
<223> OTHER INFORMATION: Xaa is non-conserved residue
<220> FEATURE:
<221> NAME/KEY: MISC_FEATURE
<222> LOCATION: (45)..(48)
<223> OTHER INFORMATION: Xaa is non-conserved residue
<220> FEATURE:
<221> NAME/KEY: MISC_FEATURE
<222> LOCATION: (50)..(51)
<223> OTHER INFORMATION: Xaa is non-conserved residue
<220> FEATURE:
<221> NAME/KEY: MISC_FEATURE
<222> LOCATION: (53)..(53)
<223> OTHER INFORMATION: Xaa is non-conserved residue
<220> FEATURE:
<221> NAME/KEY: MISC_FEATURE
<222> LOCATION: (64)..(65)
<223> OTHER INFORMATION: Xaa is non-conserved residue
<220> FEATURE:
<221> NAME/KEY: MISC_FEATURE
<222> LOCATION: (68)..(70)
<223> OTHER INFORMATION: Xaa is non-conserved residue
<220> FEATURE:
<221> NAME/KEY: MISC_FEATURE
<222> LOCATION: (72)..(75)
<223> OTHER INFORMATION: Xaa is non-conserved residue
<220> FEATURE:
<221> NAME/KEY: MISC_FEATURE
<222> LOCATION: (77)..(78)
<223> OTHER INFORMATION: Xaa is non-conserved residue
<220> FEATURE:
<221> NAME/KEY: MISC_FEATURE
<222> LOCATION: (82)..(84)
<223> OTHER INFORMATION: Xaa is non-conserved residue
<220> FEATURE:
<221> NAME/KEY: MISC_FEATURE
<222> LOCATION: (86)..(88)
<223> OTHER INFORMATION: Xaa is non-conserved residue
<220> FEATURE:
<221> NAME/KEY: MISC_FEATURE
<222> LOCATION: (90)..(92)
<223> OTHER INFORMATION: Xaa is non-conserved residue
<220> FEATURE:
<221> NAME/KEY: MISC_FEATURE
<222> LOCATION: (94)..(94)
<223> OTHER INFORMATION: Xaa is non-conserved residue
<220> FEATURE:
<221> NAME/KEY: MISC_FEATURE
<222> LOCATION: (102)..(103)
<223> OTHER INFORMATION: Xaa is non-conserved residue
<220> FEATURE:
<221> NAME/KEY: MISC_FEATURE
<222> LOCATION: (105)..(106)
<223> OTHER INFORMATION: Xaa is non-conserved residue
<220> FEATURE:
<221> NAME/KEY: MISC_FEATURE
<222> LOCATION: (108)..(108)
<223> OTHER INFORMATION: Xaa is non-conserved residue
<220> FEATURE:
<221> NAME/KEY: MISC_FEATURE
<222> LOCATION: (110)..(110)
<223> OTHER INFORMATION: Xaa is non-conserved residue
<220> FEATURE:
<221> NAME/KEY: MISC_FEATURE
<222> LOCATION: (113)..(115)
<223> OTHER INFORMATION: Xaa is non-conserved residue
<220> FEATURE:
<221> NAME/KEY: MISC_FEATURE
<222> LOCATION: (117)..(121)
<223> OTHER INFORMATION: Xaa is non-conserved residue
<220> FEATURE:
<221> NAME/KEY: MISC_FEATURE
<222> LOCATION: (123)..(125)
<223> OTHER INFORMATION: Xaa is non-conserved residue
```

```
<220> FEATURE:
<221> NAME/KEY: MISC_FEATURE
<222> LOCATION: (127)..(127)
<223> OTHER INFORMATION: Xaa is non-conserved residue
<220> FEATURE:
<221> NAME/KEY: MISC_FEATURE
<222> LOCATION: (130)..(130)
<223> OTHER INFORMATION: Xaa is non-conserved residue
<220> FEATURE:
<221> NAME/KEY: MISC_FEATURE
<222> LOCATION: (137)..(142)
<223> OTHER INFORMATION: Xaa is non-conserved residue
<220> FEATURE:
<221> NAME/KEY: MISC_FEATURE
<222> LOCATION: (146)..(146)
<223> OTHER INFORMATION: Xaa is non-conserved residue
<220> FEATURE:
<221> NAME/KEY: MISC_FEATURE
<222> LOCATION: (149)..(151)
<223> OTHER INFORMATION: Xaa is non-conserved residue
<220> FEATURE:
<221> NAME/KEY: MISC_FEATURE
<222> LOCATION: (153)..(153)
<223> OTHER INFORMATION: Xaa is non-conserved residue
<220> FEATURE:
<221> NAME/KEY: MISC_FEATURE
<222> LOCATION: (155)..(155)
<223> OTHER INFORMATION: Xaa is non-conserved residue
<220> FEATURE:
<221> NAME/KEY: MISC_FEATURE
<222> LOCATION: (159)..(160)
<223> OTHER INFORMATION: Xaa is non-conserved residue
<220> FEATURE:
<221> NAME/KEY: MISC_FEATURE
<222> LOCATION: (162)..(162)
<223> OTHER INFORMATION: Xaa is non-conserved residue
<220> FEATURE:
<221> NAME/KEY: MISC_FEATURE
<222> LOCATION: (165)..(166)
<223> OTHER INFORMATION: Xaa is non-conserved residue
<220> FEATURE:
<221> NAME/KEY: MISC_FEATURE
<222> LOCATION: (169)..(169)
<223> OTHER INFORMATION: Xaa is non-conserved residue
<220> FEATURE:
<221> NAME/KEY: MISC_FEATURE
<222> LOCATION: (171)..(174)
<223> OTHER INFORMATION: Xaa is non-conserved residue
<220> FEATURE:
<221> NAME/KEY: MISC_FEATURE
<222> LOCATION: (176)..(177)
<223> OTHER INFORMATION: Xaa is non-conserved residue
<220> FEATURE:
<221> NAME/KEY: MISC_FEATURE
<222> LOCATION: (179)..(179)
<223> OTHER INFORMATION: Xaa is non-conserved residue
<220> FEATURE:
<221> NAME/KEY: MISC_FEATURE
<222> LOCATION: (181)..(183)
<223> OTHER INFORMATION: Xaa is non-conserved residue
<220> FEATURE:
<221> NAME/KEY: MISC_FEATURE
<222> LOCATION: (185)..(186)
<223> OTHER INFORMATION: Xaa is non-conserved residue
<220> FEATURE:
<221> NAME/KEY: MISC_FEATURE
<222> LOCATION: (188)..(189)
<223> OTHER INFORMATION: Xaa is non-conserved residue
<220> FEATURE:
<221> NAME/KEY: MISC_FEATURE
<222> LOCATION: (191)..(193)
<223> OTHER INFORMATION: Xaa is non-conserved residue
<220> FEATURE:
<221> NAME/KEY: MISC_FEATURE
<222> LOCATION: (196)..(206)
<223> OTHER INFORMATION: Xaa is non-conserved residue
<220> FEATURE:
<221> NAME/KEY: MISC_FEATURE
<222> LOCATION: (208)..(215)
```

```
<223> OTHER INFORMATION: Xaa is non-conserved residue
<220> FEATURE:
<221> NAME/KEY: MISC_FEATURE
<222> LOCATION: (220)..(221)
<223> OTHER INFORMATION: Xaa is non-conserved residue
<220> FEATURE:
<221> NAME/KEY: MISC_FEATURE
<222> LOCATION: (223)..(225)
<223> OTHER INFORMATION: Xaa is non-conserved residue
<220> FEATURE:
<221> NAME/KEY: MISC_FEATURE
<222> LOCATION: (227)..(231)
<223> OTHER INFORMATION: Xaa is non-conserved residue
<220> FEATURE:
<221> NAME/KEY: MISC_FEATURE
<222> LOCATION: (233)..(238)
<223> OTHER INFORMATION: Xaa is non-conserved residue
<220> FEATURE:
<221> NAME/KEY: MISC_FEATURE
<222> LOCATION: (241)..(242)
<223> OTHER INFORMATION: Xaa is non-conserved residue
<220> FEATURE:
<221> NAME/KEY: MISC_FEATURE
<222> LOCATION: (245)..(250)
<223> OTHER INFORMATION: Xaa is non-conserved residue
<220> FEATURE:
<221> NAME/KEY: MISC_FEATURE
<222> LOCATION: (252)..(257)
<223> OTHER INFORMATION: Xaa is non-conserved residue
<220> FEATURE:
<221> NAME/KEY: MISC_FEATURE
<222> LOCATION: (259)..(260)
<223> OTHER INFORMATION: Xaa is non-conserved residue
<220> FEATURE:
<221> NAME/KEY: MISC_FEATURE
<222> LOCATION: (262)..(273)
<223> OTHER INFORMATION: Xaa is non-conserved residue
<220> FEATURE:
<221> NAME/KEY: MISC_FEATURE
<222> LOCATION: (276)..(276)
<223> OTHER INFORMATION: Xaa is non-conserved residue
<220> FEATURE:
<221> NAME/KEY: MISC_FEATURE
<222> LOCATION: (278)..(280)
<223> OTHER INFORMATION: Xaa is non-conserved residue
<220> FEATURE:
<221> NAME/KEY: MISC_FEATURE
<222> LOCATION: (286)..(286)
<223> OTHER INFORMATION: Xaa is non-conserved residue
<220> FEATURE:
<221> NAME/KEY: MISC_FEATURE
<222> LOCATION: (288)..(288)
<223> OTHER INFORMATION: Xaa is non-conserved residue
<220> FEATURE:
<221> NAME/KEY: MISC_FEATURE
<222> LOCATION: (291)..(291)
<223> OTHER INFORMATION: Xaa is non-conserved residue
<220> FEATURE:
<221> NAME/KEY: MISC_FEATURE
<222> LOCATION: (295)..(296)
<223> OTHER INFORMATION: Xaa is non-conserved residue
<220> FEATURE:
<221> NAME/KEY: MISC_FEATURE
<222> LOCATION: (299)..(299)
<223> OTHER INFORMATION: Xaa is non-conserved residue
<220> FEATURE:
<221> NAME/KEY: MISC_FEATURE
<222> LOCATION: (302)..(302)
<223> OTHER INFORMATION: Xaa is non-conserved residue
<220> FEATURE:
<221> NAME/KEY: MISC_FEATURE
<222> LOCATION: (305)..(307)
<223> OTHER INFORMATION: Xaa is non-conserved residue
<220> FEATURE:
<221> NAME/KEY: MISC_FEATURE
<222> LOCATION: (309)..(309)
<223> OTHER INFORMATION: Xaa is non-conserved residue
<220> FEATURE:
<221> NAME/KEY: MISC_FEATURE
```

```
<222> LOCATION: (318)..(318)
<223> OTHER INFORMATION: Xaa is non-conserved residue
<220> FEATURE:
<221> NAME/KEY: MISC_FEATURE
<222> LOCATION: (322)..(324)
<223> OTHER INFORMATION: Xaa is non-conserved residue
<220> FEATURE:
<221> NAME/KEY: MISC_FEATURE
<222> LOCATION: (326)..(326)
<223> OTHER INFORMATION: Xaa is non-conserved residue
<220> FEATURE:
<221> NAME/KEY: MISC_FEATURE
<222> LOCATION: (329)..(329)
<223> OTHER INFORMATION: Xaa is non-conserved residue
<220> FEATURE:
<221> NAME/KEY: MISC_FEATURE
<222> LOCATION: (331)..(332)
<223> OTHER INFORMATION: Xaa is non-conserved residue
<220> FEATURE:
<221> NAME/KEY: MISC_FEATURE
<222> LOCATION: (334)..(336)
<223> OTHER INFORMATION: Xaa is non-conserved residue
<220> FEATURE:
<221> NAME/KEY: MISC_FEATURE
<222> LOCATION: (338)..(343)
<223> OTHER INFORMATION: Xaa is non-conserved residue
<220> FEATURE:
<221> NAME/KEY: MISC_FEATURE
<222> LOCATION: (345)..(354)
<223> OTHER INFORMATION: Xaa is non-conserved residue
<220> FEATURE:
<221> NAME/KEY: MISC_FEATURE
<222> LOCATION: (356)..(360)
<223> OTHER INFORMATION: Xaa is non-conserved residue
<220> FEATURE:
<221> NAME/KEY: MISC_FEATURE
<222> LOCATION: (362)..(363)
<223> OTHER INFORMATION: Xaa is non-conserved residue
<220> FEATURE:
<221> NAME/KEY: MISC_FEATURE
<222> LOCATION: (365)..(367)
<223> OTHER INFORMATION: Xaa is non-conserved residue
<220> FEATURE:
<221> NAME/KEY: MISC_FEATURE
<222> LOCATION: (370)..(373)
<223> OTHER INFORMATION: Xaa is non-conserved residue
<220> FEATURE:
<221> NAME/KEY: MISC_FEATURE
<222> LOCATION: (378)..(379)
<223> OTHER INFORMATION: Xaa is non-conserved residue
<220> FEATURE:
<221> NAME/KEY: MISC_FEATURE
<222> LOCATION: (381)..(388)
<223> OTHER INFORMATION: Xaa is non-conserved residue
<220> FEATURE:
<221> NAME/KEY: MISC_FEATURE
<222> LOCATION: (390)..(391)
<223> OTHER INFORMATION: Xaa is non-conserved residue
<220> FEATURE:
<221> NAME/KEY: MISC_FEATURE
<222> LOCATION: (394)..(395)
<223> OTHER INFORMATION: Xaa is non-conserved residue
<220> FEATURE:
<221> NAME/KEY: MISC_FEATURE
<222> LOCATION: (397)..(399)
<223> OTHER INFORMATION: Xaa is non-conserved residue
<220> FEATURE:
<221> NAME/KEY: MISC_FEATURE
<222> LOCATION: (402)..(402)
<223> OTHER INFORMATION: Xaa is non-conserved residue
<220> FEATURE:
<221> NAME/KEY: MISC_FEATURE
<222> LOCATION: (404)..(404)
<223> OTHER INFORMATION: Xaa is non-conserved residue
<220> FEATURE:
<221> NAME/KEY: MISC_FEATURE
<222> LOCATION: (408)..(408)
<223> OTHER INFORMATION: Xaa is non-conserved residue
<220> FEATURE:
```

<221> NAME/KEY: MISC_FEATURE
<222> LOCATION: (411)..(411)
<223> OTHER INFORMATION: Xaa is non-conserved residue
<220> FEATURE:
<221> NAME/KEY: MISC_FEATURE
<222> LOCATION: (411)..(510)
<223> OTHER INFORMATION: Xaa is non-conserved residue
<220> FEATURE:
<221> NAME/KEY: MISC_FEATURE
<222> LOCATION: (413)..(413)
<223> OTHER INFORMATION: Xaa is non-conserved residue
<220> FEATURE:
<221> NAME/KEY: MISC_FEATURE
<222> LOCATION: (415)..(415)
<223> OTHER INFORMATION: Xaa is non-conserved residue
<220> FEATURE:
<221> NAME/KEY: MISC_FEATURE
<222> LOCATION: (420)..(422)
<223> OTHER INFORMATION: Xaa is non-conserved residue
<220> FEATURE:
<221> NAME/KEY: MISC_FEATURE
<222> LOCATION: (425)..(425)
<223> OTHER INFORMATION: Xaa is non-conserved residue
<220> FEATURE:
<221> NAME/KEY: MISC_FEATURE
<222> LOCATION: (427)..(432)
<223> OTHER INFORMATION: Xaa is non-conserved residue
<220> FEATURE:
<221> NAME/KEY: MISC_FEATURE
<222> LOCATION: (435)..(435)
<223> OTHER INFORMATION: Xaa is non-conserved residue
<220> FEATURE:
<221> NAME/KEY: MISC_FEATURE
<222> LOCATION: (438)..(439)
<223> OTHER INFORMATION: Xaa is non-conserved residue

<400> SEQUENCE: 61

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Ala Xaa Xaa Xaa Xaa His Gly Glu Xaa Ser Xaa Tyr
            20                  25                  30

Phe Asp Gly Trp Lys Ala Tyr Xaa Xaa Xaa Pro Phe Xaa Xaa Xaa Xaa
        35                  40                  45

Asn Xaa Xaa Gly Xaa Ile Gln Met Gly Leu Ala Glu Asn Gln Leu Xaa
    50                  55                  60

Xaa Asp Leu Xaa Xaa Xaa Trp Xaa Xaa Xaa Xaa Pro Xaa Xaa Ser Ile
65                  70                  75                  80

Cys Xaa Xaa Xaa Gly Xaa Xaa Xaa Phe Xaa Xaa Xaa Ala Xaa Phe Gln
                85                  90                  95

Asp Tyr His Gly Leu Xaa Xaa Phe Xaa Xaa Ala Xaa Ala Xaa Phe Met
            100                 105                 110

Xaa Xaa Xaa Arg Xaa Xaa Xaa Xaa Xaa Phe Xaa Xaa Xaa Arg Xaa Val
        115                 120                 125

Met Xaa Gly Gly Ala Thr Gly Ala Xaa Xaa Xaa Xaa Xaa Xaa Cys Leu
    130                 135                 140

Ala Xaa Pro Gly Xaa Xaa Xaa Leu Xaa Pro Xaa Pro Tyr Tyr Xaa Xaa
145                 150                 155                 160

Phe Xaa Arg Asp Xaa Xaa Trp Arg Xaa Gly Xaa Xaa Xaa Xaa Pro Xaa
                165                 170                 175

Xaa Cys Xaa Ser Xaa Xaa Xaa Phe Xaa Xaa Thr Xaa Xaa Ala Xaa Xaa
            180                 185                 190

Xaa Ala Tyr Xaa Xaa Xaa Xaa Xaa Xaa Xaa Xaa Xaa Xaa Xaa Gly Xaa
        195                 200                 205

Xaa Xaa Xaa Xaa Xaa Xaa Xaa Pro Leu Gly Thr Xaa Xaa Asp Xaa Xaa
    210                 215                 220
```

-continued

```
Xaa Leu Xaa Xaa Xaa Xaa Phe Xaa Xaa Xaa Xaa Xaa His Leu
225                 230                 235                 240

Xaa Xaa Asp Glu Xaa Xaa Xaa Xaa Phe Xaa Xaa Xaa Xaa Xaa
            245                 250                 255

Xaa Ser Xaa Xaa Glu Xaa Xaa Xaa Xaa Xaa Xaa Xaa Xaa Xaa
        260                 265                 270

Xaa Asp Leu Xaa His Xaa Xaa Xaa Ser Leu Ser Lys Asp Gly Xaa
            275                 280                 285

Pro Gly Xaa Arg Val Gly Xaa Xaa Tyr Ser Xaa Asn Asp Xaa Val Val
        290                 295                 300

Xaa Xaa Xaa Arg Xaa Met Ser Ser Phe Gly Leu Val Ser Xaa Gln Thr
305                 310                 315                 320

Gln Xaa Xaa Xaa Ala Xaa Met Leu Xaa Asp Xaa Xaa Phe Xaa Xaa Xaa
            325                 330                 335

Phe Xaa Xaa Xaa Xaa Xaa Xaa Arg Xaa Xaa Xaa Xaa Xaa Xaa Xaa
        340                 345                 350

Xaa Xaa Gly Xaa Xaa Xaa Xaa Ile Xaa Xaa Leu Xaa Xaa Xaa Ala
        355                 360                 365

Gly Xaa Xaa Xaa Xaa Met Asp Leu Arg Xaa Xaa Leu Xaa Xaa Xaa Xaa
    370                 375                 380

Xaa Xaa Xaa Xaa Glu Xaa Xaa Leu Trp Xaa Xaa Ile Xaa Xaa Xaa Val
385                 390                 395                 400

Lys Xaa Asn Xaa Ser Pro Gly Xaa Ser Phe Xaa Cys Xaa Glu Xaa Gly
            405                 410                 415

Trp Phe Arg Xaa Xaa Xaa Ala Asn Xaa Asp Xaa Xaa Xaa Xaa Xaa
            420                 425                 430

Ala Leu Xaa Arg Ile Xaa Xaa Phe Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa
        500                 505                 510
```

<210> SEQ ID NO 62
<211> LENGTH: 510
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE
<222> LOCATION: (1)..(20)
<223> OTHER INFORMATION: Xaa is non-conserved residue
<220> FEATURE:
<221> NAME/KEY: MISC_FEATURE
<222> LOCATION: (22)..(25)
<223> OTHER INFORMATION: Xaa is non-conserved residue
<220> FEATURE:
<221> NAME/KEY: MISC_FEATURE
<222> LOCATION: (29)..(29)
<223> OTHER INFORMATION: Xaa is non-conserved residue
<220> FEATURE:
<221> NAME/KEY: MISC_FEATURE
<222> LOCATION: (31)..(31)
<223> OTHER INFORMATION: Xaa is non-conserved residue
<220> FEATURE:

```
<221> NAME/KEY: MISC_FEATURE
<222> LOCATION: (40)..(42)
<223> OTHER INFORMATION: Xaa is non-conserved residue
<220> FEATURE:
<221> NAME/KEY: MISC_FEATURE
<222> LOCATION: (45)..(48)
<223> OTHER INFORMATION: Xaa is non-conserved residue
<220> FEATURE:
<221> NAME/KEY: MISC_FEATURE
<222> LOCATION: (50)..(51)
<223> OTHER INFORMATION: Xaa is non-conserved residue
<220> FEATURE:
<221> NAME/KEY: MISC_FEATURE
<222> LOCATION: (64)..(65)
<223> OTHER INFORMATION: Xaa is non-conserved residue
<220> FEATURE:
<221> NAME/KEY: MISC_FEATURE
<222> LOCATION: (68)..(70)
<223> OTHER INFORMATION: Xaa is non-conserved residue
<220> FEATURE:
<221> NAME/KEY: MISC_FEATURE
<222> LOCATION: (72)..(75)
<223> OTHER INFORMATION: Xaa is non-conserved residue
<220> FEATURE:
<221> NAME/KEY: MISC_FEATURE
<222> LOCATION: (77)..(78)
<223> OTHER INFORMATION: Xaa is non-conserved residue
<220> FEATURE:
<221> NAME/KEY: MISC_FEATURE
<222> LOCATION: (82)..(83)
<223> OTHER INFORMATION: Xaa is non-conserved residue
<220> FEATURE:
<221> NAME/KEY: MISC_FEATURE
<222> LOCATION: (86)..(88)
<223> OTHER INFORMATION: Xaa is non-conserved residue
<220> FEATURE:
<221> NAME/KEY: MISC_FEATURE
<222> LOCATION: (90)..(92)
<223> OTHER INFORMATION: Xaa is non-conserved residue
<220> FEATURE:
<221> NAME/KEY: MISC_FEATURE
<222> LOCATION: (94)..(94)
<223> OTHER INFORMATION: Xaa is non-conserved residue
<220> FEATURE:
<221> NAME/KEY: MISC_FEATURE
<222> LOCATION: (102)..(103)
<223> OTHER INFORMATION: Xaa is non-conserved residue
<220> FEATURE:
<221> NAME/KEY: MISC_FEATURE
<222> LOCATION: (105)..(106)
<223> OTHER INFORMATION: Xaa is non-conserved residue
<220> FEATURE:
<221> NAME/KEY: MISC_FEATURE
<222> LOCATION: (108)..(108)
<223> OTHER INFORMATION: Xaa is non-conserved residue
<220> FEATURE:
<221> NAME/KEY: MISC_FEATURE
<222> LOCATION: (110)..(110)
<223> OTHER INFORMATION: Xaa is non-conserved residue
<220> FEATURE:
<221> NAME/KEY: MISC_FEATURE
<222> LOCATION: (113)..(115)
<223> OTHER INFORMATION: Xaa is non-conserved residue
<220> FEATURE:
<221> NAME/KEY: MISC_FEATURE
<222> LOCATION: (117)..(118)
<223> OTHER INFORMATION: Xaa is non-conserved residue
<220> FEATURE:
<221> NAME/KEY: MISC_FEATURE
<222> LOCATION: (120)..(121)
<223> OTHER INFORMATION: Xaa is non-conserved residue
<220> FEATURE:
<221> NAME/KEY: MISC_FEATURE
<222> LOCATION: (124)..(125)
<223> OTHER INFORMATION: Xaa is non-conserved residue
<220> FEATURE:
<221> NAME/KEY: MISC_FEATURE
<222> LOCATION: (130)..(130)
<223> OTHER INFORMATION: Xaa is non-conserved residue
```

```
<220> FEATURE:
<221> NAME/KEY: MISC_FEATURE
<222> LOCATION: (137)..(137)
<223> OTHER INFORMATION: Xaa is non-conserved residue
<220> FEATURE:
<221> NAME/KEY: MISC_FEATURE
<222> LOCATION: (139)..(139)
<223> OTHER INFORMATION: Xaa is non-conserved residue
<220> FEATURE:
<221> NAME/KEY: MISC_FEATURE
<222> LOCATION: (141)..(142)
<223> OTHER INFORMATION: Xaa is non-conserved residue
<220> FEATURE:
<221> NAME/KEY: MISC_FEATURE
<222> LOCATION: (146)..(146)
<223> OTHER INFORMATION: Xaa is non-conserved residue
<220> FEATURE:
<221> NAME/KEY: MISC_FEATURE
<222> LOCATION: (150)..(150)
<223> OTHER INFORMATION: Xaa is non-conserved residue
<220> FEATURE:
<221> NAME/KEY: MISC_FEATURE
<222> LOCATION: (155)..(155)
<223> OTHER INFORMATION: Xaa is non-conserved residue
<220> FEATURE:
<221> NAME/KEY: MISC_FEATURE
<222> LOCATION: (159)..(160)
<223> OTHER INFORMATION: Xaa is non-conserved residue
<220> FEATURE:
<221> NAME/KEY: MISC_FEATURE
<222> LOCATION: (162)..(162)
<223> OTHER INFORMATION: Xaa is non-conserved residue
<220> FEATURE:
<221> NAME/KEY: MISC_FEATURE
<222> LOCATION: (165)..(166)
<223> OTHER INFORMATION: Xaa is non-conserved residue
<220> FEATURE:
<221> NAME/KEY: MISC_FEATURE
<222> LOCATION: (169)..(169)
<223> OTHER INFORMATION: Xaa is non-conserved residue
<220> FEATURE:
<221> NAME/KEY: MISC_FEATURE
<222> LOCATION: (172)..(172)
<223> OTHER INFORMATION: Xaa is non-conserved residue
<220> FEATURE:
<221> NAME/KEY: MISC_FEATURE
<222> LOCATION: (174)..(174)
<223> OTHER INFORMATION: Xaa is non-conserved residue
<220> FEATURE:
<221> NAME/KEY: MISC_FEATURE
<222> LOCATION: (177)..(177)
<223> OTHER INFORMATION: Xaa is non-conserved residue
<220> FEATURE:
<221> NAME/KEY: MISC_FEATURE
<222> LOCATION: (179)..(179)
<223> OTHER INFORMATION: Xaa is non-conserved residue
<220> FEATURE:
<221> NAME/KEY: MISC_FEATURE
<222> LOCATION: (181)..(183)
<223> OTHER INFORMATION: Xaa is non-conserved residue
<220> FEATURE:
<221> NAME/KEY: MISC_FEATURE
<222> LOCATION: (185)..(185)
<223> OTHER INFORMATION: Xaa is non-conserved residue
<220> FEATURE:
<221> NAME/KEY: MISC_FEATURE
<222> LOCATION: (188)..(189)
<223> OTHER INFORMATION: Xaa is non-conserved residue
<220> FEATURE:
<221> NAME/KEY: MISC_FEATURE
<222> LOCATION: (191)..(193)
<223> OTHER INFORMATION: Xaa is non-conserved residue
<220> FEATURE:
<221> NAME/KEY: MISC_FEATURE
<222> LOCATION: (196)..(204)
<223> OTHER INFORMATION: Xaa is non-conserved residue
<220> FEATURE:
<221> NAME/KEY: MISC_FEATURE
<222> LOCATION: (211)..(215)
```

```
<223> OTHER INFORMATION: Xaa is non-conserved residue
<220> FEATURE:
<221> NAME/KEY: MISC_FEATURE
<222> LOCATION: (220)..(221)
<223> OTHER INFORMATION: Xaa is non-conserved residue
<220> FEATURE:
<221> NAME/KEY: MISC_FEATURE
<222> LOCATION: (224)..(225)
<223> OTHER INFORMATION: Xaa is non-conserved residue
<220> FEATURE:
<221> NAME/KEY: MISC_FEATURE
<222> LOCATION: (227)..(228)
<223> OTHER INFORMATION: Xaa is non-conserved residue
<220> FEATURE:
<221> NAME/KEY: MISC_FEATURE
<222> LOCATION: (230)..(231)
<223> OTHER INFORMATION: Xaa is non-conserved residue
<220> FEATURE:
<221> NAME/KEY: MISC_FEATURE
<222> LOCATION: (233)..(238)
<223> OTHER INFORMATION: Xaa is non-conserved residue
<220> FEATURE:
<221> NAME/KEY: MISC_FEATURE
<222> LOCATION: (242)..(242)
<223> OTHER INFORMATION: Xaa is non-conserved residue
<220> FEATURE:
<221> NAME/KEY: MISC_FEATURE
<222> LOCATION: (247)..(250)
<223> OTHER INFORMATION: Xaa is non-conserved residue
<220> FEATURE:
<221> NAME/KEY: MISC_FEATURE
<222> LOCATION: (252)..(255)
<223> OTHER INFORMATION: Xaa is non-conserved residue
<220> FEATURE:
<221> NAME/KEY: MISC_FEATURE
<222> LOCATION: (260)..(260)
<223> OTHER INFORMATION: Xaa is non-conserved residue
<220> FEATURE:
<221> NAME/KEY: MISC_FEATURE
<222> LOCATION: (262)..(273)
<223> OTHER INFORMATION: Xaa is non-conserved residue
<220> FEATURE:
<221> NAME/KEY: MISC_FEATURE
<222> LOCATION: (279)..(280)
<223> OTHER INFORMATION: Xaa is non-conserved residue
<220> FEATURE:
<221> NAME/KEY: MISC_FEATURE
<222> LOCATION: (286)..(286)
<223> OTHER INFORMATION: Xaa is non-conserved residue
<220> FEATURE:
<221> NAME/KEY: MISC_FEATURE
<222> LOCATION: (288)..(288)
<223> OTHER INFORMATION: Xaa is non-conserved residue
<220> FEATURE:
<221> NAME/KEY: MISC_FEATURE
<222> LOCATION: (291)..(291)
<223> OTHER INFORMATION: Xaa is non-conserved residue
<220> FEATURE:
<221> NAME/KEY: MISC_FEATURE
<222> LOCATION: (302)..(302)
<223> OTHER INFORMATION: Xaa is non-conserved residue
<220> FEATURE:
<221> NAME/KEY: MISC_FEATURE
<222> LOCATION: (305)..(307)
<223> OTHER INFORMATION: Xaa is non-conserved residue
<220> FEATURE:
<221> NAME/KEY: MISC_FEATURE
<222> LOCATION: (318)..(318)
<223> OTHER INFORMATION: Xaa is non-conserved residue
<220> FEATURE:
<221> NAME/KEY: MISC_FEATURE
<222> LOCATION: (322)..(323)
<223> OTHER INFORMATION: Xaa is non-conserved residue
<220> FEATURE:
<221> NAME/KEY: MISC_FEATURE
<222> LOCATION: (326)..(326)
<223> OTHER INFORMATION: Xaa is non-conserved residue
<220> FEATURE:
<221> NAME/KEY: MISC_FEATURE
```

```
<222> LOCATION: (329)..(329)
<223> OTHER INFORMATION: Xaa is non-conserved residue
<220> FEATURE:
<221> NAME/KEY: MISC_FEATURE
<222> LOCATION: (331)..(332)
<223> OTHER INFORMATION: Xaa is non-conserved residue
<220> FEATURE:
<221> NAME/KEY: MISC_FEATURE
<222> LOCATION: (334)..(336)
<223> OTHER INFORMATION: Xaa is non-conserved residue
<220> FEATURE:
<221> NAME/KEY: MISC_FEATURE
<222> LOCATION: (339)..(343)
<223> OTHER INFORMATION: Xaa is non-conserved residue
<220> FEATURE:
<221> NAME/KEY: MISC_FEATURE
<222> LOCATION: (345)..(347)
<223> OTHER INFORMATION: Xaa is non-conserved residue
<220> FEATURE:
<221> NAME/KEY: MISC_FEATURE
<222> LOCATION: (349)..(354)
<223> OTHER INFORMATION: Xaa is non-conserved residue
<220> FEATURE:
<221> NAME/KEY: MISC_FEATURE
<222> LOCATION: (357)..(360)
<223> OTHER INFORMATION: Xaa is non-conserved residue
<220> FEATURE:
<221> NAME/KEY: MISC_FEATURE
<222> LOCATION: (362)..(363)
<223> OTHER INFORMATION: Xaa is non-conserved residue
<220> FEATURE:
<221> NAME/KEY: MISC_FEATURE
<222> LOCATION: (365)..(367)
<223> OTHER INFORMATION: Xaa is non-conserved residue
<220> FEATURE:
<221> NAME/KEY: MISC_FEATURE
<222> LOCATION: (370)..(370)
<223> OTHER INFORMATION: Xaa is non-conserved residue
<220> FEATURE:
<221> NAME/KEY: MISC_FEATURE
<222> LOCATION: (372)..(373)
<223> OTHER INFORMATION: Xaa is non-conserved residue
<220> FEATURE:
<221> NAME/KEY: MISC_FEATURE
<222> LOCATION: (378)..(379)
<223> OTHER INFORMATION: Xaa is non-conserved residue
<220> FEATURE:
<221> NAME/KEY: MISC_FEATURE
<222> LOCATION: (381)..(386)
<223> OTHER INFORMATION: Xaa is non-conserved residue
<220> FEATURE:
<221> NAME/KEY: MISC_FEATURE
<222> LOCATION: (388)..(388)
<223> OTHER INFORMATION: Xaa is non-conserved residue
<220> FEATURE:
<221> NAME/KEY: MISC_FEATURE
<222> LOCATION: (390)..(391)
<223> OTHER INFORMATION: Xaa is non-conserved residue
<220> FEATURE:
<221> NAME/KEY: MISC_FEATURE
<222> LOCATION: (394)..(394)
<223> OTHER INFORMATION: Xaa is non-conserved residue
<220> FEATURE:
<221> NAME/KEY: MISC_FEATURE
<222> LOCATION: (398)..(399)
<223> OTHER INFORMATION: Xaa is non-conserved residue
<220> FEATURE:
<221> NAME/KEY: MISC_FEATURE
<222> LOCATION: (408)..(408)
<223> OTHER INFORMATION: Xaa is non-conserved residue
<220> FEATURE:
<221> NAME/KEY: MISC_FEATURE
<222> LOCATION: (411)..(411)
<223> OTHER INFORMATION: Xaa is non-conserved residue
<220> FEATURE:
<221> NAME/KEY: MISC_FEATURE
<222> LOCATION: (413)..(413)
<223> OTHER INFORMATION: Xaa is non-conserved residue
<220> FEATURE:
```

```
<221> NAME/KEY: MISC_FEATURE
<222> LOCATION: (415)..(415)
<223> OTHER INFORMATION: Xaa is non-conserved residue
<220> FEATURE:
<221> NAME/KEY: MISC_FEATURE
<222> LOCATION: (421)..(421)
<223> OTHER INFORMATION: Xaa is non-conserved residue
<220> FEATURE:
<221> NAME/KEY: MISC_FEATURE
<222> LOCATION: (425)..(425)
<223> OTHER INFORMATION: Xaa is non-conserved residue
<220> FEATURE:
<221> NAME/KEY: MISC_FEATURE
<222> LOCATION: (427)..(432)
<223> OTHER INFORMATION: Xaa is non-conserved residue
<220> FEATURE:
<221> NAME/KEY: MISC_FEATURE
<222> LOCATION: (435)..(435)
<223> OTHER INFORMATION: Xaa is non-conserved residue
<220> FEATURE:
<221> NAME/KEY: MISC_FEATURE
<222> LOCATION: (438)..(439)
<223> OTHER INFORMATION: Xaa is non-conserved residue
<220> FEATURE:
<221> NAME/KEY: MISC_FEATURE
<222> LOCATION: (441)..(476)
<223> OTHER INFORMATION: Xaa is non-conserved residue
<220> FEATURE:
<221> NAME/KEY: MISC_FEATURE
<222> LOCATION: (478)..(510)
<223> OTHER INFORMATION: Xaa is non-conserved residue

<400> SEQUENCE: 62

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Ala Xaa Xaa Xaa His Gly Glu Xaa Ser Xaa Tyr
            20                  25                  30

Phe Asp Gly Trp Lys Ala Tyr Xaa Xaa Xaa Pro Phe Xaa Xaa Xaa Xaa
                35                  40                  45

Asn Xaa Xaa Gly Val Ile Gln Met Gly Leu Ala Glu Asn Gln Leu Xaa
        50                  55                  60

Xaa Asp Leu Xaa Xaa Xaa Trp Xaa Xaa Xaa Xaa Pro Xaa Xaa Ser Ile
65                  70                  75                  80

Cys Xaa Xaa Glu Gly Xaa Xaa Xaa Phe Xaa Xaa Xaa Ala Xaa Phe Gln
                85                  90                  95

Asp Tyr His Gly Leu Xaa Xaa Phe Xaa Xaa Ala Xaa Ala Xaa Phe Met
                100                 105                 110

Xaa Xaa Xaa Arg Xaa Xaa Arg Xaa Xaa Phe Asp Xaa Xaa Arg Val Val
            115                 120                 125

Met Xaa Gly Gly Ala Thr Gly Ala Xaa Glu Xaa Leu Xaa Xaa Cys Leu
        130                 135                 140

Ala Xaa Pro Gly Asp Xaa Phe Leu Val Pro Xaa Pro Tyr Tyr Xaa Xaa
145                 150                 155                 160

Phe Xaa Arg Asp Xaa Xaa Trp Arg Xaa Gly Val Xaa Leu Xaa Pro Ile
        165                 170                 175

Xaa Cys Xaa Ser Xaa Xaa Xaa Phe Xaa Ile Thr Xaa Xaa Ala Xaa Xaa
            180                 185                 190

Xaa Ala Tyr Xaa Xaa Xaa Xaa Xaa Xaa Xaa Xaa Val Lys Gly Leu
            195                 200                 205

Leu Ile Xaa Xaa Xaa Xaa Xaa Pro Leu Gly Thr Xaa Xaa Asp Arg Xaa
        210                 215                 220

Xaa Leu Xaa Xaa Leu Xaa Xaa Phe Xaa Xaa Xaa Xaa Xaa Xaa His Leu
225                 230                 235                 240
```

```
Val Xaa Asp Glu Ile Tyr Xaa Xaa Xaa Phe Xaa Xaa Xaa Phe
            245                 250                 255

Val Ser Ile Xaa Glu Xaa Xaa Xaa Xaa Xaa Xaa Xaa Xaa Xaa
            260                 265                 270

Xaa Asp Leu Ile His Ile Xaa Xaa Ser Leu Ser Lys Asp Xaa Gly Xaa
        275                 280                 285

Pro Gly Xaa Arg Val Gly Ile Val Tyr Ser Tyr Asn Asp Xaa Val Val
        290                 295                 300

Xaa Xaa Xaa Arg Lys Met Ser Ser Phe Gly Leu Val Ser Xaa Gln Thr
305                 310                 315                 320

Gln Xaa Xaa Leu Ala Xaa Met Leu Xaa Asp Xaa Xaa Phe Xaa Xaa Xaa
            325                 330                 335

Phe Leu Xaa Xaa Xaa Xaa Xaa Arg Xaa Xaa Xaa Arg Xaa Xaa Xaa Xaa
            340                 345                 350

Xaa Xaa Gly Leu Xaa Xaa Xaa Ile Xaa Xaa Leu Xaa Xaa Xaa Xaa Ala
        355                 360                 365

Gly Xaa Phe Xaa Xaa Met Asp Leu Arg Xaa Xaa Leu Xaa Xaa Xaa Xaa
        370                 375                 380

Xaa Xaa Asp Xaa Glu Xaa Xaa Leu Trp Xaa Val Ile Ile Xaa Xaa Val
385                 390                 395                 400

Lys Leu Asn Val Ser Pro Gly Xaa Ser Phe Xaa Cys Xaa Glu Xaa Gly
            405                 410                 415

Trp Phe Arg Val Xaa Phe Ala Asn Xaa Asp Xaa Xaa Xaa Xaa Xaa Xaa
            420                 425                 430

Ala Leu Xaa Arg Ile Xaa Xaa Phe Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Leu Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa
            500                 505                 510

<210> SEQ ID NO 63
<211> LENGTH: 503
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE
<222> LOCATION: (1)..(17)
<223> OTHER INFORMATION: Xaa is non-conserved residue
<220> FEATURE:
<221> NAME/KEY: MISC_FEATURE
<222> LOCATION: (20)..(26)
<223> OTHER INFORMATION: Xaa is non-conserved residue
<220> FEATURE:
<221> NAME/KEY: MISC_FEATURE
<222> LOCATION: (29)..(30)
<223> OTHER INFORMATION: Xaa is non-conserved residue
<220> FEATURE:
<221> NAME/KEY: MISC_FEATURE
<222> LOCATION: (32)..(32)
<223> OTHER INFORMATION: Xaa is non-conserved residue
<220> FEATURE:
<221> NAME/KEY: MISC_FEATURE
<222> LOCATION: (35)..(35)
<223> OTHER INFORMATION: Xaa is non-conserved residue
<220> FEATURE:
```

```
<221> NAME/KEY: MISC_FEATURE
<222> LOCATION: (38)..(39)
<223> OTHER INFORMATION: Xaa is non-conserved residue
<220> FEATURE:
<221> NAME/KEY: MISC_FEATURE
<222> LOCATION: (41)..(43)
<223> OTHER INFORMATION: Xaa is non-conserved residue
<220> FEATURE:
<221> NAME/KEY: MISC_FEATURE
<222> LOCATION: (45)..(49)
<223> OTHER INFORMATION: Xaa is non-conserved residue
<220> FEATURE:
<221> NAME/KEY: MISC_FEATURE
<222> LOCATION: (59)..(60)
<223> OTHER INFORMATION: Xaa is non-conserved residue
<220> FEATURE:
<221> NAME/KEY: MISC_FEATURE
<222> LOCATION: (63)..(65)
<223> OTHER INFORMATION: Xaa is non-conserved residue
<220> FEATURE:
<221> NAME/KEY: MISC_FEATURE
<222> LOCATION: (69)..(69)
<223> OTHER INFORMATION: Xaa is non-conserved residue
<220> FEATURE:
<221> NAME/KEY: MISC_FEATURE
<222> LOCATION: (71)..(72)
<223> OTHER INFORMATION: Xaa is non-conserved residue
<220> FEATURE:
<221> NAME/KEY: MISC_FEATURE
<222> LOCATION: (74)..(88)
<223> OTHER INFORMATION: Xaa is non-conserved residue
<220> FEATURE:
<221> NAME/KEY: MISC_FEATURE
<222> LOCATION: (90)..(92)
<223> OTHER INFORMATION: Xaa is non-conserved residue
<220> FEATURE:
<221> NAME/KEY: MISC_FEATURE
<222> LOCATION: (94)..(97)
<223> OTHER INFORMATION: Xaa is non-conserved residue
<220> FEATURE:
<221> NAME/KEY: MISC_FEATURE
<222> LOCATION: (105)..(107)
<223> OTHER INFORMATION: Xaa is non-conserved residue
<220> FEATURE:
<221> NAME/KEY: MISC_FEATURE
<222> LOCATION: (109)..(110)
<223> OTHER INFORMATION: Xaa is non-conserved residue
<220> FEATURE:
<221> NAME/KEY: MISC_FEATURE
<222> LOCATION: (112)..(115)
<223> OTHER INFORMATION: Xaa is non-conserved residue
<220> FEATURE:
<221> NAME/KEY: MISC_FEATURE
<222> LOCATION: (117)..(119)
<223> OTHER INFORMATION: Xaa is non-conserved residue
<220> FEATURE:
<221> NAME/KEY: MISC_FEATURE
<222> LOCATION: (122)..(125)
<223> OTHER INFORMATION: Xaa is non-conserved residue
<220> FEATURE:
<221> NAME/KEY: MISC_FEATURE
<222> LOCATION: (127)..(131)
<223> OTHER INFORMATION: Xaa is non-conserved residue
<220> FEATURE:
<221> NAME/KEY: MISC_FEATURE
<222> LOCATION: (134)..(134)
<223> OTHER INFORMATION: Xaa is non-conserved residue
<220> FEATURE:
<221> NAME/KEY: MISC_FEATURE
<222> LOCATION: (137)..(137)
<223> OTHER INFORMATION: Xaa is non-conserved residue
<220> FEATURE:
<221> NAME/KEY: MISC_FEATURE
<222> LOCATION: (139)..(139)
<223> OTHER INFORMATION: Xaa is non-conserved residue
<220> FEATURE:
<221> NAME/KEY: MISC_FEATURE
<222> LOCATION: (143)..(143)
<223> OTHER INFORMATION: Xaa is non-conserved residue
```

-continued

```
<220> FEATURE:
<221> NAME/KEY: MISC_FEATURE
<222> LOCATION: (145)..(145)
<223> OTHER INFORMATION: Xaa is non-conserved residue
<220> FEATURE:
<221> NAME/KEY: MISC_FEATURE
<222> LOCATION: (147)..(147)
<223> OTHER INFORMATION: Xaa is non-conserved residue
<220> FEATURE:
<221> NAME/KEY: MISC_FEATURE
<222> LOCATION: (150)..(153)
<223> OTHER INFORMATION: Xaa is non-conserved residue
<220> FEATURE:
<221> NAME/KEY: MISC_FEATURE
<222> LOCATION: (155)..(155)
<223> OTHER INFORMATION: Xaa is non-conserved residue
<220> FEATURE:
<221> NAME/KEY: MISC_FEATURE
<222> LOCATION: (157)..(157)
<223> OTHER INFORMATION: Xaa is non-conserved residue
<220> FEATURE:
<221> NAME/KEY: MISC_FEATURE
<222> LOCATION: (170)..(170)
<223> OTHER INFORMATION: Xaa is non-conserved residue
<220> FEATURE:
<221> NAME/KEY: MISC_FEATURE
<222> LOCATION: (175)..(176)
<223> OTHER INFORMATION: Xaa is non-conserved residue
<220> FEATURE:
<221> NAME/KEY: MISC_FEATURE
<222> LOCATION: (180)..(183)
<223> OTHER INFORMATION: Xaa is non-conserved residue
<220> FEATURE:
<221> NAME/KEY: MISC_FEATURE
<222> LOCATION: (185)..(185)
<223> OTHER INFORMATION: Xaa is non-conserved residue
<220> FEATURE:
<221> NAME/KEY: MISC_FEATURE
<222> LOCATION: (187)..(187)
<223> OTHER INFORMATION: Xaa is non-conserved residue
<220> FEATURE:
<221> NAME/KEY: MISC_FEATURE
<222> LOCATION: (189)..(190)
<223> OTHER INFORMATION: Xaa is non-conserved residue
<220> FEATURE:
<221> NAME/KEY: MISC_FEATURE
<222> LOCATION: (192)..(193)
<223> OTHER INFORMATION: Xaa is non-conserved residue
<220> FEATURE:
<221> NAME/KEY: MISC_FEATURE
<222> LOCATION: (196)..(197)
<223> OTHER INFORMATION: Xaa is non-conserved residue
<220> FEATURE:
<221> NAME/KEY: MISC_FEATURE
<222> LOCATION: (199)..(201)
<223> OTHER INFORMATION: Xaa is non-conserved residue
<220> FEATURE:
<221> NAME/KEY: MISC_FEATURE
<222> LOCATION: (203)..(212)
<223> OTHER INFORMATION: Xaa is non-conserved residue
<220> FEATURE:
<221> NAME/KEY: MISC_FEATURE
<222> LOCATION: (214)..(214)
<223> OTHER INFORMATION: Xaa is non-conserved residue
<220> FEATURE:
<221> NAME/KEY: MISC_FEATURE
<222> LOCATION: (223)..(229)
<223> OTHER INFORMATION: Xaa is non-conserved residue
<220> FEATURE:
<221> NAME/KEY: MISC_FEATURE
<222> LOCATION: (231)..(235)
<223> OTHER INFORMATION: Xaa is non-conserved residue
<220> FEATURE:
<221> NAME/KEY: MISC_FEATURE
<222> LOCATION: (237)..(242)
<223> OTHER INFORMATION: Xaa is non-conserved residue
<220> FEATURE:
<221> NAME/KEY: MISC_FEATURE
<222> LOCATION: (246)..(246)
```

```
<223> OTHER INFORMATION: Xaa is non-conserved residue
<220> FEATURE:
<221> NAME/KEY: MISC_FEATURE
<222> LOCATION: (252)..(252)
<223> OTHER INFORMATION: Xaa is non-conserved residue
<220> FEATURE:
<221> NAME/KEY: MISC_FEATURE
<222> LOCATION: (254)..(255)
<223> OTHER INFORMATION: Xaa is non-conserved residue
<220> FEATURE:
<221> NAME/KEY: MISC_FEATURE
<222> LOCATION: (257)..(264)
<223> OTHER INFORMATION: Xaa is non-conserved residue
<220> FEATURE:
<221> NAME/KEY: MISC_FEATURE
<222> LOCATION: (266)..(288)
<223> OTHER INFORMATION: Xaa is non-conserved residue
<220> FEATURE:
<221> NAME/KEY: MISC_FEATURE
<222> LOCATION: (290)..(290)
<223> OTHER INFORMATION: Xaa is non-conserved residue
<220> FEATURE:
<221> NAME/KEY: MISC_FEATURE
<222> LOCATION: (292)..(292)
<223> OTHER INFORMATION: Xaa is non-conserved residue
<220> FEATURE:
<221> NAME/KEY: MISC_FEATURE
<222> LOCATION: (294)..(294)
<223> OTHER INFORMATION: Xaa is non-conserved residue
<220> FEATURE:
<221> NAME/KEY: MISC_FEATURE
<222> LOCATION: (307)..(310)
<223> OTHER INFORMATION: Xaa is non-conserved residue
<220> FEATURE:
<221> NAME/KEY: MISC_FEATURE
<222> LOCATION: (313)..(320)
<223> OTHER INFORMATION: Xaa is non-conserved residue
<220> FEATURE:
<221> NAME/KEY: MISC_FEATURE
<222> LOCATION: (322)..(323)
<223> OTHER INFORMATION: Xaa is non-conserved residue
<220> FEATURE:
<221> NAME/KEY: MISC_FEATURE
<222> LOCATION: (328)..(330)
<223> OTHER INFORMATION: Xaa is non-conserved residue
<220> FEATURE:
<221> NAME/KEY: MISC_FEATURE
<222> LOCATION: (336)..(337)
<223> OTHER INFORMATION: Xaa is non-conserved residue
<220> FEATURE:
<221> NAME/KEY: MISC_FEATURE
<222> LOCATION: (339)..(341)
<223> OTHER INFORMATION: Xaa is non-conserved residue
<220> FEATURE:
<221> NAME/KEY: MISC_FEATURE
<222> LOCATION: (343)..(343)
<223> OTHER INFORMATION: Xaa is non-conserved residue
<220> FEATURE:
<221> NAME/KEY: MISC_FEATURE
<222> LOCATION: (345)..(346)
<223> OTHER INFORMATION: Xaa is non-conserved residue
<220> FEATURE:
<221> NAME/KEY: MISC_FEATURE
<222> LOCATION: (348)..(350)
<223> OTHER INFORMATION: Xaa is non-conserved residue
<220> FEATURE:
<221> NAME/KEY: MISC_FEATURE
<222> LOCATION: (352)..(357)
<223> OTHER INFORMATION: Xaa is non-conserved residue
<220> FEATURE:
<221> NAME/KEY: MISC_FEATURE
<222> LOCATION: (359)..(361)
<223> OTHER INFORMATION: Xaa is non-conserved residue
<220> FEATURE:
<221> NAME/KEY: MISC_FEATURE
<222> LOCATION: (363)..(368)
<223> OTHER INFORMATION: Xaa is non-conserved residue
<220> FEATURE:
<221> NAME/KEY: MISC_FEATURE
```

-continued

```
<222> LOCATION: (371)..(373)
<223> OTHER INFORMATION: Xaa is non-conserved residue
<220> FEATURE:
<221> NAME/KEY: MISC_FEATURE
<222> LOCATION: (375)..(376)
<223> OTHER INFORMATION: Xaa is non-conserved residue
<220> FEATURE:
<221> NAME/KEY: MISC_FEATURE
<222> LOCATION: (379)..(381)
<223> OTHER INFORMATION: Xaa is non-conserved residue
<220> FEATURE:
<221> NAME/KEY: MISC_FEATURE
<222> LOCATION: (383)..(383)
<223> OTHER INFORMATION: Xaa is non-conserved residue
<220> FEATURE:
<221> NAME/KEY: MISC_FEATURE
<222> LOCATION: (386)..(386)
<223> OTHER INFORMATION: Xaa is non-conserved residue
<220> FEATURE:
<221> NAME/KEY: MISC_FEATURE
<222> LOCATION: (388)..(393)
<223> OTHER INFORMATION: Xaa is non-conserved residue
<220> FEATURE:
<221> NAME/KEY: MISC_FEATURE
<222> LOCATION: (395)..(405)
<223> OTHER INFORMATION: Xaa is non-conserved residue
<220> FEATURE:
<221> NAME/KEY: MISC_FEATURE
<222> LOCATION: (408)..(415)
<223> OTHER INFORMATION: Xaa is non-conserved residue
<220> FEATURE:
<221> NAME/KEY: MISC_FEATURE
<222> LOCATION: (418)..(418)
<223> OTHER INFORMATION: Xaa is non-conserved residue
<220> FEATURE:
<221> NAME/KEY: MISC_FEATURE
<222> LOCATION: (420)..(420)
<223> OTHER INFORMATION: Xaa is non-conserved residue
<220> FEATURE:
<221> NAME/KEY: MISC_FEATURE
<222> LOCATION: (427)..(427)
<223> OTHER INFORMATION: Xaa is non-conserved residue
<220> FEATURE:
<221> NAME/KEY: MISC_FEATURE
<222> LOCATION: (429)..(429)
<223> OTHER INFORMATION: Xaa is non-conserved residue
<220> FEATURE:
<221> NAME/KEY: MISC_FEATURE
<222> LOCATION: (433)..(435)
<223> OTHER INFORMATION: Xaa is non-conserved residue
<220> FEATURE:
<221> NAME/KEY: MISC_FEATURE
<222> LOCATION: (439)..(442)
<223> OTHER INFORMATION: Xaa is non-conserved residue
<220> FEATURE:
<221> NAME/KEY: MISC_FEATURE
<222> LOCATION: (445)..(446)
<223> OTHER INFORMATION: Xaa is non-conserved residue
<220> FEATURE:
<221> NAME/KEY: MISC_FEATURE
<222> LOCATION: (448)..(449)
<223> OTHER INFORMATION: Xaa is non-conserved residue
<220> FEATURE:
<221> NAME/KEY: MISC_FEATURE
<222> LOCATION: (451)..(503)
<223> OTHER INFORMATION: Xaa is non-conserved residue

<400> SEQUENCE: 63

Xaa Xaa Xaa Xaa Xaa Xaa Xaa Xaa Xaa Xaa Xaa Xaa Xaa Xaa Xaa Xaa
1               5                   10                  15

Xaa Leu Ser Xaa Xaa Xaa Xaa Xaa Xaa His Gly Xaa Xaa Ser Xaa
            20                  25                  30

Tyr Phe Xaa Gly Trp Xaa Xaa Tyr Xaa Xaa Pro Xaa Xaa Xaa Xaa
        35                  40                  45

Xaa Asn Pro Ser Gly Ile Ile Gln Met Gly Xaa Xaa Glu Asn Xaa Xaa
```

-continued

```
            50                  55                  60
Xaa Phe Asp Leu Xaa Glu Xaa Xaa Leu Xaa Xaa Xaa Xaa Xaa Xaa
65                  70                  75                  80

Xaa Xaa Xaa Xaa Xaa Xaa Xaa Gly Xaa Xaa Xaa Phe Xaa Xaa Xaa
                    85                  90                  95

Xaa Leu Phe Gln Asp Tyr His Gly Xaa Xaa Phe Xaa Xaa Ala Xaa
                100                 105                 110

Xaa Xaa Xaa Met Xaa Xaa Xaa Arg Gly Xaa Xaa Xaa Xaa Phe Xaa Xaa
                115                 120                 125

Xaa Xaa Xaa Val Leu Xaa Ala Gly Xaa Thr Xaa Ala Asn Glu Xaa Leu
130                 135                 140

Xaa Phe Xaa Leu Ala Xaa Xaa Xaa Ala Xaa Leu Xaa Pro Thr Pro
145                 150                 155                 160

Tyr Tyr Pro Gly Phe Asp Arg Asp Leu Xaa Trp Arg Thr Gly Xaa Xaa
                165                 170                 175

Ile Val Pro Xaa Xaa Xaa Xaa Ser Xaa Asn Xaa Phe Xaa Xaa Thr Xaa
                180                 185                 190

Xaa Ala Leu Xaa Xaa Ala Xaa Xaa Ala Xaa Xaa Xaa Xaa Xaa Xaa
                195                 200                 205

Xaa Xaa Xaa Xaa Leu Xaa Thr Asn Pro Ser Asn Pro Leu Gly Xaa Xaa
                210                 215                 220

Xaa Xaa Xaa Xaa Xaa Leu Xaa Xaa Xaa Xaa Phe Xaa Xaa Xaa
225                 230                 235                 240

Xaa Xaa Ile His Leu Xaa Ser Asp Glu Ile Tyr Xaa Gly Xaa Xaa Phe
                245                 250                 255

Xaa Xaa Xaa Xaa Xaa Xaa Xaa Ser Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa
                275                 280                 285

Arg Xaa His Xaa Val Xaa Ser Leu Ser Lys Asp Leu Gly Leu Pro Gly
290                 295                 300

Phe Arg Xaa Xaa Xaa Xaa Tyr Ser Xaa Xaa Xaa Xaa Xaa Xaa Xaa
305                 310                 315                 320

Ala Xaa Xaa Met Ser Ser Phe Xaa Xaa Xaa Ser Ser Gln Thr Gln Xaa
                325                 330                 335

Xaa Leu Xaa Xaa Xaa Leu Xaa Asp Xaa Xaa Phe Xaa Xaa Xaa Tyr Xaa
                340                 345                 350

Xaa Xaa Xaa Xaa Xaa Arg Xaa Xaa Xaa Arg Xaa Xaa Xaa Xaa Xaa
                355                 360                 365

Gly Leu Xaa Xaa Xaa Gly Xaa Xaa Cys Leu Xaa Xaa Xaa Ala Xaa Leu
370                 375                 380

Phe Xaa Trp Xaa Xaa Xaa Xaa Xaa Leu Xaa Xaa Xaa Xaa Xaa Xaa
385                 390                 395                 400

Xaa Xaa Xaa Xaa Xaa Leu Trp Xaa Xaa Xaa Xaa Xaa Xaa Xaa Leu
                405                 410                 415

Asn Xaa Ser Xaa Gly Ser Ser Cys His Cys Xaa Glu Xaa Gly Trp Phe
                420                 425                 430

Xaa Xaa Xaa Phe Ala Asn Xaa Xaa Xaa Xaa Thr Leu Xaa Xaa Ala Xaa
                435                 440                 445

Xaa Arg Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa
465                 470                 475                 480
```

```
Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa
            500

<210> SEQ ID NO 64
<211> LENGTH: 503
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE
<222> LOCATION: (1)..(17)
<223> OTHER INFORMATION: Xaa is non-conserved residue
<220> FEATURE:
<221> NAME/KEY: MISC_FEATURE
<222> LOCATION: (20)..(26)
<223> OTHER INFORMATION: Xaa is non-conserved residue
<220> FEATURE:
<221> NAME/KEY: MISC_FEATURE
<222> LOCATION: (30)..(30)
<223> OTHER INFORMATION: Xaa is non-conserved residue
<220> FEATURE:
<221> NAME/KEY: MISC_FEATURE
<222> LOCATION: (32)..(32)
<223> OTHER INFORMATION: Xaa is non-conserved residue
<220> FEATURE:
<221> NAME/KEY: MISC_FEATURE
<222> LOCATION: (35)..(35)
<223> OTHER INFORMATION: Xaa is non-conserved residue
<220> FEATURE:
<221> NAME/KEY: MISC_FEATURE
<222> LOCATION: (38)..(39)
<223> OTHER INFORMATION: Xaa is non-conserved residue
<220> FEATURE:
<221> NAME/KEY: MISC_FEATURE
<222> LOCATION: (42)..(43)
<223> OTHER INFORMATION: Xaa is non-conserved residue
<220> FEATURE:
<221> NAME/KEY: MISC_FEATURE
<222> LOCATION: (46)..(49)
<223> OTHER INFORMATION: Xaa is non-conserved residue
<220> FEATURE:
<221> NAME/KEY: MISC_FEATURE
<222> LOCATION: (52)..(52)
<223> OTHER INFORMATION: Xaa is non-conserved residue
<220> FEATURE:
<221> NAME/KEY: MISC_FEATURE
<222> LOCATION: (54)..(54)
<223> OTHER INFORMATION: Xaa is non-conserved residue
<220> FEATURE:
<221> NAME/KEY: MISC_FEATURE
<222> LOCATION: (63)..(65)
<223> OTHER INFORMATION: Xaa is non-conserved residue
<220> FEATURE:
<221> NAME/KEY: MISC_FEATURE
<222> LOCATION: (71)..(71)
<223> OTHER INFORMATION: Xaa is non-conserved residue
<220> FEATURE:
<221> NAME/KEY: MISC_FEATURE
<222> LOCATION: (74)..(88)
<223> OTHER INFORMATION: Xaa is non-conserved residue
<220> FEATURE:
<221> NAME/KEY: MISC_FEATURE
<222> LOCATION: (90)..(92)
<223> OTHER INFORMATION: Xaa is non-conserved residue
<220> FEATURE:
<221> NAME/KEY: MISC_FEATURE
<222> LOCATION: (96)..(97)
<223> OTHER INFORMATION: Xaa is non-conserved residue
<220> FEATURE:
<221> NAME/KEY: MISC_FEATURE
<222> LOCATION: (106)..(107)
<223> OTHER INFORMATION: Xaa is non-conserved residue
<220> FEATURE:
```

```
<221> NAME/KEY: MISC_FEATURE
<222> LOCATION: (110)..(110)
<223> OTHER INFORMATION: Xaa is non-conserved residue
<220> FEATURE:
<221> NAME/KEY: MISC_FEATURE
<222> LOCATION: (112)..(114)
<223> OTHER INFORMATION: Xaa is non-conserved residue
<220> FEATURE:
<221> NAME/KEY: MISC_FEATURE
<222> LOCATION: (117)..(119)
<223> OTHER INFORMATION: Xaa is non-conserved residue
<220> FEATURE:
<221> NAME/KEY: MISC_FEATURE
<222> LOCATION: (122)..(122)
<223> OTHER INFORMATION: Xaa is non-conserved residue
<220> FEATURE:
<221> NAME/KEY: MISC_FEATURE
<222> LOCATION: (124)..(125)
<223> OTHER INFORMATION: Xaa is non-conserved residue
<220> FEATURE:
<221> NAME/KEY: MISC_FEATURE
<222> LOCATION: (127)..(130)
<223> OTHER INFORMATION: Xaa is non-conserved residue
<220> FEATURE:
<221> NAME/KEY: MISC_FEATURE
<222> LOCATION: (134)..(134)
<223> OTHER INFORMATION: Xaa is non-conserved residue
<220> FEATURE:
<221> NAME/KEY: MISC_FEATURE
<222> LOCATION: (137)..(137)
<223> OTHER INFORMATION: Xaa is non-conserved residue
<220> FEATURE:
<221> NAME/KEY: MISC_FEATURE
<222> LOCATION: (139)..(139)
<223> OTHER INFORMATION: Xaa is non-conserved residue
<220> FEATURE:
<221> NAME/KEY: MISC_FEATURE
<222> LOCATION: (143)..(143)
<223> OTHER INFORMATION: Xaa is non-conserved residue
<220> FEATURE:
<221> NAME/KEY: MISC_FEATURE
<222> LOCATION: (145)..(145)
<223> OTHER INFORMATION: Xaa is non-conserved residue
<220> FEATURE:
<221> NAME/KEY: MISC_FEATURE
<222> LOCATION: (147)..(147)
<223> OTHER INFORMATION: Xaa is non-conserved residue
<220> FEATURE:
<221> NAME/KEY: MISC_FEATURE
<222> LOCATION: (150)..(153)
<223> OTHER INFORMATION: Xaa is non-conserved residue
<220> FEATURE:
<221> NAME/KEY: MISC_FEATURE
<222> LOCATION: (155)..(155)
<223> OTHER INFORMATION: Xaa is non-conserved residue
<220> FEATURE:
<221> NAME/KEY: MISC_FEATURE
<222> LOCATION: (175)..(176)
<223> OTHER INFORMATION: Xaa is non-conserved residue
<220> FEATURE:
<221> NAME/KEY: MISC_FEATURE
<222> LOCATION: (181)..(183)
<223> OTHER INFORMATION: Xaa is non-conserved residue
<220> FEATURE:
<221> NAME/KEY: MISC_FEATURE
<222> LOCATION: (185)..(185)
<223> OTHER INFORMATION: Xaa is non-conserved residue
<220> FEATURE:
<221> NAME/KEY: MISC_FEATURE
<222> LOCATION: (187)..(187)
<223> OTHER INFORMATION: Xaa is non-conserved residue
<220> FEATURE:
<221> NAME/KEY: MISC_FEATURE
<222> LOCATION: (189)..(189)
<223> OTHER INFORMATION: Xaa is non-conserved residue
<220> FEATURE:
<221> NAME/KEY: MISC_FEATURE
<222> LOCATION: (192)..(193)
<223> OTHER INFORMATION: Xaa is non-conserved residue
```

-continued

```
<220> FEATURE:
<221> NAME/KEY: MISC_FEATURE
<222> LOCATION: (197)..(197)
<223> OTHER INFORMATION: Xaa is non-conserved residue
<220> FEATURE:
<221> NAME/KEY: MISC_FEATURE
<222> LOCATION: (199)..(201)
<223> OTHER INFORMATION: Xaa is non-conserved residue
<220> FEATURE:
<221> NAME/KEY: MISC_FEATURE
<222> LOCATION: (203)..(206)
<223> OTHER INFORMATION: Xaa is non-conserved residue
<220> FEATURE:
<221> NAME/KEY: MISC_FEATURE
<222> LOCATION: (208)..(209)
<223> OTHER INFORMATION: Xaa is non-conserved residue
<220> FEATURE:
<221> NAME/KEY: MISC_FEATURE
<222> LOCATION: (211)..(211)
<223> OTHER INFORMATION: Xaa is non-conserved residue
<220> FEATURE:
<221> NAME/KEY: MISC_FEATURE
<222> LOCATION: (223)..(229)
<223> OTHER INFORMATION: Xaa is non-conserved residue
<220> FEATURE:
<221> NAME/KEY: MISC_FEATURE
<222> LOCATION: (231)..(232)
<223> OTHER INFORMATION: Xaa is non-conserved residue
<220> FEATURE:
<221> NAME/KEY: MISC_FEATURE
<222> LOCATION: (234)..(235)
<223> OTHER INFORMATION: Xaa is non-conserved residue
<220> FEATURE:
<221> NAME/KEY: MISC_FEATURE
<222> LOCATION: (237)..(242)
<223> OTHER INFORMATION: Xaa is non-conserved residue
<220> FEATURE:
<221> NAME/KEY: MISC_FEATURE
<222> LOCATION: (252)..(252)
<223> OTHER INFORMATION: Xaa is non-conserved residue
<220> FEATURE:
<221> NAME/KEY: MISC_FEATURE
<222> LOCATION: (254)..(255)
<223> OTHER INFORMATION: Xaa is non-conserved residue
<220> FEATURE:
<221> NAME/KEY: MISC_FEATURE
<222> LOCATION: (257)..(264)
<223> OTHER INFORMATION: Xaa is non-conserved residue
<220> FEATURE:
<221> NAME/KEY: MISC_FEATURE
<222> LOCATION: (266)..(267)
<223> OTHER INFORMATION: Xaa is non-conserved residue
<220> FEATURE:
<221> NAME/KEY: MISC_FEATURE
<222> LOCATION: (269)..(285)
<223> OTHER INFORMATION: Xaa is non-conserved residue
<220> FEATURE:
<221> NAME/KEY: MISC_FEATURE
<222> LOCATION: (287)..(288)
<223> OTHER INFORMATION: Xaa is non-conserved residue
<220> FEATURE:
<221> NAME/KEY: MISC_FEATURE
<222> LOCATION: (294)..(294)
<223> OTHER INFORMATION: Xaa is non-conserved residue
<220> FEATURE:
<221> NAME/KEY: MISC_FEATURE
<222> LOCATION: (308)..(309)
<223> OTHER INFORMATION: Xaa is non-conserved residue
<220> FEATURE:
<221> NAME/KEY: MISC_FEATURE
<222> LOCATION: (313)..(316)
<223> OTHER INFORMATION: Xaa is non-conserved residue
<220> FEATURE:
<221> NAME/KEY: MISC_FEATURE
<222> LOCATION: (319)..(320)
<223> OTHER INFORMATION: Xaa is non-conserved residue
<220> FEATURE:
<221> NAME/KEY: MISC_FEATURE
<222> LOCATION: (322)..(322)
```

```
<223> OTHER INFORMATION: Xaa is non-conserved residue
<220> FEATURE:
<221> NAME/KEY: MISC_FEATURE
<222> LOCATION: (328)..(328)
<223> OTHER INFORMATION: Xaa is non-conserved residue
<220> FEATURE:
<221> NAME/KEY: MISC_FEATURE
<222> LOCATION: (336)..(337)
<223> OTHER INFORMATION: Xaa is non-conserved residue
<220> FEATURE:
<221> NAME/KEY: MISC_FEATURE
<222> LOCATION: (339)..(340)
<223> OTHER INFORMATION: Xaa is non-conserved residue
<220> FEATURE:
<221> NAME/KEY: MISC_FEATURE
<222> LOCATION: (343)..(343)
<223> OTHER INFORMATION: Xaa is non-conserved residue
<220> FEATURE:
<221> NAME/KEY: MISC_FEATURE
<222> LOCATION: (345)..(346)
<223> OTHER INFORMATION: Xaa is non-conserved residue
<220> FEATURE:
<221> NAME/KEY: MISC_FEATURE
<222> LOCATION: (348)..(350)
<223> OTHER INFORMATION: Xaa is non-conserved residue
<220> FEATURE:
<221> NAME/KEY: MISC_FEATURE
<222> LOCATION: (353)..(357)
<223> OTHER INFORMATION: Xaa is non-conserved residue
<220> FEATURE:
<221> NAME/KEY: MISC_FEATURE
<222> LOCATION: (361)..(361)
<223> OTHER INFORMATION: Xaa is non-conserved residue
<220> FEATURE:
<221> NAME/KEY: MISC_FEATURE
<222> LOCATION: (363)..(365)
<223> OTHER INFORMATION: Xaa is non-conserved residue
<220> FEATURE:
<221> NAME/KEY: MISC_FEATURE
<222> LOCATION: (367)..(368)
<223> OTHER INFORMATION: Xaa is non-conserved residue
<220> FEATURE:
<221> NAME/KEY: MISC_FEATURE
<222> LOCATION: (371)..(373)
<223> OTHER INFORMATION: Xaa is non-conserved residue
<220> FEATURE:
<221> NAME/KEY: MISC_FEATURE
<222> LOCATION: (376)..(376)
<223> OTHER INFORMATION: Xaa is non-conserved residue
<220> FEATURE:
<221> NAME/KEY: MISC_FEATURE
<222> LOCATION: (379)..(381)
<223> OTHER INFORMATION: Xaa is non-conserved residue
<220> FEATURE:
<221> NAME/KEY: MISC_FEATURE
<222> LOCATION: (383)..(383)
<223> OTHER INFORMATION: Xaa is non-conserved residue
<220> FEATURE:
<221> NAME/KEY: MISC_FEATURE
<222> LOCATION: (386)..(386)
<223> OTHER INFORMATION: Xaa is non-conserved residue
<220> FEATURE:
<221> NAME/KEY: MISC_FEATURE
<222> LOCATION: (388)..(393)
<223> OTHER INFORMATION: Xaa is non-conserved residue
<220> FEATURE:
<221> NAME/KEY: MISC_FEATURE
<222> LOCATION: (396)..(403)
<223> OTHER INFORMATION: Xaa is non-conserved residue
<220> FEATURE:
<221> NAME/KEY: MISC_FEATURE
<222> LOCATION: (405)..(405)
<223> OTHER INFORMATION: Xaa is non-conserved residue
<220> FEATURE:
<221> NAME/KEY: MISC_FEATURE
<222> LOCATION: (408)..(409)
<223> OTHER INFORMATION: Xaa is non-conserved residue
<220> FEATURE:
<221> NAME/KEY: MISC_FEATURE
```

-continued

```
<222> LOCATION: (411)..(415)
<223> OTHER INFORMATION: Xaa is non-conserved residue
<220> FEATURE:
<221> NAME/KEY: MISC_FEATURE
<222> LOCATION: (420)..(420)
<223> OTHER INFORMATION: Xaa is non-conserved residue
<220> FEATURE:
<221> NAME/KEY: MISC_FEATURE
<222> LOCATION: (427)..(427)
<223> OTHER INFORMATION: Xaa is non-conserved residue
<220> FEATURE:
<221> NAME/KEY: MISC_FEATURE
<222> LOCATION: (429)..(429)
<223> OTHER INFORMATION: Xaa is non-conserved residue
<220> FEATURE:
<221> NAME/KEY: MISC_FEATURE
<222> LOCATION: (433)..(435)
<223> OTHER INFORMATION: Xaa is non-conserved residue
<220> FEATURE:
<221> NAME/KEY: MISC_FEATURE
<222> LOCATION: (440)..(442)
<223> OTHER INFORMATION: Xaa is non-conserved residue
<220> FEATURE:
<221> NAME/KEY: MISC_FEATURE
<222> LOCATION: (445)..(445)
<223> OTHER INFORMATION: Xaa is non-conserved residue
<220> FEATURE:
<221> NAME/KEY: MISC_FEATURE
<222> LOCATION: (449)..(449)
<223> OTHER INFORMATION: Xaa is non-conserved residue
<220> FEATURE:
<221> NAME/KEY: MISC_FEATURE
<222> LOCATION: (452)..(455)
<223> OTHER INFORMATION: Xaa is non-conserved residue
<220> FEATURE:
<221> NAME/KEY: MISC_FEATURE
<222> LOCATION: (457)..(503)
<223> OTHER INFORMATION: Xaa is non-conserved residue

<400> SEQUENCE: 64

Xaa Xaa Xaa Xaa Xaa Xaa Xaa Xaa Xaa Xaa Xaa Xaa Xaa Xaa Xaa Xaa
1               5                   10                  15

Xaa Leu Ser Xaa Xaa Xaa Xaa Xaa Xaa His Gly Gln Xaa Ser Xaa
            20                  25                  30

Tyr Phe Xaa Gly Trp Xaa Xaa Tyr Glu Xaa Xaa Pro Tyr Xaa Xaa Xaa
        35                  40                  45

Xaa Asn Pro Xaa Gly Xaa Ile Gln Met Gly Leu Ala Glu Asn Xaa Xaa
    50                  55                  60

Xaa Phe Asp Leu Leu Glu Xaa Trp Leu Xaa Xaa Xaa Xaa Xaa Xaa Xaa
65                  70                  75                  80

Xaa Xaa Xaa Xaa Xaa Xaa Xaa Gly Xaa Xaa Xaa Phe Arg Glu Xaa
                85                  90                  95

Xaa Leu Phe Gln Asp Tyr His Gly Leu Xaa Xaa Phe Lys Xaa Ala Xaa
            100                 105                 110

Xaa Xaa Phe Met Xaa Xaa Xaa Arg Gly Xaa Lys Xaa Phe Xaa Xaa
        115                 120                 125

Xaa Xaa Ile Val Leu Xaa Ala Gly Xaa Thr Xaa Ala Asn Glu Xaa Leu
        130                 135                 140

Xaa Phe Xaa Leu Ala Xaa Xaa Xaa Ala Xaa Leu Leu Pro Thr Pro
145                 150                 155                 160

Tyr Tyr Pro Gly Phe Asp Arg Asp Leu Lys Trp Arg Thr Gly Xaa Xaa
                165                 170                 175

Ile Val Pro Ile Xaa Xaa Xaa Ser Xaa Asn Xaa Phe Xaa Ile Thr Xaa
            180                 185                 190

Xaa Ala Leu Glu Xaa Ala Xaa Xaa Xaa Ala Xaa Xaa Xaa Xaa Leu Xaa
            195                 200                 205
```

```
Xaa Lys Xaa Val Leu Ile Thr Asn Pro Ser Asn Pro Leu Gly Xaa Xaa
    210                 215                 220

Xaa Xaa Xaa Xaa Xaa Leu Xaa Xaa Leu Xaa Xaa Phe Xaa Xaa Xaa Xaa
225                 230                 235                 240

Xaa Xaa Ile His Leu Ile Ser Asp Glu Ile Tyr Xaa Gly Xaa Xaa Phe
                245                 250                 255

Xaa Xaa Xaa Xaa Xaa Xaa Xaa Ser Xaa Xaa Glu Xaa Xaa Xaa Xaa
            260                 265                 270

Xaa Xaa Xaa Xaa Xaa Xaa Xaa Xaa Xaa Xaa Xaa Xaa Val Xaa Xaa
            275                 280                 285

Arg Val His Ile Val Xaa Ser Leu Ser Lys Asp Leu Gly Leu Pro Gly
    290                 295                 300

Phe Arg Val Xaa Xaa Ile Tyr Ser Xaa Xaa Xaa Val Val Xaa Xaa
305             310                 315                 320

Ala Xaa Lys Met Ser Ser Phe Xaa Leu Val Ser Ser Gln Thr Gln Xaa
                325                 330                 335

Xaa Leu Xaa Xaa Leu Leu Xaa Asp Xaa Xaa Phe Xaa Xaa Xaa Tyr Ile
            340                 345                 350

Xaa Xaa Xaa Xaa Xaa Arg Leu Lys Xaa Arg Xaa Xaa Xaa Leu Xaa Xaa
            355                 360                 365

Gly Leu Xaa Xaa Xaa Gly Ile Xaa Cys Leu Xaa Xaa Xaa Ala Xaa Leu
370                 375                 380

Phe Xaa Trp Xaa Xaa Xaa Xaa Xaa Leu Leu Xaa Xaa Xaa Xaa Xaa
385                 390                 395                 400

Xaa Xaa Xaa Met Xaa Leu Trp Xaa Xaa Ile Xaa Xaa Xaa Xaa Xaa Leu
                405                 410                 415

Asn Ile Ser Xaa Gly Ser Ser Cys His Cys Xaa Glu Xaa Gly Trp Phe
            420                 425                 430

Xaa Xaa Xaa Phe Ala Asn Met Xaa Xaa Xaa Thr Leu Xaa Leu Ala Leu
            435                 440                 445

Xaa Arg Leu Xaa Xaa Xaa Xaa Asp Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa
            500

<210> SEQ ID NO 65
<211> LENGTH: 498
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE
<222> LOCATION: (1)..(9)
<223> OTHER INFORMATION: Xaa is non-conserved residue
<220> FEATURE:
<221> NAME/KEY: MISC_FEATURE
<222> LOCATION: (14)..(15)
<223> OTHER INFORMATION: Xaa is non-conserved residue
<220> FEATURE:
<221> NAME/KEY: MISC_FEATURE
<222> LOCATION: (17)..(20)
<223> OTHER INFORMATION: Xaa is non-conserved residue
<220> FEATURE:
<221> NAME/KEY: MISC_FEATURE
```

```
<222> LOCATION: (23)..(24)
<223> OTHER INFORMATION: Xaa is non-conserved residue
<220> FEATURE:
<221> NAME/KEY: MISC_FEATURE
<222> LOCATION: (29)..(29)
<223> OTHER INFORMATION: Xaa is non-conserved residue
<220> FEATURE:
<221> NAME/KEY: MISC_FEATURE
<222> LOCATION: (32)..(33)
<223> OTHER INFORMATION: Xaa is non-conserved residue
<220> FEATURE:
<221> NAME/KEY: MISC_FEATURE
<222> LOCATION: (35)..(37)
<223> OTHER INFORMATION: Xaa is non-conserved residue
<220> FEATURE:
<221> NAME/KEY: MISC_FEATURE
<222> LOCATION: (39)..(39)
<223> OTHER INFORMATION: Xaa is non-conserved residue
<220> FEATURE:
<221> NAME/KEY: MISC_FEATURE
<222> LOCATION: (41)..(43)
<223> OTHER INFORMATION: Xaa is non-conserved residue
<220> FEATURE:
<221> NAME/KEY: MISC_FEATURE
<222> LOCATION: (45)..(46)
<223> OTHER INFORMATION: Xaa is non-conserved residue
<220> FEATURE:
<221> NAME/KEY: MISC_FEATURE
<222> LOCATION: (48)..(48)
<223> OTHER INFORMATION: Xaa is non-conserved residue
<220> FEATURE:
<221> NAME/KEY: MISC_FEATURE
<222> LOCATION: (60)..(60)
<223> OTHER INFORMATION: Xaa is non-conserved residue
<220> FEATURE:
<221> NAME/KEY: MISC_FEATURE
<222> LOCATION: (63)..(63)
<223> OTHER INFORMATION: Xaa is non-conserved residue
<220> FEATURE:
<221> NAME/KEY: MISC_FEATURE
<222> LOCATION: (65)..(65)
<223> OTHER INFORMATION: Xaa is non-conserved residue
<220> FEATURE:
<221> NAME/KEY: MISC_FEATURE
<222> LOCATION: (67)..(70)
<223> OTHER INFORMATION: Xaa is non-conserved residue
<220> FEATURE:
<221> NAME/KEY: MISC_FEATURE
<222> LOCATION: (72)..(72)
<223> OTHER INFORMATION: Xaa is non-conserved residue
<220> FEATURE:
<221> NAME/KEY: MISC_FEATURE
<222> LOCATION: (74)..(79)
<223> OTHER INFORMATION: Xaa is non-conserved residue
<220> FEATURE:
<221> NAME/KEY: MISC_FEATURE
<222> LOCATION: (82)..(83)
<223> OTHER INFORMATION: Xaa is non-conserved residue
<220> FEATURE:
<221> NAME/KEY: MISC_FEATURE
<222> LOCATION: (86)..(87)
<223> OTHER INFORMATION: Xaa is non-conserved residue
<220> FEATURE:
<221> NAME/KEY: MISC_FEATURE
<222> LOCATION: (89)..(89)
<223> OTHER INFORMATION: Xaa is non-conserved residue
<220> FEATURE:
<221> NAME/KEY: MISC_FEATURE
<222> LOCATION: (96)..(96)
<223> OTHER INFORMATION: Xaa is non-conserved residue
<220> FEATURE:
<221> NAME/KEY: MISC_FEATURE
<222> LOCATION: (98)..(98)
<223> OTHER INFORMATION: Xaa is non-conserved residue
<220> FEATURE:
<221> NAME/KEY: MISC_FEATURE
<222> LOCATION: (100)..(101)
<223> OTHER INFORMATION: Xaa is non-conserved residue
<220> FEATURE:
```

```
<221> NAME/KEY: MISC_FEATURE
<222> LOCATION: (103)..(103)
<223> OTHER INFORMATION: Xaa is non-conserved residue
<220> FEATURE:
<221> NAME/KEY: MISC_FEATURE
<222> LOCATION: (105)..(105)
<223> OTHER INFORMATION: Xaa is non-conserved residue
<220> FEATURE:
<221> NAME/KEY: MISC_FEATURE
<222> LOCATION: (108)..(110)
<223> OTHER INFORMATION: Xaa is non-conserved residue
<220> FEATURE:
<221> NAME/KEY: MISC_FEATURE
<222> LOCATION: (112)..(114)
<223> OTHER INFORMATION: Xaa is non-conserved residue
<220> FEATURE:
<221> NAME/KEY: MISC_FEATURE
<222> LOCATION: (120)..(122)
<223> OTHER INFORMATION: Xaa is non-conserved residue
<220> FEATURE:
<221> NAME/KEY: MISC_FEATURE
<222> LOCATION: (124)..(126)
<223> OTHER INFORMATION: Xaa is non-conserved residue
<220> FEATURE:
<221> NAME/KEY: MISC_FEATURE
<222> LOCATION: (130)..(130)
<223> OTHER INFORMATION: Xaa is non-conserved residue
<220> FEATURE:
<221> NAME/KEY: MISC_FEATURE
<222> LOCATION: (132)..(134)
<223> OTHER INFORMATION: Xaa is non-conserved residue
<220> FEATURE:
<221> NAME/KEY: MISC_FEATURE
<222> LOCATION: (136)..(136)
<223> OTHER INFORMATION: Xaa is non-conserved residue
<220> FEATURE:
<221> NAME/KEY: MISC_FEATURE
<222> LOCATION: (142)..(142)
<223> OTHER INFORMATION: Xaa is non-conserved residue
<220> FEATURE:
<221> NAME/KEY: MISC_FEATURE
<222> LOCATION: (146)..(146)
<223> OTHER INFORMATION: Xaa is non-conserved residue
<220> FEATURE:
<221> NAME/KEY: MISC_FEATURE
<222> LOCATION: (148)..(148)
<223> OTHER INFORMATION: Xaa is non-conserved residue
<220> FEATURE:
<221> NAME/KEY: MISC_FEATURE
<222> LOCATION: (155)..(155)
<223> OTHER INFORMATION: Xaa is non-conserved residue
<220> FEATURE:
<221> NAME/KEY: MISC_FEATURE
<222> LOCATION: (160)..(161)
<223> OTHER INFORMATION: Xaa is non-conserved residue
<220> FEATURE:
<221> NAME/KEY: MISC_FEATURE
<222> LOCATION: (164)..(164)
<223> OTHER INFORMATION: Xaa is non-conserved residue
<220> FEATURE:
<221> NAME/KEY: MISC_FEATURE
<222> LOCATION: (166)..(169)
<223> OTHER INFORMATION: Xaa is non-conserved residue
<220> FEATURE:
<221> NAME/KEY: MISC_FEATURE
<222> LOCATION: (171)..(172)
<223> OTHER INFORMATION: Xaa is non-conserved residue
<220> FEATURE:
<221> NAME/KEY: MISC_FEATURE
<222> LOCATION: (174)..(174)
<223> OTHER INFORMATION: Xaa is non-conserved residue
<220> FEATURE:
<221> NAME/KEY: MISC_FEATURE
<222> LOCATION: (176)..(176)
<223> OTHER INFORMATION: Xaa is non-conserved residue
<220> FEATURE:
<221> NAME/KEY: MISC_FEATURE
<222> LOCATION: (178)..(178)
<223> OTHER INFORMATION: Xaa is non-conserved residue
```

```
<220> FEATURE:
<221> NAME/KEY: MISC_FEATURE
<222> LOCATION: (180)..(180)
<223> OTHER INFORMATION: Xaa is non-conserved residue
<220> FEATURE:
<221> NAME/KEY: MISC_FEATURE
<222> LOCATION: (184)..(184)
<223> OTHER INFORMATION: Xaa is non-conserved residue
<220> FEATURE:
<221> NAME/KEY: MISC_FEATURE
<222> LOCATION: (187)..(188)
<223> OTHER INFORMATION: Xaa is non-conserved residue
<220> FEATURE:
<221> NAME/KEY: MISC_FEATURE
<222> LOCATION: (191)..(192)
<223> OTHER INFORMATION: Xaa is non-conserved residue
<220> FEATURE:
<221> NAME/KEY: MISC_FEATURE
<222> LOCATION: (194)..(198)
<223> OTHER INFORMATION: Xaa is non-conserved residue
<220> FEATURE:
<221> NAME/KEY: MISC_FEATURE
<222> LOCATION: (201)..(201)
<223> OTHER INFORMATION: Xaa is non-conserved residue
<220> FEATURE:
<221> NAME/KEY: MISC_FEATURE
<222> LOCATION: (203)..(203)
<223> OTHER INFORMATION: Xaa is non-conserved residue
<220> FEATURE:
<221> NAME/KEY: MISC_FEATURE
<222> LOCATION: (216)..(217)
<223> OTHER INFORMATION: Xaa is non-conserved residue
<220> FEATURE:
<221> NAME/KEY: MISC_FEATURE
<222> LOCATION: (219)..(220)
<223> OTHER INFORMATION: Xaa is non-conserved residue
<220> FEATURE:
<221> NAME/KEY: MISC_FEATURE
<222> LOCATION: (222)..(222)
<223> OTHER INFORMATION: Xaa is non-conserved residue
<220> FEATURE:
<221> NAME/KEY: MISC_FEATURE
<222> LOCATION: (225)..(226)
<223> OTHER INFORMATION: Xaa is non-conserved residue
<220> FEATURE:
<221> NAME/KEY: MISC_FEATURE
<222> LOCATION: (228)..(233)
<223> OTHER INFORMATION: Xaa is non-conserved residue
<220> FEATURE:
<221> NAME/KEY: MISC_FEATURE
<222> LOCATION: (236)..(237)
<223> OTHER INFORMATION: Xaa is non-conserved residue
<220> FEATURE:
<221> NAME/KEY: MISC_FEATURE
<222> LOCATION: (242)..(242)
<223> OTHER INFORMATION: Xaa is non-conserved residue
<220> FEATURE:
<221> NAME/KEY: MISC_FEATURE
<222> LOCATION: (244)..(244)
<223> OTHER INFORMATION: Xaa is non-conserved residue
<220> FEATURE:
<221> NAME/KEY: MISC_FEATURE
<222> LOCATION: (248)..(248)
<223> OTHER INFORMATION: Xaa is non-conserved residue
<220> FEATURE:
<221> NAME/KEY: MISC_FEATURE
<222> LOCATION: (250)..(250)
<223> OTHER INFORMATION: Xaa is non-conserved residue
<220> FEATURE:
<221> NAME/KEY: MISC_FEATURE
<222> LOCATION: (254)..(255)
<223> OTHER INFORMATION: Xaa is non-conserved residue
<220> FEATURE:
<221> NAME/KEY: MISC_FEATURE
<222> LOCATION: (258)..(271)
<223> OTHER INFORMATION: Xaa is non-conserved residue
<220> FEATURE:
<221> NAME/KEY: MISC_FEATURE
<222> LOCATION: (273)..(275)
```

```
<223> OTHER INFORMATION: Xaa is non-conserved residue
<220> FEATURE:
<221> NAME/KEY: MISC_FEATURE
<222> LOCATION: (277)..(278)
<223> OTHER INFORMATION: Xaa is non-conserved residue
<220> FEATURE:
<221> NAME/KEY: MISC_FEATURE
<222> LOCATION: (280)..(281)
<223> OTHER INFORMATION: Xaa is non-conserved residue
<220> FEATURE:
<221> NAME/KEY: MISC_FEATURE
<222> LOCATION: (288)..(288)
<223> OTHER INFORMATION: Xaa is non-conserved residue
<220> FEATURE:
<221> NAME/KEY: MISC_FEATURE
<222> LOCATION: (297)..(298)
<223> OTHER INFORMATION: Xaa is non-conserved residue
<220> FEATURE:
<221> NAME/KEY: MISC_FEATURE
<222> LOCATION: (301)..(301)
<223> OTHER INFORMATION: Xaa is non-conserved residue
<220> FEATURE:
<221> NAME/KEY: MISC_FEATURE
<222> LOCATION: (303)..(304)
<223> OTHER INFORMATION: Xaa is non-conserved residue
<220> FEATURE:
<221> NAME/KEY: MISC_FEATURE
<222> LOCATION: (307)..(308)
<223> OTHER INFORMATION: Xaa is non-conserved residue
<220> FEATURE:
<221> NAME/KEY: MISC_FEATURE
<222> LOCATION: (310)..(310)
<223> OTHER INFORMATION: Xaa is non-conserved residue
<220> FEATURE:
<221> NAME/KEY: MISC_FEATURE
<222> LOCATION: (325)..(325)
<223> OTHER INFORMATION: Xaa is non-conserved residue
<220> FEATURE:
<221> NAME/KEY: MISC_FEATURE
<222> LOCATION: (328)..(329)
<223> OTHER INFORMATION: Xaa is non-conserved residue
<220> FEATURE:
<221> NAME/KEY: MISC_FEATURE
<222> LOCATION: (331)..(331)
<223> OTHER INFORMATION: Xaa is non-conserved residue
<220> FEATURE:
<221> NAME/KEY: MISC_FEATURE
<222> LOCATION: (333)..(334)
<223> OTHER INFORMATION: Xaa is non-conserved residue
<220> FEATURE:
<221> NAME/KEY: MISC_FEATURE
<222> LOCATION: (336)..(337)
<223> OTHER INFORMATION: Xaa is non-conserved residue
<220> FEATURE:
<221> NAME/KEY: MISC_FEATURE
<222> LOCATION: (339)..(340)
<223> OTHER INFORMATION: Xaa is non-conserved residue
<220> FEATURE:
<221> NAME/KEY: MISC_FEATURE
<222> LOCATION: (343)..(344)
<223> OTHER INFORMATION: Xaa is non-conserved residue
<220> FEATURE:
<221> NAME/KEY: MISC_FEATURE
<222> LOCATION: (347)..(349)
<223> OTHER INFORMATION: Xaa is non-conserved residue
<220> FEATURE:
<221> NAME/KEY: MISC_FEATURE
<222> LOCATION: (351)..(356)
<223> OTHER INFORMATION: Xaa is non-conserved residue
<220> FEATURE:
<221> NAME/KEY: MISC_FEATURE
<222> LOCATION: (359)..(360)
<223> OTHER INFORMATION: Xaa is non-conserved residue
<220> FEATURE:
<221> NAME/KEY: MISC_FEATURE
<222> LOCATION: (364)..(364)
<223> OTHER INFORMATION: Xaa is non-conserved residue
<220> FEATURE:
<221> NAME/KEY: MISC_FEATURE
```

```
<222> LOCATION: (367)..(368)
<223> OTHER INFORMATION: Xaa is non-conserved residue
<220> FEATURE:
<221> NAME/KEY: MISC_FEATURE
<222> LOCATION: (374)..(374)
<223> OTHER INFORMATION: Xaa is non-conserved residue
<220> FEATURE:
<221> NAME/KEY: MISC_FEATURE
<222> LOCATION: (376)..(378)
<223> OTHER INFORMATION: Xaa is non-conserved residue
<220> FEATURE:
<221> NAME/KEY: MISC_FEATURE
<222> LOCATION: (380)..(382)
<223> OTHER INFORMATION: Xaa is non-conserved residue
<220> FEATURE:
<221> NAME/KEY: MISC_FEATURE
<222> LOCATION: (384)..(389)
<223> OTHER INFORMATION: Xaa is non-conserved residue
<220> FEATURE:
<221> NAME/KEY: MISC_FEATURE
<222> LOCATION: (391)..(391)
<223> OTHER INFORMATION: Xaa is non-conserved residue
<220> FEATURE:
<221> NAME/KEY: MISC_FEATURE
<222> LOCATION: (395)..(397)
<223> OTHER INFORMATION: Xaa is non-conserved residue
<220> FEATURE:
<221> NAME/KEY: MISC_FEATURE
<222> LOCATION: (399)..(400)
<223> OTHER INFORMATION: Xaa is non-conserved residue
<220> FEATURE:
<221> NAME/KEY: MISC_FEATURE
<222> LOCATION: (402)..(402)
<223> OTHER INFORMATION: Xaa is non-conserved residue
<220> FEATURE:
<221> NAME/KEY: MISC_FEATURE
<222> LOCATION: (405)..(405)
<223> OTHER INFORMATION: Xaa is non-conserved residue
<220> FEATURE:
<221> NAME/KEY: MISC_FEATURE
<222> LOCATION: (409)..(409)
<223> OTHER INFORMATION: Xaa is non-conserved residue
<220> FEATURE:
<221> NAME/KEY: MISC_FEATURE
<222> LOCATION: (411)..(411)
<223> OTHER INFORMATION: Xaa is non-conserved residue
<220> FEATURE:
<221> NAME/KEY: MISC_FEATURE
<222> LOCATION: (414)..(414)
<223> OTHER INFORMATION: Xaa is non-conserved residue
<220> FEATURE:
<221> NAME/KEY: MISC_FEATURE
<222> LOCATION: (423)..(423)
<223> OTHER INFORMATION: Xaa is non-conserved residue
<220> FEATURE:
<221> NAME/KEY: MISC_FEATURE
<222> LOCATION: (427)..(429)
<223> OTHER INFORMATION: Xaa is non-conserved residue
<220> FEATURE:
<221> NAME/KEY: MISC_FEATURE
<222> LOCATION: (431)..(432)
<223> OTHER INFORMATION: Xaa is non-conserved residue
<220> FEATURE:
<221> NAME/KEY: MISC_FEATURE
<222> LOCATION: (436)..(436)
<223> OTHER INFORMATION: Xaa is non-conserved residue
<220> FEATURE:
<221> NAME/KEY: MISC_FEATURE
<222> LOCATION: (438)..(440)
<223> OTHER INFORMATION: Xaa is non-conserved residue
<220> FEATURE:
<221> NAME/KEY: MISC_FEATURE
<222> LOCATION: (442)..(452)
<223> OTHER INFORMATION: Xaa is non-conserved residue
<220> FEATURE:
<221> NAME/KEY: MISC_FEATURE
<222> LOCATION: (454)..(460)
<223> OTHER INFORMATION: Xaa is non-conserved residue
<220> FEATURE:
```

```
<221> NAME/KEY: MISC_FEATURE
<222> LOCATION: (462)..(462)
<223> OTHER INFORMATION: Xaa is non-conserved residue
<220> FEATURE:
<221> NAME/KEY: MISC_FEATURE
<222> LOCATION: (464)..(464)
<223> OTHER INFORMATION: Xaa is non-conserved residue
<220> FEATURE:
<221> NAME/KEY: MISC_FEATURE
<222> LOCATION: (466)..(468)
<223> OTHER INFORMATION: Xaa is non-conserved residue
<220> FEATURE:
<221> NAME/KEY: MISC_FEATURE
<222> LOCATION: (470)..(475)
<223> OTHER INFORMATION: Xaa is non-conserved residue
<220> FEATURE:
<221> NAME/KEY: MISC_FEATURE
<222> LOCATION: (477)..(498)
<223> OTHER INFORMATION: Xaa is non-conserved residue

<400> SEQUENCE: 65

Xaa Xaa Xaa Xaa Xaa Xaa Xaa Xaa Gln Leu Leu Ser Xaa Xaa Ala
1               5                   10                  15

Xaa Xaa Xaa Xaa His Gly Xaa Xaa Ser Ser Tyr Phe Xaa Gly Trp Xaa
            20                  25                  30

Xaa Tyr Xaa Xaa Xaa Pro Xaa Asp Xaa Xaa Xaa Asn Xaa Xaa Gly Xaa
        35                  40                  45

Ile Gln Met Gly Leu Ala Glu Asn Gln Leu Ser Xaa Asp Leu Xaa Glu
    50                  55                  60

Xaa Trp Xaa Xaa Xaa Xaa Pro Xaa Ala Xaa Xaa Xaa Xaa Xaa Gly
65                  70                  75                  80

Ala Xaa Xaa Phe Arg Xaa Xaa Ala Xaa Phe Gln Asp Tyr His Gly Xaa
                85                  90                  95

Pro Xaa Phe Xaa Xaa Ala Xaa Ala Xaa Phe Met Xaa Xaa Xaa Arg Xaa
        100                 105                 110

Xaa Xaa Val Thr Phe Asp Pro Xaa Xaa Xaa Val Xaa Xaa Xaa Gly Ala
            115                 120                 125

Thr Xaa Ala Xaa Xaa Xaa Leu Xaa Phe Cys Leu Ala Asp Xaa Gly Asp
    130                 135                 140

Ala Xaa Leu Xaa Pro Thr Pro Tyr Tyr Pro Xaa Phe Asp Arg Asp Xaa
145                 150                 155                 160

Xaa Trp Arg Xaa Gly Xaa Xaa Xaa Xaa Pro Xaa Xaa Cys Xaa Ser Xaa
                165                 170                 175

Asn Xaa Phe Xaa Leu Thr Arg Xaa Ala Leu Xaa Xaa Ala Tyr Xaa Xaa
            180                 185                 190

Ala Xaa Xaa Xaa Xaa Xaa Arg Val Xaa Gly Xaa Leu Ile Thr Asn Pro
        195                 200                 205

Ser Asn Pro Leu Gly Thr Thr Xaa Xaa Arg Xaa Xaa Leu Xaa Met Leu
    210                 215                 220

Xaa Xaa Phe Xaa Xaa Xaa Xaa Xaa His Leu Xaa Xaa Asp Glu Ile
225                 230                 235                 240

Tyr Xaa Gly Xaa Val Phe Ala Xaa Pro Xaa Phe Val Ser Xaa Xaa Glu
        245                 250                 255

Val Xaa Xaa Xaa Xaa Xaa Xaa Xaa Xaa Xaa Xaa Xaa Xaa Xaa Gly
    260                 265                 270

Xaa Xaa Xaa Asp Xaa Xaa His Xaa Xaa Tyr Ser Leu Ser Lys Asp Xaa
        275                 280                 285

Gly Leu Pro Gly Phe Arg Val Gly Xaa Xaa Tyr Ser Xaa Asn Xaa Xaa
    290                 295                 300
```

```
Val Val Xaa Xaa Ala Xaa Lys Met Ser Ser Phe Gly Leu Val Ser Ser
305                 310                 315                 320

Gln Thr Gln His Xaa Leu Ala Xaa Xaa Leu Xaa Asp Xaa Xaa Phe Xaa
                325                 330                 335

Xaa Arg Xaa Xaa Ala Glu Xaa Xaa Arg Arg Xaa Xaa Xaa Arg Xaa Xaa
            340                 345                 350

Xaa Xaa Xaa Xaa Gly Leu Xaa Xaa Val Gly Ile Xaa Cys Leu Xaa Xaa
            355                 360                 365

Asn Ala Gly Leu Phe Xaa Trp Xaa Xaa Xaa Arg Xaa Xaa Xaa Arg Xaa
            370                 375                 380

Xaa Xaa Xaa Xaa Xaa Glu Xaa Glu Leu Trp Xaa Xaa Xaa Val Xaa Xaa
385                 390                 395                 400

Val Xaa Leu Asn Xaa Ser Pro Gly Xaa Ser Xaa His Cys Xaa Glu Pro
        405                 410                 415

Gly Trp Phe Arg Val Cys Xaa Ala Asn Met Xaa Xaa Xaa Thr Xaa Xaa
            420                 425                 430

Val Ala Leu Xaa Arg Xaa Xaa Xaa Phe Xaa Xaa Xaa Xaa Xaa Xaa Xaa
            435                 440                 445

Xaa Xaa Xaa Xaa Ala Xaa Xaa Xaa Xaa Xaa Xaa Pro Xaa Arg Xaa
            450                 455                 460

Ser Xaa Xaa Xaa Arg Xaa Xaa Xaa Xaa Xaa Ala Xaa Xaa Xaa Xaa
465                 470                 475                 480

Xaa Xaa Xaa Xaa Xaa Xaa Xaa Xaa Xaa Xaa Xaa Xaa Xaa Xaa Xaa
                485                 490                 495

Xaa Xaa
```

<210> SEQ ID NO 66
<211> LENGTH: 498
<212> TYPE: PRT
<213> ORGANISM: Artificial
<220> FEATURE:
<223> OTHER INFORMATION: Consensus Protein Sequence
<220> FEATURE:
<221> NAME/KEY: MISC_FEATURE
<222> LOCATION: (1)..(9)
<223> OTHER INFORMATION: Xaa is non-conserved residue
<220> FEATURE:
<221> NAME/KEY: MISC_FEATURE
<222> LOCATION: (15)..(15)
<223> OTHER INFORMATION: Xaa is non-conserved residue
<220> FEATURE:
<221> NAME/KEY: MISC_FEATURE
<222> LOCATION: (17)..(20)
<223> OTHER INFORMATION: Xaa is non-conserved residue
<220> FEATURE:
<221> NAME/KEY: MISC_FEATURE
<222> LOCATION: (24)..(24)
<223> OTHER INFORMATION: Xaa is non-conserved residue
<220> FEATURE:
<221> NAME/KEY: MISC_FEATURE
<222> LOCATION: (29)..(29)
<223> OTHER INFORMATION: Xaa is non-conserved residue
<220> FEATURE:
<221> NAME/KEY: MISC_FEATURE
<222> LOCATION: (32)..(33)
<223> OTHER INFORMATION: Xaa is non-conserved residue
<220> FEATURE:
<221> NAME/KEY: MISC_FEATURE
<222> LOCATION: (36)..(37)
<223> OTHER INFORMATION: Xaa is non-conserved residue
<220> FEATURE:
<221> NAME/KEY: MISC_FEATURE
<222> LOCATION: (41)..(43)
<223> OTHER INFORMATION: Xaa is non-conserved residue
<220> FEATURE:
<221> NAME/KEY: MISC_FEATURE

```
<222> LOCATION: (45)..(46)
<223> OTHER INFORMATION: Xaa is non-conserved residue
<220> FEATURE:
<221> NAME/KEY: MISC_FEATURE
<222> LOCATION: (60)..(60)
<223> OTHER INFORMATION: Xaa is non-conserved residue
<220> FEATURE:
<221> NAME/KEY: MISC_FEATURE
<222> LOCATION: (65)..(65)
<223> OTHER INFORMATION: Xaa is non-conserved residue
<220> FEATURE:
<221> NAME/KEY: MISC_FEATURE
<222> LOCATION: (67)..(70)
<223> OTHER INFORMATION: Xaa is non-conserved residue
<220> FEATURE:
<221> NAME/KEY: MISC_FEATURE
<222> LOCATION: (74)..(79)
<223> OTHER INFORMATION: Xaa is non-conserved residue
<220> FEATURE:
<221> NAME/KEY: MISC_FEATURE
<222> LOCATION: (82)..(83)
<223> OTHER INFORMATION: Xaa is non-conserved residue
<220> FEATURE:
<221> NAME/KEY: MISC_FEATURE
<222> LOCATION: (86)..(86)
<223> OTHER INFORMATION: Xaa is non-conserved residue
<220> FEATURE:
<221> NAME/KEY: MISC_FEATURE
<222> LOCATION: (89)..(89)
<223> OTHER INFORMATION: Xaa is non-conserved residue
<220> FEATURE:
<221> NAME/KEY: MISC_FEATURE
<222> LOCATION: (98)..(98)
<223> OTHER INFORMATION: Xaa is non-conserved residue
<220> FEATURE:
<221> NAME/KEY: MISC_FEATURE
<222> LOCATION: (101)..(101)
<223> OTHER INFORMATION: Xaa is non-conserved residue
<220> FEATURE:
<221> NAME/KEY: MISC_FEATURE
<222> LOCATION: (108)..(108)
<223> OTHER INFORMATION: Xaa is non-conserved residue
<220> FEATURE:
<221> NAME/KEY: MISC_FEATURE
<222> LOCATION: (110)..(110)
<223> OTHER INFORMATION: Xaa is non-conserved residue
<220> FEATURE:
<221> NAME/KEY: MISC_FEATURE
<222> LOCATION: (112)..(113)
<223> OTHER INFORMATION: Xaa is non-conserved residue
<220> FEATURE:
<221> NAME/KEY: MISC_FEATURE
<222> LOCATION: (120)..(121)
<223> OTHER INFORMATION: Xaa is non-conserved residue
<220> FEATURE:
<221> NAME/KEY: MISC_FEATURE
<222> LOCATION: (125)..(126)
<223> OTHER INFORMATION: Xaa is non-conserved residue
<220> FEATURE:
<221> NAME/KEY: MISC_FEATURE
<222> LOCATION: (130)..(130)
<223> OTHER INFORMATION: Xaa is non-conserved residue
<220> FEATURE:
<221> NAME/KEY: MISC_FEATURE
<222> LOCATION: (132)..(132)
<223> OTHER INFORMATION: Xaa is non-conserved residue
<220> FEATURE:
<221> NAME/KEY: MISC_FEATURE
<222> LOCATION: (134)..(134)
<223> OTHER INFORMATION: Xaa is non-conserved residue
<220> FEATURE:
<221> NAME/KEY: MISC_FEATURE
<222> LOCATION: (136)..(136)
<223> OTHER INFORMATION: Xaa is non-conserved residue
<220> FEATURE:
<221> NAME/KEY: MISC_FEATURE
<222> LOCATION: (142)..(142)
<223> OTHER INFORMATION: Xaa is non-conserved residue
<220> FEATURE:
```

-continued

```
<221> NAME/KEY: MISC_FEATURE
<222> LOCATION: (155)..(155)
<223> OTHER INFORMATION: Xaa is non-conserved residue
<220> FEATURE:
<221> NAME/KEY: MISC_FEATURE
<222> LOCATION: (160)..(161)
<223> OTHER INFORMATION: Xaa is non-conserved residue
<220> FEATURE:
<221> NAME/KEY: MISC_FEATURE
<222> LOCATION: (164)..(164)
<223> OTHER INFORMATION: Xaa is non-conserved residue
<220> FEATURE:
<221> NAME/KEY: MISC_FEATURE
<222> LOCATION: (166)..(167)
<223> OTHER INFORMATION: Xaa is non-conserved residue
<220> FEATURE:
<221> NAME/KEY: MISC_FEATURE
<222> LOCATION: (169)..(169)
<223> OTHER INFORMATION: Xaa is non-conserved residue
<220> FEATURE:
<221> NAME/KEY: MISC_FEATURE
<222> LOCATION: (172)..(172)
<223> OTHER INFORMATION: Xaa is non-conserved residue
<220> FEATURE:
<221> NAME/KEY: MISC_FEATURE
<222> LOCATION: (174)..(174)
<223> OTHER INFORMATION: Xaa is non-conserved residue
<220> FEATURE:
<221> NAME/KEY: MISC_FEATURE
<222> LOCATION: (176)..(176)
<223> OTHER INFORMATION: Xaa is non-conserved residue
<220> FEATURE:
<221> NAME/KEY: MISC_FEATURE
<222> LOCATION: (178)..(178)
<223> OTHER INFORMATION: Xaa is non-conserved residue
<220> FEATURE:
<221> NAME/KEY: MISC_FEATURE
<222> LOCATION: (180)..(180)
<223> OTHER INFORMATION: Xaa is non-conserved residue
<220> FEATURE:
<221> NAME/KEY: MISC_FEATURE
<222> LOCATION: (184)..(184)
<223> OTHER INFORMATION: Xaa is non-conserved residue
<220> FEATURE:
<221> NAME/KEY: MISC_FEATURE
<222> LOCATION: (187)..(188)
<223> OTHER INFORMATION: Xaa is non-conserved residue
<220> FEATURE:
<221> NAME/KEY: MISC_FEATURE
<222> LOCATION: (191)..(192)
<223> OTHER INFORMATION: Xaa is non-conserved residue
<220> FEATURE:
<221> NAME/KEY: MISC_FEATURE
<222> LOCATION: (194)..(194)
<223> OTHER INFORMATION: Xaa is non-conserved residue
<220> FEATURE:
<221> NAME/KEY: MISC_FEATURE
<222> LOCATION: (196)..(198)
<223> OTHER INFORMATION: Xaa is non-conserved residue
<220> FEATURE:
<221> NAME/KEY: MISC_FEATURE
<222> LOCATION: (216)..(217)
<223> OTHER INFORMATION: Xaa is non-conserved residue
<220> FEATURE:
<221> NAME/KEY: MISC_FEATURE
<222> LOCATION: (219)..(220)
<223> OTHER INFORMATION: Xaa is non-conserved residue
<220> FEATURE:
<221> NAME/KEY: MISC_FEATURE
<222> LOCATION: (222)..(222)
<223> OTHER INFORMATION: Xaa is non-conserved residue
<220> FEATURE:
<221> NAME/KEY: MISC_FEATURE
<222> LOCATION: (225)..(226)
<223> OTHER INFORMATION: Xaa is non-conserved residue
<220> FEATURE:
<221> NAME/KEY: MISC_FEATURE
<222> LOCATION: (228)..(232)
<223> OTHER INFORMATION: Xaa is non-conserved residue
```

```
<220> FEATURE:
<221> NAME/KEY: MISC_FEATURE
<222> LOCATION: (237)..(237)
<223> OTHER INFORMATION: Xaa is non-conserved residue
<220> FEATURE:
<221> NAME/KEY: MISC_FEATURE
<222> LOCATION: (242)..(242)
<223> OTHER INFORMATION: Xaa is non-conserved residue
<220> FEATURE:
<221> NAME/KEY: MISC_FEATURE
<222> LOCATION: (244)..(244)
<223> OTHER INFORMATION: Xaa is non-conserved residue
<220> FEATURE:
<221> NAME/KEY: MISC_FEATURE
<222> LOCATION: (248)..(248)
<223> OTHER INFORMATION: Xaa is non-conserved residue
<220> FEATURE:
<221> NAME/KEY: MISC_FEATURE
<222> LOCATION: (250)..(250)
<223> OTHER INFORMATION: Xaa is non-conserved residue
<220> FEATURE:
<221> NAME/KEY: MISC_FEATURE
<222> LOCATION: (255)..(255)
<223> OTHER INFORMATION: Xaa is non-conserved residue
<220> FEATURE:
<221> NAME/KEY: MISC_FEATURE
<222> LOCATION: (259)..(271)
<223> OTHER INFORMATION: Xaa is non-conserved residue
<220> FEATURE:
<221> NAME/KEY: MISC_FEATURE
<222> LOCATION: (273)..(275)
<223> OTHER INFORMATION: Xaa is non-conserved residue
<220> FEATURE:
<221> NAME/KEY: MISC_FEATURE
<222> LOCATION: (277)..(277)
<223> OTHER INFORMATION: Xaa is non-conserved residue
<220> FEATURE:
<221> NAME/KEY: MISC_FEATURE
<222> LOCATION: (281)..(281)
<223> OTHER INFORMATION: Xaa is non-conserved residue
<220> FEATURE:
<221> NAME/KEY: MISC_FEATURE
<222> LOCATION: (288)..(288)
<223> OTHER INFORMATION: Xaa is non-conserved residue
<220> FEATURE:
<221> NAME/KEY: MISC_FEATURE
<222> LOCATION: (297)..(297)
<223> OTHER INFORMATION: Xaa is non-conserved residue
<220> FEATURE:
<221> NAME/KEY: MISC_FEATURE
<222> LOCATION: (301)..(301)
<223> OTHER INFORMATION: Xaa is non-conserved residue
<220> FEATURE:
<221> NAME/KEY: MISC_FEATURE
<222> LOCATION: (303)..(304)
<223> OTHER INFORMATION: Xaa is non-conserved residue
<220> FEATURE:
<221> NAME/KEY: MISC_FEATURE
<222> LOCATION: (307)..(308)
<223> OTHER INFORMATION: Xaa is non-conserved residue
<220> FEATURE:
<221> NAME/KEY: MISC_FEATURE
<222> LOCATION: (310)..(310)
<223> OTHER INFORMATION: Xaa is non-conserved residue
<220> FEATURE:
<221> NAME/KEY: MISC_FEATURE
<222> LOCATION: (325)..(325)
<223> OTHER INFORMATION: Xaa is non-conserved residue
<220> FEATURE:
<221> NAME/KEY: MISC_FEATURE
<222> LOCATION: (328)..(328)
<223> OTHER INFORMATION: Xaa is non-conserved residue
<220> FEATURE:
<221> NAME/KEY: MISC_FEATURE
<222> LOCATION: (331)..(331)
<223> OTHER INFORMATION: Xaa is non-conserved residue
<220> FEATURE:
<221> NAME/KEY: MISC_FEATURE
<222> LOCATION: (333)..(333)
```

```
<223> OTHER INFORMATION: Xaa is non-conserved residue
<220> FEATURE:
<221> NAME/KEY: MISC_FEATURE
<222> LOCATION: (336)..(337)
<223> OTHER INFORMATION: Xaa is non-conserved residue
<220> FEATURE:
<221> NAME/KEY: MISC_FEATURE
<222> LOCATION: (343)..(344)
<223> OTHER INFORMATION: Xaa is non-conserved residue
<220> FEATURE:
<221> NAME/KEY: MISC_FEATURE
<222> LOCATION: (348)..(349)
<223> OTHER INFORMATION: Xaa is non-conserved residue
<220> FEATURE:
<221> NAME/KEY: MISC_FEATURE
<222> LOCATION: (351)..(351)
<223> OTHER INFORMATION: Xaa is non-conserved residue
<220> FEATURE:
<221> NAME/KEY: MISC_FEATURE
<222> LOCATION: (353)..(356)
<223> OTHER INFORMATION: Xaa is non-conserved residue
<220> FEATURE:
<221> NAME/KEY: MISC_FEATURE
<222> LOCATION: (359)..(360)
<223> OTHER INFORMATION: Xaa is non-conserved residue
<220> FEATURE:
<221> NAME/KEY: MISC_FEATURE
<222> LOCATION: (364)..(364)
<223> OTHER INFORMATION: Xaa is non-conserved residue
<220> FEATURE:
<221> NAME/KEY: MISC_FEATURE
<222> LOCATION: (367)..(368)
<223> OTHER INFORMATION: Xaa is non-conserved residue
<220> FEATURE:
<221> NAME/KEY: MISC_FEATURE
<222> LOCATION: (374)..(374)
<223> OTHER INFORMATION: Xaa is non-conserved residue
<220> FEATURE:
<221> NAME/KEY: MISC_FEATURE
<222> LOCATION: (376)..(377)
<223> OTHER INFORMATION: Xaa is non-conserved residue
<220> FEATURE:
<221> NAME/KEY: MISC_FEATURE
<222> LOCATION: (380)..(380)
<223> OTHER INFORMATION: Xaa is non-conserved residue
<220> FEATURE:
<221> NAME/KEY: MISC_FEATURE
<222> LOCATION: (384)..(384)
<223> OTHER INFORMATION: Xaa is non-conserved residue
<220> FEATURE:
<221> NAME/KEY: MISC_FEATURE
<222> LOCATION: (386)..(387)
<223> OTHER INFORMATION: Xaa is non-conserved residue
<220> FEATURE:
<221> NAME/KEY: MISC_FEATURE
<222> LOCATION: (389)..(389)
<223> OTHER INFORMATION: Xaa is non-conserved residue
<220> FEATURE:
<221> NAME/KEY: MISC_FEATURE
<222> LOCATION: (396)..(396)
<223> OTHER INFORMATION: Xaa is non-conserved residue
<220> FEATURE:
<221> NAME/KEY: MISC_FEATURE
<222> LOCATION: (399)..(400)
<223> OTHER INFORMATION: Xaa is non-conserved residue
<220> FEATURE:
<221> NAME/KEY: MISC_FEATURE
<222> LOCATION: (402)..(402)
<223> OTHER INFORMATION: Xaa is non-conserved residue
<220> FEATURE:
<221> NAME/KEY: MISC_FEATURE
<222> LOCATION: (409)..(409)
<223> OTHER INFORMATION: Xaa is non-conserved residue
<220> FEATURE:
<221> NAME/KEY: MISC_FEATURE
<222> LOCATION: (411)..(411)
<223> OTHER INFORMATION: Xaa is non-conserved residue
<220> FEATURE:
<221> NAME/KEY: MISC_FEATURE
```

```
<222> LOCATION: (414)..(414)
<223> OTHER INFORMATION: Xaa is non-conserved residue
<220> FEATURE:
<221> NAME/KEY: MISC_FEATURE
<222> LOCATION: (423)..(423)
<223> OTHER INFORMATION: Xaa is non-conserved residue
<220> FEATURE:
<221> NAME/KEY: MISC_FEATURE
<222> LOCATION: (427)..(429)
<223> OTHER INFORMATION: Xaa is non-conserved residue
<220> FEATURE:
<221> NAME/KEY: MISC_FEATURE
<222> LOCATION: (436)..(436)
<223> OTHER INFORMATION: Xaa is non-conserved residue
<220> FEATURE:
<221> NAME/KEY: MISC_FEATURE
<222> LOCATION: (439)..(440)
<223> OTHER INFORMATION: Xaa is non-conserved residue
<220> FEATURE:
<221> NAME/KEY: MISC_FEATURE
<222> LOCATION: (442)..(449)
<223> OTHER INFORMATION: Xaa is non-conserved residue
<220> FEATURE:
<221> NAME/KEY: MISC_FEATURE
<222> LOCATION: (451)..(452)
<223> OTHER INFORMATION: Xaa is non-conserved residue
<220> FEATURE:
<221> NAME/KEY: MISC_FEATURE
<222> LOCATION: (454)..(460)
<223> OTHER INFORMATION: Xaa is non-conserved residue
<220> FEATURE:
<221> NAME/KEY: MISC_FEATURE
<222> LOCATION: (462)..(462)
<223> OTHER INFORMATION: Xaa is non-conserved residue
<220> FEATURE:
<221> NAME/KEY: MISC_FEATURE
<222> LOCATION: (464)..(464)
<223> OTHER INFORMATION: Xaa is non-conserved residue
<220> FEATURE:
<221> NAME/KEY: MISC_FEATURE
<222> LOCATION: (466)..(468)
<223> OTHER INFORMATION: Xaa is non-conserved residue
<220> FEATURE:
<221> NAME/KEY: MISC_FEATURE
<222> LOCATION: (470)..(475)
<223> OTHER INFORMATION: Xaa is non-conserved residue
<220> FEATURE:
<221> NAME/KEY: MISC_FEATURE
<222> LOCATION: (477)..(498)
<223> OTHER INFORMATION: Xaa is non-conserved residue

<400> SEQUENCE: 66

Xaa Xaa Xaa Xaa Xaa Xaa Xaa Xaa Xaa Gln Leu Leu Ser Arg Xaa Ala
1               5                   10                  15

Xaa Xaa Xaa Xaa His Gly Glu Xaa Ser Ser Tyr Phe Xaa Gly Trp Xaa
            20                  25                  30

Xaa Tyr Asp Xaa Xaa Pro Phe Asp Xaa Xaa Xaa Asn Xaa Xaa Gly Val
        35                  40                  45

Ile Gln Met Gly Leu Ala Glu Asn Gln Leu Ser Xaa Asp Leu Ile Glu
    50                  55                  60

Xaa Trp Xaa Xaa Xaa Xaa Pro Glu Ala Xaa Xaa Xaa Xaa Xaa Xaa Gly
65                  70                  75                  80

Ala Xaa Xaa Phe Arg Xaa Ile Ala Xaa Phe Gln Asp Tyr His Gly Leu
            85                  90                  95

Pro Xaa Phe Arg Xaa Ala Met Ala Lys Phe Met Xaa Gln Xaa Arg Xaa
            100                 105                 110

Xaa Lys Val Thr Phe Asp Pro Xaa Xaa Val Val Met Xaa Xaa Gly Ala
        115                 120                 125

Thr Xaa Ala Xaa Asp Xaa Leu Xaa Phe Cys Leu Ala Asp Xaa Gly Asp
130                 135                 140
```

```
Ala Tyr Leu Val Pro Thr Pro Tyr Tyr Pro Xaa Phe Asp Arg Asp Xaa
145                 150                 155                 160

Xaa Trp Arg Xaa Gly Xaa Xaa Leu Xaa Pro Ile Xaa Cys Xaa Ser Xaa
            165                 170                 175

Asn Xaa Phe Xaa Leu Thr Arg Xaa Ala Leu Xaa Xaa Ala Tyr Xaa Xaa
        180                 185                 190

Ala Xaa Arg Xaa Xaa Xaa Arg Val Lys Gly Val Leu Ile Thr Asn Pro
        195                 200                 205

Ser Asn Pro Leu Gly Thr Thr Xaa Xaa Arg Xaa Xaa Leu Xaa Met Leu
210                 215                 220

Xaa Xaa Phe Xaa Xaa Xaa Xaa Val His Leu Ile Xaa Asp Glu Ile
225                 230                 235                 240

Tyr Xaa Gly Xaa Val Phe Ala Xaa Pro Xaa Phe Val Ser Ile Xaa Glu
            245                 250                 255

Val Ile Xaa Xaa Xaa Xaa Xaa Xaa Xaa Xaa Xaa Xaa Xaa Gly
            260                 265                 270

Xaa Xaa Xaa Asp Xaa Val His Ile Xaa Tyr Ser Leu Ser Lys Asp Xaa
        275                 280                 285

Gly Leu Pro Gly Phe Arg Val Gly Xaa Val Tyr Ser Xaa Asn Xaa Xaa
        290                 295                 300

Val Val Xaa Xaa Ala Xaa Lys Met Ser Ser Phe Gly Leu Val Ser Ser
305                 310                 315                 320

Gln Thr Gln His Xaa Leu Ala Xaa Met Leu Xaa Asp Xaa Glu Phe Xaa
                325                 330                 335

Xaa Arg Phe Leu Ala Glu Xaa Xaa Arg Arg Leu Xaa Xaa Arg Xaa Asp
            340                 345                 350

Xaa Xaa Xaa Xaa Gly Leu Xaa Xaa Val Gly Ile Xaa Cys Leu Xaa Xaa
            355                 360                 365

Asn Ala Gly Leu Phe Xaa Trp Xaa Xaa Leu Arg Xaa Met Leu Arg Xaa
            370                 375                 380

Lys Xaa Xaa Asp Xaa Glu Leu Glu Leu Trp Arg Xaa Ile Val Xaa Xaa
385                 390                 395                 400

Val Xaa Leu Asn Val Ser Pro Gly Xaa Ser Xaa His Cys Xaa Glu Pro
            405                 410                 415

Gly Trp Phe Arg Val Cys Xaa Ala Asn Met Xaa Xaa Xaa Thr Met Glu
            420                 425                 430

Val Ala Leu Xaa Arg Ile Xaa Xaa Phe Xaa Xaa Xaa Xaa Xaa Xaa Xaa
            435                 440                 445

Xaa Lys Xaa Xaa Ala Xaa Xaa Xaa Xaa Xaa Xaa Pro Xaa Arg Xaa
    450                 455                 460

Ser Xaa Xaa Xaa Arg Xaa Xaa Xaa Xaa Ala Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa
```